(12) United States Patent
Karsten et al.

(10) Patent No.: US 11,564,948 B2
(45) Date of Patent: Jan. 31, 2023

(54) THERAPEUTIC METHODS USING ERYTHROCYTES

(71) Applicant: Sangui Bio Pty Ltd, Manly (AU)

(72) Inventors: Elisabeth Karsten, Northmead (AU); Ben Herbert, North Epping (AU); Alan Liddle, Manly (AU); Cameron Hill, St. Leonards (AU)

(73) Assignee: Sangui Bio Pty Ltd, Manly (AU)

( * ) Notice: Subject to any disclaimer, the term of this patent is extended or adjusted under 35 U.S.C. 154(b) by 448 days.

(21) Appl. No.: 16/064,973

(22) PCT Filed: Dec. 22, 2016

(86) PCT No.: PCT/AU2016/000404
§ 371 (c)(1),
(2) Date: Jun. 21, 2018

(87) PCT Pub. No.: WO2017/106899
PCT Pub. Date: Jun. 29, 2017

(65) Prior Publication Data
US 2019/0000884 A1   Jan. 3, 2019

(30) Foreign Application Priority Data

Dec. 22, 2015 (AU) ............................ 2015905309

(51) Int. Cl.
*A61K 35/18* (2015.01)
*C12N 5/078* (2010.01)

(52) U.S. Cl.
CPC ............ *A61K 35/18* (2013.01); *C12N 5/0641* (2013.01); *C12N 2500/35* (2013.01); *C12N 2501/20* (2013.01); *C12N 2502/1114* (2013.01); *C12N 2502/1323* (2013.01); *C12N 2502/1352* (2013.01); *C12N 2502/256* (2013.01); *C12N 2502/28* (2013.01); *C12N 2502/30* (2013.01)

(58) Field of Classification Search
CPC combination set(s) only.
See application file for complete search history.

(56) References Cited

U.S. PATENT DOCUMENTS

| | | | |
|---|---|---|---|
| 4,931,276 A | 6/1990 | Franco et al. | |
| 5,858,358 A * | 1/1999 | June | C07K 14/705 424/130.1 |
| 10,273,455 B2 * | 4/2019 | Baek | C12N 5/0641 |
| 2008/0095749 A1 * | 4/2008 | Aggarwal | A61K 35/28 424/93.7 |
| 2009/0054741 A1 | 2/2009 | Mcaleer | |
| 2012/0195869 A1 | 8/2012 | Terman | |
| 2014/0154221 A1 * | 6/2014 | Castro | A61P 1/04 435/375 |
| 2018/0306817 A1 | 10/2018 | Karsten et al. | |
| 2020/0096512 A1 | 3/2020 | Herbert et al. | |

FOREIGN PATENT DOCUMENTS

| | | | | |
|---|---|---|---|---|
| CN | 1662817 A | 8/2005 | | |
| CN | 1969184 A | 5/2007 | | |
| CN | 101248187 A | 8/2008 | | |
| FR | 2778851 | * 11/1999 | ............ | A61K 38/55 |
| JP | 2007510149 A | 4/2007 | | |
| JP | 2012530133 A | 11/2012 | | |
| JP | 2013501926 A | 1/2013 | | |
| JP | 2015055620 A | 3/2015 | | |
| JP | 2015523384 A | 8/2015 | | |
| WO | WO 1992/005801 | 4/1992 | | |
| WO | WO 2002007752 A2 | 1/2002 | | |
| WO | WO 2002007752 A3 | 1/2002 | | |
| WO | WO 2003087833 A2 | 10/2003 | | |
| WO | WO 2003087833 A3 | 10/2003 | | |
| WO | WO 2005045441 A1 | 5/2005 | | |
| WO | WO 2005103678 A2 | 11/2005 | | |
| WO | WO 2005103678 A3 | 11/2005 | | |
| WO | WO 2006081324 A2 | 8/2006 | | |
| WO | WO 2006081324 A3 | 8/2006 | | |
| WO | WO 2008134526 A2 | 11/2008 | | |
| WO | WO 2008134526 A3 | 11/2008 | | |
| WO | WO 2009/019317 | 2/2009 | | |
| WO | WO 2009111595 A2 | 9/2009 | | |
| WO | WO 2009/137629 | 11/2009 | | |
| WO | WO 2010147621 A1 | 12/2010 | | |
| WO | WO 2011018288 A1 | 2/2011 | | |
| WO | WO 2011/091154 | 7/2011 | | |
| WO | WO 2011127056 A2 | 10/2011 | | |
| WO | WO 2011127056 A3 | 10/2011 | | |
| WO | WO 2012166055 A1 | 12/2012 | | |
| WO | WO 2013/045885 | 4/2013 | | |
| WO | WO 2013/139906 | 9/2013 | | |

(Continued)

OTHER PUBLICATIONS

Antunes, Immunology and Cell Biology, 2011, 89:111-121. (Year: 2011).*
Fonseca et al, Blood, 2011, 97:3152-3160. (Year: 2011).*
Fredriksson et al, Inflammation, 2003, 27(2):71-78. (Year: 2003).*
Machine translation of specification of FR 2778851 (3 pages) (Year: 1999).*
Anderson et al, J Immunol, 2018, 201 (5): 1343-1351. (Year: 2018).*
Sut et al, Blood Transfusion, 2017, 15: 145-152. (Year: 2017).*
Watkins et al, Jan. 2015, 22(1): 38-46. (Year: 2015).*
Translation of FR 2778851, date of publication 1998. (Year: 1998).*
International Search Report dated Aug. 17, 2017 for PCT/AU2016/000404.
Day, Michael J. et al., "Expression and Regulation of Erythrocyte Auto-Antibodies in Mice Following Immunization with Rat Erythrocytes," *Eur. J. Immunol.*, 19:5 (1989) 795-801.
Zhou, Jingling et al., "Opsonization of Malaria-Infected Erythrocytes Activates the Inflammasome and Enhances Inflammatory Cytokine Secretion by Human Macrophages," *Malaria Journal*, 11:343 (2012) 1-13.

(Continued)

*Primary Examiner* — Allison M Fox
(74) *Attorney, Agent, or Firm* — Jones Day

(57) ABSTRACT

The present disclosure relates to methods for modulating the level of proteins in a subject or in target cells by priming red blood cells with various agents or conditions that modulate the levels of proteins associated with red blood cells and administering the primed red blood cells to a subject. The disclosed methods represent a novel use of red blood cells primed to express a number of proteins, as cell therapies for numerous diseases or disorders.

15 Claims, 232 Drawing Sheets

(56) References Cited

FOREIGN PATENT DOCUMENTS

| WO | WO 2013156806 A2 | 10/2013 |
|---|---|---|
| WO | WO 2013156806 A3 | 10/2013 |
| WO | WO 2014011901 A2 | 1/2014 |
| WO | WO 2014011901 A3 | 1/2014 |
| WO | WO 2014181309 A1 | 11/2014 |
| WO | WO 2016/187353 | 11/2016 |
| WO | WO 2017059477 A1 | 4/2017 |
| WO | WO 2018112500 A1 | 6/2018 |

OTHER PUBLICATIONS

Anniss et al., 2005, "Proteomic analysis of supernatants of stored red blood cell products", Transfusion, 45(9):1426-1433.
Ayache et al, 2006, "Effects of storage time and exogenous protease inhibitors on plasma protein levels", Am J Clin Pathol., 126(2):174-184.
Baruchel et al., 2015, "Updated Clinical Activity of Graspa Versus Native 1-Asparaginase in Combination with Cooprall Regimen in Phase 3 Randomized Trial in Patients with Relapsed Acute Lymphoblastic Leukemia (NCT01518517)", Blood, 126(23):3723.
Bjork et al., 1996, "A new enzyme activity in human blood cells and isolation of the responsible protein (D-dopachrome tautomerase) from erythrocytes", Eur J Haematol, 57(3):254-256.
Bowyer et al, 2011, "Global profiling of proteolysis during rupture of Plasmodium falciparum from the host erythrocyte", Mol Cell Proteomics, 10(5):M110.001636 (14 pages).
Bruil et al., 1995, "The mechanisms of leukocyte removal by filtration", Transfus Med Rev., 9(2):145-166.
Cassell et al., 1962, "Transfusion of buffy coat-poor red cell suspensions prepared by dextran sedimentation: description of newly designed equipment and evaluation of its use", Transfusion, 2:216-220.
D'Amici et al, 2007, "Proteomic analysis of RBC membrane protein degradation during blood storage", J Proteome Res., 6(8):3242-3255.
Dalton, 2017, "Blood tests at your fingertips", Chemical & Engineering News, 95(1):16-19.
Danesh et al., 2014, "Exosomes from red blood cell units bind to monocytes and induce proinflammatory cytokines, boosting T-cell responses in vitro", Blood, 123(5):687-696 (Epub 2013).
Dzieciatkowska et al., 2013, "Proteomic analysis of the supernatant of red blood cell units: the effects of storage and leucoreduction", Vox Sang, 105(3):210-218.
Ferru et al., 2012, "A new method for the capture of surface proteins in Plasmodium falciparum parasitized erythrocyte", J Infect Dev Ctries, 6(6):536-541.
Hansell et al., 2011, "DARC and D6: silent partners in chemokine regulation?", Immunol Cell Biol., 89(2):197-206 (Epub 2010).
Haudek et al., 2009, "Proteome maps of the main human peripheral blood constituents", J Proteome Res., 8(8):3834-3843.
International Search Report and Written Opinion for International Patent Application No. PCT/AU2016/000341 (published as WO 2017059477) dated Dec. 20, 2016 (13 pages).
International Search Report and Written Opinion for International Patent Application No. PCT/AU2016/000404 (published as WO 2017106899) dated Aug. 17, 2017 (17 pages).
International Search Report and Written Opinion for International Patent Application No. PCT/AU2017/000282 (published as WO 2018112500) dated Feb. 28, 2018 (22 pages).
Karsten et al., 2018, "Red blood cells are dynamic reservoirs of cytokines", Sci Rep., 8(1):3101 (12 pages).
Li et al, 2006, "Development and characterization of dried blood spot materials for the measurement of immunoreactive trypsinogen", J Med Screen, 13(2):79-84.
Makinen et al., 1977, "Migration inhibition factor and the blood clotting system: effects of defibrination, heparin and thrombin", Clin Exp Immunol., 29(1):181-186.
Mayeux, 2004, "Biomarkers: potential uses and limitations", NeuroRx, 1(2):182-188.
Mayr et al., 2008, "Duffy antigen modifies the chemokine response in human endotoxemia", Crit Care Med., 36(1):159-165.
McDade et al., 2007, "What a drop can do: dried blood spots as a minimally invasive method for integrating biomarkers into population-based research", Demography, 44(4):899-925.
Oliveri et al, 2001, "The effect of protease inhibitors on the two-dimensional electrophoresis pattern of red blood cell membranes", Electrophoresis, 22(3):560-565.
Pasini et al., 2006, "In-depth analysis of the membrane and cytosolic proteome of red blood cells", Blood, 108(3):791-801.
Pasini et al., 2010, "Red blood cell (RBC) membrane proteomics—Part I: Proteomics and RBC physiology", J Proteomics, 73(3):403-420 (Epub 2009).
Rubin et al., 2012, "Red blood cell microparticles: clinical relevance", Transfus Med Hemother, 39(5):342-347.
Schnabel et al., 2010, "Duffy antigen receptor for chemokines (Darc) polymorphism regulates circulating concentrations of monocyte chemoattractant protein-1 and other inflammatory mediators", Blood, 115(26):5289-5299 (Epub 2009).
Sirchia et al., 1980, "Evaluation of three procedures for the preparation of leukocyte-poor and leukocyte-free red blood cells for transfusion", Vox Sang, 38(4):197-204.
Tenczar, 1973, "Comparison of inverted centrifugation, saline washing, and dextran sedimentation in the preparation of leukocyte-poor red cells", Transfusion, 13(4):183-188.
Villanueva et al., 1988, "Chromatography, flow injection analysis and electrophoresis in computer-assisted comparative biochemistry: its application and possibilities in clinical research. Preliminary studies on Crohn's disease", J Chromatogr, 440:261-273.
Waikar et al., 2012, "Imperfect gold standards for kidney injury biomarker evaluation", J Am Soc Nephrol., 23(1):13-21 (Epub 2011).
Zaccaria et al., 2015, "Accessing to the minor proteome of red blood cells through the influence of the nanoparticle surface properties on the corona composition", Int J Nanomedicine, 10:1869-1883.
Zecher et al., 2014, "Erythrocyte-derived microvesicles amplify systemic inflammation by thrombin-dependent activation of complement", Arterioscler Thromb Vasc Biol., 34(2):313-320 (Epub 2013).
Zeng et al., 2014, "Mechanical response of red blood cells entering a constriction", Biomicrofluidics, 8(6):064123.
Darbonne et al., 1991, "Red blood cells are a sink for interleukin 8, a leukocyte chemotaxin", J Clin Invest, 88(4):1362-1369.
Hanahan et al., 1974, "The preparation of red cell ghosts (membranes)", Methods Enzymol., 31:168-172.
Kumar et al., 2015, "Enrichment of reticulocytes from whole blood using aqueous multiphase systems of polymers," Am. J. Hematol., 90(1):31-36 (Epub 2014).
Sparrow et al., 2004, "Supernatant from stored red blood cell primes inflammatory cells: influence of prestorage white cell reduction", Transfusion, 44(5):722-730.

\* cited by examiner

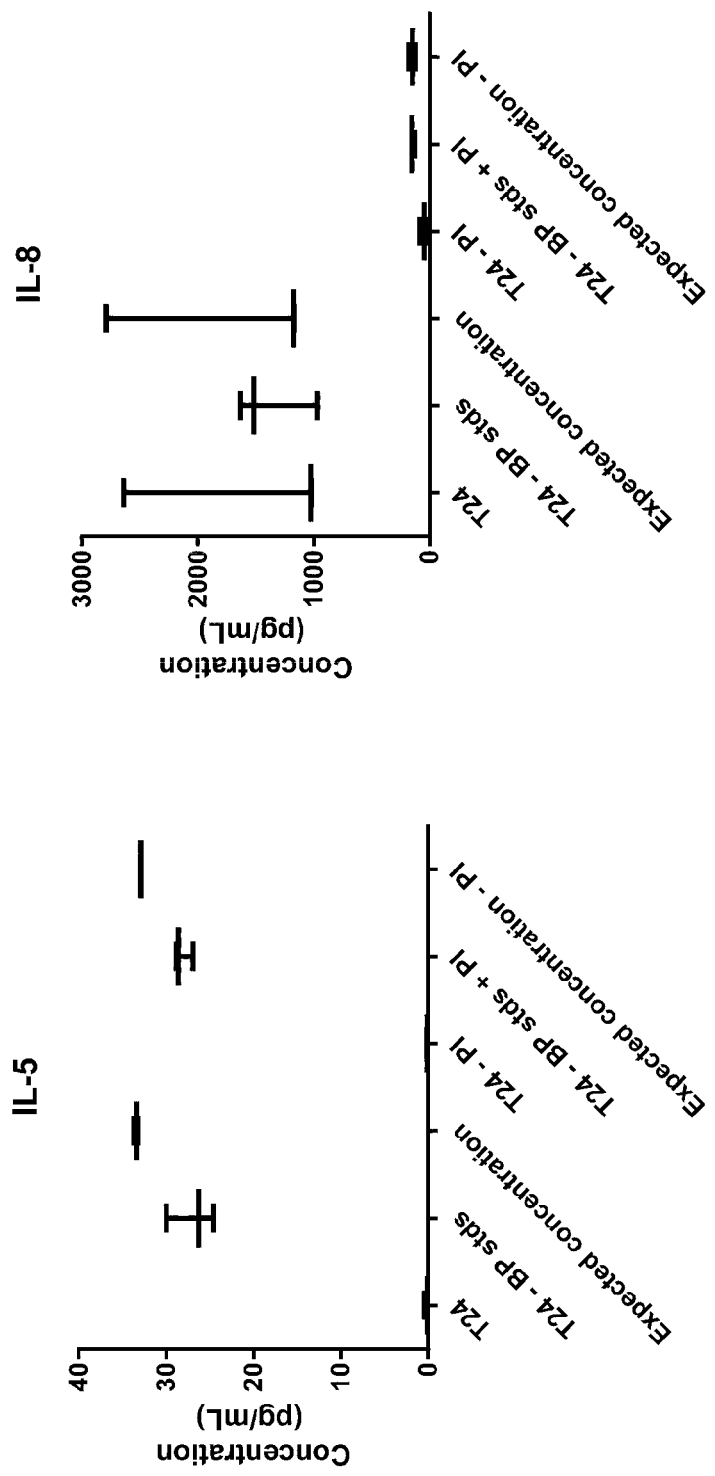

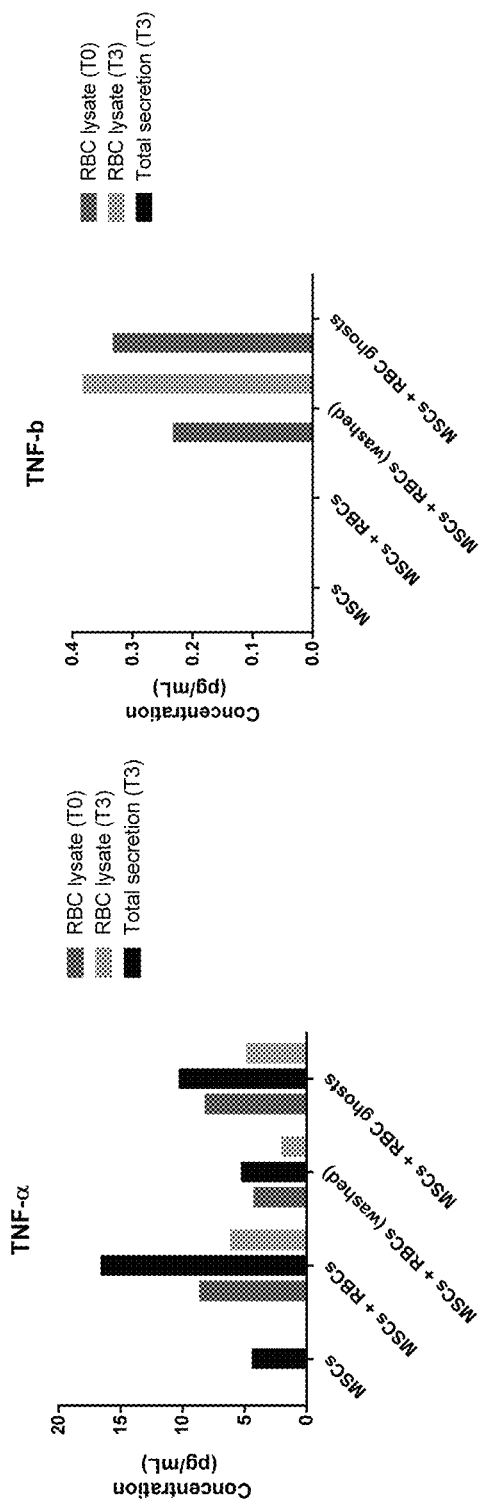
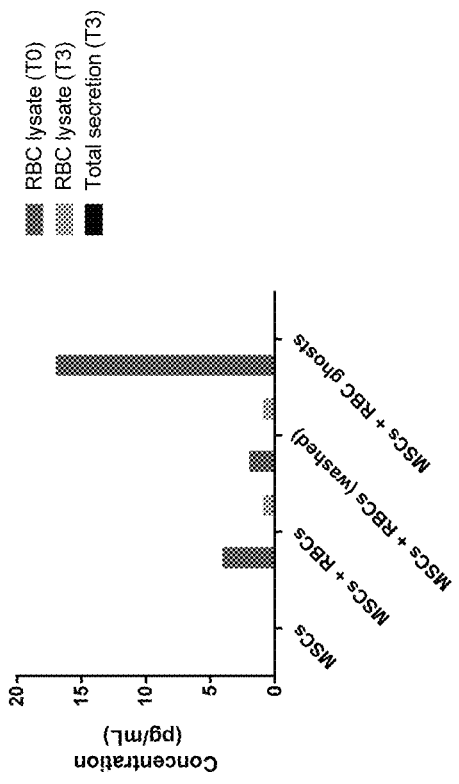
FIG. 19M
FIG. 19N
FIG. 19O

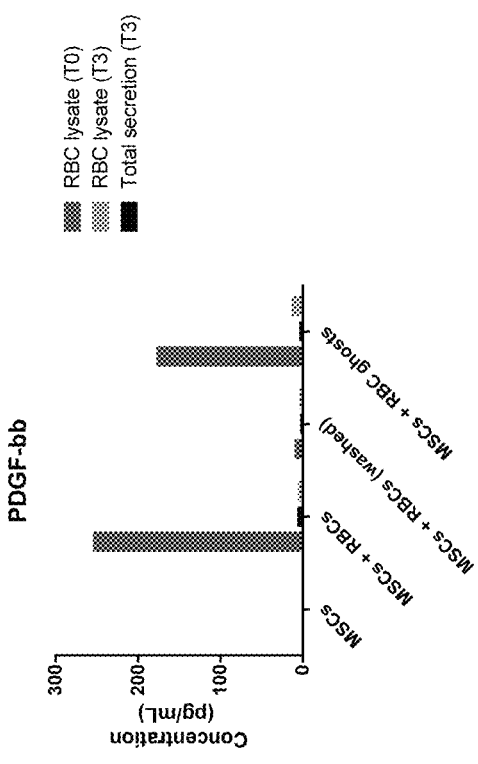
FIG. 22J
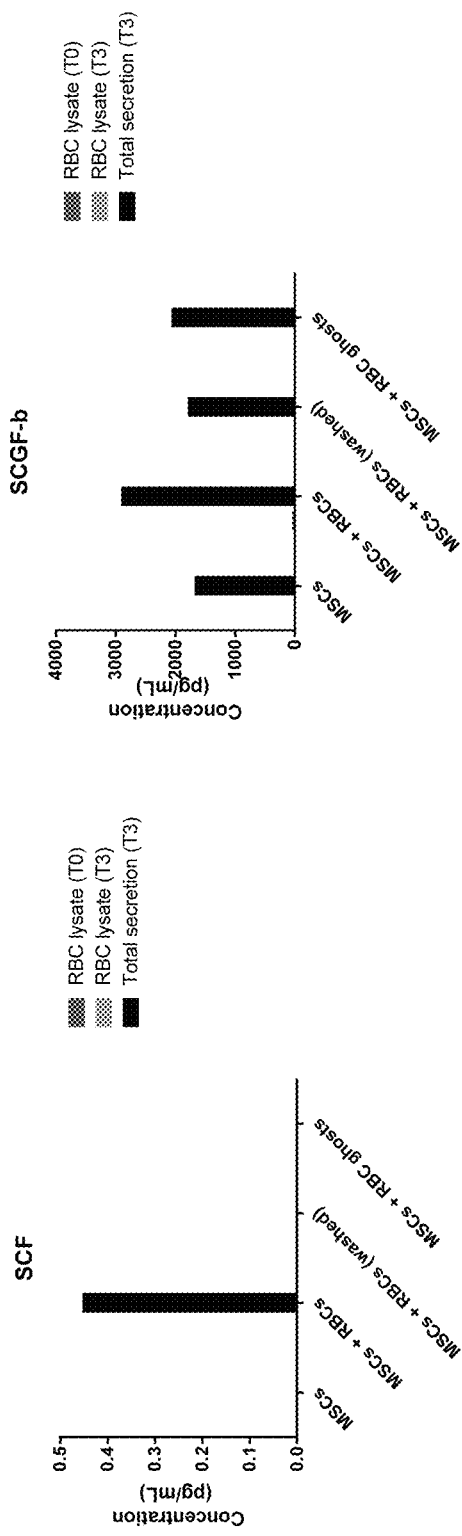
FIG. 22L
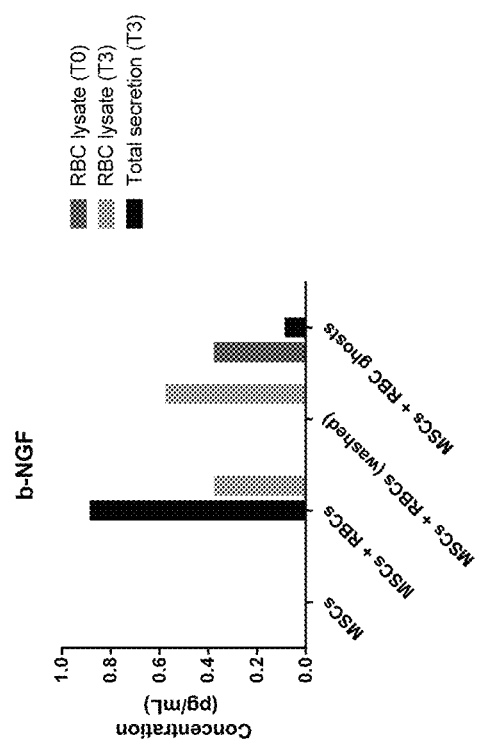
FIG. 22I
FIG. 22K

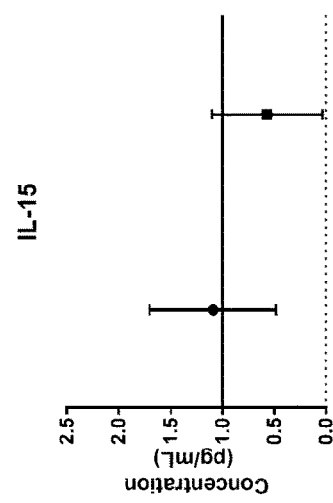
FIG. 28G  FIG. 28H  FIG. 28I
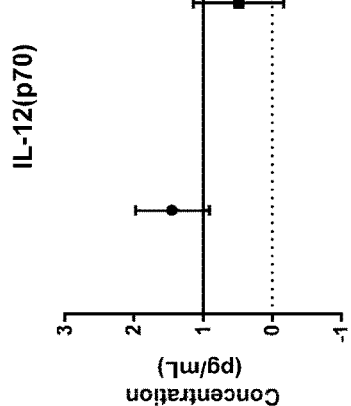
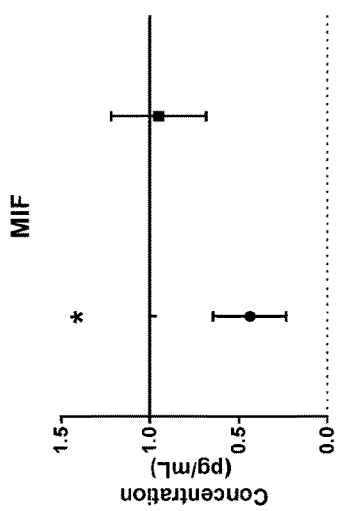
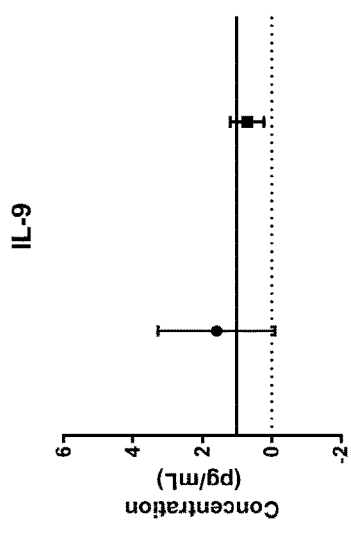
FIG. 28J  FIG. 28K  FIG. 28L

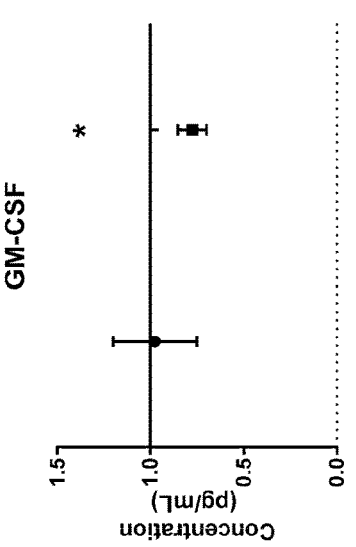
FIG. 31A bFGF
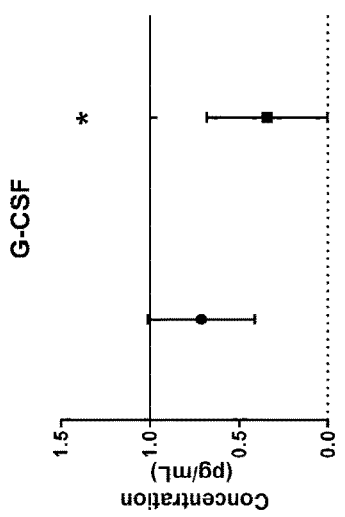
FIG. 31B G-CSF
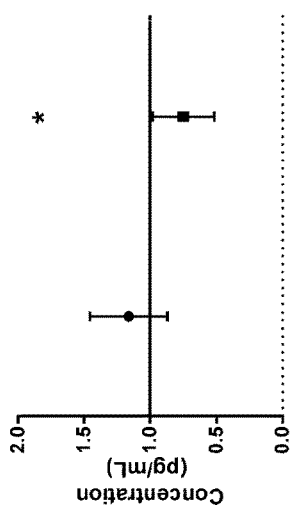
FIG. 31C GM-CSF
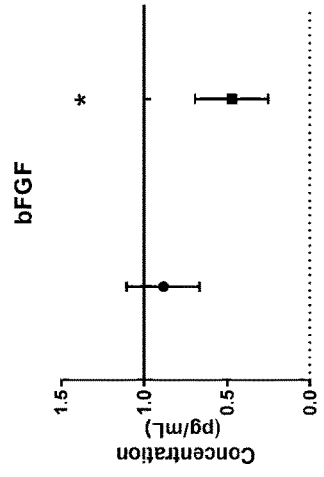
FIG. 31D HGF
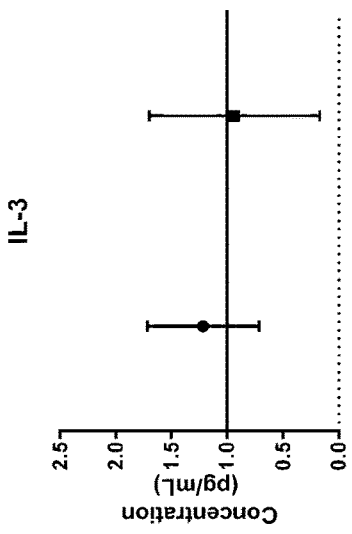
FIG. 31E IL-3
FIG. 31F IL-7

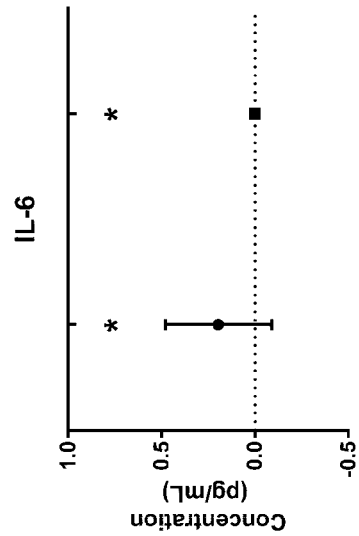
FIG. 32A
FIG. 32B
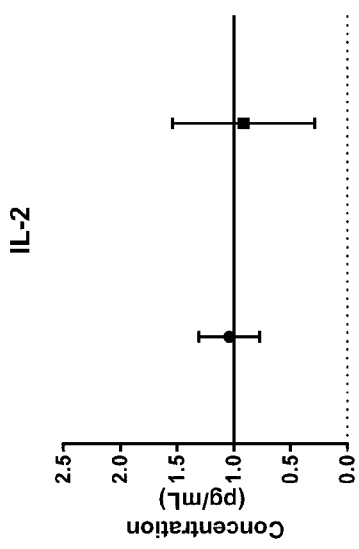
FIG. 32C
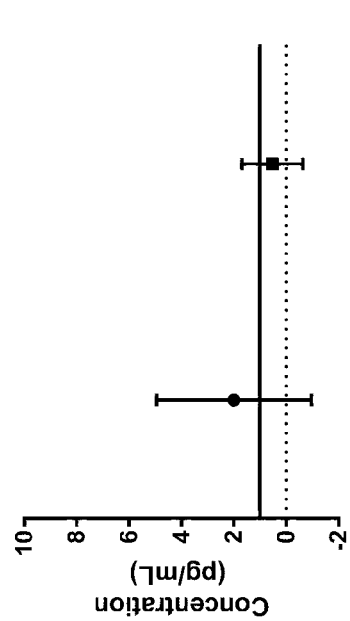
FIG. 32D

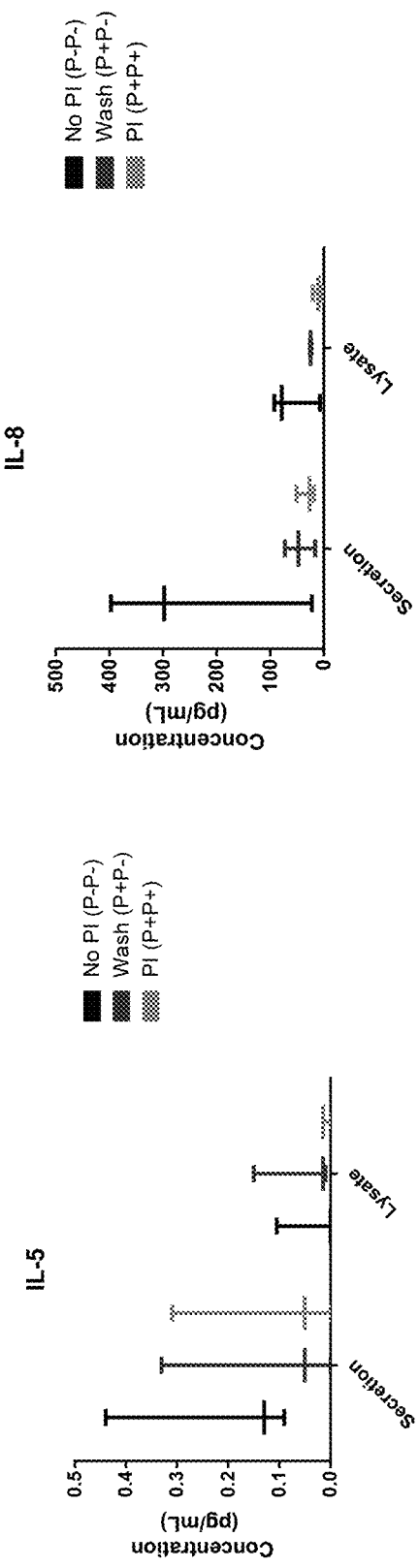
FIG. 33E
FIG. 33F
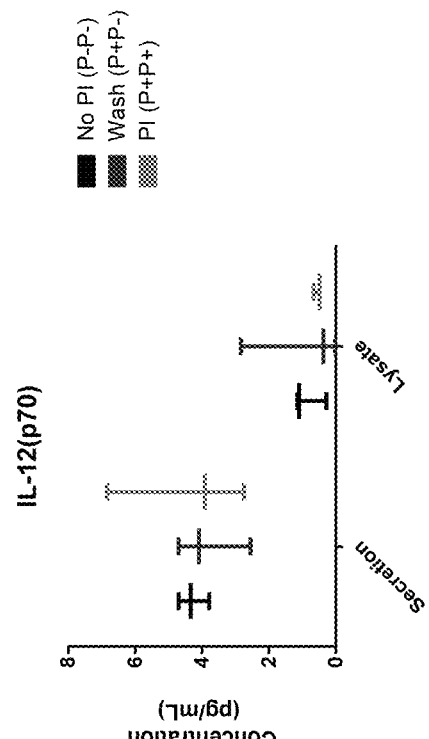
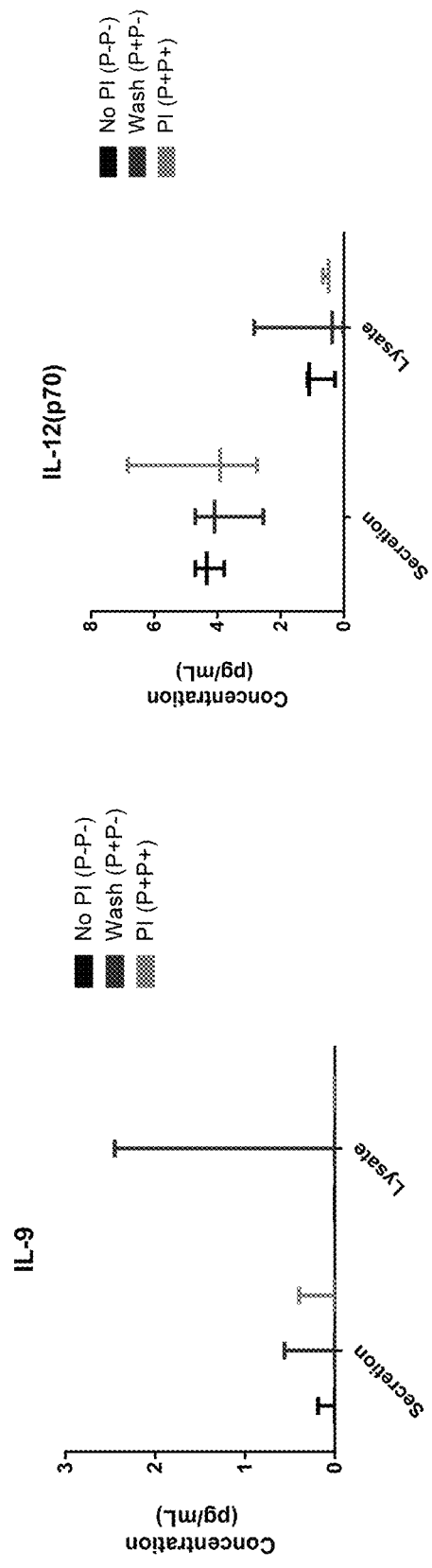
FIG. 33G
FIG. 33H

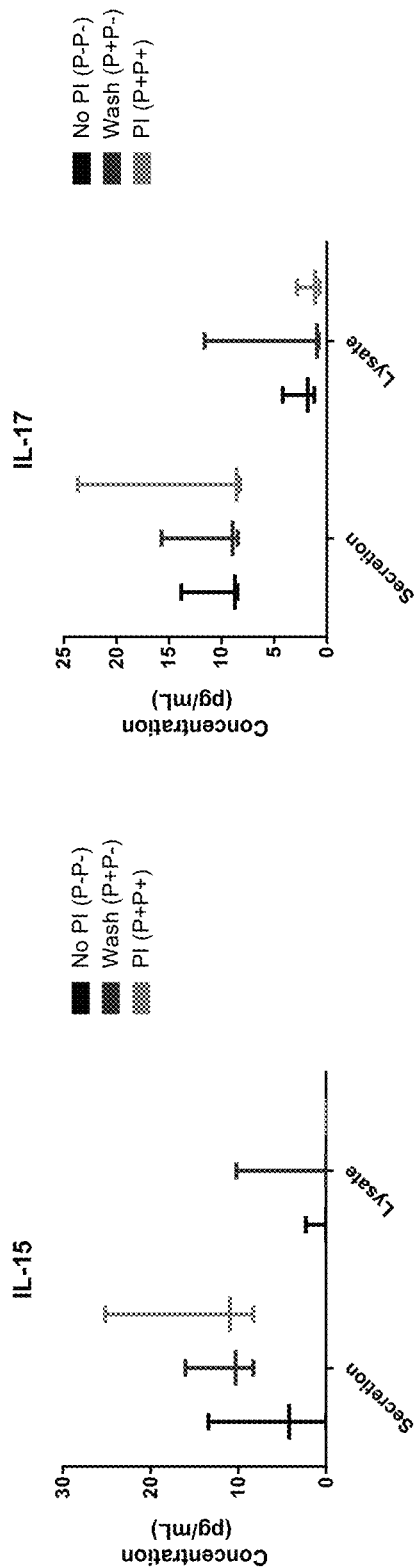
FIG. 33I
FIG. 33J
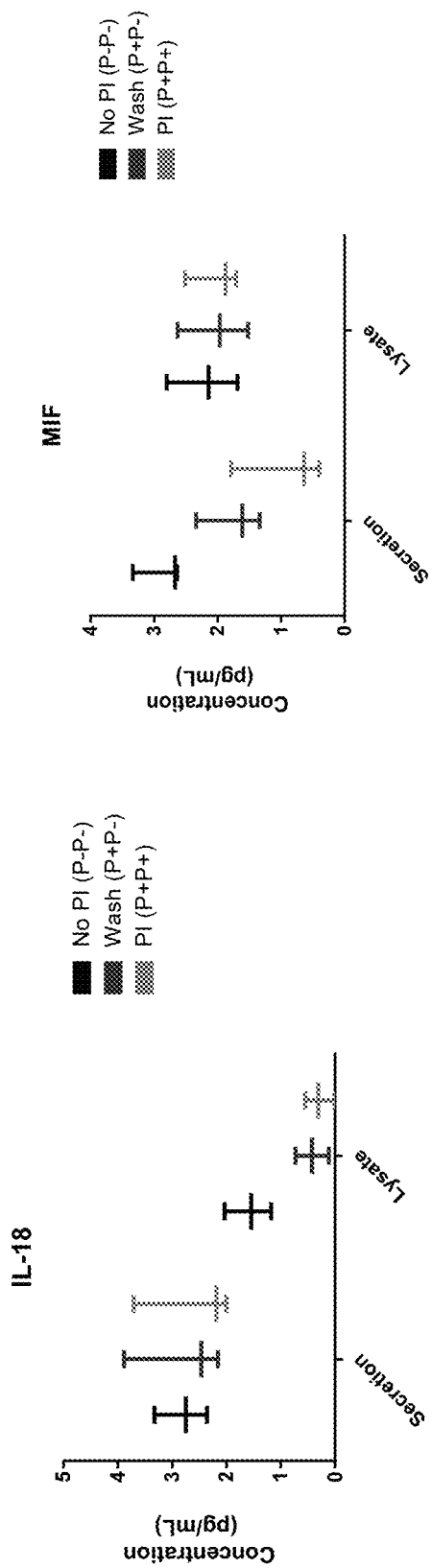
FIG. 33K
FIG. 33L

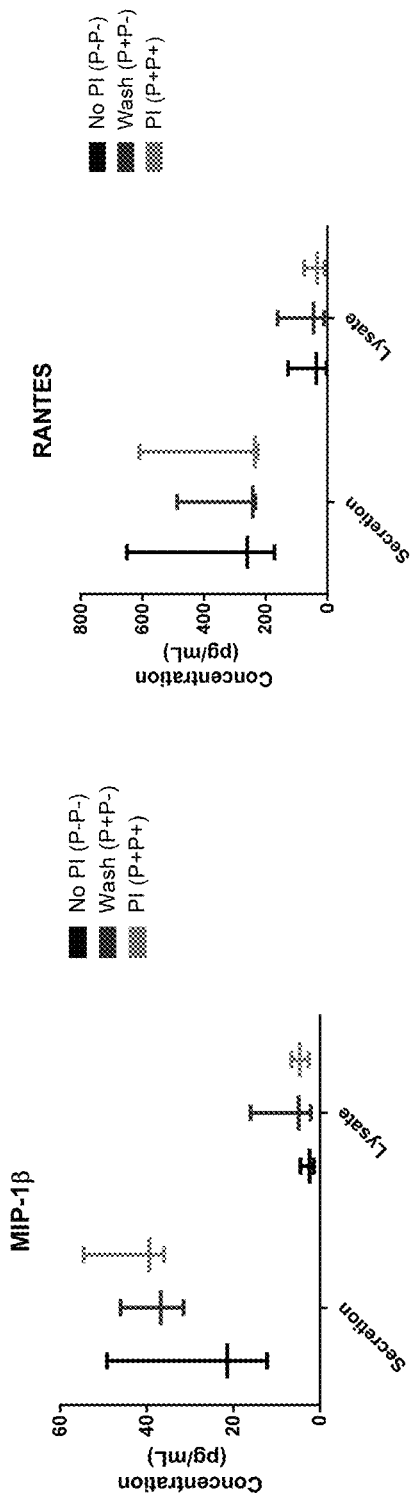
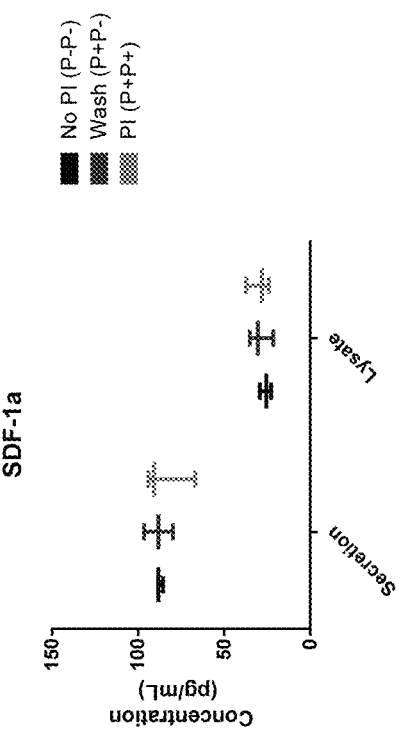
FIG. 35J
FIG. 35I
FIG. 35K

THERAPEUTIC METHODS USING ERYTHROCYTES

TECHNICAL FIELD

The present disclosure relates generally to the field of haematology. More specifically, the present disclosure relates to modified red blood cells (RBCs)/erythrocytes and cell therapies that utilise them.

CROSS REFERENCE TO RELATED APPLICATION

This application is the National Phase application of International Application No. PCT/AU2016/000404, filed 22 Dec. 2016, which designates the United States and was published in English, which claims priority to and is related to Australian Application No. 2015905309 entitled "Therapeutic Methods Using Erythrocytes" filed on 22 Dec. 2015. These applications are incorporated herein by reference in their entirety. In addition, the other references or publications referred to in the present disclosure are also hereby incorporated by reference in their entirety.

BACKGROUND

Cell therapies have emerged as a promising form of treatment for numerous diseases and conditions including cancer, infectious diseases, transplantation, autoimmune disorders, infectious disease, inflammation, and immune deficiency. Such therapies are also used as an adjunct to standard treatments.

In many cases, cell therapies seek to modulate elements of the patient's own immune system to alleviate the disease or condition in question. The immune system consists of a network of tissues, organs, and cells such as T-lymphocytes, B-lymphocytes, NK cells, monocytes/macrophages, cytokines and the like. Cell therapies may alter the activity of signaling molecules known as cytokines that mediate/regulate numerous processes including immunity, inflammation and haematopoiesis.

RBCs are an abundant cellular component of blood accounting for 40%-50% of its volume. Despite this, they are given scant consideration in the design of therapeutic approaches with the exception of those intended to treat diseases and conditions directly involving RBCs. RBCs are traditionally thought to have little if any involvement in the generation of immune responses, or in cell development, growth, and repair. They have thus been overlooked as a potential means of manipulating these processes. For example, the use of RBCs to regulate the cytokine milieu has not been considered or demonstrated.

Although there have been some encouraging outcomes arising from some cell therapies to date, improvements are needed to increase the effectiveness of existing and future treatments. These improved treatments may rely, at least in part, on utilising RBCs given that they are an abundant cell type in the blood.

SUMMARY

The present inventors have surprisingly identified that RBCs play a significant role in regulating the cytokine milieu by secretion and/or sequestration of various proteins such as cytokines, chemokines, and growth factors.

Without being bound to theory, it is postulated that RBCs may act as a reservoir for various proteins that may be released under various conditions. As demonstrated herein, RBCs may be induced to sequester or release these proteins, thus providing a means of regulating other cell types and biological processes. This in turn facilitates the design of improved therapeutic approaches.

Non-limiting embodiments of the present disclosure are listed below.

Certain embodiments are to methods for modulating the levels of at least one protein in a subject comprising producing primed red blood cells by contacting red blood cells with at least one agent or at least one condition that modulates the level of one or more red blood cell proteins and administering to the subject one or more primed red blood cell components selected from the group consisting of the primed red blood cells, supernatant obtained from incubation or culture of the primed red blood cells, lysate obtained from the primed red blood cells, membranes obtained from the primed red blood cells, and red blood cell ghosts or membranes produced from the primed red blood cells, wherein administering the one or more primed red blood cell components to the subject modulates the levels of at least one protein in the subject. In some embodiments, the one or more primed red blood cell components are obtained during priming of the red blood cells and/or after priming of the red blood cells. In other embodiments, the red blood cells are obtained from the subject. In yet other embodiments, the red blood cells are not obtained from the subject. In other embodiments, the one or more primed red blood cell components administered is the supernatant obtained from incubation or culture of the primed red blood cells.

In some other embodiments, the at least one agent is one or more agents selected from the group consisting of proteins, enzymes, nucleic acids, protease inhibitors, protein denaturation agents, RNA stabilisers, anti-coagulants, and cells. In other embodiments, the at least one agent is selected from the group consisting of protease inhibitors, anti-coagulants, cancer cells, stem cells, and immune cells. In yet other embodiments, the at least one condition is shear stress, hypoxia, or hyperoxia. In other embodiments, the red blood cells are obtained from one or more sources selected from the group consisting of at least one subject, at least one cell bank, and at least one cell line. In still other embodiments, the subject is a human or a non-human mammal. In certain embodiments, the one or more primed red blood cell components are administered to the subject through one or more methods selected from the group consisting of systemically, locally, intravenously, subcutaneously, intra-articularly, intramuscularly, intrathecally, and intraperitoneally.

In still other embodiments, the one or more red blood cell proteins are selected from the group consisting of chemokines, cytokines, growth factors, receptors, intracellular signal transmitters, hormones, nuclear transcription factors, neurotransmitters, extracellular matrix components, and enzymes. In some embodiments, the one or more red blood cell proteins are cytokines, chemokines, or growth factors.

Certain embodiments are to methods of modulating the activity of target cells comprising producing primed red blood cells by contacting red blood cells with at least one agent or at least one condition that modulates the level of one or more red blood cell proteins and mixing the target cells with one or more primed red blood cell components selected from the group consisting of the primed red blood cells, supernatant obtained from incubating or culturing the primed red blood cells, lysate obtained from the primed red blood cells, membranes obtained from the primed red blood cells, and red blood cell ghosts or membranes produced from the primed red blood cells, wherein mixing the target cells with the one or more primed red blood cell components modulates the activity of the target cells. In some embodiments, the primed red blood cells modulate one or more activities of the target cells selected from the group consisting of cell signaling, immune response, cell development, cell growth, inhibition of cell growth, cell death, and cell repair. In other embodiments, the target cells are one or more selected from the group consisting of immune cells, immortalized cells, cancer cells, stem cells, endothelial cells, fibroblasts, and synovial cells. In still other embodiments, the immune cells are one or more selected from the group consisting of T-lymphocytes, B-lymphocytes, monocytes, macrophages, dendritic cells, natural killer cells, neutrophils, eosinophils, and basophils. In still other embodiments, the cancer cells are one or more selected from the group consisting of tumor cells, solid tumor cells, disseminated tumor cells, and/or cancerous blood cells. In yet other embodiments, the stem cells are one or more selected from the group consisting of totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, and mesenchymal stem cells.

In certain embodiments, the mixing comprises a process selected from the group consisting of incubating, culturing, co-culturing, and combining the target cells with the primed red blood cells. In other embodiments, the target cells are from a subject. In still other embodiments, the target cells are within a subject.

In yet other embodiments, the target cells are administered to a subject. In still other embodiments, one or more target cell components selected from the group consisting of target cells, target cell ghosts, target cell membranes, target cell lysates, target cell fractions, and supernatant produced by incubating or culturing target cells are administered to a subject. In some embodiments, one or more of the primed red blood cells, primed red blood cell components, target cells, and target cell components are administered to the subject by one or more routes selected from the group consisting of systemically, locally, intravenously, subcutaneously, intra-articularly, intramuscularly, intrathecally, and intraperitoneally.

In certain other embodiments, the subject has a disease or disorder.

Certain embodiments are to methods of preventing, treating, or ameliorating a disease or disorder comprising administering to a subject in need thereof red blood cells and/or target cells produced according to one or more of the methods provided herein. In some embodiments, the red blood cells and/or target cells are administered to the subject by one or more routes selected from the group consisting of systemically, locally, intravenously, subcutaneously, intra-articularly, intramuscularly, intrathecally, and intraperitoneally. In other embodiments, the subject is a human or non-human mammal. In yet other embodiments, the disease or disorder is selected from the group consisting of cancer, infectious disease, organ failure, autoimmune disease, autoimmune disorders, inflammation, and immune deficiency.

In some embodiments, there is an increase and/or decrease in the level of one or more of the proteins associated with red blood cells. In other embodiments, there is an increase and/or decrease in the level of at least one of the one or more proteins associated with the red blood cells. In certain other embodiments, there is an increase in the level of at least one of the one or more proteins associated with the red blood cells. In still other embodiments, there is a decrease in the level of at least one of the one or more proteins associated with the red blood cells.

In yet other embodiments, the level of the one or more proteins associated with red blood cells is measured using one or more antibodies. In some other embodiments, the one or more proteins are selected from the group consisting of chemokines, cytokines, growth factors, receptors, intracellular signal transmitters, hormones, nuclear transcription factors, neurotransmitters, and extracellular matrix components, and enzymes. In still other embodiments, the one or more proteins are selected from the group consisting of chemokines, cytokines, and growth factors.

In other embodiments, the at least one agent is one or more agents selected from the group consisting of proteins, enzymes, nucleic acids, protease inhibitors, protein denaturation agents, RNA stabilizers, anticoagulants, and cells. In some embodiments, the at least one condition is shear stress, hypoxia, or hyperoxia. In still other embodiments, the primed red blood cells modulate the activity of one or more target cells. In yet other embodiments, the primed red blood cells are administered to a subject.

Certain embodiments are to methods of priming red blood cells, the method comprising measuring the level of one of more proteins associated with the red blood cells, contacting the red blood cells with at least one agent or at least one condition, measuring the level of the one or more proteins associated with the red blood cells, and comparing the level of the one or more proteins associated with the red blood cells before being contacted with the at least one agent or at least one condition with the level of the one or more proteins associated with the red blood cells after being contacted with the at least one agent or at least one condition, wherein a difference in the level of at least one of the one or more proteins associated with red blood cells indicates that the red blood cell has been primed. In some embodiments, the level of one or more proteins, two or more proteins, three of more proteins, four or more proteins, five or more proteins, six or more proteins, seven or more proteins, eight or more proteins, nine or more proteins, ten or more proteins, eleven or more proteins, twelve or more proteins, thirteen or more proteins, fourteen or more proteins, or fifteen or more proteins associated with red blood cells is measured. In other embodiments, the level of three of more proteins associated with red blood cells is measured. In still other embodiments, wherein there is a difference in the level of at least one, at least two, at least three, at least four, at least five, at least six, at least seven, at least eight, at least nine, at least ten, at least eleven, at least twelve, at least thirteen, at least fourteen, or at least fifteen of the one or more proteins associated with the red blood cells. In still other embodiments, there is a difference in the level of at least three proteins associated with the red blood cells. In certain other embodiments, the difference in the level of the one or more proteins associated with red blood cells before being contacted with at least one agent or at least one condition compared to the level of the one or more proteins associated with red blood cells after being contacted with at least one agent or at least one conditions is determined by a statistical analysis selected from the group consisting of a Student's T test, an ANOVA test, a mixed-effects model, a Mann-Whitney test, a Wilcoxon rank sum, and a Speannans rank correlation.

Certain embodiments are to methods for increasing or decreasing levels of a target protein on or within cells of a subject, the method comprising treating red blood cells (RBCs) to increase or decrease levels of a target protein present within the RBCs and/or associated with a surface of the RBCs, and administering to the subject one or more of (i) the RBCs after said treating, (ii) RBC lysate, RBC membranes, and/or RBC ghosts obtained from lysing the RBCs during and/or after said treating, (iii) cell wash obtained from washing the RBCs during and/or after said treating, (iv) culture supernatant obtained from a culture of the RBCs generated during and/or after said treating, (v) combinations of (i)-(iv) to thereby increase or decrease the levels of the target protein on or within the cells. In some embodiments, the RBCs subjected to the treating are obtained from the subject. In another embodiment, the RBCs subjected to said treating are not obtained from the subject.

In certain embodiments, the RBCs administered to the subject are RBCs ghosts. In certain other embodiments, increasing or decreasing levels of a target protein induces or modulates cell signaling, an immune response, cell development, cell growth, inhibition of cell growth, cell death, and/or cell repair. In other embodiments, the increasing or decreasing levels of a target protein induces or modulates an immune response in the subject. In certain other embodiments, (i) the RBCs, (ii) the RBC lysate, RBC membranes, and/or RBC ghosts, (iii) the cell wash, (iv) the culture supernatant, or (v) combinations of (i)-(iv) are administered to the subject systemically, locally, intravenously, subcutaneously, intra-articularly, intramuscularly, intrathecally, and/or intraperitoneally. In some other embodiments, the subject is a mammalian subject, a human subject, or both.

Certain embodiments are to methods for inducing or modulating the function of target cells, the method comprising treating RBCs to increase or decrease levels of a target protein present within or associated with a surface of the RBCs, and mixing the target cells with one or more of (i) the RBCs after said treating, (ii) RBC lysate, RBC membranes, and/or RBC ghosts obtained from lysing the RBCs during and/or after said treating, (iii) cell wash obtained from washing the RBCs during and/or after said treating, (iv) culture supernatant obtained from a culture of the RBCs generated during and/or after said treating, (v) combinations of (i)-(iv) to thereby induce or modulate the function of the target cells. In some embodiments, the target cells are one or more of immune cells, cancer cells, stem cells, endothelial cells, fibroblasts, synovial cells, and/or myeloid cells. In yet other embodiments, the immune cells are one or more of T-lymphocytes, B-lymphocytes, monocytes, macrophages, dendritic cells, natural killer cells, neutrophils, eosinophils, and/or basophils. In some other embodiments, the cancer cells are one or more of tumour cells, solid tumour cells, disseminated tumour cells, and/or cancerous blood cells. In still other embodiments, the stem cells are one or more of: totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, mesenchymal stem cells, or combination thereof.

In certain embodiments, the target cells are stem cells and the mixing primes the stem cells towards a specific cell lineage. In certain other embodiments, the methods further comprise administering to a subject suffering from or susceptible to developing a given disease or disorder (i) the target cells after said mixing, (ii) target cell lysate, target cell membranes, and/or target cell ghosts obtained from lysing the target cells during and/or after said treating, (iii) cell wash obtained from washing the target cells during and/or after said treating, (iv) culture supernatant obtained from a culture of the target cells generated during and/or after said treating, (v) or combinations of (i)-(iv). In other embodiments, (i) the target cells, (ii) the target cell lysate, target cell membranes, and/or target cell ghosts, (iii) the target cell wash, (iv) the target cell culture supernatant, or (v) combinations of (i)-(iv) are administered to the subject systemically, locally, intravenously, subcutaneously, intra-articularly, intramuscularly, intrathecally, and/or intraperitoneally.

In certain embodiments, the method further comprises administering to the subject: (i) the RBCs, (ii) the RBC lysate, RBC membranes, and/or RBC ghosts, (iii) the cell wash, (iv) the culture supernatant, or (v) combinations of (i)-(iv). In some embodiments, (i) the RBCs, (ii) the RBC lysate, RBC membranes, and/or RBC ghosts, (iii) the cell wash, (iv) the culture supernatant, or (v) combinations of (i)-(iv) are administered to the subject systemically, locally, intravenously, subcutaneously, intra-articularly, intramuscularly, intrathecally, and/or intraperitoneally. In certain other aspects, (i) the target cells, (ii) the target cell lysate, target cell membranes, and/or target cell ghosts, (iii) the target cell wash, (iv) the target cell culture supernatant, or (v) combinations of (i)-(iv) are administered to the subject locally, and (i) the RBCs, (ii) the RBC lysate, RBC membranes, and/or RBC ghosts, (iii) the cell wash, (iv) the culture supernatant, or (v)

combinations of (i)-(iv) are administered to the subject systemically or locally.

In certain embodiments, the subject is a mammalian subject, a human subject, or both. In certain other embodiments, the subject is suffering from a tissue injury, cancer, an inflammatory disease or condition, or an immune disorder. In some other embodiments, the RBCs and/or the target cells are obtained from the subject. In still other embodiments, the RBCs and/or the target cells are not obtained from the subject.

In certain other embodiments, the treating comprises one or more of: contacting the red blood cells with a protease inhibitor, contacting the red blood cells with an anticoagulant, lysing the red blood cells, subjecting the red blood cells to shear stress, treating the red blood cells with oxygen, and/or depriving the red blood cells of oxygen. In other embodiments, the protease inhibitor is selected from the group consisting of: aprotinin, leupeptin, $\alpha$2-macroglobulin, antipain dihydrochloride, calpain inhibitor I, calpain inhibitor II, chymostatin, TLCK (CAS 131918-97-3), trypsin-inhibitor, Pefabloc SC (Roche), PMSF (C6H5CH2SO2F—Thermo Fisher Scientific), cOmplete protease inhibitor cocktail (Roche), or combinations thereof. In some embodiments, the anticoagulant is selected from the group.

In certain other embodiments, the target protein is one or more of a cytokine, a chemokine, or a growth factor. In still other embodiments, the target protein is an inflammatory cytokine or an inflammatory chemokine. In certain embodiments, the levels of the target protein are increased. In other embodiments, the target protein is selected from the group consisting of: CTACK, GRO-$\alpha$, BFGF, G-CSF, CM-CSF, HGF, IFN-$\alpha$2, IFN-$\gamma$, IL-1$\alpha$, IL-1$\beta$, IL-2, IL-2r$\alpha$, IL-3, IL-4, IL-5, IL-6, IL-7, IL-8, IL-9, IL-10, IL-12-40, IL-12p70, IL-13, IL-15, IL-16, IL-17, IL-18, IP-10, LIF, MCP-1, M-CSF, MIF, MIG, MIP-1$\alpha$, MIP-1$\beta$, $\beta$-NGF, PDGF-bb, RANTES, SDF-1$\alpha$, TNF-$\alpha$, TNF-$\beta$, TRAIL, VEGF, or combinations thereof. In certain other embodiments, the levels of the target protein are decreased. In some embodiments, the target protein is selected from the group consisting of: IFN-α2, IFN-γ, IL-1β, IL-8, IL-9, IL-12p70, IL-16, IL-17, IL-18, MIF, TNF-α, IL-2rα, IL-4, CTACK, GRO-α, IL-18, MCP-1, MIP-1 GRO-α, MIP-1β, RANTES, SDF-1α, βFGF, G-CSF, GM-CSF, HGF, IL-3, IP-10, M-CSF, PDFG-bb, VEGF, IL-2, IL-6, IL-12p40, and combinations thereof.

In certain embodiments, the method is used as an adjunct therapy. In other embodiments, the method is used as an adjunct therapy for treatment of tissue injury, cancer, an inflammatory disease or condition, and/or an immune disorder.

BRIEF DESCRIPTION OF THE FIGURES

Exemplary embodiments of the present disclosure will now be described, by way of example only, with reference to the accompanying figures.

FIG. 22A-FIG. 22M is a series of graphs showing the concentration of growth factors in the lysate of RBCs before and after incubation with MSCs and the secretion of MSCs and/or RBCs after 72 hours at 37° C. as measured by BioPlex and reported as pg/mL (20 million RBCs in 100 uL PBS). Data presented as mean±SD (n=1).

FIG. 31A-FIG. 31M is a series of graphs showing the concentration of growth factors released or secreted from RBCs into PBS over 24 hours and in the corresponding RBC lysate at 37° C. with or without protease inhibitors (PI) as measured by BioPlex and reported as pg/mL (20 million RBCs in 100 uL PBS). Data presented as fold change after addition of PI±95% CI, where ● represents fold change in secretion with addition of PI compared to the no Pt, and ■ represents fold change in concentration in lysate with addition of PI compared to the no PI control (n=7).

FIG. 32A-FIG. 32D is a series of graphs showing the concentration of cytokines with multiple functions released or secreted from RBCs into PBS over 24 hours and in the corresponding RBC lysate at 37° C. with or without protease inhibitors (PI) as measured by BioPlex and reported as pg/mL (20 million RBCs in 100 uL PBS). Data presented as fold change after addition of PI±95% CI, where ● represents fold change in secretion with addition of PI compared to the no PI, and u represents fold change in concentration in lysate with addition of PI compared to the no PI control (n=7).

FIG. 35A-FIG. 35K is a series of graphs showing the concentration of chemokines released or secreted from RBCs into PBS over 48 hours and in the corresponding RBC lysate at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).

DEFINITIONS

Figure 1:
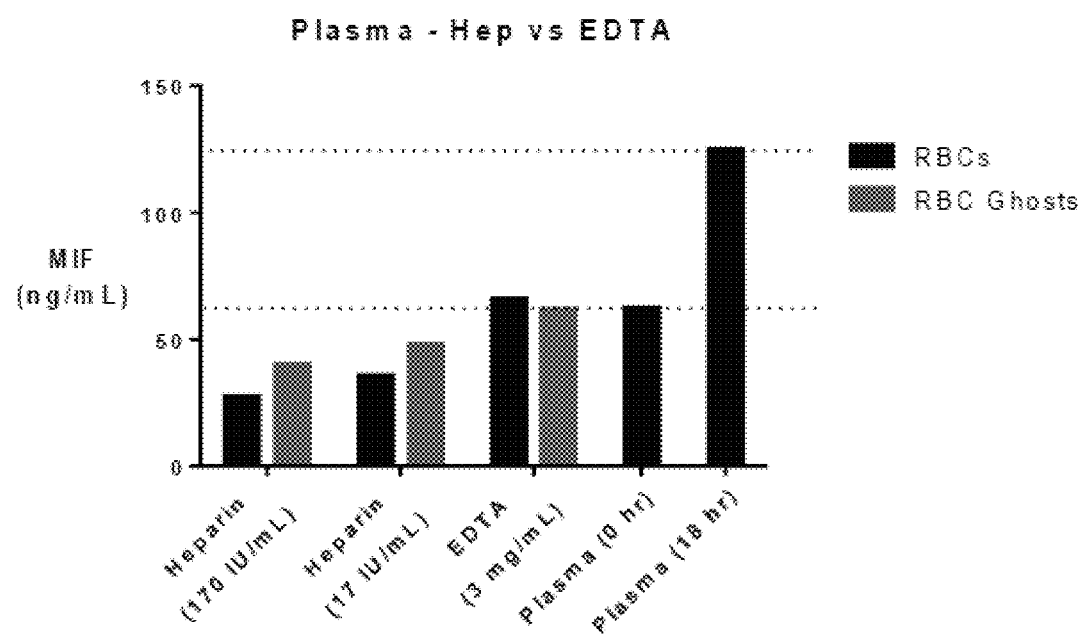
FIG. 1 Macrophage migration inhibitory factor (MIF) concentration in the plasma containing RBCs or ghosts incubated or cultured with varying concentrations of heparin and EDTA (n=1).

As used in this application, the singular form "a", "an" and "the" include plural references unless the context clearly dictates otherwise. For example, the term "a cell lysate" includes multiple cell lysates.

As used herein, the term "comprising" means "including." Variations of the word "comprising", such as "comprise" and "comprises," have correspondingly varied meanings. Thus, for example, a method "comprising" steps 'A' and 'B' may consist exclusively of steps 'A' and 'B' or may include one or more additional steps (e.g. steps 'A', 'B', and 'C').

As used herein the terms "red blood cells", "RBCs", and "erythrocytes" refers to a collection of cells that may comprise more than 99.5%, more than 99.6%, more than 99.7%, more than 99.75%, more than 99.8%, more than 99.85%, more than 99.9%, more than 99.5%, approximately 100% red blood cells, or 100% red blood cells as achieved by one or more red blood cell isolation or purification techniques (e.g., leukodepletion, red blood cell depletion, platelet depletion, and the like). RBCs will be understood to encompass whole RBCs, RBC ghosts, RBC membranes, RBC lysates, RBC fractions, glycolipid receptors isolated from RBCs, and combinations thereof.

As used herein, the term "red blood cell components", "red blood cell products", or "RBC products" refer to the parts of or associated with red blood cells, including whole RBCs, RBC ghosts, RBC membranes, RBC lysates, RBC fractions, glycolipid receptors isolated from RBCs and supernatant produced by incubating or culturing red blood cells in, for instance, a media/medium.

As used herein, the term "RBC ghosts" will be understood to refer to RBCs from which some (e.g. more than: 10%, 20%, 30%, 40%, 50%, 60%, 70%, 80%, 90%, 95%) of the cytoplasmic protein has been removed. The cytoplasmic protein may be removed, for example, by lysis and washing of the RBCs.

As used herein, the term "protein" refers to a polymer made up of amino acids linked together by peptide bonds.

As used herein, the term "red blood cell proteins" or "proteins associated with red blood cells" refers to proteins associated with or in the vicinity of red blood cells, including proteins located intracellularly (e.g., found within a red blood cell or within a red blood cell lysate), partially or completely at the surface of the red blood cell (e.g., in the red blood cell membrane), or proteins released or released or secreted from red blood cells into the external milieu (e.g., media or plasma/serum). Red blood cell proteins include proteins added externally (e.g., purified, recombinant, and/or plasmid/vector-expressed proteins) that are, for instance, internalized by or externalized by red blood cells, or specifically or non-specifically bound to the surface of red blood cells.

As used herein, the term red blood cell protein "release or secretion" or proteins "released or secreted" by red blood cells refers to proteins that have moved by active or inactive mechanisms from (i) the intracellular region or interior of an RBC to the surface and/or extracellular or exterior region of the RBC (e.g., plasma, serum, or medium) or (ii) moved from the extracellular or exterior region of the RBC (from, e.g., the plasma, serum or medium) to the surface and/or extracellular region or the exterior of the RBC. Proteins may be bound to the surface of the red blood cells by cell surface-protein binding interactions known in the art (e.g., receptors, covalent attachment, noncovalent attachment, adhesion). Surface-bound proteins may be released back into the extracellular or exterior region of the RBC (e.g., into the plasma, serum, or medium).

As used herein, the term "agent" refers to one or more substances that have an effect (e.g., an effect on cellular activity and/or protein levels) on cells (e.g., red blood cells or target cells) and includes, for example, proteins (e.g., synthetic, purified, recombinant, or vector-expressed proteins), enzymes (e.g., substances that accelerate or catalyse chemical reactions, e.g., protein reactions), nucleic acids (e.g., RNA, DNA, or synthetic nucleic acids), protease inhibitors (e.g., specific or non-specific protease inhibitors), protein denaturation agents (e.g., oxidizing or reducing reagents), RNA stabilisers (e.g., chemical (e.g., RNAse inactivation agents), small molecule, or biological (e.g., aminoglycosides) agents), anti-coagulants (e.g., coumarins, heparins, chelating agents (e.g., EDTA, EGTA)), chemical agents (e.g., synthesized or naturally occurring chemical compounds), and cells (e.g., primary cells or other healthy/normal cells from a subject, cancer cells, immortalized cells, or cell lines (e.g., cell lines derived from a subject (e.g., human)), including, e.g., immune cells, stem cells, endothelial cells, fibroblasts, and synovial cells).

As used herein, the term "primed" or "treated" red blood cells or RBCs refers to an increase or decrease in the presence or level of red blood cell proteins after the red blood cells have been contacted with (e.g., incubated, cultured, or combined with) an agent(s) or exposed to a particular condition(s) (e.g., shear stress, hypoxia, hyperoxia).

As used herein, the term "primed red blood cell components" refers to red blood cell components that have been derived from red blood cells that have been primed or treated with an agent(s) or condition(s).

As used herein, the term "target cells" refers to one or more cells that are to be contacted with primed red blood cells or primed red blood cell components, and may include primary cells or other healthy/normal cells from a subject, cancer cells, immortalized cells, or cell lines (e.g., cell lines derived from a subject (e.g., human)). In some embodiments, target cells include immune cells, stem cells, endothelial cells, fibroblasts, or synovial cells.

As used herein, the term "target cell components" or "target cell products" refers to parts of or associated with target cells, including whole cells, target cell ghosts, target cell membranes, target cell lysates, target cell fractions, glycolipid receptors isolated from target cells and supernatant produced by incubating or culturing target cells in, for instance, a media/medium.

As used herein, a "media" or "medium" refers to a composition having the ability to maintain the viability of cells or cell components. The media can stimulate cell growth and proliferation (e.g., cell culture media) or maintain cells at a particular and/or existing growth state (e.g., cell incubation media). Non-limiting examples of media include isotonic salt solution, balanced salt solution, saline, phosphate buffered saline (PBS), hank's balanced salt solution (HBSS), Earles' balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and Iscove's Modified Dulbecco's Media (IMDM).

As used herein, a "cell supernatant" will be understood to mean a cell incubation or culture medium used to incubate or culture a population cells at a given temperature or a given range of temperatures for a given time period, for example, more than: 5 minutes, 10 minutes, 20 minutes, 30 minutes, 1 hour, 2 hours, 3 hours, 6 hours, 12 hours, 24 hours, 48 hours, 72 hours, 96 hours, or 120 hours.

As used herein, a "cell wash" will be understood to mean a liquid that has been used to rinse a population of cells, and differs from a cell supernatant as defined above insofar as the cell wash is not also used as a medium for cell culture. Accordingly, a fluid used to generate a "cell wash" may be mixed with the cell population for a period of less than: 30 minutes, 20 minutes, 15 minutes, 10 minutes, 5 minutes, 4, minutes, 3 minutes, 2 minutes, 1 minute, or 30 seconds.

As used herein, the term "protease inhibitor" refers to a substance (e.g., protein or to chemical substance) that blocks or reduces the catalytic (e.g., proteolytic) activity of a protease enzyme. A protease inhibitor may block the ability of a protease to cleave the peptide bond of a given protein, typically by blocking the active site of the protease and preventing its access to a substrate. By way of non-limiting example, protease inhibitors may include non-specific protease inhibitors (e.g., protease inhibitors not specific to a particular protein or class of proteins), specific protease inhibitors (e.g., protease inhibitor specific to a particular protein or substrate, e.g., serine protease inhibitors, cysteine protease inhibitors, metalloprotease inhibitors, and aspartic protease inhibitors), or dual-, multi- or pan-specific protease inhibitors, e.g., protease inhibitors specific for one or more proteins or one or more classes of proteins, e.g., a serine and cysteine protease inhibitor).

As used herein, the term "shear stress" refers to the ratio of force to area.

As used herein, the term "subject" includes one or more animals including, for example, bovine, equine, ovine, primate, avian and rodent species. The subject may be an animal in which the blood comprises red blood cells (e.g., a mammal, bird, fish, reptile, or amphibian). In some embodiments, the subject may be a mammal such as, for example, a human or a non-human mammal. In another embodiment, the subject may be a mouse, rat, hamster, ferret, gerbil, rabbit, monkey, chimpanzee, horse, pony, donkey, sheep, pig, chicken, goat, cat, or dog.

As used herein, the term "treatment" or "therapy" refers to one or more protocols, methods and/or agents that can be used in preventing, managing, alleviating, or ameliorating a disease, disorder, or condition, including in the prevention, alleviation, or amelioration of one or more symptoms of a disease, disorder, or condition and/or a symptom related thereto. In certain embodiments, the terms "treatment" and "treatments" refer to a biological therapy, supportive therapy, and/or other therapies useful in the prevention, management, alleviation, and/or amelioration of a disease, disorder, or condition known to one of skill in the art, such as medical personnel.

As used herein, the term "adjunct therapy" will be understood to mean a therapy that is given in addition to a primary, main, or initial therapy to maximize the effectiveness of the primary, main, or initial therapy. An adjunct therapy may be administered by the same route as or by a different route than an initial therapy. Any adjunct therapy may also be administered at the same time as or at a different time than a primary therapy.

Descriptions of prior art documents herein, or statements herein derived from or based on those documents, are not an admission that the documents or derived statements are part of the common general knowledge of the relevant art.

For the purposes of description all documents referred to herein are hereby incorporated by reference in their entirety unless otherwise stated.

The subject headings used in the detailed description are included for the ease of reference or the reader and should not be used to limit the subject matter found throughout the disclosure or the claims. The subject headings should not be used in construing the scope of the claims or the claim limitations.

DETAILED DESCRIPTION

The role of RBCs in modulating immune responses by influencing the availability of proteins such as cytokines and chemokines that regulate the activity of other cells in the body is largely unrecognised. The present inventors have determined that RBCs may sequester or release a range of proteins under various conditions, including cytokines, chemokines, and growth factors. Thus, although previously unrecognised, RBCs appear to play a significant role in regulating the availability of various factors that have an influence on cell signaling, immune response, cell development, cell growth, inhibition of cell growth, cell death, and cell repair.

The following description conveys exemplary embodiments of the present disclosure in sufficient detail to enable those of ordinary skill in the art to practice it. Features or limitations of the various embodiments described do not necessarily limit other embodiments of the present disclosure or the present disclosure as a whole. Hence, the following detailed description does not limit the scope of the present disclosure, which is defined only by the claims.

Red Blood Cells

Red blood cells (RBCs) for use in the methods of the present disclosure may be obtained from a suitable source, including from a subject (in, e.g., a blood sample), an existing blood collection/reservoir (e.g., a blood bank), other commercial sources (e.g., red blood cell suppliers) and the like. In some embodiments, the red blood cells are obtained from the subject to which the primed red blood cell components or target cell components may be administered to (e.g., a subject in need of a treatment or therapy). In other embodiments, red blood cells may be obtained from another/different subject (e.g., a blood-type matched donor (e.g., a family member)).

Exemplary methods for the collection of blood and separation or isolation of RBCs are known to those of ordinary skill in the art and include, for example, centrifugation, magnetic bead technologies, fluorescence activated cell sorting, dextran sedimentation, density gradient separation, leukoreduction filtration, and the like. Suitable methodologies are disclosed, for example, in the following references: Dextran sedimentation—Tenczar F J. Comparison of inverted centrifugation, saline washing, and dextran sedimentation in the preparation of leukocyte-poor red cells. Transfusion, 13(4) 1973; Density gradient separation—Vettore L, De Matteis M C, Zampini P. A new density gradient system for the separation of human red blood cells. American Journal of Hematology, 8(3) 1980; Leukoreduction filtration—AuBuchon J P, Elfath M D, Popovsky M A, Stromberg R R, Pickard C, Herschel L, Whitley P, McNeil D, Arnold N, O'Conner J L. Evaluation of a new prestorage leukoreduction filter for red blood cell units. Vox *Sanguinis*, 72(2) 1997.

In some embodiments, RBCs primed or treated to induce or trigger the release, retention, or sequestration of proteins may comprise or consist of RBC ghosts. The RBC ghosts may, for example, have more than: 10%, 20%, 30%, 40%, 50%, 60%, 70%, 80%, 90%, 95%; 99% or 99.5% or all their cytoplasmic protein removed. The RBC ghosts may be produced using known techniques such as, for example, hypotonic hemolysis. (see, for example, Bramley T A, Coleman R, Finean J B. Chemical, enzymological and permeability properties of human erythrocyte ghosts prepared by hypotonic lysis in media of different osmolarities. Biochimica et Biophysica Acta—Biomembranes, 241(3) 1971).

In other embodiments, RBCs primed to induce the release, retention, or sequestration of proteins may comprise or consist of RBC membranes or RBC membrane fragments. These may be produced using known techniques such as, for example, hypotonic hemolysis, and freeze-thawing of lysates.

In some embodiments, RBCs may be washed to remove proteins associated with the outer membrane. Cell washes may be performed using suitable media such as, for example, phosphate buffered saline (PBS), an isotonic salt solution, a growth medium, a culture medium, or combinations thereof. Non-limiting examples of suitable media for use as cell wash liquid and/or cell culture media in the methods of the present disclosure include one or more of the following: isotonic salt solution, balanced salt solution, saline, phosphate buffered saline (PBS), hank's balanced salt solution (HBSS), Earle's balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), Iscove's Modified Dulbecco's Media (IMDM), or combinations thereof.

In other embodiments, RBCs may be lysed and lysates and/or RBC membranes isolated. The RBC membranes may be washed to remove associated proteins. Additionally or alternatively, RBC membranes may be treated to directly or indirectly bind to desired target proteins.

Red Blood Cell Proteins

The present disclosure relies at least in part on the determination by the inventors that RBCs may act as a reservoir for various proteins (e.g. cytokines and chemokines). As demonstrated herein, RBCs harbour these proteins internally and/or on their outer membranes, often in significant quantities. The present inventors have shown that RBCs may be manipulated to sequester, retain, or release these proteins (e.g. cyokines, chemokines and growth factors). This provides a means of influencing processes including cell growth, cell death, cell differentiation, and/or immune responses.

In some embodiments, proteins sequestered or retained by RBCs are localised internally. Hence, external proteins may be internalised by RBCs. Proteins released or secreted by RBCs may move or be transported from inside the cell across the cell membrane and into the external milieu.

In other embodiments, proteins sequestered, retained, released, or secreted by the RBCs are localised on the cell surface. The proteins may be bound directly to the RBC outer membrane, or indirectly bound to the outer membrane via one or more RBC membrane proteins and/or molecules.

A number of proteins may be modulated by the methods of the present disclosure, with non-limiting examples including signalling molecules, e.g., chemokines, cytokines, growth factors, receptors, intracellular signal transmitters, hormones, nuclear transcription factors, neurotransmitters, and extracellular matrix components, and enzymes. For instance, growth factors can include those that stimulate the growth, proliferation, healing, or differentiation of, for example, skin cells (e.g., epidermal growth factor (EGF), keratinocyte growth factor (KGF), migration stimulating factor (MSF)), nerve cells/nervous system (e.g., neuregulins (e.g., neuregulin 1-4) and neurotrophins (e.g., nerve growth factor (NGF), brain-derived neurotrophic factor (BDNF), neurotrophin-3 (NT-3), neurotrophin-4 (NT-4))), connective tissue and mesenchymal cells (e.g., fibroblast growth factor (FGF)), blood vessel cells (e.g., platelet-derived growth factor (PDGF), placental growth factor (PGF), vascular endothelial growth factor (VEGF)), blood cells (e.g., erythropoietin, granulocyte colony stimulating factor (G-CSF), granulocyte macrophage colony-stimulating factor (GM-CSF)), and cell proliferation (e.g., insulin-like growth factor (IGF-1), insulin-like growth factor-2 (IGF-2)) along with pleitropic growth factors (e.g, transforming growth factor-beta (TGF-β), transforming growth factor-beta (TGF-α), tumor necrosis factor (TNF)).

Receptors can include intracellular receptors (e.g., nuclear (e.g., transcription factors), cytoplasmic (e.g., steroid), and endoplasmic recticulum (e.g., $IP_3$) receptors) or cell surface receptors (e.g., ion channel-linked, G-protein-linked, enzyme-linked, toll gate, and ligand gated receptors, integrins). Hormones can include lipid-derived (e.g., prostaglandins, leukotrienes, prostacylins, thromboxane); amino acid-derived (e.g., epinephrine, melatonin, thyroxine); peptide (e.g., amylin, adiponenctin, angiotensinogen, calcitonin, brain natriuretic peptide (BNP), erythropoietin, follicle-stimulating hormone (FSH), ghrelin, glucagon-like peptide-1 (GLP-1), human chorionic gonadotropin (hCG), insulin, insulin-like growth factor (IGF), and the like); and steroids (e.g., androgen, estrogen, glucocorticoid, progestogen, secosteroid, and the like). Intracellular signal transmitters or transducers can include families of proteins and protein kinases (e.g., Ras and Src families), and Wnt signalling family proteins. Neurotransmitters can include amino acids, peptides (e.g., β-endorphin, opioid), monoamines, trace amines, purines, and gasotransmitters. Nuclear transcription factors can include modulators of DNA transcription (e.g., fos, myc, N-myc), and modulators of mRNA transcription, and suppressors of cell division (e.g., p53, pRb). Enzymes can include oxidoreductases (e.g., alcohol, aldehyde, amino acid, sulphur, diphenol, peroxidises, and the like) NADH, NADPH, nucleases, proteases, kinases, transferases, hydrolases, lyases, isomerases, and ligases.

While not imparting particular limitation to the type(s) of proteins that may be sequestered, retained and/or released by RBCs in accordance with the present disclosure, non-limiting examples include chemokines, cytokines and growth factors.

In certain embodiments and again without particular limitation, the proteins that may be sequestered, retained and/or released by the RBC include one or more of the proteins as set out in Table 1.

TABLE 1

Non-limiting examples of individual proteins that may be sequestered and/or released by RBC according to the present disclosure.

| Single Protein (acronym) | Single Protein (full name) |
|---|---|
| basic FGF | basic fibroblast growth factor |
| CTACK (CCL27) | cutaneous T cell-attracting chemokine |
| Eotaxin 1 | CCL11 #1 |
| G-CSF (GCSF) | granulocyte-colony stimulating factor |
| GM-CSF (CSF2) | granulocyte-macrophage colony-stimulating factor |
| HGF | hepatocyte growth factor |
| IFN-α2 | interferon alpha subtype α2 |
| IFN-γ | interferon gamma |
| IL-10 | interleukin 10 |
| IL-12 (IL-12p70) | interleukin 12 p35 and p40 heterodimer |
| IL-13 | interleukin 13 |

TABLE 1-continued

Non-limiting examples of individual proteins that may be sequestered and/or released by RBC according to the present disclosure.

| Single Protein (acronym) | Single Protein (full name) |
| --- | --- |
| IL-12p40 | interleukin 12 p40 subunit |
| IL-15 | interleukin 15 |
| IL-16 | interleukin 16 |
| IL-17A | interleukin 17A |
| IL-18 | interleukin 18 |
| IL-1α | interleukin 1 alpha |
| IL-1β | interleukin 1 beta |
| IL-2 | interleukin 2 |
| IL-2ra | interleukin 2 receptor alpha chain |
| IL-3 | interleukin 3 |
| IL-4 | Interleukin 4 |
| IL-5 | interleukin 5 |
| IL-6 | interleukin 6 |
| IL-7 | interleukin 7 |
| IL-9 | interleukin 9 |
| IP-10 (CXCL10) | interferon gamma-induced protein 10 |
| LIF | leukaemia inhibitory factor |
| M-CSF (CSF1) | macrophage colony-stimulating factor |
| MIG (CXCL9) | monokine induced by IFNγ, Chemokine (C—X—C motif) ligand 9 |
| MIP-1α (CCL3) | macrophage inflammatory protein-1 alpha |
| MIP-1β (CCL4) | macrophage inflammatory protein-1 alpha |
| βNGF | beta nerve growth factor |
| PDGF-BB | platelet-derived growth factor B chain homodimer |
| SDF-1α (CXCL12) | stromal cell-derived factor 1 |
| TNF-α (cachexin) | tumour necrosis factor alpha |
| TNF-β (lymphotoxin) | tumour necrosis factor-beta |
| TRAIL | TNF-related apoptosis-inducing ligand |
| VEGF | vascular endothelial growth factor |
| IL-8 | interleukin 8 |
| MCP-1 (CCL2) | monocyte chemoattractant protein-1 |
| MGSA | maintenance of genome stability protein A |
| PGE-2 | prostaglandin E2 |
| RANTES (CCL5) | regulated on activation, normal T cell expressed and secreted |
| MIF (MMIF) | macrophage migration inhibitory factor |
| GRO-α (CXCL1) | Growth-regulated oncogene α |
| CRP | C-reactive protein |
| DDT (MIF-2) | D-dopachrome tautomerase |

In certain embodiments, the level of at least one protein is modulated in a subject by the methods provided herein. In other embodiments, the level of at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins is modulated in a subject. In some embodiments, the level of at least two proteins is modulated in a subject. In other embodiments, the level of at least three proteins is modulated in a subject. In still other embodiments, the level of at least four proteins is modulated in a subject. In other embodiments, the level of at least five proteins is modulated in a subject. In another embodiment, the level of at least six proteins is modulated in a subject. In some other embodiments, the level of at least seven proteins is modulated in a subject. In another embodiment, the level of at least eight proteins is modulated in a subject. In still other embodiments, the level of at least nine proteins is modulated in a subject. In yet other embodiments, the level of at least ten proteins is modulated in a subject.

In certain embodiments, contacting red blood cells with an agent(s) modulates the level of one or more red blood cell proteins, two or more red blood cell proteins, three or more red blood cell proteins, four or more red blood cell proteins, five or more red blood cell proteins, six or more red blood cell proteins, seven or more red blood cell proteins, eight or more red blood cell proteins, nine or more red blood cell proteins, ten or more red blood cell proteins, eleven or more red blood cell proteins, twelve or more red blood cell proteins, thirteen or more red blood cell proteins, fourteen or more red blood cell proteins, fifteen or more red blood cell proteins, sixteen or more red blood cell proteins, seventeen or more red blood cell proteins, eighteen or more red blood cell proteins, nineteen or more red blood cell proteins, twenty or more red blood cell proteins, twenty-one or more red blood cell proteins, twenty-two or more red blood cell proteins, twenty-three or more red blood cell proteins, twenty-four or more red blood cell proteins, twenty-five or more red blood cell proteins, twenty-six or more red blood cell proteins, twenty-seven or more red blood cell proteins, twenty-eight or more red blood cell proteins, twenty-nine or more red blood cell proteins, or thirty or more red blood cell proteins. In some embodiments, an agent(s) modulates the level of two or more red blood cell proteins. In other embodiments, an agent(s) modulates the level of three or more red blood cell proteins. In still other embodiments, an agent(s) modulates the level of four or more red blood cell proteins. In some other embodiments, an agent(s) modulates the level of five or more red blood cell proteins. In other embodiments, an agent(s) modulates the level of six or more red blood cell proteins. In still other embodiments, an agent(s) modulates the level of seven or more red blood cell proteins. In yet other embodiments, an agent(s) modulates the level of eight or more red blood cell proteins. In some other embodiments, an agent(s) modulates the level of nine or more red blood cell proteins. In other embodiments, an agent(s) modulates the level of ten or more red blood cell proteins.

Red Blood Cell Priming

According to methods of the present disclosure, RBCs may be primed or treated with a variety of agents or various environmental conditions to modulate the levels of red blood cell proteins. In certain embodiments, methods are provided for priming red blood cells by measuring the difference in the level of one or more red blood cell proteins before and after the red blood cells are contacted with an agent or condition.

In certain embodiments, the level of one or more proteins associated with red blood cells, two or more proteins associated with red blood cells, three or more proteins associated with red blood cells, four or more proteins associated with red blood cells, five or more proteins associated with red blood cells, six or more proteins associated with red blood cells, seven or more proteins associated with red blood cells, eight or more proteins associated with red blood cells, nine or more proteins associated with red blood cells, ten or more proteins associated with red blood cells, eleven or more proteins associated with red blood cells, twelve or more proteins associated with red blood cells, thirteen or more proteins associated with red blood cells, fourteen or more proteins associated with red blood cells, fifteen or more proteins associated with red blood cells, sixteen or more proteins associated with red blood cells, seventeen or more proteins associated with red blood cells, eighteen or more proteins associated with red blood cells, nineteen or more proteins associated with red blood cells, or twenty or more proteins associated with red blood cells are measured. In some embodiments, the level of two or more proteins associated with red blood cells are measured. In other embodiments, the level of three or more proteins associated with red blood cells are measured. In still other embodiments, the level of four or more proteins associated with red blood cells are measured. In some other embodiments, the level of five or more proteins associated with red blood cells are measured. In other embodiments, the level of six or more proteins associated with red blood cells are measured. In still other embodiments, the level of seven or more proteins associated with red blood cells are measured. In yet other embodiments, the level of eight or more proteins associated with red blood cells are measured. In some other embodiments, the level of nine or more proteins associated with red blood cells are measured. In other embodiments, the level of ten or more proteins associated with red blood cells are measured In certain embodiments, change in the levels of the red blood cell-associated protein(s) is different or substantially different. The different or substantially different level of the one or more proteins may range from, for example, protein levels that are different (e.g., not within a relevant statistical analysis as determined by one of skill in the art) to protein levels that are more than those determined to be similar by a person of ordinary skill in the art by, for example, a statistical analysis or a threshold fold difference (e.g., proteins levels more than two-fold different). In some embodiments, the level of one or more proteins associated with red blood cells before and after being contacted with an agent(s) or condition(s) is different. In yet other embodiments, the level of one or more proteins associated with red blood cells before and after being contacted with an agent(s) or condition(s) is substantially different. In other embodiments, the difference in the level of one or more proteins associated with red blood cells before and after being contacted with an agent(s) or condition(s) is substantially different as determined by statistical methods available to one skilled in the art (e.g., a Students T-test with a p-value of 0.05 or higher). A number of methods of statistical analyses are appropriate to determine the difference in the level of proteins associated with red blood cells before and after being contacted with an agent(s) or a condition(s) including, for example, a Student's T test, an ANOVA test, a mixed-effects model, a Mann-Whitney test, a Wilcoxon rank sum, or a Spearmans rank correlation. The difference in the levels of the protein(s) associated with red blood cells may be due to, in some embodiments, an increase in the levels of one or more proteins; in other embodiments, a decrease in the levels of one or more proteins; or in still other embodiments, both an increase and a decrease in the levels of one or more proteins.

In certain embodiments, a agent or condition induces or triggers the release of proteins. The proteins may be transported from the cell interior across the cell membrane and into the external milieu, or alternatively they may be released from the outer surface membrane of the RBC. Additionally or alternatively, RBCs may be primed or treated to induce the sequestration of external proteins. The proteins may be sequestered into the cell interior, and/or onto the outer surface membrane of the RBC. Additionally or alternatively, RBCs may be primed or treated to promote the retention of proteins located within the RBC and/or on the surface or membrane of the RBC.

The following are non-limiting examples of specific agents/treatments or conditions that may be applied to RBCs in accordance with the present disclosure. In some embodiments, RBCs may be primed or treated with an agent to induce the release, retention, or sequestration of proteins. Exemplary agents may be one or more of the following: proteins, enzymes, nucleic acids, protease inhibitors, protein denaturation agents, RNA stabilisers, anticoagulants, cells, or combinations thereof. In particular, RBCs may be primed with one or more proteins (e.g., synthesized, purified, recombinant, and/or vector-expressed proteins), enzymes (e.g., substances that accelerate or catalyze chemical reactions, e.g., protein reactions), nucleic acids (e.g., RNA, DNA, or synthetic nucleic acids), protease inhibitors (e.g., specific or non-specific protease inhibitors), protein denaturation agents (e.g., oxidizing or reducing reagents), RNA stabilisers (e.g., chemical (e.g., RNAse inactivation agents), small molecule, or biological (e.g., aminoglycosides) agents), anti-coagulents (e.g., coumarins, heparins, chelating agents (e.g., EDTA, EGTA)), chemical agents (e.g., synthesized or naturally occurring chemical compounds), and cells (e.g., primary cells or other healthy/normal cells from a subject, cancer cells, immortalized cells, cell lines (e.g., cell lines derived from a subject)).

In some embodiments, the protease inhibitor may, for example, be selected from aprotinin, leupeptin, α2-macroglobulin, antipain dihydrochloride, calpain inhibitor I, calpain inhibitor II, chymostatin, TLCK (CAS 131918-97-3), trypsin-inhibitor, Pefabloc SC (Roche), PMSF ($C_6H_5CH_2SO_2F$—Thermo Fisher Scientific), complete protease inhibitor cocktail (Roche), or combinations thereof.

In other embodiments, the anti-coagulant may, for example, be selected from heparin, ethylenediaminetetraacetic acid (EDTA), EDTA disodium salt, EDTA tetrasodium salt, EDTA dipotassium salt, EDTA diammonium salt, ethylenebis(oxyethylenenitrilo)tetraacetic acid (EGTA), EDTA trisodium salt, EDTA tripotassium salt, ethylene glycol-O,O-bis(2-aminoethyl)-N,N,N,N-tetraacetic acid, N-(2-hydroxyethyl)ethylenediamine-N,N,N-triacetic acid trisodium salt, citrate, acid-citrate-dextrose, di-ammonium hydrogen citrate, di-ammonium tartrate, warfarin, N-(2-bis (carboxymethyl)aminoethyl)-N-(2-hydroxyethyl)glycin salt dihydrate, citric acid, citric acid monosodium salt, citric acid disodium salt, citric acid trisodium salt, citric acid monopotassium salt, citric acid tripotassium salt, protein C/protein S, nitrilotriacetic acid, potassium sodium tartrate, potassium hydrogen D-tartrate, L-tartaric acid monosodium salt, L-tartaric acid disodium salt, L-tartaric acid dipotassium salt, streptokinase, protamine sulfate, tris(carboxymethyl)amine, anti-thrombin III, phenprocoumon, hirudin, nicoumalone, Coumadin, glycosaminoglycans, ibuprofen, acetylsalicylic acid, indomethacin, prostaglandins, sulfinpyrazone, urokinase, hirulog, tissue plasminogen activator, coumarin, and combinations thereof.

Thus, in some embodiments, RBCs are primed with a protease inhibitor (e.g. cOmplete protease inhibitor cocktail (Roche)), and induced to secrete/release one or more of the following proteins: IFN-α2, IFN-γ, IL-1β, IL-8, IL-9, IL-12p70, IL-16, IL17, IL-18, MIF, TNF-α, IL-2rα, IL-4, CTACK, GRO-α, IL-18, MCP-1, MIP-1 GRO-α, MIP-13, RANTES, SDF-1α, βFGF, G-CSF, GM-CSF, HGF, IL-3, IP-10, M-CSF, PDFG-bb, VEGF, IL-2, IL-6, IL-12p40. In other embodiments, RBCs are primed or treated with a protease inhibitor and induced to retain and/or sequester one or more of the following proteins: CTACK, GRO-α, βFGF, G-CSF, CM-CSF, HGF, IFN-α2, IFN-γ, IL-1α, IL-1β, IL-2, IL-2rα, IL-3, IL-4, IL-5, IL-6, IL-7, IL-8, IL-9, IL-10, IL-12-40, IL-12p70, IL-13, IL-15, IL-16, IL-17, IL-18, IP-10, LIF, MCP-1, M-CSF, MIF, MIG, MIP-1α, MIP-1β, β-NGF, PDGF-bb, RANTES, SDF-1α, TNF-α, TNF-β, TRAIL, of VEGF.

In further embodiments, RBCs are primed with an anticoagulant (e.g., coumarin, heparin and/or EDTA) and induced to secrete/release one or more proteins (e.g., MIF).

In other embodiments, RBCs are primed with protein denaturation agents (e.g., chemical agents) that may include formamide, guanidine (isothiocyanate, thiocyanate, HCl), sodium dodecyl sulphate (SDS), or urea.

In yet other embodiments, RBCs are primed with nucleic acids like RNA, DNA, or artificial nucleic acids. RBCs may be primed with the nucleic acids directly (e.g., transformation, transfection, transduction, or injection) or indirectly through, for example, a vehicle (e.g., a virus or polymer).

In another embodiments, the RBC are primed with RNA stabilizers (e.g., RNAases or aminoglycosides).

In still other embodiments, RBCs are primed with cells, including one cell type and/or cell line or several cell types and/or cell lines. In some embodiments, the cells are immune cells, cancer cells, stem cells, endothelial cells, fibroblasts, synovial cells, and myeloid cells. The immune cells may, for example, be one or more of the following: T-lymphocytes, B-lymphocytes, monocytes, macrophages, dendritic cells, natural killer cells, neutrophils, eosinophils, or basophils. The cancer cells may, for example, be one or more of tumour cells, solid tumour cells, disseminated tumour cells, cancerous blood cells. The stem cells may, for example, be one or more of the following: totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, mesenchymal stem cells, or combinations thereof. In still other embodiments, the cells may be those of numerous cell lines known to one of skill in the art including, for example, HUVEC, HEK-293, HT-29, MEWO, Jurkat, MCF-7, or A549 cells, and the like.

In certain aspects of the disclosure, RBCs may be subjected to certain conditions to prime the RBCs. In some embodiments, RBCs may be subjected to shear stress to induce the release, retention, or sequestration of proteins. RBC are constantly subjected to shear forces in vivo when travelling from venous circulation into capillary beds. This may be emulated by suitable means such as, for example, forcing the RBC through a narrow gauge needle. The shear forces may impart a pressure on the RBC that exceeds standard blood pressure in a given individual, for example, 1.1, 1.2, 1.3, 1.4, 1.5, 1.6, 1.7, 1.8, 1.9, 2, 3, 4, 5 or more than 5 times.

In still other embodiments, RBCs may be primed or treated with excess oxygen, or alternatively deprived of oxygen to induce the release, retention, or sequestration of proteins. For example, RBCs may be primed or treated with excess oxygen (e.g., hyperoxic conditions) in culture for a suitable time period such that they become highly oxygenated. In yet other embodiments, RBCs may be primed or treated with hypoxic media (e.g., hypoxic PBS), sealed, and cultured for a suitable time period such that they become deoxygenated.

Subjects

Certain embodiments relate to subjects according to the methods provided herein. The subject may be an animal that includes, for example, bovine, equine, ovine, primate, avian or rodent species. The subject may be an animal in which the blood comprises red blood cells (e.g., a mammal, bird, fish, reptile, or amphibian). In some embodiments, the subject may be a mammal such as, for example, a human or a non-human mammal. In another embodiment, the subject may be a mouse, rat, hamster, ferret, gerbil, rabbit, monkey, chimpanzee, horse, pony, donkey, sheep, pig, chicken, goat, cat, or dog. The subject may be suffering from a disease or condition such as, for example, a tissue injury, cancer, an inflammatory disease or condition, and/or an immune disorder. The subject may be receiving a primary therapy for the disease or condition, and the methods of the present disclosure may be used as an adjunct therapy. Alternatively, the methods of the disclosure may be used as a primary therapy for a subject and another therapy used as an adjunct therapy. In some embodiments, an adjunct therapy (e.g., primed red blood cells and/or target cells) may be administered to the subject by the same route as the primary therapy or a different route than the primary therapy. In other embodiments, an adjunct therapy may be administered to the subject at a different time (e.g., dosing schedule) than the primary therapy or the same time as the primary therapy.

Cell Therapies

Experimental data provided in the Examples of the present specification demonstrate that RBC may be primed or treated to sequester, retain, or release proteins (e.g. cytokines, chemokines, and/or growth factors).

The present disclosure provides methods for increasing or decreasing levels of a target protein on, within, or surrounding the cells of a subject. The present disclosure also provides methods for inducing or modulating the activity of target cell types and cell populations (in vitro, ex vivo or in vivo).

Certain embodiments are directed to methods that comprise priming or treating RBCs to increase or decrease levels of one or more proteins (e.g, target proteins) present within the RBC and/or associated with a surface of the RBC. RBCs may be primed or treated prior to administration to the subject or mixing with target cells such as, for example, by priming or treating with a protease inhibitor, priming or treating with an anticoagulant, lysing the RBCs and optionally isolating RBC membranes, washing the RBCs, subjecting the RBCs to shear stress, priming or treating the RBCs with oxygen, depriving the RBCs of oxygen, and/or combinations thereof.

In some embodiments, the primed or treated RBCs and/or primed or treated RBC components or products (e.g., RBC membranes, RBC lysates, RBC washes, RBC culture supernatants, RBC ghosts) may be administered to a subject to modulate the activity/function of a target cell population(s) in vivo. One or more of the following: whole RBC, lysed RBC, RBC ghosts, isolated RBC membranes, washed RBC, wash solution from washed RBC, RBC supernatant from cultured RBC, RBC subjected to shear stress, RBC primed or treated with oxygen, RBC deprived of oxygen, or to combinations thereof, may be administered to the subject. The lysed RBC, isolated RBC membranes, and washed RBC may be primed or treated with a protease inhibitor, anti-coagulant, cells, or combinations thereof, or may be produced from whole RBC primed or treated with a protease inhibitor, anti-coagulant, cells, or combinations thereof. RBCs subjected to shear stress, RBC primed or treated with oxygen, and RBC deprived of oxygen may also be pre- or post-treated or primed with a protease inhibitor, anti-coagulant, cells, or combinations thereof.

The primed or treated RBCs and/or primed or treated RBC components or products may be administered to the subject locally or systemically. For example, the RBCs/RBC components or products may be administered intravenously, epicutaneously, subcutaneously, intra-articularly, via a mucous membranes (e.g. inhalation, rectal), intramuscularly, intracerebrally, intrathecally, and/or intraperitoneally. In some embodiments, administration of the RBCs to the subject may induce and/or modulate one or more immune response(s) in the subject. Additionally or alternatively, administration of the RBCs to the subject may induce and/or modulate cell development. Additionally or alternatively, administration of the RBCs to the subject may induce and/or modulate cell growth. Additionally or alternatively, administration of the RBCs to the subject may induce and/or modulate cell death. Additionally or alternatively, administration of the RBCs to the subject may induce and/or modulate cell repair.

In some embodiments, the primed or treated RBCs and/or primed or treated RBC components or products (e.g. RBC membranes, RBC lysates, RBC washes, RBC culture supernatants, RBC ghosts) may be mixed with target cells in vitro or ex vivo to form a mixture (e.g., a cell culture). Mixing of RBCs and target cells may include, for example, combining, incubating, culturing, and/or co-culturing the cells on a substrate (e.g., cell culture plate or flask) or in suspension (e.g., in a tube or flask). Non-limiting examples of suitable target cells include, but are not limited to, immune cells, stem cells, endothelial cells, fibroblasts, synovial cells, and/or myeloid cells. The mixture may, if desired, be maintained for a time period suitable to achieve modification of cell activity (e.g. target cell activity, and/or RBC activity if present), and/or the sequestration of target protein(s), and/or the release of target proteins from cells in the mixture (e.g. target cell activity and/or RBC activity if present). The target cells and/or target cell product(s) (e.g. target cell membranes, target cell lysates, target cell washes, target cell ghosts) may be administered to a subject. The target cells and/or target cell product(s) may be administered to the subject with or without other components from the mixture such as, for example, supernatant from the mixture, and/or RBC from the mixture, and/or RBC components or products (e.g., RBC membranes, RBC lysates, RBC washes, RBC ghosts) from the mixture. One or more components of the mixture may be administered to the subject locally (e.g., topical) or systemically (e.g., enteral, parenteral). For example, the component(s) may be administered intravenously, epicutaneously, subcutaneously, intra-articularly, via a mucous membranes (e.g., inhalation, rectal), intramuscularly, intracerebrally, intrathecally, and/or intraperitoneally. In some embodiments, target cells and/or target cell product(s) from the mixture may be administered to the subject locally or systemically. Again by way of non-limiting example, the target cells and/or target cell product(s) from the mixture may be administered to the subject locally, and RBCs and/or RBC components or products may be administered systemically to the subject. Additionally or alternatively, the target cells and/or target cell product(s) from the mixture may be administered to the subject systemically, and RBC and/or RBC components or products may be administered systemically to the subject. Administration of one or more components (e.g., supernatant, target cells, target cell product(s), RBC, and/or RBC product(s) of the mixture to the subject may induce and/or modulate one or more of the following: cell signaling, immune response, cell development, cell growth, inhibition of cell growth, cell death, and cell repair in vivo.

RBCs, RBC components or products, target cells, and target cell components or products used in the methods of the present disclosure may be obtained or derived from individual(s) of one or more species that differ from the species of the subject to which they are administered (i.e., allogeneic). The individual(s) and subject may be mammalian.

RBCs, RBC components or products, target cells, and target cell components or products used in the methods of the present disclosure may be obtained or derived from individual(s) of a species that is the same as that of the species of the subject to which they are administered (i.e., allogeneic). The individual(s) may have the same blood type as the subject, or a different blood type compared to that of the subject. The individual(s) and subject may be mammalian (e.g., human).

RBCs, RBC components or products, target cells, and target cell components or products used in the methods of the present disclosure may be obtained or derived from the subject to which they are administered (i.e., autologous). The subject may be mammalian (e.g., human).

In embodiments in which the RBCs, RBC components or products, target cells, and target cell components or products are obtained or derived from individual(s) that are not the subject, standard methods for the collection and separation of cells may be used as are known to those of ordinary skill in the art (e.g. centrifugation, magnetic bead technologies, fluorescence activated cell sorting, dextran sedimentation, density gradient separation, leukoreduction filtration, and the like).

In embodiments in which RBCs are obtained from the subject for treatment and re-administration to the subject, methods for the collection of blood and separation of RBC may be used as are known to those of ordinary skill in the art (e.g. apheresis/erythropheresis, centrifugation, magnetic bead technologies, fluorescence activated cell sorting, dextran sedimentation, density gradient separation, leukoreduction filtration, and the like).

Administration of RBCs, RBC components or products, target cells, and/or target cell components or products to a subject in accordance with the methods of the present disclosure may provide a favourable outcome in the prevention and/or treatment of diseases and conditions.

By way of non-limiting example, treating RBCs with an agent or condition may prime them to sequester certain target proteins once administered to the subject. Additionally or alternatively, RBCs may be primed to release one or more target proteins (i.e., one or more target protein types) once mixed with target cells and/or upon administration to the subject. Without imparting particular limitations, the target protein(s) may be chemokine(s), cytokine(s) and/or growth factor(s). Non-limiting examples of suitable proteins are listed in Table 1 above.

Non-limiting examples of target cells in the subject that may be induced or modulated upon administration of the primed or treated RBCs include, but are not limited to, immune cells, cancer cells, stem cells, endothelial cells, fibroblasts, synovial cells, and myeloid cells. The immune cells may, for example, be one or more of the following: T-lymphocytes, B-lymphocytes, monocytes, macrophages, dendritic cells, natural killer cells, neutrophils, eosinophils, basophils. The cancer cells may, for example, be one or more of tumour cells, solid tumour cells, disseminated tumour cells, cancerous blood cells. The stem cells may, for example, be one or more of the following: totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, mesenchymal stem cells, or combinations thereof.

Target cells (e.g., immune cells, stem cells, endothelial cells, fibroblasts, synovial cells, and/or myeloid cells) and target cell components or products administered to the subject after mixing with primed or treated RBC/primed or treated RBC components or products may have numerous biological effects including, but not limited to, the induction and/or modulation of cell development, cell growth, cell death, cell repair, and/or immune responses.

For example, the modulated activity of a stem cell may include one or more of the following: altered lineage, altered cytokine secretion profile, altered stem cell homing, altered engraftment potential, increased or reduced proliferation capacity, or combinations thereof.

Target cells administered to the subject may be isolated/purified from other components that they have been mixed with such as RBCs, or alternatively administered to the subject together with other component(s) (e.g, RBC components).

Medicaments

The present disclosure provides medicaments for performing the methods of the present disclosure.

In some embodiments, the medicaments comprise RBC that have been primed or treated in accordance with the present disclosure to increase or decrease levels of one or more proteins or target proteins present within and/or associated with a surface of the RBC.

The medicament may comprise primed or treated RBCs that have been obtained from a subject to which the medicament is to be administered. Additionally or alternatively, the medicament may comprise primed or treated RBs that have been obtained from an individual of the same species to the subject to which the medicament is to be administered. The individual of the same species may or may not have the same blood type as the subject. Additionally or alternatively, the medicament may comprise primed or treated RBCs that have been obtained from an individual of a different species to the subject to which the medicament is to be administered.

In other embodiments, the medicaments comprise target cells that have been mixed (e.g., cultured) with primed or treated RBCs/RBC components or products in accordance with the present disclosure. By way of non-limiting example, the target cells may be immune cells, stem cells, endothelial cells, fibroblasts, synovial cells, and/or myeloid cells. The immune cells may, for example, be one or more of T-lymphocytes, B-lymphocytes, monocytes, macrophages, dendritic cells, natural killer cells, neutrophils, eosinophils, and/or basophils. The cancer cells may, for example, be one or more of the following: tumour cells, solid tumour cells, disseminated tumour cells, cancerous blood cells. The stem cells may, for example, be one or more of totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, mesenchymal stem cells, or combinations thereof. These medicaments may further comprise other additional component(s) of the mixture such as, for example, RBCs and/or RBC components or products.

In some embodiments, the present disclosure provides use of RBCs primed or treated to increase or decrease levels of one or more proteins or target proteins present within and/or associated with a surface of the RBC, and/or a product or component of the primed or treated RBCs selected from one or more of a lysate, membrane preparation, ghost, wash, and/or culture supernatant, in the preparation of a medicament for inducing or modulating one or more of cell signaling, immune response(s), cell development, cell growth, inhibition of cell growth, cell death, and/or cell repair in a subject.

In other embodiments, the present disclosure provides RBC primed or treated to increase or decrease levels of a target protein present within and/or associated with a surface of the RBC, and/or a product of the primed or treated RBC selected from one or more of a lysate, membrane preparation, ghost, wash, and culture supernatant, for use in inducing or modulating one or more of cell signaling, immune response(s), cell development, cell growth, inhibition of cell growth, cell death, and/or cell repair in a subject.

In some embodiments, the present disclosure provides use of target cells in the preparation of a medicament for preventing or treating a disease or condition, wherein the target cells have been mixed with RBCs primed or treated to increase or decrease levels of one or more proteins or target proteins present within and/or associated with a surface of the RBC, and/or a product or component of the primed or treated RBCs selected from one or more of a lysate, membrane preparation, ghost, wash, and culture supernatant.

In other embodiments, the present disclosure provides target cells for use in preventing or treating a disease or condition, wherein the target cells have been mixed with RBCs primed or treated to increase or decrease levels of one or more proteins or target proteins present within and/or associated with a surface of the RBC, and/or a product of the primed or treated RBC selected from one or more of a lysate, membrane preparation, ghost, wash, and culture supernatant.

In accordance with one or more of the embodiments set out herein, the RBCs may be contacted with an agent according to the methods provided herein. The target protein(s) may be one or more of IFN-α2, IFN-γ, IL-1β, IL-8, IL-9, IL-12p70, IL-16, IL17, IL-18, MIF, TNF-α, IL-2rα, IL-4, CTACK, GRO-α, IL-18, MCP-1, MIP-1 GRO-α, MIP-1β, RANTES, SDF-1α, βFGF, G-CSF, GM-CSF, HGF, IL-3, IP-10, M-CSF, PDFG-bb, VEGF, IL-2, IL-6, IL-12p40, CTACK, GRO-α, βFGF, G-CSF, CM-CSF, HGF, IFN-α2, IFN-γ, IL-1α, IL-1β, IL-2, IL-2rα, IL-3, IL-4, IL-5, IL-6, IL-7, IL-8, IL-9, IL-10, IL-12-40, IL-12p70, IL-13, IL-15, IL-16, IL-17, IL-18, IP-10, LIF, MCP-1, M-CSF, MIF, MIG, MIP-1α, MIP-1β, β-NGF, PDGF-bb, RANTES, SDF-1α, TNF-α, TNF-β, TRAIL, VEGF. The target cells may be one or more of those set out previously. The subject may be mammalian (e.g., human). The subject may be suffering from a disease or condition (e.g., a tissue injury, cancer, an inflammatory disease or condition, an immune disorder).

Medicaments according to the present disclosure may comprise a pharmaceutically acceptable carrier, excipient, diluent and/or adjuvant. "Pharmaceutically acceptable" carriers, excipients, diluents and/or adjuvants as contemplated herein are substances which do not produce adverse reaction(s) when administered to a particular recipient such as a human or non-human animal. Pharmaceutically acceptable carriers, excipients, diluents and adjuvants are generally also compatible with other ingredients of the medicaments such as, for example, RBCs, RBC components or products, target cells, or target cell components or products. Non-limiting examples of suitable excipients, diluents, and carriers may be found in the "*Handbook of Pharmaceutical Excipients*" 4th Edition, (2003) Rowe et al. (Eds), The Pharmaceutical Press, London, American Pharmaceutical Association, Washington.

Adjuvant(s) may be included in the medicaments of the present disclosure. Suitable adjuvants may be included. In general, adjuvant activity in the context of the medicaments include, but is not limited to, the ability to enhance the immune response (quantitatively or qualitatively) induced by immunogenic components in the medicament (e.g., RBCs, RBC components or products, target cells, target cell components or to products). This may reduce the dose or level of the immunogenic components required to produce an immune response and/or reduce the number or the frequency of dosages required to produce the desired immune response.

An adjuvant may enhance the immune response induced and/or enhanced by component(s) of the medicament thereby improving therapeutic outcomes. The adjuvant may enable the induction of immunity utilising a lower dose of other active component(s) (e.g., RBC, RBC components or products, target cells, target cell components or products).

Non-limiting examples of adjuvants suitable for inclusion in the medicaments and methods for their preparation include Typically medicaments according to the present disclosure may be administered locally or systemically. For example, the medicaments may be administered intravenously, epicutaneously, subcutaneously, intra-artcularly, via a mucous membranes (e.g. inhalation, rectal), intramuscularly, intracerebrally, intrathecally, and/or intraperitoneally. In some embodiments, the medicaments may comprise separate components that are not administered together. For example, the medicament may comprise a first component of primed or treated RBCs and/or RBC components or products and a second component of target cells and/or target cell components or products that have been mixed with the primed or treated RBCs/RBC components or products. The RBCs and/or RBC components or products may be administered by a first administration route (e.g., a systemic route) and the target cells and/or target cell components or products may be administered by a second different route (e.g., a local route), or vice versa.

In general, the medicaments are administered in a manner compatible with the route of administration and physical characteristics of the recipient (including health status) and in such a way that it elicits the desired effect(s) (i.e., therapeutically effective, immunogenic and/or protective).

For example, the appropriate dosage of a given medicament may depend on a variety of factors including, but not limited to, a subject's physical characteristics (e.g., age, weight, sex), whether the medicament is being used as single agent or adjuvant therapy, the progression of a given disease state, and other factors that may be recognised by one skilled in the art. Various general considerations that may be considered when determining an appropriate dosage of a given medicament of the present disclosure are described, for example, in Gennaro et al. (Eds), (1990), "*Remington's Pharmaceutical Sciences*", Mack Publishing Co., Easton, Pa., USA; and Gilman et al., (Eds), (1990), "*Goodman And Gilman's: The Pharmacological Bases of Therapeulics*", Pergamon Press.

In general, medicaments of the present disclosure may be administered to a subject in an amount of from about 50 micrograms to about 5 mg of active component(s) (e.g, RBCs, RBC components or products, target cells, target cell components or products). In some embodiments, the dosage is in an amount of from about 50 micrograms to about 500 micrograms.

One skilled in the art would be able, by routine experimentation, to determine an effective, non-toxic amount of RBC and/or stem cells thereof to include in a medicament of the disclosure for the desired therapeutic outcome.

Generally, an effective dosage is expected to be in the range of about 0.0001 mg to about 1000 mg of active component(s) (e.g., RBCs, RBC components or products, target cells, target cell components or products) per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$ of active component(s) (e.g., RBCs, RBC components or products, target cells, target cell components or products). Generally, an effective dosage is expected to be in the range of about 25 to about 500 mg/m$^2$, about 25 to about 350 mg/m$^2$, about 25 to about 300 mg/$^2$, about 25 to about 250 mg/m$^2$, about 50 to about 250 mg/m$^2$, and about 75 to about 150 mg/m$^2$.

Typically, in therapeutic applications, the treatment would be for the duration of the infection, disease state or condition. Further, it will be apparent to one of ordinary skill in the art that the optimal quantity and spacing of individual dosages may be determined by the nature and extent of the infection, disease state or condition being treated, the form, route and site of administration, and the nature of the particular individual being treated. Also, such optimum conditions may be determined by known techniques.

In many instances, it may be desirable to have several or multiple administrations of a medicament of present disclosure. For example, medicaments of the disclosure may be administered 1, 2, 3, 4, 5, 6, 7, 8, 9, 10, or more times. The administrations may be from about one to about twelve week intervals, and in certain embodiments from about one to about four week intervals. Periodic re-administration may be desirable in the case of recurrent exposure to a particular pathogen targeted by a medicament of the disclosure.

Medicaments according to the present disclosure may be administered as an adjunct to a primary therapy for the disease or condition. Accordingly, a medicament according to the present disclosure may be an "adjunct medicament".

It may also be apparent to one of ordinary skill in the art that the optimal course of treatment may be ascertained using conventional course of treatment determination tests.

It will be appreciated by persons of ordinary skill in the art that numerous variations and/or modifications may be made to the present disclosure as disclosed in the embodiments provided herein without departing from the spirit or scope of the present disclosure as broadly described. The present embodiments are, therefore, to be considered as illustrative and not restrictive.

EXAMPLES

The present disclosure will now be described with reference to specific example(s), which should not be construed as in any way limiting.

Figure 2:
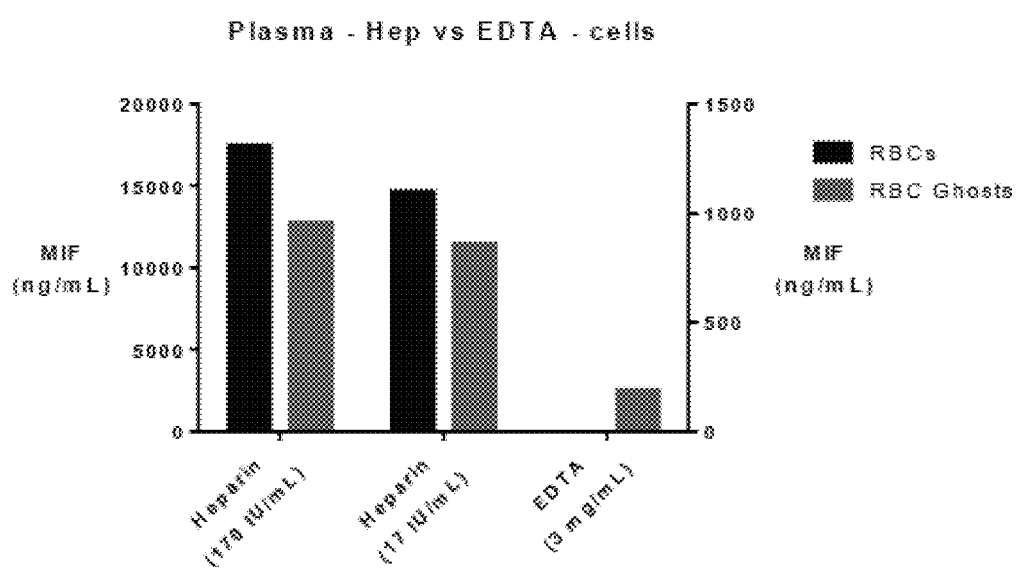
FIG. 2 MIF concentration of RBC lysate and ghost 'lysate' after being incubated or cultured in plasma with varying concentrations of heparin and EDTA (n=1).

Example 1. Effect of Different Anticoagulants (Heparin and EDTA) on RBC and RBC Ghost Uptake During Culture Up to 18 Hours To determine if the presence of anticoagulants alter the capacity for protein binding to red blood cells, these cells were incubated in plasma with or without heparin or EDTA. Whole blood from healthy volunteers was collected into EDTA vacutainers (3 mg/mL). Plasma was collected from blood collected into hepain and citrate vacutainers. RBCs were isolated from anticoagulated whole blood using dextran sedimentation (6% dextran, 1 hour, room temperature) and were washed twice in phosphate buffered saline (PBS). RBC ghosts were isolated by lysing the RBCs in hypotonic water for 5 minutes with the inclusion of protease inhibitors (Roche cOmplete protease inhibitor cocktail). The ghosts were then isolated by centrifugation (16,000 g, 20 minutes) and were resuspended in PBS. Following isolation, 10 million RBCs (or ghost of 10 million RBCs) were resuspended in either PBS or plasma with the addition of heparin (17 IU/mL or 1700 IU/mL) or EDTA (30 mg/mL). The red blood cells or ghosts were then cultured for 0, 1, or 18 hours at 37° C. As controls, EDTA plasma containing heparin or EDTA were culture under the same conditions. Following incubation, the cell free supernatants was collected and stored at −80° C. Prior to analysis, samples were subjected to ×3 freeze-thaw cycles. MIF concentration of the samples was quantified using a MIF ELISA. After 18 hours in culture, MIF levels in plasma alone had increased by approximately 50% and the levels of MIF in the plasma of the red blood cell samples containing red blood cells decreased indicating that the MIF had bound to the intact cells (FIG. 1). RBC ghosts were also able to bind MIF, thus indicating that intact cells are not needed for this binding activity (FIG. 1). Addition of EDTA to the cell suspensions resulted in substantially less MIF in the RBC lysates and ghosts 'lysates' than heparin treatment (FIG. 2). These results indicate that the addition of anticoagulants to red blood cell cultures may affect the amount of protein in the cells and the capacity to bind more protein.

Figure 3:
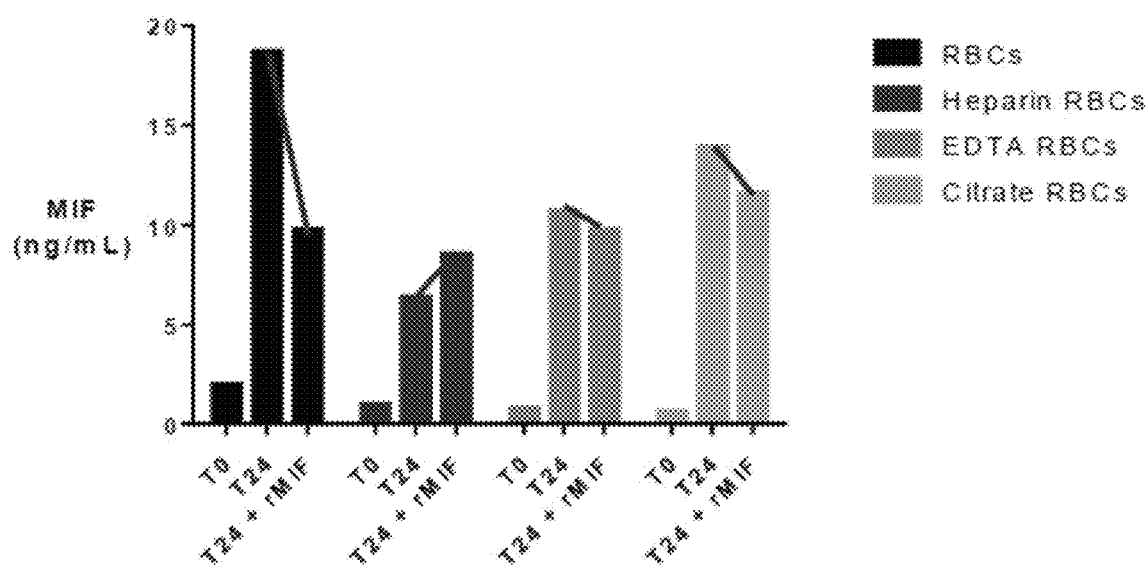
FIG. 3 RBCs collected in heparin, EDTA, citrate, or no anticoagulant and cultured in PBS for 24 hours with or without rMIF (n=1).
Figure 4B:
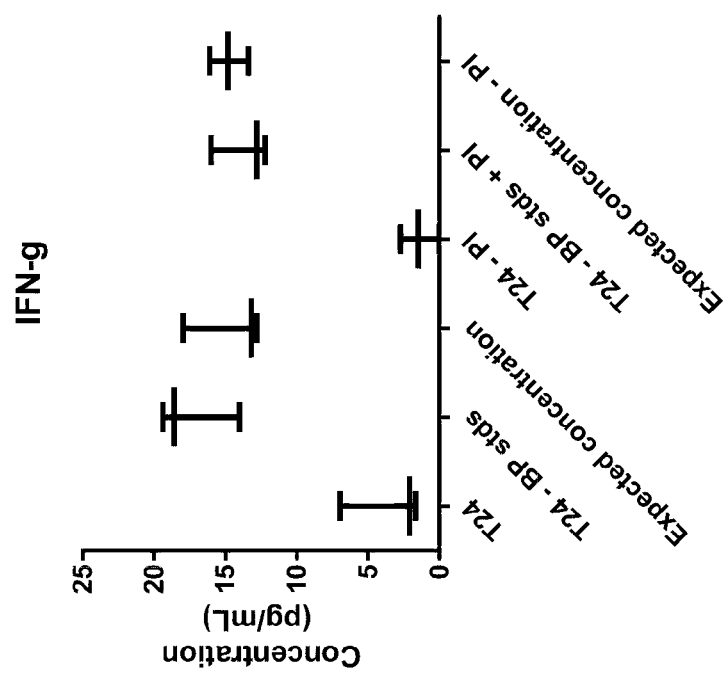
FIG. 4A-FIG. 4O Summary of pro-inflammatory proteins released or secreted from RBCs into PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 4A:
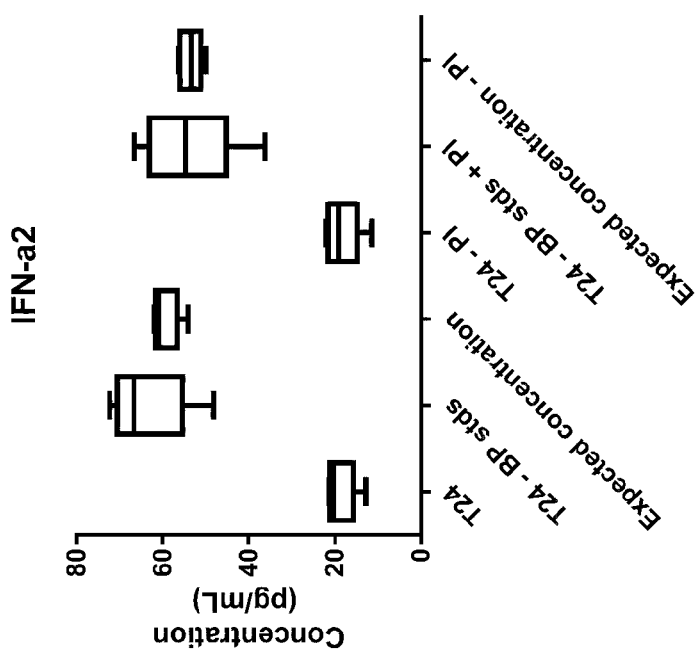
Figure 4C:
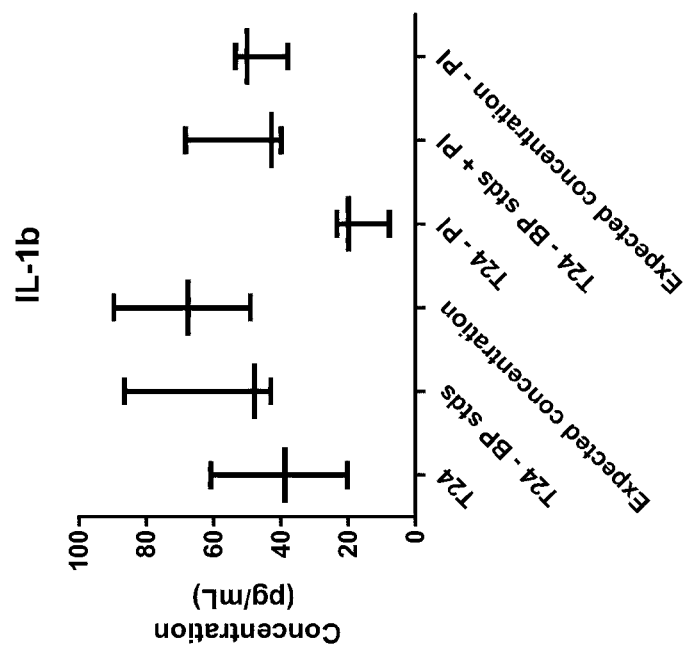
Figure 4D:
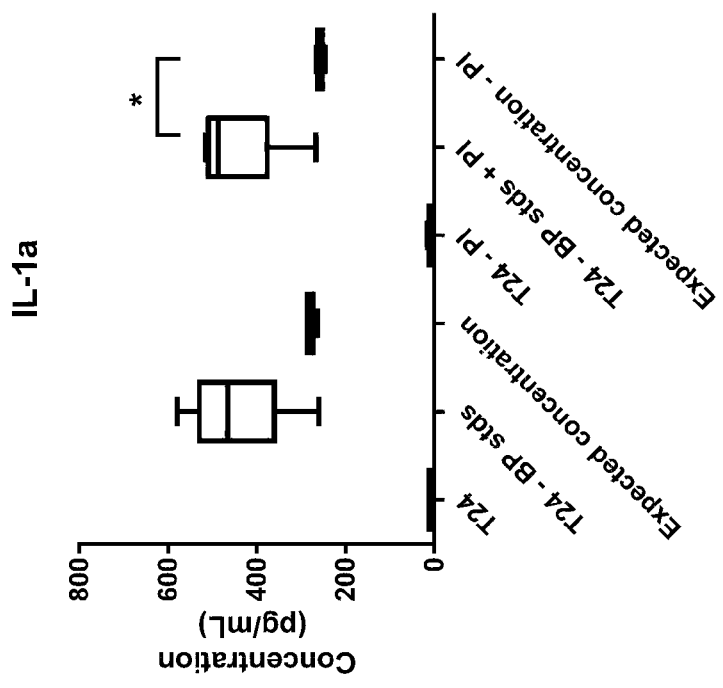
Figure 4H:
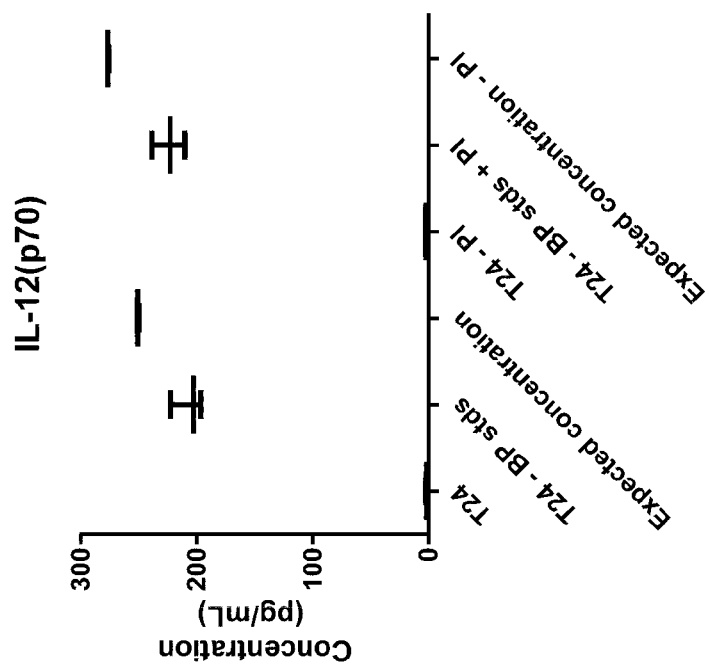
Figure 4G:
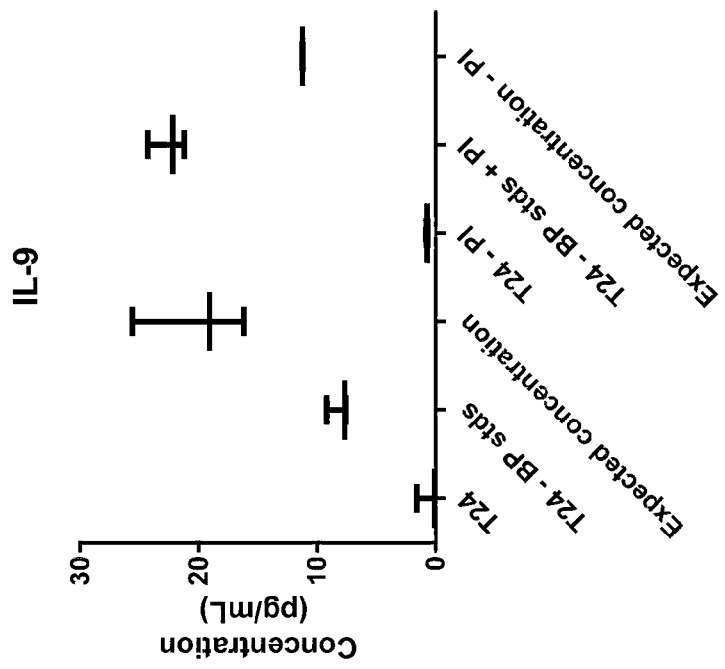
Figures 4I, 4J:
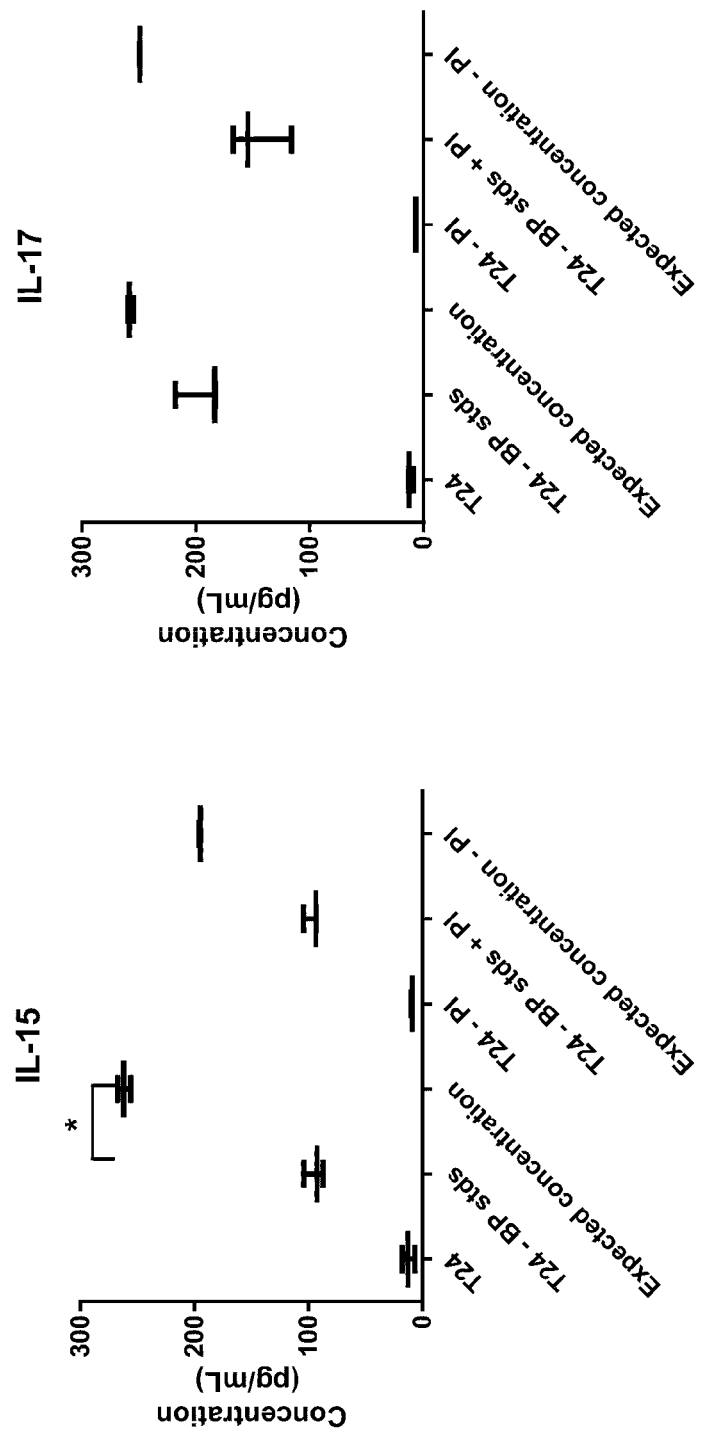
Figures 4K, 4L:
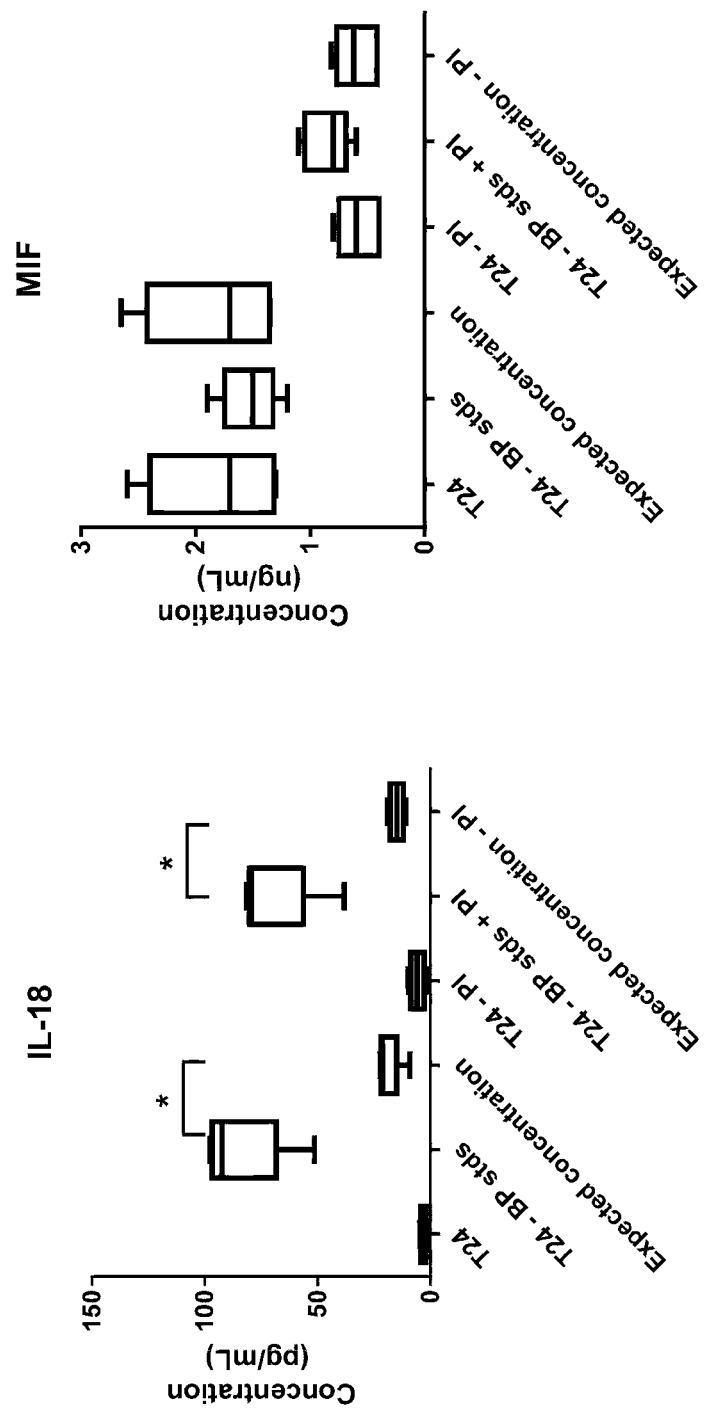
Figure 4N:
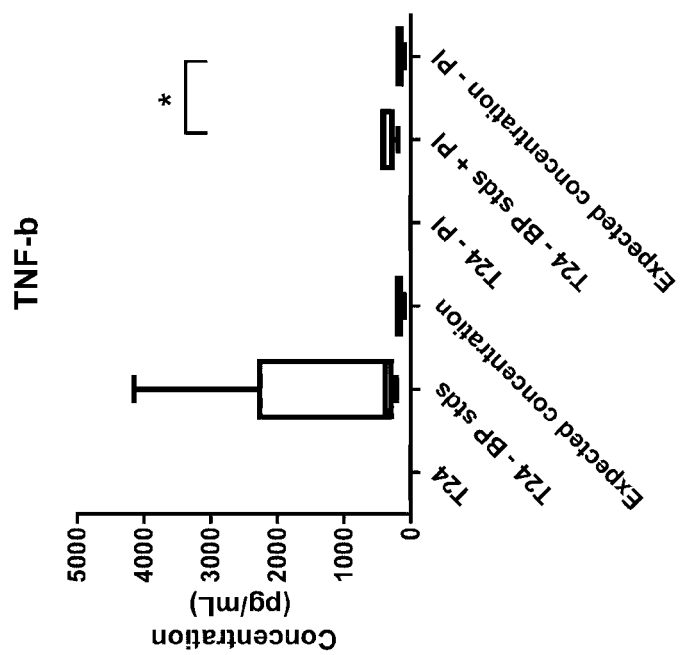
Figure 4M:
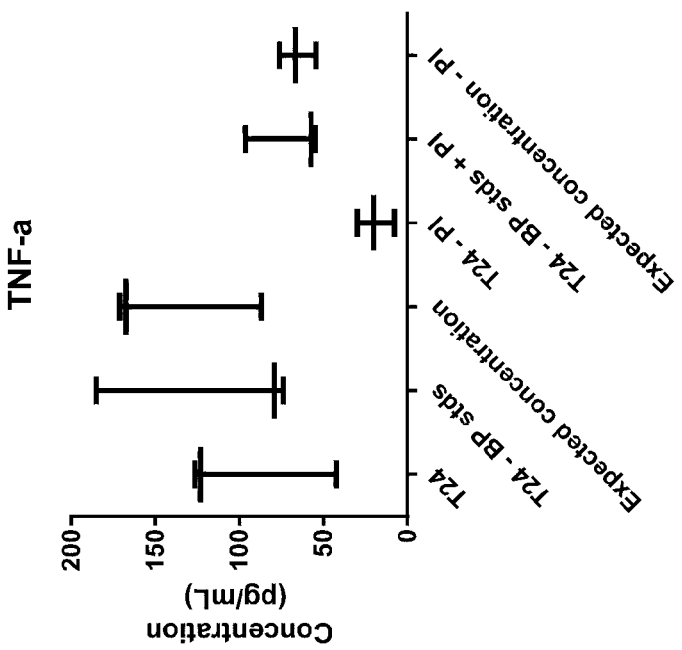
Figure 4O:
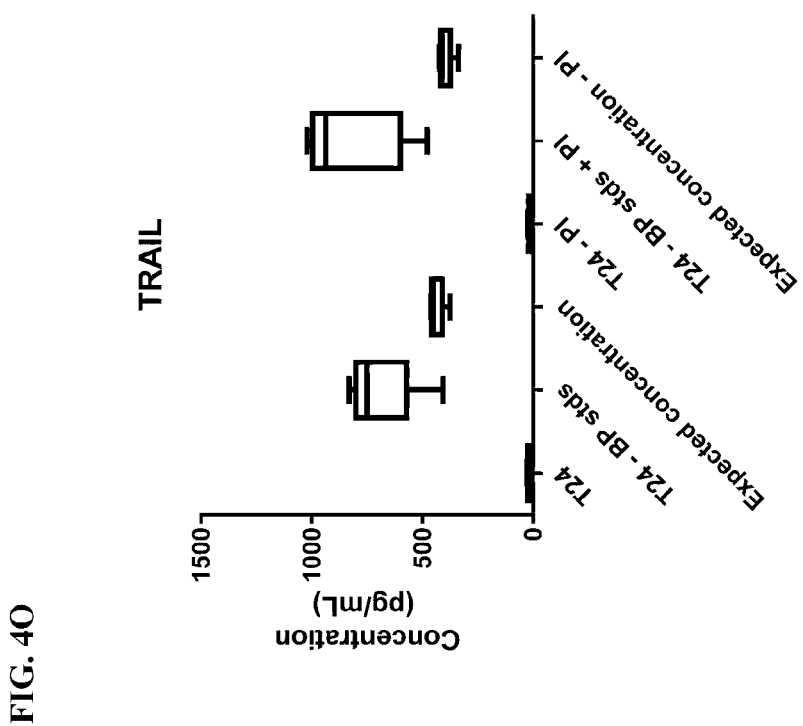
Figure 5B:
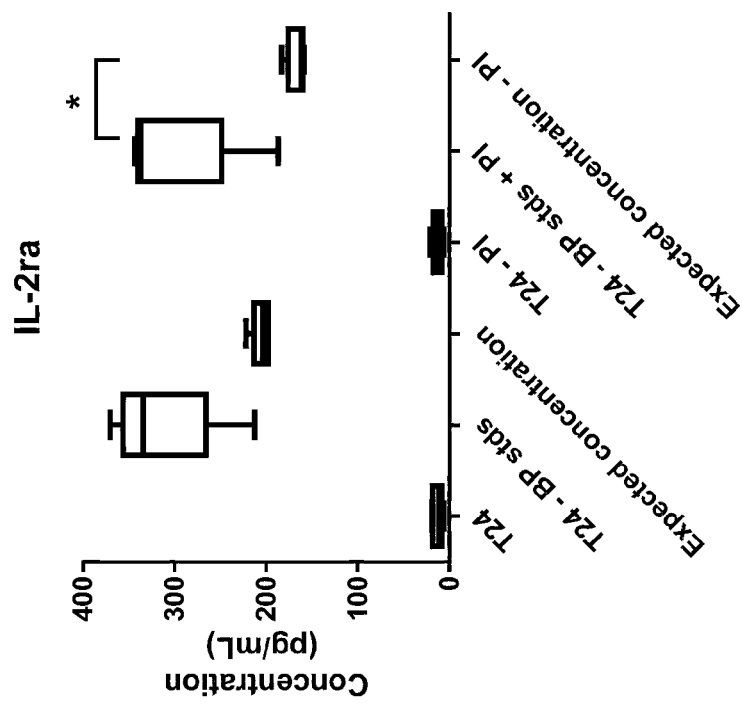
FIG. 5A-FIG. 5E is a series of graphs showing the concentration of anti-inflammatory proteins released or secreted from RBCs into PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 5A:
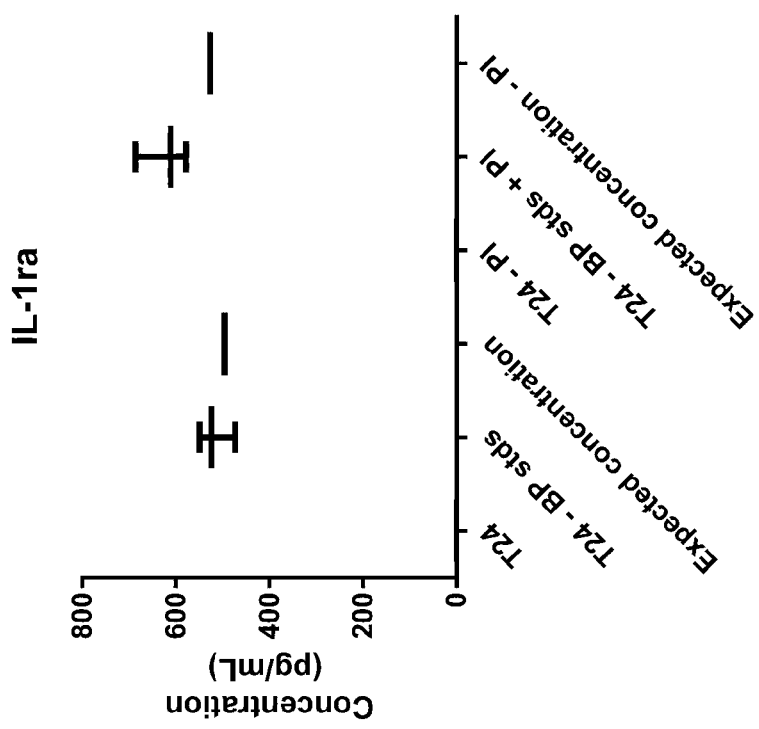
Figure 5D:
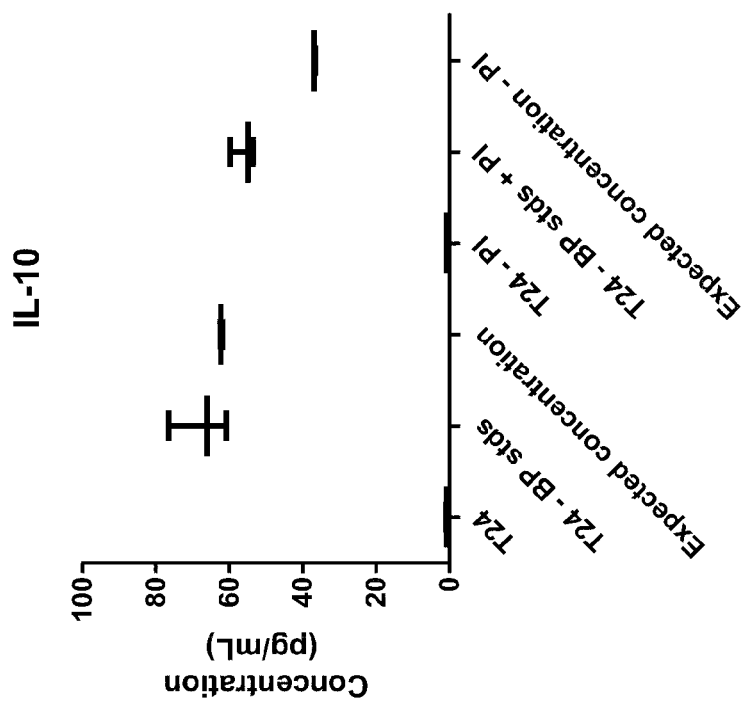
Figure 5C:
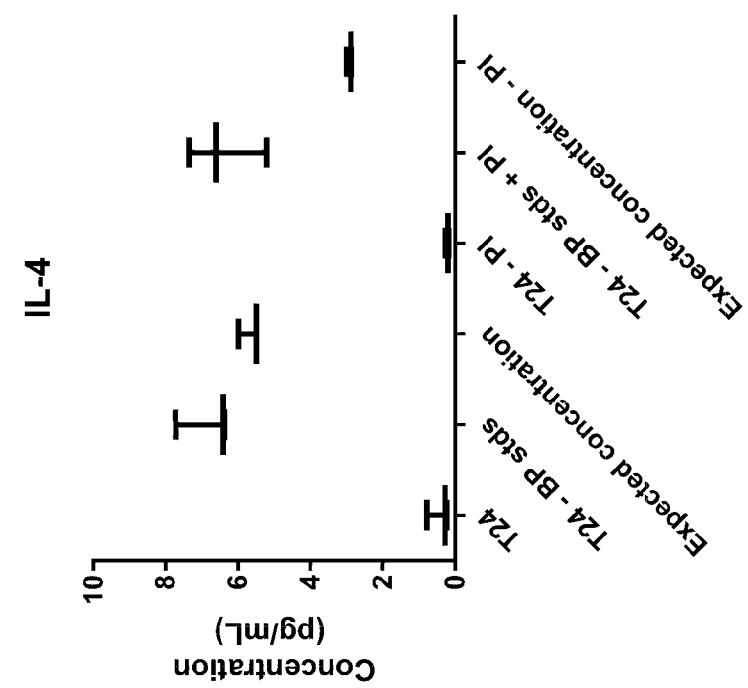
Figure 5E:
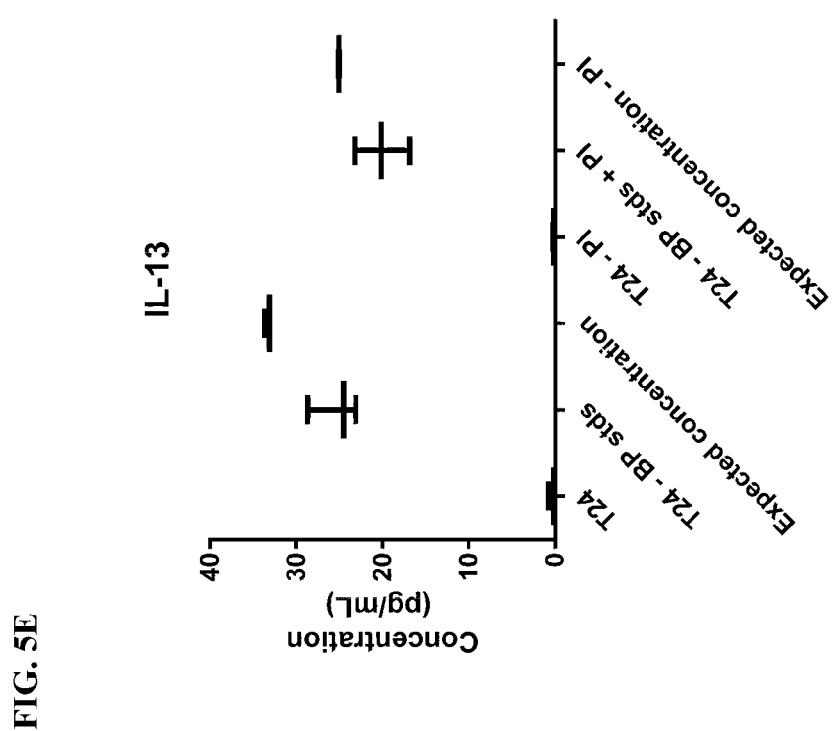
Figure 6A:
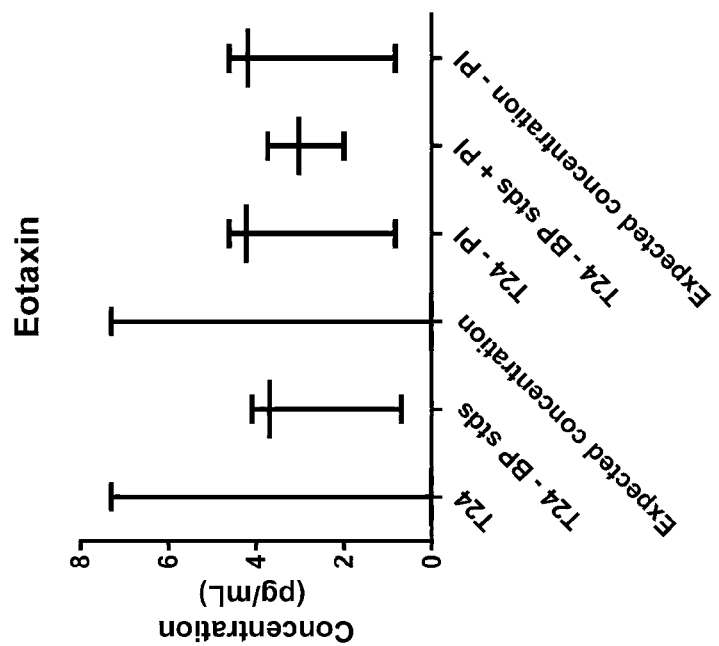
FIG. 6A-FIG. 6K is a series of graphs showing the concentration of chemokines released or secreted from RBCs into PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 6B:
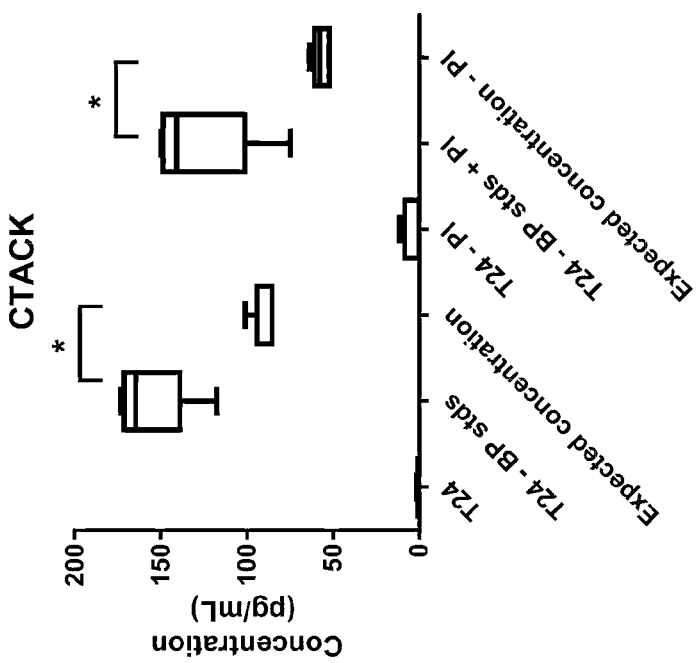
Figure 6D:
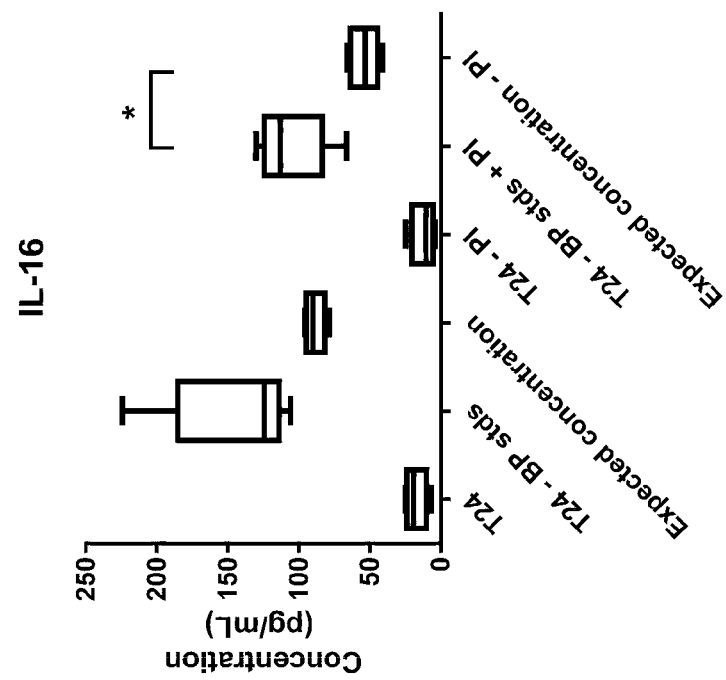
Figure 6C:
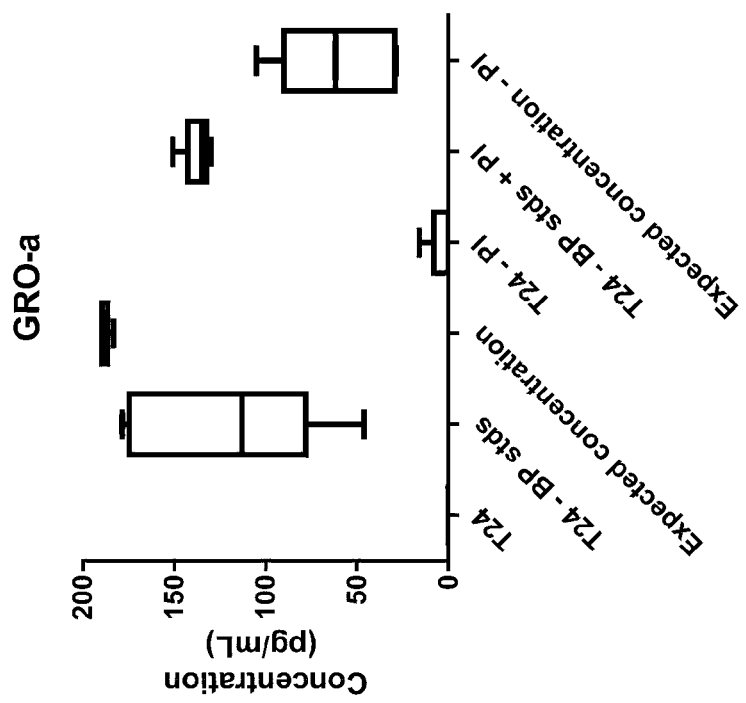
Figure 6F:
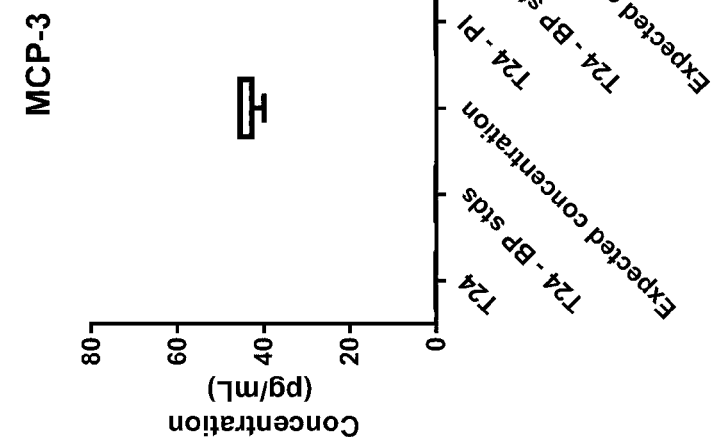
Figure 6E:
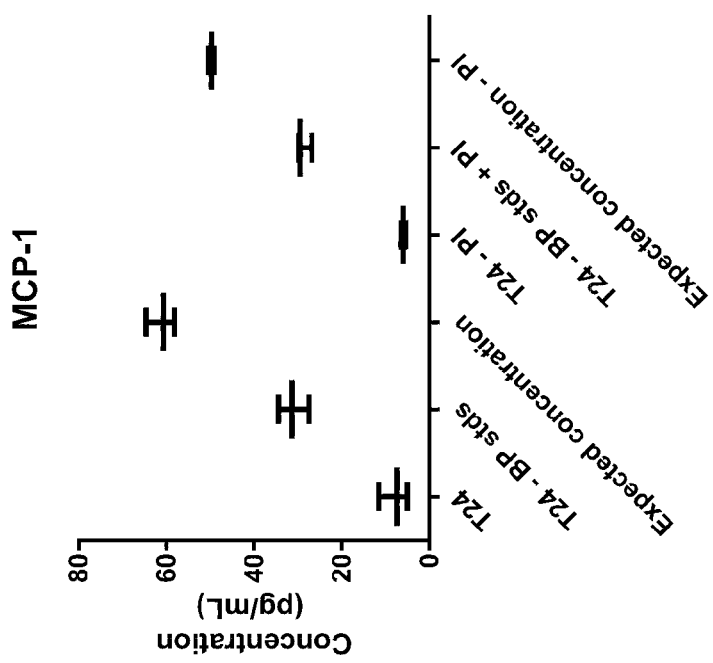
Figure 6H:
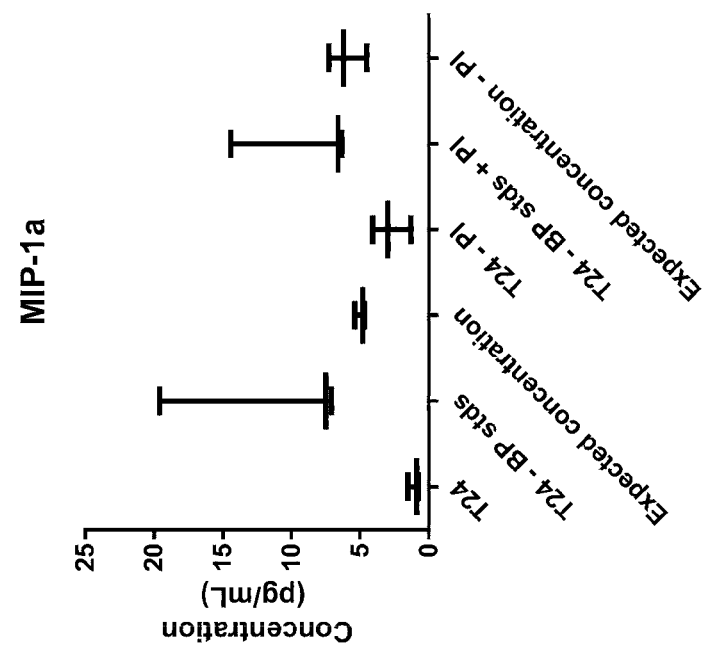
Figure 6G:
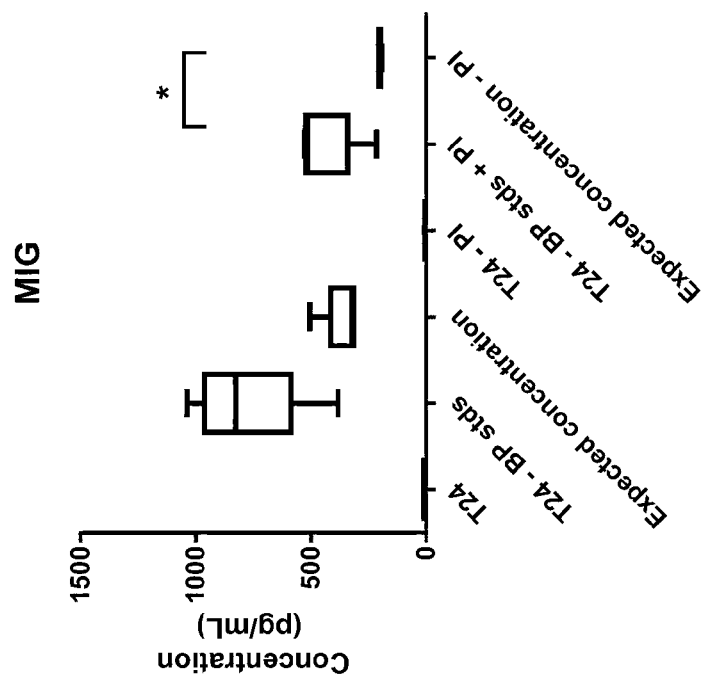
Figure 6J:
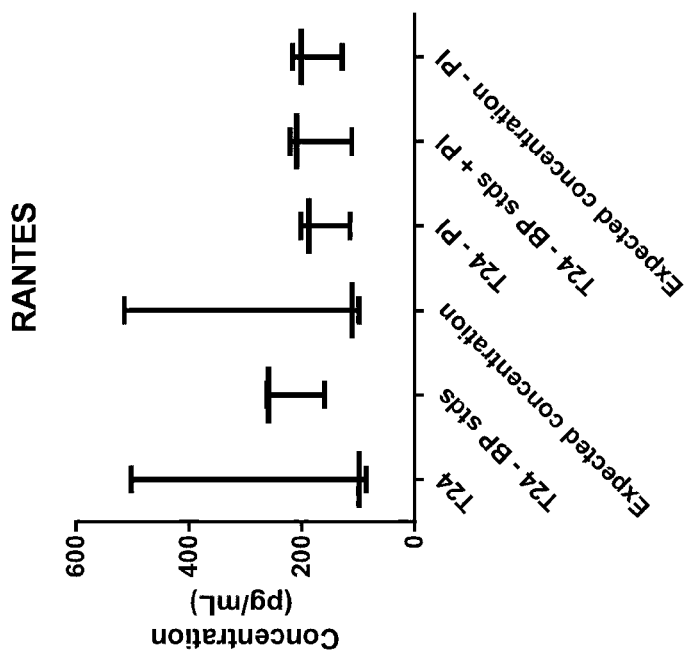
Figure 6I:
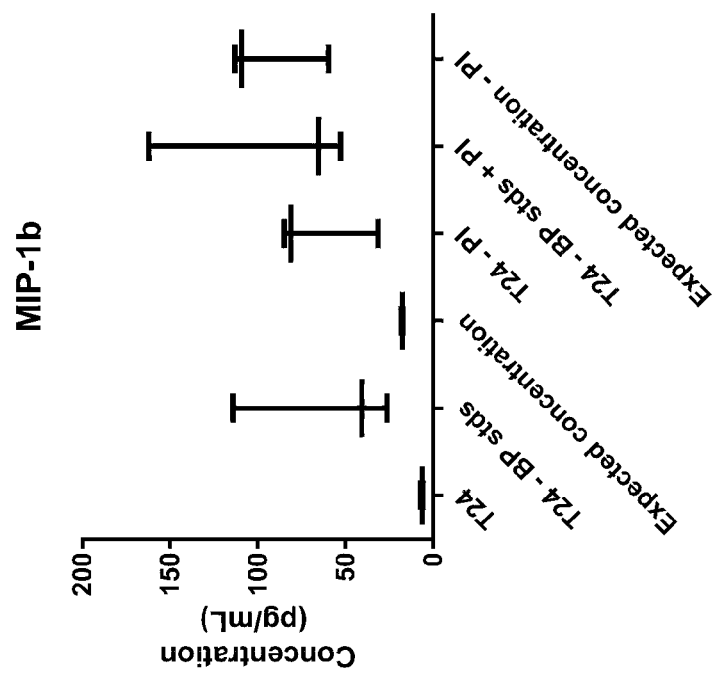
Figure 6K:
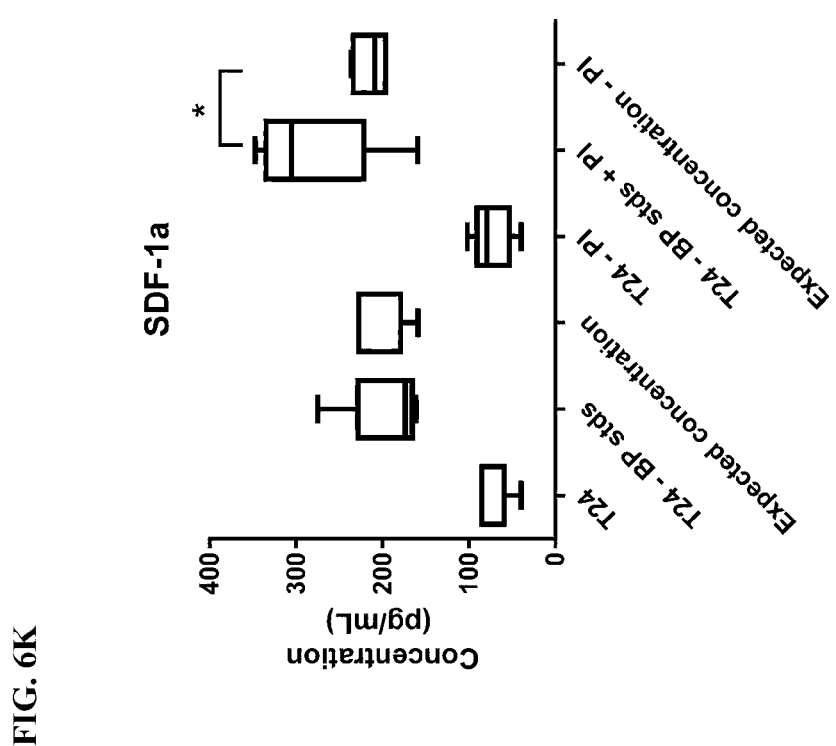
Figure 7A:
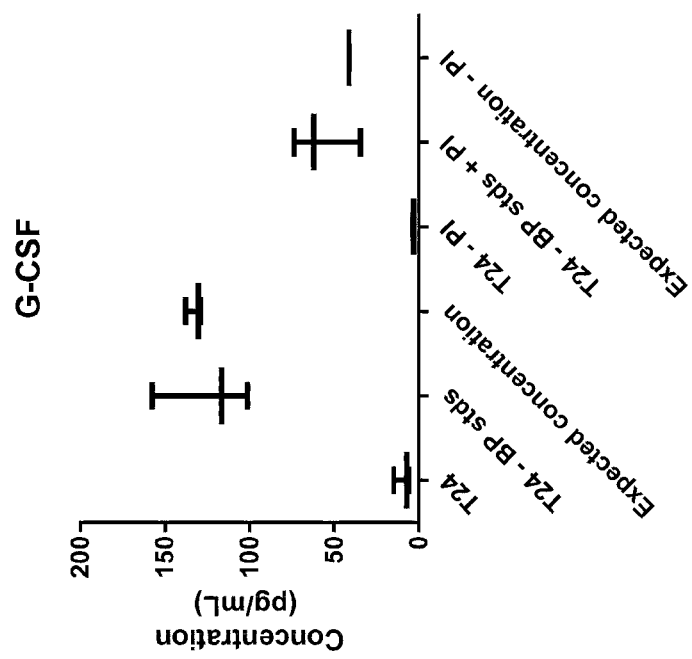
FIG. 7A-FIG. 7M is a series of graphs showing the concentration of growth factors released or secreted from RBCs into PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 7B:
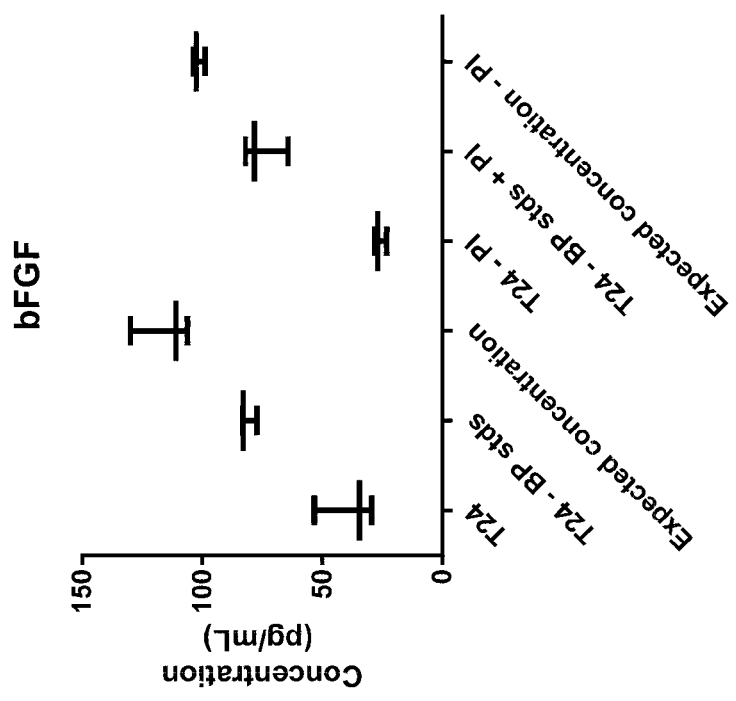
Figure 7D:
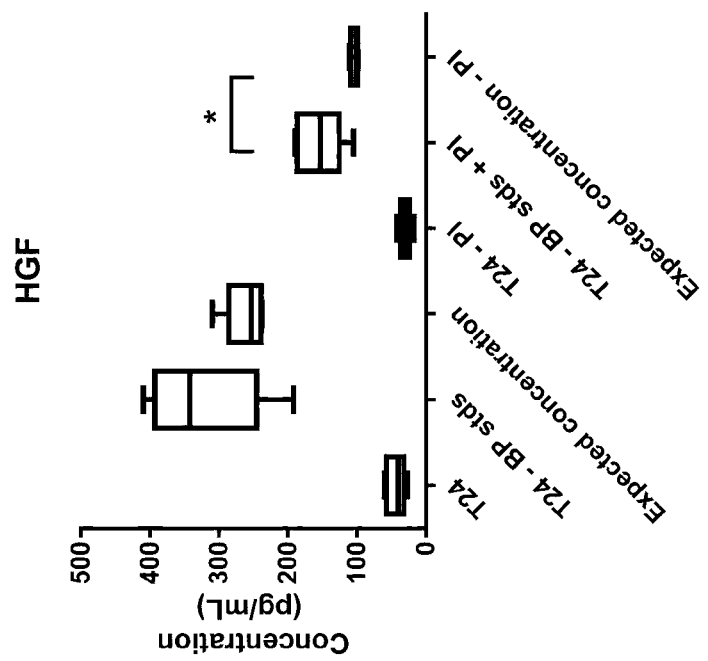
Figure 7C:
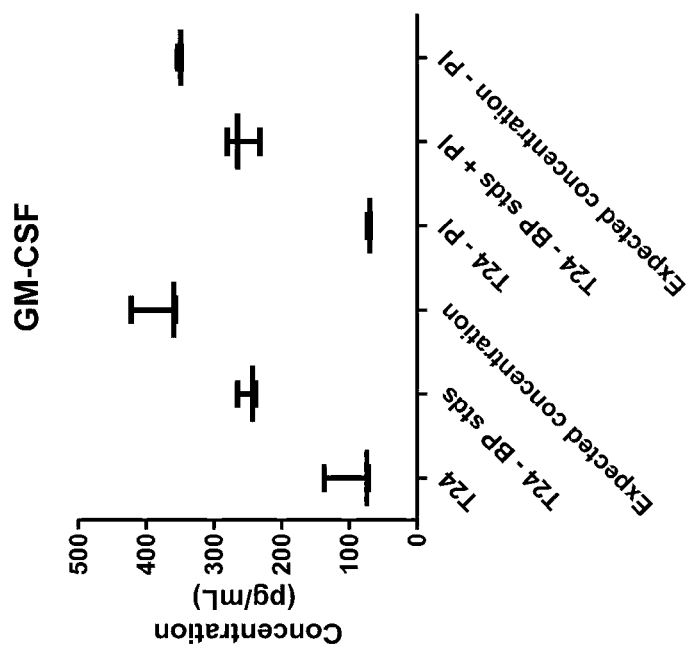
Figure 7F:
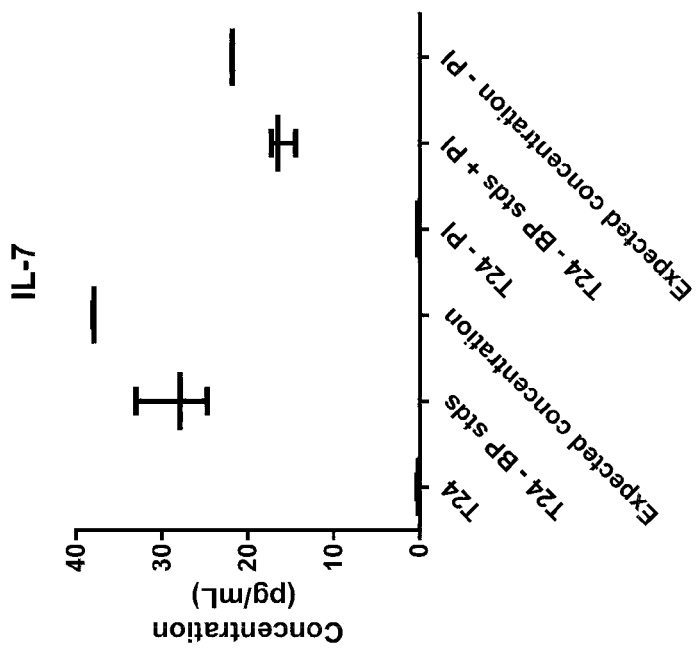
Figure 7E:
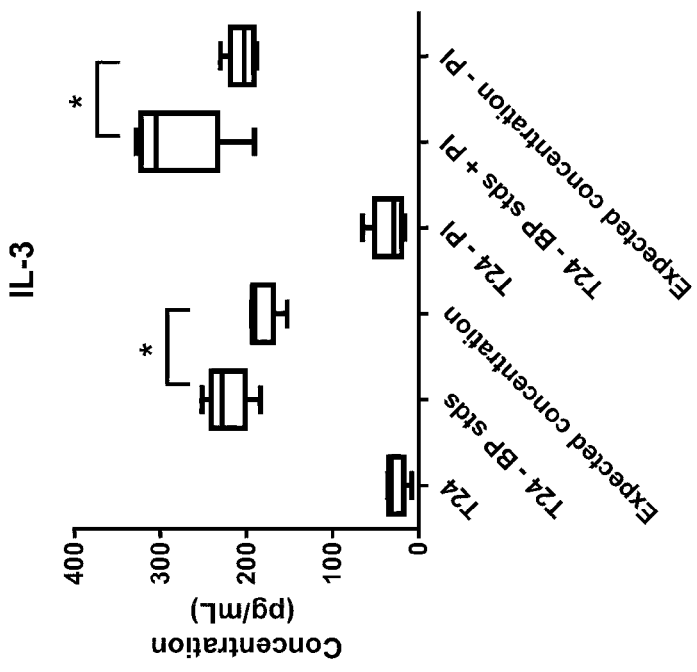
Figure 7H:
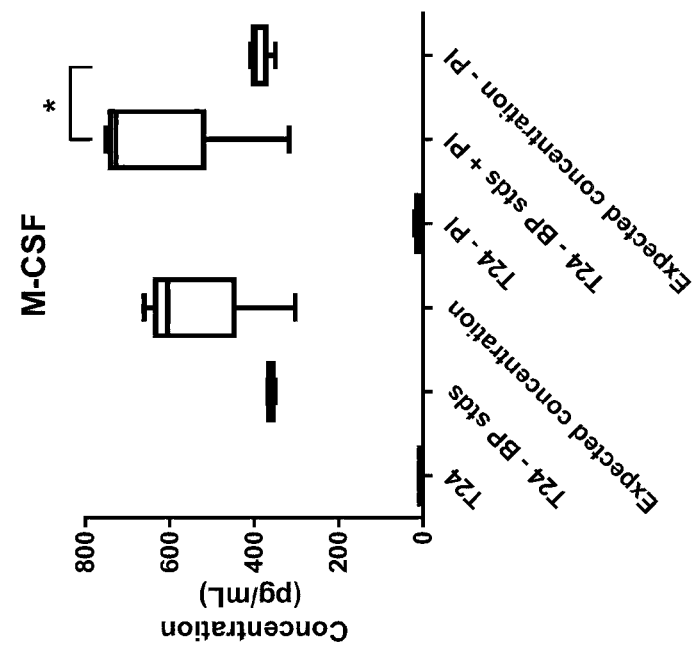
Figure 7G:
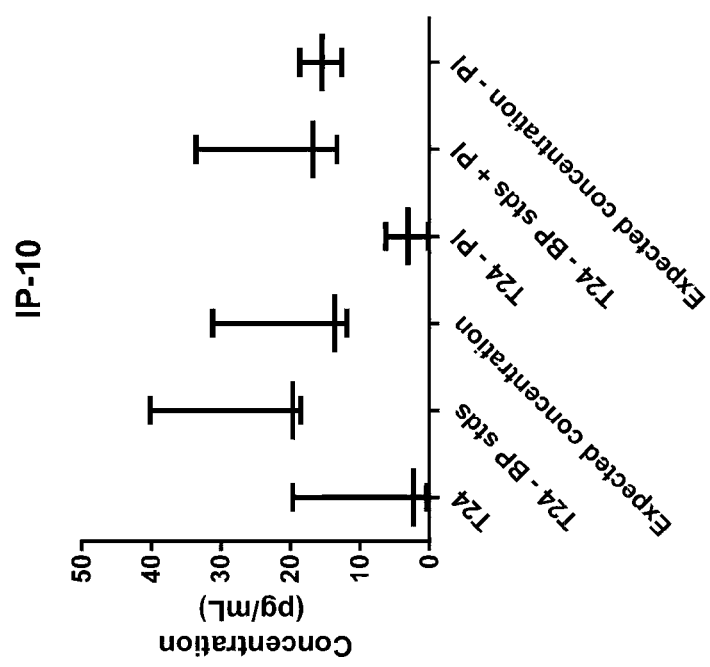
Figures 7I, 7J:
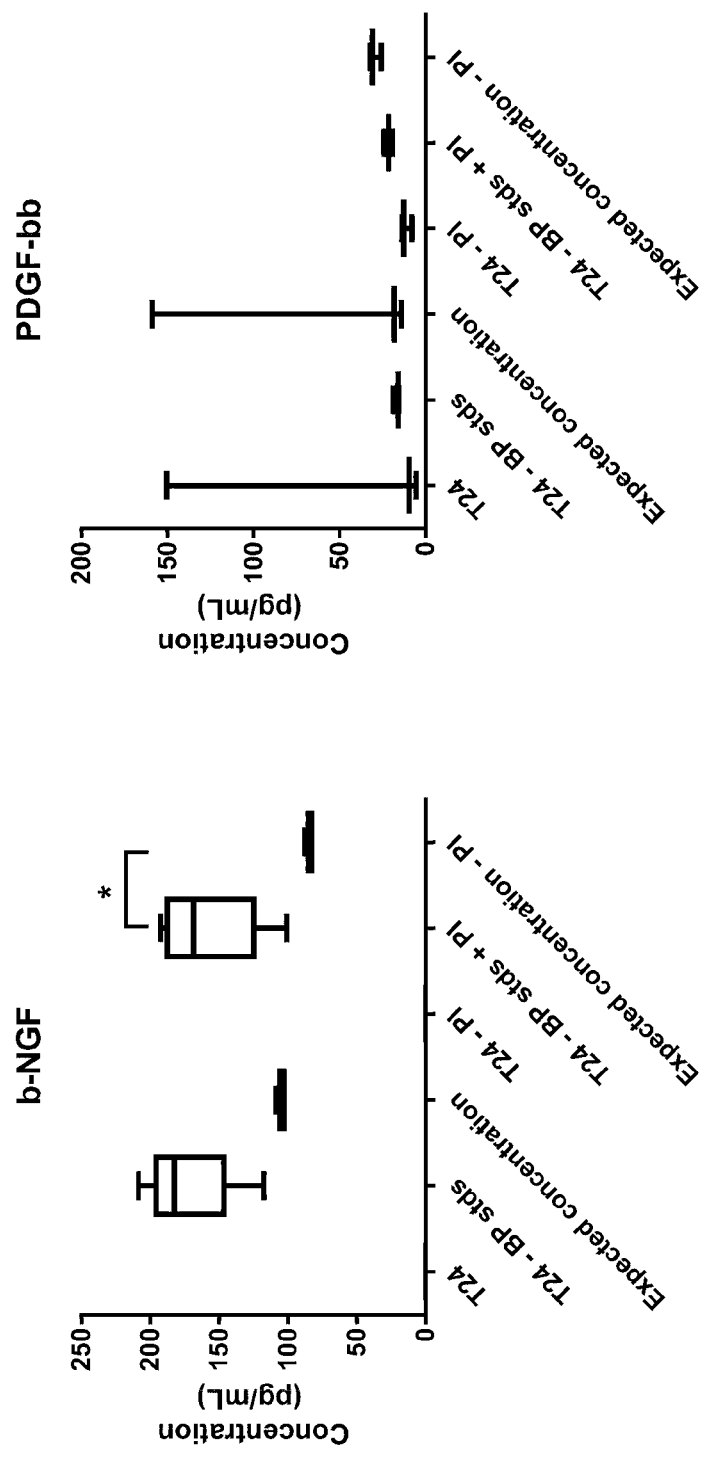
Figure 7L:
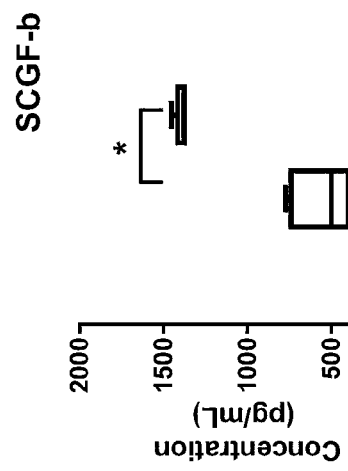
Figure 7K:
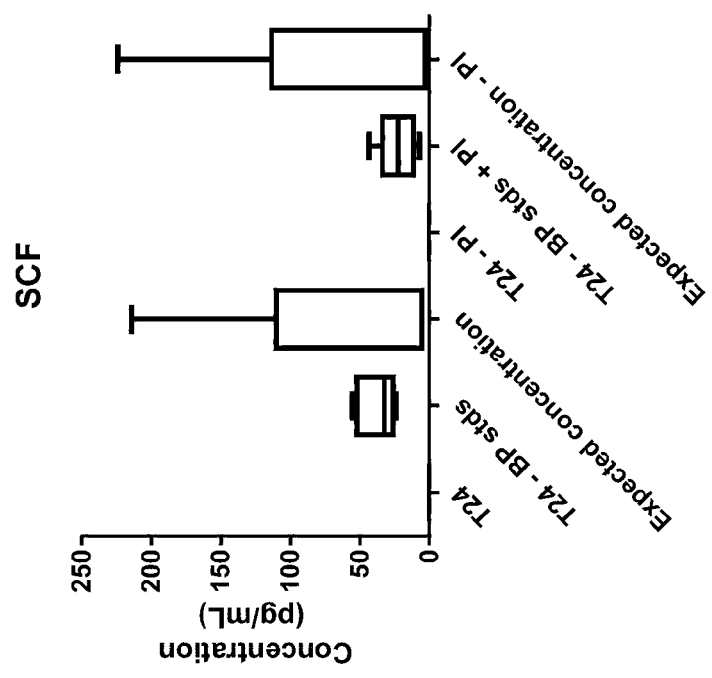
Figure 7M:
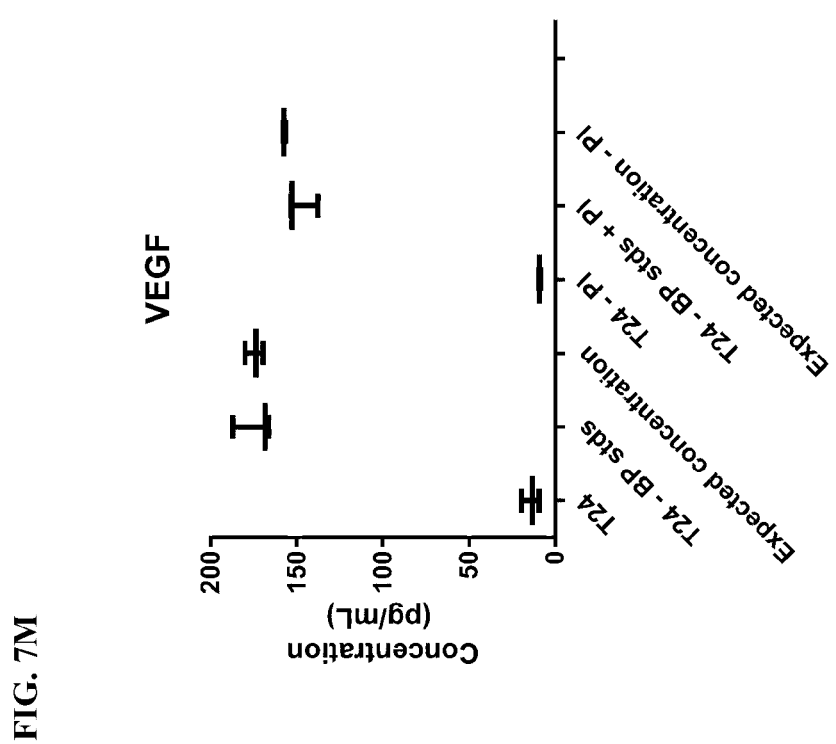
Figure 8B:
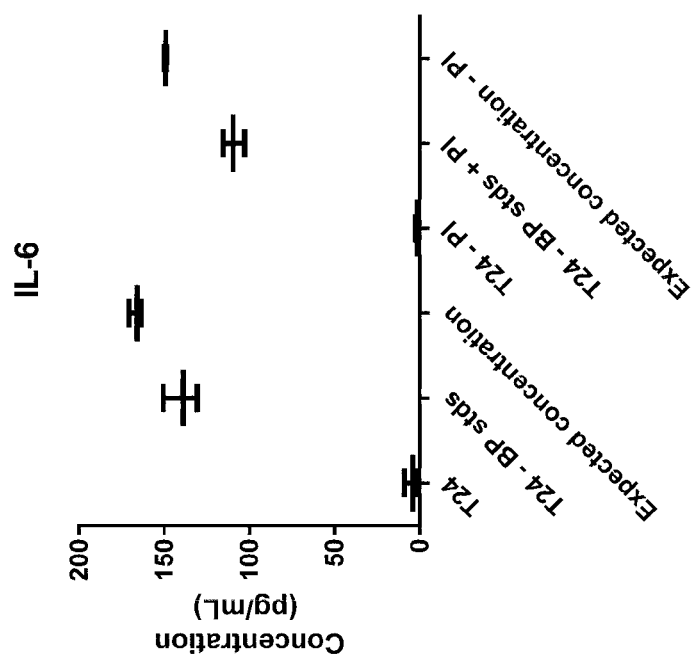
FIG. 8A-FIG. 8D is a series of graphs showing the concentration of proteins with multiple functions released or secreted from RBCs into PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 8A:
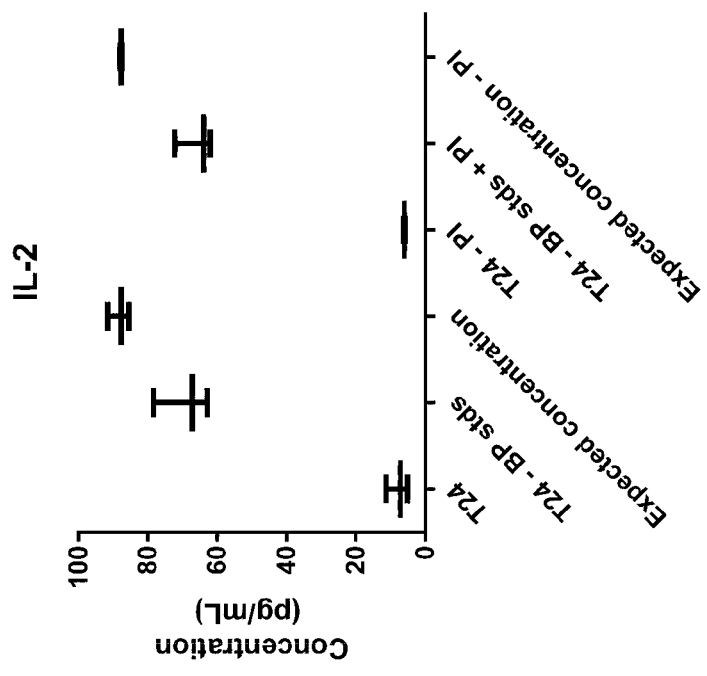
Figures 8C, 8D:
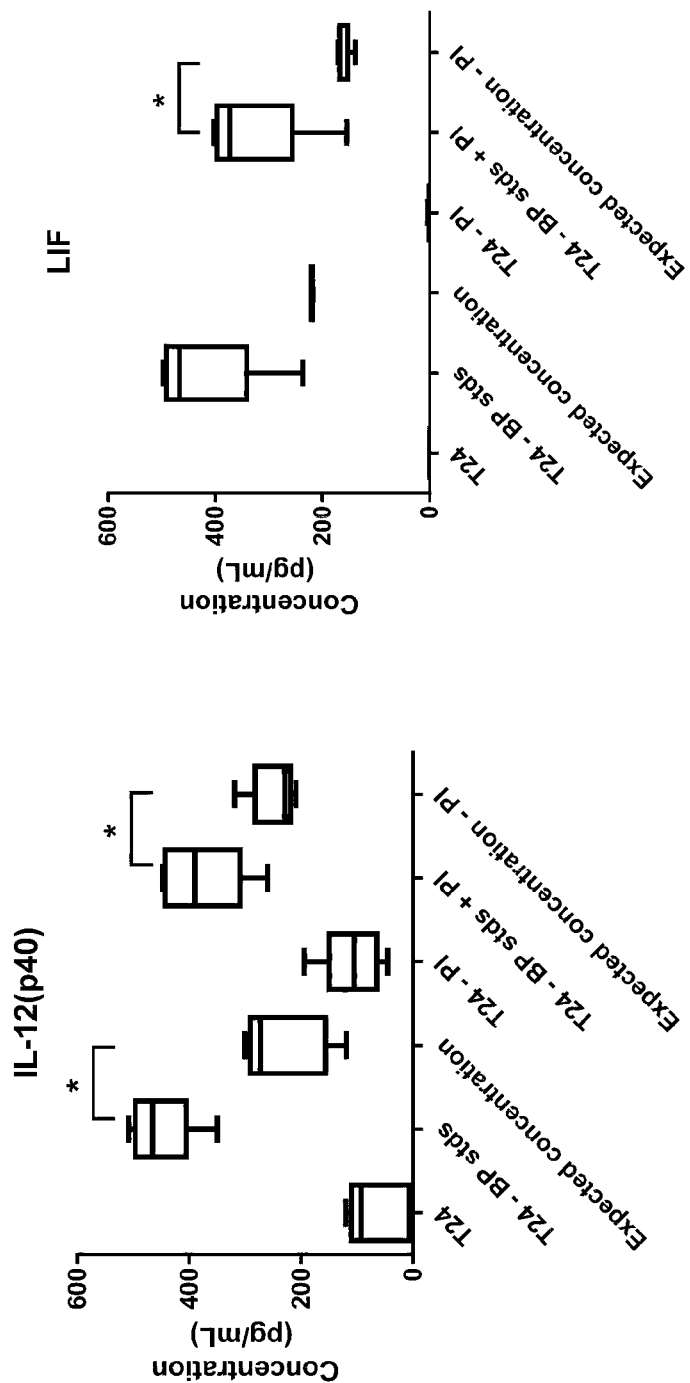
Figure 9B:
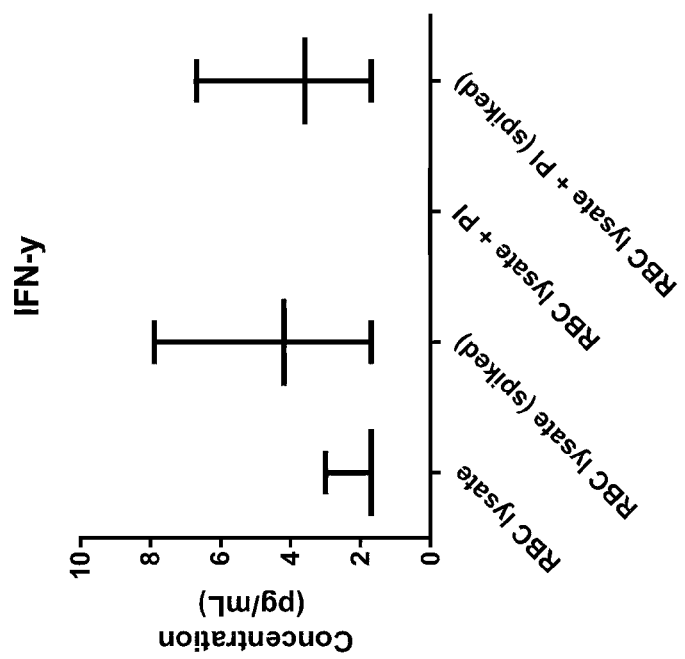
FIG. 9A-FIG. 9O is a series of graphs showing the concentration of pro-inflammatory cytokines in the lysate of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 9A:
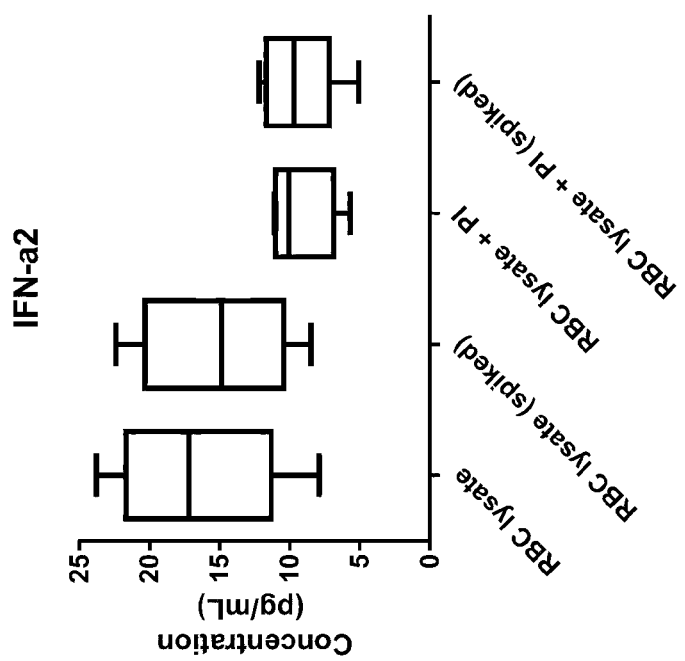
Figure 9C:
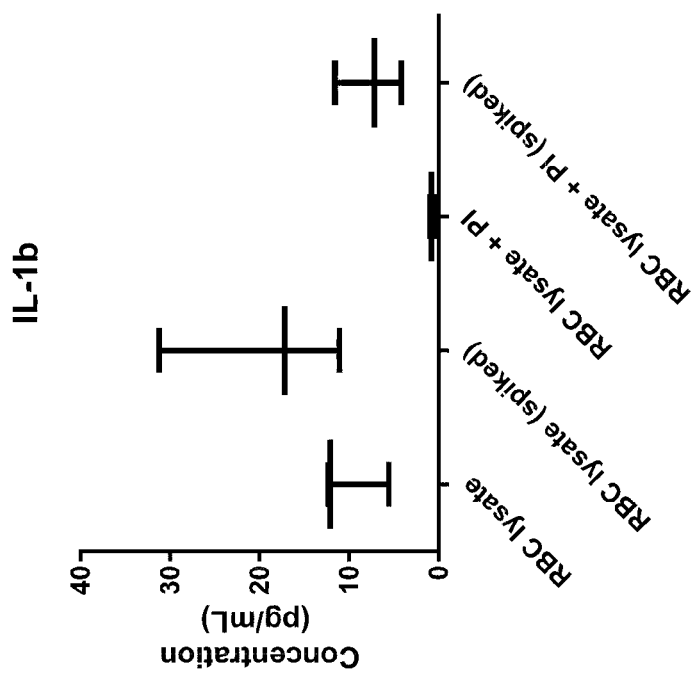
Figure 9D:
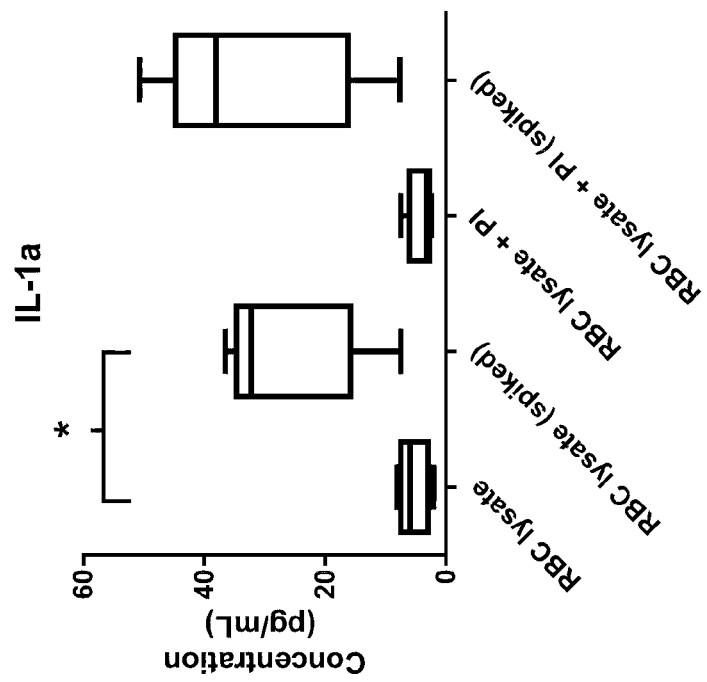
Figure 9F:
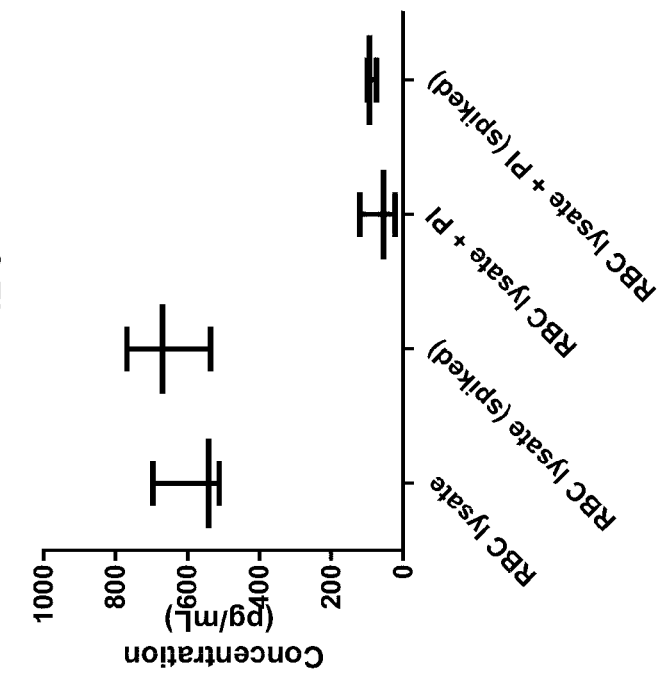
Figure 9E:
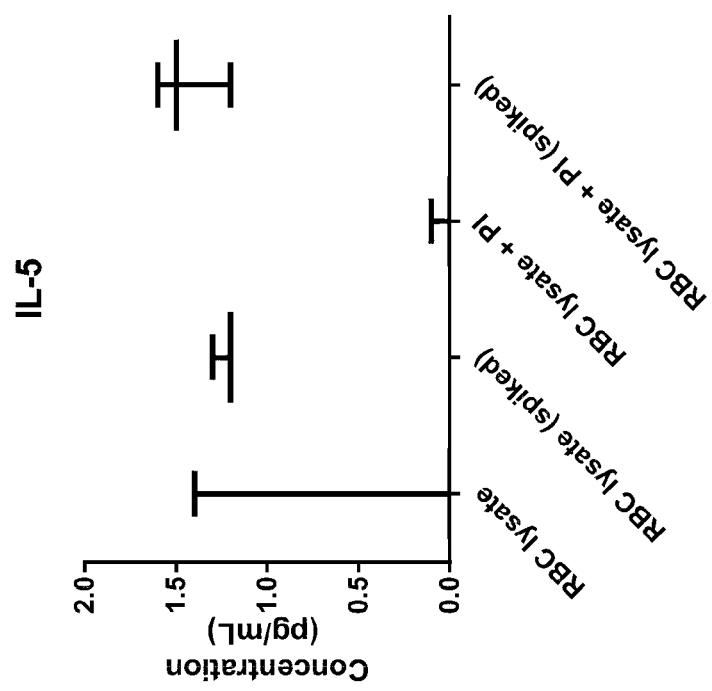
Figure 9H:
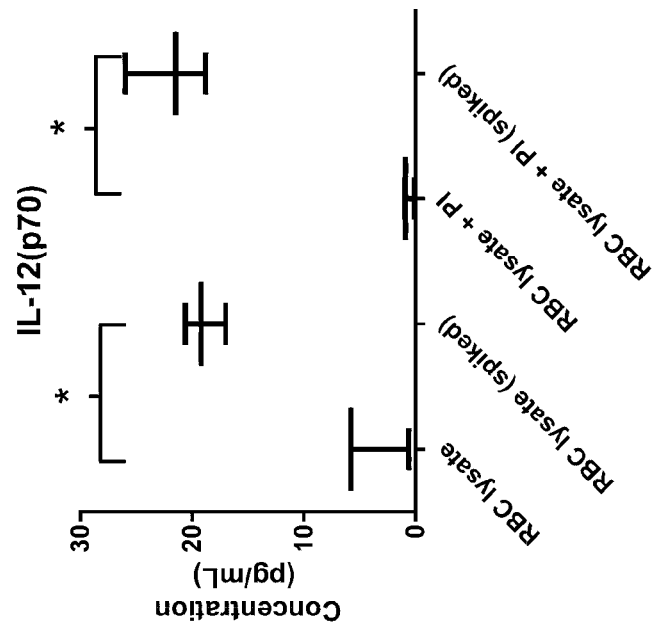
Figure 9G:
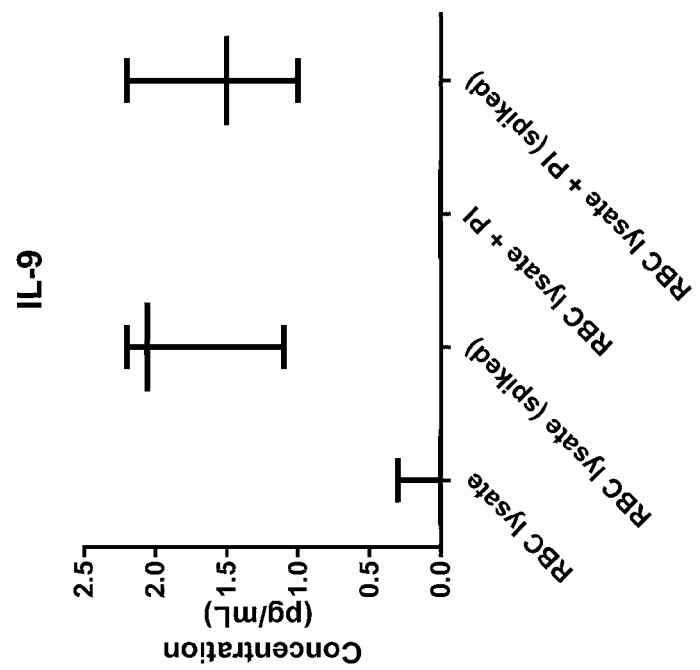
Figure 9J:
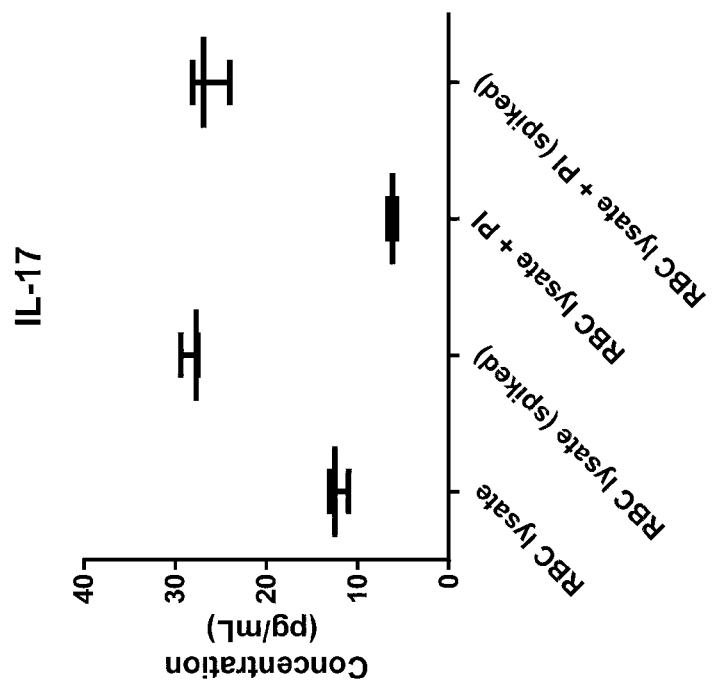
Figure 9I:
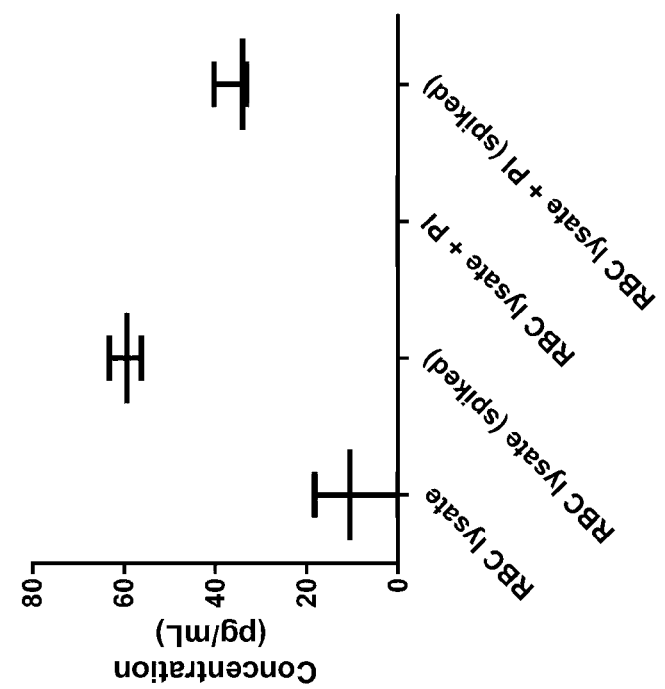
Figures 9K, 9L:
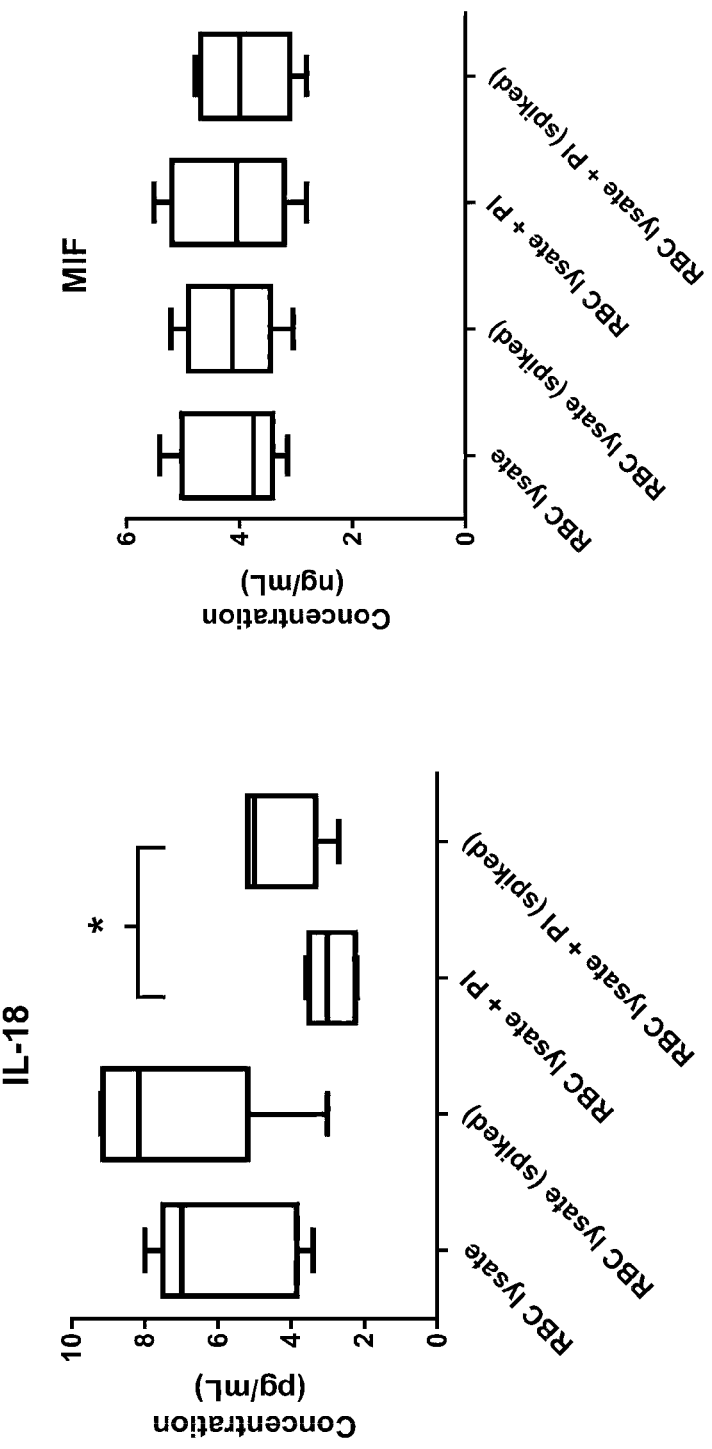
Figure 9N:
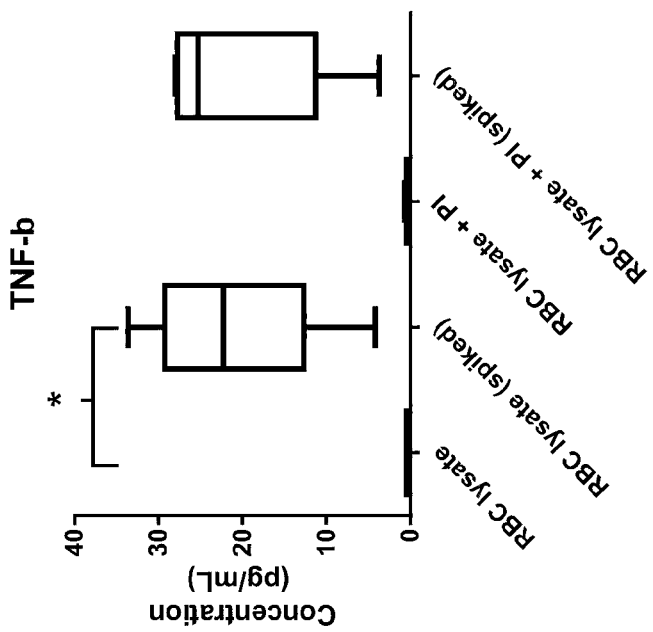
Figure 9M:
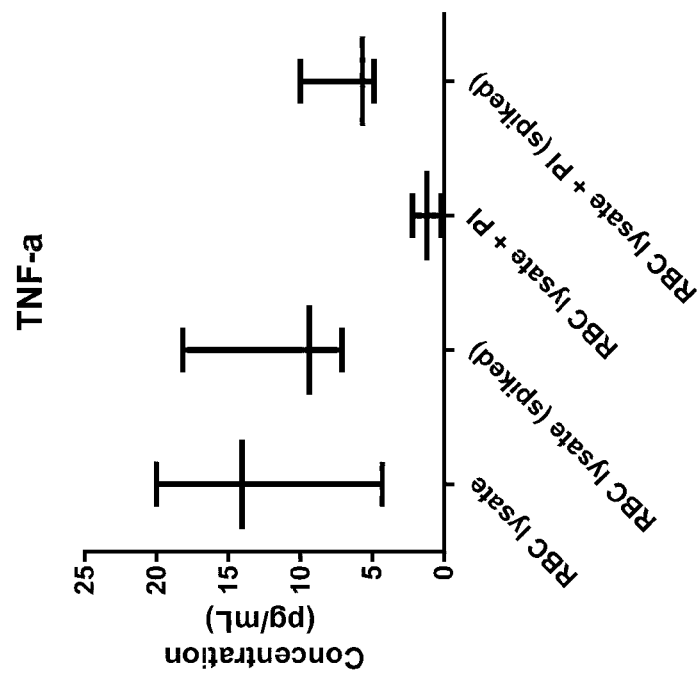
Figure 9O:
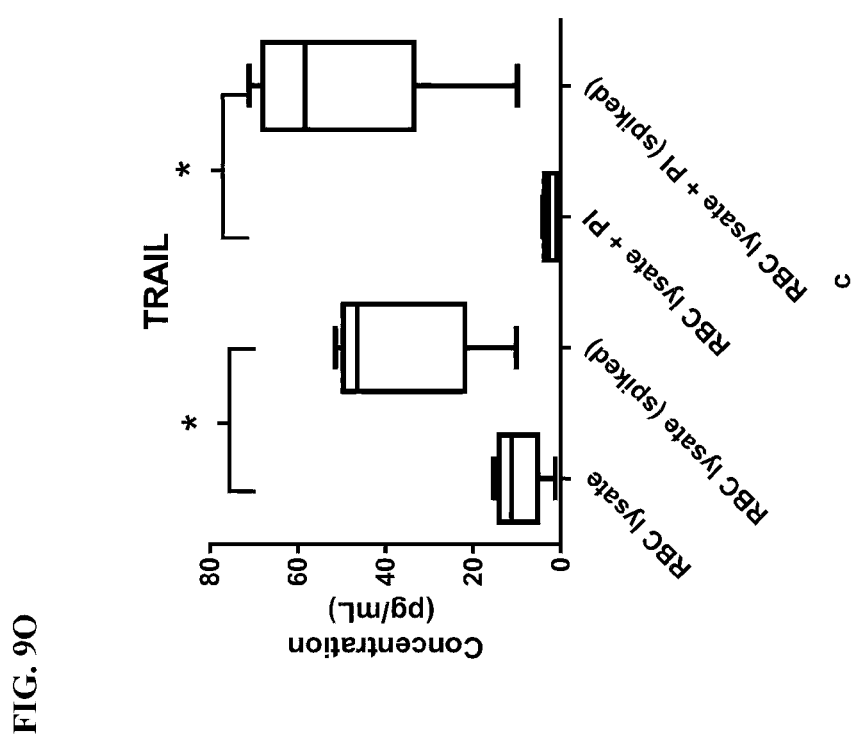
Figure 10B:
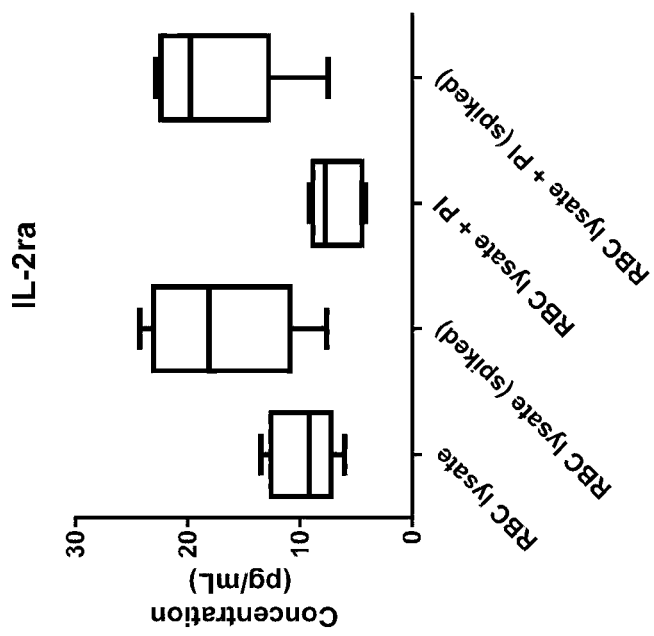
FIG. 10A-FIG. 10E is a series of graphs showing the concentration of anti-inflammatory cytokines in the lysate of RBCs after incubation in PBS with and without protease inhibitors and BioPlex standards over 24 hours at 37° C. as measured by BioPlex and reported as pg/mL (20 million RBCs in 100 uL PBS). Data presented as mean=SD, * indicates a significant difference of $p<0.05$ (n=3 for 27-plex, n=5 for 21-plex).
Figure 10A:
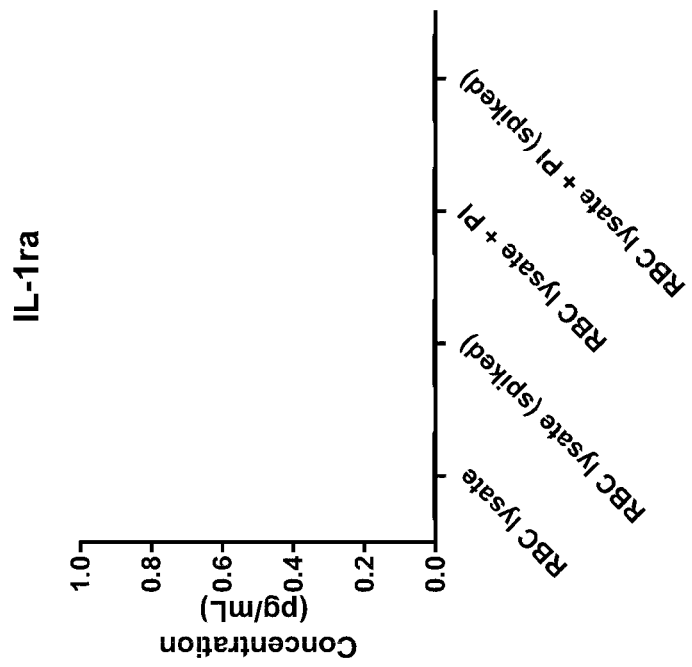
Figure 10D:
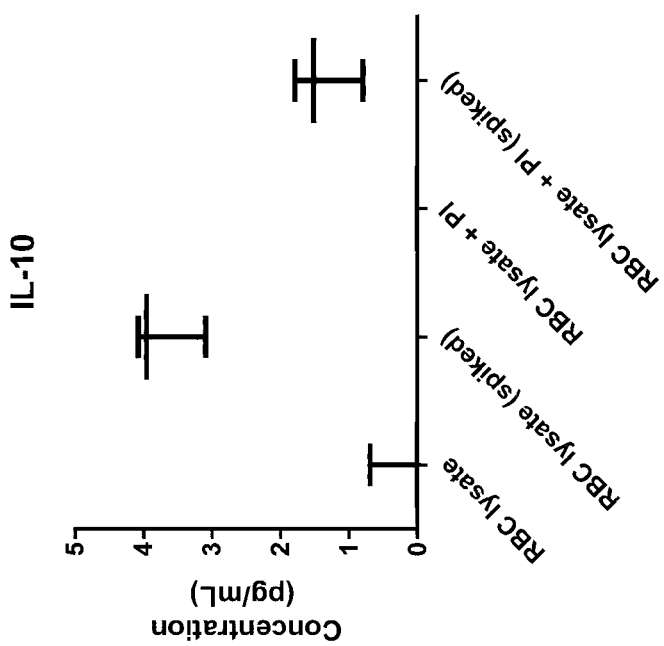
Figure 10C:
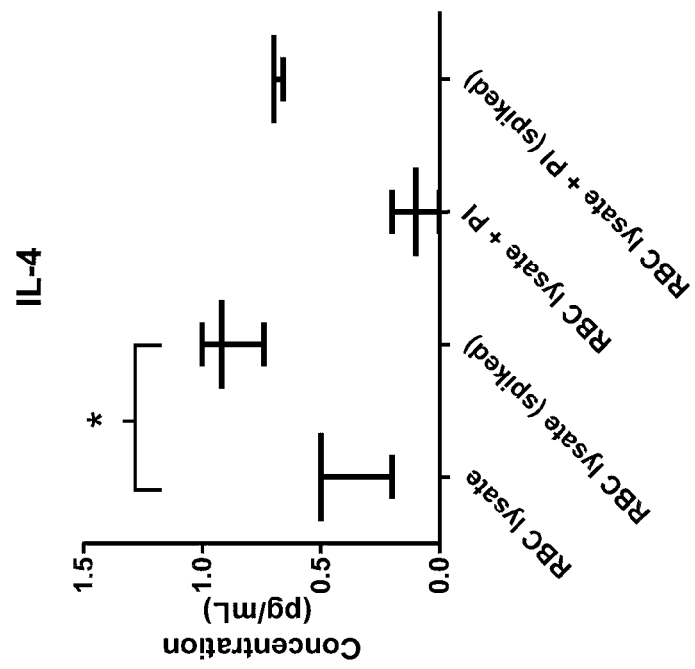
Figure 10E:
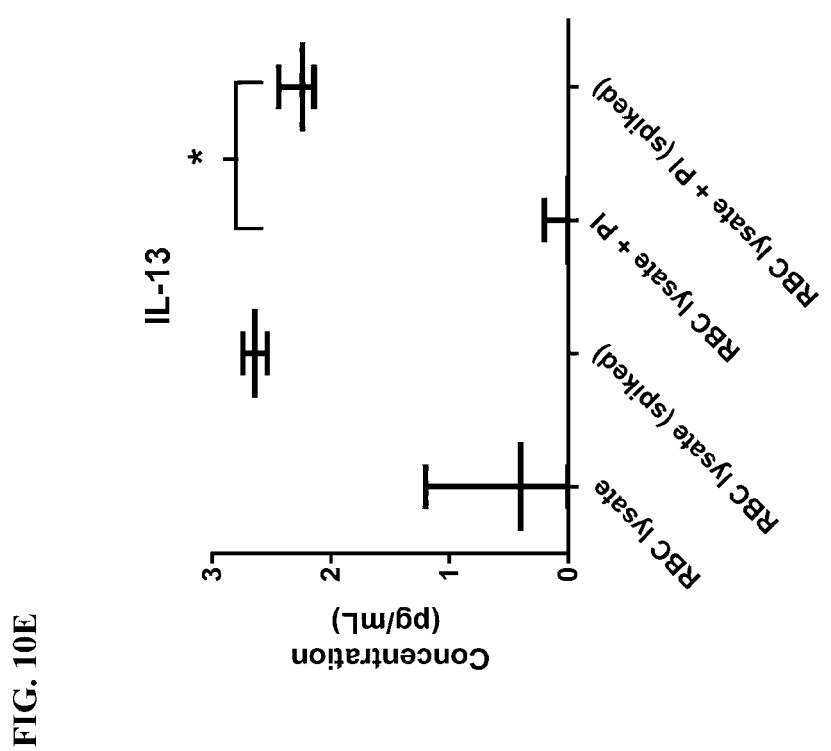
Figure 11B:
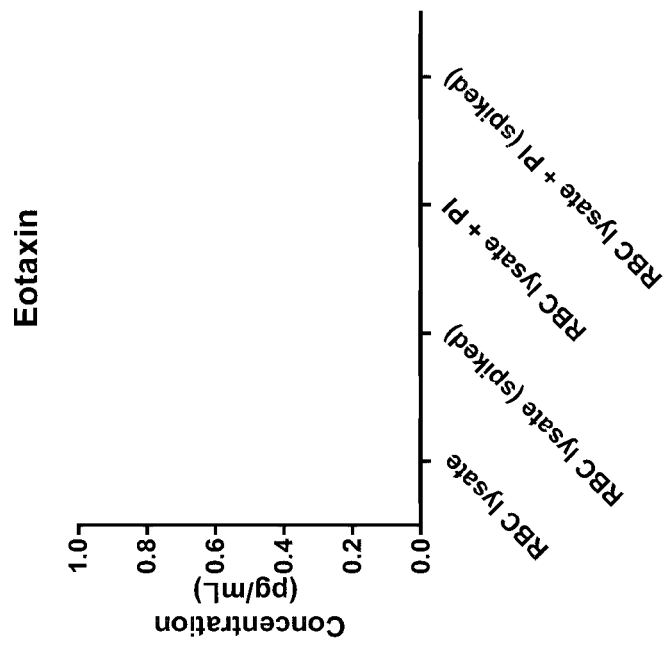
FIG. 11A-FIG. 11K is a series of graphs showing the concentration of chemokines in the lysate of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 11A:
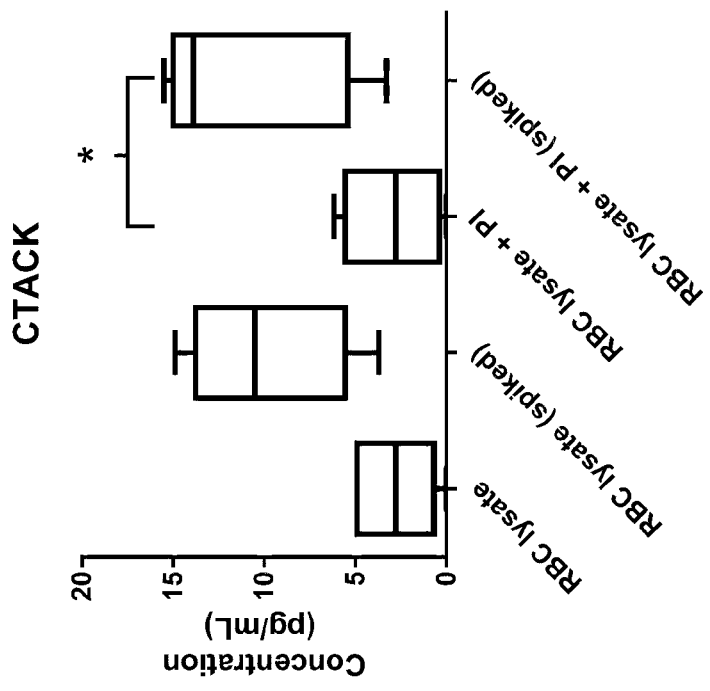
Figure 11D:
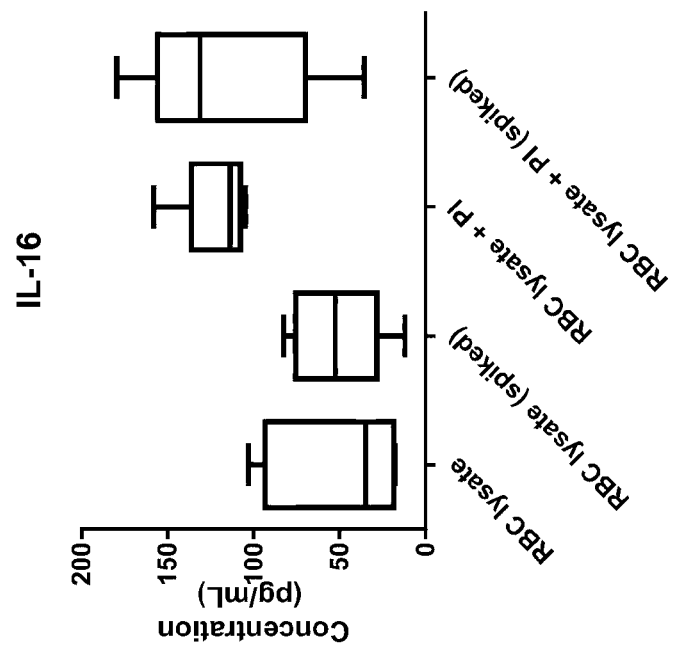
Figure 11C:
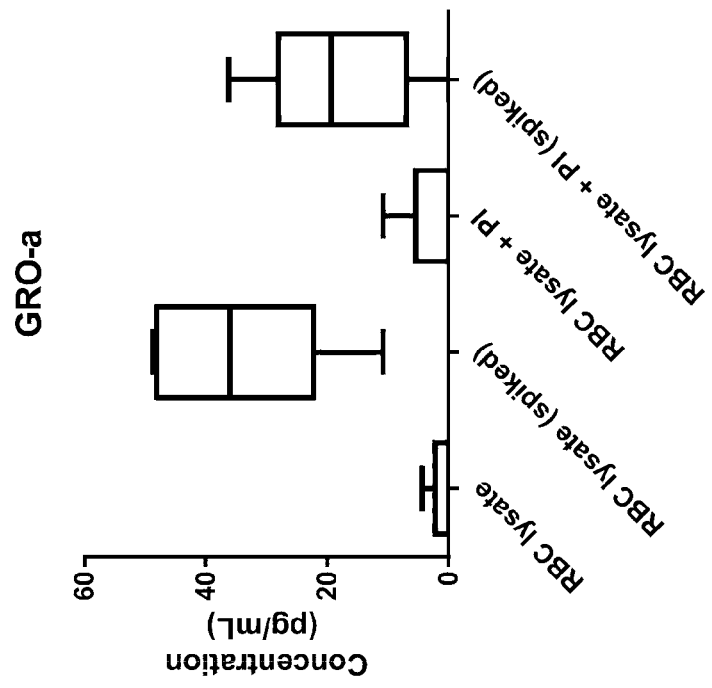
Figure 11F:
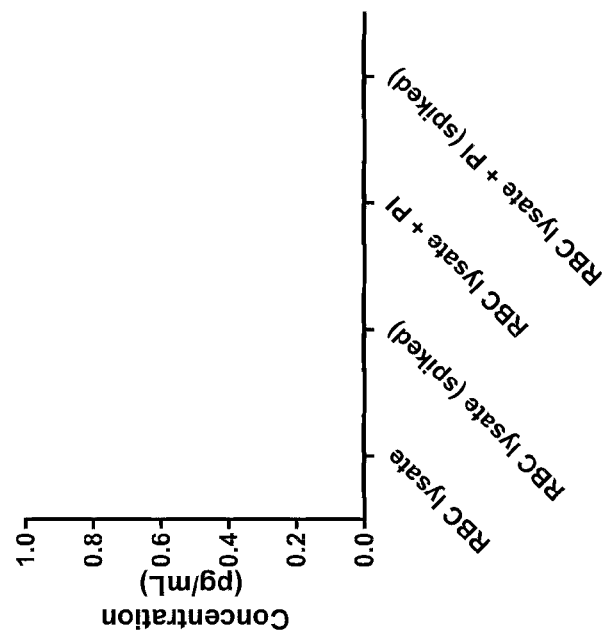
Figure 11E:
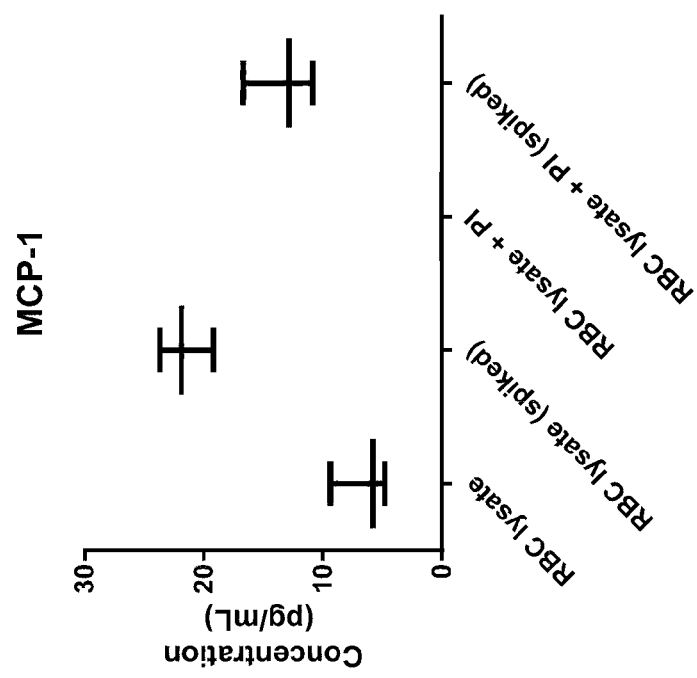
Figure 11H:
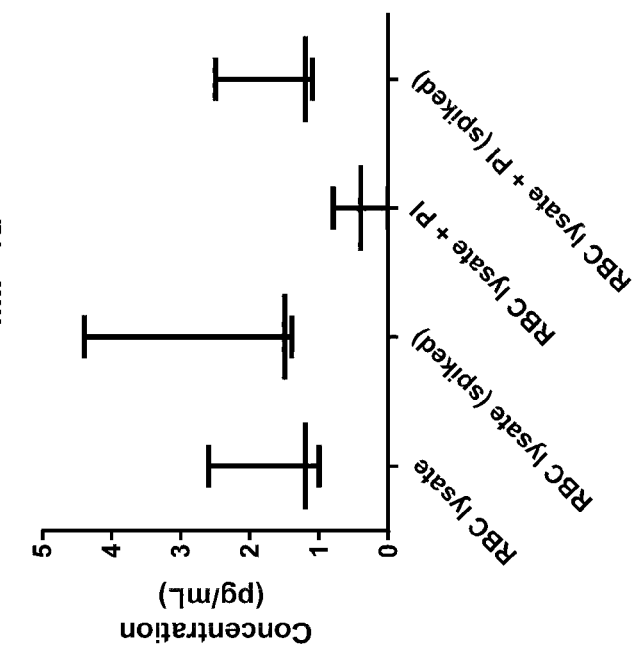
Figure 11G:
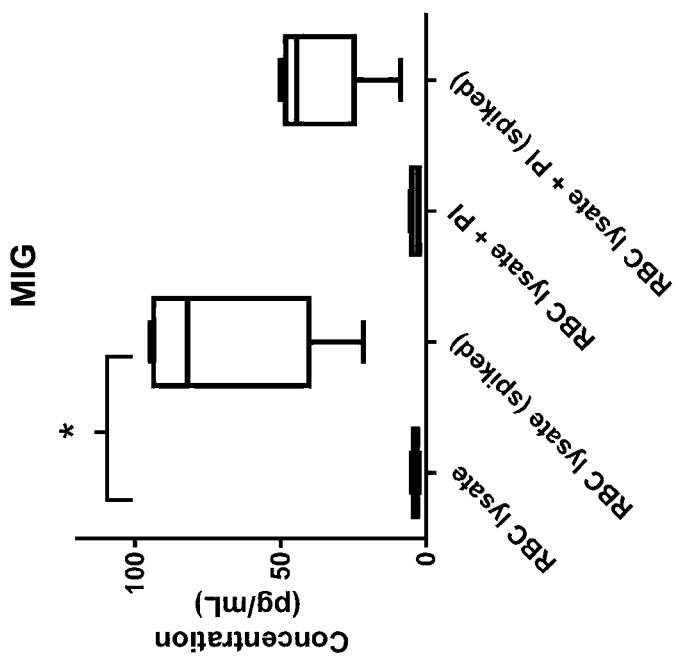
Figures 11I, 11J:
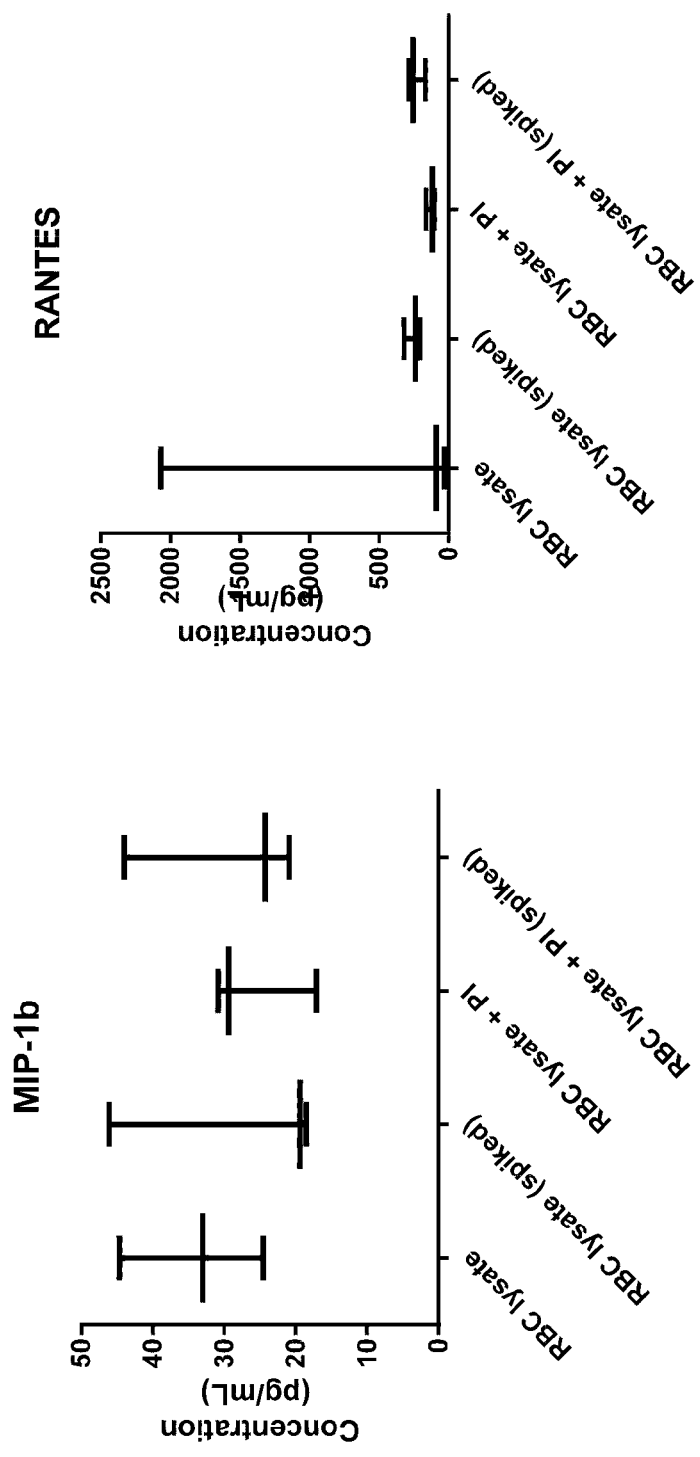
Figure 11K:
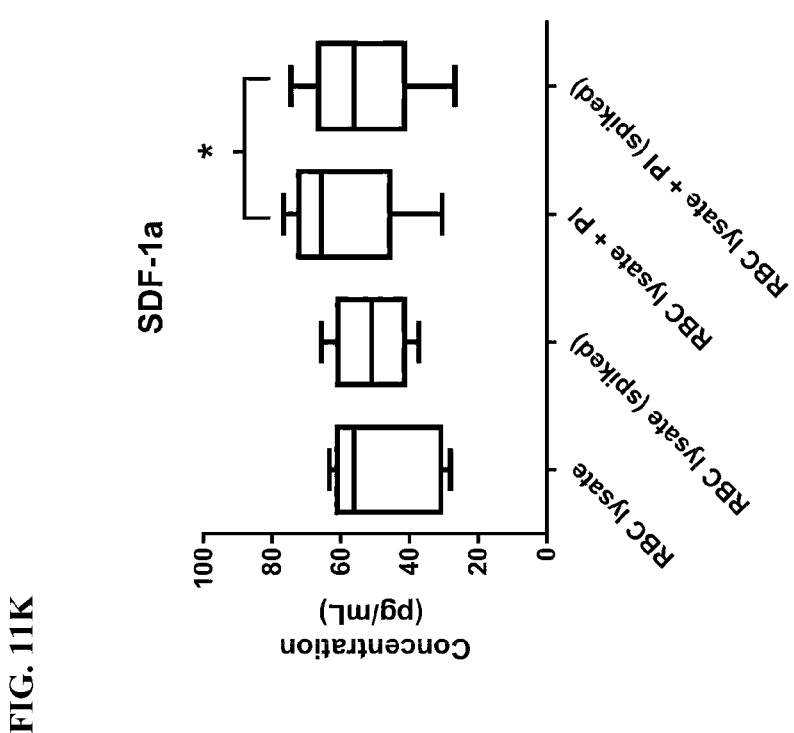
Figure 12A:
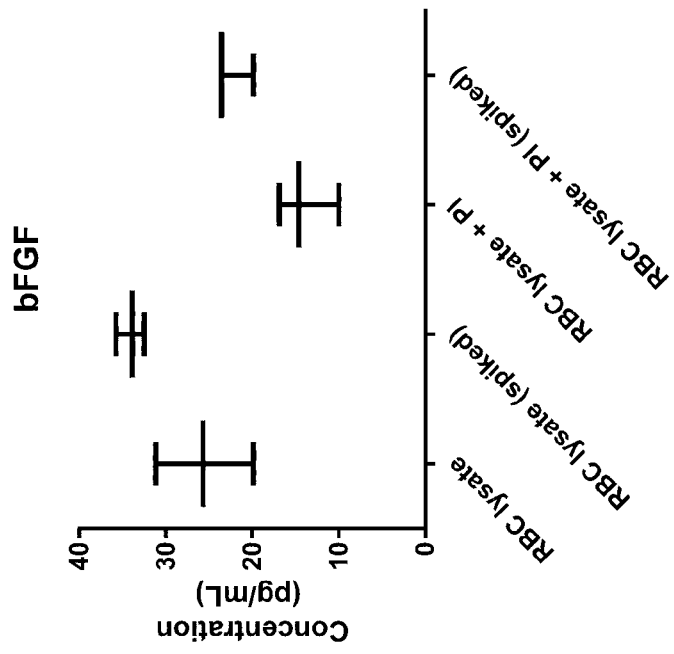
FIG. 12A-FIG. 12M is a series of graphs showing the concentration of growth factors in the lysate of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 12B:
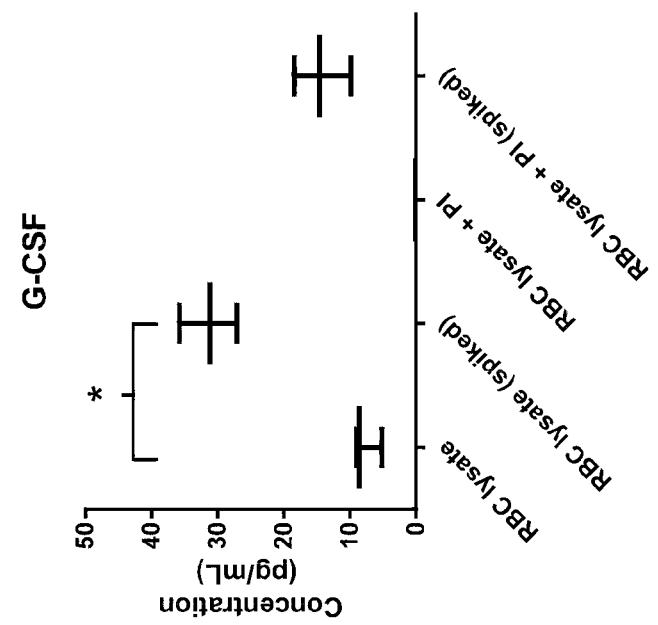
Figure 12D:
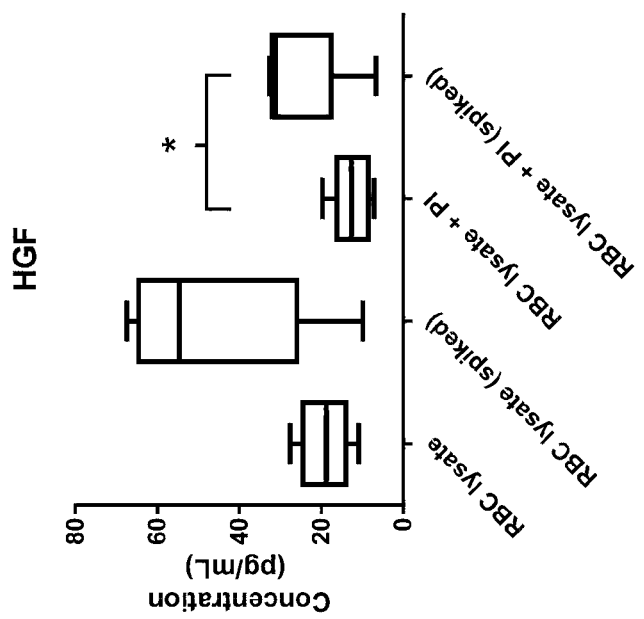
Figure 12C:
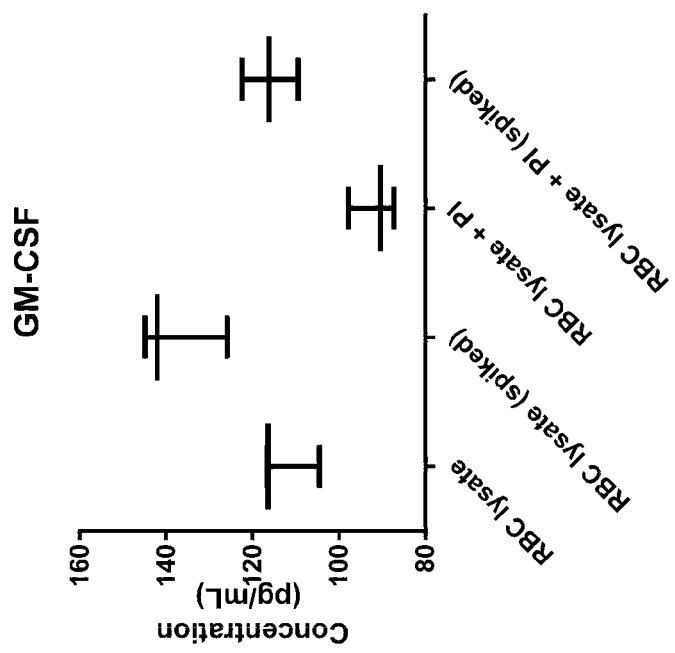
Figure 12F:
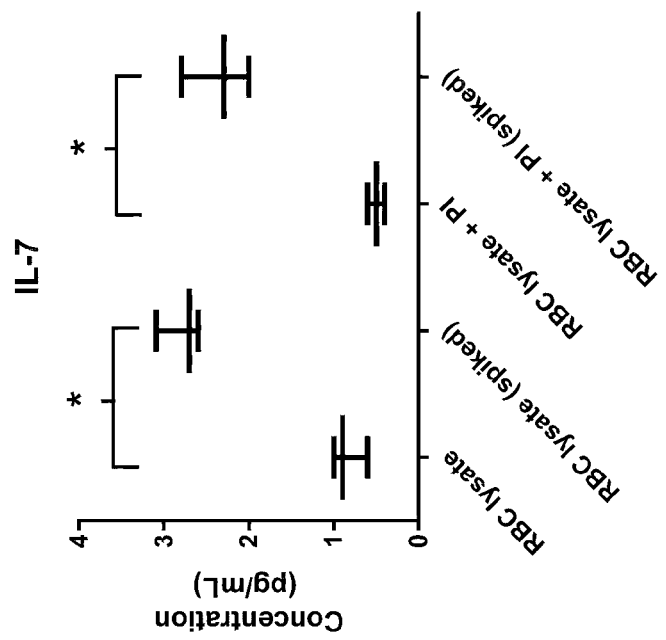
Figure 12E:
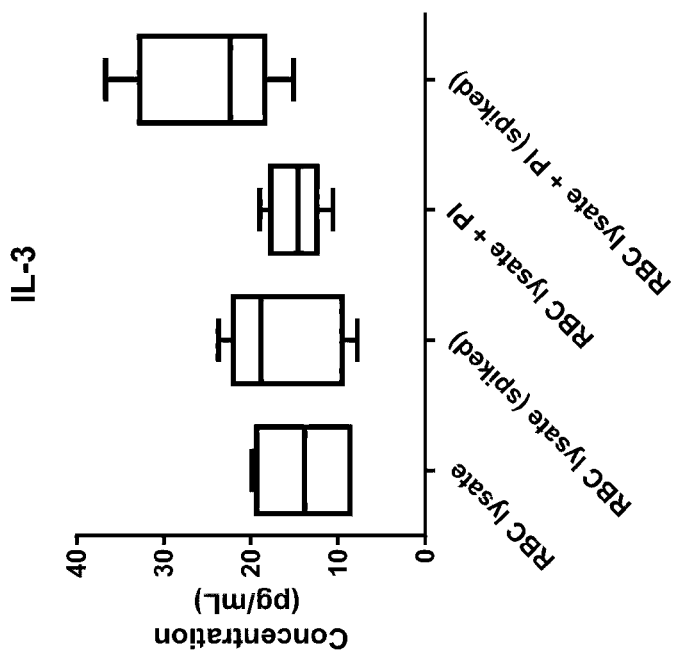
Figure 12H:
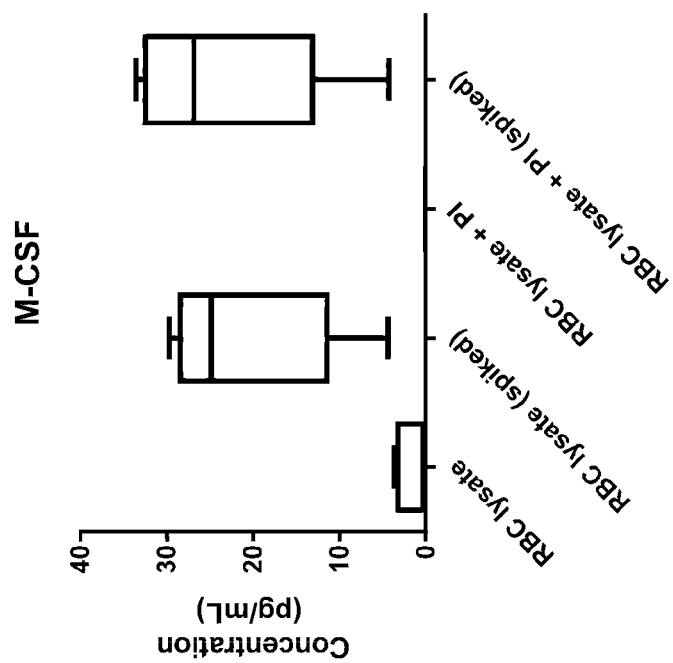
Figure 12G:
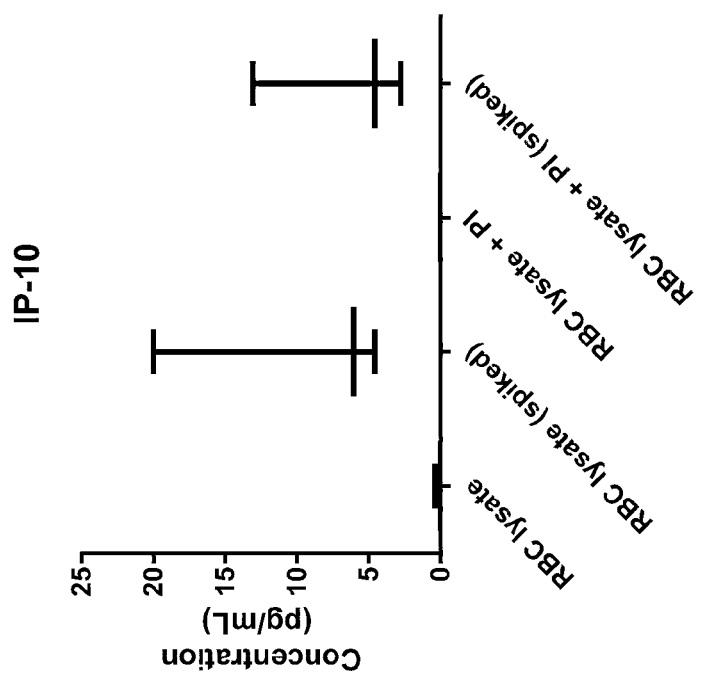
Figure 12J:
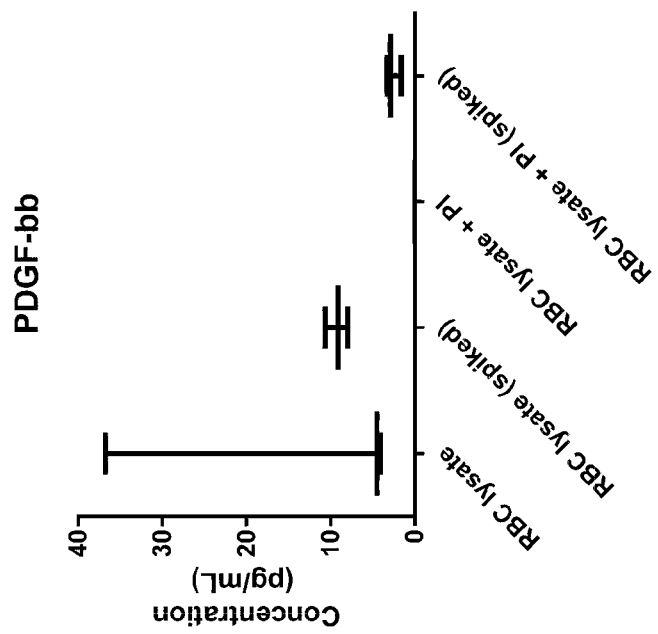
Figure 12I:
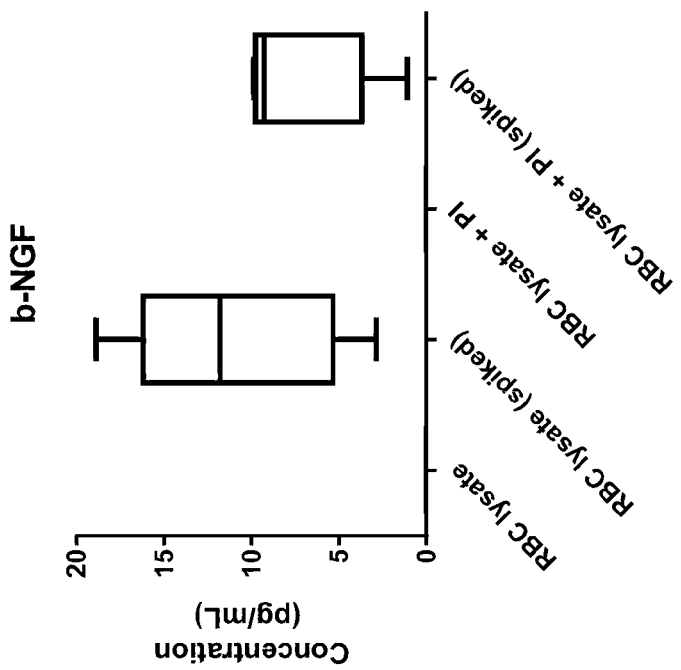
Figure 12L:
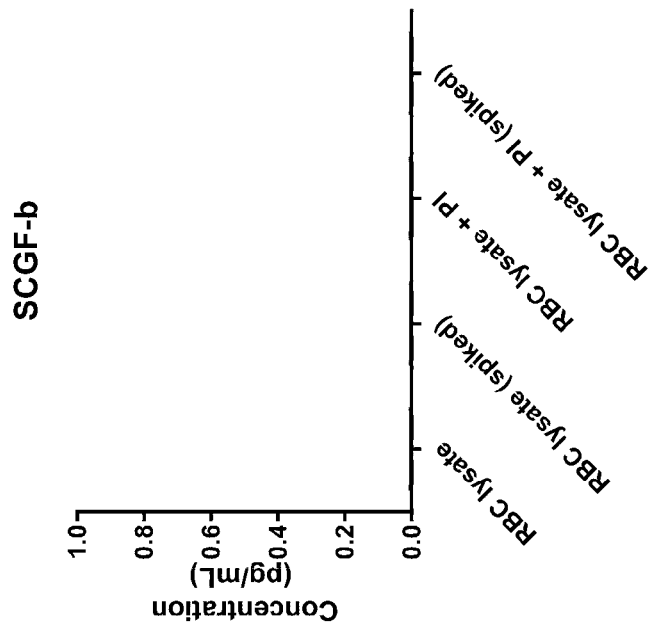
Figure 12K:
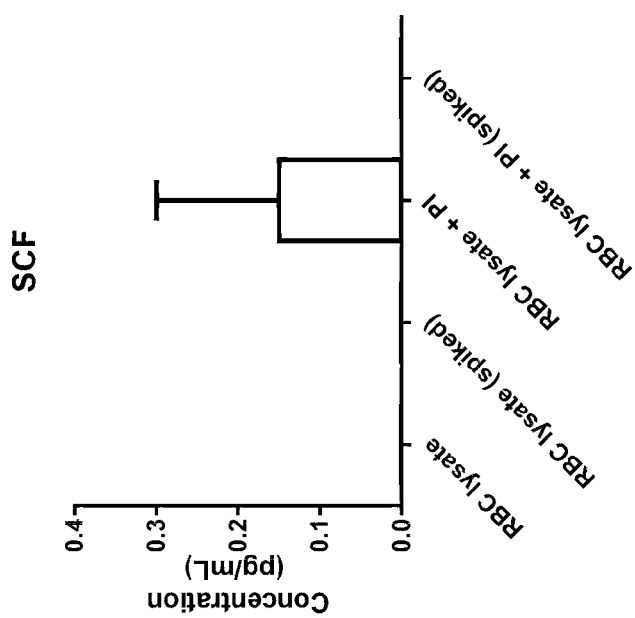
Figure 12M:
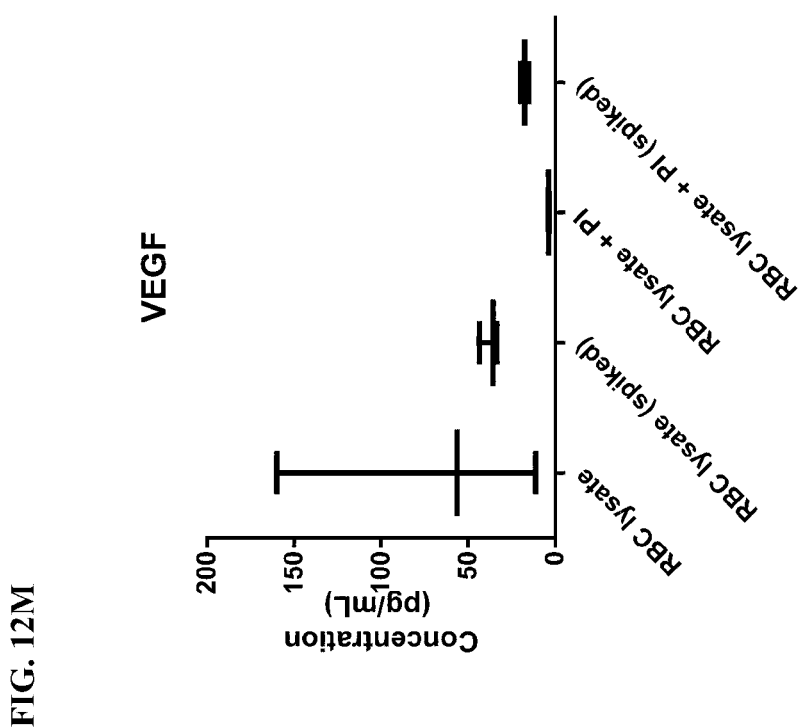
Figure 13A:
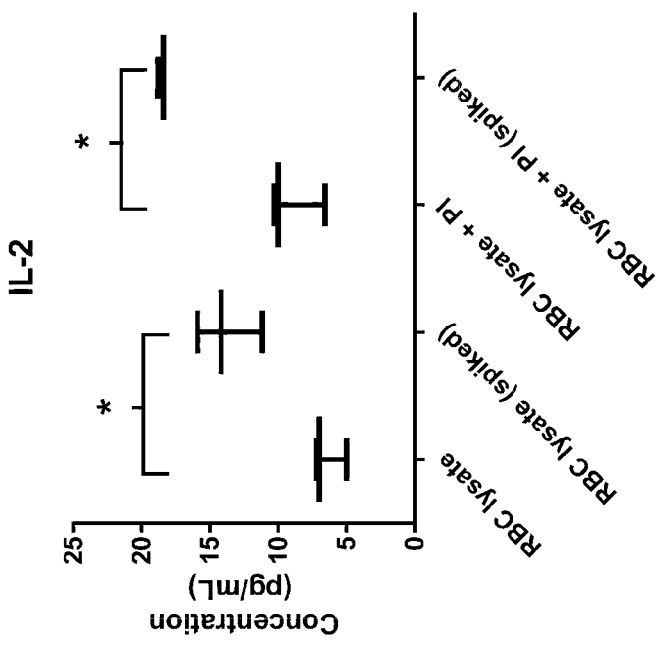
FIG. 13A-FIG. 13D is a series of graphs showing the concentration of cytokines with multiple factors in the lysate of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 13B:
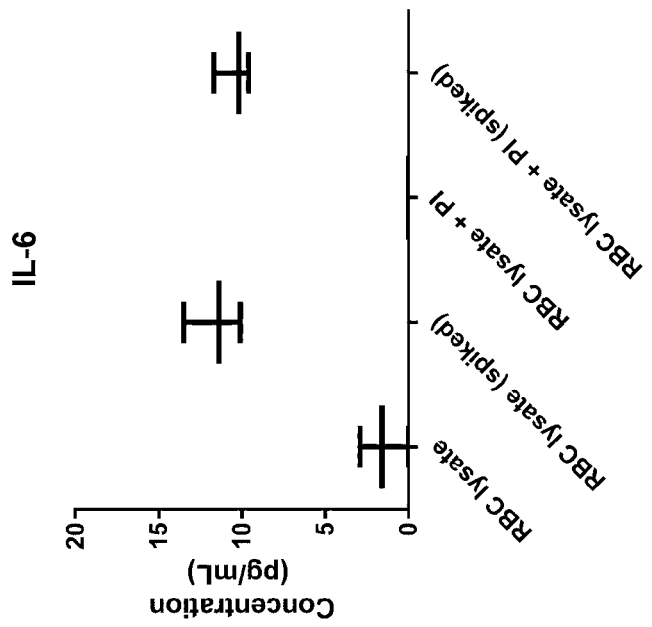
Figure 13C:
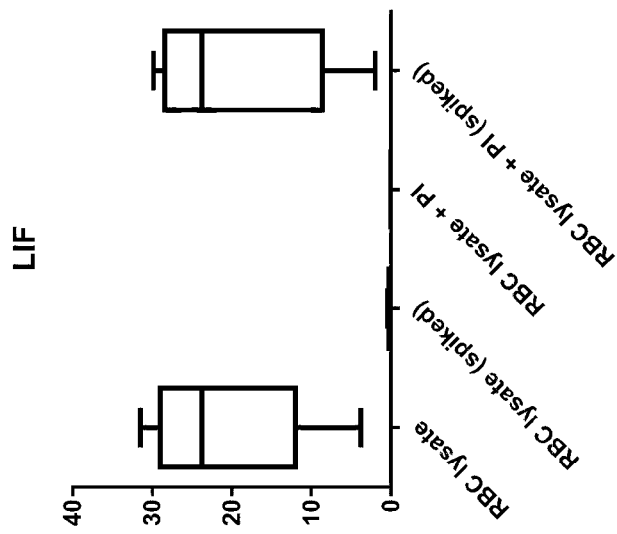
Figure 13D:
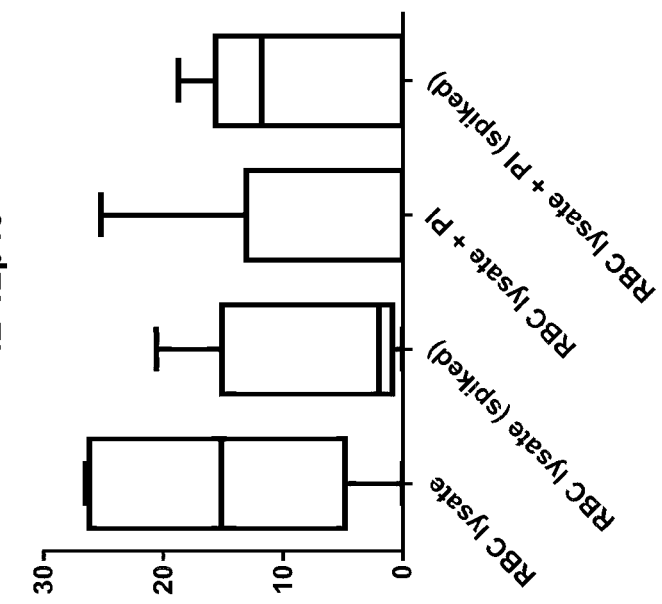
Figure 14B:
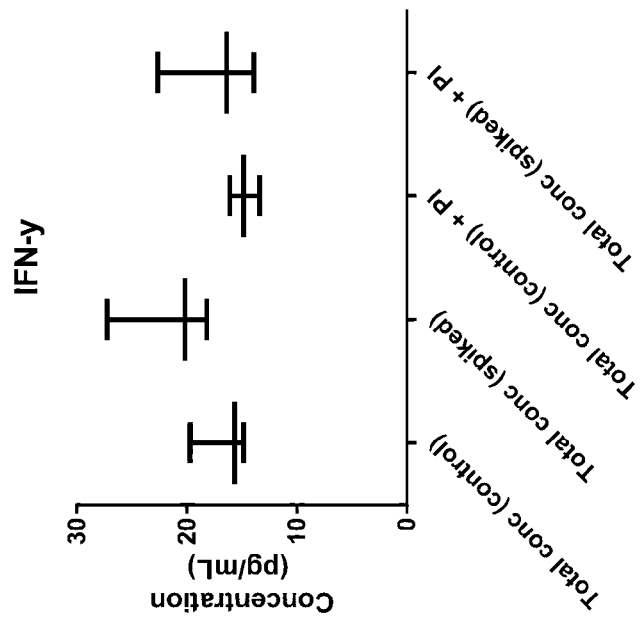
FIG. 14A-FIG. 14O is a series of graphs showing the concentration of pro-inflammatory cytokines in the secretion, lysate, and recombinant protein spike of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 14A:
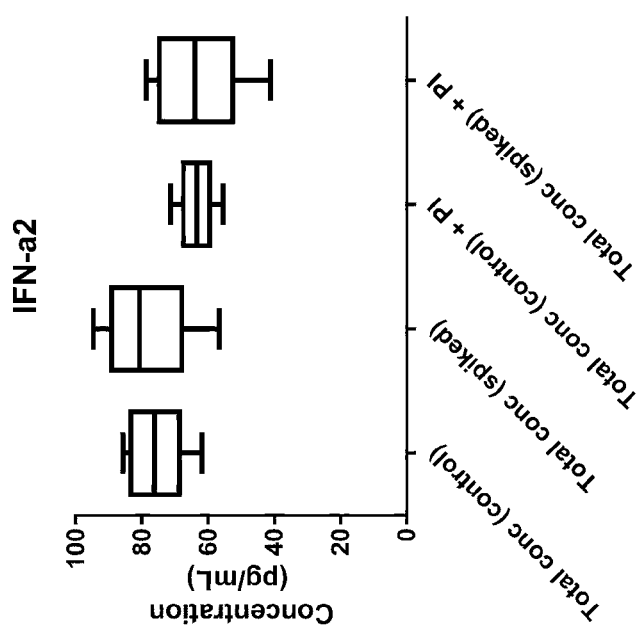
Figure 14D:
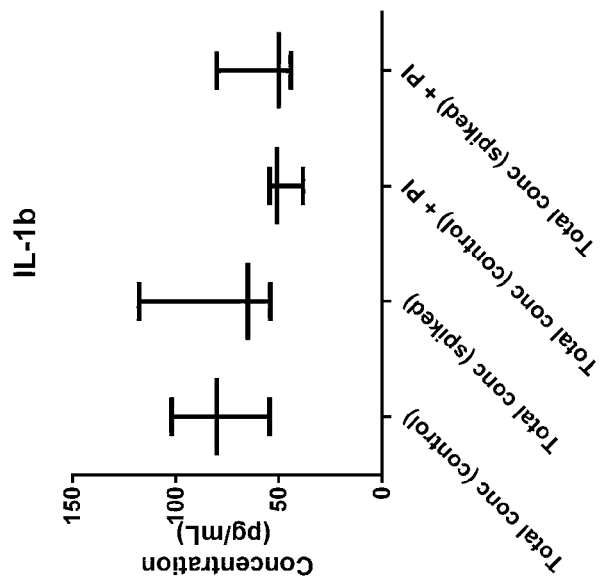
Figure 14C:
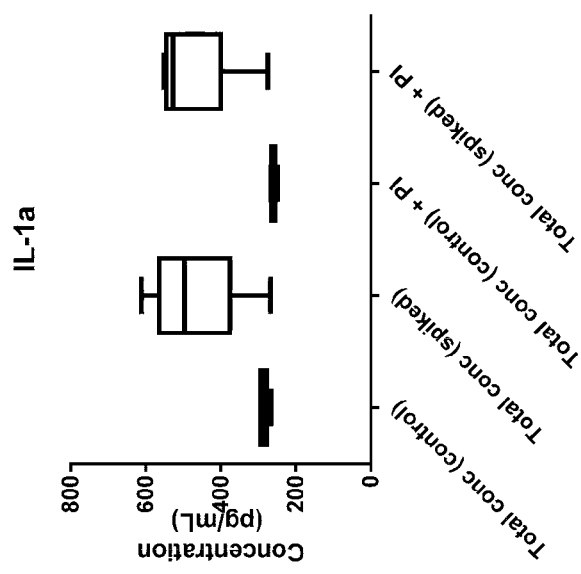
Figure 14F:
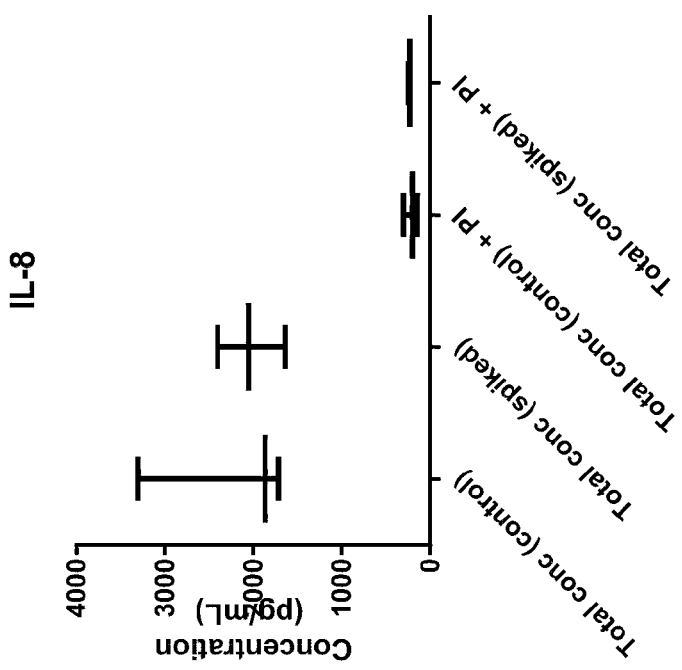
Figure 14E:
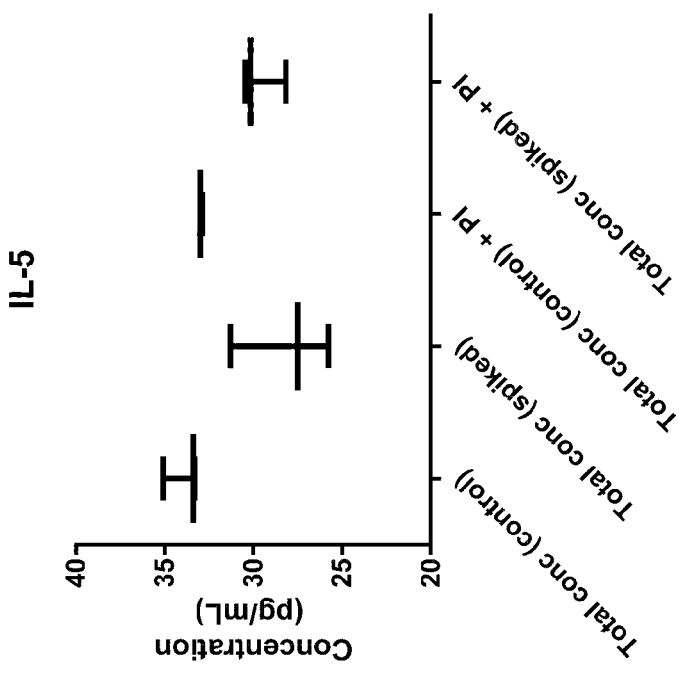
Figure 14H:
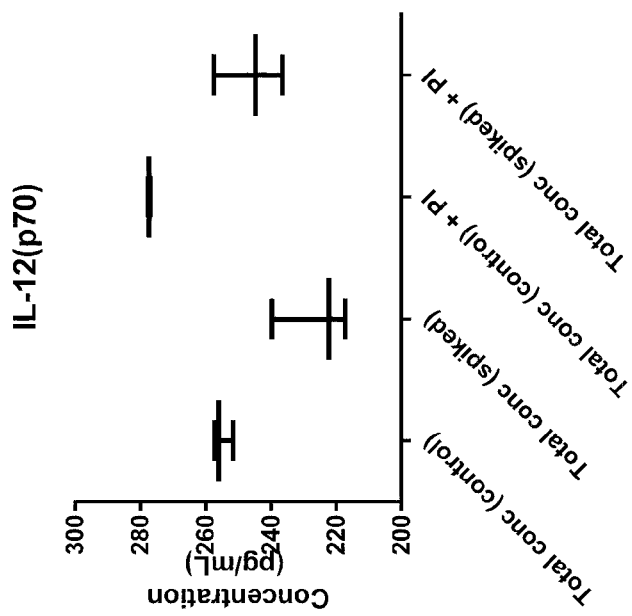
Figure 14G:
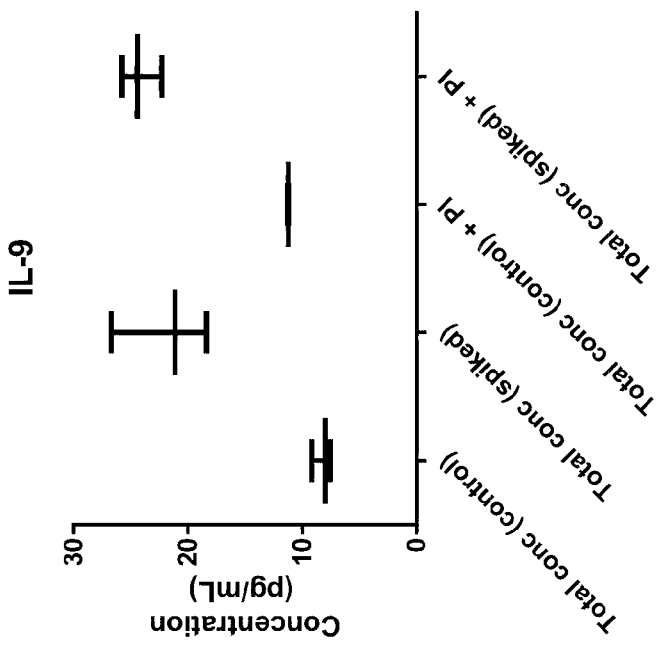
Figure 14J:
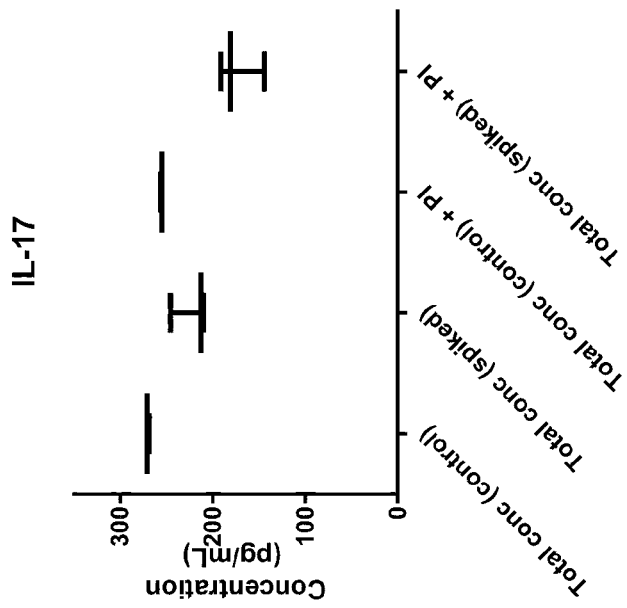
Figure 14I:
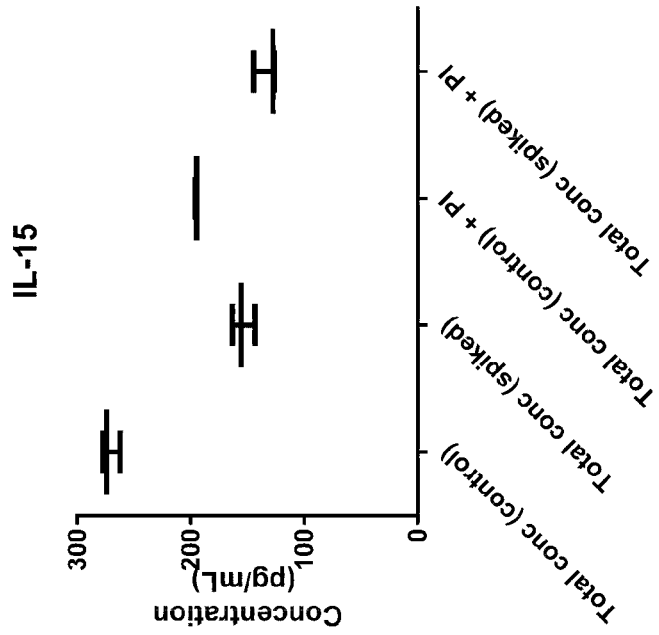
Figure 14L:
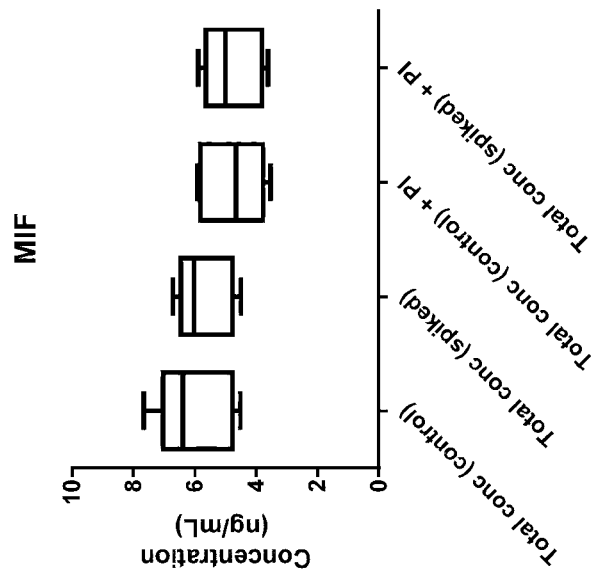
Figure 14K:
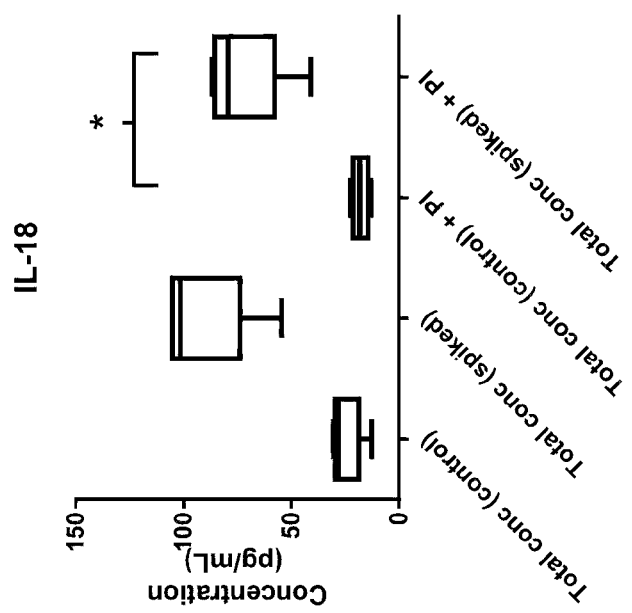
Figure 14N:
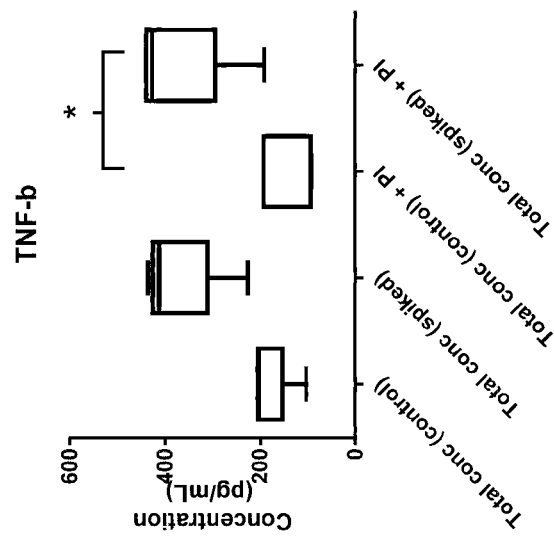
Figure 14M:
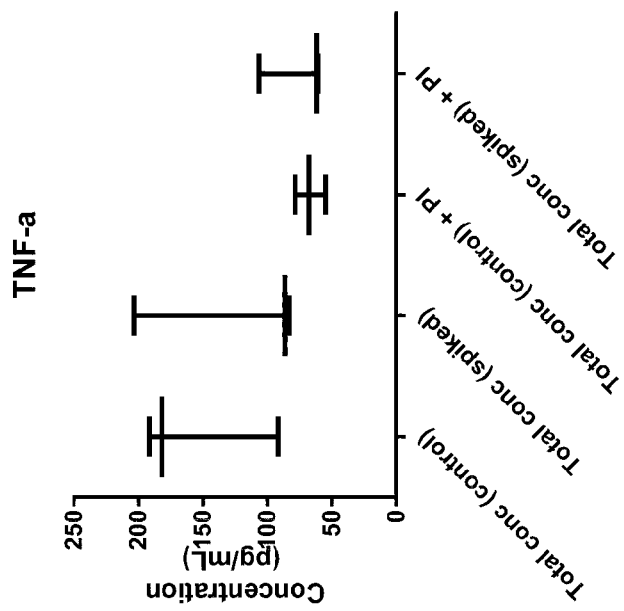
Figure 14O:
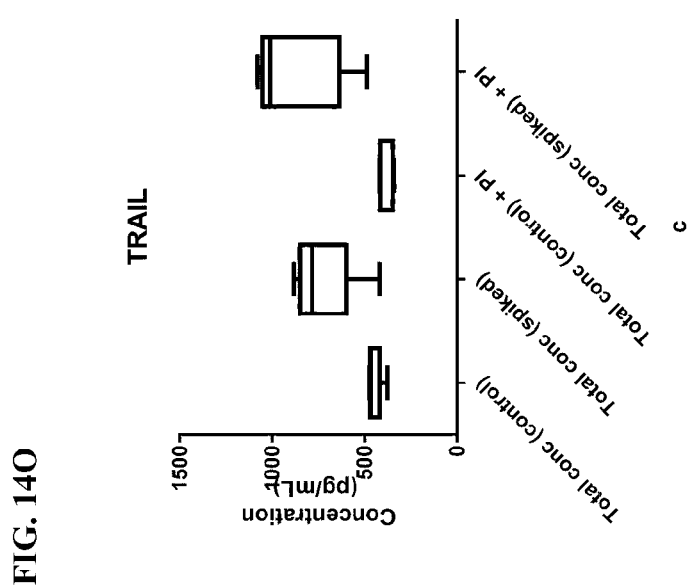
Figure 15B:
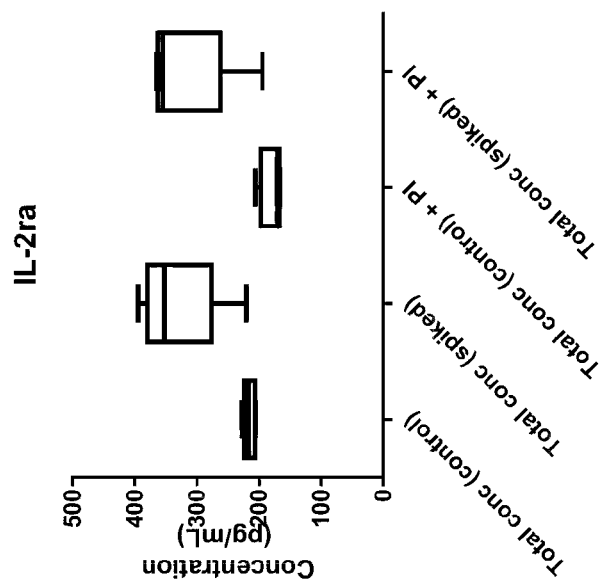
FIG. 15A-FIG. 15E is a series of graphs showing the concentration of anti-inflammatory cytokines in the secretion, lysate, and recombinant protein spike of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 15A:
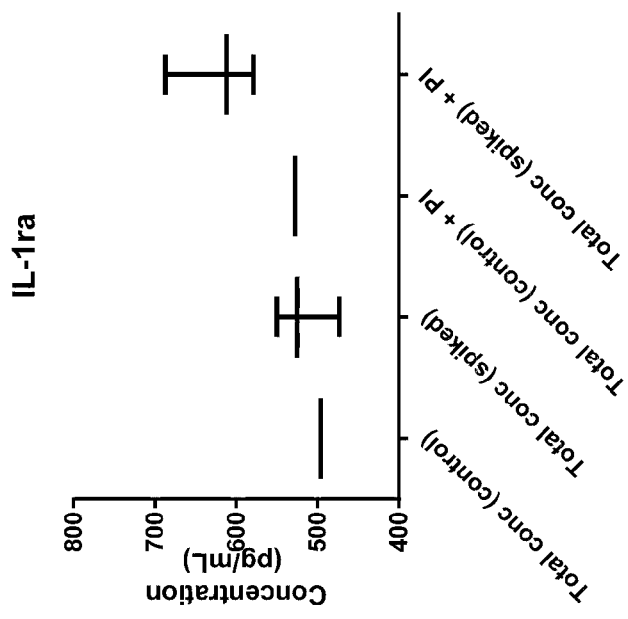
Figure 15D:
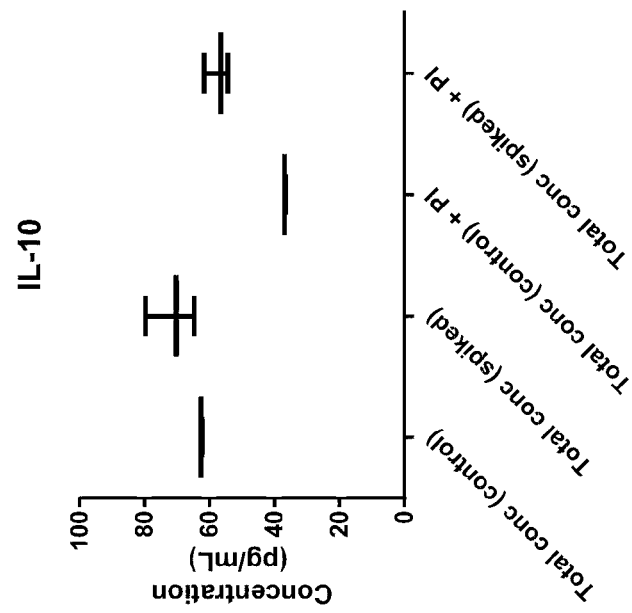
Figure 15C:
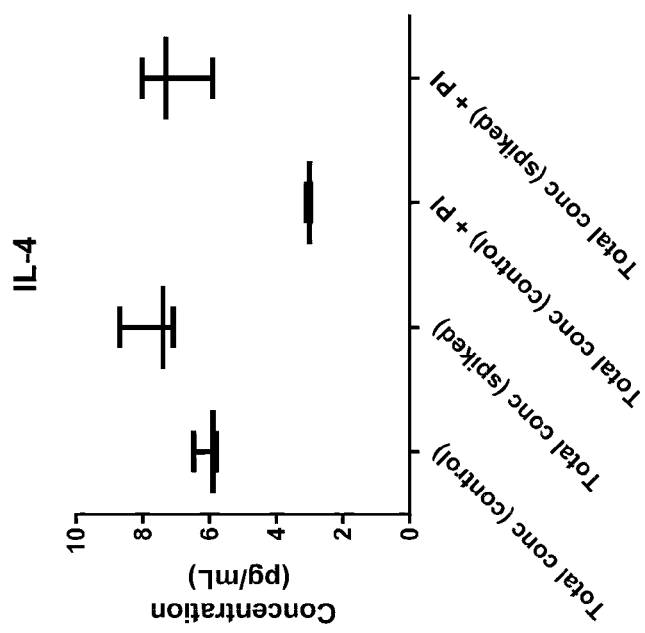
Figure 15E:
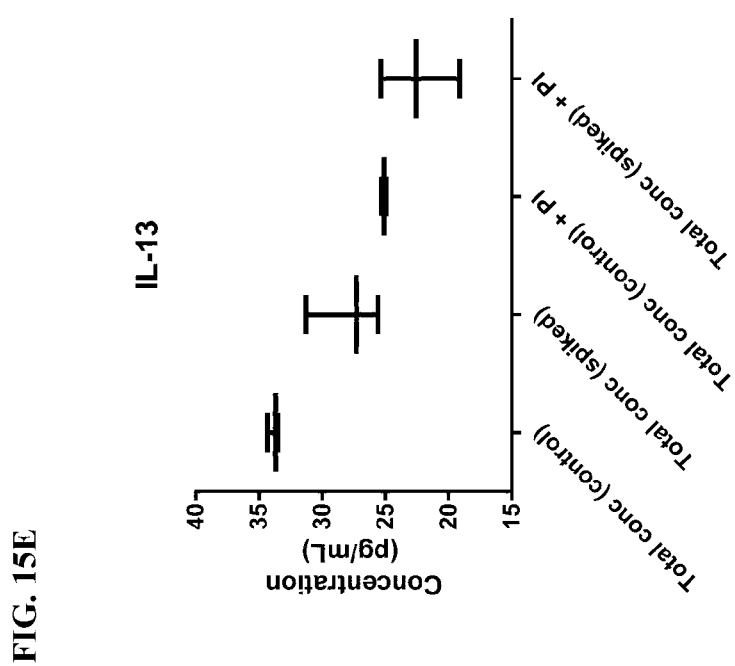
Figure 16B:
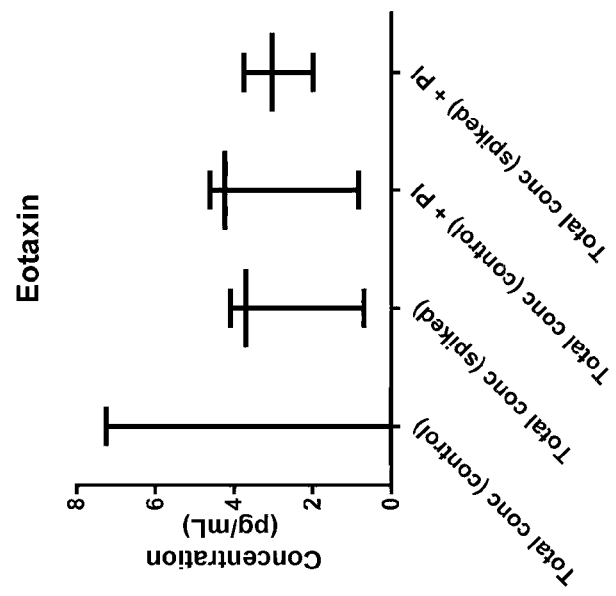
FIG. 16A-FIG. 16K is a series of graphs showing the concentration of chemokines in the secretion, lysate, and recombinant protein spike of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 16A:
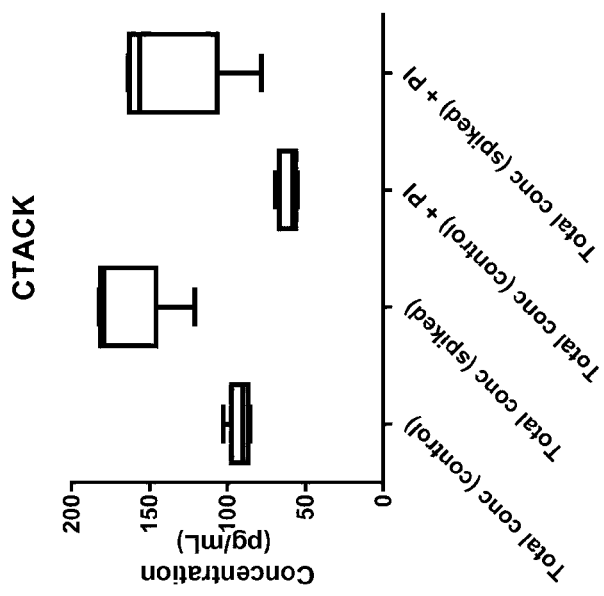
Figure 16D:
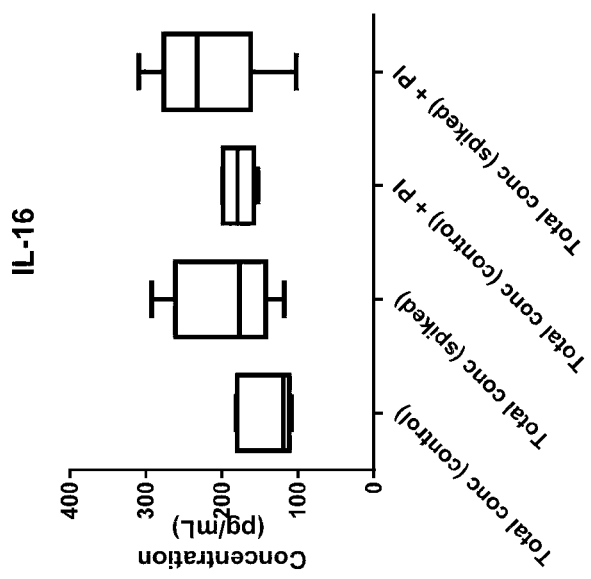
Figure 16C:
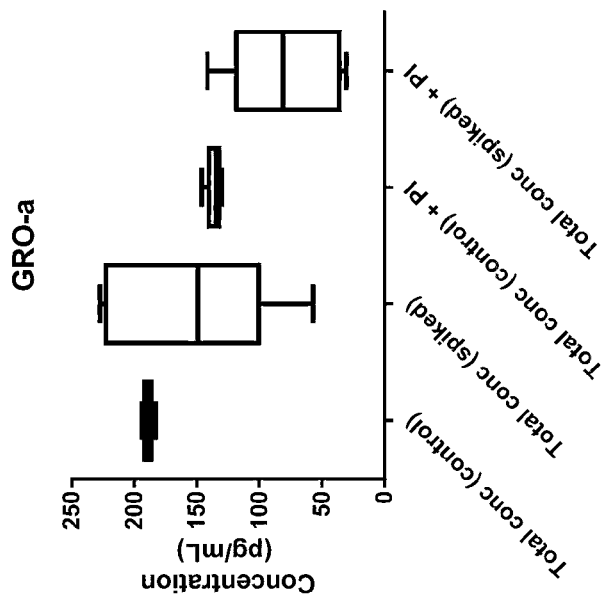
Figure 16F:
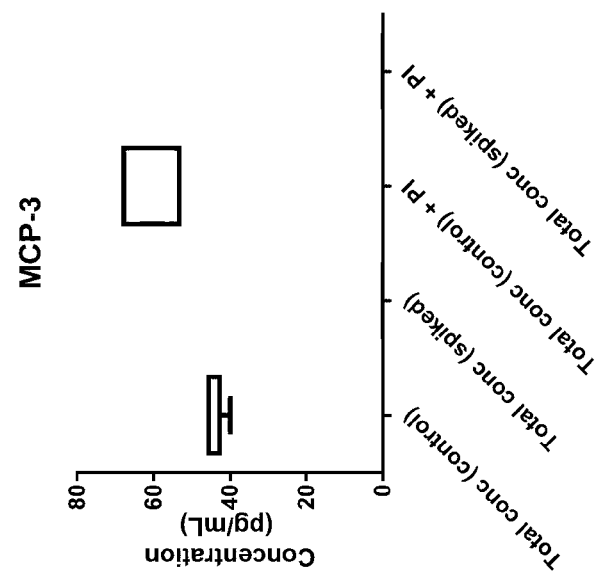
Figure 16E:
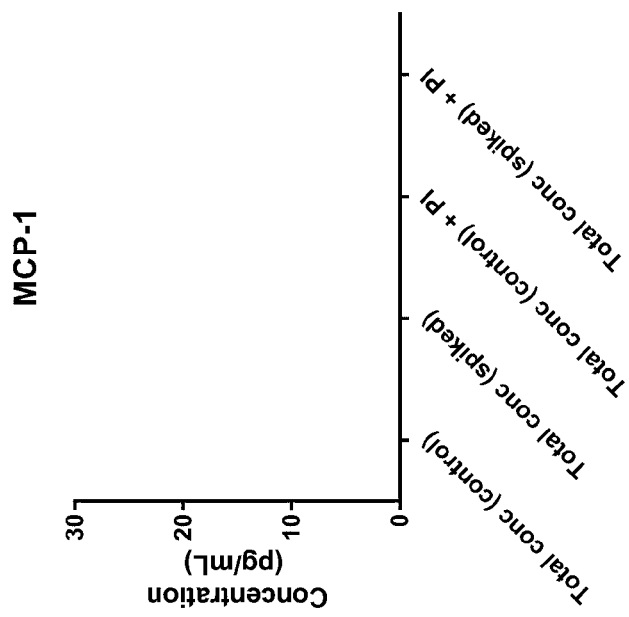
Figure 16H:
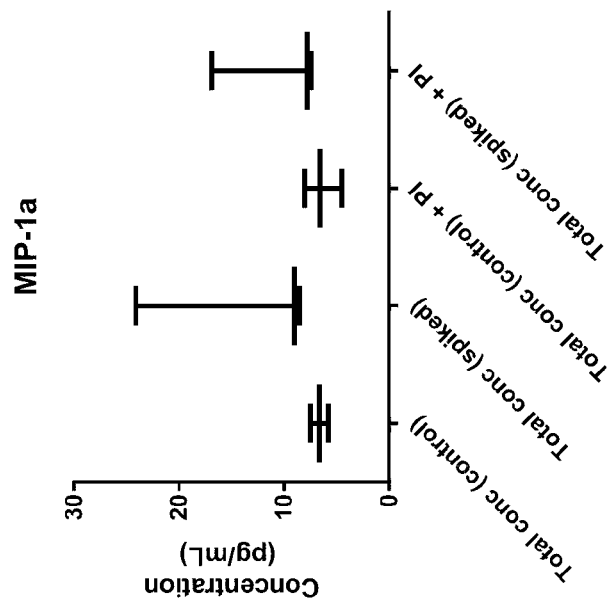
Figure 16G:
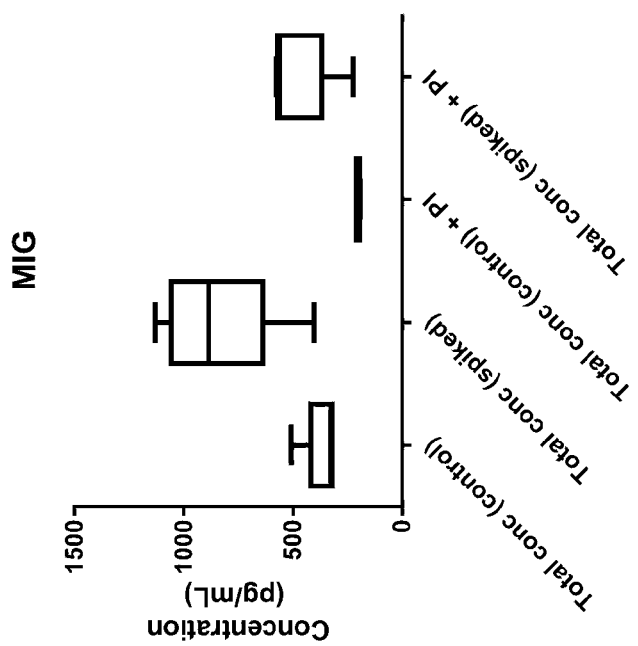
Figure 16J:
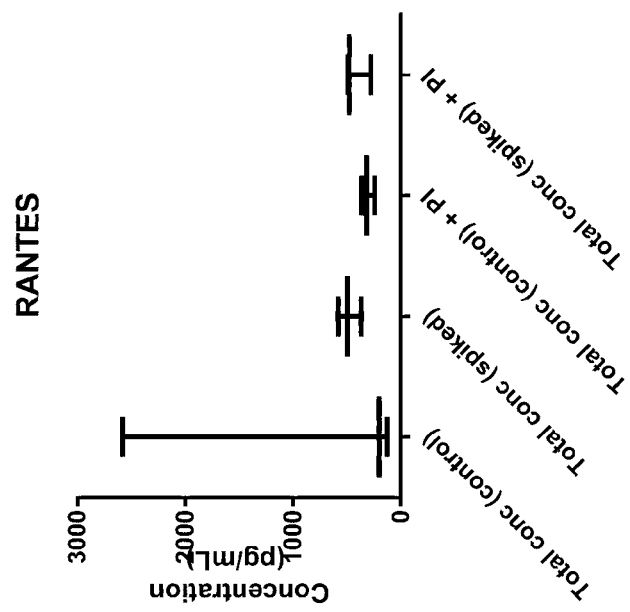
Figure 16I:
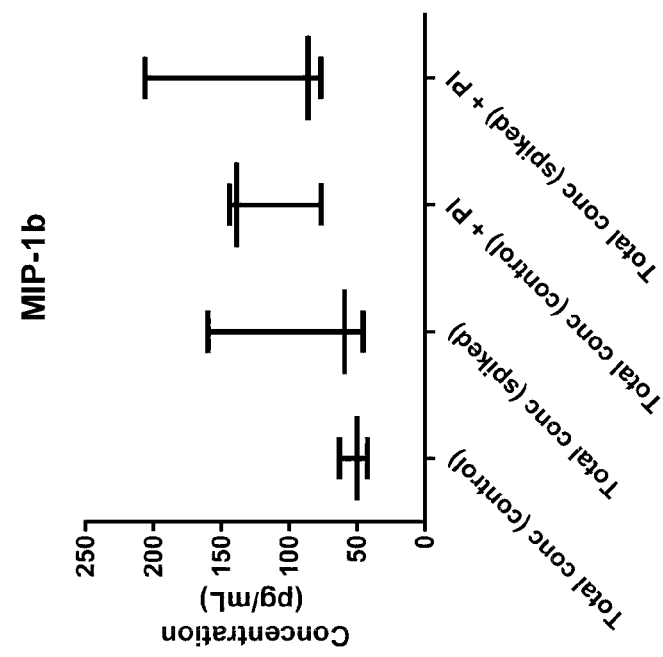
Figure 16K:
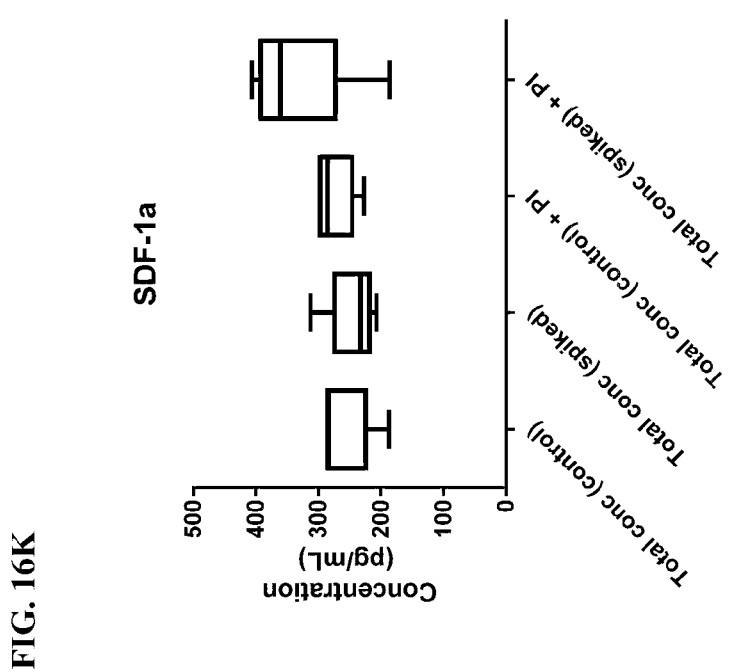
Figure 17A:
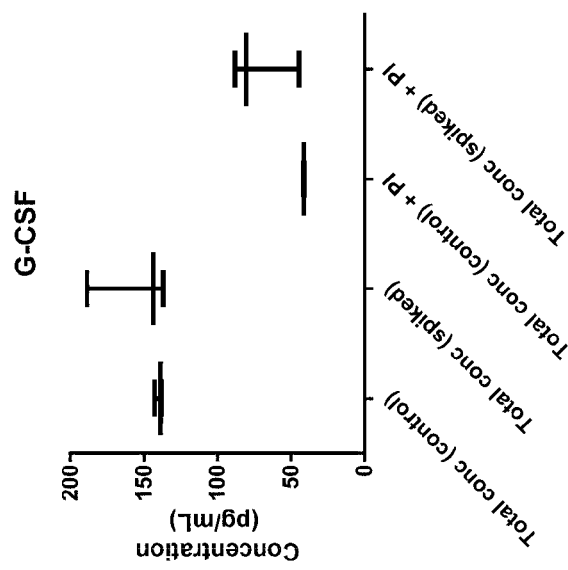
FIG. 17A-FIG. 17M is a series of graphs showing the concentration of growth factors in the secretion, lysate, and recombinant protein spike of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of $p<0.05$ (n=3 for 27-plex, n=5 for 21-plex).
Figure 17B:
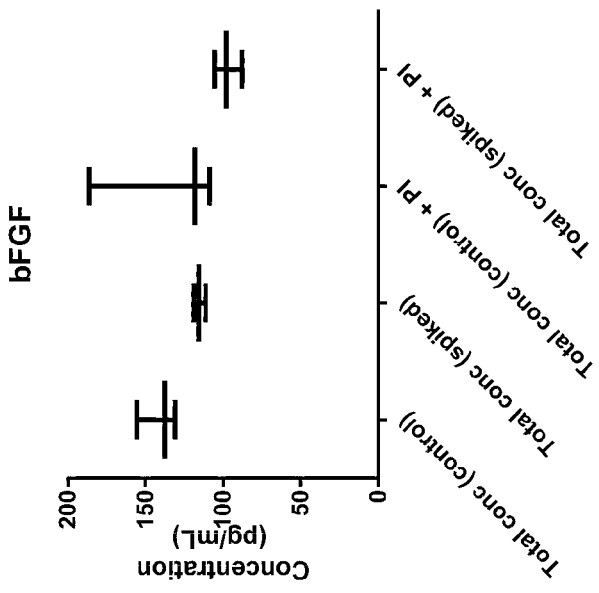
Figure 17D:
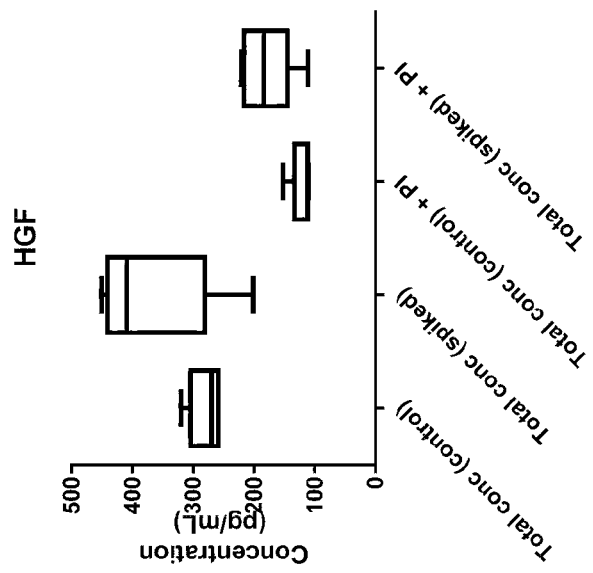
Figure 17C:
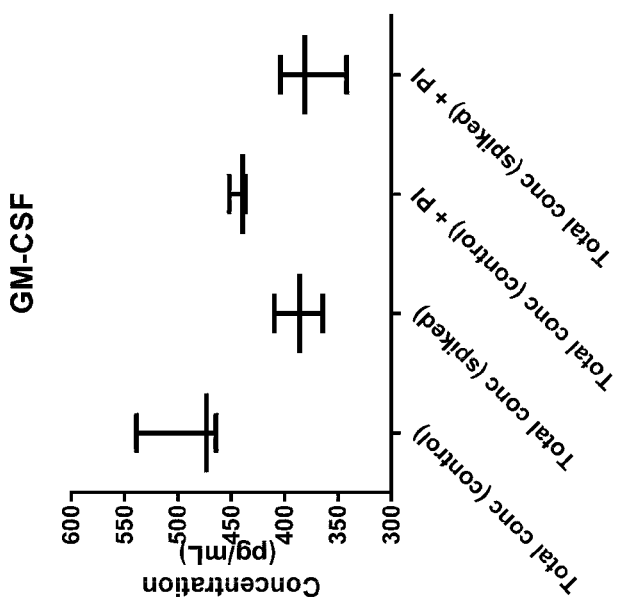
Figure 17F:
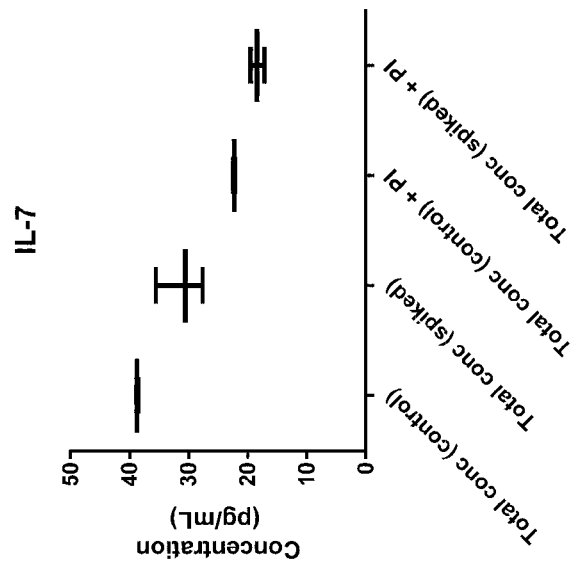
Figure 17E:
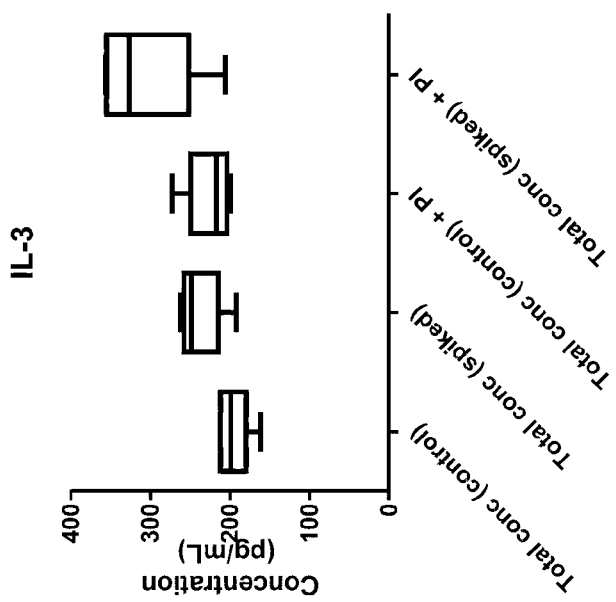
Figure 17H:
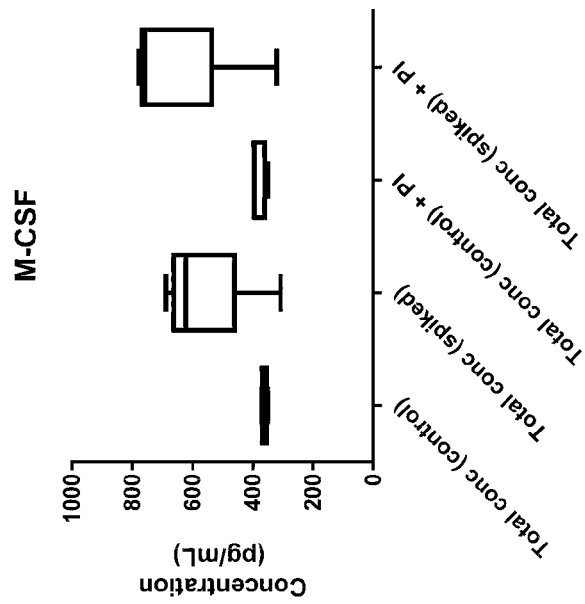
Figure 17G:
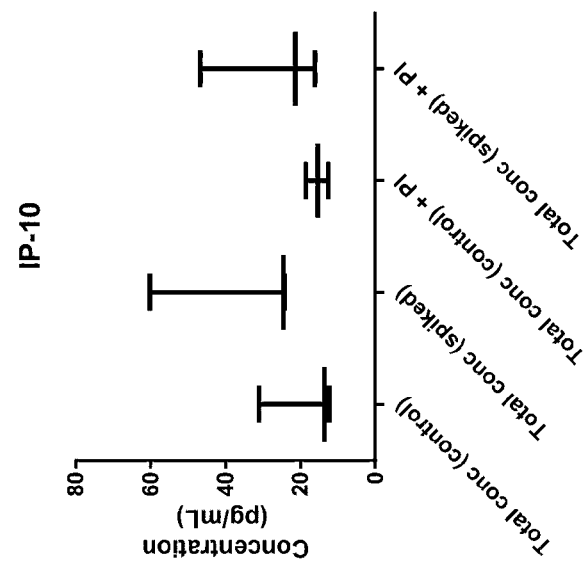
Figures 17I, 17J:
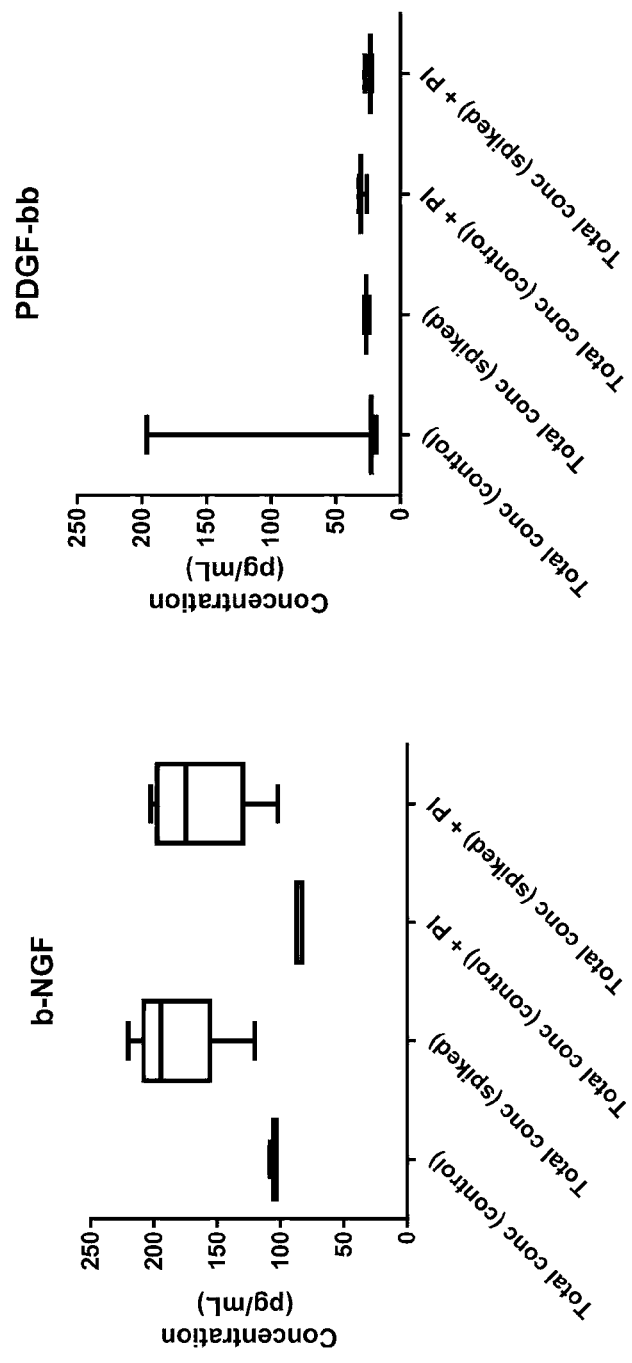
Figure 17L:
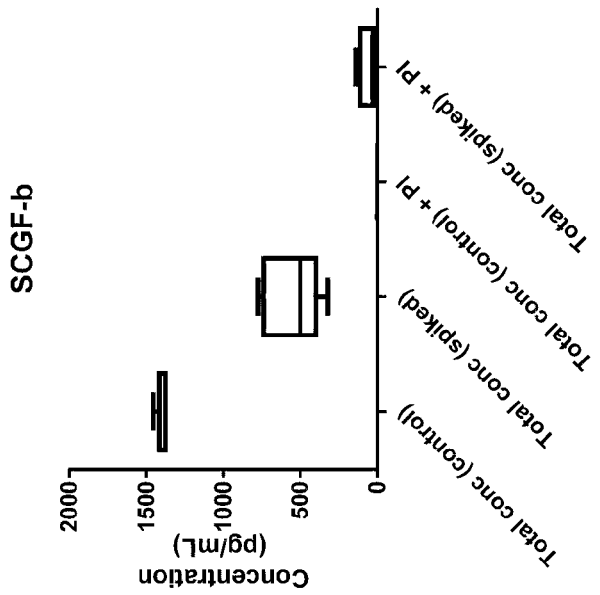
Figure 17K:
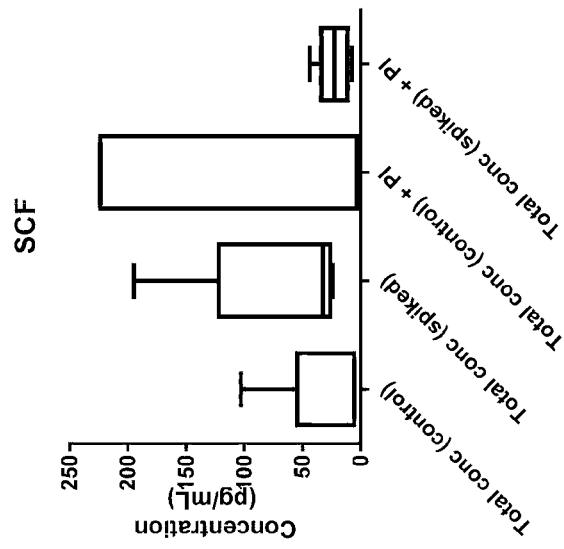
Figure 17M:
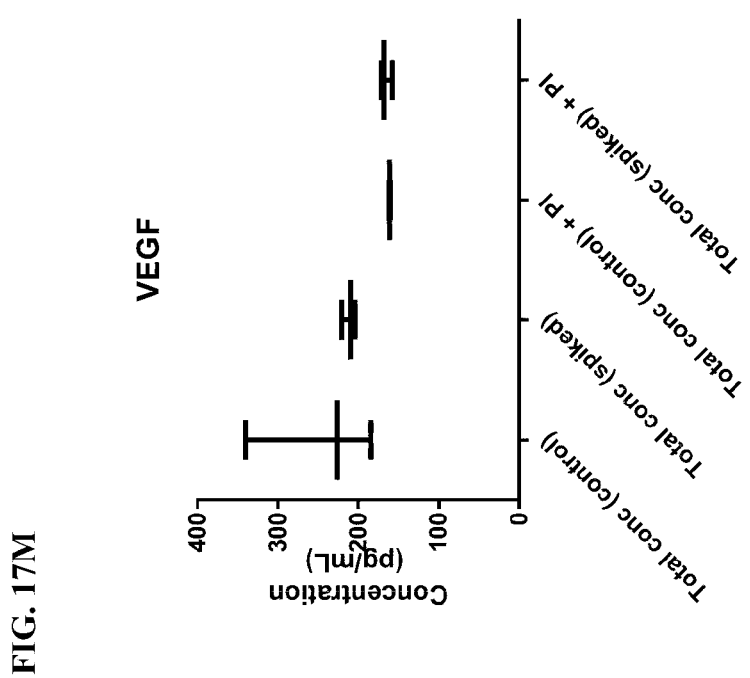
Figure 18B:
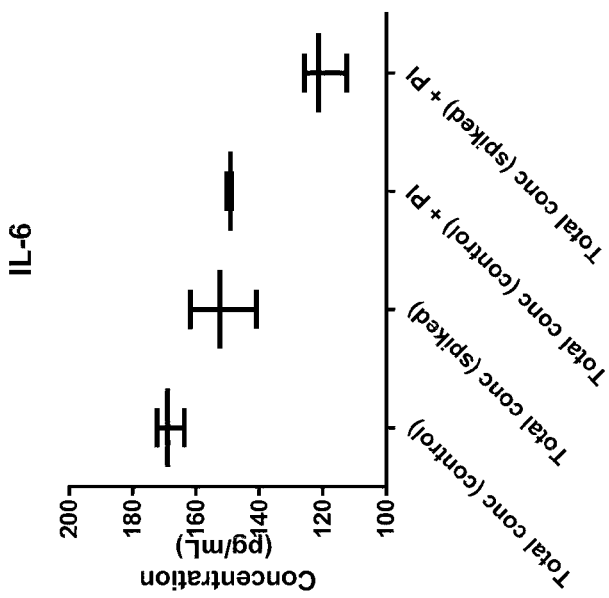
FIG. 18A-FIG. 18D is a series of graphs showing the concentration of cytokines with multiple functions in the secretion, lysate, and recombinant protein spike of RBCs after incubation in PBS with and without protease inhibitors and BioPlex standards over 24 hours at 37° C. as measured by BioPlex and reported as pg/mL (20 million RBCs in 100 uL PBS). Data presented as mean±SD, * indicates a significant difference of p<0.05 (n=3 for 27-plex, n=5 for 21-plex).
Figure 18A:
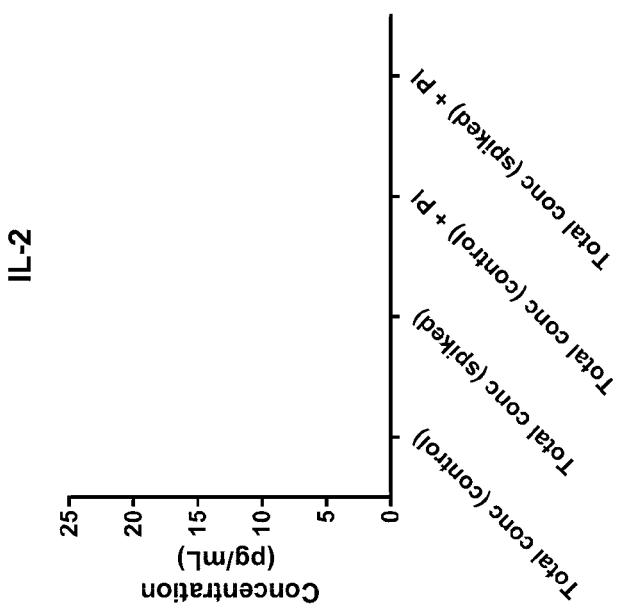
Figure 18D:
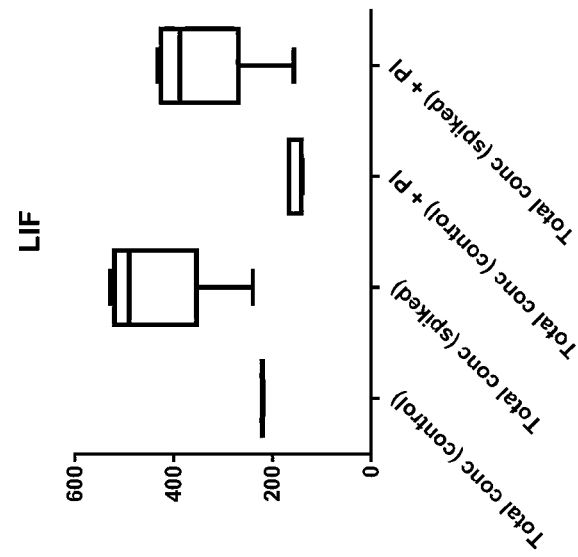
Figure 18C:
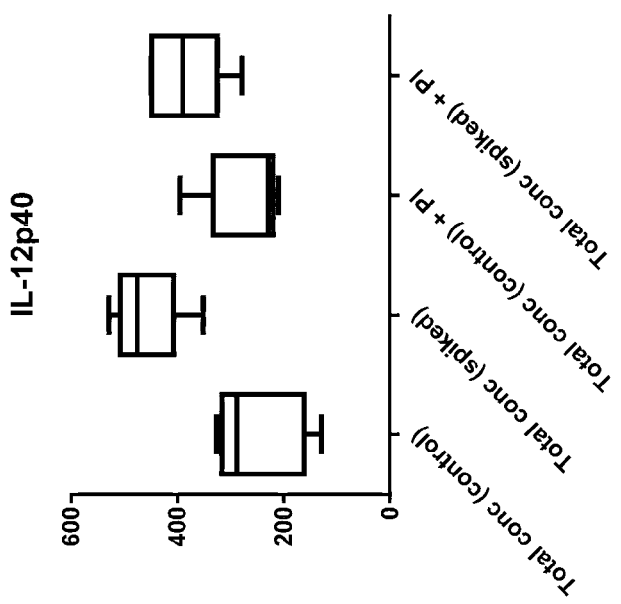
Figure 19A:
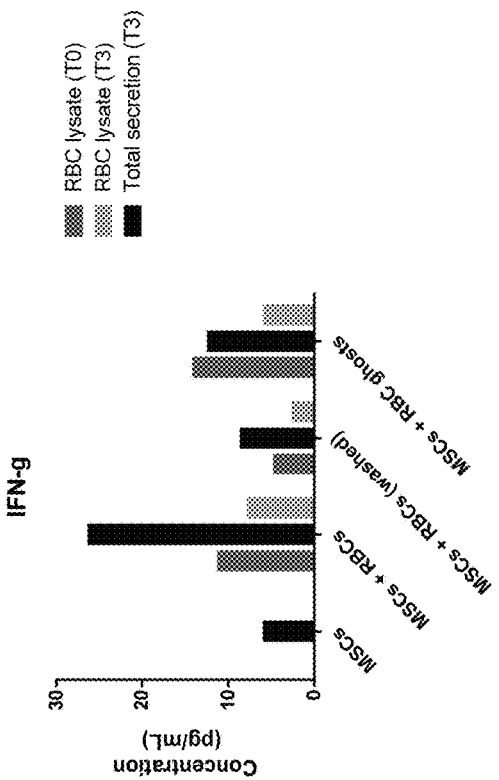
FIG. 19A-FIG. 19O is a series of graphs showing the concentration of pro-inflammatory cytokines in the lysate of RBCs before and after incubation with MSCs and the secretion of MSCs and/or RBCs after 72 hours at 37° C. as measured by BioPlex and reported as pg/mL (20 million RBCs in 100 uL PBS). Data presented as mean±SD (n=1).
Figure 19B:
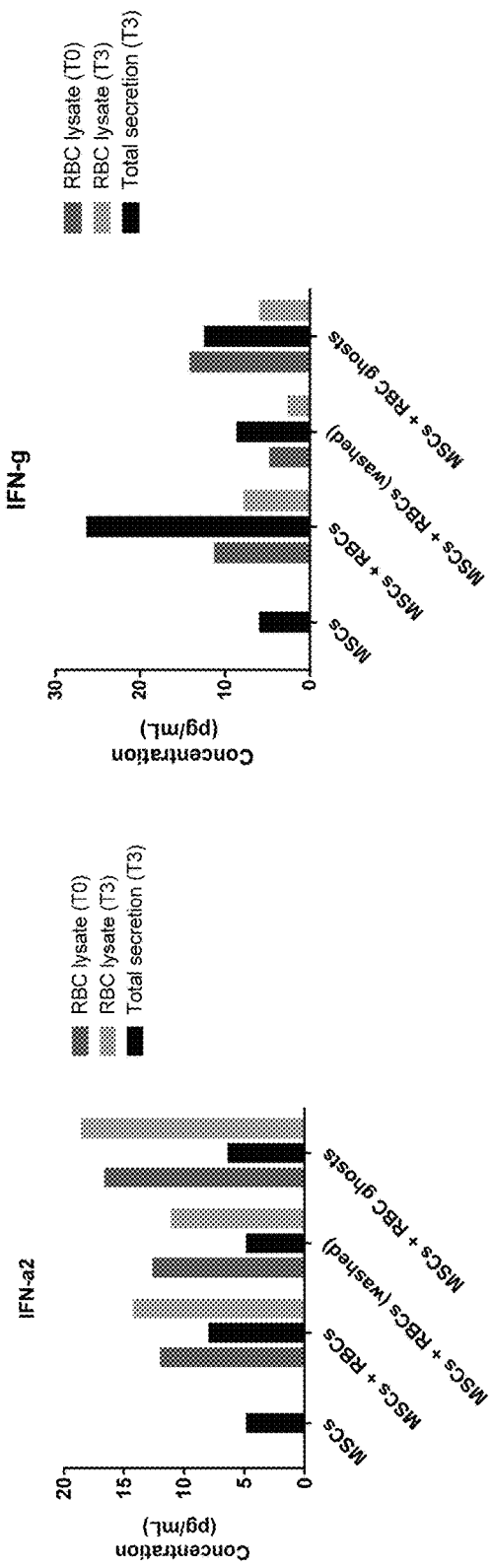
Figure 19C:
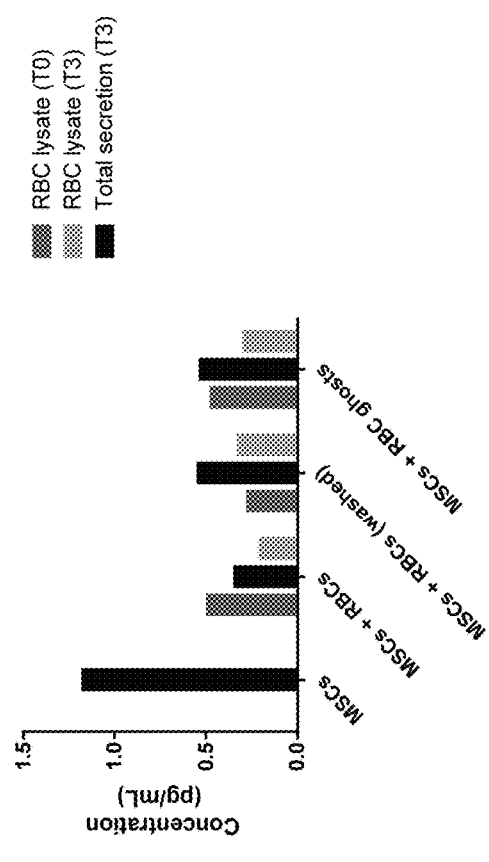
Figure 19D:
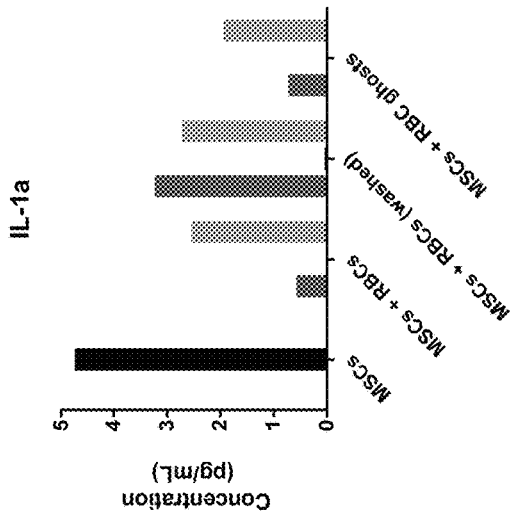
Figure 19E:
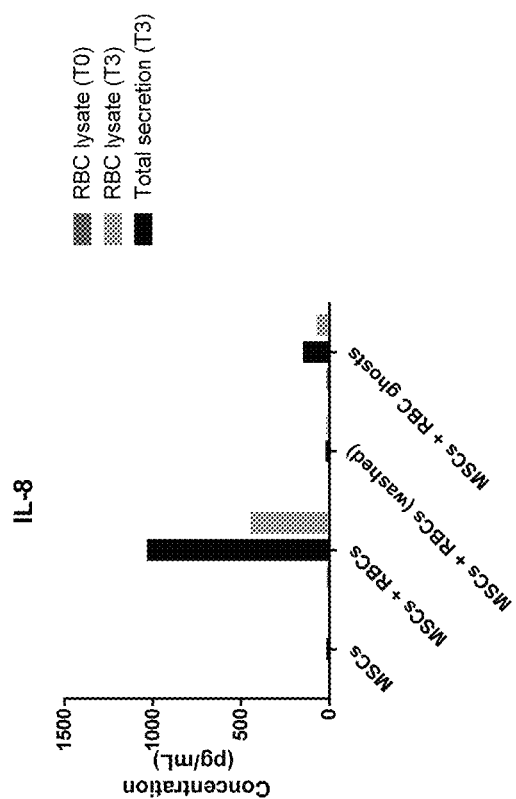
Figure 19F:
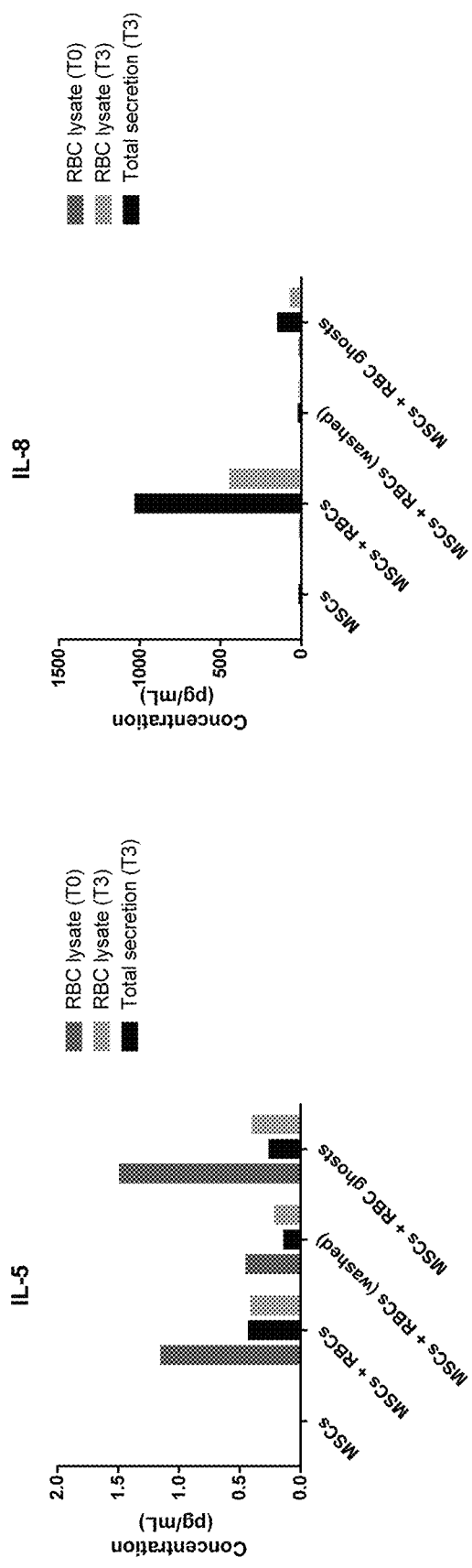
Figure 19G:
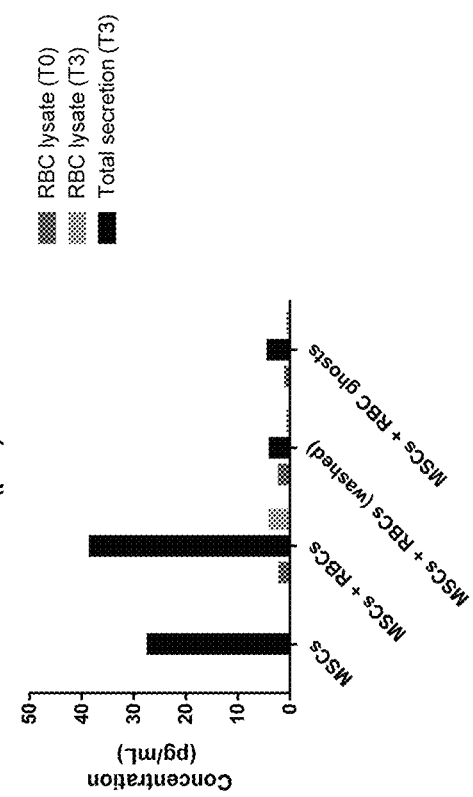
Figure 19H:
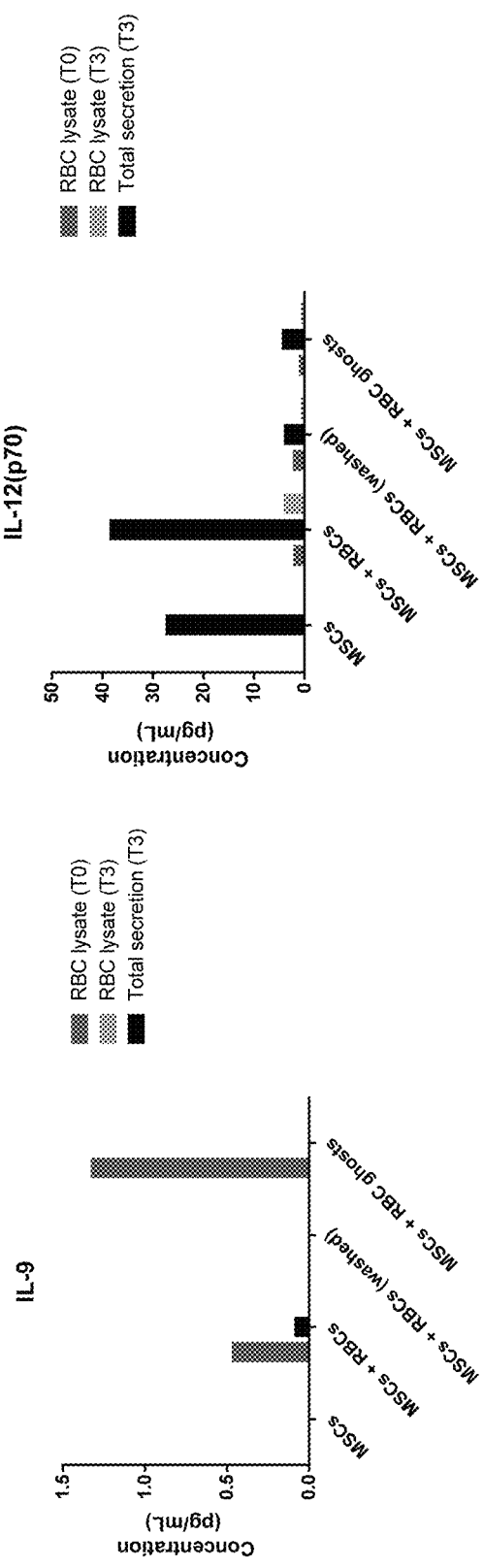
Figure 19I:
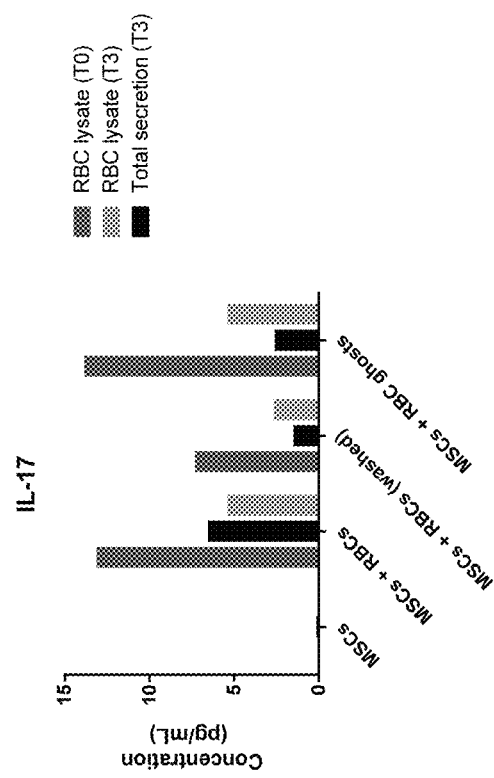
Figure 19J:
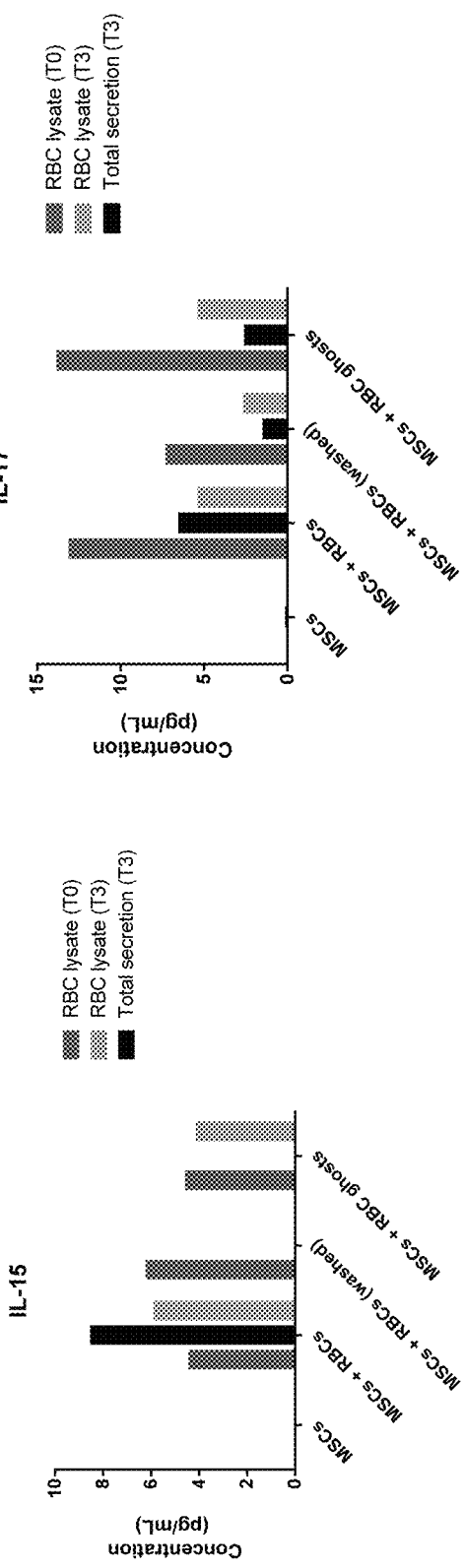
Figure 19K:
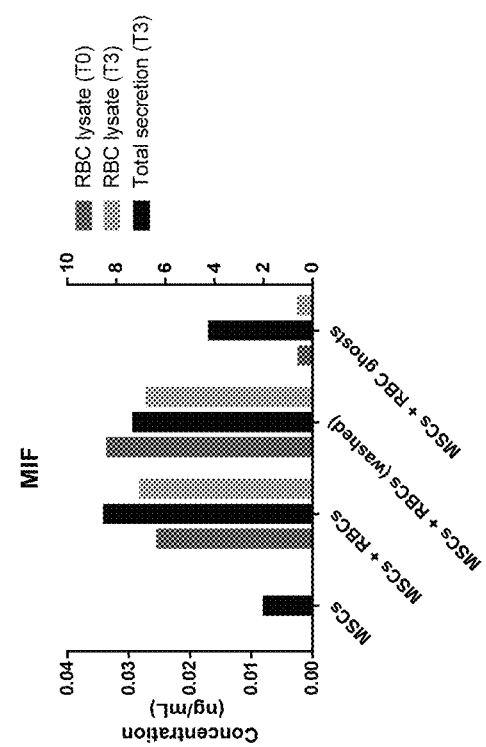
Figure 19L:
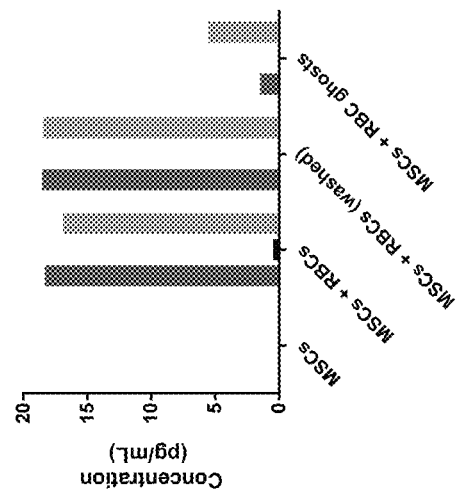
Figure 20A:
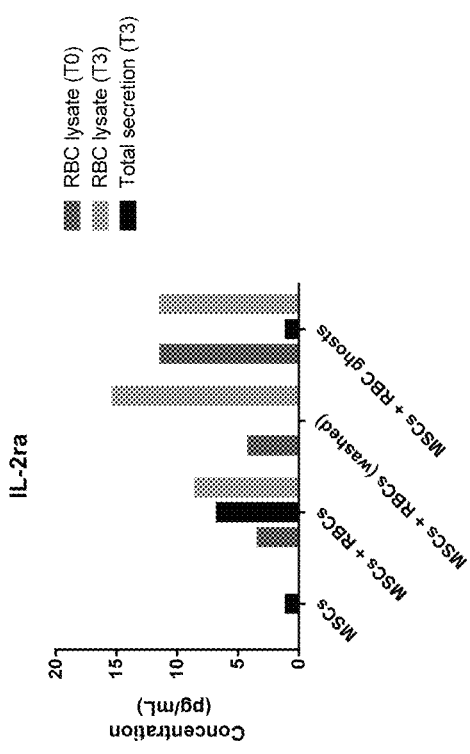
FIG. 20A-FIG. 20E is a series of graphs showing the concentration of anti-inflammatory cytokines in the lysate of RBCs before and after incubation with MSCs and the secretion of MSCs and/or RBCs after 72 hours at 37° C. as measured by BioPlex and reported as pg/mL (20 million RBCs in 100 uL PBS). Data presented as mean±SD (n=1).
Figure 20B:
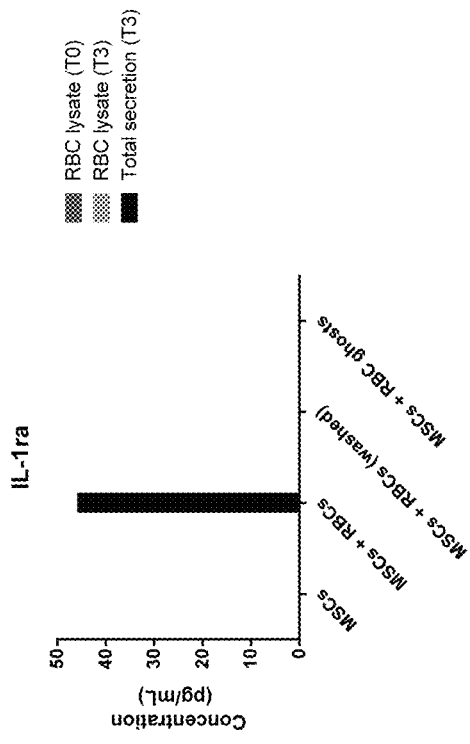
Figure 20C:
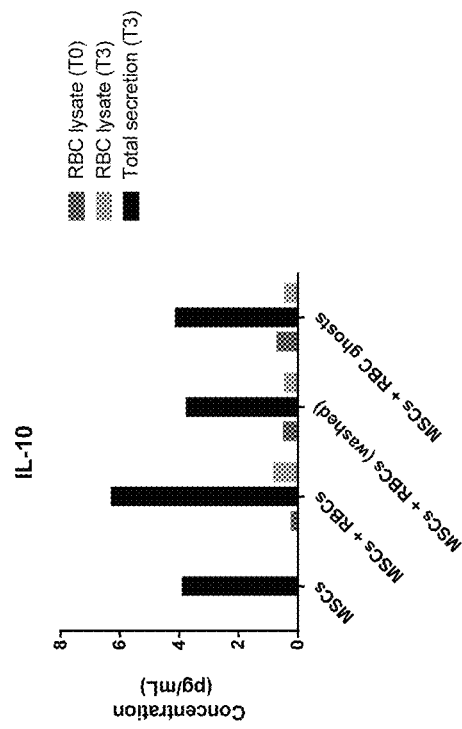
Figure 20D:
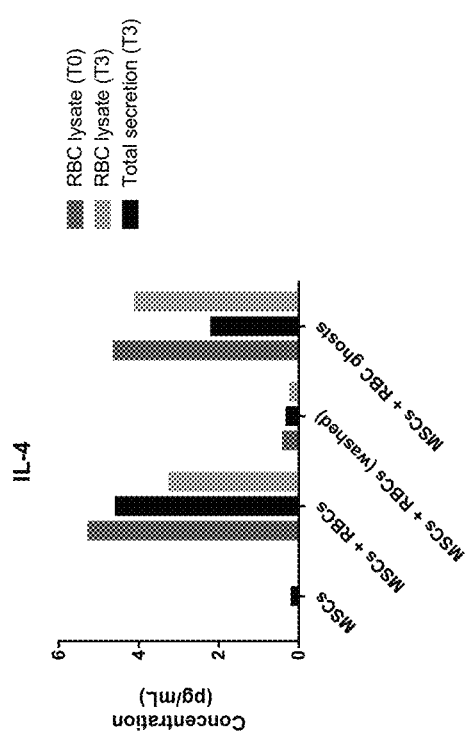
Figure 20E:
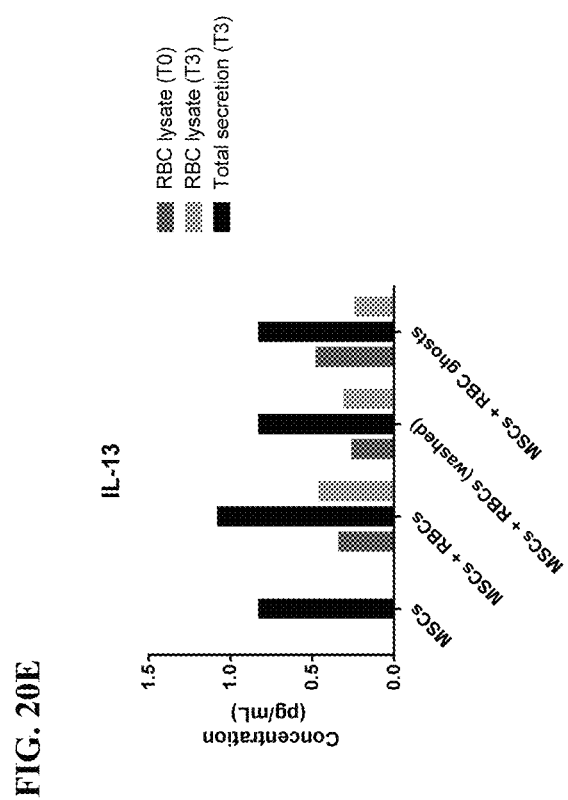
Figure 21A:
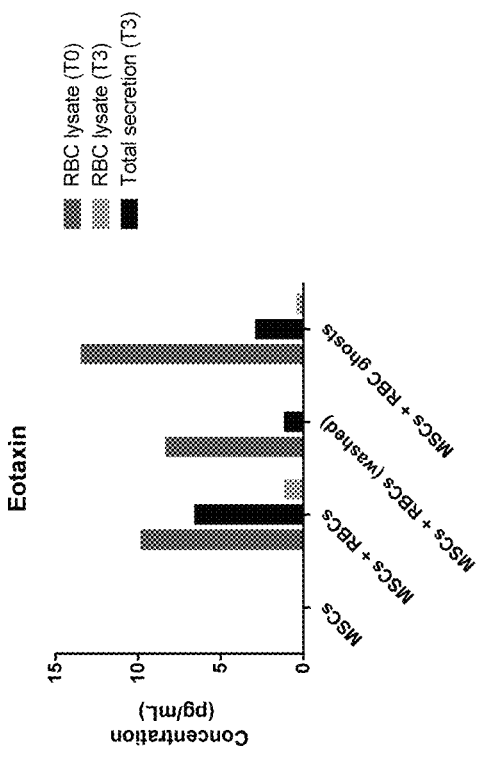
FIG. 21A-FIG. 21K is a series of graphs showing the concentration of chemokines in the lysate of RBCs before and after incubation with MSCs and the secretion of MSCs and/or RBCs after 72 hours at 37° C. as measured by BioPlex and reported as pg/mL (20 million RBCs in 100 uL PBS). Data presented as mean±SD (n=1).
Figure 21B:
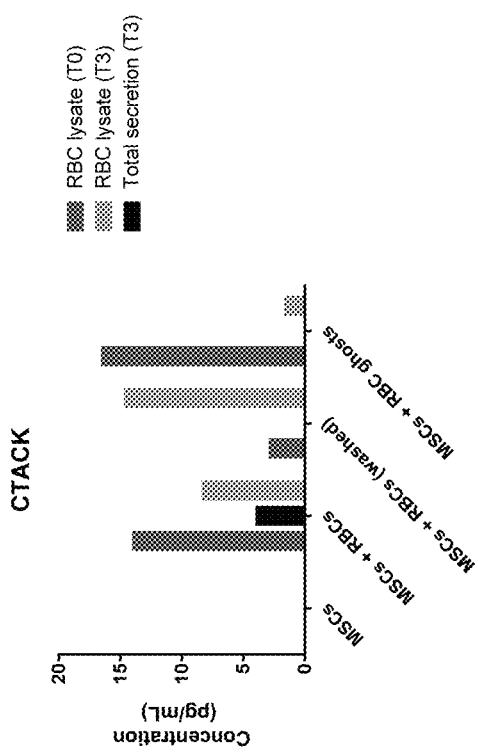
Figure 21C:
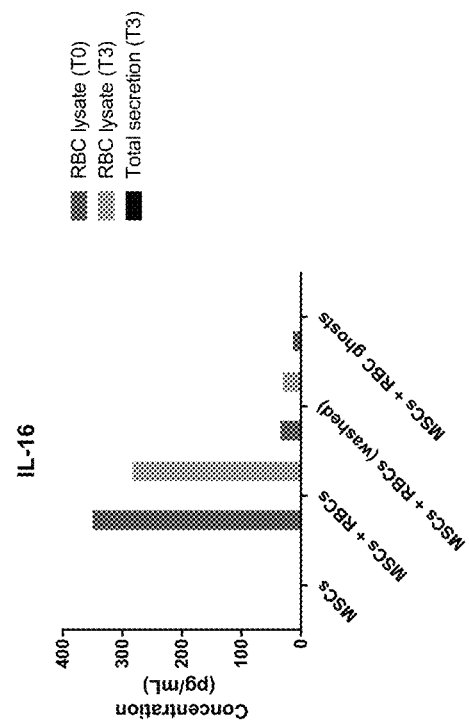
Figure 21D:
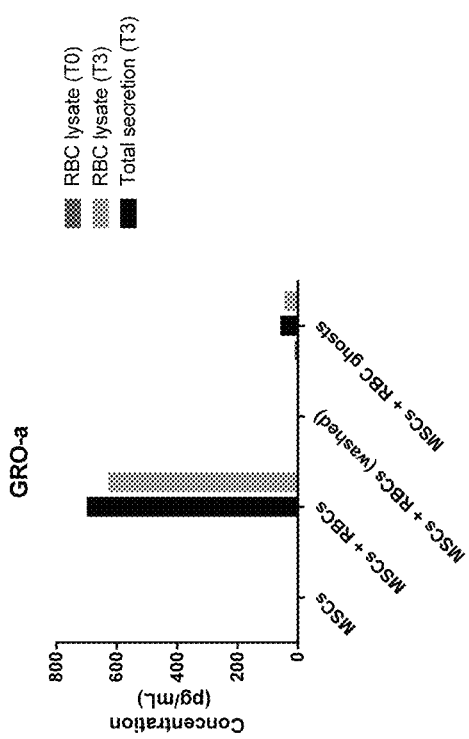
Figure 21E:
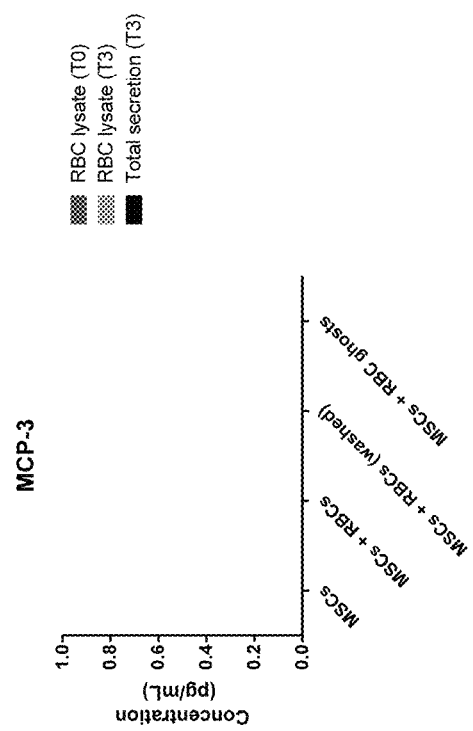
Figure 21G:
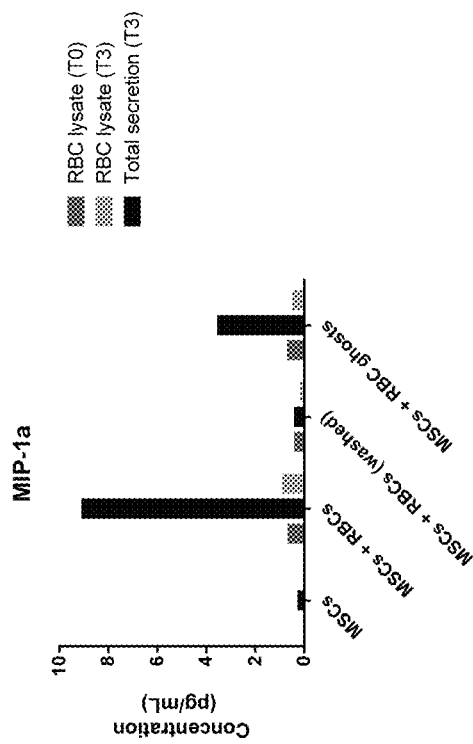
Figure 21F:
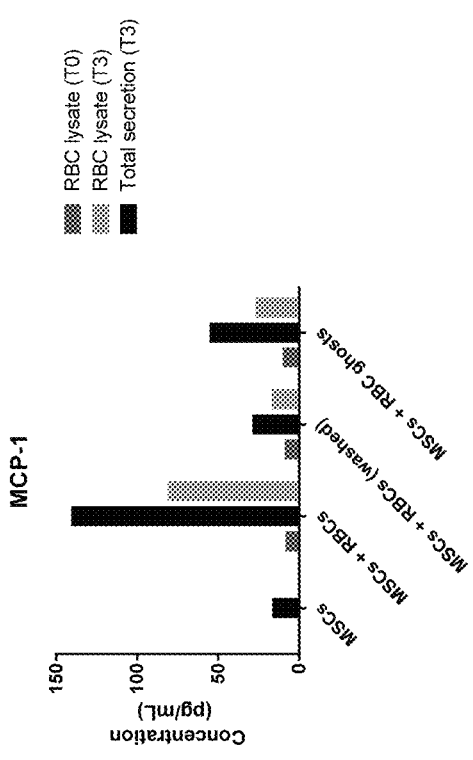
Figure 21H:
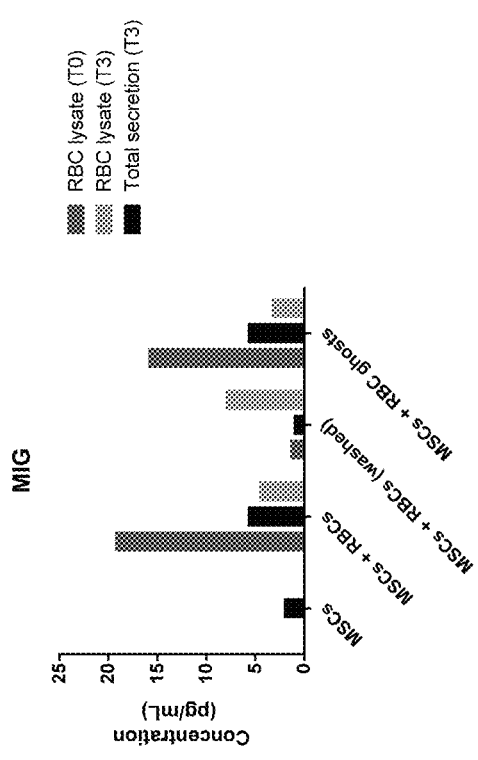
Figure 21J:
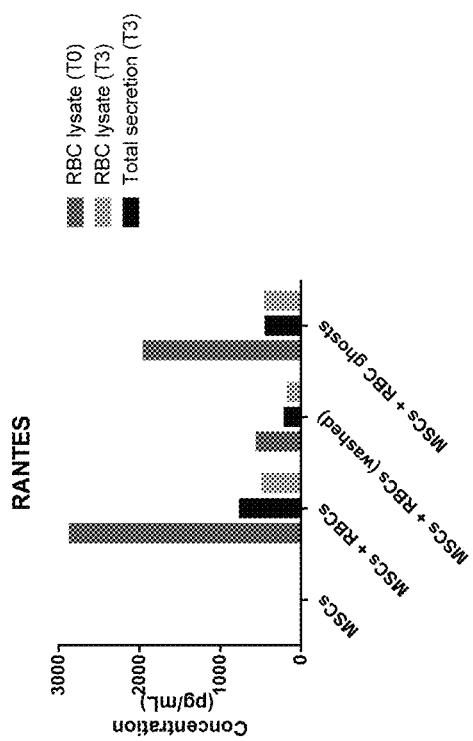
Figure 21I:
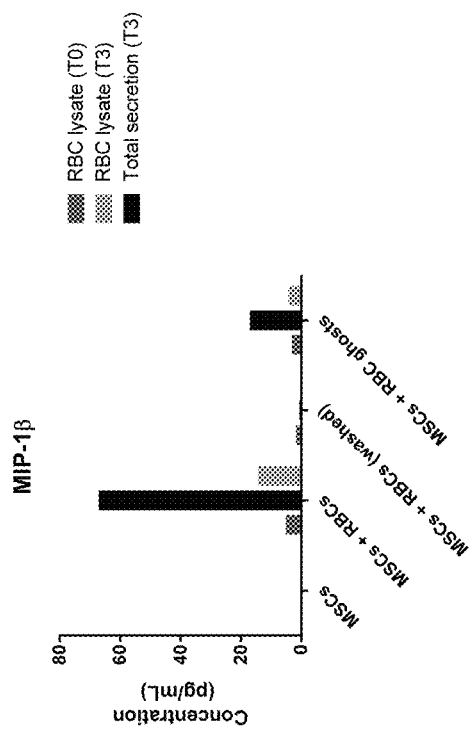
Figure 21K:
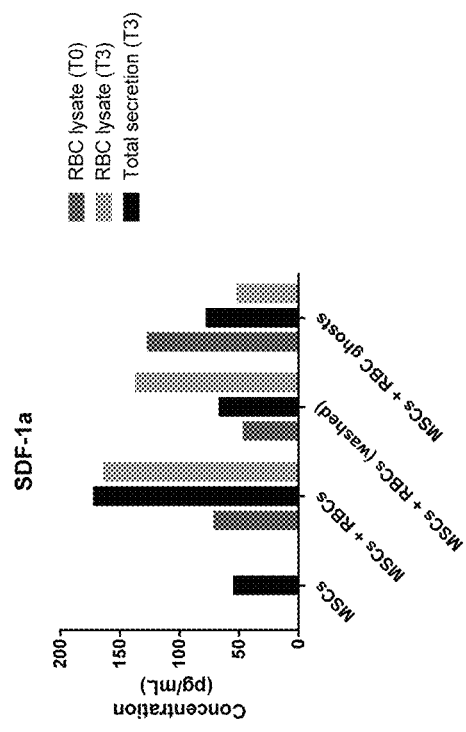
Figure 22B:
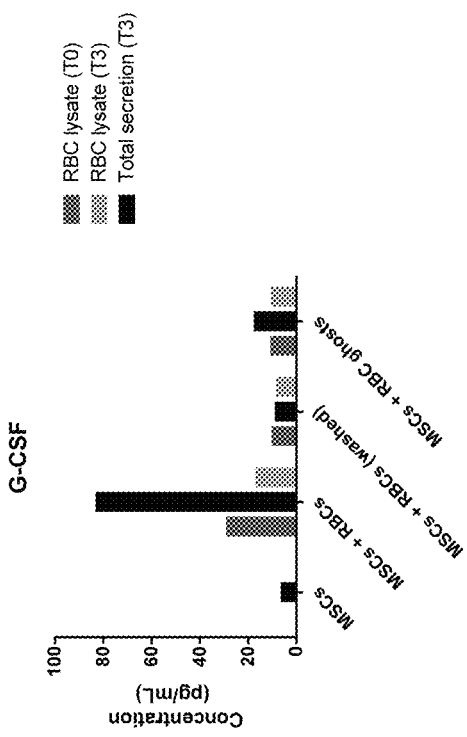
Figure 22D:
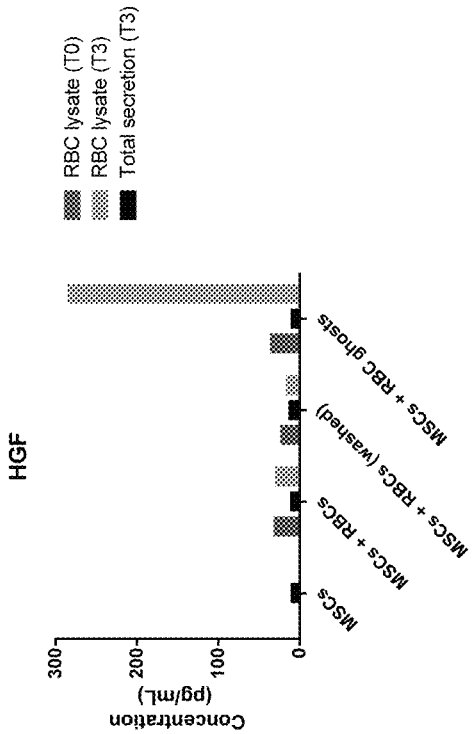
Figure 22A:
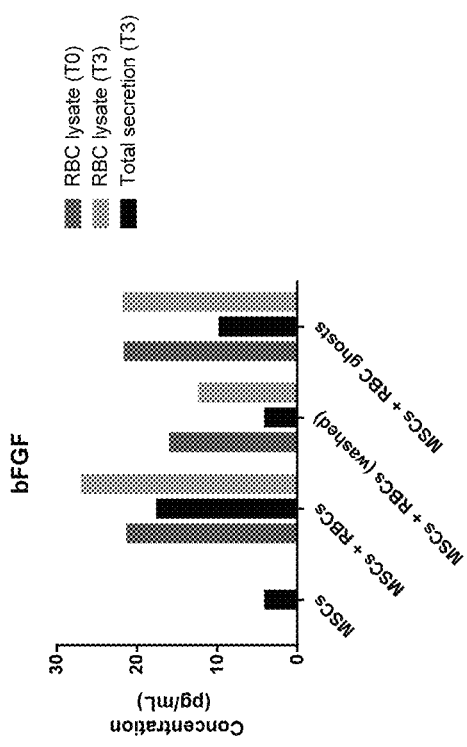
Figure 22C:
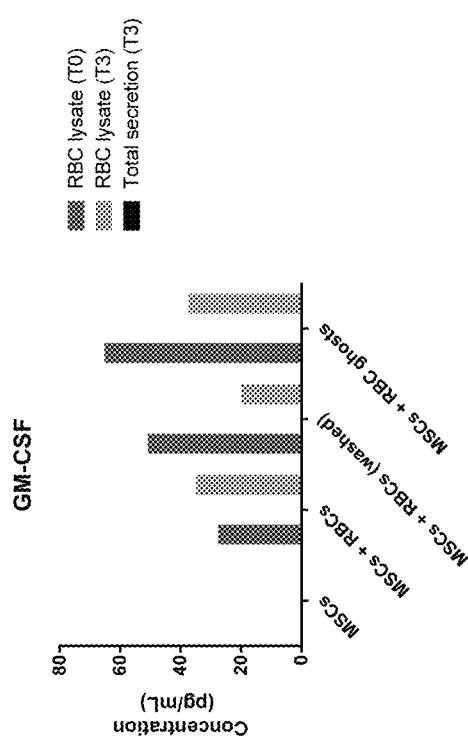
Figure 22E:
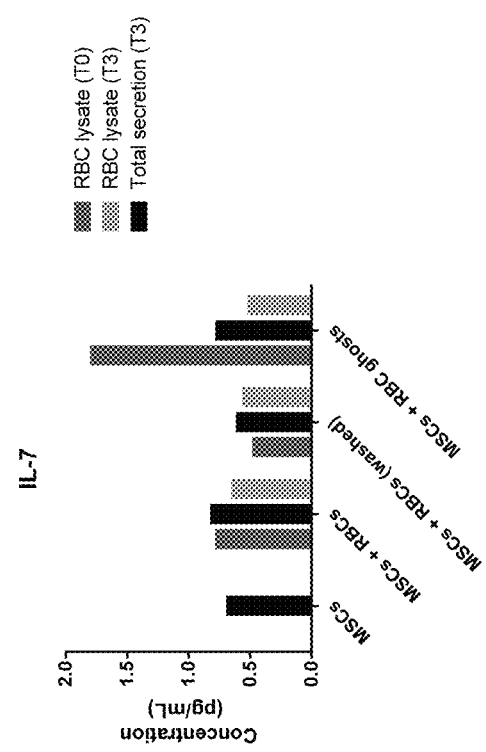
Figure 22F:
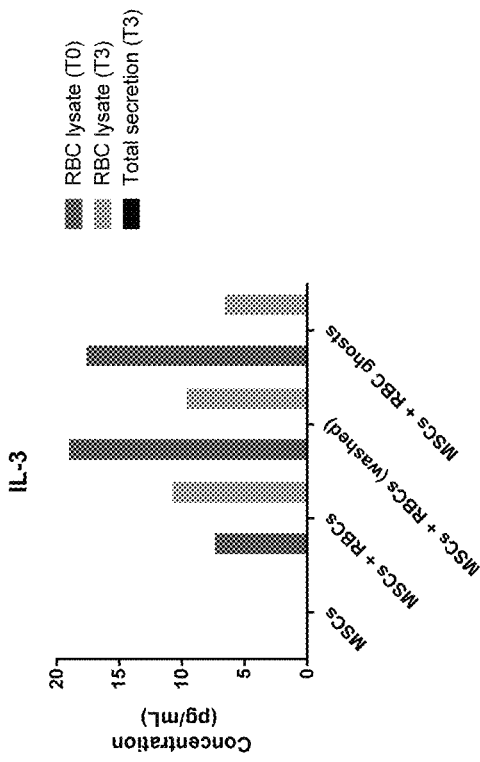
Figure 22G:
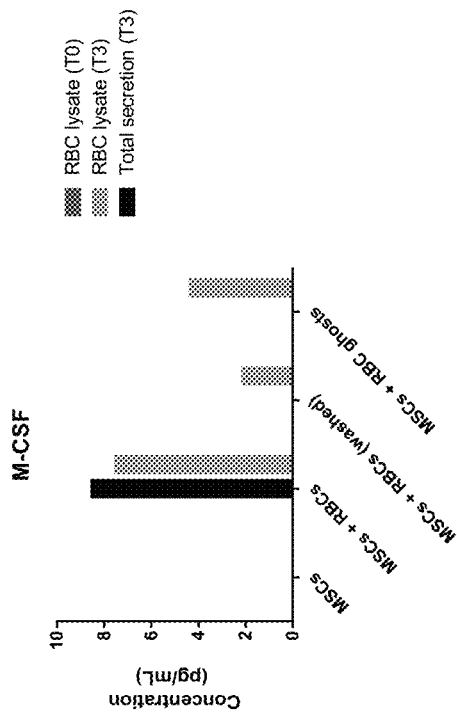
Figure 22H:
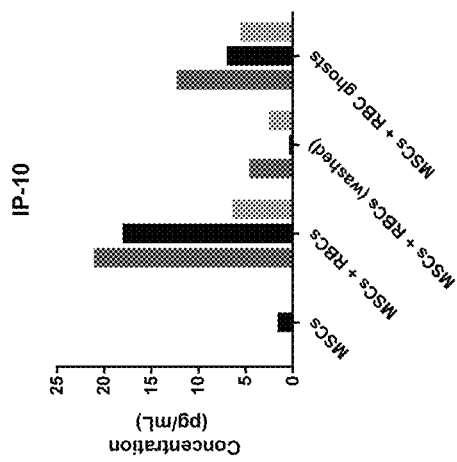
Figure 22M:
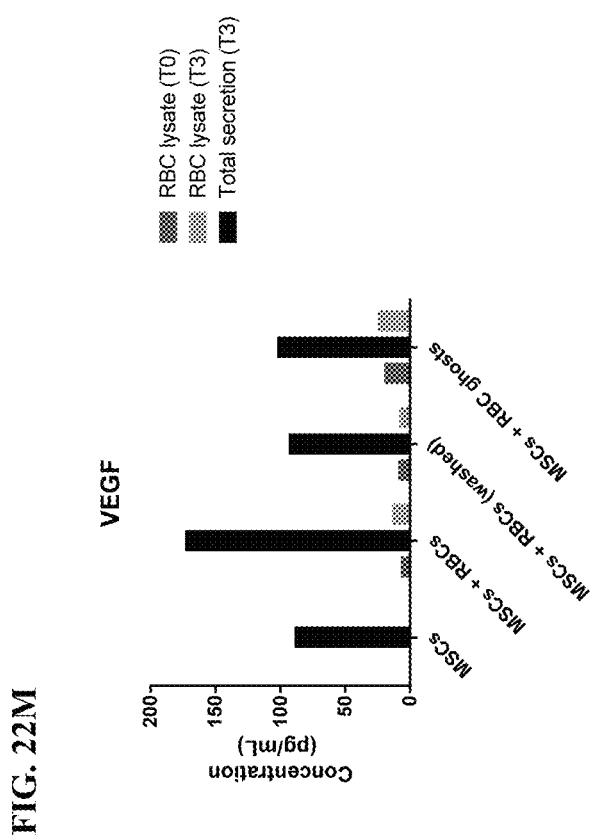
Figure 23A:
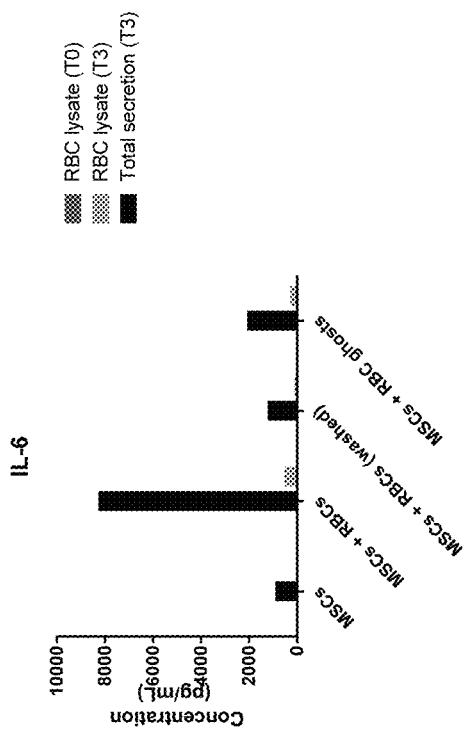
FIG. 23A-FIG. 23D is a series of graphs showing the concentration of proteins with multiple functions in the lysate of RBCs before and after incubation with MSCs and the secretion of MSCs and/or RBCs after 72 hours at 37° C. as measured by BioPlex and reported as pg/mL (20 million RBCs in 100 uL PBS). Data presented as mean±SD (n=1).
Figure 23B:
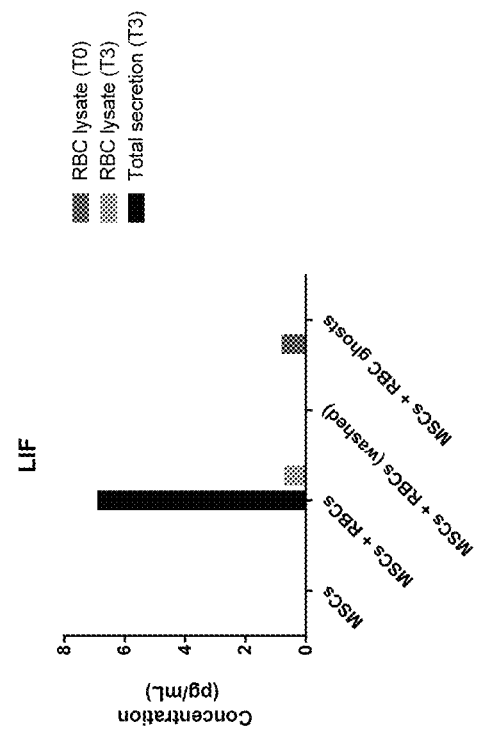
Figure 23C:
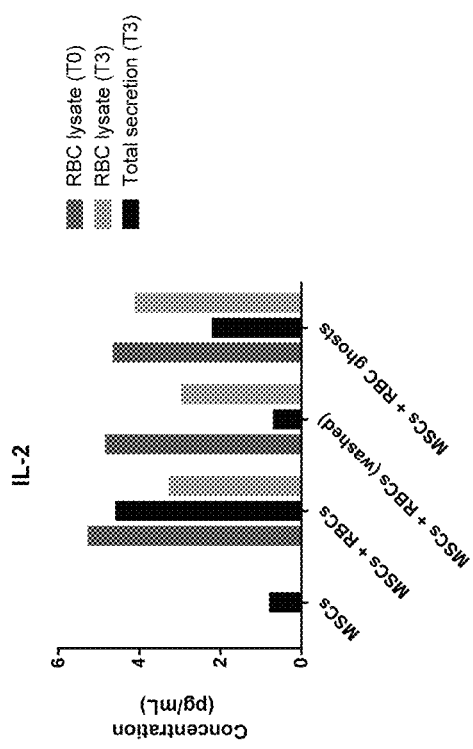
Figure 23D:
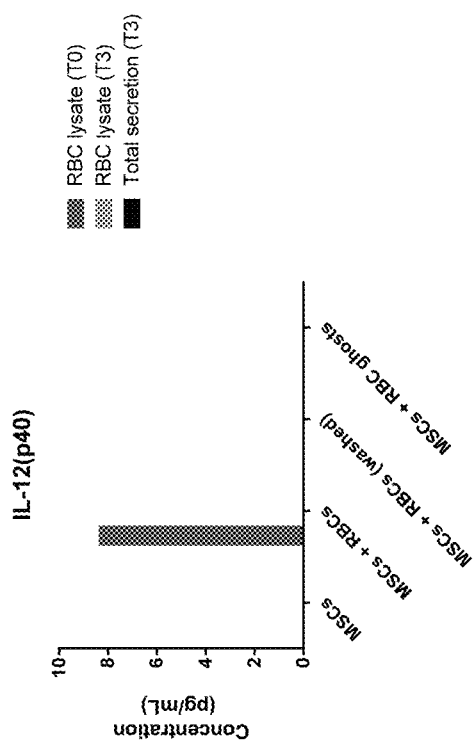
Figure 24:
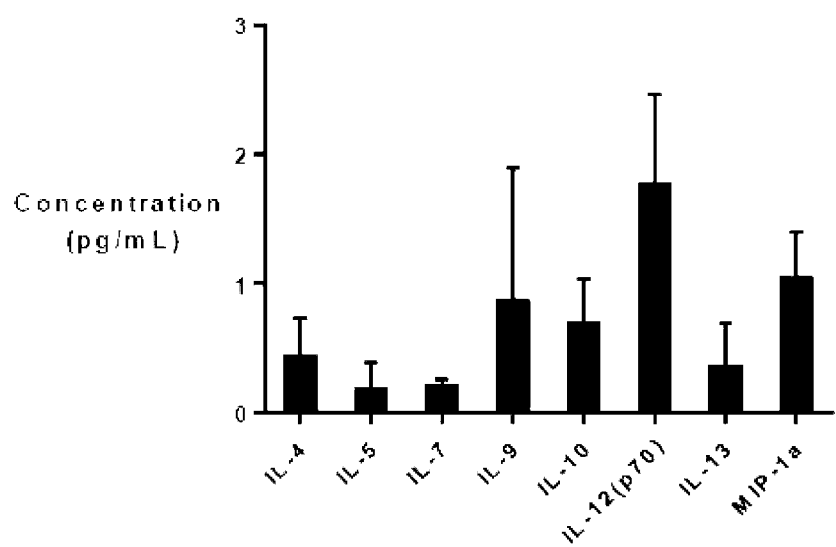
FIG. 24 is a series of graphs showing the concentration of proteins released or secreted from RBCs into PBS over 24 hours at 37° C. as measured by BioPlex and reported as pg/mL (20 million RBCs in 100 uL PBS). Data presented as mean±SD (n=3).
Figure 25:
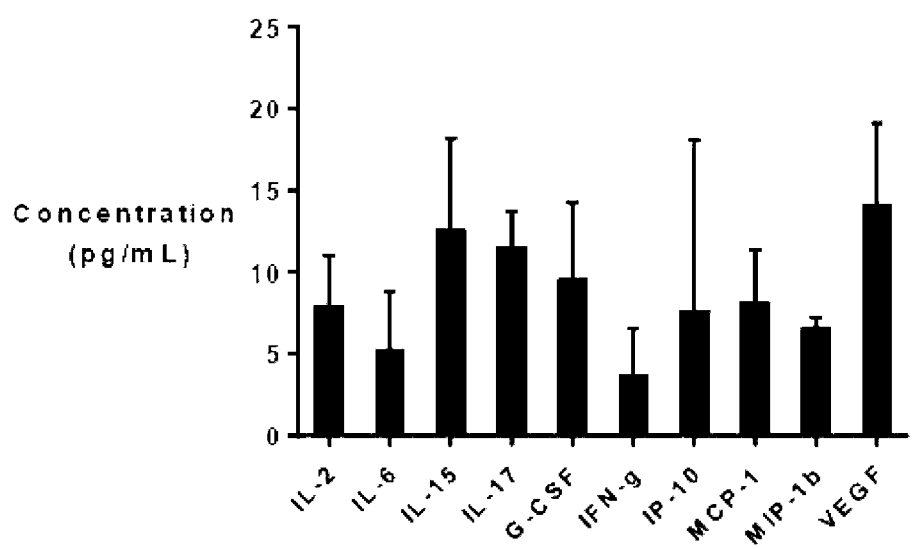
FIG. 25 is a series of graphs showing the concentration of proteins released or secreted from RBCs into PBS over 24 hours at 37° C. as measured by BioPlex and reported as pg/mL (20 million RBCs in 100 uL PBS). Data presented as mean±SD (n=3).
Figure 26:
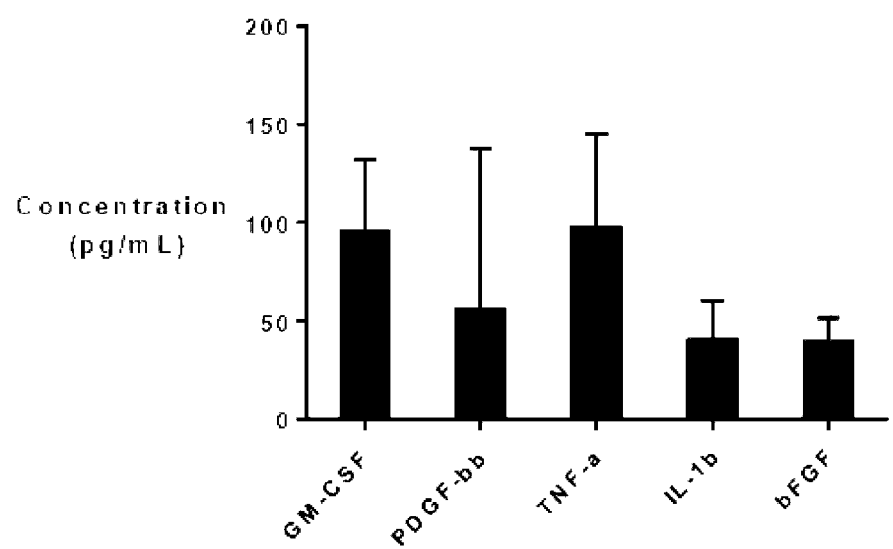
FIG. 26 is a series of graphs showing the concentration of proteins released or secreted from RBCs into PBS over 24 hours at 37° C. as measured by BioPlex and reported as pg/mL (20 million RBCs in 100 uL PBS). Data presented as mean±SD (n=3).
Figure 27:
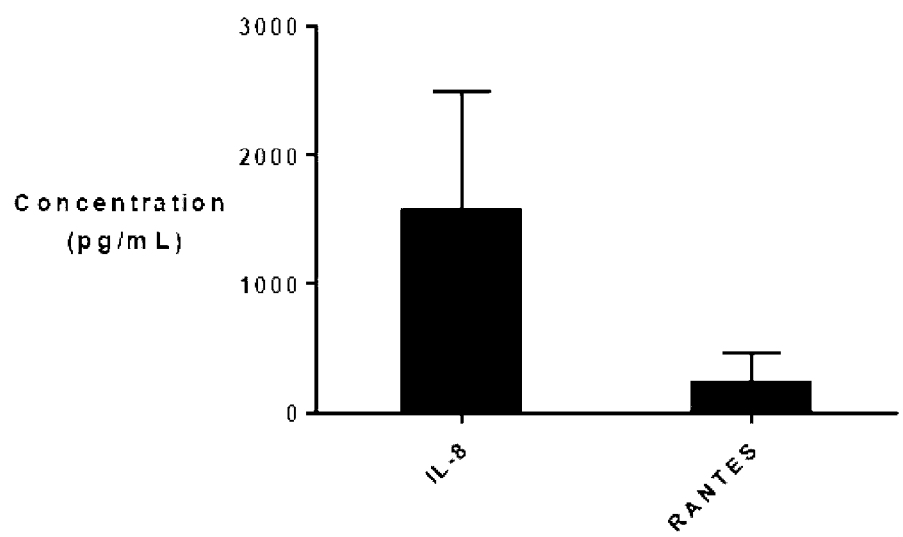
FIG. 27 is a series of graphs showing the concentration of proteins released or secreted from RBCs into PBS over 24 hours at 37° C. as measured by BioPlex and reported as pg/mL (20 million RBCs in 100 uL PBS). Data presented as mean±SD (n=3).
Figure 28A:
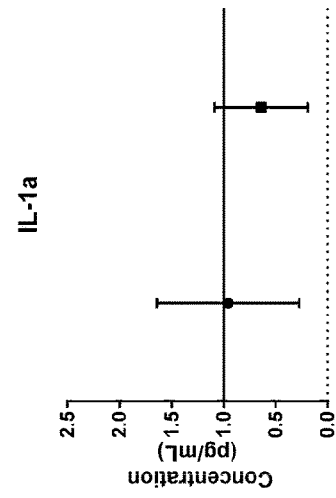
FIG. 28A-FIG. 28O is a series of graphs showing the concentration of pro-inflammatory cytokines released or secreted from RBCs into PBS over 24 hours and in the corresponding RBC lysate at 37° C. with or without protease inhibitors (PI) as measured by BioPlex and reported as pg/mL (20 million RBCs in 100 uL PBS). Data presented as fold change after addition of PI±95% CI, where ● represents fold change in secretion with addition of PI compared to the no PI, and ■ represents fold change in concentration in lysate with addition of PI compared to the no PI control (n=7).
Figure 28B:
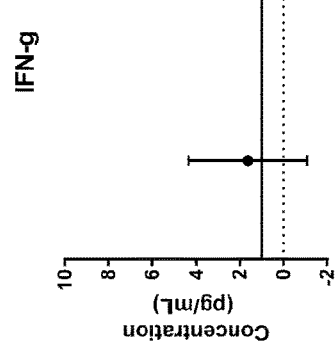
Figure 28C:
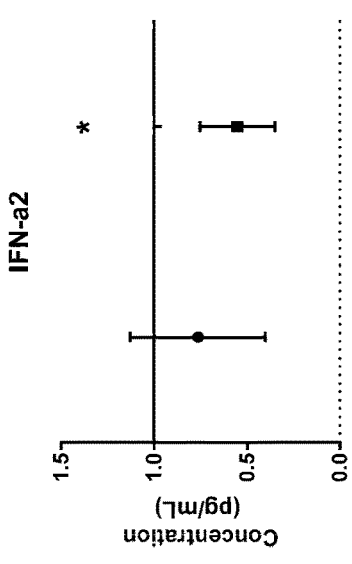
Figure 28D:
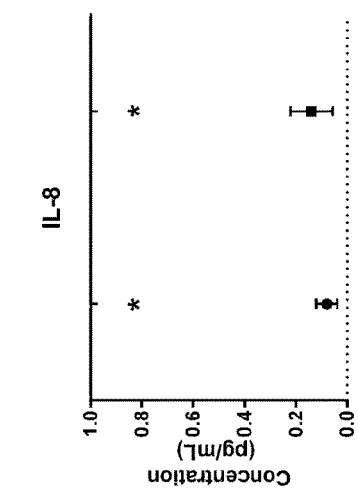
Figure 28E:
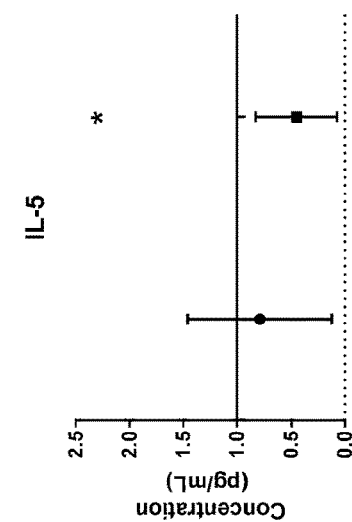
Figure 28F:
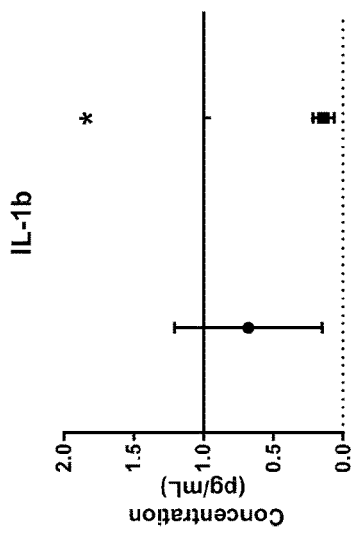
Figure 28O:
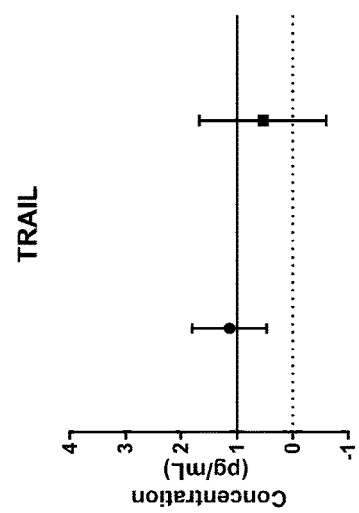
Figure 28N:
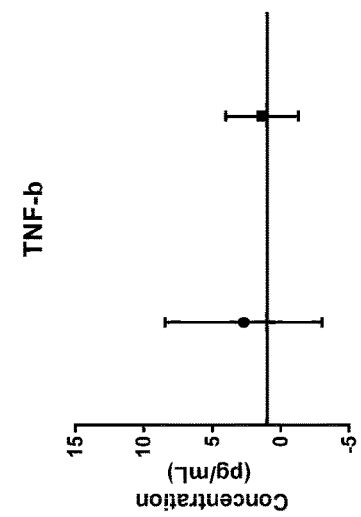
Figure 28M:
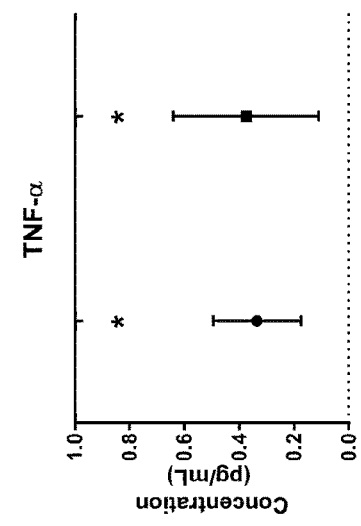
Figure 29C:
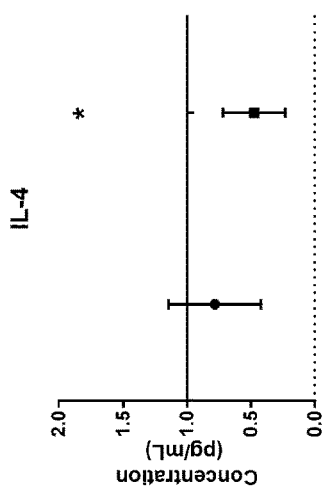
FIG. 29A-FIG. 29E is a series of graphs showing the concentration of anti-inflammatory cytokines released or secreted from RBCs into PBS over 24 hours and in the corresponding RBC lysate at 37° C. with or without protease inhibitors (PI) as measured by BioPlex and reported as pg/mL (20 million RBCs in 100 uL PBS). Data presented as fold change after addition of PI 95% CI, where ● represents fold change in secretion with addition of PI compared to the no PI, and ■ represents fold change in concentration in lysate with addition of PI compared to the no PI control (n=7).
Figure 29B:
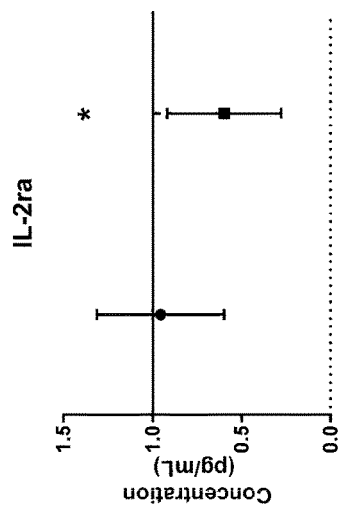
Figure 29E:
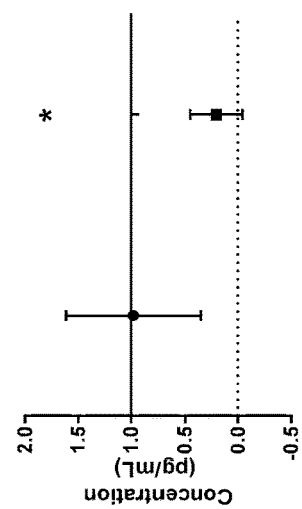
Figure 29A:
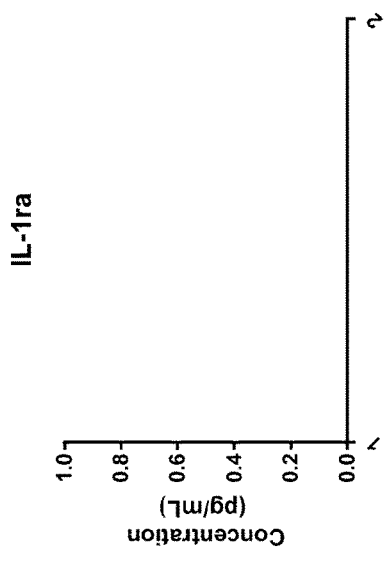
Figure 29D:
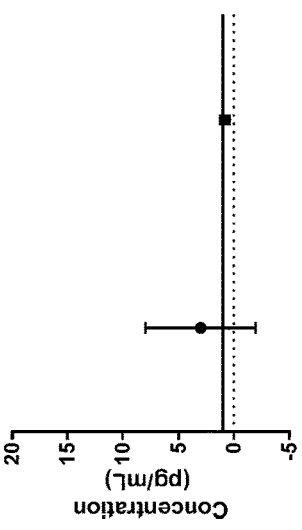
Figure 30C:
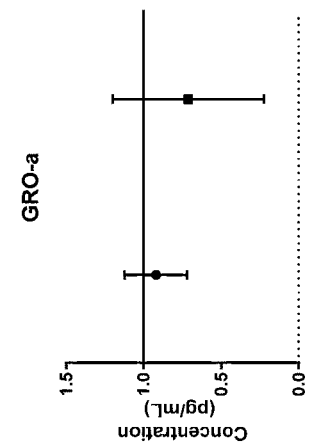
FIG. 30A-FIG. 30K is a series of graphs showing the concentration of chemokines released or secreted from RBCs into PBS over 24 hours and in the corresponding RBC lysate at 37° C. with or without protease inhibitors (PI) as measured by BioPlex and reported as pg/mL (20 million RBCs in 100 uL PBS). Data presented as fold change after addition of PI±95% Cl, where ● represents fold change in secretion with addition of PI compared to the no PI, and ■ represents fold change in concentration in lysate with addition of PI compared to the no PI control (n=7).
Figure 30B:
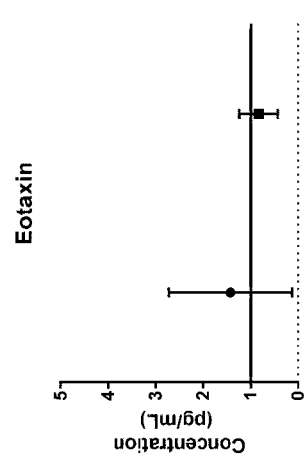
Figure 30A:
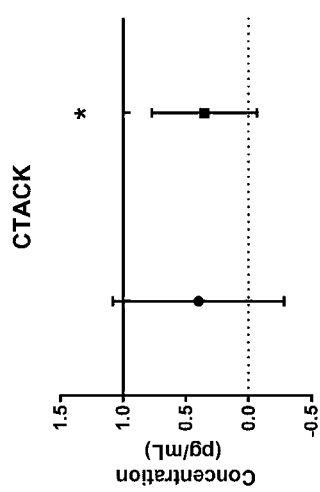
Figure 30F:
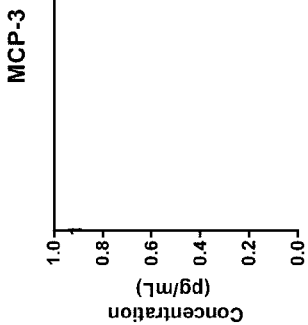
Figure 30E:
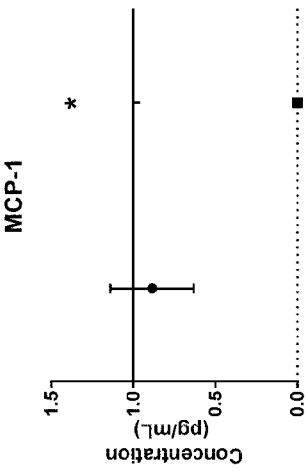
Figure 30D:
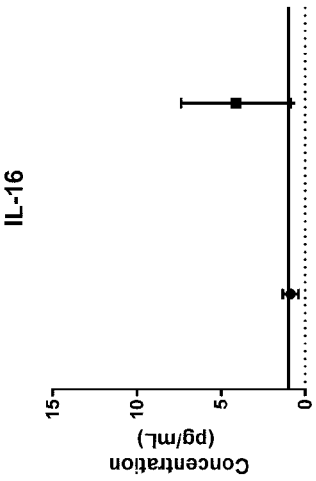
Figure 30I:
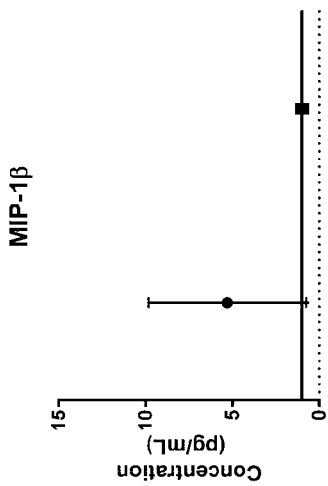
Figure 30H:
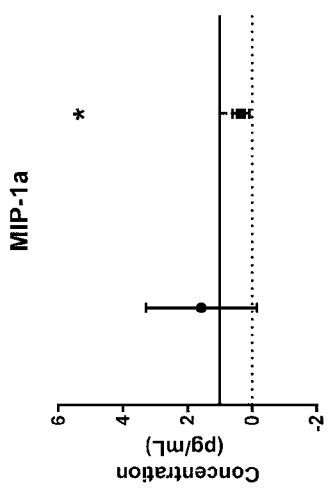
Figure 30K:
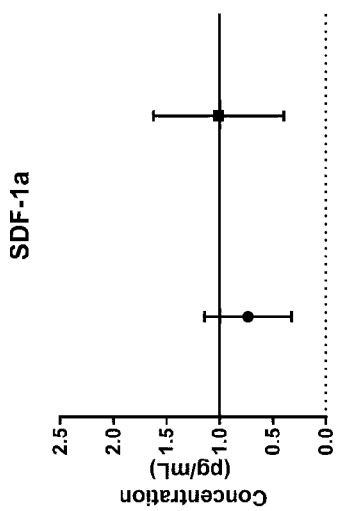
Figure 30G:
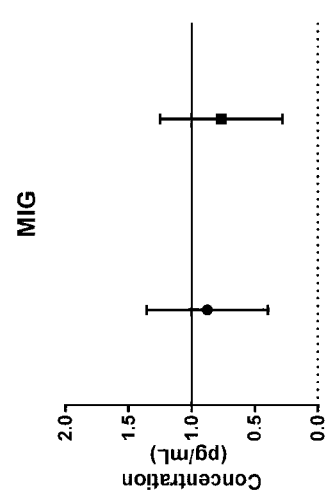
Figure 30J:
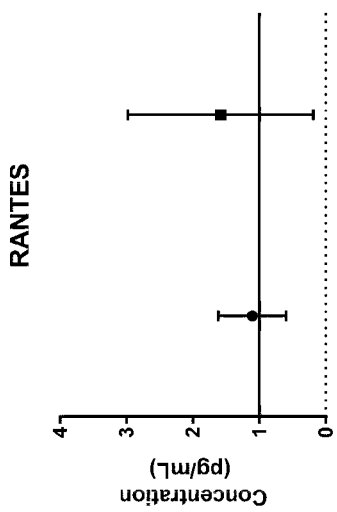
Figure 31I:
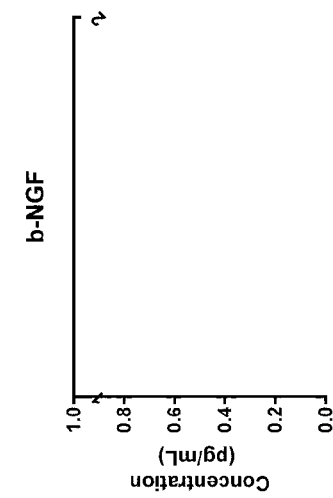
Figure 31H:
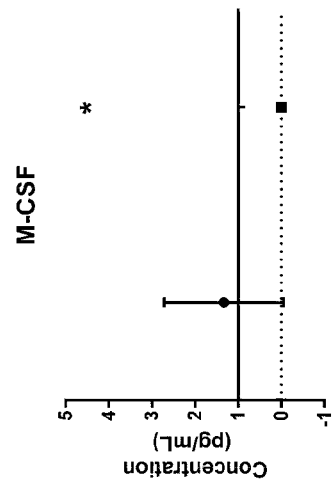
Figure 31G:
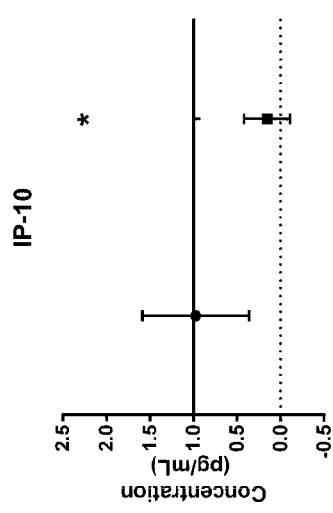
Figure 31L:
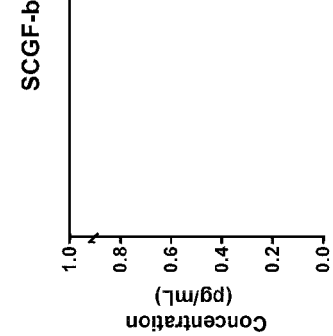
Figure 31K:
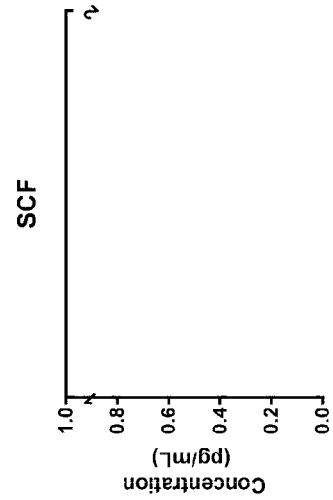
Figure 31J:
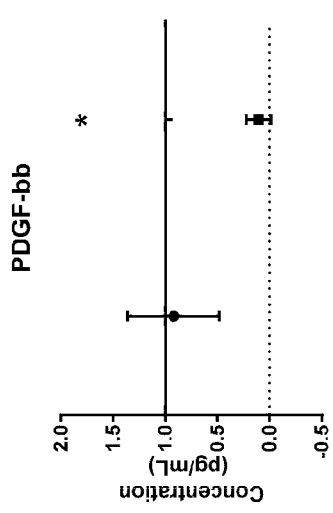
Figure 31M:
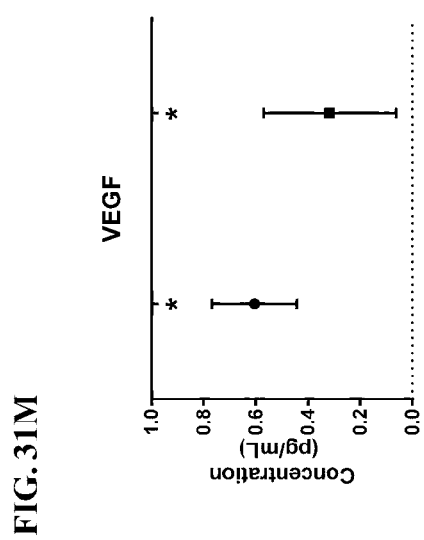
Figure 33A:
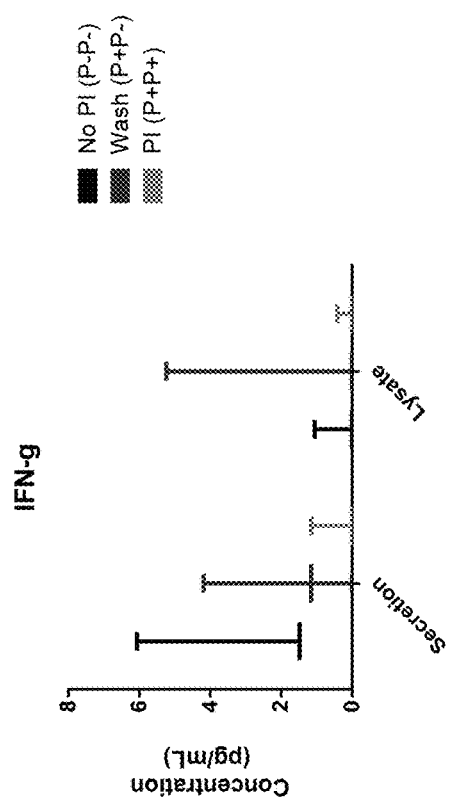
FIG. 33A-FIG. 33O is a series of graphs showing the concentration of pro-inflammatory cytokines released or secreted from RBCs into PBS over 48 hours and in the corresponding RBC lysate at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 33B:
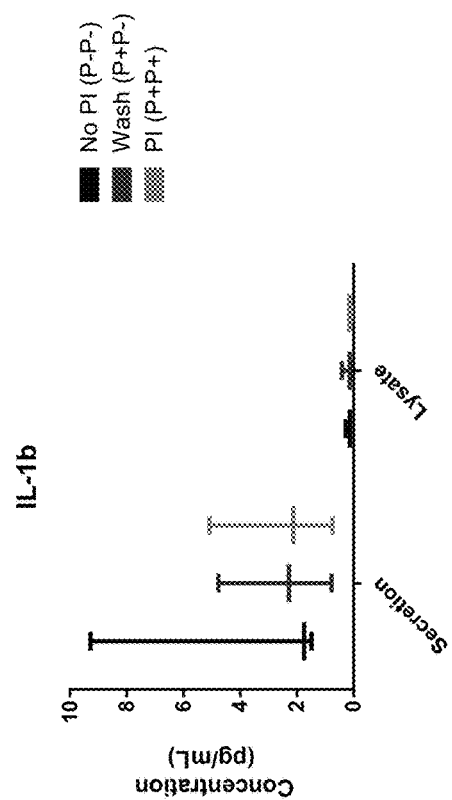
Figure 33C:
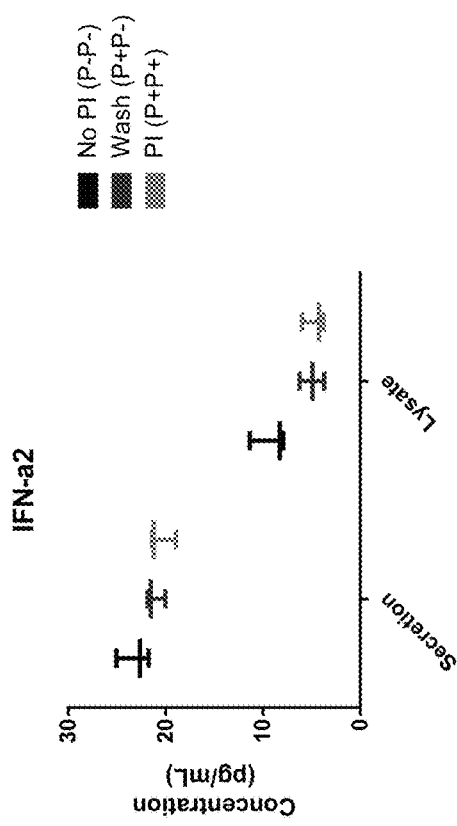
Figure 33D:
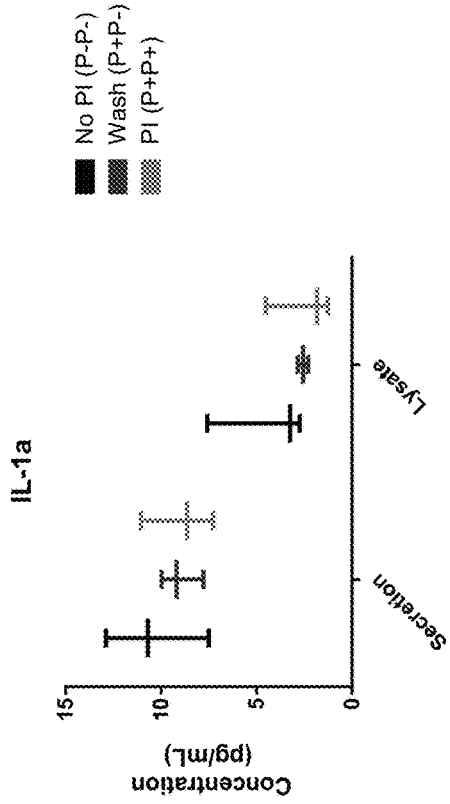
Figure 33N:
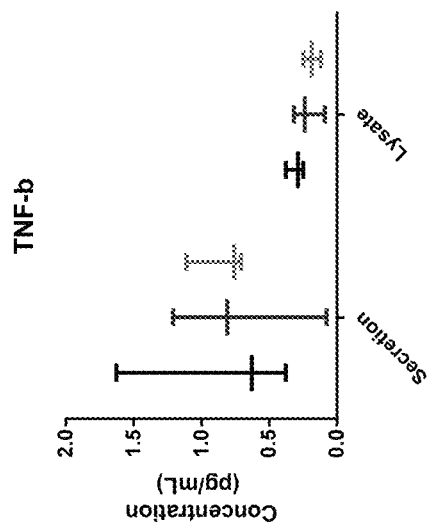
Figure 33M:
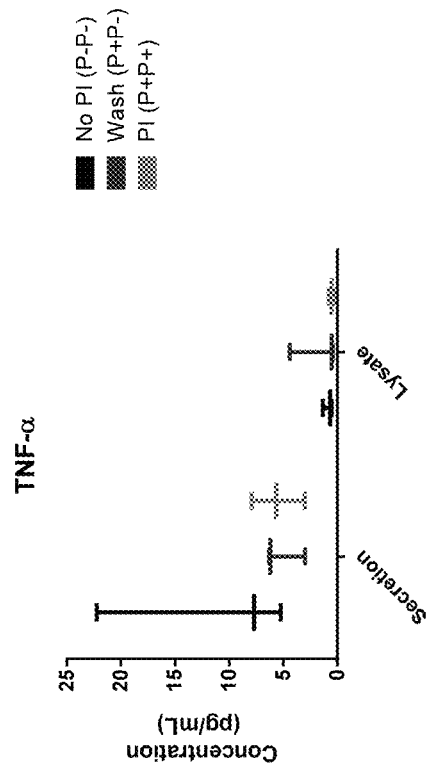
Figure 33O:
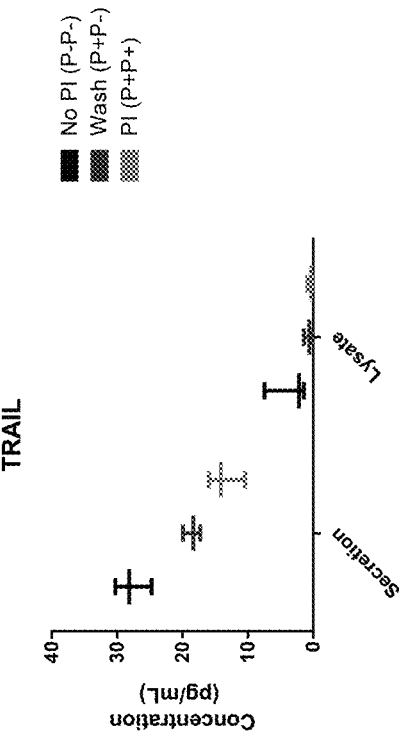
Figure 34A:
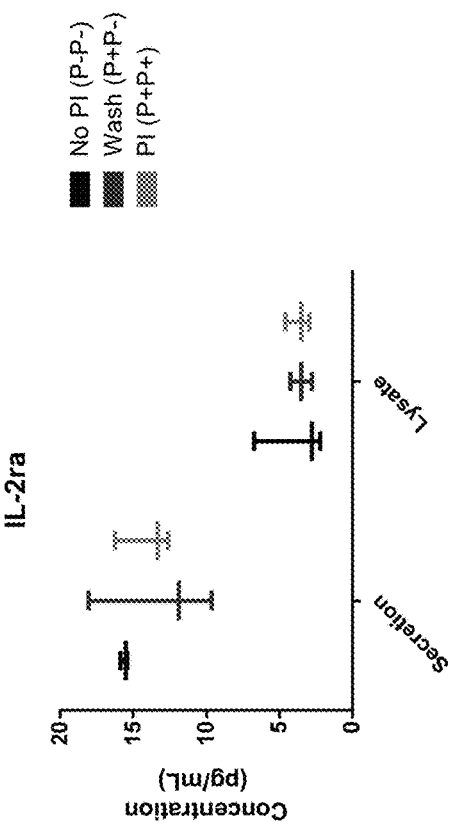
FIG. 34A-FIG. 34E is a series of graphs showing the concentration of anti-inflammatory cytokines released or secreted from RBCs into PBS over 48 hours and in the corresponding RBC lysate at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 34B:
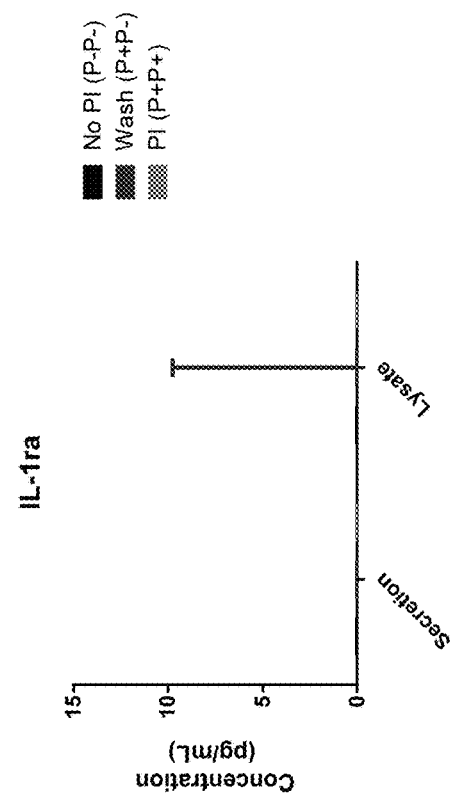
Figure 34C:
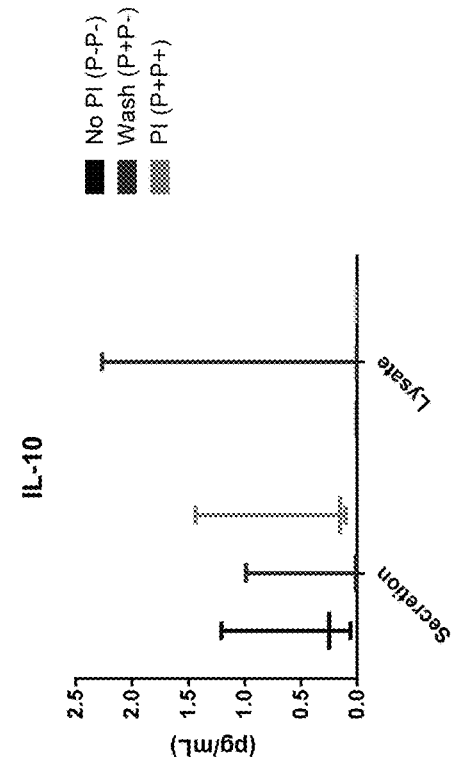
Figure 34D:
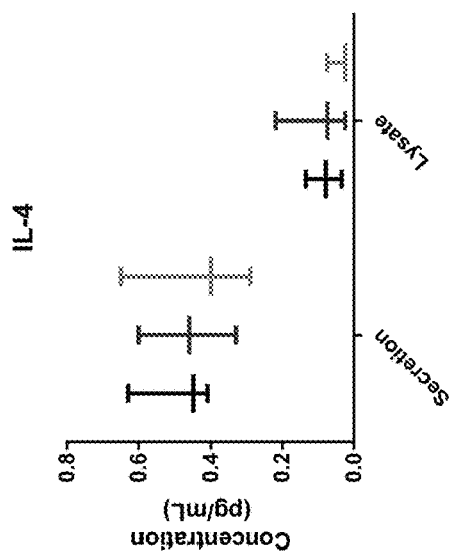
Figure 34E:
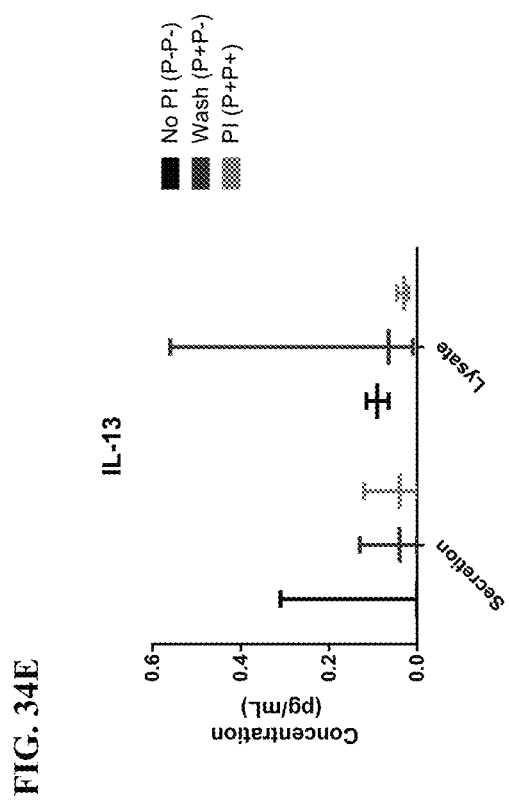
Figure 35B:
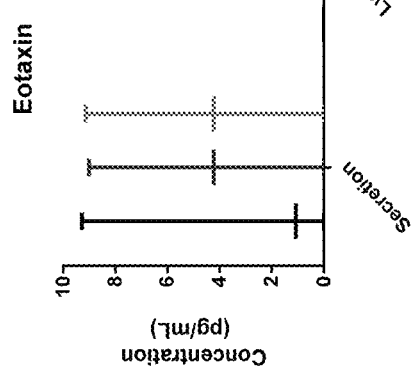
Figure 35D:
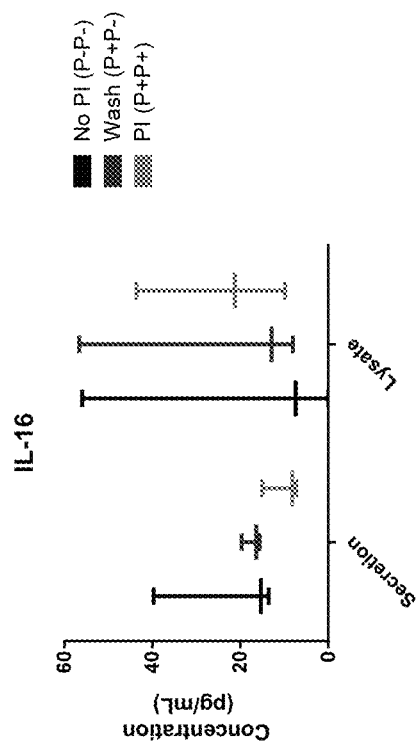
Figure 35A:
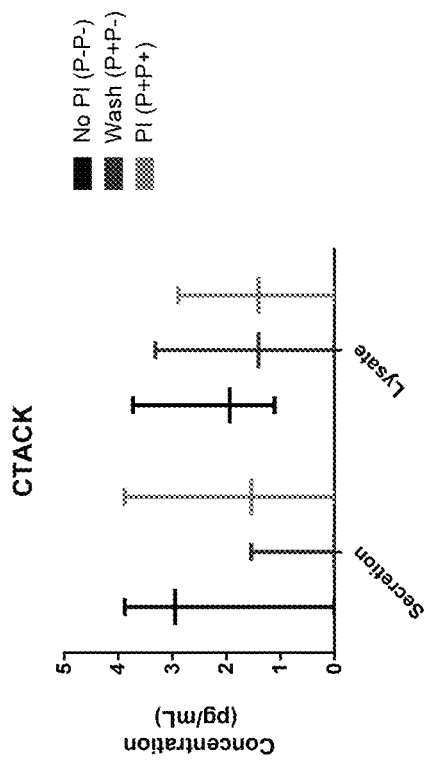
Figure 35C:
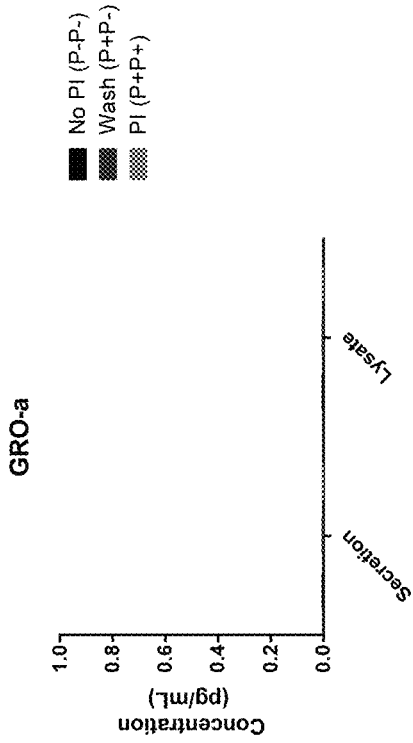
Figure 35E:
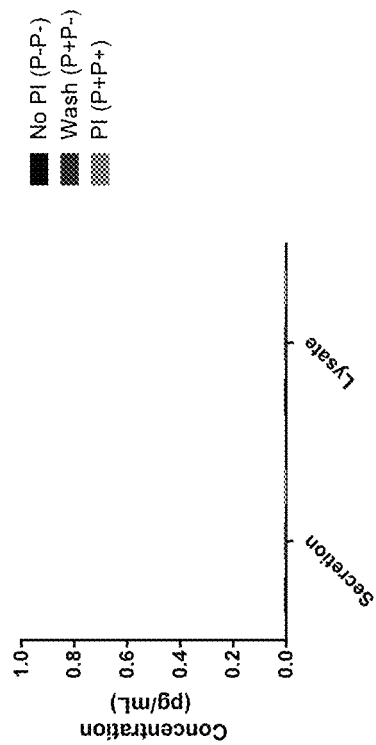
Figure 35F:
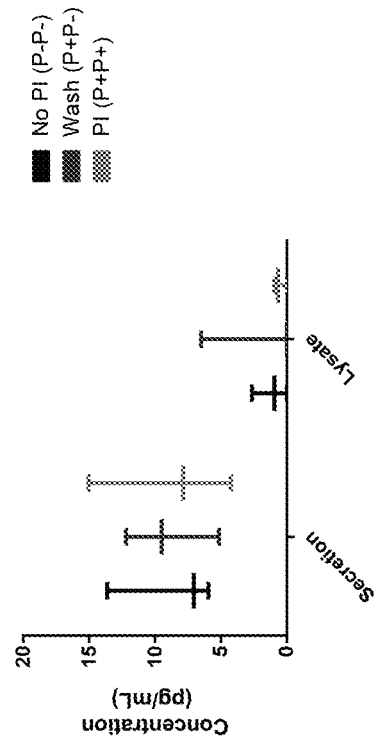
Figure 35G:
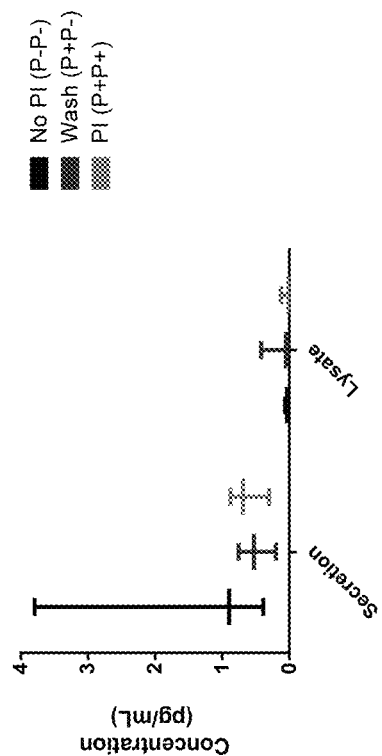
Figure 35H:
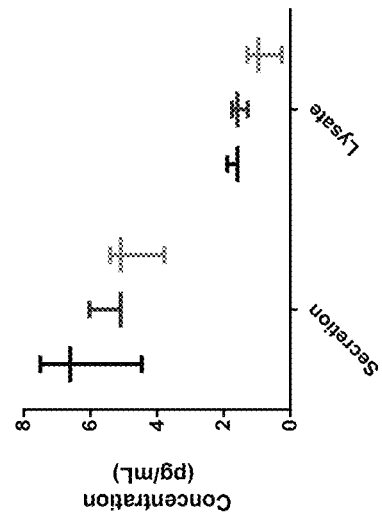
Figure 36B:
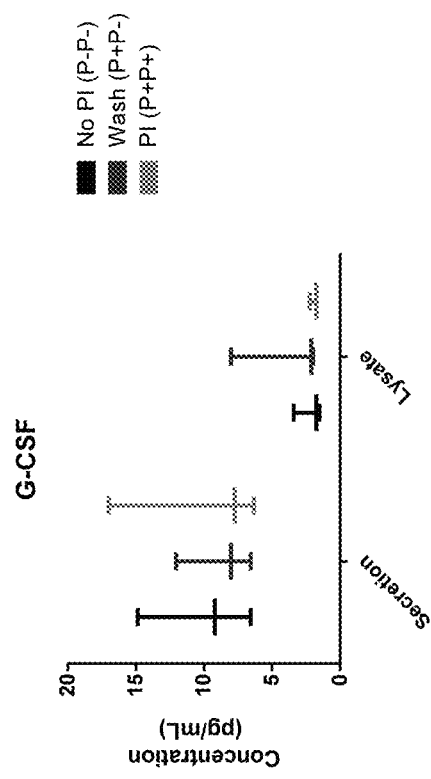
FIG. 36A-FIG. 36H is a series of graphs showing the concentration of growth factors released or secreted from RBCs into PBS over 48 hours and in the corresponding RBC lysate at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 36D:
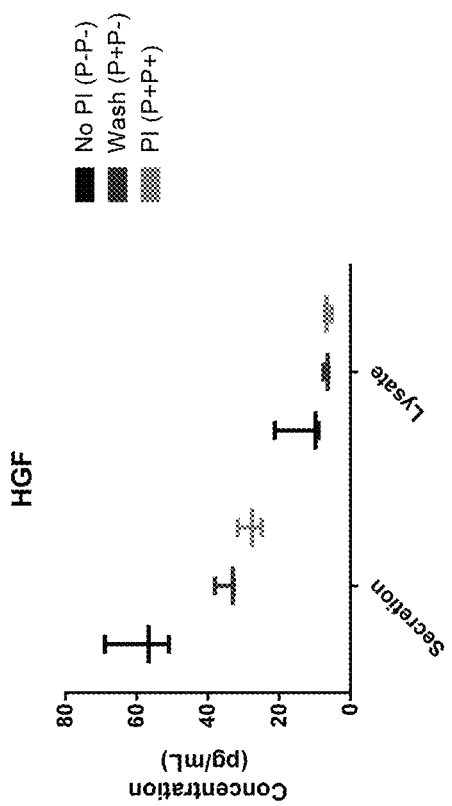
Figure 36A:
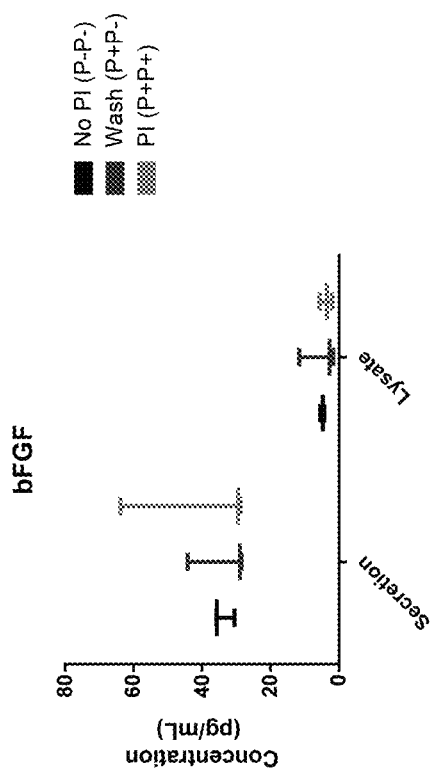
Figure 36C:
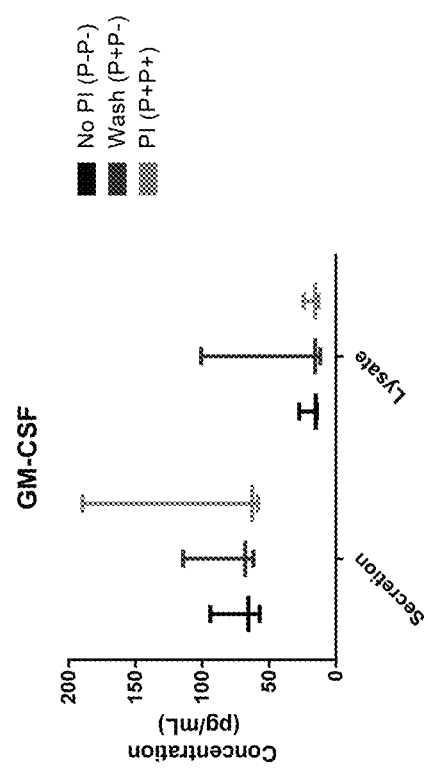
Figure 36E:
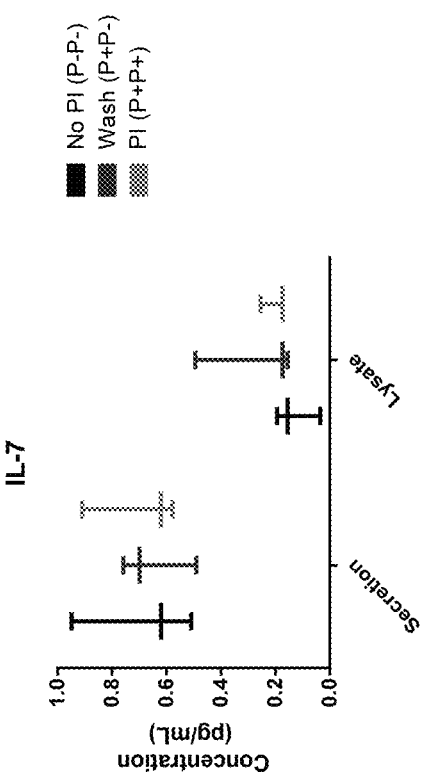
Figure 36F:
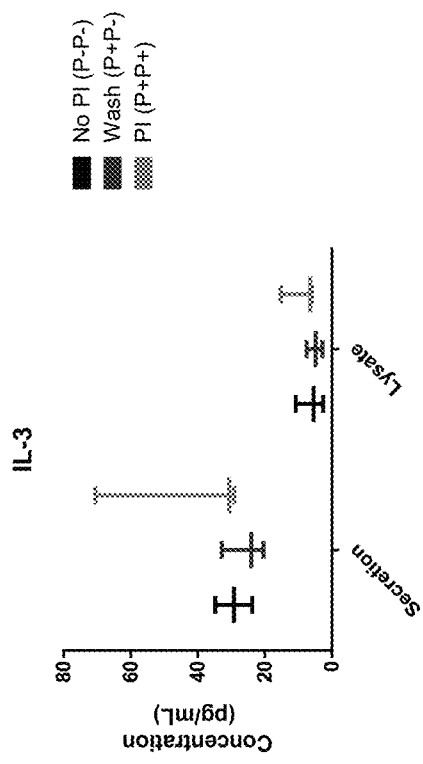
Figure 36G:
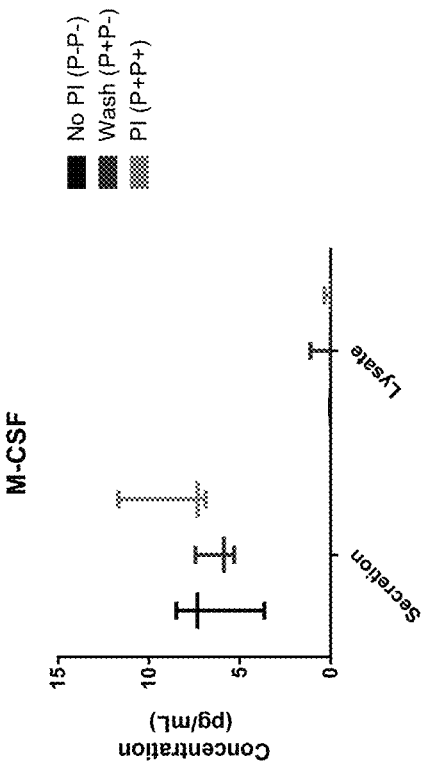
Figure 36H:
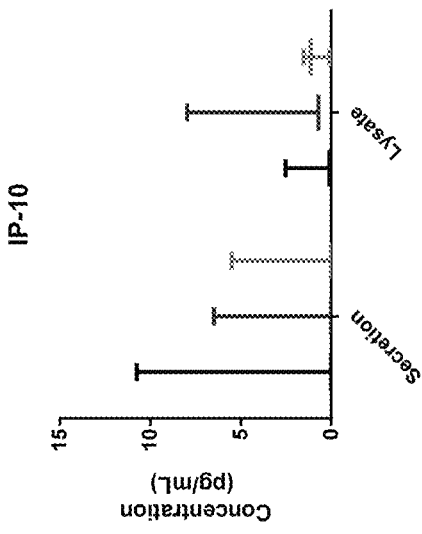
Figure 37A:
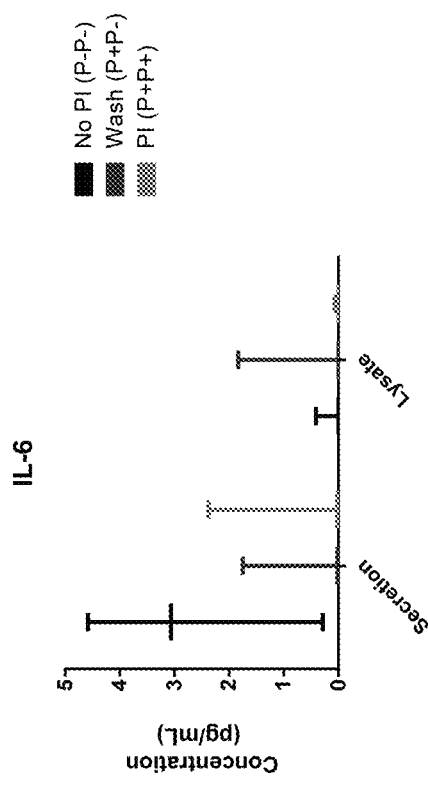
FIG. 37A-FIG. 37D is a series of graphs showing the concentration of cytokines with multiple factors released or secreted from RBCs into PBS over 48 hours and in the corresponding RBC lysate at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 37B:
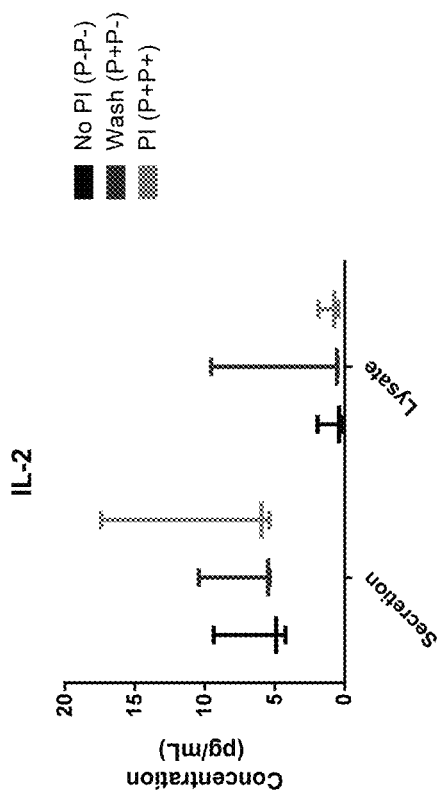
Figure 37C:
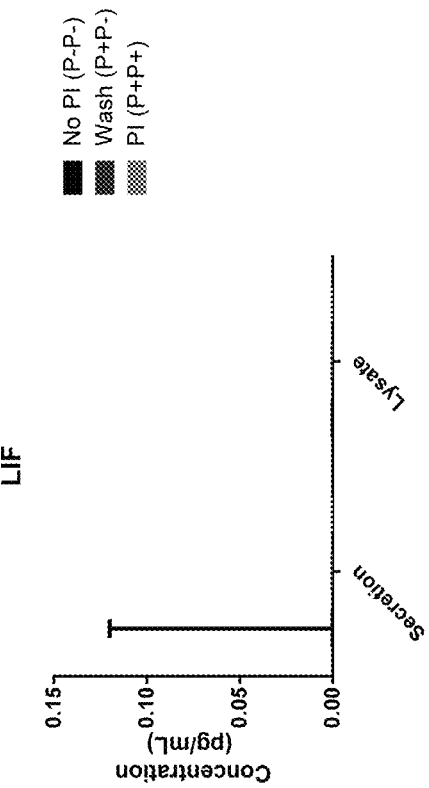
Figure 37D:
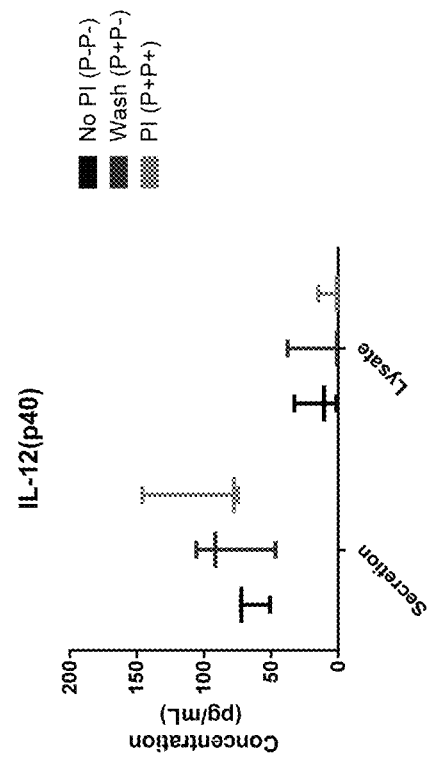
Figure 38A:
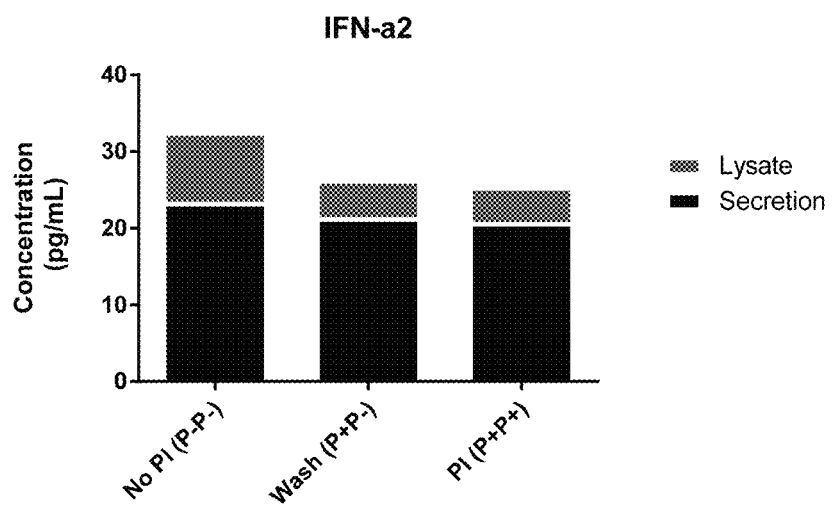
FIG. 38A-FIG. 38O is a series of graphs showing the total measured pro-inflammatory cytokines released or secreted from and in the lysate of RBCs after 48 hours incubation at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3). Total concentration of proteins (secretion+lysate)
Figure 38B:
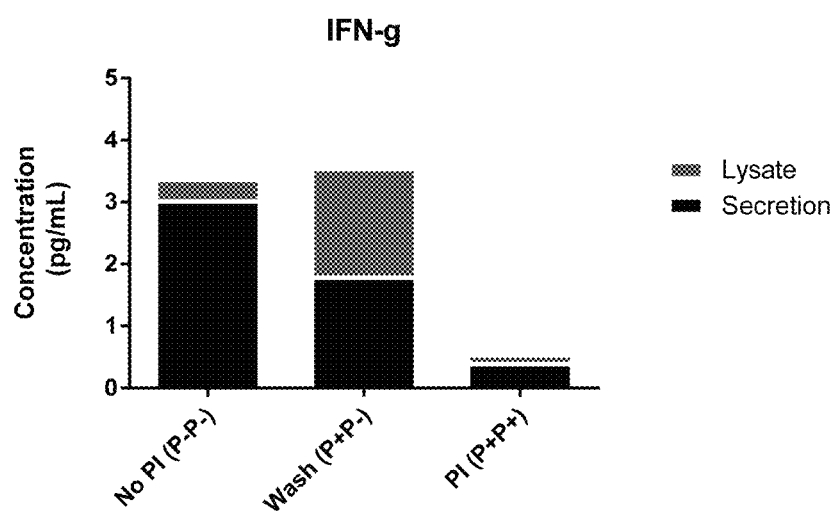
Figure 38C:
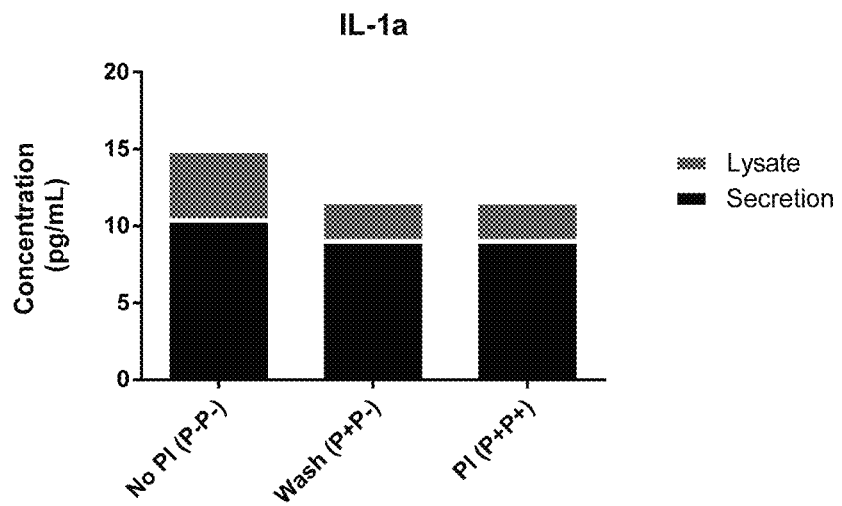
Figure 38D:
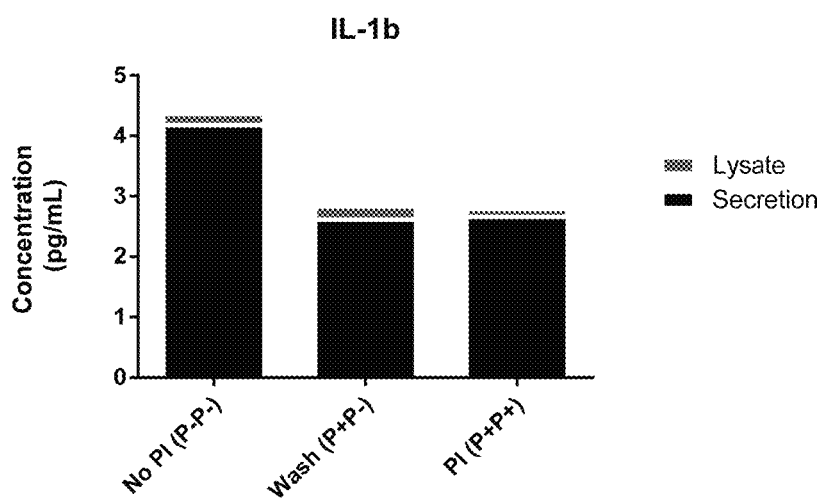
Figure 38E:
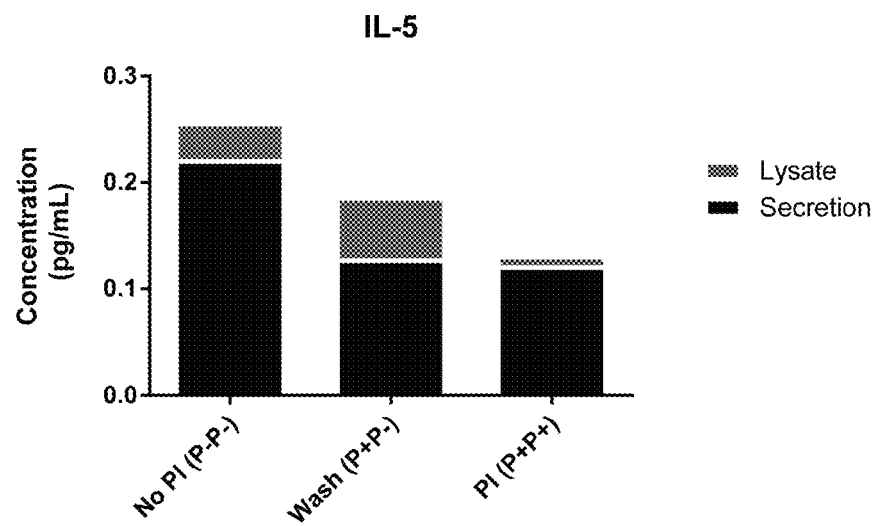
Figure 38F:
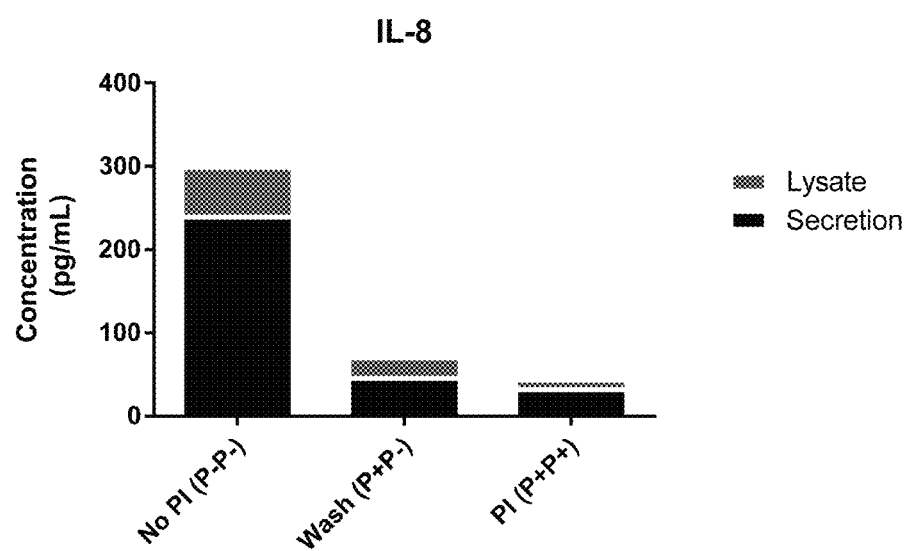
Figure 38G:
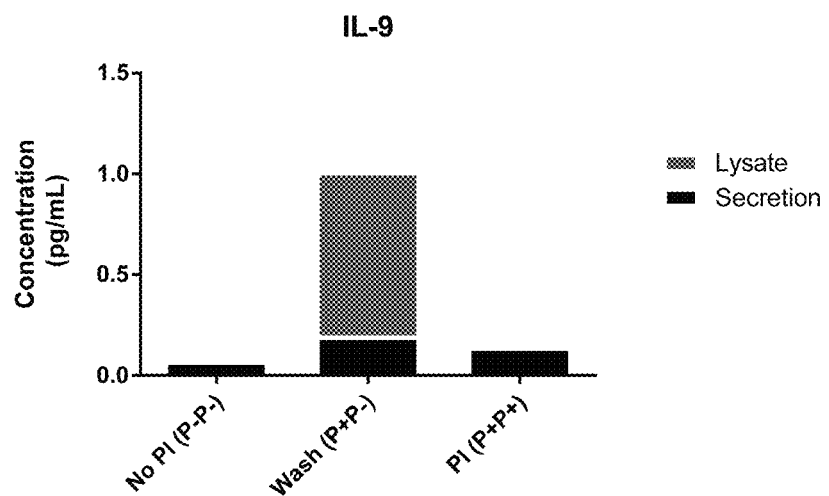
Figure 38H:
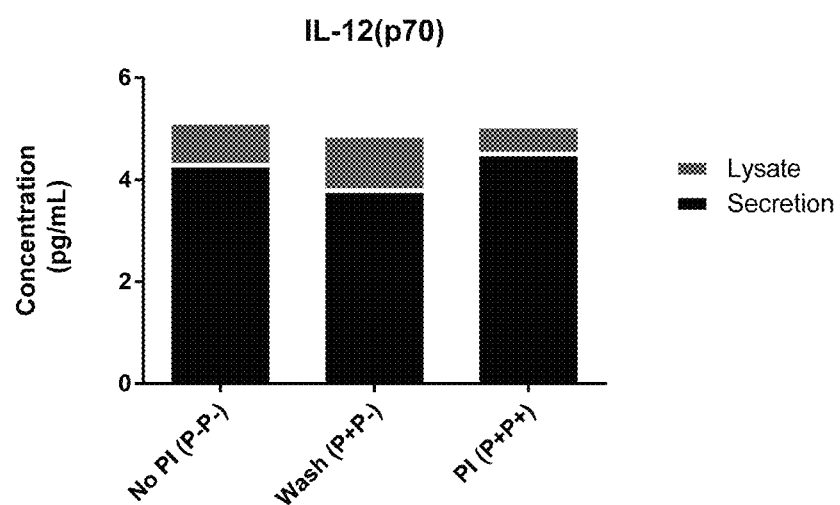
Figure 38I:
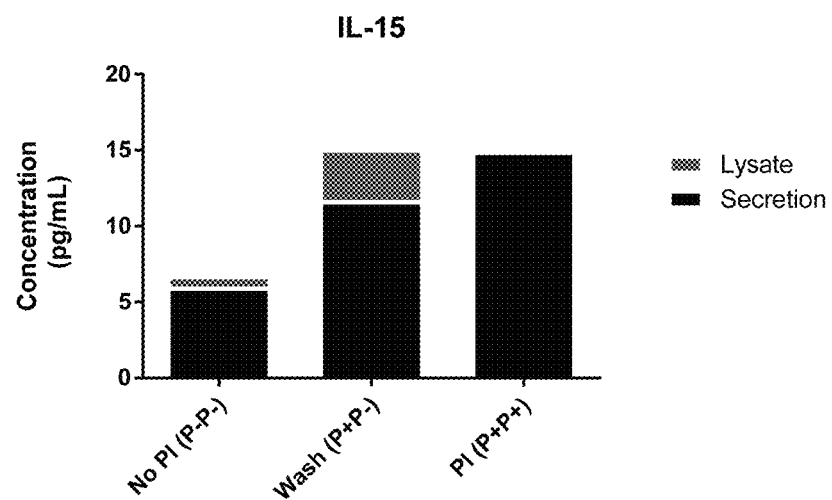
Figure 38J:
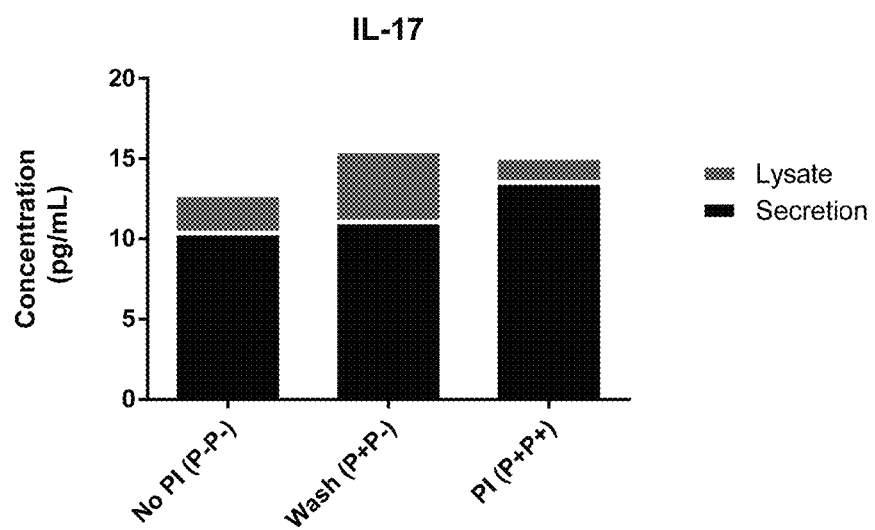
Figure 38K:
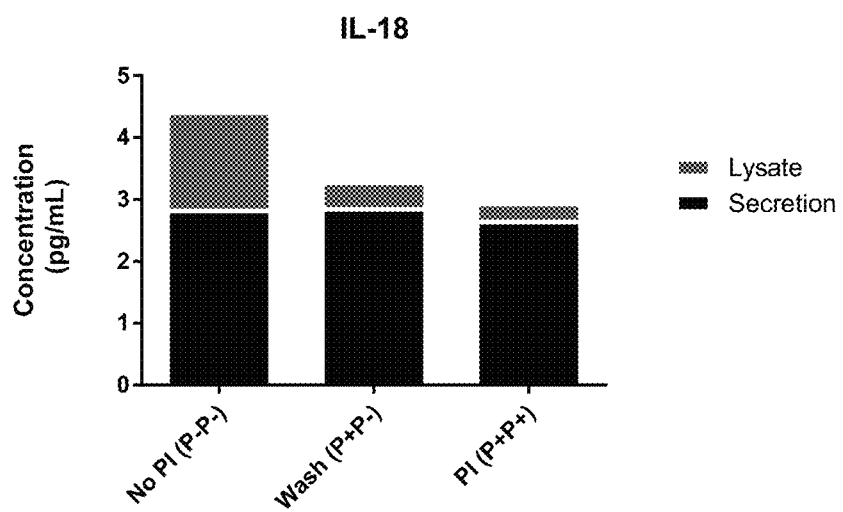
Figure 38L:
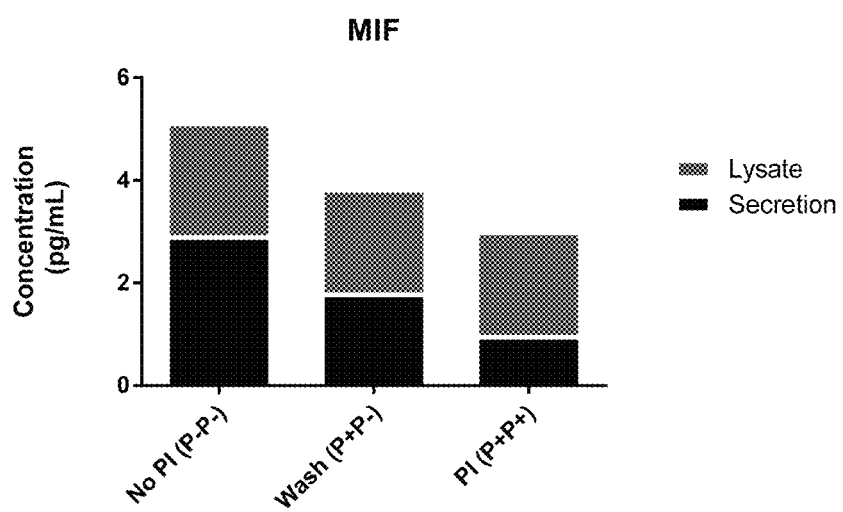
Figure 38M:
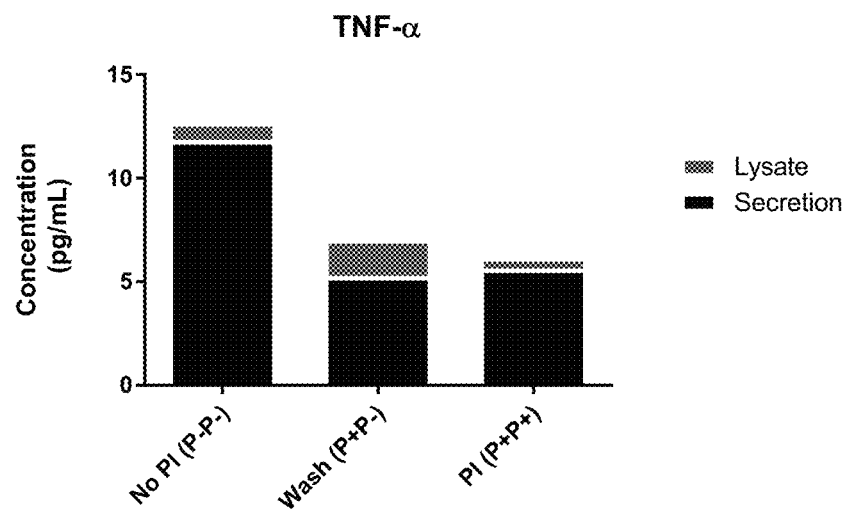
Figure 38N:
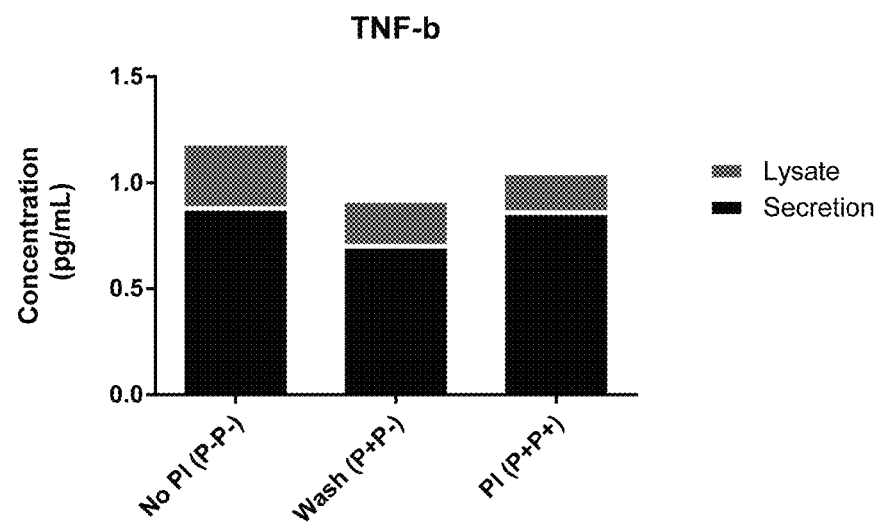
Figure 38O:
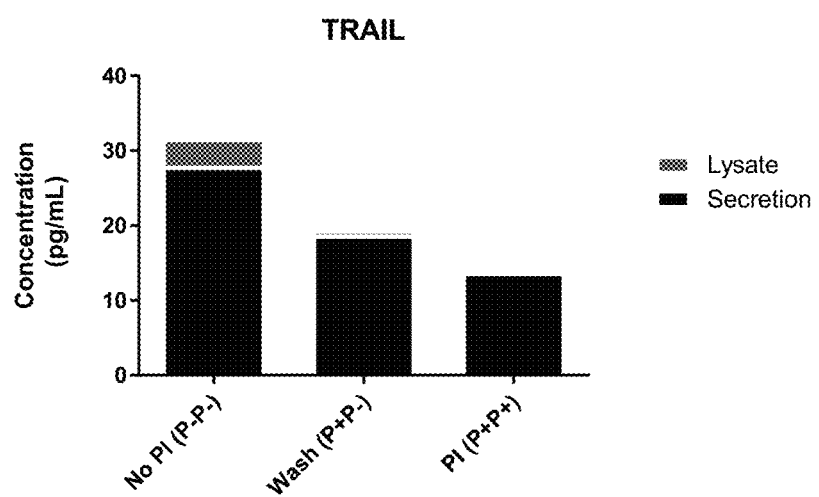
Figure 39A:
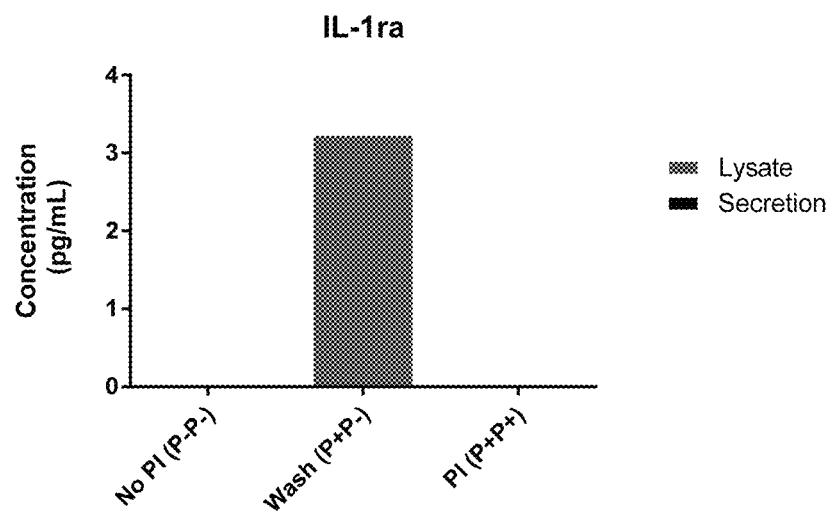
FIG. 39A-FIG. 39E is a series of graphs showing the total measured anti-inflammatory cytokines released or secreted from and in the lysate of RBCs after 48 hours incubation at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 39B:
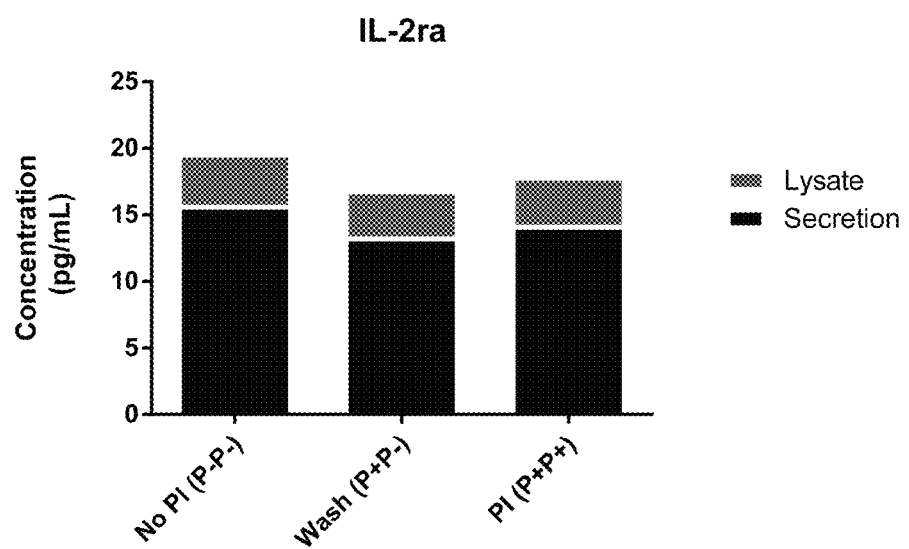
Figure 39C:
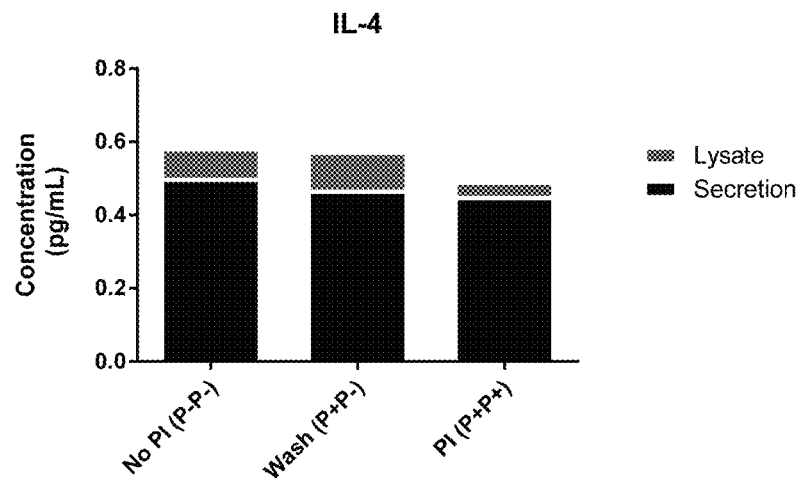
Figure 39D:
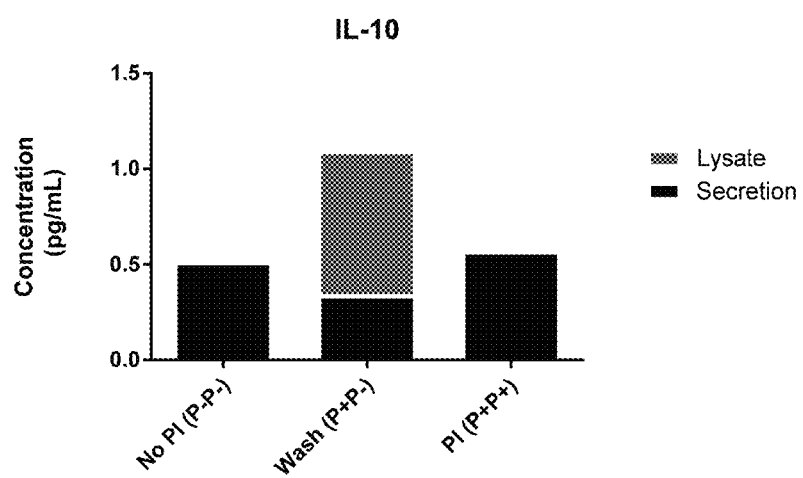
Figure 39E:
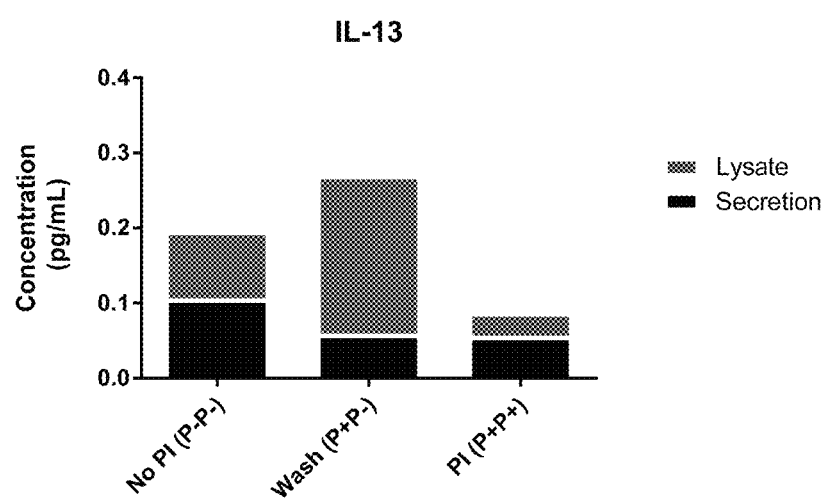
Figure 40A:
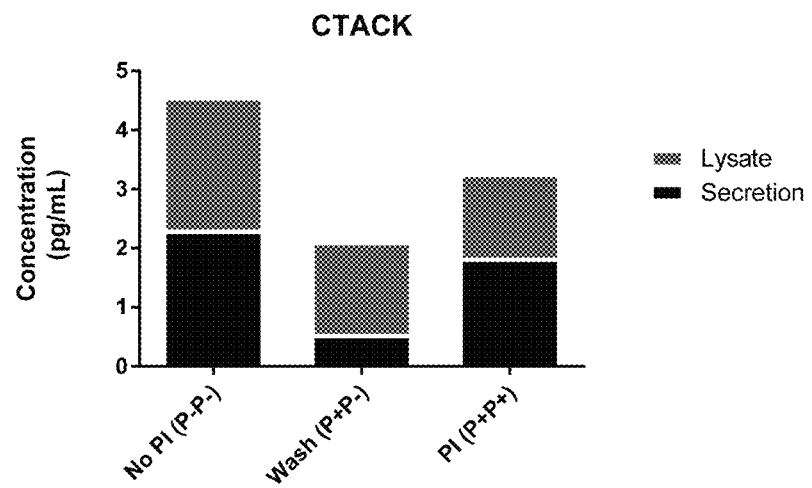
FIG. 40A-FIG. 40K is a series of graphs showing the total measured chemokines released or secreted from and in the lysate of RBCs after 48 hours incubation at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 40B:
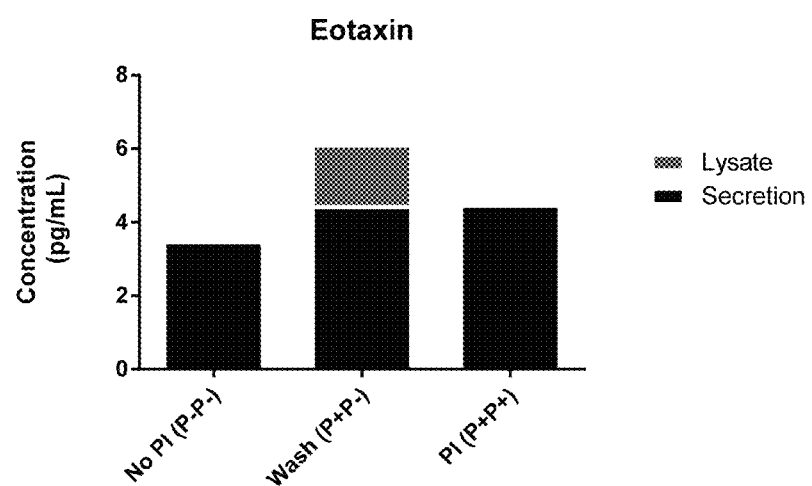
Figure 40C:
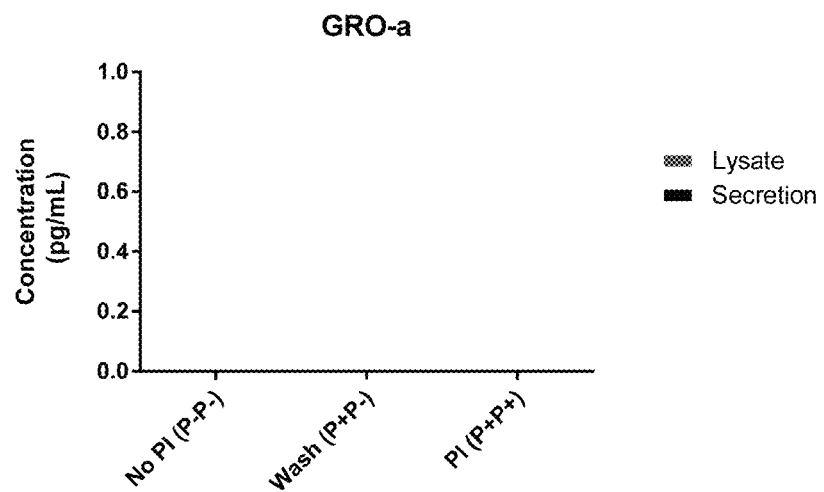
Figure 40D:
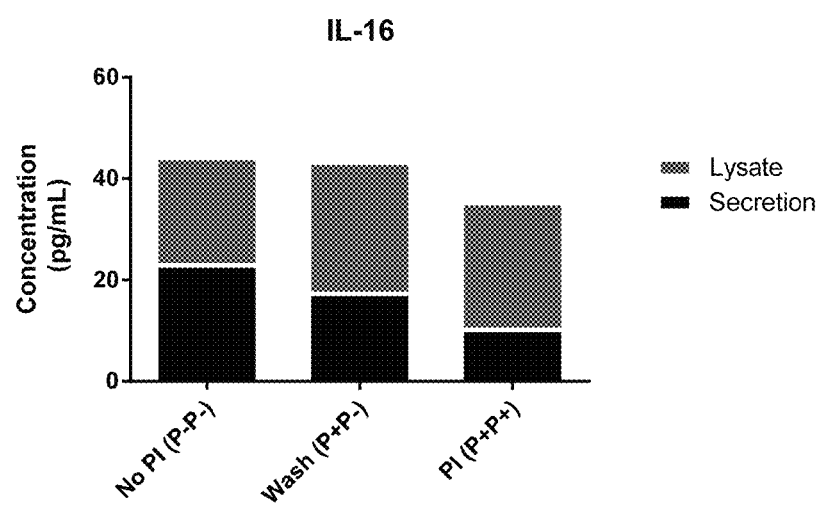
Figure 40E:
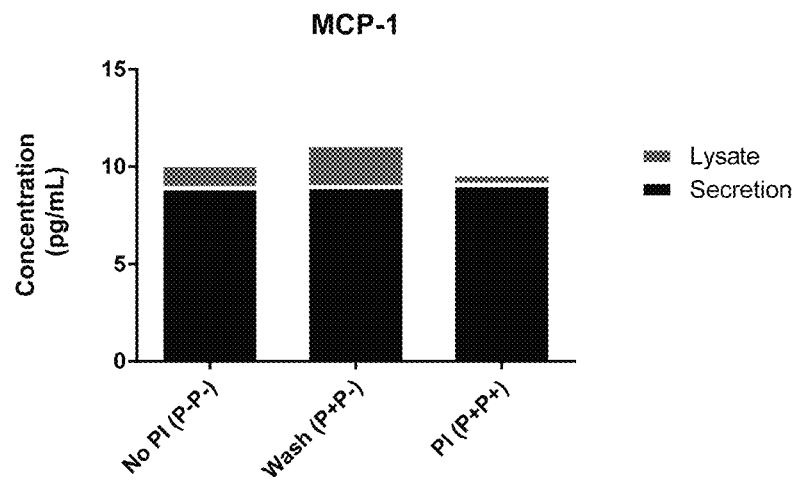
Figure 40F:
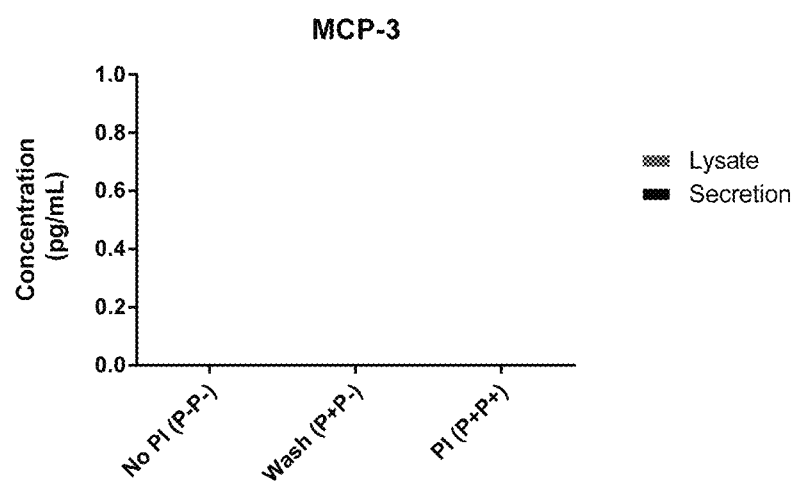
Figure 40G:
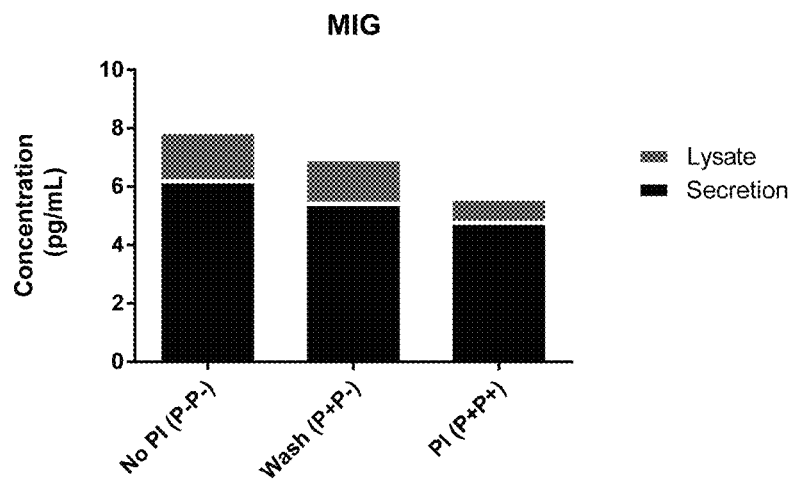
Figure 40H:
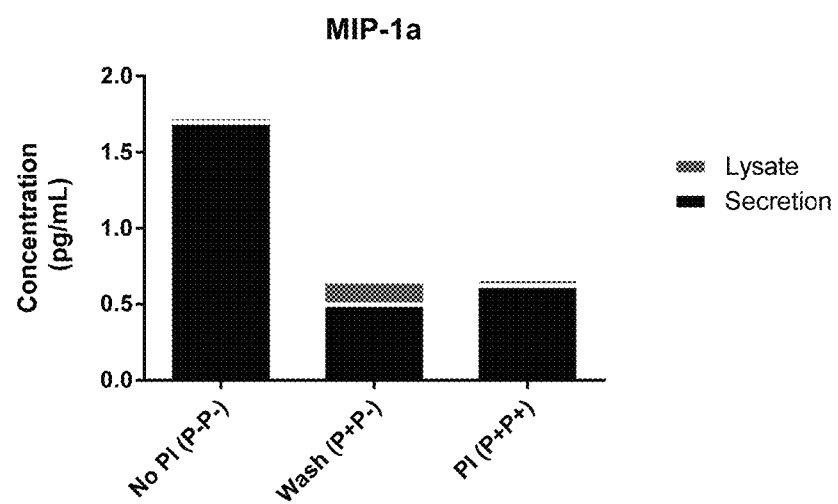
Figure 40I:
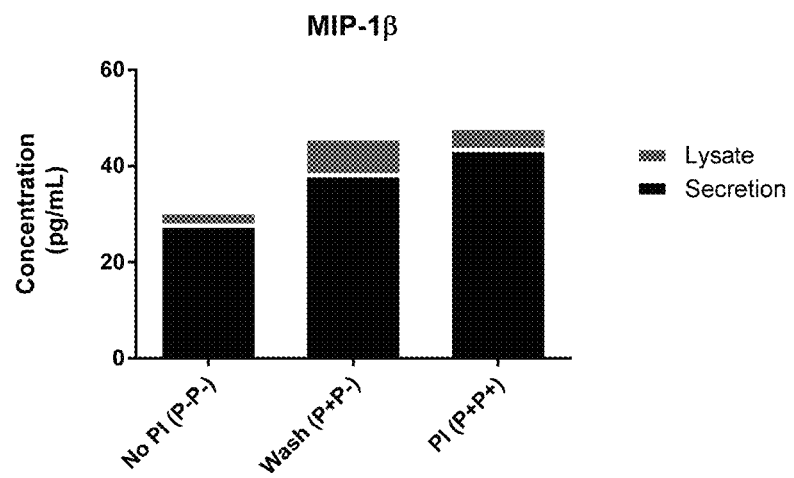
Figure 40J:
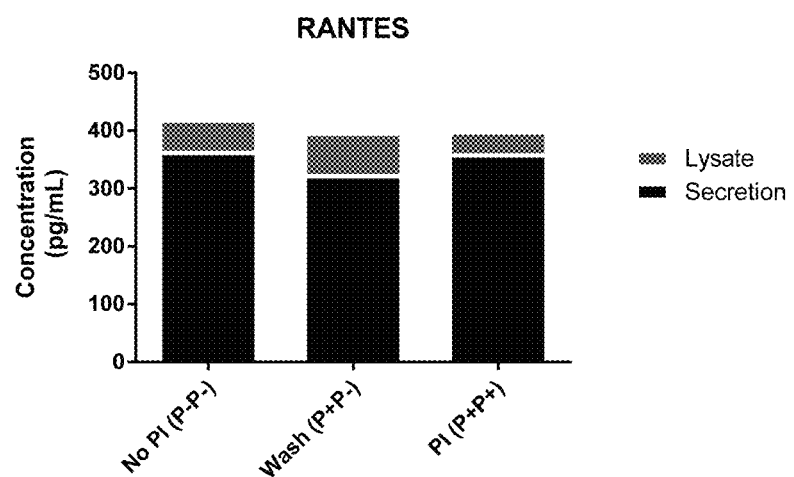
Figure 40K:
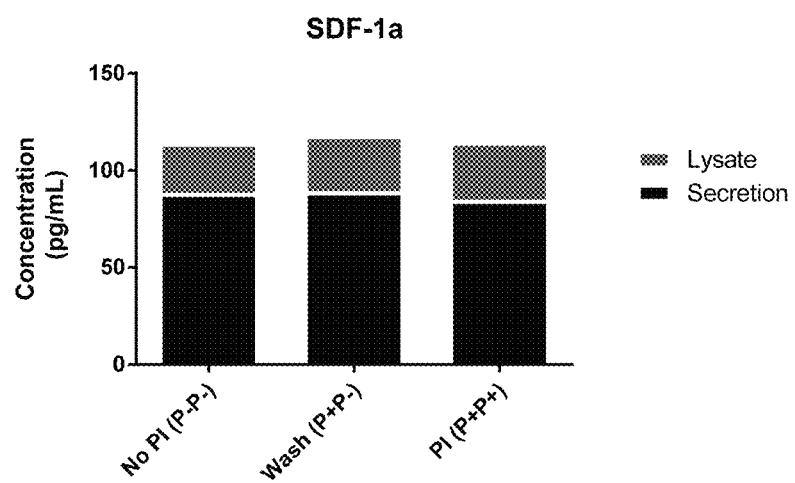
Figure 41A:
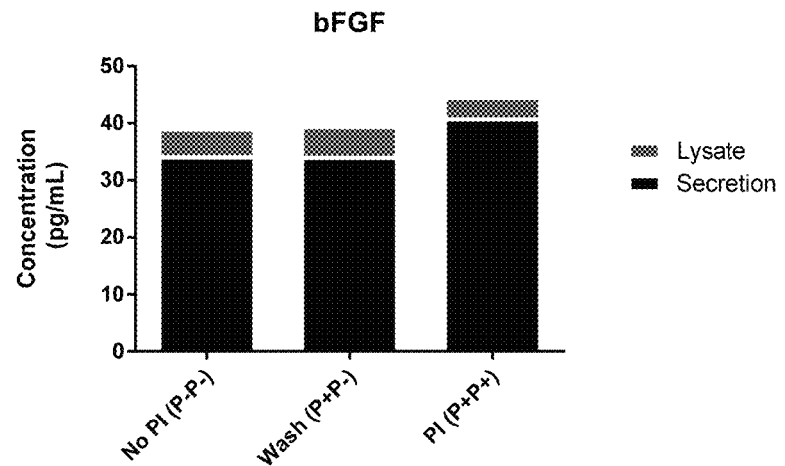
FIG. 41A-FIG. 41H is a series of graphs showing the total measured growth factors released or secreted from and in the lysate of RBCs after 48 hours incubation at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 41B:
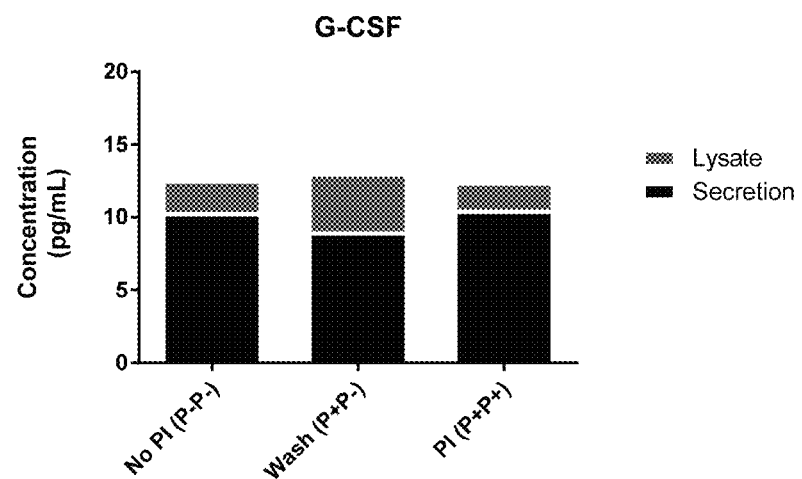
Figure 41C:
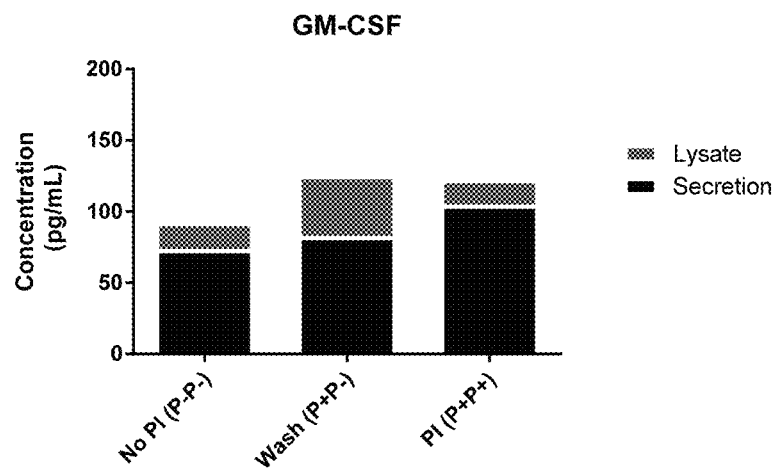
Figure 41D:
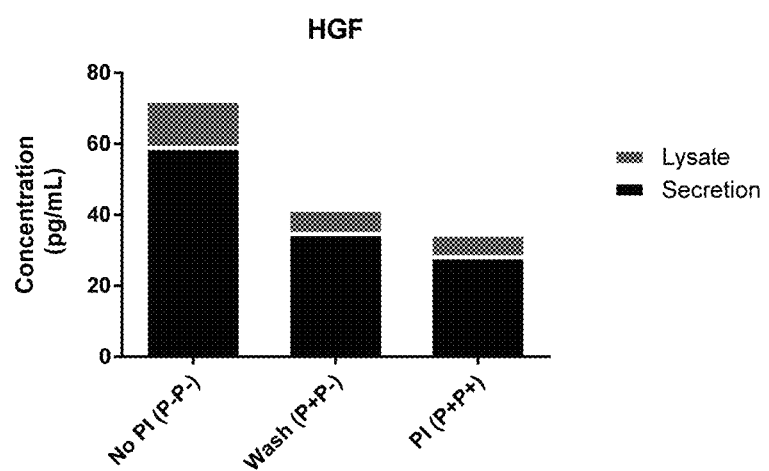
Figure 41E:
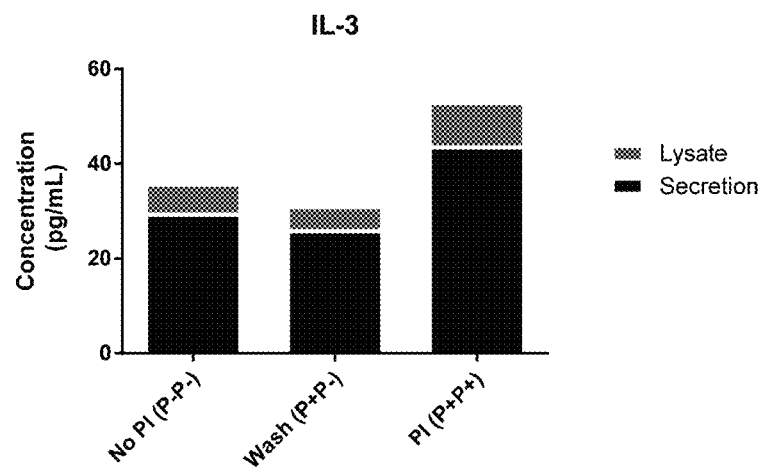
Figure 41F:
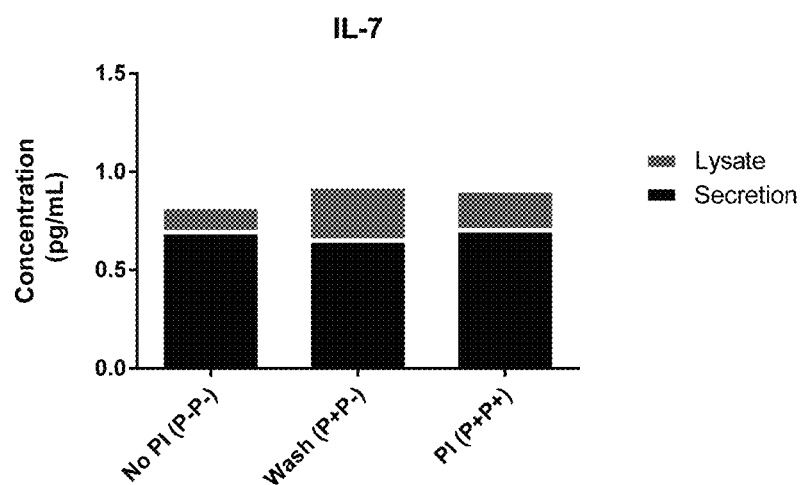
Figure 41G:
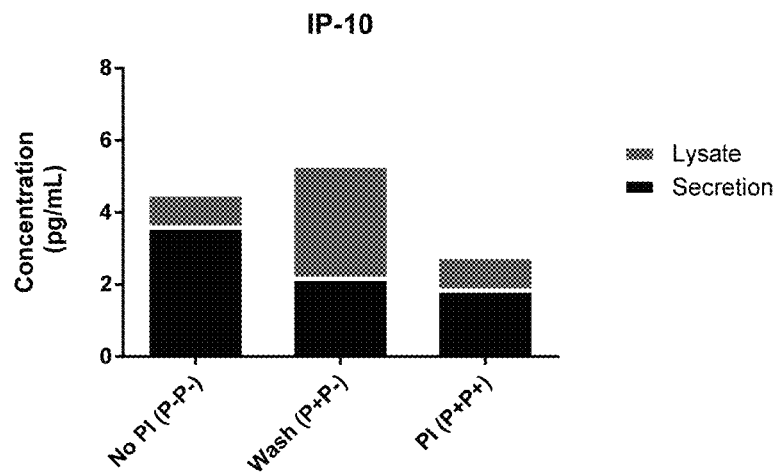
Figure 41H:
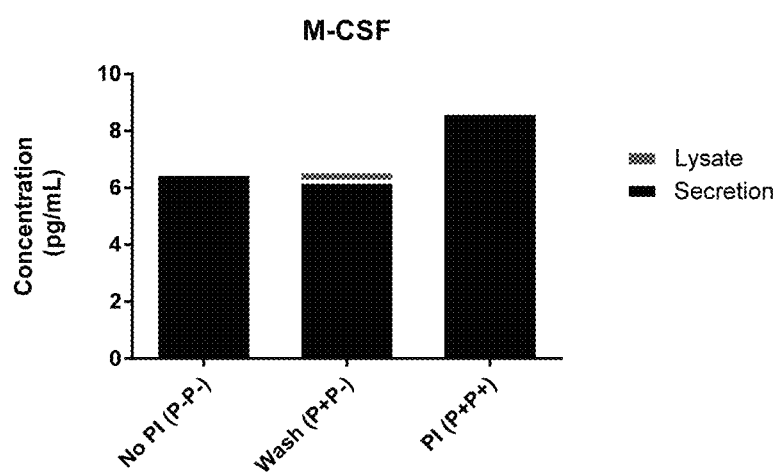
Figure 42A:
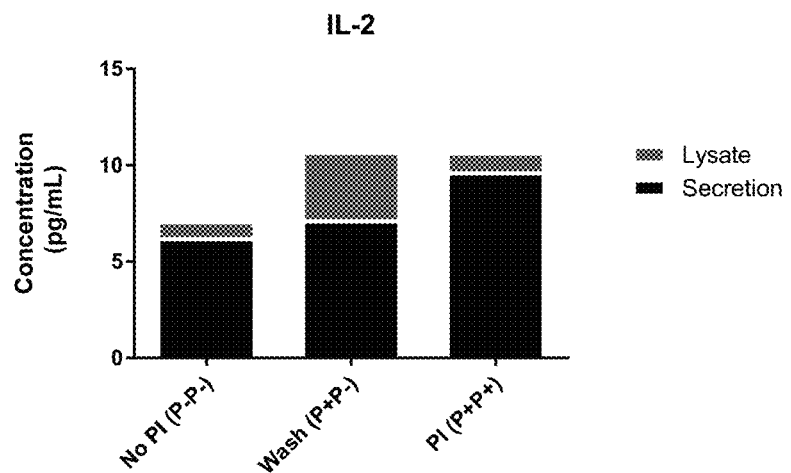
FIG. 42A-FIG. 42D is a series of graphs showing the total measured cytokines with multiple functions released or secreted from and in the lysate of RBCs after 48 hours incubation at 37° C. with or without protease inhibitors (PI) as measured by BioPlex and reported as pg/mL (20 million RBCs in 100 uL PBS). Cells were washed in PBS at 24 hours and resuspend in PBS with or without protease inhibitors. Data presented as mean±SD (n=3).
Figure 42B:
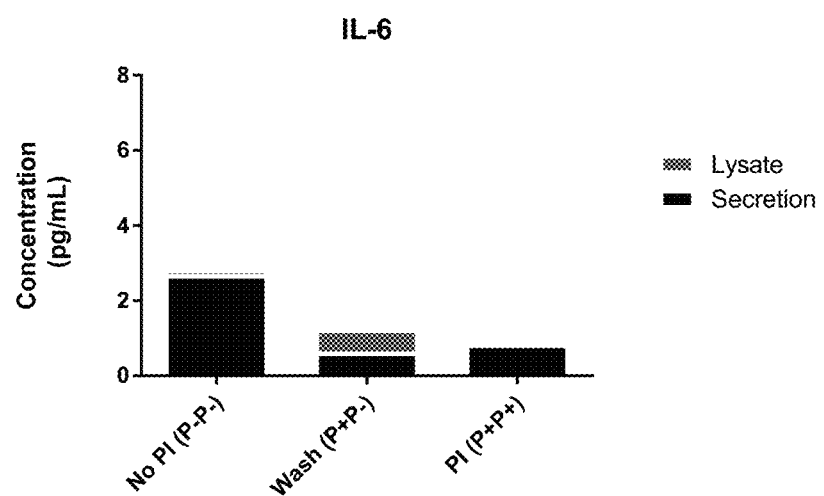
Figure 42C:
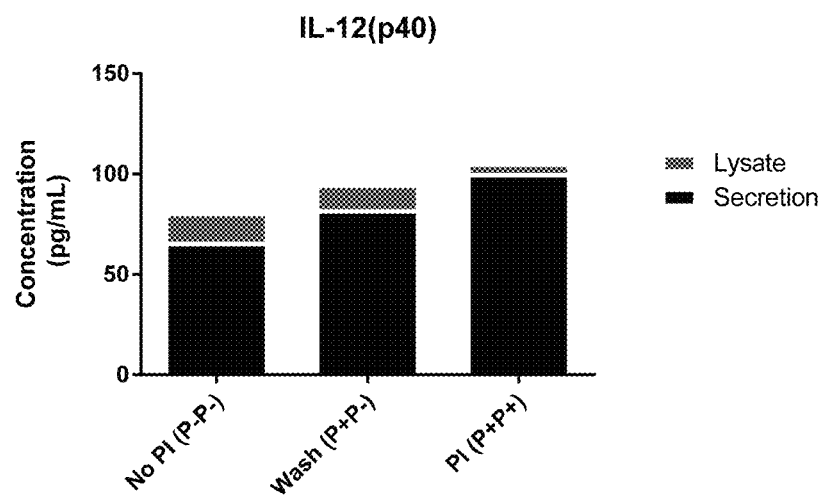
Figure 42D:
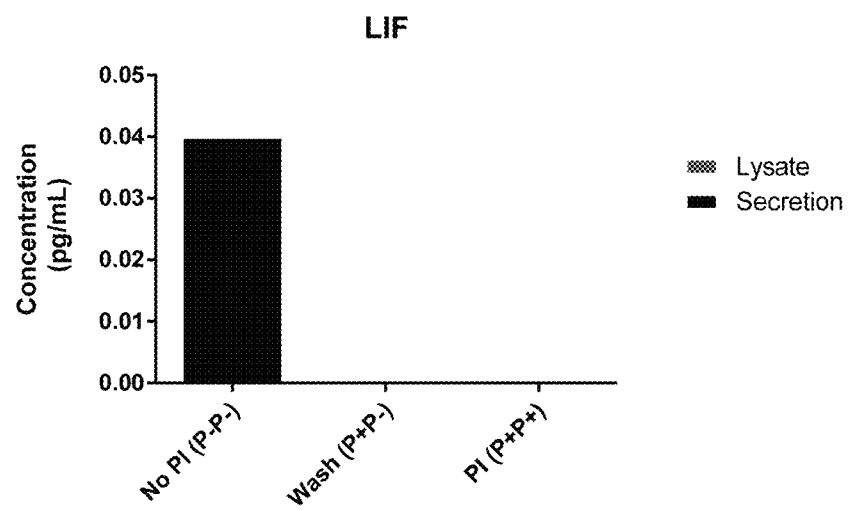

Example 2. Effect of Different Anticoagulants (Heparin, EDTA, and Citrate) at the Time of Blood Collection on the Binding Capacity of Red Blood Cells To determine if the anticoagulant used at the time of blood collection altered the capacity for protein binding to red blood cells, whole blood was collected into a variety of collection tubes containing anticoagulants. Whole blood from healthy volunteers was collected into either heparin vacutainers, EDTA vacutainers, or sodium citrate vacutainers. An aliquot of blood was collected without any anticoagulant, and coagulation was prevented by immediate dilution in PBS and cell washing. Following collection, RBCs were isolated from whole blood using dextran sedimentation (6% dextran, 1 hour, room temperature) and were washed twice in PBS. These RBCs were then resuspended in PBS (100 million cells/mL) and in the presence or absence of recombinant MIF (5 ng per test). This cell suspension was incubated for up to 24 hours (37° C., 5% $CO_2$). Following incubation, the cell free supernatants was collected and stored at −80° C. Prior to analysis, samples were subjected to ×2 freeze-thaw cycles. MIF concentration of the samples was quantified using a MIF ELISA. The addition of recombinant MIF (rMIF) to the cell suspensions altered the final concentration of MIF in the supernatant after 24 hours. In all but the heparin treated RBCs, the final concentration of MIF after rMIF incubation was lower than the control (FIG. 3). This demonstrates that either the addition of rMIF slowed overall secretion of endogenous MIF, or that the addition of rMIF increased the rate of MIF uptake, or that the rMIF accelerated protease activity and thus MIF degradation. The anticoagulants had a clear effect on the amount of MIF that was sequestered by the RBCs.

Example 3: Effect of Culturing RBCs in the Presence of Recombinant Proteins (BioPlex Standards)

Addition of recombinant MIF to RBCs in culture results in a much lower yield of MIF in the secretome than would be expected. To investigate if the same will be seen with the addition of other recombinant proteins (in the form of BioPlex standards), RBCs were incubated in the presence of a cocktail of recombinant protein. Whole blood was collected from healthy volunteers into EDTA vacutainers. RBCs were isolated using dextran sedimentation (6% dextran, 1 hour, room temperature). After sedimentation, RBCs were washed once in PBS, and then 20 million RBCs were resuspened in 100 µL PBS or 100 µL PBS containing protease inhibitors, with or without the addition of recombinant cytokines (BioPlex standards, 25 µL, standard 3). These cell suspensions were then incubated for 24 hours (37° C., 5% CO$_2$). Following incubation, the supernanat and the cells were separated by centrifugation, and each component were from at −80° C.

The samples were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

A number of proteins were released from RBCs cultured in PBS for 24 hours at 37° C. See FIG. 4A-FIG. 8D for protein classification as anti-inflammatory, pro-inflammatory, chemokines, or growth factors. The concentration of some cytokines in RBC lysates increased significantly ($p<0.05$) after incubation with recombinant proteins including IL-1α, IL-12p70, and TRAIL. Addition of protease inhibitors also had an effect on the amount of protein that was bound by the red blood cells particularly for IL-18, CTACK and SDF-1α (FIG. 9A-FIG. 13D). The total measured cytokines for both the cell free supernatant and the cell lysates are outlined in FIG. 14A-FIG. 18D. The total concentration of cytokines was reduced for a number of proteins with the inclusion of protease inhibitors, such as for IL-8, IL-10, and GRO-α (FIG. 14A-FIG. 18D). Protease inhibitors have an effect on the secretion profile of RBCs. In many cases, the use of protease inhibitors results in a smaller standard deviation. The protease inhibitors may be targeting a specific cell type or population of RBCs (i.e. older RBCs), thus reducing variability in the samples.

Example 4. Effect of Culturing MSCs in the Presence of RBCs or RBC Derivatives RBCs (and RBC derivatives) contain large concentrations of cytokines. In vivo RBCs and mesenchymal stem cells (MSCs) are frequently in contact, particularly in situations such as wound healing where a number of cells are present and are signaling. In a simplified model of this RBCs (and RBC derivatives) were incubated with MSCs and the secretion profile was assessed. Primary MSCs were cultured to confluence at passage 2 and were trypsonised were seeded into T25 flasks (10,000 cells per mL) in culture media (DMEM+10% FBS). These cells were incubated for 3 days (37° C., 5% CO$_2$) after which the media was replaced and RBCs, washed RBCs, or RBC ghosts (500 million cells per condition) were added to the relevant flasks. To prepare the red blood cells, whole blood was collected into EDTA vacutainers. RBCs were isolated by dextran sedimentation (6% dextran, 60 minutes, room temperature). Following sedimentation, the RBCs were washed once in PBS. To produce 'washed RBCs', the isolated RBCs were washed twice more in PBS by excessively shaking the cell suspension and centrifuging the cells. RBC ghosts were isolated by lying the RBCs in hypotonic water for 5 minutes. The ghosts were then isolated by centrifugation (16,000 g, 20 minutes) and were resuspended in PBS.

The MSCs were primed or treated with either nothing, intact RBCs, washed RBCs, or with RBC ghosts. These were then incubated for 72 hours (37° C., 5% CO$_2$). After incubation, the conditioned media and the RBCs or RBC ghosts were separated by centrifugation. The MSCs were trypsonised and the MSCs and RBCs were counted using flow cytometry and a haemotology analyser respectively. The conditioned media and RBCs were frozen at −80° C., and samples were subjected to 3× freeze/thaw cycles to lyse all the cells.

The samples were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

The secretion profile of the MSCs changed notably with the addition of RBCs. Less of a change was observed with the washed RBCs and the ghosts. The concentration of a number of cytokines increased in the RBC lysate after culture, indicating that the cells bound some of the extracellular cytokines, particularly IL-8 and IL-6 (FIG. 19A-FIG. 23D). Cell counts differed according to the culture conditions. MSCs cultured with RBCs had the highest yield of MSCs after culture. Similarly, after culture, there was a higher yield of RBCs that the washed RBCs (Table 2). Incubation with intacts RBCs had a major effect on the secretion profile and proliferation of MSCs, and the RBCs sequestered a proportion of certain cytokines (i.e. IL-8), this may be part of a RBC cytokine buffering system.

TABLE 2

Cell count and viability of MSCs after culture with or without RBC (or RBC derivatives) as measured by flow cytometry for the MSCs and the hematology analyser for the RBCs (n = 1).

| Conditions | MSCs | | RBCs |
|---|---|---|---|
| | Av. Viability (%) | Total # | |
| MSCs | 99 | 241,000 | — |
| MSCs + RBCs | 98.7 | 338,000 | 483,000,000 |
| MSCs + washed RBCs | 98.3 | 317,000 | 435,000,000 |
| MSCs + ghosts | 99.7 | 312,000 | — |

Example 5. Effect of Shear Force on RBCs

RBCs are constantly subjected to shear forces in vivo when travelling from venous circulation into capillary beds. The release of proteins from RBCs or whole blood (WB) in response to mechanical stress was tested. Whole blood was collected from healthy volunteers into EDTA vacutainers. RBCs were then isolated by dextran sedimentation (6% dextran, 1 hour, room temperature). Following sedimentation, the isolated RBCs were washed once in PBS and were resuspended in PBS to achieve a 40% haematocrit. An aliquot of the WB or RBCs were then subjected to mechanical stress by adding 500 μL of the blood sample to a 1 mL insulin syringe with a 29 gauge needle. Using a weight, the blood was slowly forced out of the needle and was collected at the bottom. The WB or RBCs were either analysed immediately (fresh), after 1 hour at room temperature (fresh+1 hr) or were freeze-thawed to lyse all of the cells (frozen) before analysis. All blood samples were run on the iChroma machine with the hsCRP kits according to the manufacturer's instructions.

Mechanical stress did have an effect on the overall levels of CRP (Table 3), suggesting that CRP was unbound or produced immediately after stress. Of note, 1 hour after the mechanical stress, the levels of CRP dropped in the WB sample from 0.95 mg/L to 0.21 mg/L, but did not change in the control (unstressed) sample. This suggests that enzymes may have been activated causing degradation of CRP. RBC lysis did not appear to have occurred after being pushing through the needle.

In this instance, the RBCs do not appear to be the major contributor of CRP in WB. The distribution of CRP in blood appears to vary day to day. The levels of CRP increased immediately after mechanical stress. This suggests that the CRP was unbounbg or was produced immediately, which enabled detection by the antibody.

TABLE 3

CRP levels (mg/L) in whole blood (WB) and red blood cells (RBCs) with and without mechanical stress stimuli (needle). CRP levels were measured using hsCRP kits on the iChroma instrument.

| Sample type | | Collection details | [CRP] mg/L | Adjusted [CRP] mg/L |
|---|---|---|---|---|
| WB | (fresh) | Subject 1 | 0.76 | 0.76 |
| | (frozen) | | 0.80 | 0.80 |
| | (fresh) + 1 hr | | 0.88 | 0.88 |
| WB (needle) | (fresh) | Subject 1 | 0.95 | 0.95 |
| | (frozen) | | 0.98 | 0.98 |
| | (fresh) + 1 hr | | 0.21 | 0.21 |
| RBCs | (fresh) | Subject 1 | <0.1 | <0.1 |
| | (frozen) | | <0.1 | <0.1 |
| RBCs (needle) | (fresh) | Subject 1 | 0.11 | 0.11 |
| | (frozen) | | <0.1 | <0.1 |

Example 6. Effect of Hypoxia on RBC and RBC Ghost Activity

Blood is a highly oxygenated environment and changes in oxygen content is likely to have secondary effects on protein content. In order to test if the MIF concentration of RBCs is affected by altered oxygen conditions, RBCs were incubated in hypoxic PBS. Hypoxic PBS was produced by incubating PBS in a nitrogen chamber for ≥18 hours (5% $CO_2$, 3% $O_2$, 92% $N_2$). Whole blood was collected from healthy volunteers into EDTA vacutainers. RBCs were then isolated by dextran sedimentation (6% dextran, 1 hour, room temperature). Following sedimentation, the isolated RBCs were washed twice in PBS. RBC ghosts were isolated by lysed the RBCs in hypotonic water for 5 minutes. The ghosts were then isolated by centrifugation (16,000 g, 20 minutes). The intact RBCs or RBC ghosts (10 million) were added to hypoxic PBS or normoxic PBS (100 μL) in Eppendorf tubes with 17 IU/mL of heparin. These tubes were then completely sealed and the cell suspensions were incubated for 1 hour or 18 hours (37° C.). Following incubation, the conditioned PBS was collected and stored at −80° C. and was subjected to ×3 freeze-thaw cycles. The RBCs or RBC ghosts 'primed' under hypoxic conditions were then added to autologous plasma and were then incubated for a further 1 or 18 hours (37° C.). Following this incubation, the supernatant (conditioned plasma) was collected and stored at −80° C. and was subjected to ×3 freeze-thaw cycles.

Hypoxia noticeably decreased MIF release from RBCs, but did not seem to affect release of MIF from RBC ghosts (Table 4). This supports that protein release is somehow linked to oxygen content. The concentration of MIF in RBC lysates incubated under hypoxic conditions was much lower than the RBC control (0 hours), it is likely that protein degradation was occurring during culture (Table 5).

Hypoxia had an effect on the released MIF levels from RBCs and the intracellular MIF concentration. It is possible that protein degradation occurred as a result of the hypoxic environment (Table 5). IF the opposite is true (hyper-oxidataive environment), it may be a way to modulate protein levels and binding to RBCs.

TABLE 4

MIF release from RBCs and ghosts incubated in PBS or hypoxic PBS for 18 hours with heparin (17 IU/mL), (n - 1).

| Sample | | MIF (ng/mL) |
|---|---|---|
| PBS | RBCs | 14.95 |
| Hypoxic PBS | RBCs | 5.87 |
| PBS | Ghosts | 16.01 |
| Hypoxic PBS | Ghosts | 15.40 |

TABLE 5

RBC lysate and RBC ghost 'lysate' incubated in PBS or hypoxic PBS for 18 hours with heparin (17 IU/mL), (n = 1).

| Sample | | MIF (ng/mL) |
|---|---|---|
| Hypoxic PBS | RBCs | 10,147 |
| | RBCs - 0 hrs | 17,658 |
| Hypoxic PBS | Ghosts | 678 |

Example 7. Identification of Proteins Released or Secreted from RBCs Over Time A number of proteins have been identified in RBC lysates. To investigate if RBCs may also secrete these proteins, RBCs were incubated overnight in PBS and the conditioned media was analysed. Analysis of the secretome negates possible issues with haemolgobin that is present in RBC lysates. Whole blood was collected from healthy volunteers into EDTA vacutainers. RBCs were then isolated by dextran sedimentation (6% dextran, 1 hour, room temperature). Following sedimentation, the isolated RBCs were washed twice in PBS. Isolated RBCs were aliquoted to 20 million cells in 100 μL of PBS with or without protease inhibitors.

These cell suspensions were then incubated at for 24 hours (37° C., 5% $CO_2$). After incubation, the conditioned media and the cells were separated by centrifugation. These samples were then frozen at −80° C. and the samples were subjected to 3× freeze/thaw cycles to ensure complete cellular lysis. Following lysis, the red blood cell lysates and conditioned media samples were diluted in PBS to the equivalent of 400 million cells/mL. These samples were then analysed on the multiplex cytokine assays. Two multiplex assays were utilised. The first was the 27-plex human cytokine panel that assays for FGF basic, Eotaxin, G-CSF, GM-CSF, IFN-γ, IL-β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

A number of proteins were released or secreted after the RBCs were incubated in PBS for 24 hours (FIG. 24A-FIG. 27). FIG. 24A-FIG. 27 are separated according to the mean detected concentration of each protein. The addition of protease inhbitors during RBC culture also altered protein release. Inclusion of protease inhibtiors in the cell suspensions typically resulted in lower detectable concentrations in both the conditioned media and the cell lysate, although there were some exceptions such as MIP-1β (FIG. 28A-FIG. 42D). The inclusion of protease inhibitors also reduced the biological variation between biological replicates in the concentration of cytokines.

Example 8. Modulation of Protease Inhibitor Effect

The inclusion of protease inhibitors to a blood sample during storage at 37° C. alters the secretion profile of RBCs. In order to test if this activity was irreversible, the protease inhibitors were washed off RBCs after incubation for 24 hours and the cells were incubated for a further 24 hours to monitor differences in the cytokine profile of the resulting conditioned media. Whole blood was collected from healthy volunteers into EDTA vacutainers. RBCs were isolated by dextran sedimentation (6% dextran, 1 hour, room temperature). Following sedimentation, the isolated RBCs were washed twice in PBS. Isolated RBCs were in aliquots of 20 million cells in PBS or PBS with protease inhibitors (100 µL) as outlined in Table 5. The cell suspensions were then incubated for 24 hours (37° C., 5% $CO_2$). After incubation, the supernatant and the cells were separated by centrifugation and the supernant was collected and frozen at −80° C. The remaining cells were washed twice in PBS and were then resuspended in an aliquot of fresh PBS or PBS with protease inhibitors (100 µL) as outlined in Table 5. These cell suspensions were then incubation for an additional 24 hours (37° C., 5% $CO_2$). After incubation, the cells and supernatant were separated by centrifugation, and these samples were frozen at −80° C. and were subjected to 3× freeze/thaw cycles to ensure complete lysis.

The samples were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminexr® 200™ system (Bio-Rad) and fluorescent values were collected. The calibration curve for each cytokine was analysed with 5 parametric logistic curve regression using BioPlex manager software (ver. 5.0, Bio-Rad, USA).

Example 9. Red Blood Cell Secretions after Priming with Various Cell Types

Whole blood was collected from healthy volunteers (n=1). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

Cells representing neutral tissues such as endothelial (HUVEC), primary fibroblast, renal cells (HEK-293) were chosen along with representative cancer cell lines from bowel cancer (HT-29) and melanoma (MEWO). Cell lines were expanded in culture media consisting of (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, cells were seeded into T75 flasks at a concentration of $0.1 \times 10^6$ cells per mL of culture media and were incubated for 24 hours to ensure plate adherence (37° C., 5% $CO_2$). After incubation, the conditions as outlined in Table 6 were prepared using freshly isolated red blood cells. For co-culture with red blood cells the total volume of culture media in T75 flasks was 18 mL.

TABLE 6

Co-culture conditions for all representative cell lines and red blood cells (RBCs) at a ratio of 1:100 at 37° C., 5% $CO_2$ for 72 hours.

| Condition | Label | Flask size | Cells seeded | Red blood cell number |
|---|---|---|---|---|
| Cells:RBCs (1:100) | Primed | T75 | $2 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were washed once with PBS and counted using a haematology analyser (Coulter Act Diff, Beckman Coulter).

The red blood cells were then diluted in PBS to the equivalent of 400 million cells/mL. The red blood cells were next incubated in PBS for 24 hours, at 37° C. and 5% $CO_2$. After the incubation, the red blood cells were removed by centrifugation (500 g, 10 minutes) and the supernatants containing the red blood cell secretions were retained and analysed. Two multiplex assays were utilised: the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 43A:
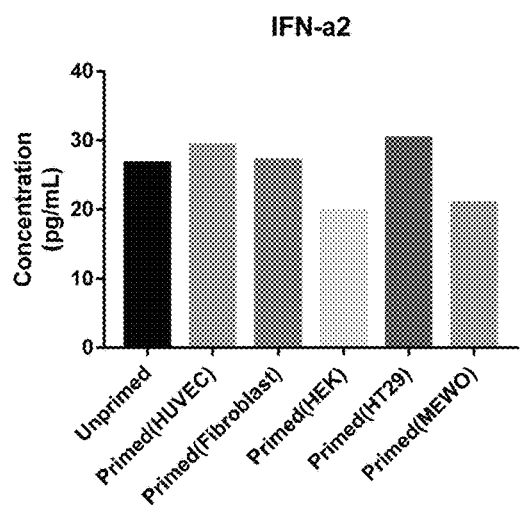
FIG. 43A-43VV is a series of graphs showing the concentration of proteins released from red blood cells following co-culture for 3 days with (primed RBCs) or without (unprimed RBCs) representative cell lines.
Figure 43B:
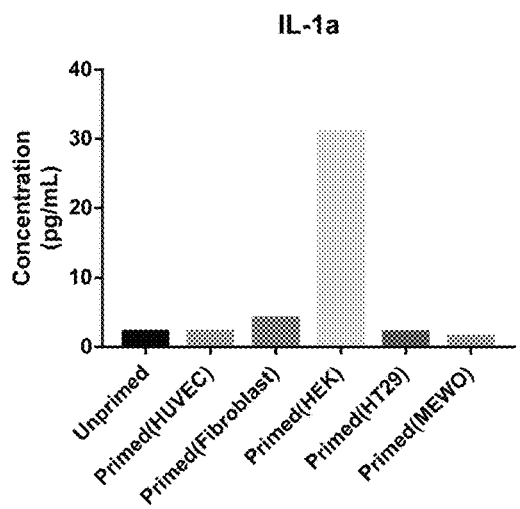
Figure 43C:
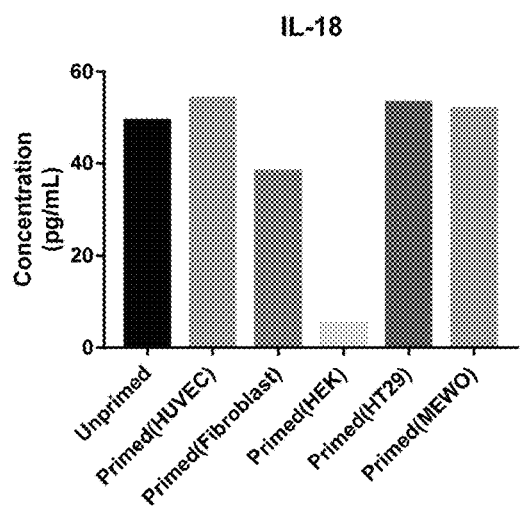
Figure 43D:
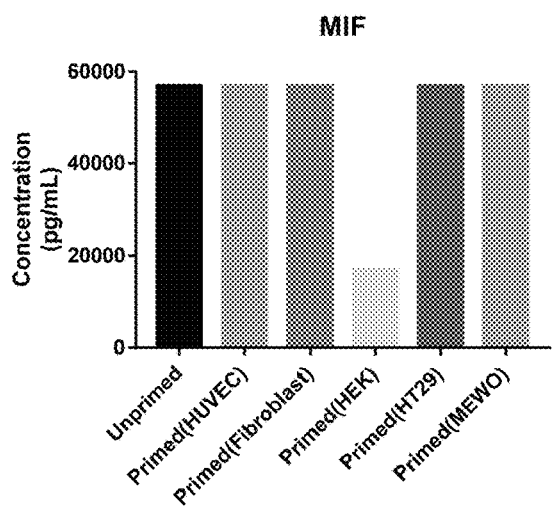
Figure 43E:
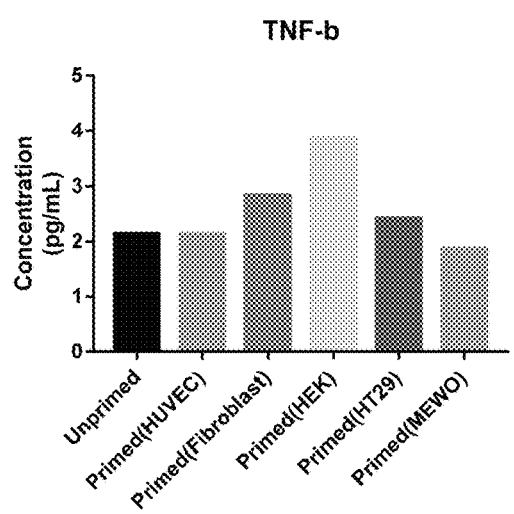
Figure 43F:
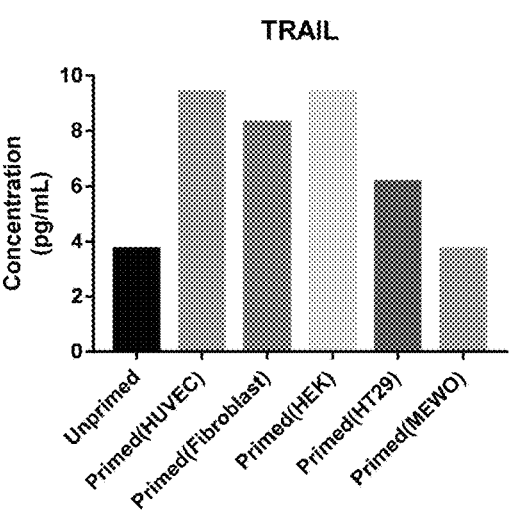
Figure 43G:
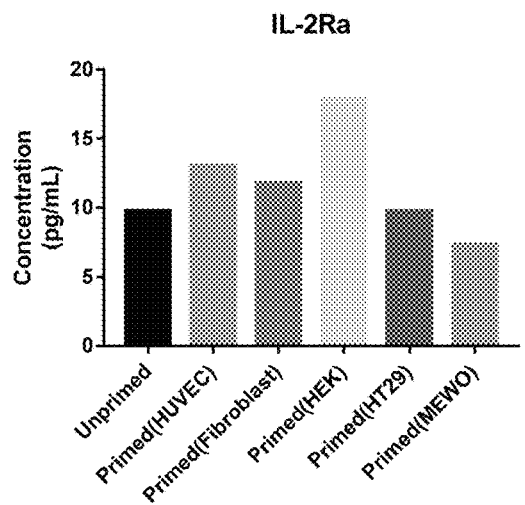
Figure 43H:
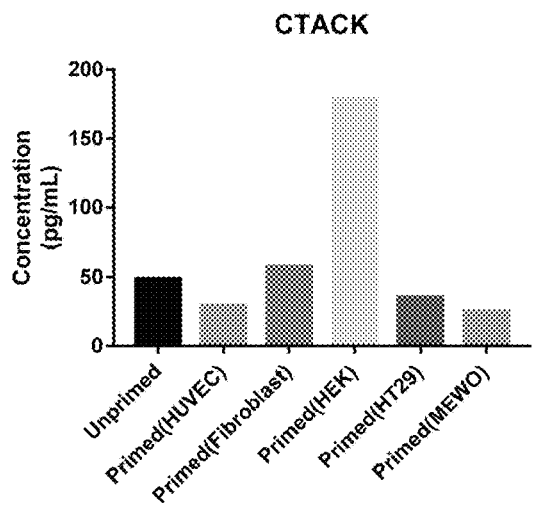
Figure 43I:
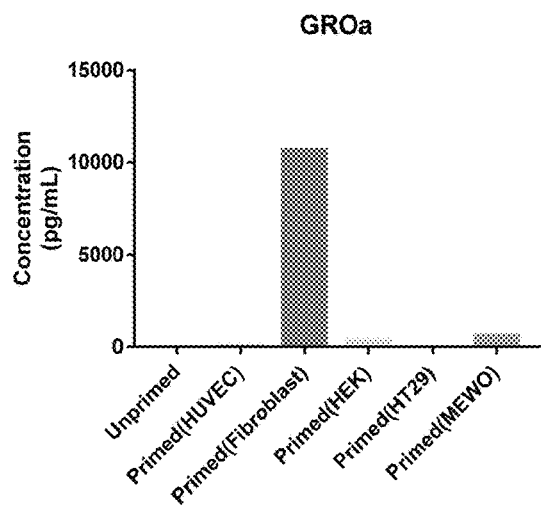
Figure 43J:
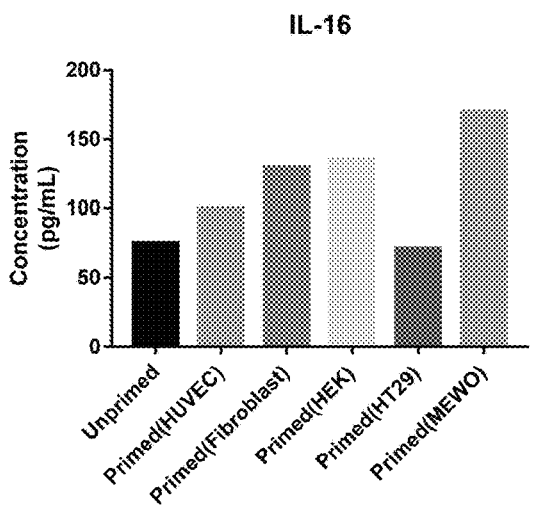
Figure 43K:
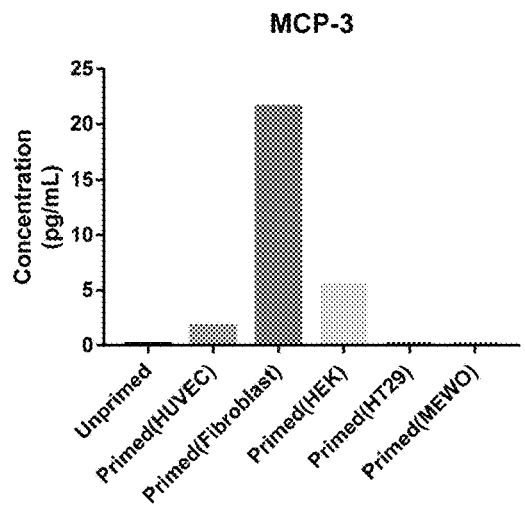
Figure 43L:
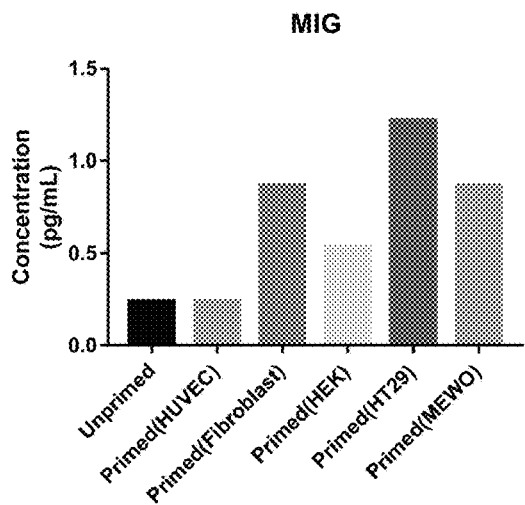
Figure 43M:
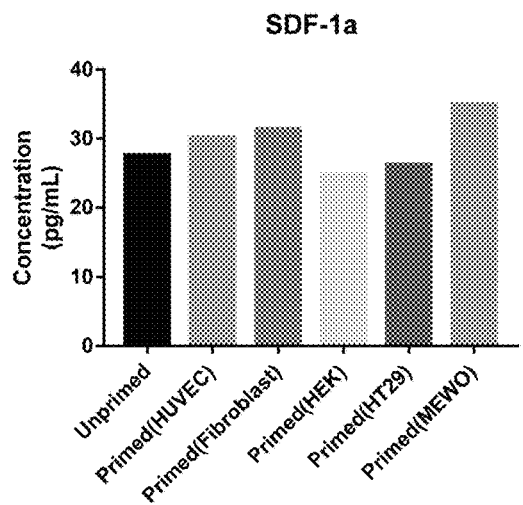
Figure 43N:
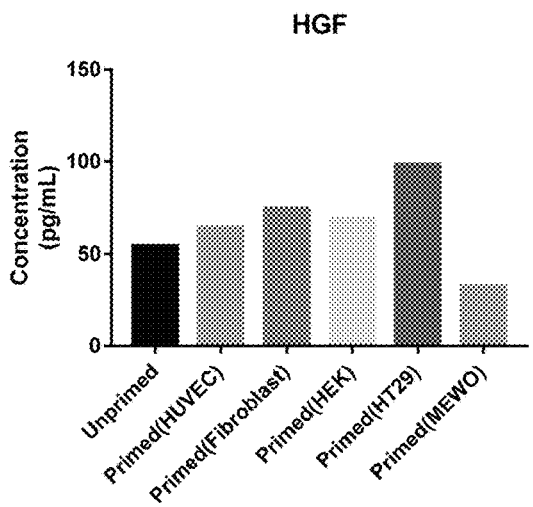
Figure 43O:
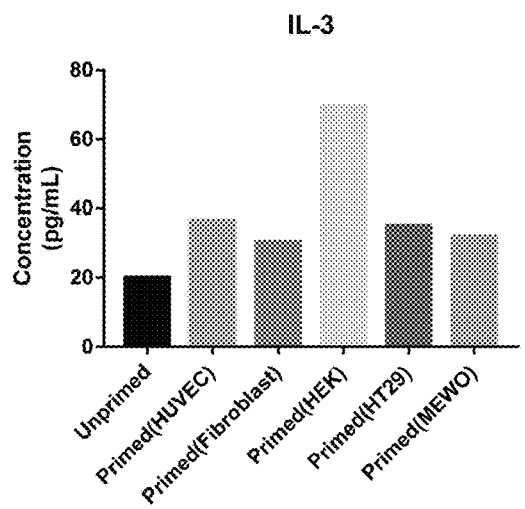
Figure 43P:
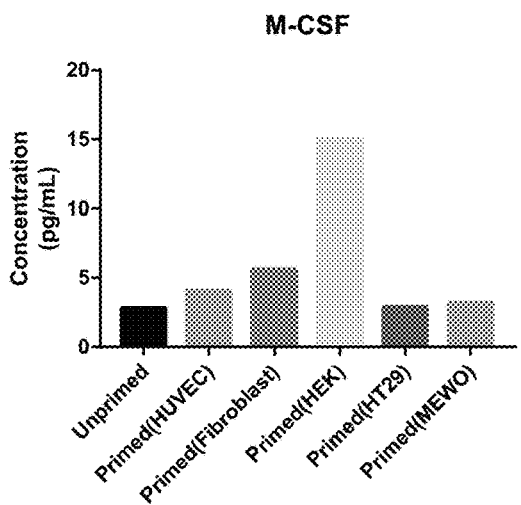
Figure 43Q:
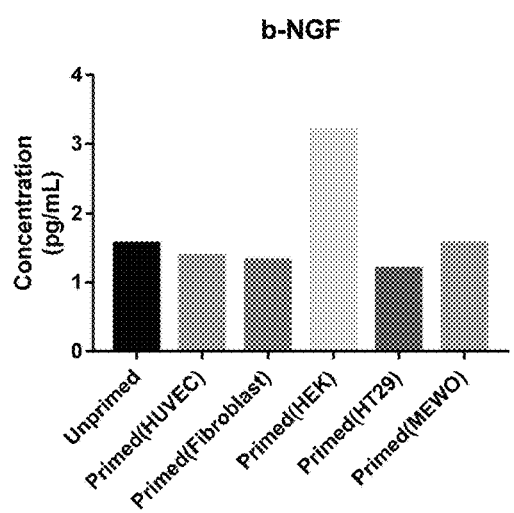
Figure 43R:
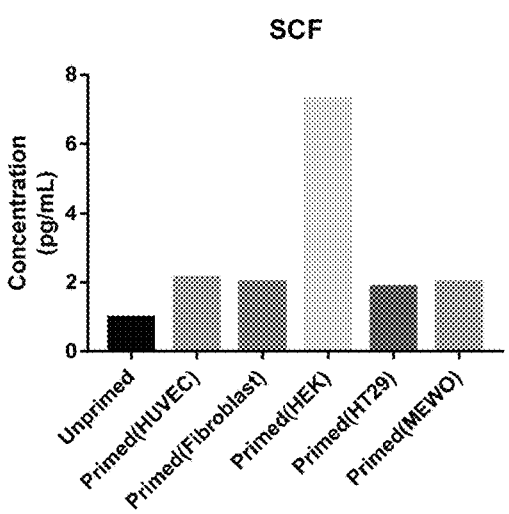
Figure 43S:
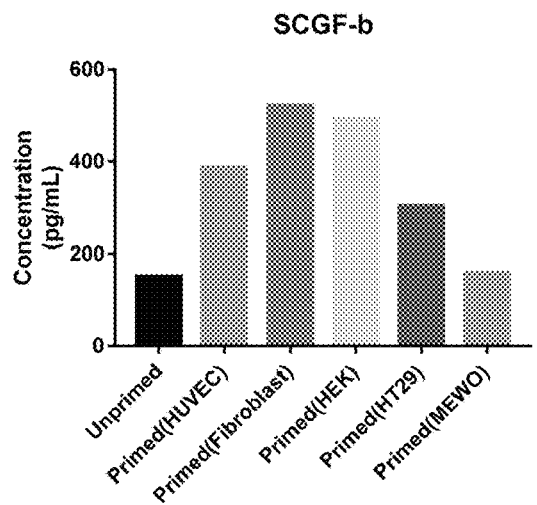
Figure 43T:
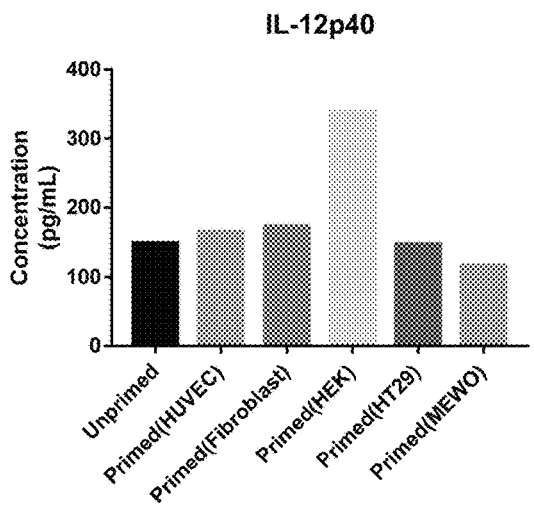
Figure 43U:
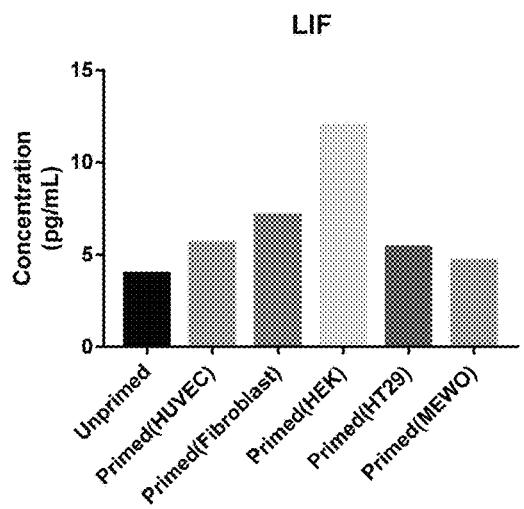
Figure 43V:
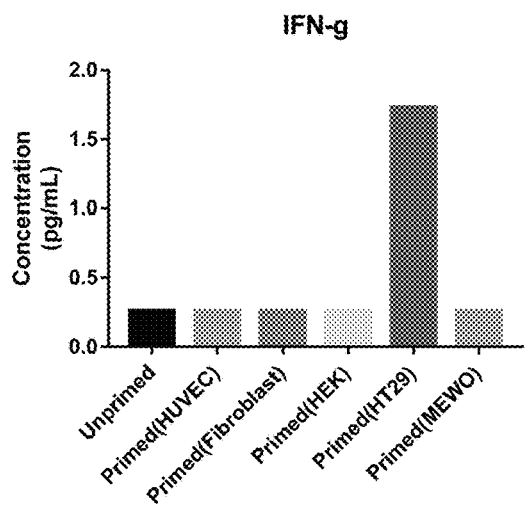
Figure 43W:
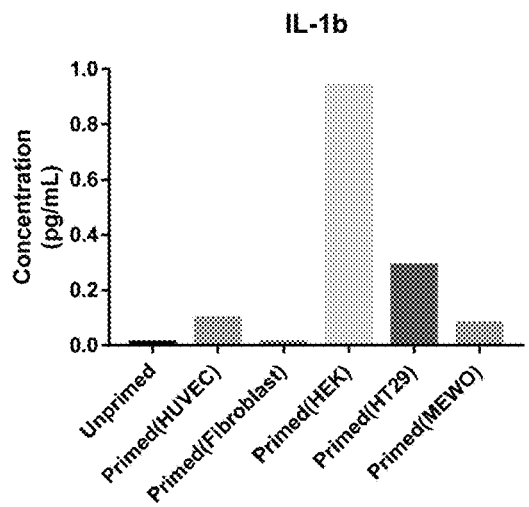
Figure 43X:
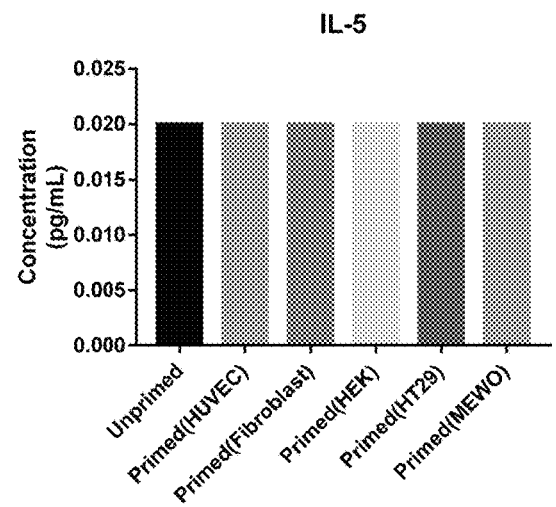
Figure 43Y:
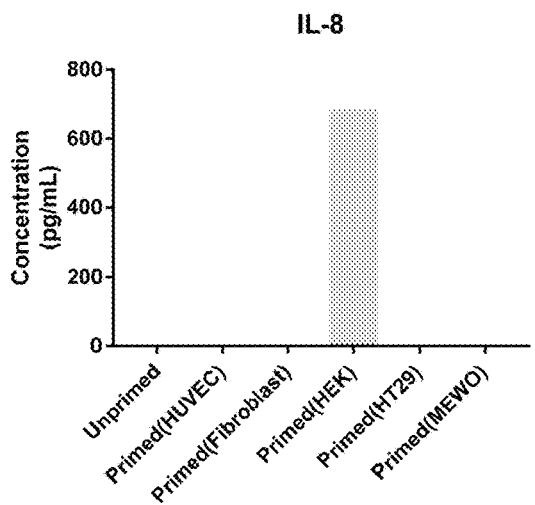
Figure 43Z:
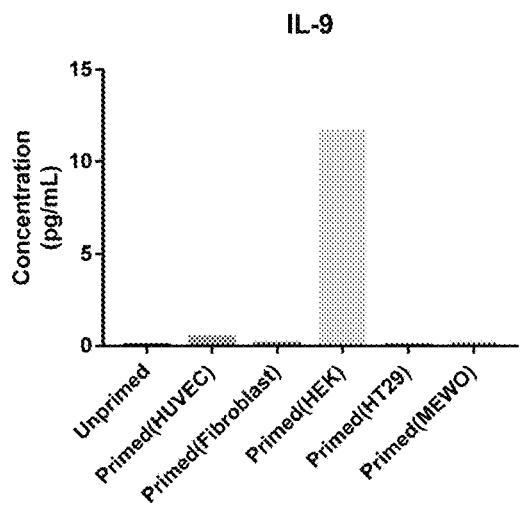
Figure 43A:
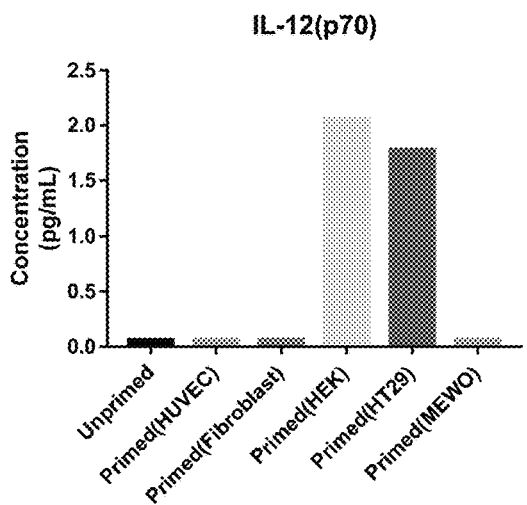
Figure 43B:
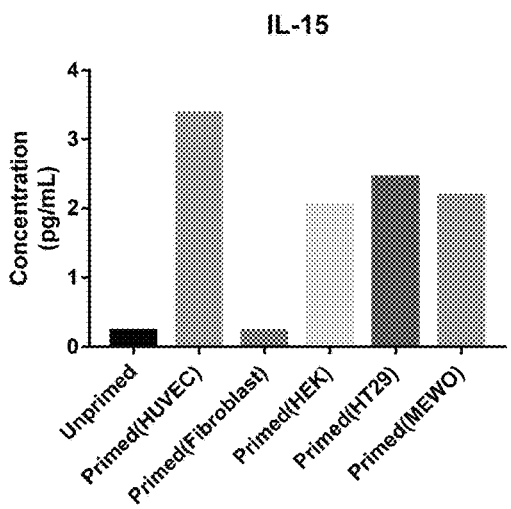
Figure 43C:
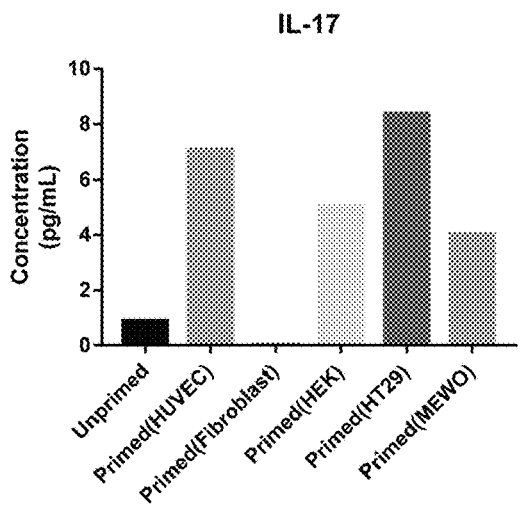
Figure 43D:
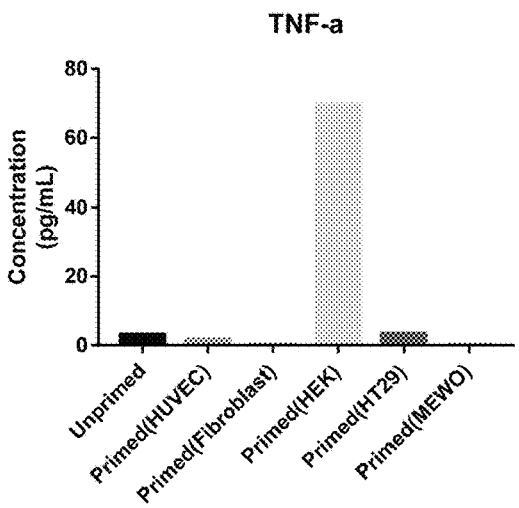
Figure 43E:
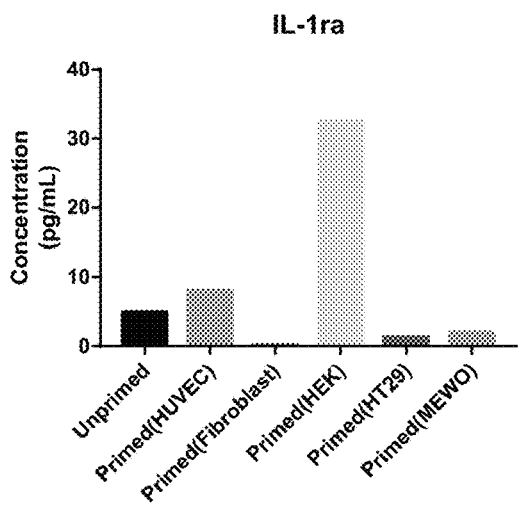
Figure 43F:
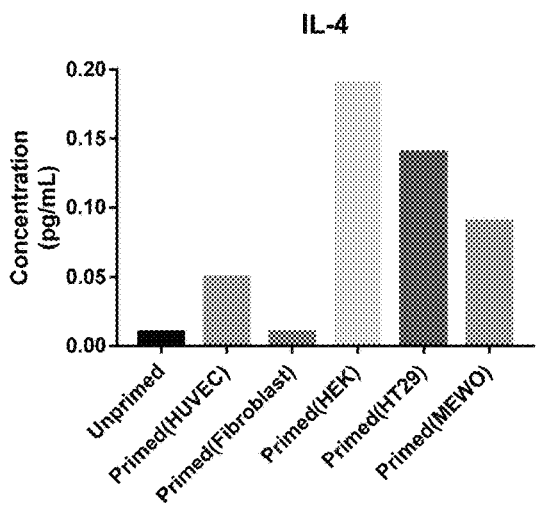
Figure 43G:
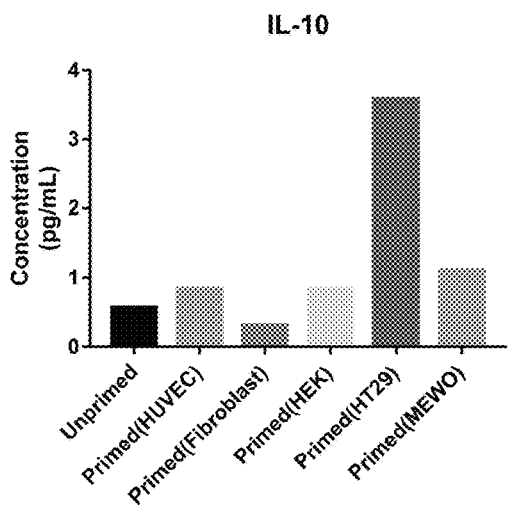
Figure 43H:
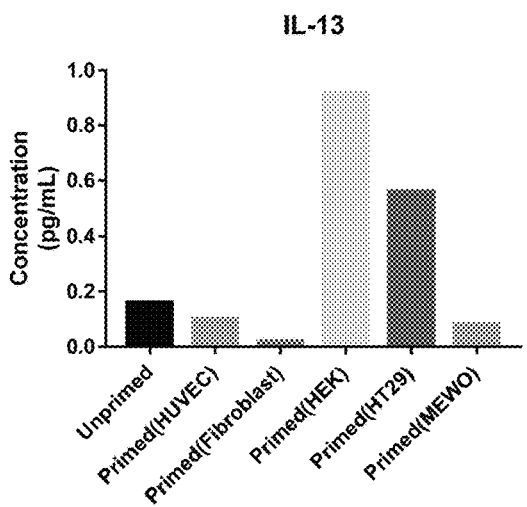
Figure 43I:
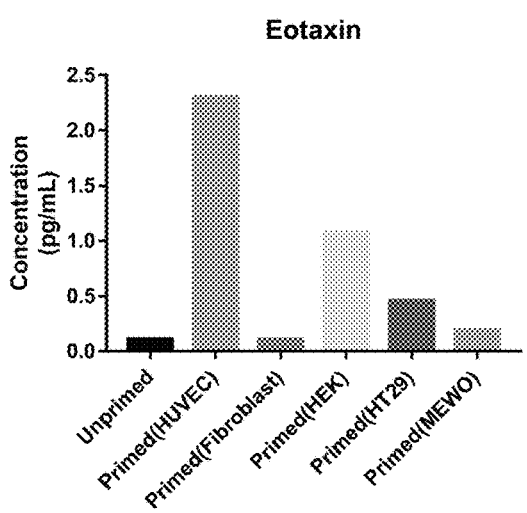
Figure 43J:
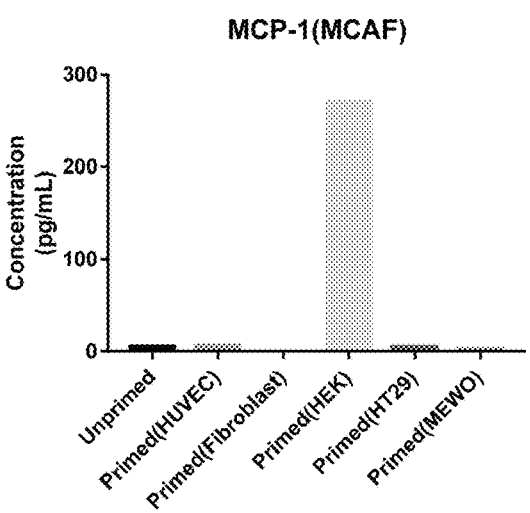
Figure 43K:
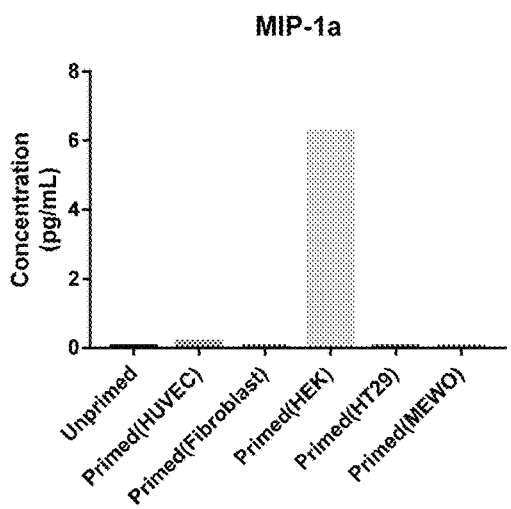
Figure 43L:
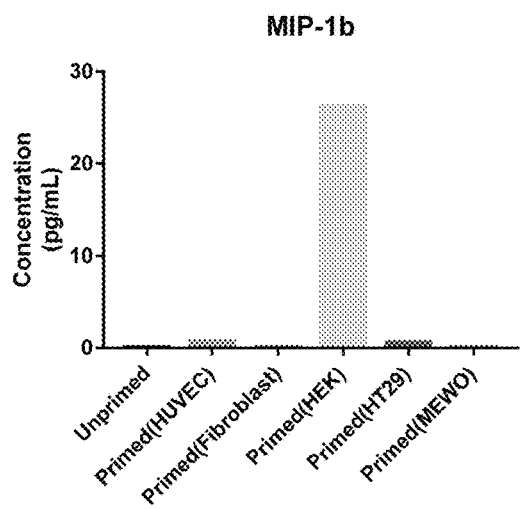
Figure 43M:
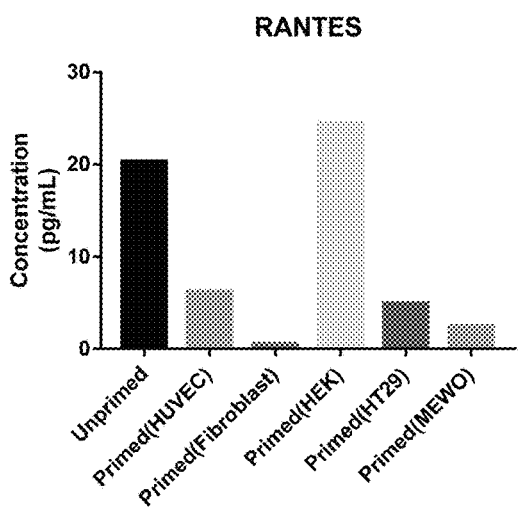
Figure 43N:
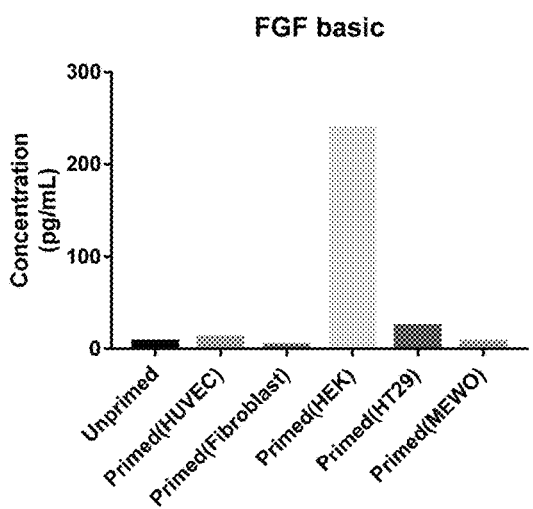
Figure 43O:
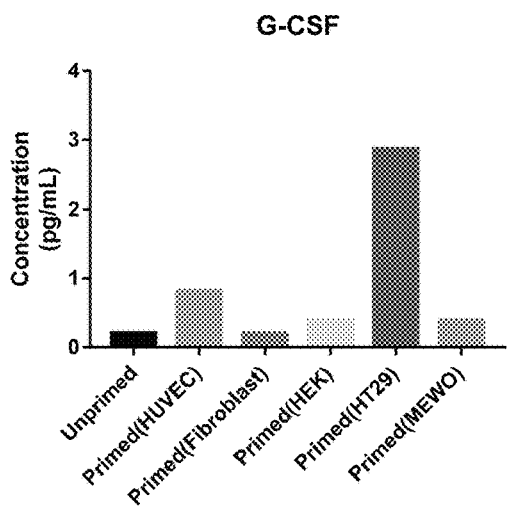
Figure 43P:
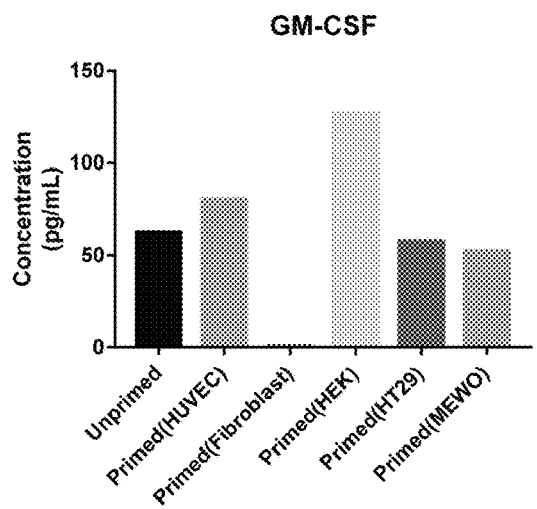
Figure 43Q:
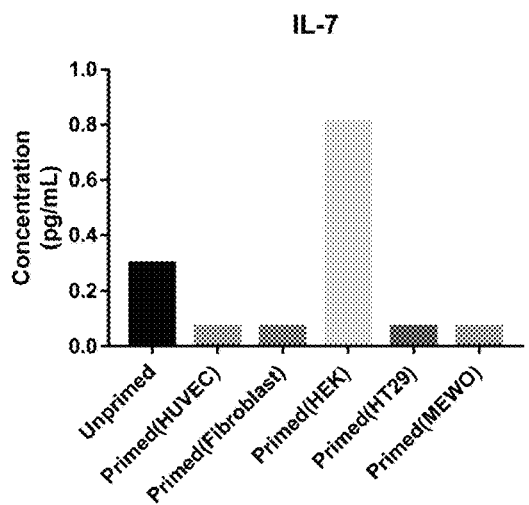
Figure 43R:
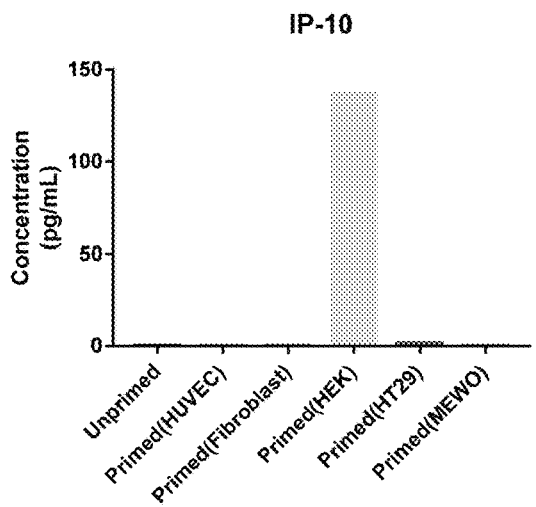
Figure 43S:
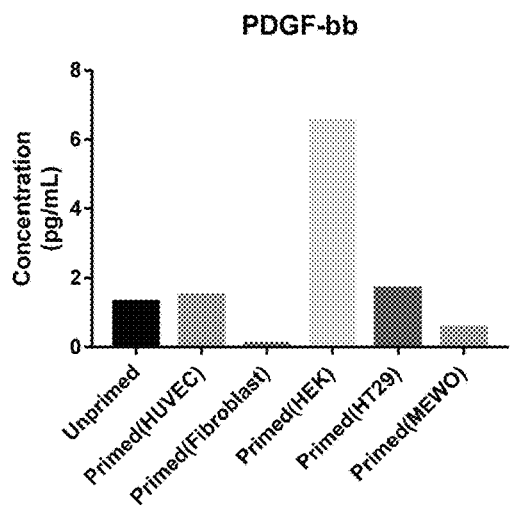
Figure 43T:
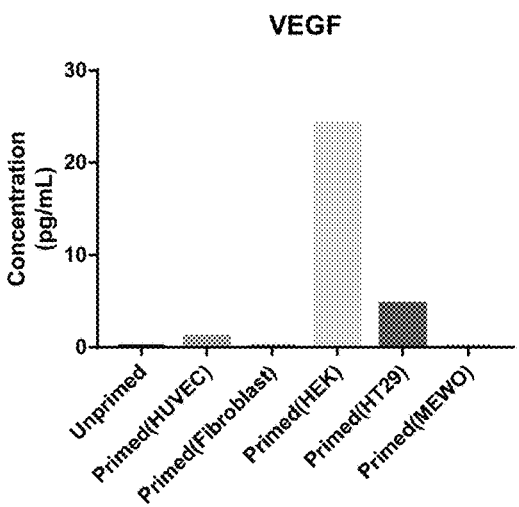
Figure 43U:
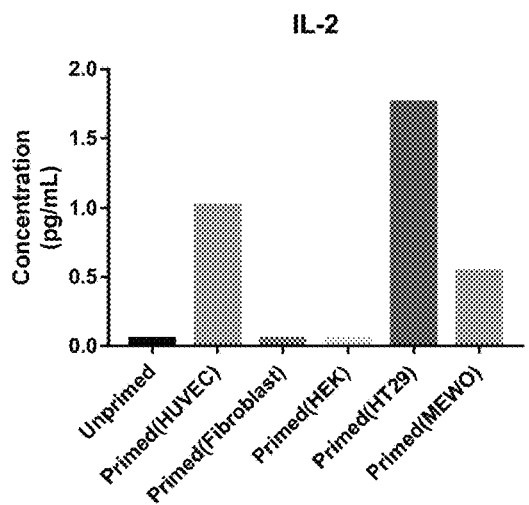
Figure 43V:
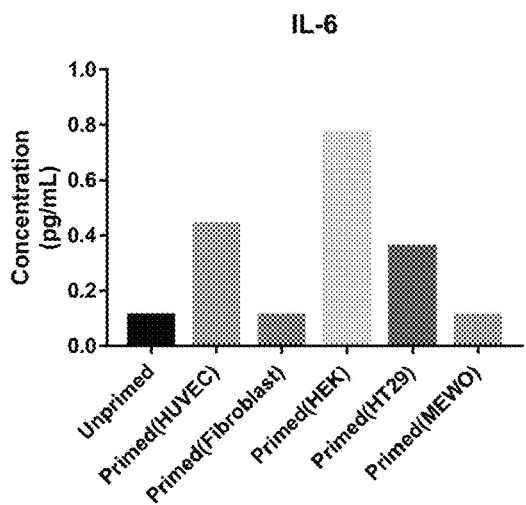

As shown in FIG. 43A-43VV, the cytokines released or secreted by red blood cells were altered by the 'priming' process which, in this instance, was co-culture with a number of different cell lines. The red blood cell secretion profiles were not only changed after priming, but also each cell type differentially primed the red blood cells with different concentrations of cytokines. For example priming RBCs with HEK cells produced considerable increases in cytokines such as IP-10, VEGF, FGF-basic, MCP-1 and CTACK. In contrast, priming the RBCs with primary fibroblasts resulted in large increases in GROa and MCP-3. These results demonstrated that the red blood cell cytokine secretion profile was subject to change depending on its environment. In addition the data showed that different cell types were able to produce primed red blood cells with significantly different cytokine profiles.

Example 10. Red Blood Cell Secretions after Priming with Immortalised Human T Lymphocytes (Jurkat Cells) in Suspension Whole blood was collected from healthy volunteers (n=1). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to the cellular suspension at a 1:4 ratio (dextran:cell suspension). This solution was left at room temperature for 30 minutes for red blood cell sedimentation to the bottom of the tube. After this time, the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

Jurkat cells were expanded in culture media (RPMI with 10% FBS and 1% antibiotic-antimycotic, v/v) at 37° C. and 5% $CO_2$. Cells were passaged twice a week and were counted using a haemocytometer; viability was determined with trypan blue staining.

For co-culture experiments, Jurkat cells were seeded into T75 flasks at a concentration of $0.1 \times 10^6$ cells per mL of culture media and were incubated for 24 hours to ensure plate adherence (37° C., 5 (% $CO_2$). After incubation, the conditions as outlined in Table 7 were prepared using freshly isolated red blood cells. For co-culture with red blood cells, the total volume of culture media in T75 flasks was 18 mL.

TABLE 7

Co-culture conditions for Jurkat cells and red blood cells (RBCs) at a ratio of 1:100 at 37° C., 5% $CO_2$ for 72 hours.

| Condition | Label | Flask size | Jurkat cells seeded | Red blood cell number |
|---|---|---|---|---|
| Jurkat cells:RBCs (1:100) | Primed | T75 | $2 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were the separated from the Jurkat cells using Ficoll density separation according to the manufacturer's instructions. The red blood cell fraction was washed once with PBS and counted using a haematology analyser (Coulter Act Diff, Beckman Coulter).

The red blood cells were then diluted in PBS to the equivalent of 400 million cells/mL. The red blood cells were then incubated in PBS for 24 hours, at 37° C. and 5% $CO_2$. After the incubation, the red blood cells were removed by centrifugation (500 g, 10 minutes) and the supernatants containing the red blood cell secretions were retained and analysed. Two multiplex assays were utilised. The 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 44A:
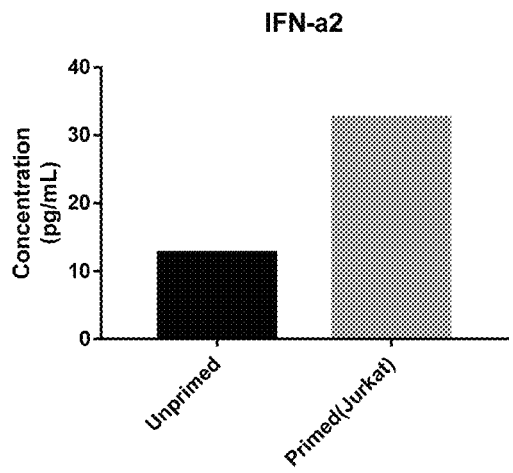
FIG. 44A-44VV is a series of graphs showing the concentration of released or secreted proteins from red blood cells following co-culture for 3 days with (primed) or without (unprimed) cells from the T lymphocyte cell line (Jurkat).
Figure 44B:
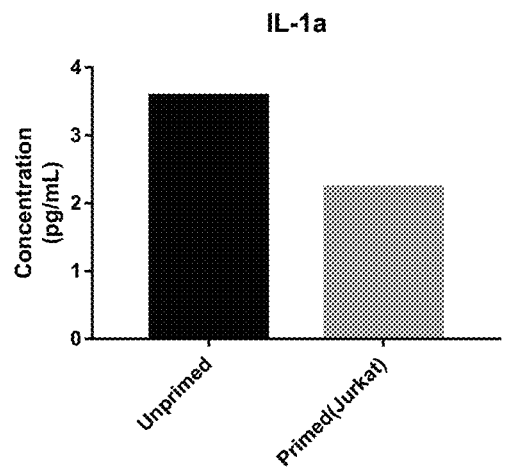
Figure 44C:
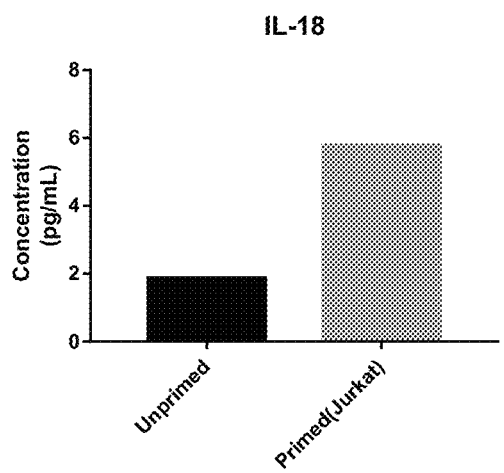
Figure 44D:
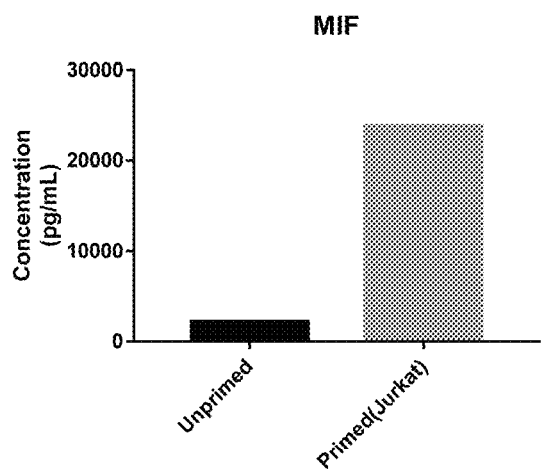
Figure 44E:
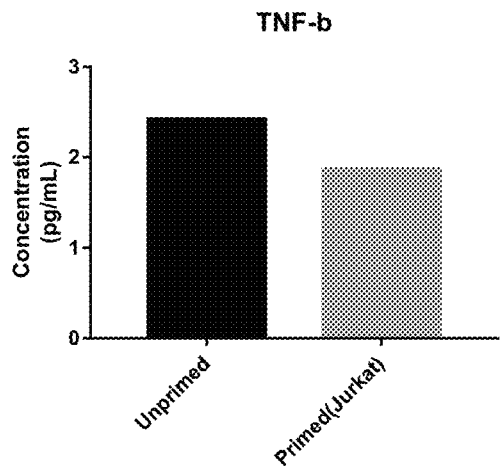
Figure 44F:
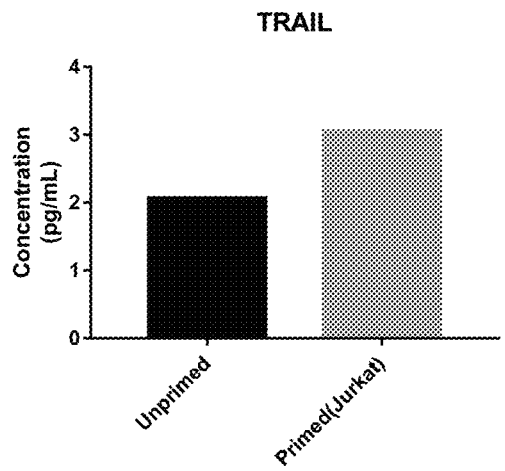
Figure 44G:
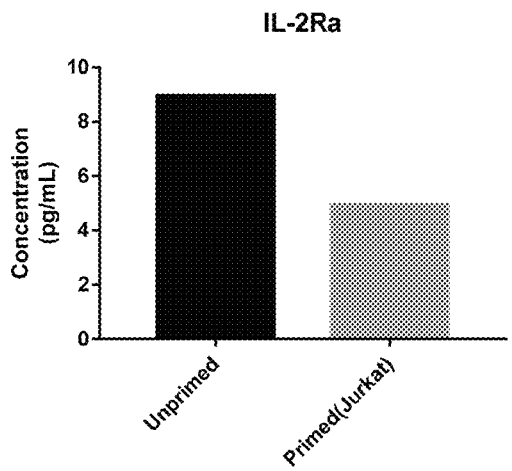
Figure 44H:
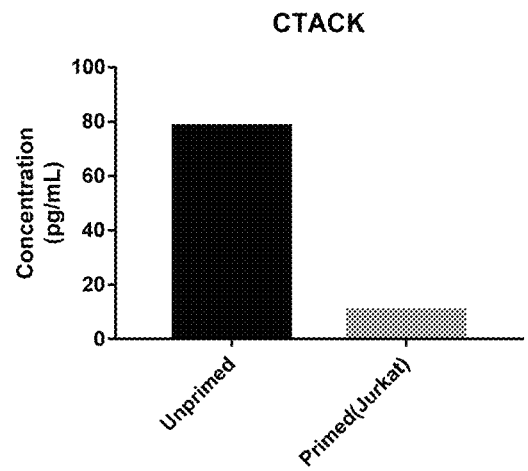
Figure 44I:
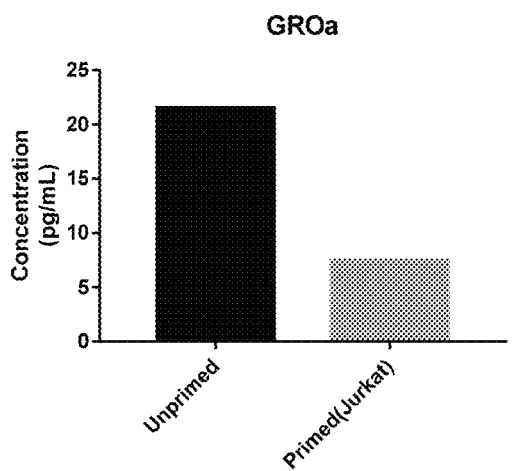
Figure 44J:
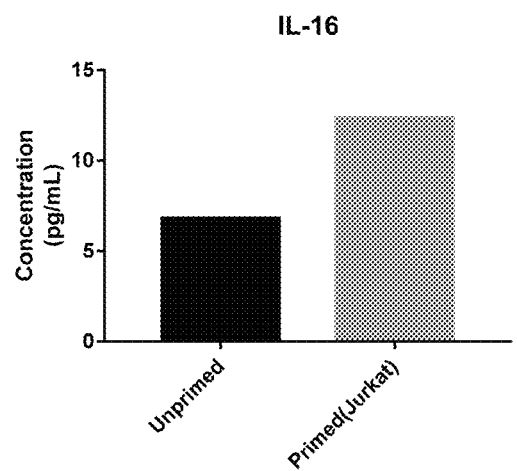
Figure 44K:
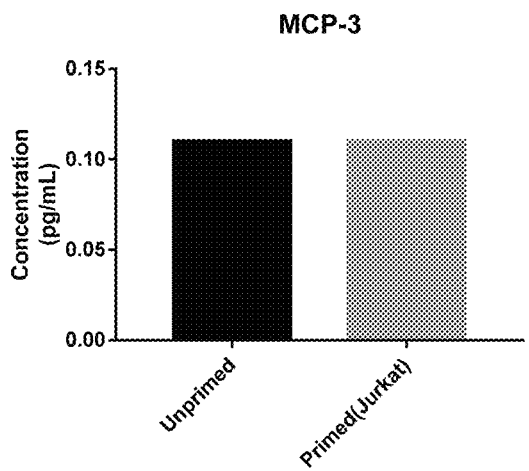
Figure 44L:
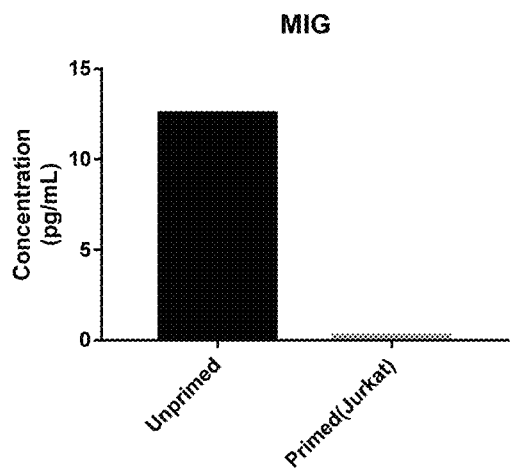
Figure 44M:
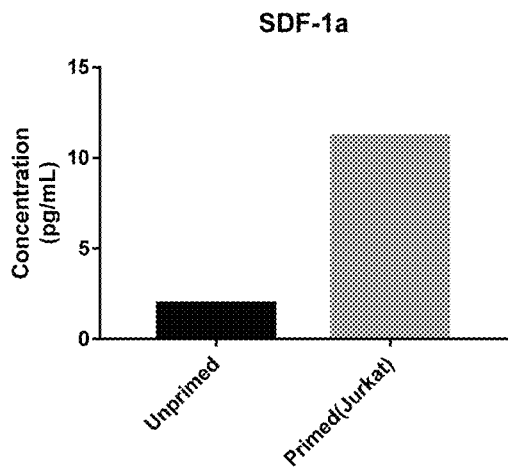
Figure 44N:
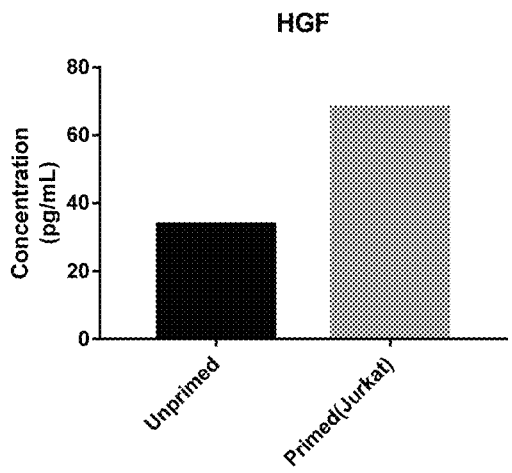
Figure 44O:
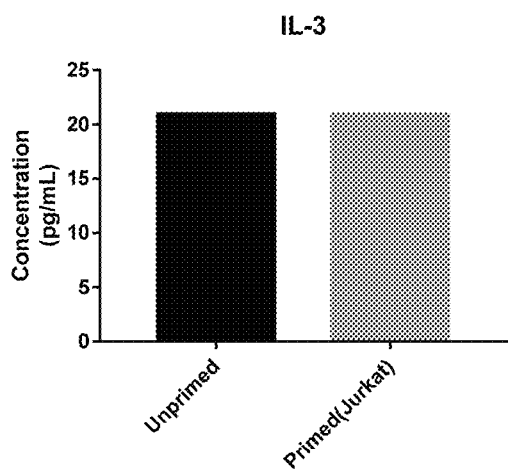
Figure 44P:
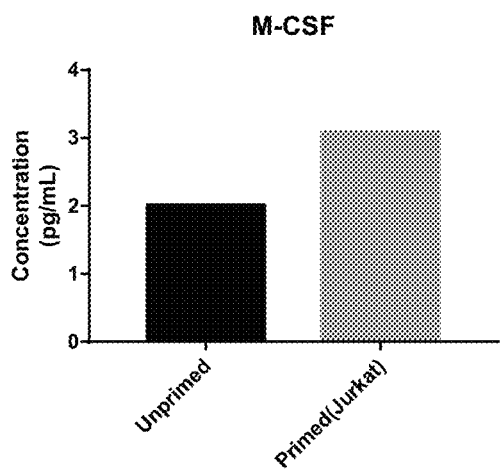
Figure 44Q:
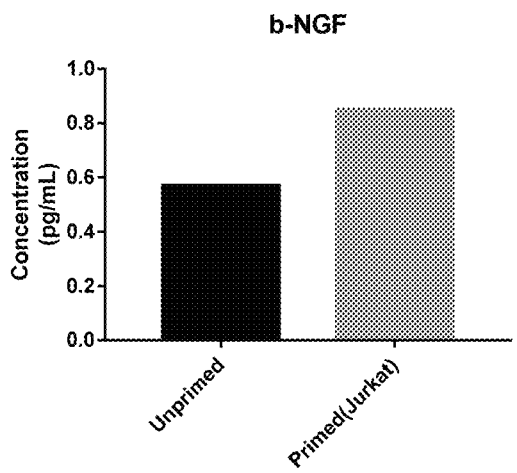
Figure 44R:
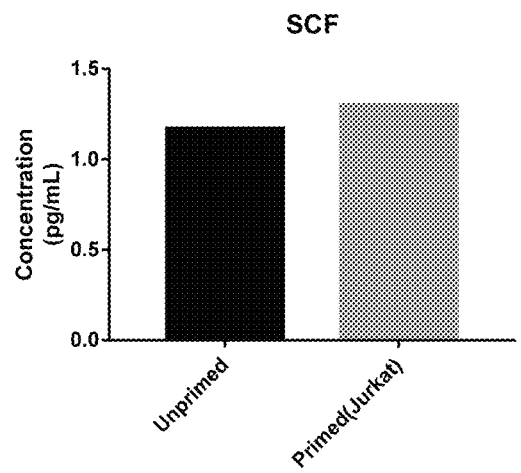
Figure 44S:
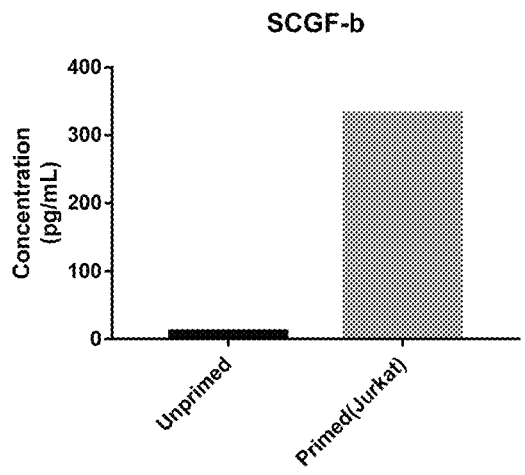
Figure 44T:
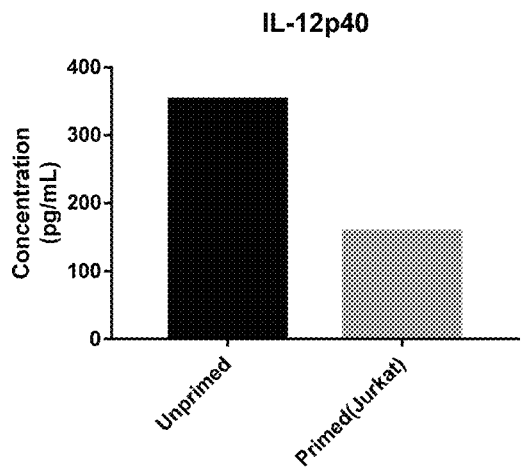
Figure 44U:
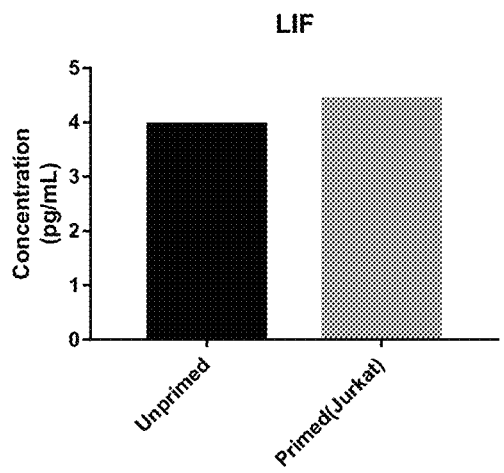
Figure 44V:
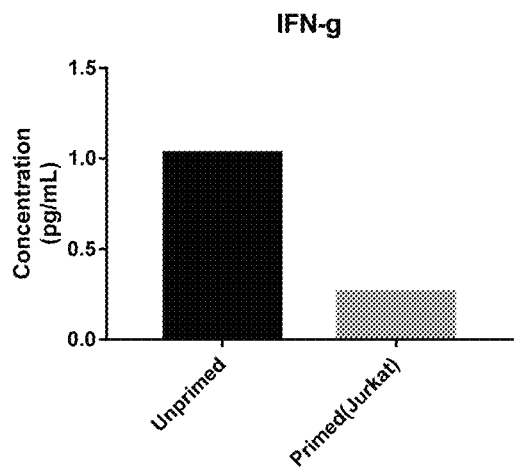
Figure 44W:
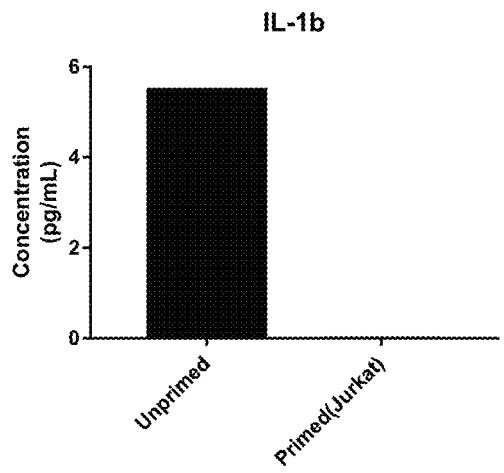
Figure 44X:
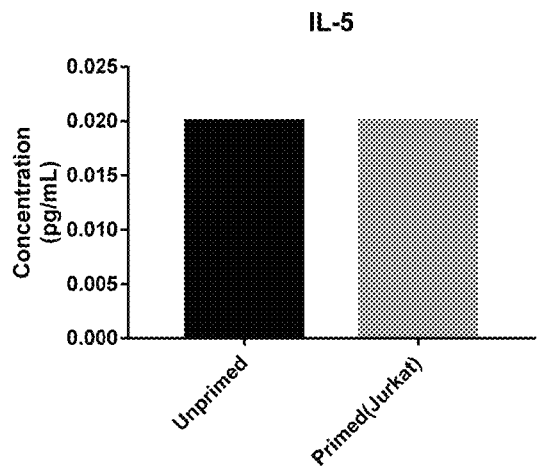
Figure 44Y:
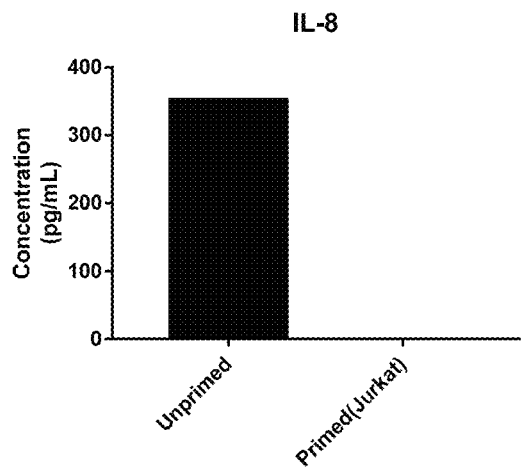
Figure 44Z:
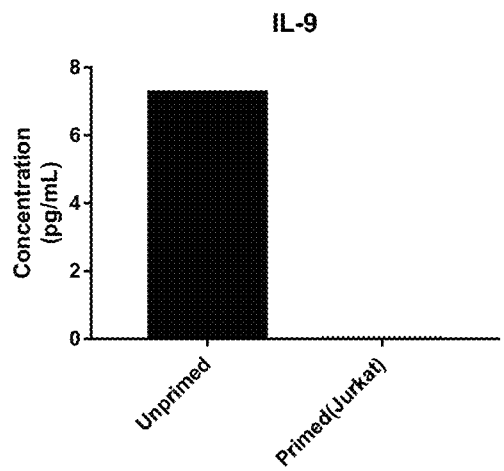
Figure 44A:
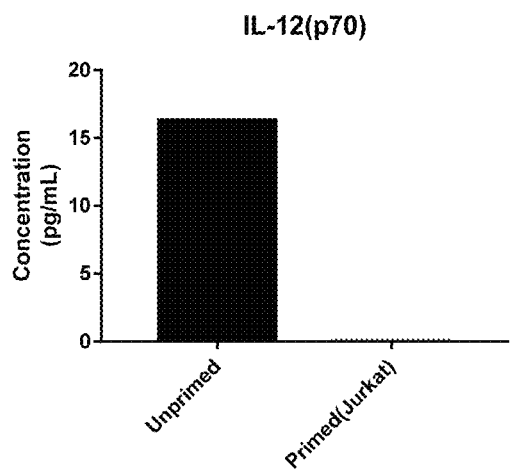
Figure 44B:
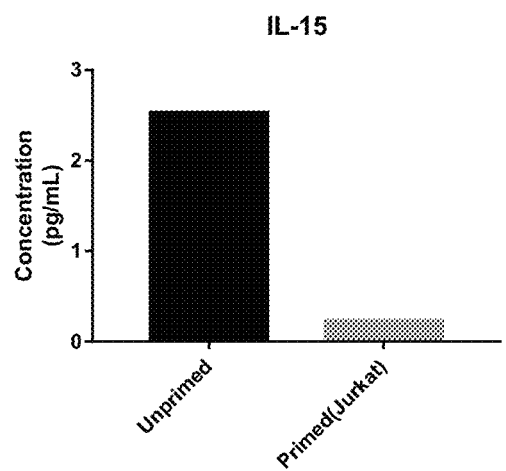
Figure 44C:
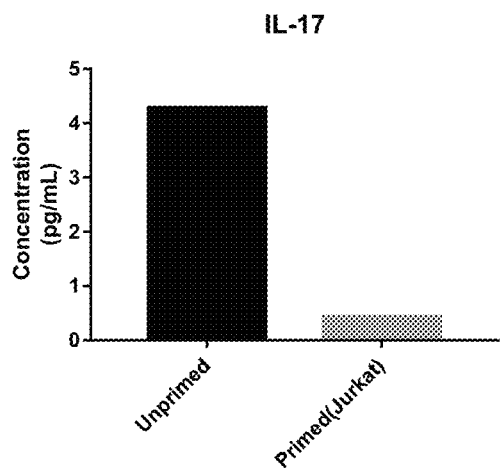
Figure 44D:
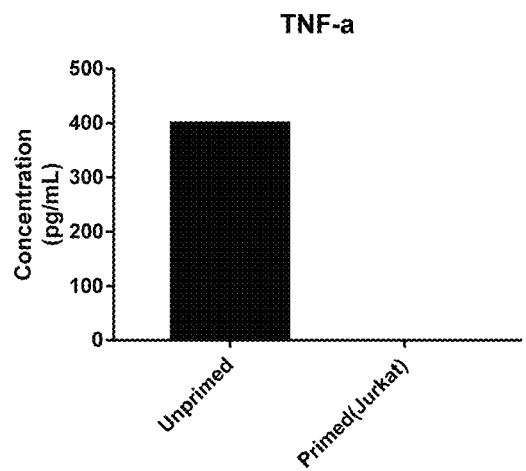
Figure 44E:
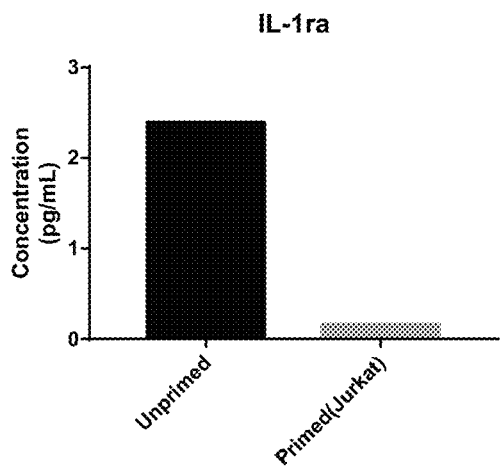
Figure 44F:
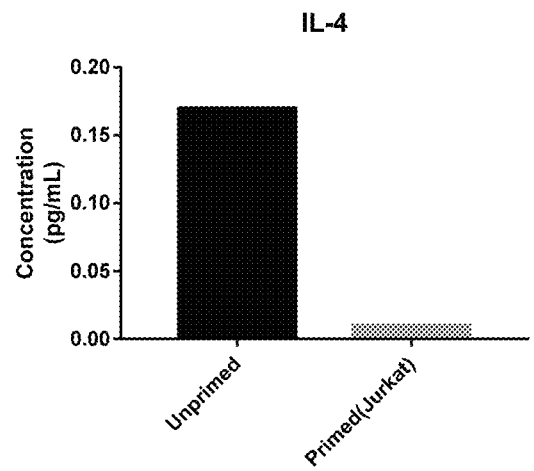
Figure 44G:
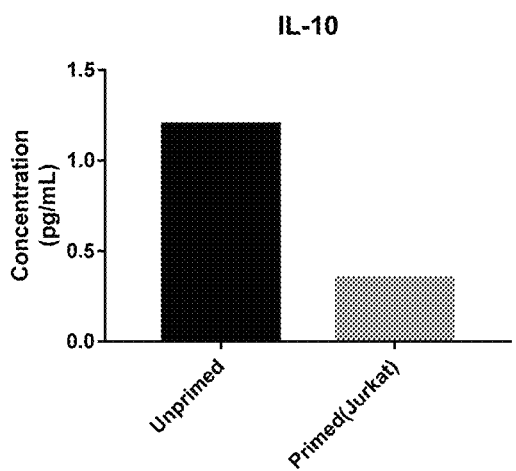
Figure 44H:
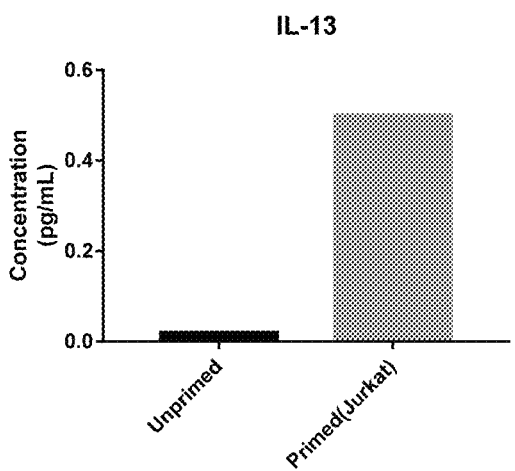
Figure 44I:
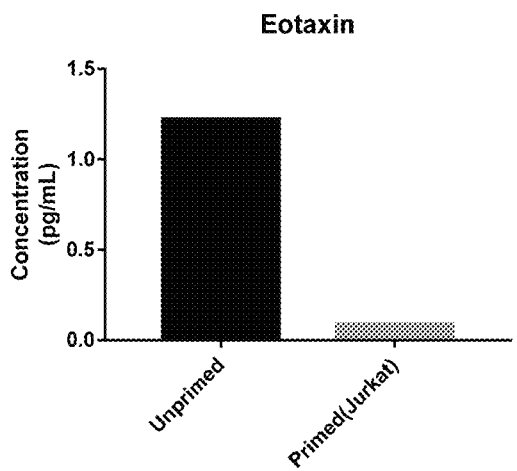
Figure 44J:
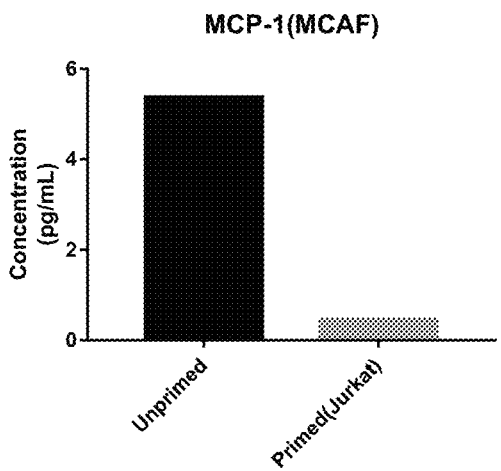
Figure 44K:
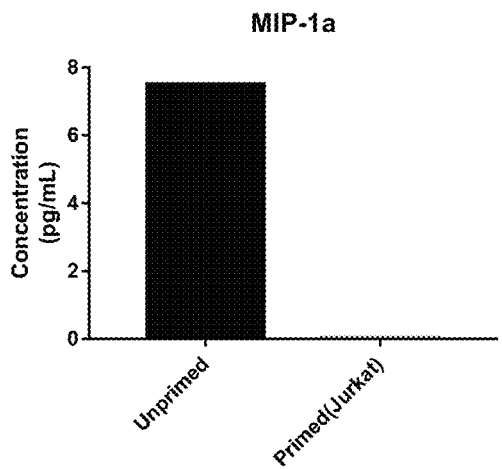
Figure 44L:
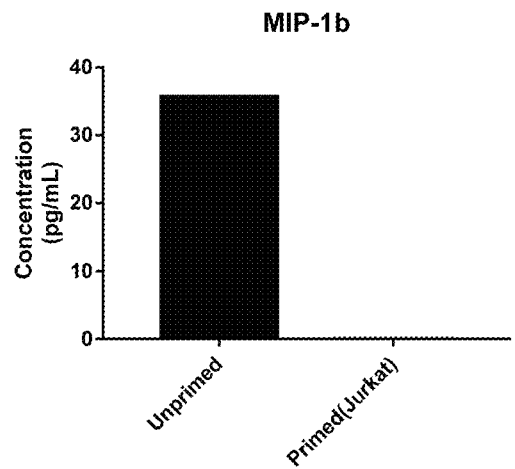
Figure 44M:
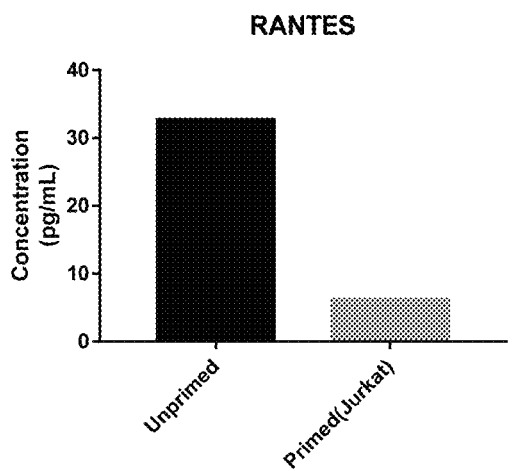
Figure 44N:
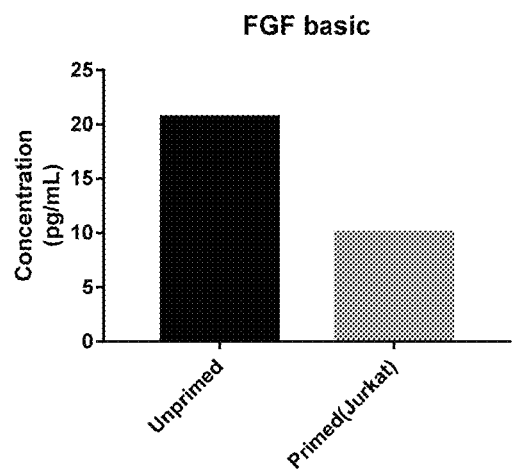
Figure 44O:
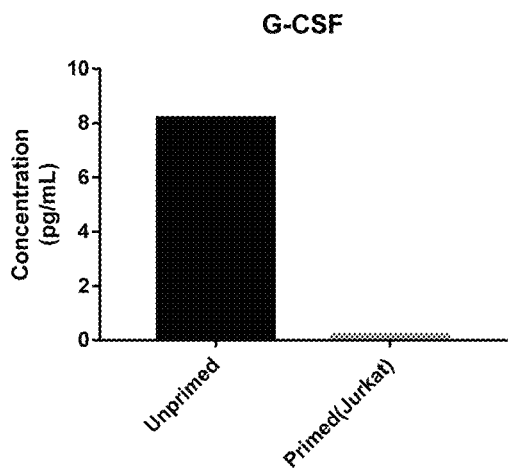
Figure 44P:
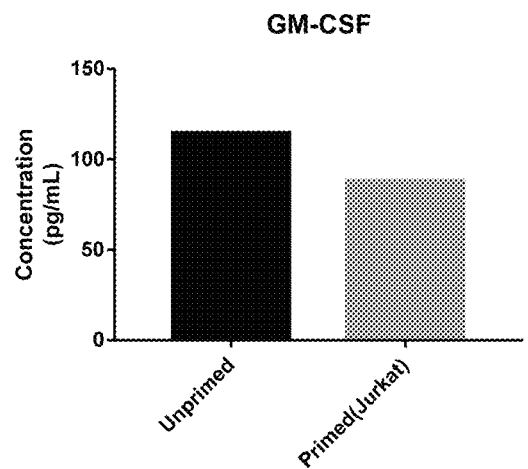
Figure 44Q:
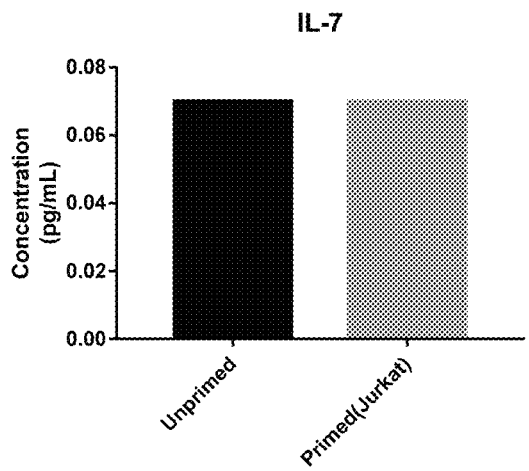
Figure 44R:
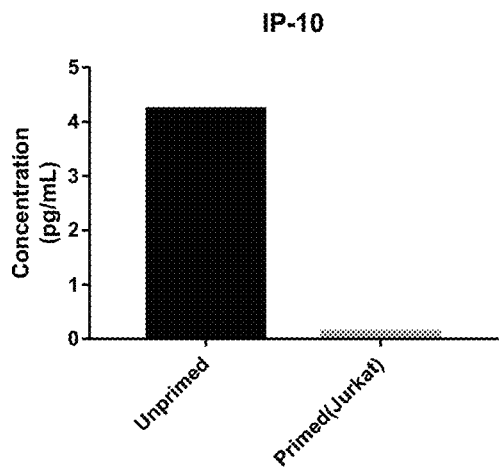
Figure 44S:
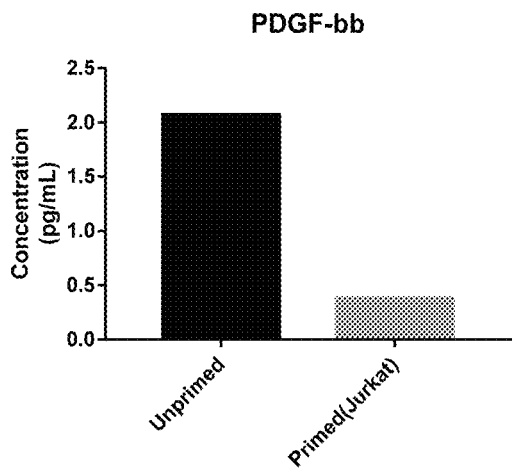
Figure 44T:
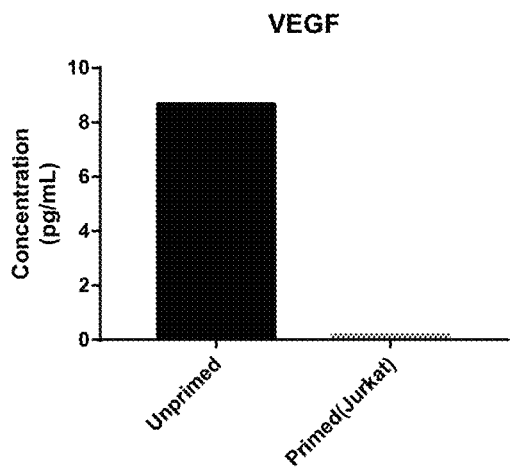
Figure 44U:
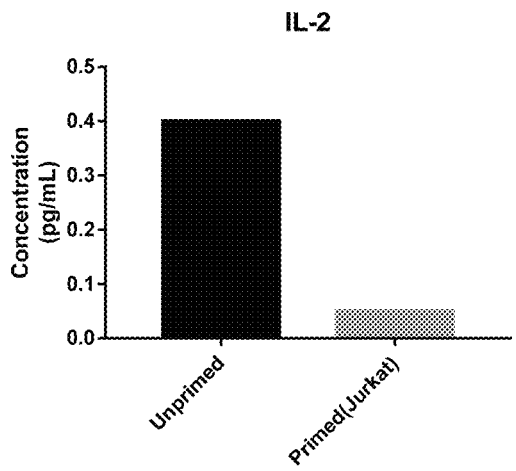
Figure 44V:
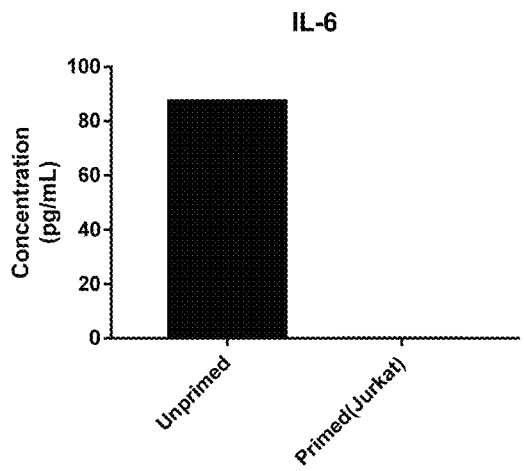

As shown in FIG. 44A-44V, the cytokines released or secreted by red blood cells were altered by the 'priming' process, which in this instance was co-culture with Jurkat cells (an immortalised T lymphocyte cell line). The red blood cell secretion concentration of proteins such as IFN-α2, MIF, SCGF-b were all increased markedly following co-culture priming. Whilst the levels of proteins such as GROa, CTACK, IL-8, TNF-a, RANTES, and IL6 all decreased measurably following co-culture priming. These results demonstrated that this priming effect may occur in various culturing conditions, and with non-adherent cells.

Example 11. Red Blood Cells Following Priming with Mesenchymal Stem Cells (MSCs)

11.1. RBC Membranes

Whole blood was collected from healthy volunteers (n≥3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then suspended in $ddH_2O$ to lyse the cells. This solution was vortexed and then centrifuged (15000 g, 20 minutes) to pellet the membranes. This process was repeated and the resulting pellet was resuspended in PBS and used for priming experiments.

MSCs were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MSCs were seeded into T75 flasks at a concentration of $0.1 \times 10^6$ cells per mL of culture media and were incubated for 24 hours to ensure plate adherence (37° C., 5% $CO_2$). After incubation, the conditions as outlined in Table 8 were prepared using freshly isolated red blood cells. For co-culture with red blood cells the total volume of culture media in T75 flasks was 18 mL.

TABLE 8

Co-culture conditions for MSCs and red blood cells membranes at a ratio of 1:100 at 37° C., 5% $CO_2$ for 72 hours.

| Condition | Label | Flask size | MSCs seeded | Equivalent RBC membrane number |
|---|---|---|---|---|
| MSCs:RBC membranes (1:100) | Primed | T75 | $2 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cell membranes were isolated by centrifugation out of the conditioned media (15000 g, 20 minutes). Any remaining particulates in the conditioned media were removed by centrifugation (2000 g, 10 minutes) after which it was stored at −80° C. The red blood cell membranes were washed once with PBS (15000 g, 20 minutes).

The red blood cell membranes were then diluted (based on the original number of red blood cells used) in PBS to the equivalent of the membranes from 400 million cells/mL. The primed and unprimed red blood cell membranes were subjected to 3 freeze-thaw cycles to ensure complete lysis. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 45A:
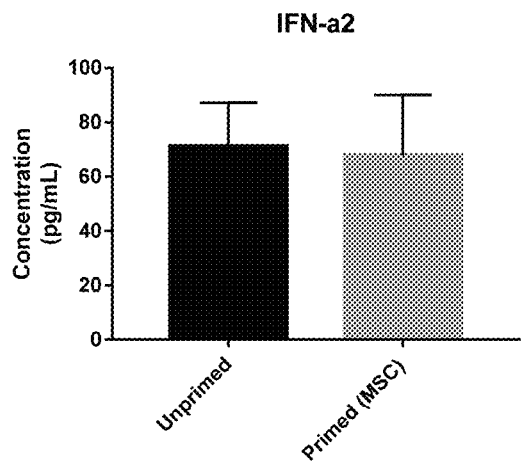
FIG. 45A-45VV is a series of graphs showing the concentration of proteins in red blood cell membranes following co-culture for 3 days with (primed) or without (unprimed) mesenchymal stem cells (MSCs). Significant differences (p<0.05) were determined using Student's T-tests.
Figure 45B:
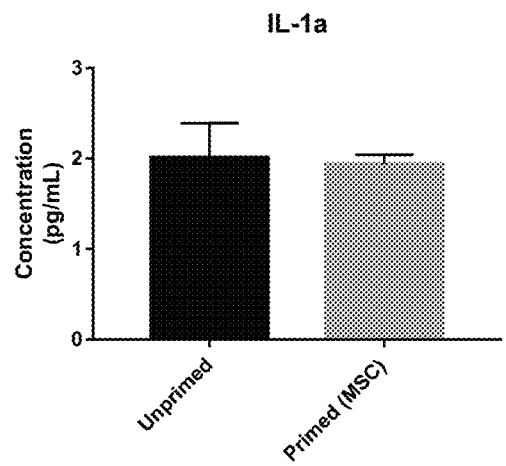
Figure 45C:
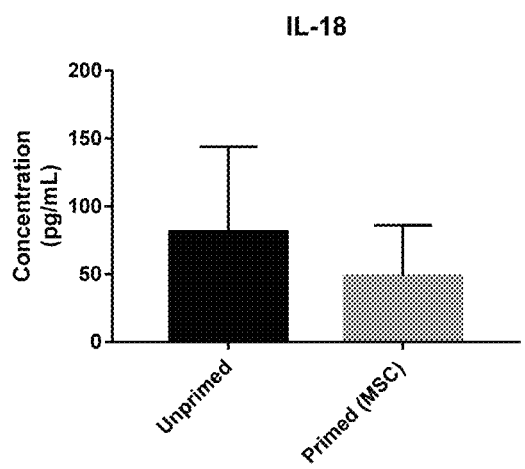
Figure 45D:
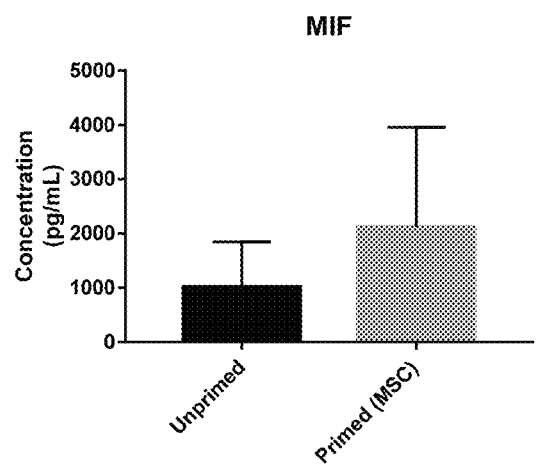
Figure 45E:
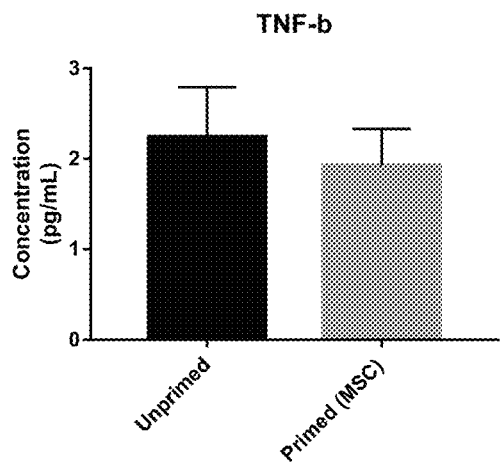
Figure 45F:
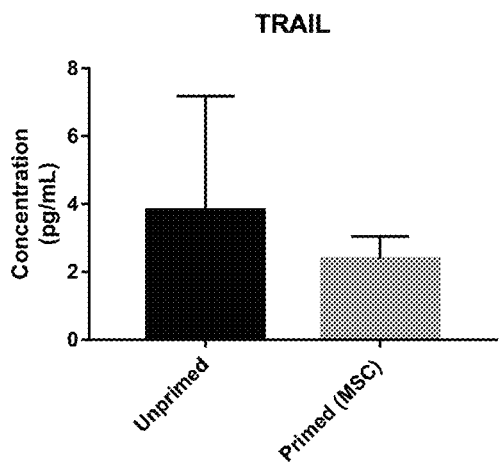
Figure 45G:
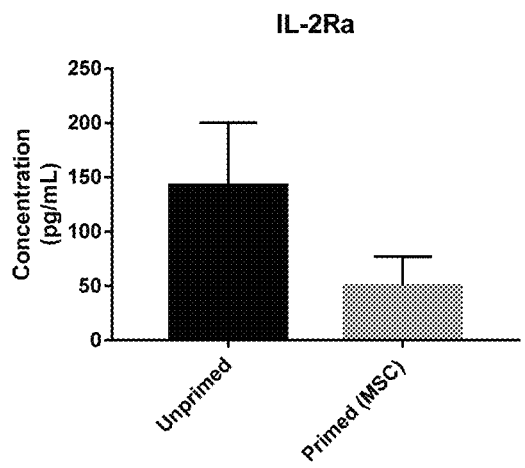
Figure 45H:
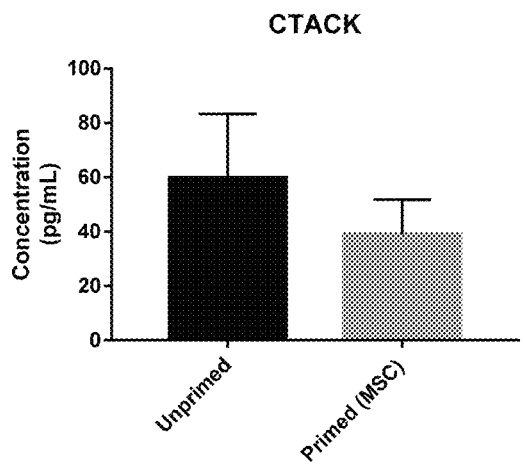
Figure 45I:
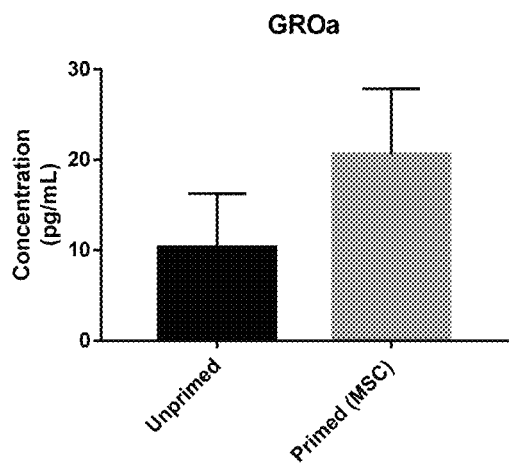
Figure 45J:
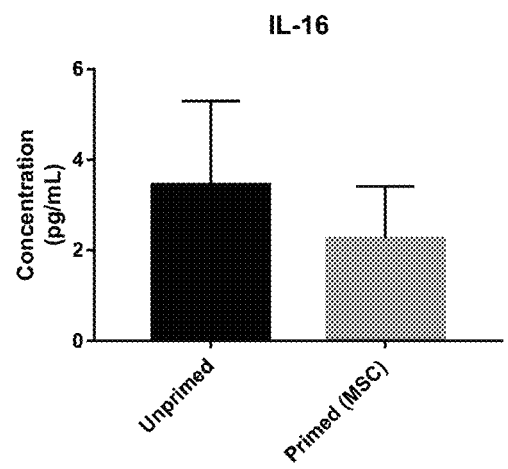
Figure 45K:
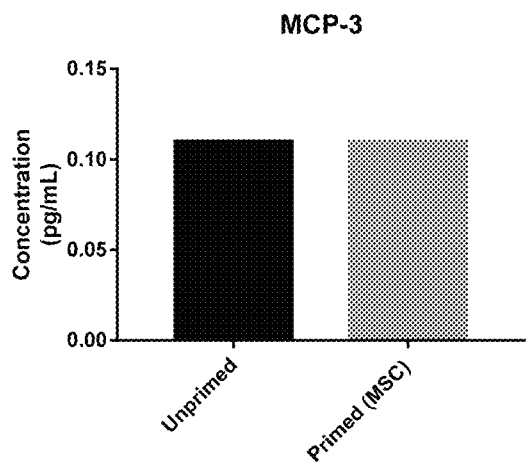
Figure 45L:
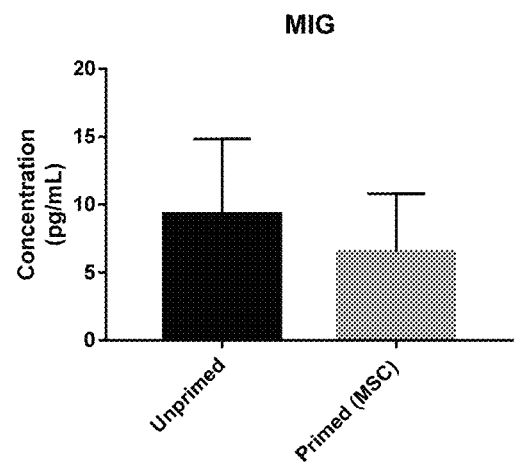
Figure 45M:
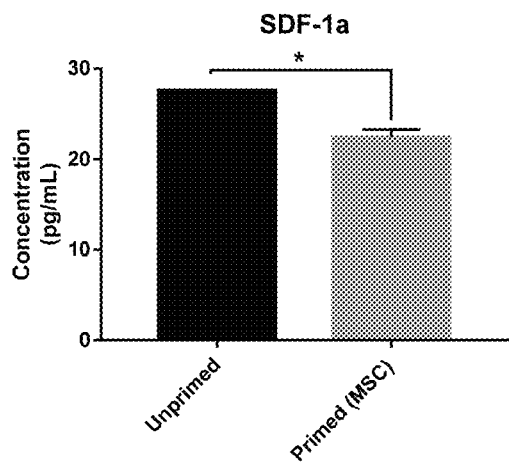
Figure 45N:
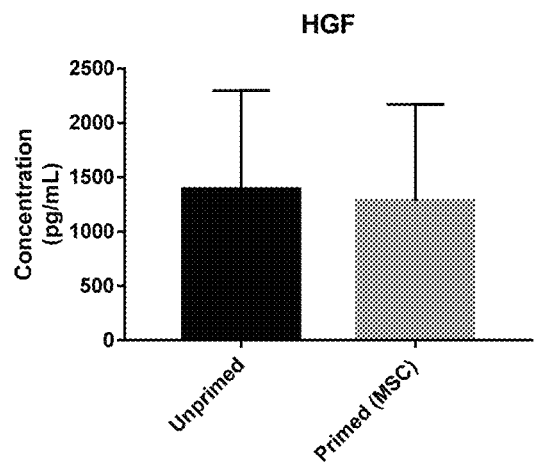
Figure 45O:
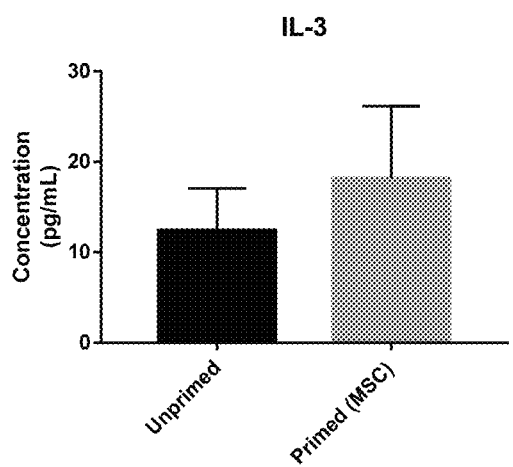
Figure 45P:
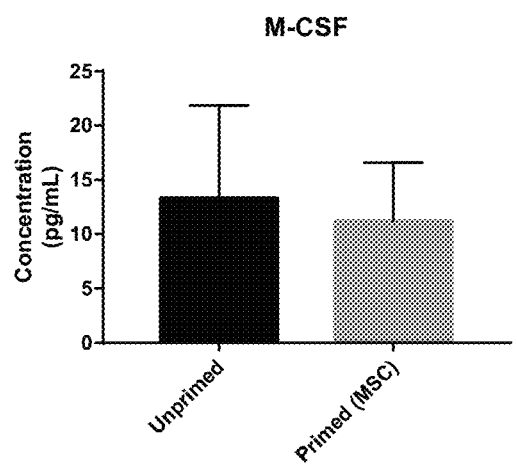
Figure 45Q:
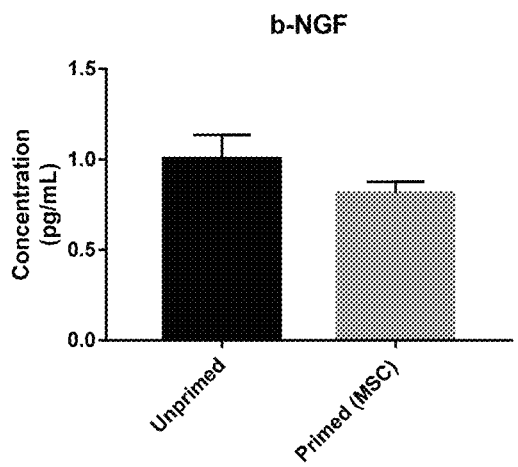
Figure 45R:
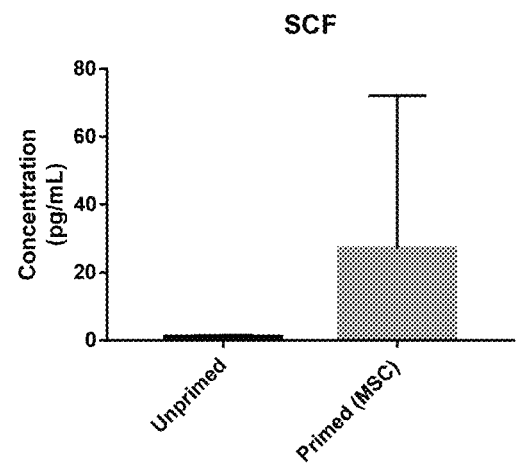
Figure 45S:
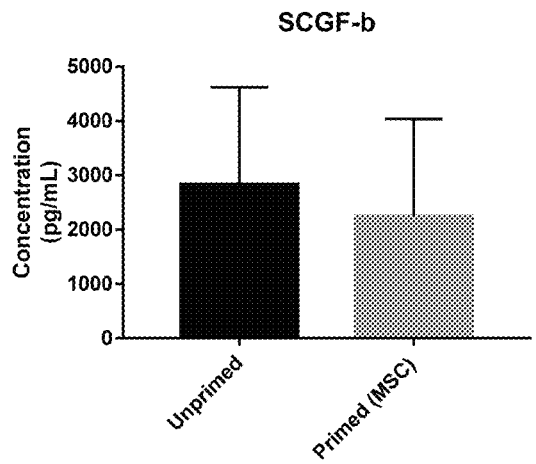
Figure 45T:
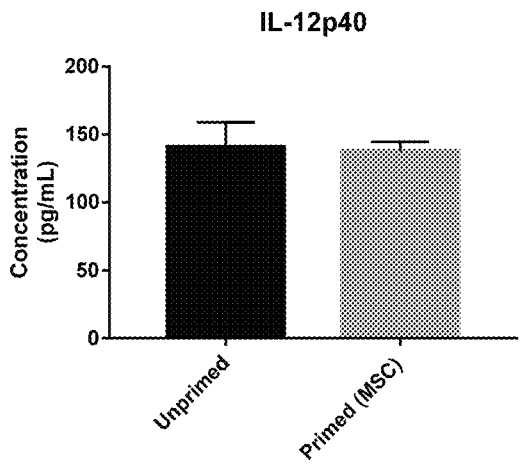
Figure 45U:
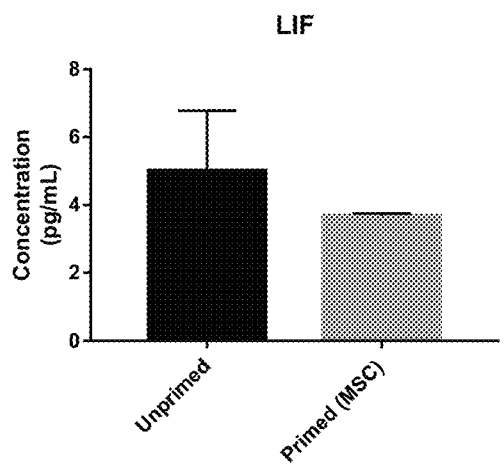
Figure 45V:
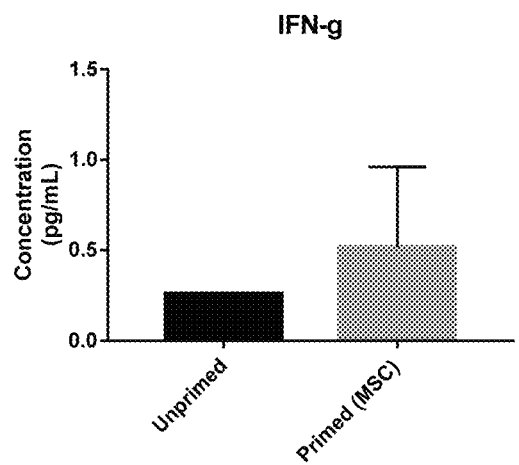
Figure 45W:
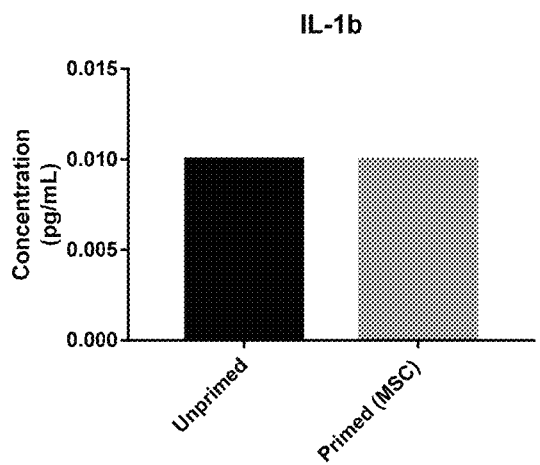
Figure 45X:
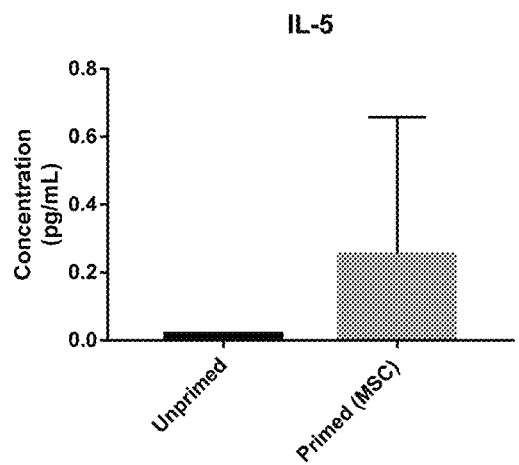
Figure 45Y:
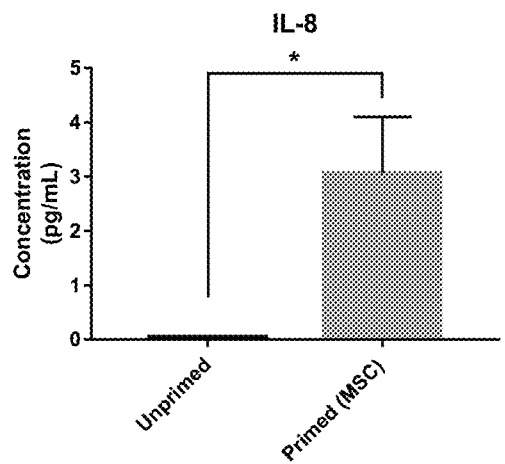
Figure 45Z:
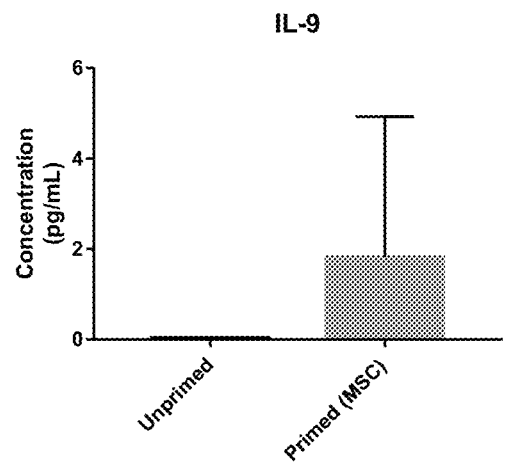
Figure 45A:
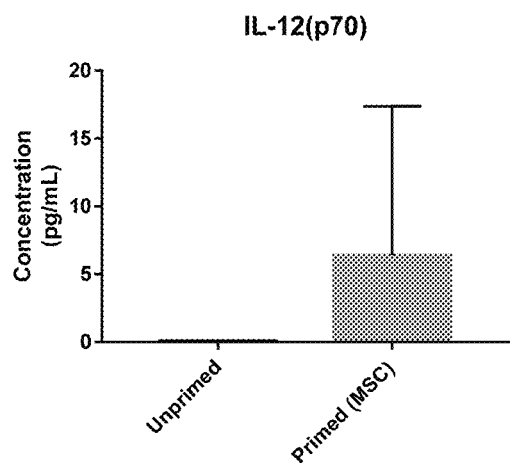
Figure 45B:
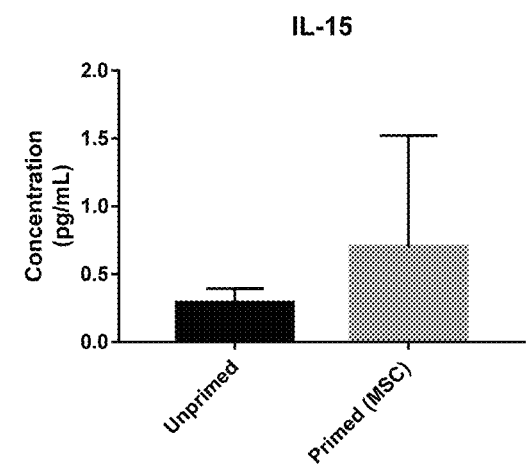
Figure 45C:
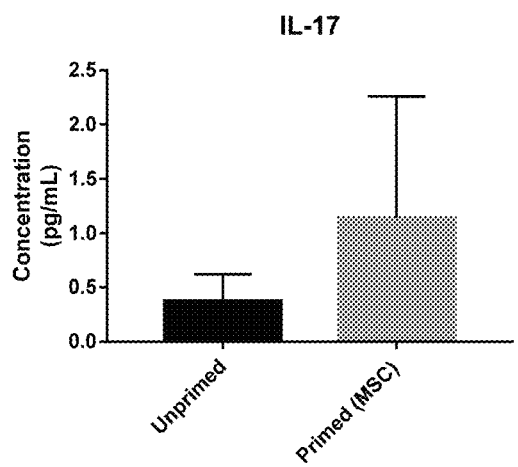
Figure 45D:
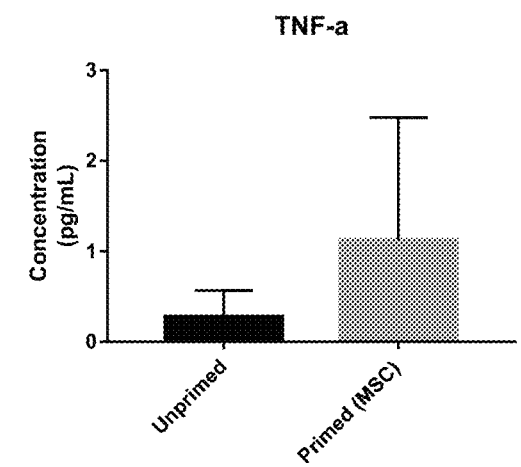
Figure 45E:
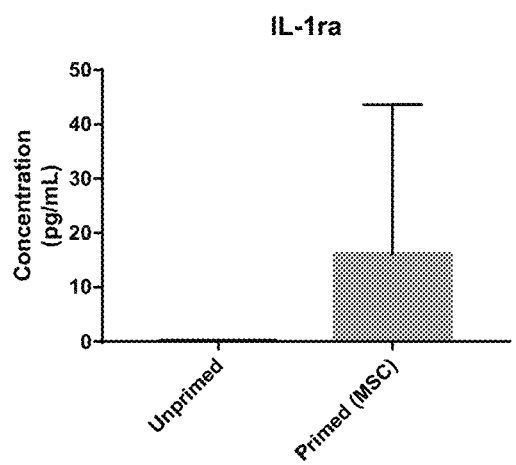
Figure 45F:
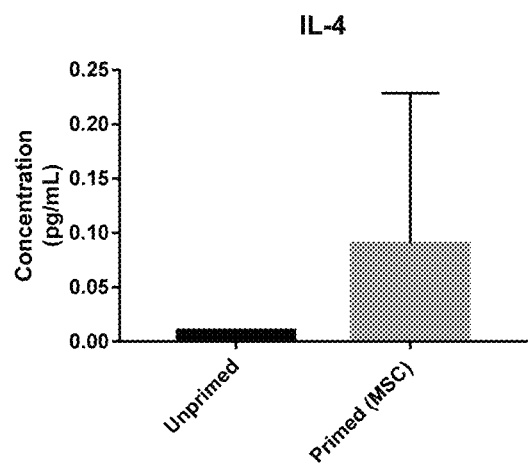
Figure 45G:
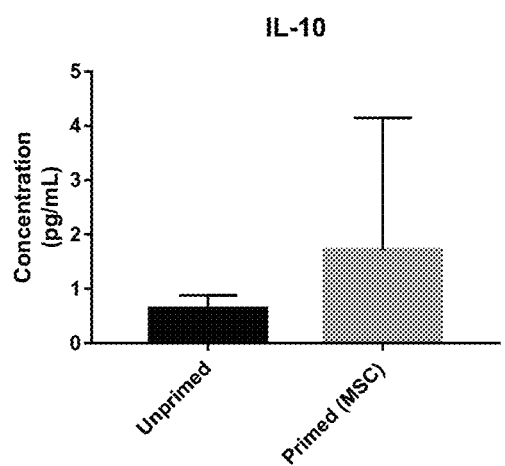
Figure 45H:
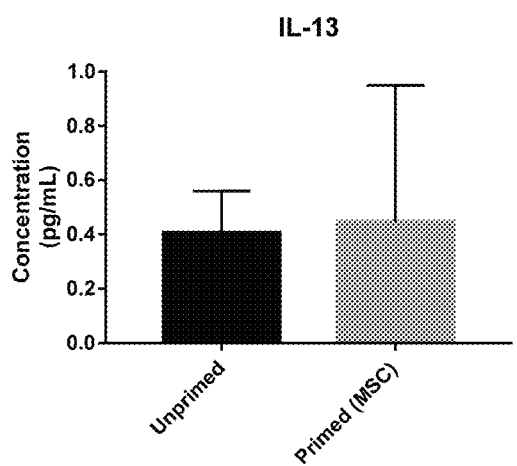
Figure 45I:
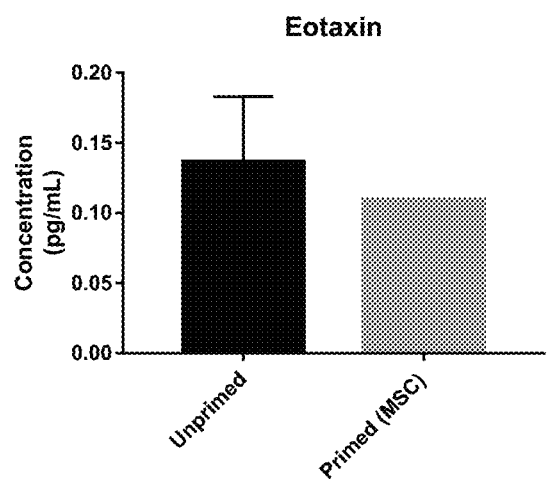
Figure 45J:
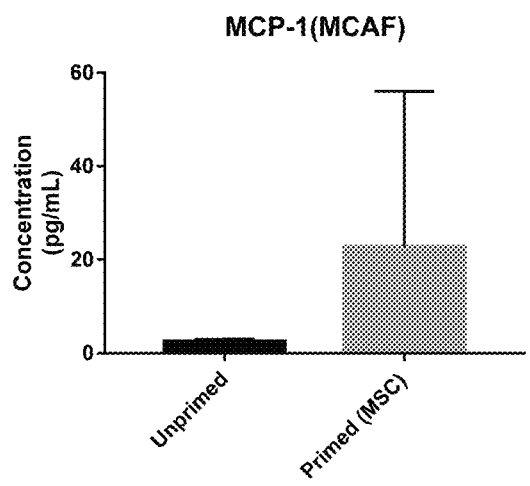
Figure 45K:
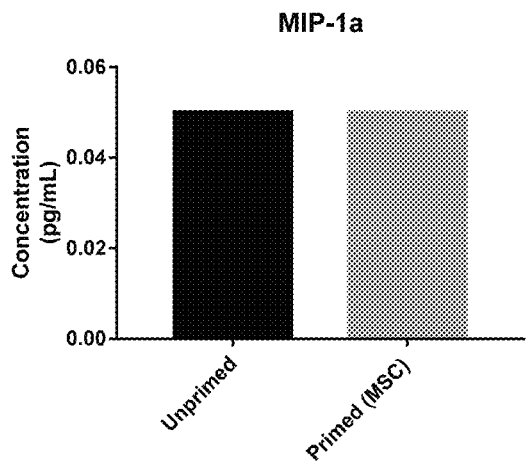
Figure 45L:
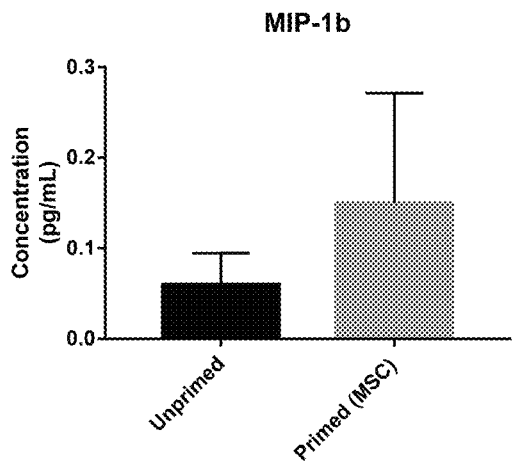
Figure 45M:
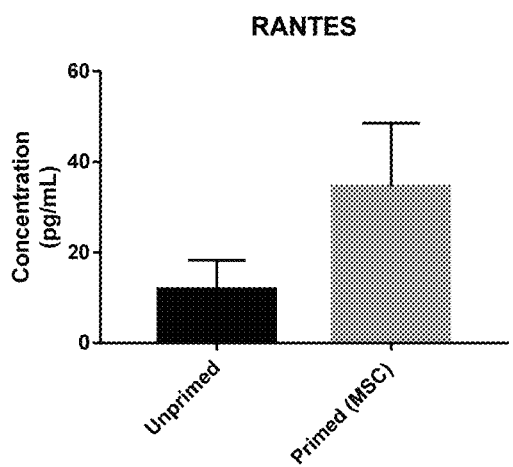
Figure 45N:
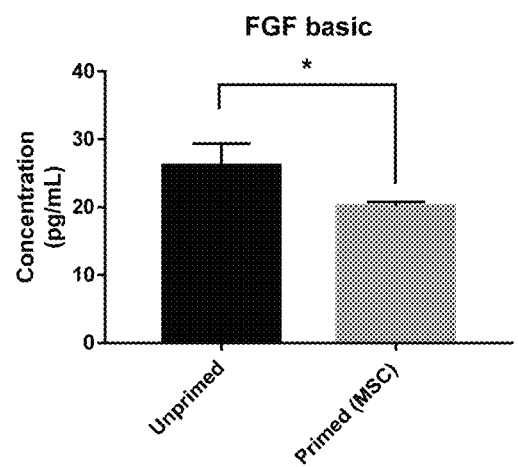
Figure 45O:
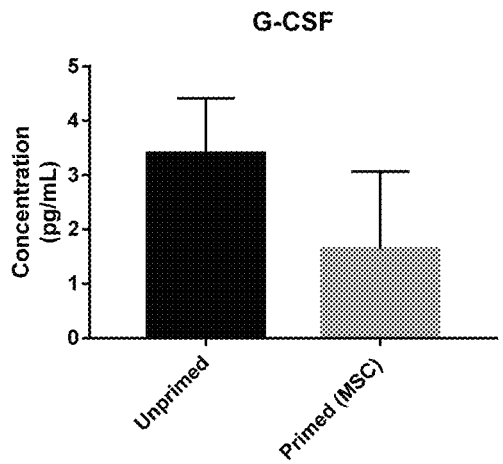
Figure 45P:
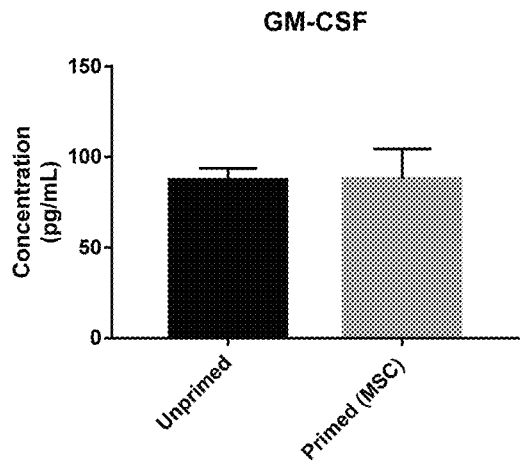
Figure 45Q:
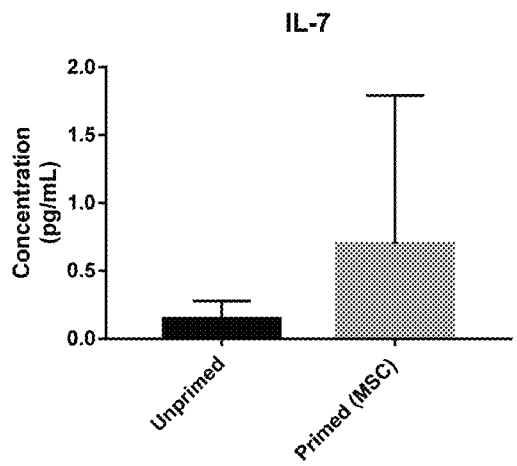
Figure 45R:
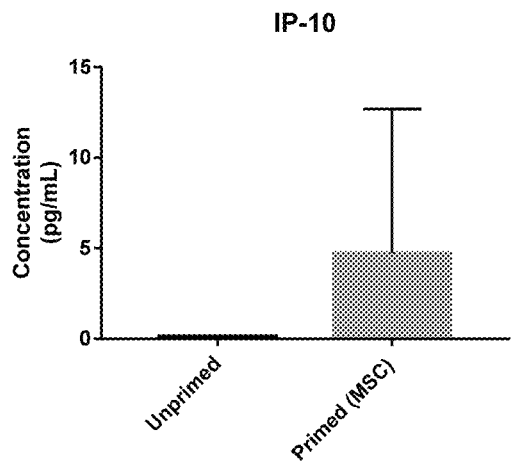
Figure 45S:
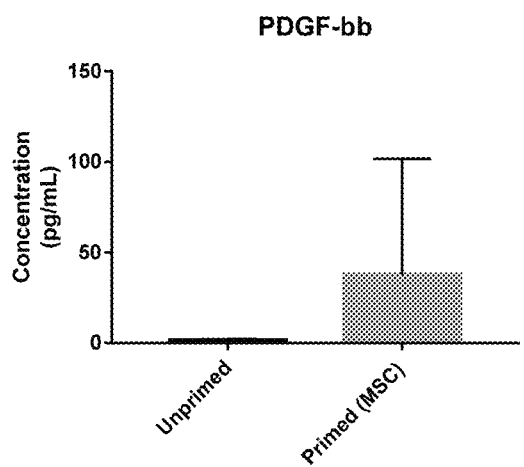
Figure 45T:
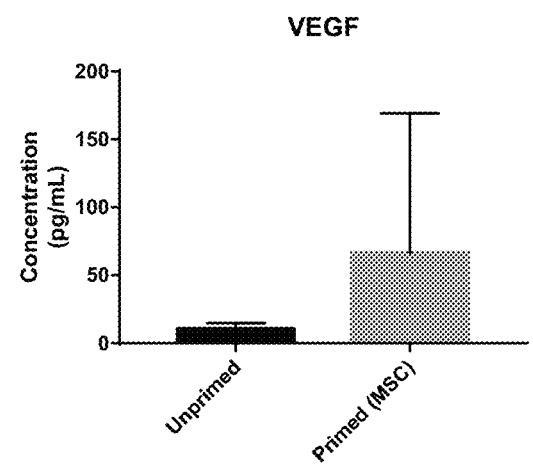
Figure 45U:
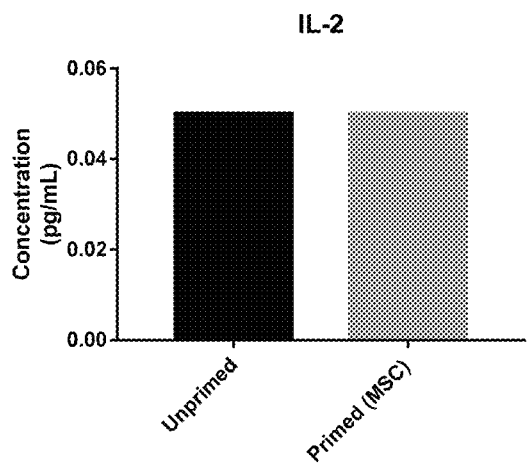
Figure 45V:
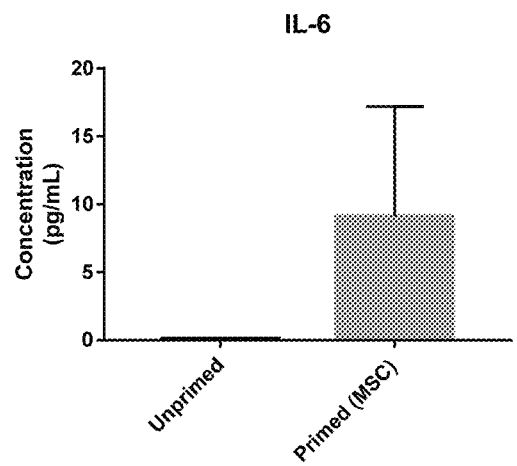

As shown in FIG. 45A-45VV, the cytokine profile of the red blood cell membranes was altered by the 'priming' process, which in this instance was co-culture with mesenchymal stem cells (MSCs). The red blood cell membrane concentration of IL-8, was significantly increased following co-culture priming. Whilst the levels of a few proteins such as FGF-basic and SDF-1a decreased significantly following co-culture priming. The results demonstrated that the cytokine profile of red blood cell membranes were subject to change depending on their environment. None of the cytokines were significantly different after priming in the whole red blood cell lysis experiment, indicating that the membrane has different cytokine binding properties to the red blood cell as a whole.

11.2 RBC Membrane Secretions

Whole blood was collected from healthy volunteers (n+3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then suspended in $ddH_2O$ to lyse the cells. This solution was vortexed and then centrifuged (15000 g, 20 minutes) to pellet the membranes. This process was repeated and the resulting pellet was suspended in PBS and used for priming experiments.

Mesenchymal stem cells (MSCs) isolated from adipose tissue were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MSCs were seeded into T75 flasks at a concentration of $0.1 \times 10^6$ cells per mL of ADSC culture media and were incubated for 24 hours to ensure plate adherence (37° C., 5% $CO_2$). After incubation, the conditions as outlined in Table 9 were prepared using freshly isolated red blood cells. For co-culture with red blood cells the total volume of culture media in T75 flasks was 18 mL.

TABLE 9

Co-culture conditions for MSCs and red blood cells (RBCs) at a ratio of 1:100 at 37° C., 5% $CO_2$ for 72 hours.

| Condition | Label | Flask size | MSCs seeded | Red blood cell derived membranes |
|---|---|---|---|---|
| MSCs:RBC membraness (1:100) | Primed | T75 | $2 \times 10^6$ | $200 \times 10^6$ |
| RBC membranes | Unprimed | T75 | — | $200 \times 10^6$ |

Cells were then incubated for 72 hours at 37° C. with 5% $CO_2$. Following incubation, the red blood cell membranes were isolated by centrifugation out of the conditioned media (15000 g, 20 minutes). Any remaining particulates in the conditioned media were removed by centrifugation (2000 g, 10 minutes) after which it was stored at −80° C. The red blood cell membranes were washed once with PBS (15000 g, 20 minutes).

The red blood cell membranes were then diluted (based on the original number of red blood cells used) in PBS to the equivalent of the membranes from 400 million cells/mL. The membranes were then incubated in PBS for 24 hours, at 37° C. and 5% $CO_2$. After the incubation the red blood cell membranes were removed by centrifugation (15000 g, 20 minutes) the supernatant containing the membrane secretions were retained and analysed. Two multiplex assays were utilised. The 27-plex human cytokine panel that assays for FGF basic, Eotaxin, G-CSF, GM-CSF, IFN-γ, IL-β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 46A:
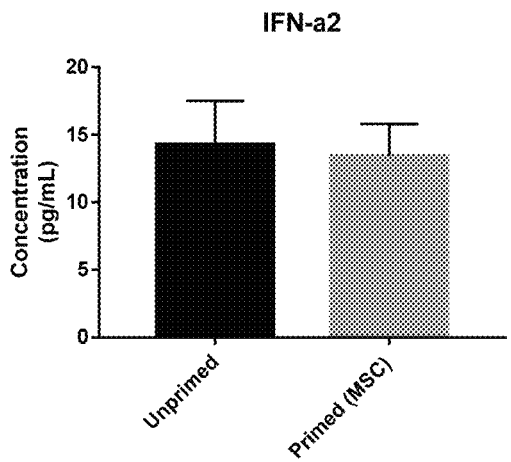
FIG. 46A-46VV is a series of graphs showing the concentration of proteins released by red blood cell membranes following co-culture for 3 days with (primed) or to without (unprimed) mesenchymal stem cells (MSCs). Significant differences (p<0.05) were determined using Student's T-tests.
Figure 46B:
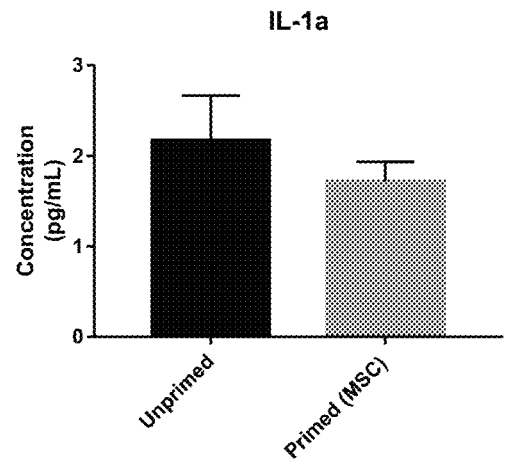
Figure 46C:
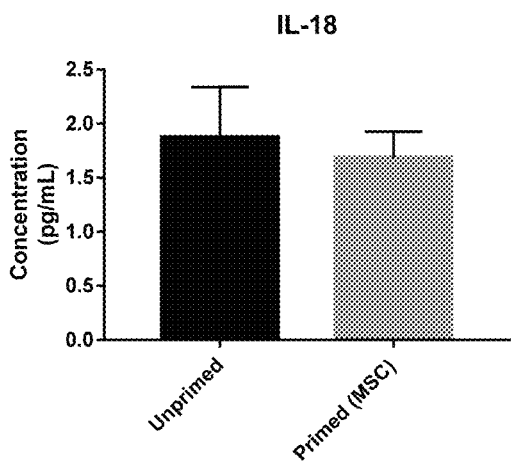
Figure 46D:
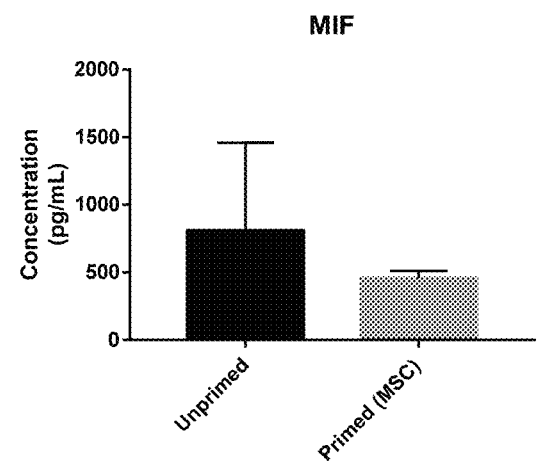
Figure 46E:
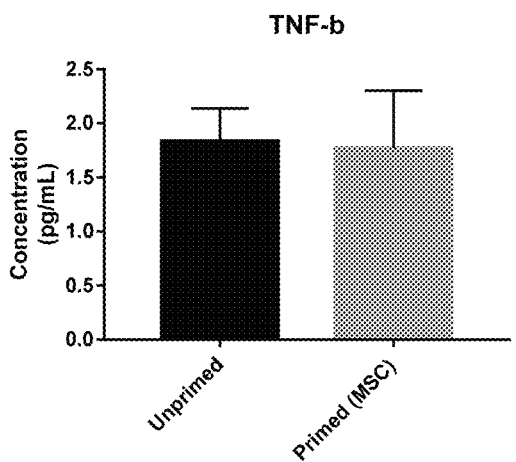
Figure 46F:
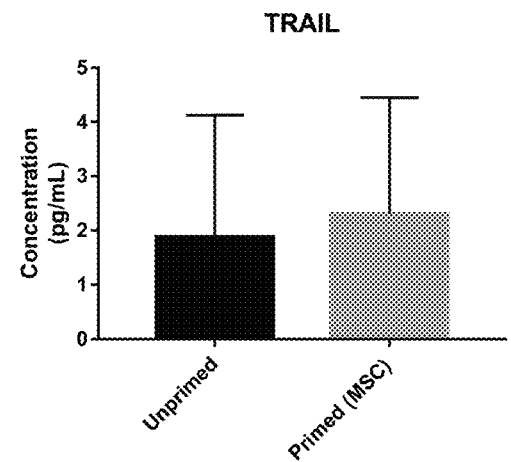
Figure 46G:
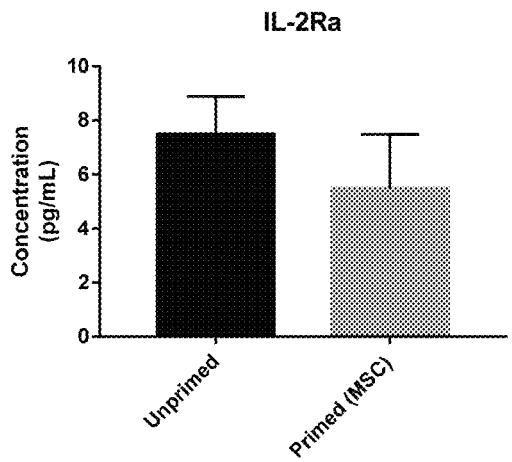
Figure 46H:
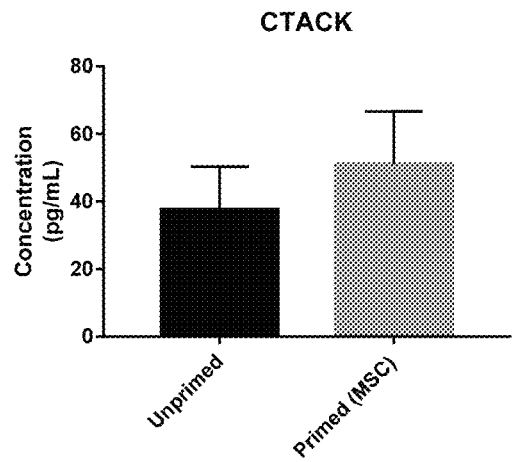
Figure 46I:
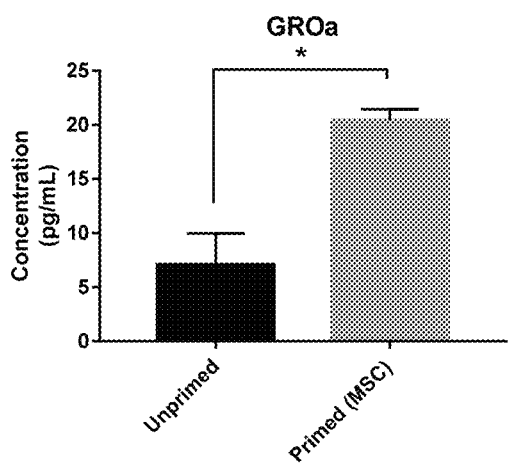
Figure 46J:
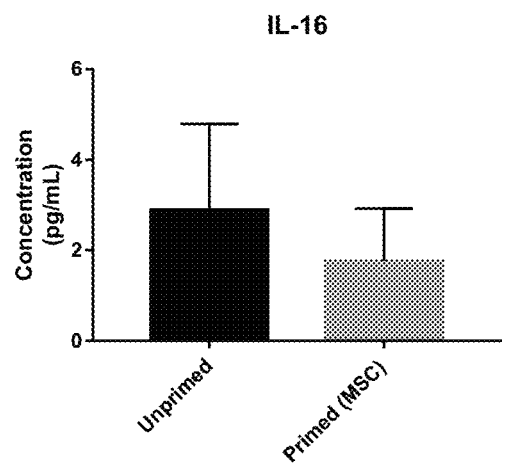
Figure 46K:
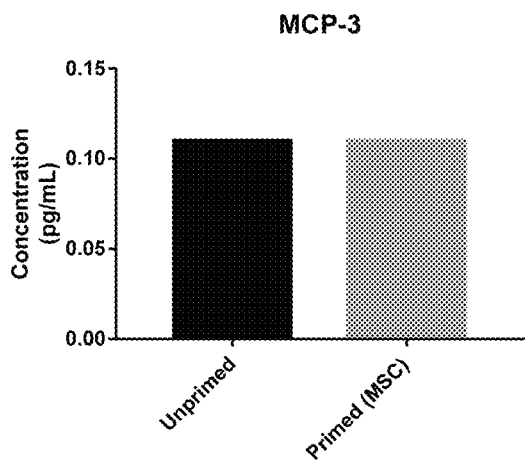
Figure 46L:
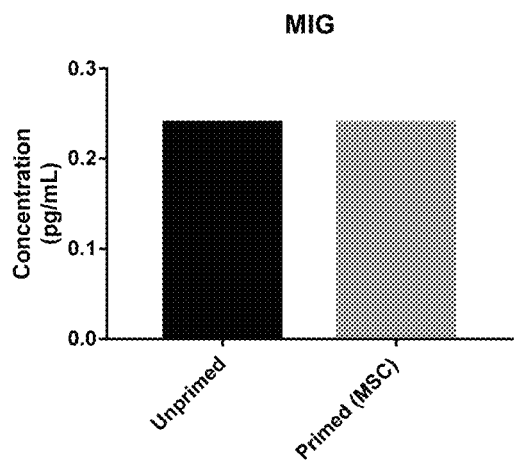
Figure 46M:
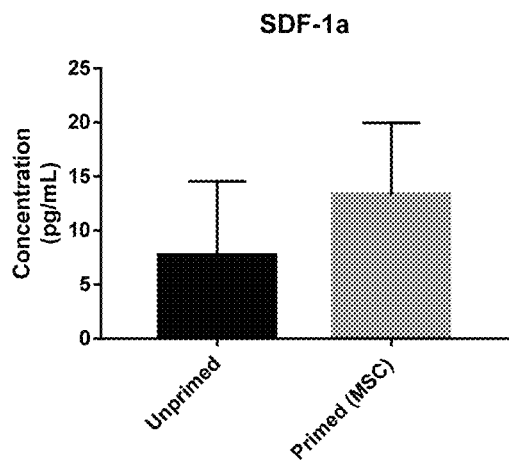
Figure 46N:
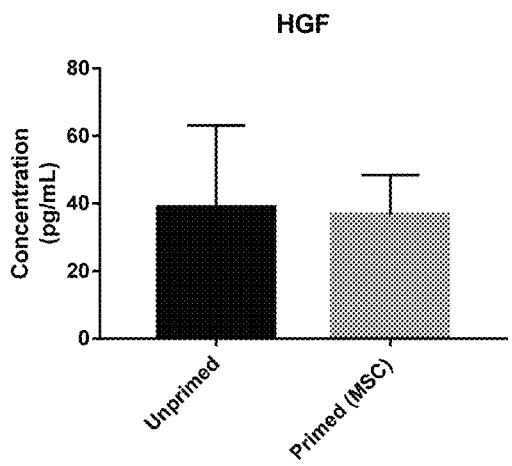
Figure 46O:
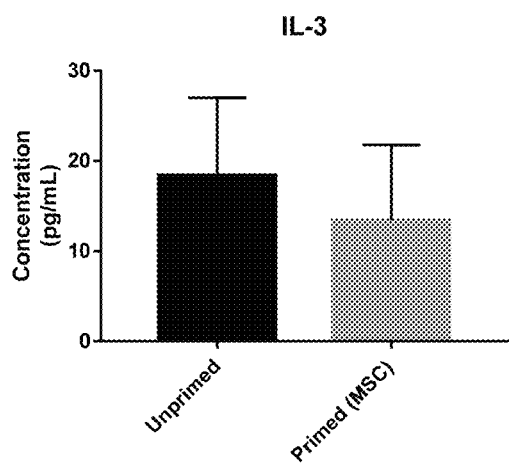
Figure 46P:
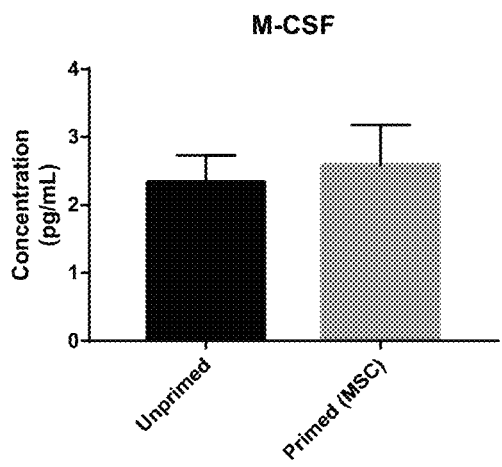
Figure 46Q:
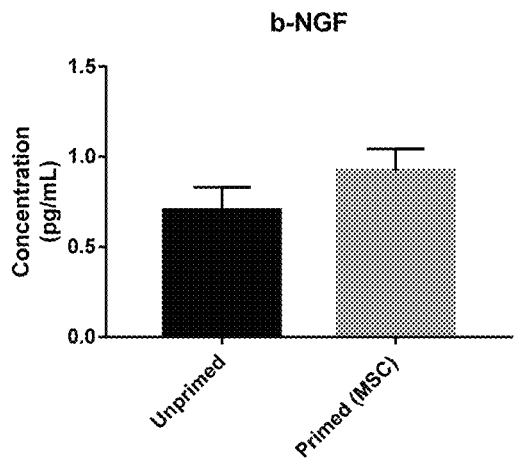
Figure 46R:
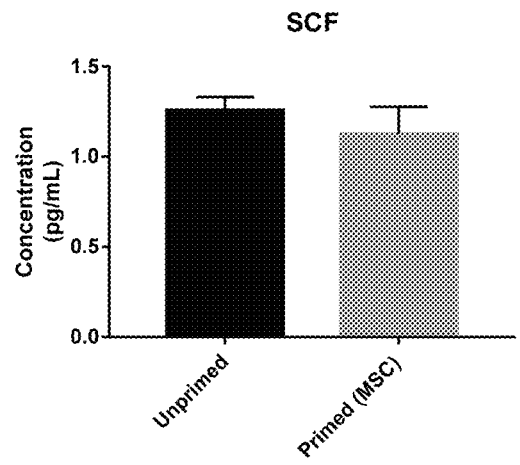
Figure 46S:
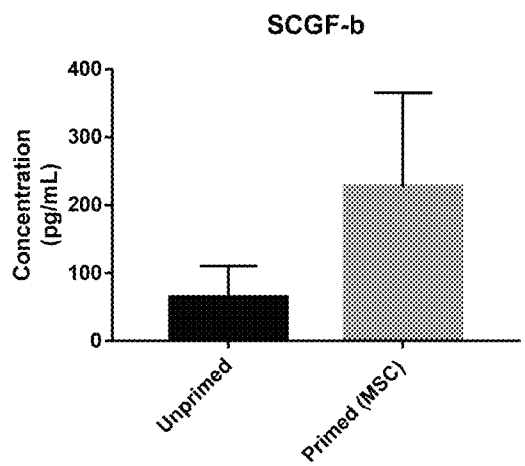
Figure 46T:
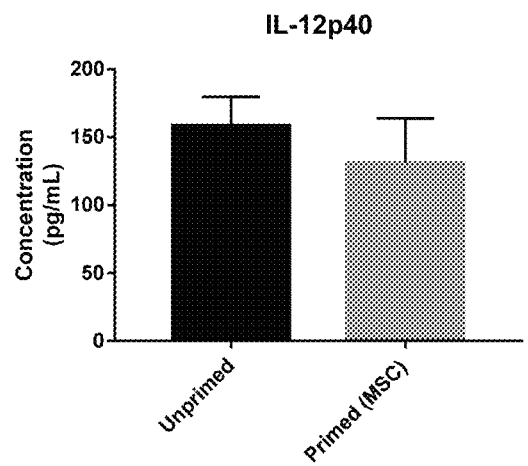
Figure 46U:
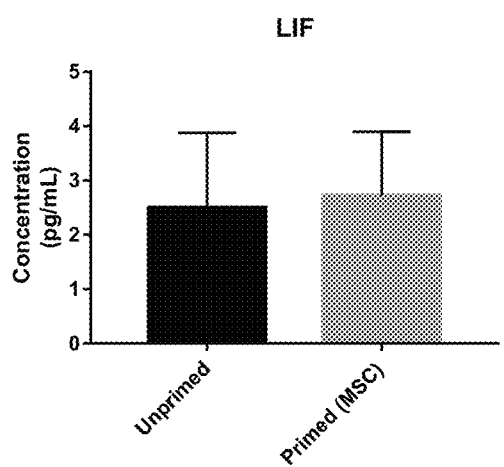
Figure 46V:
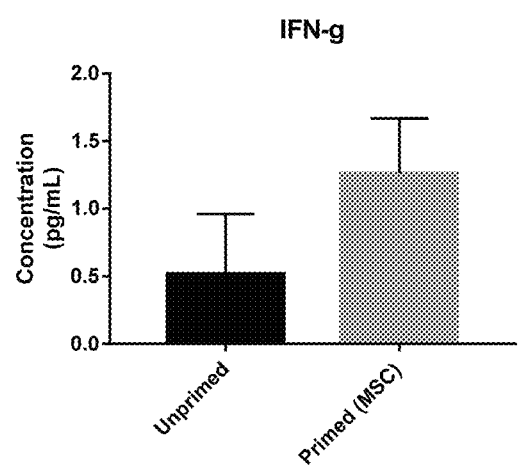
Figure 46W:
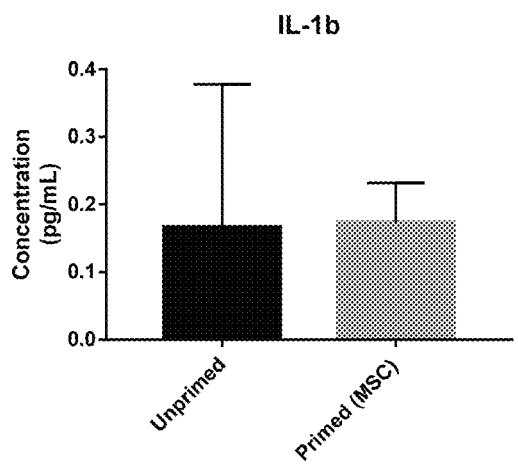
Figure 46X:
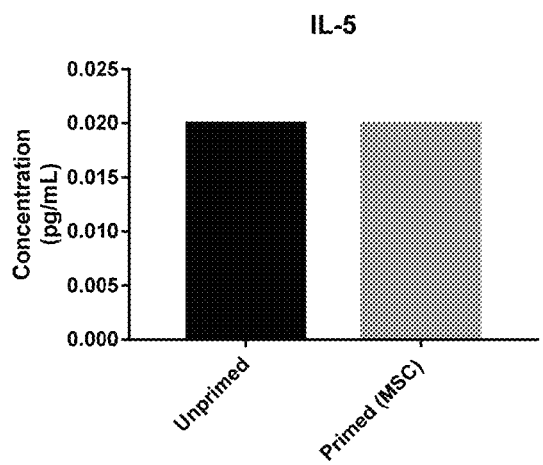
Figure 46Y:
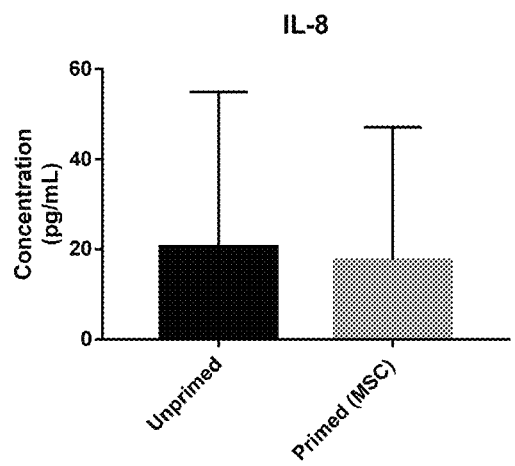
Figure 46Z:
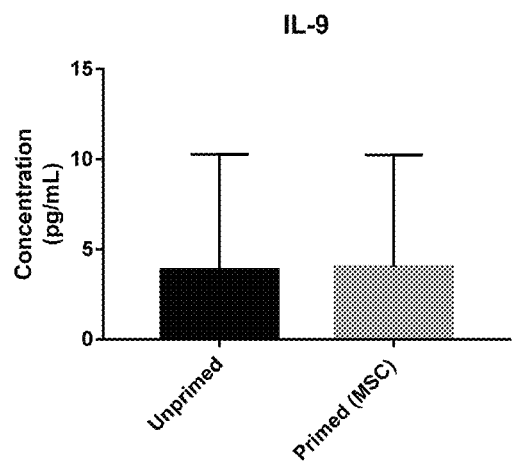
Figure 46A:
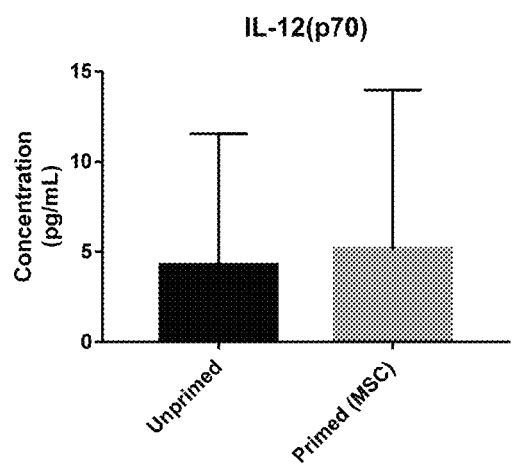
Figure 46B:
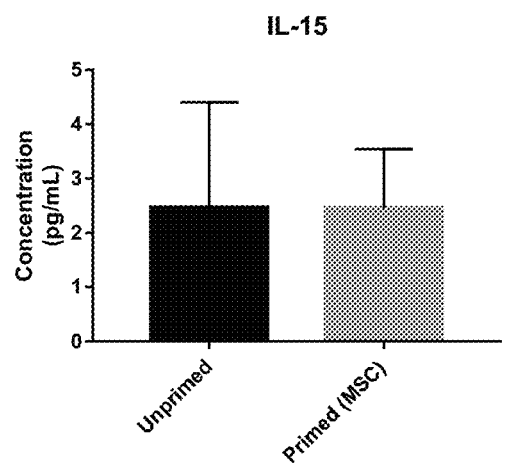
Figure 46C:
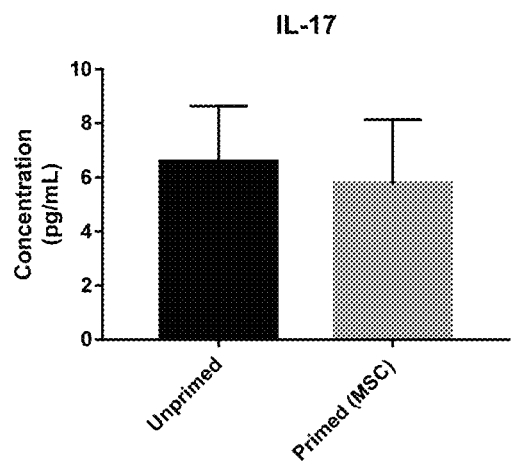
Figure 46D:
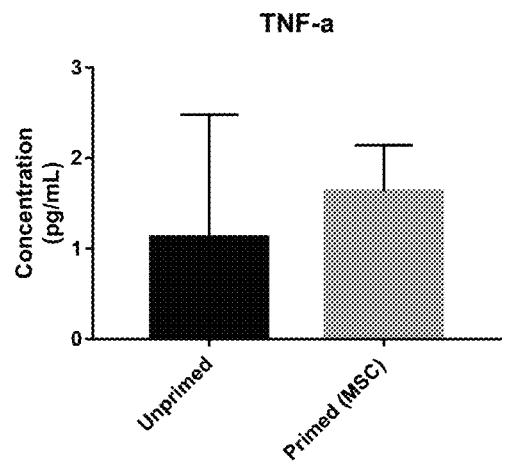
Figure 46E:
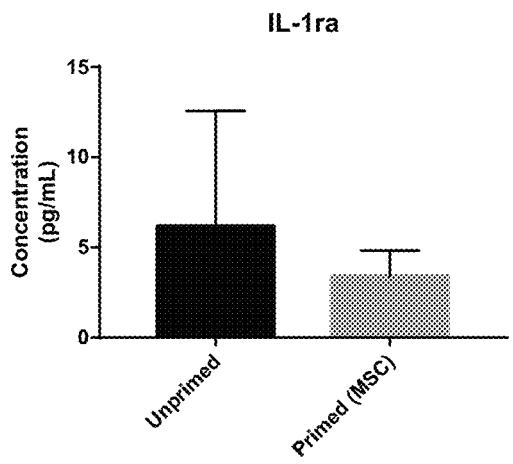
Figure 46F:
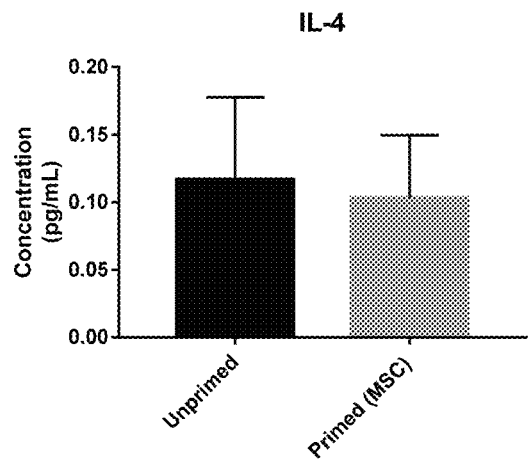
Figure 46G:
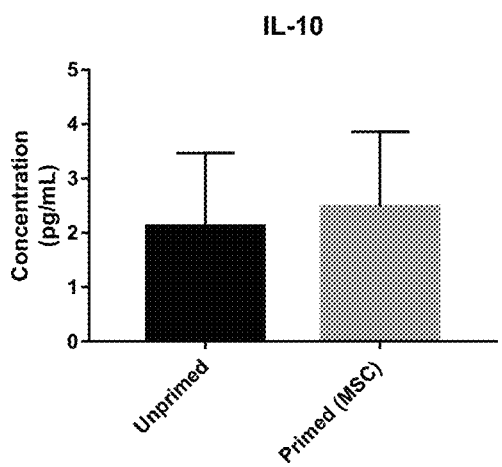
Figure 46H:
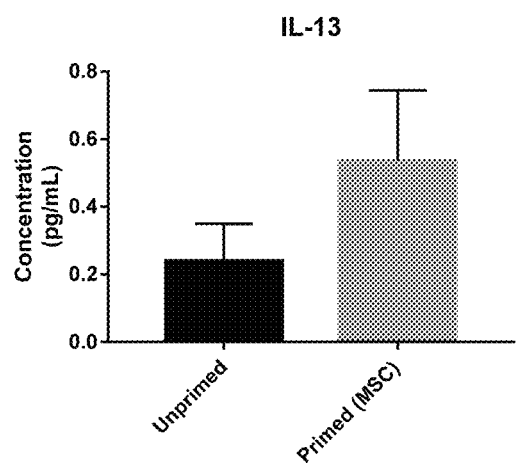
Figure 46I:
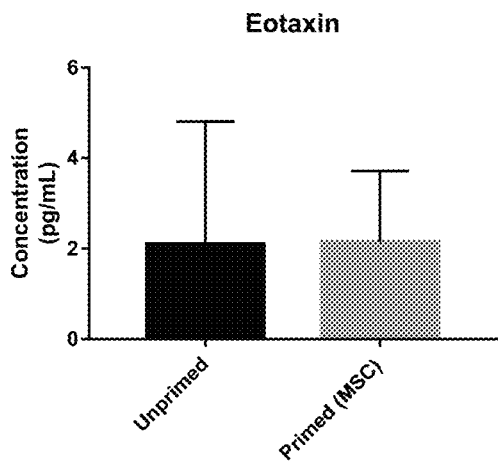
Figure 46J:
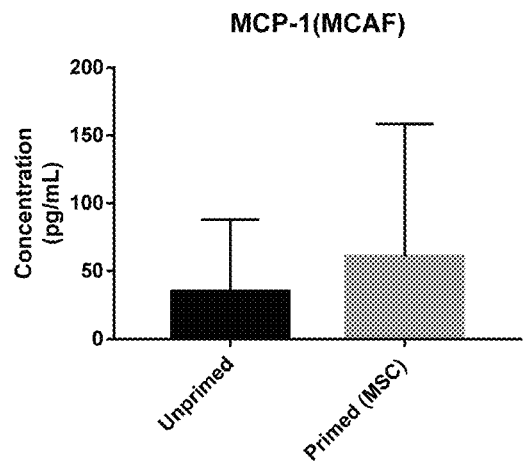
Figure 46K:
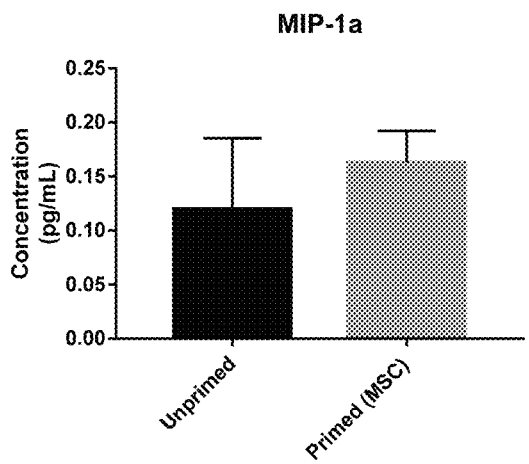
Figure 46L:
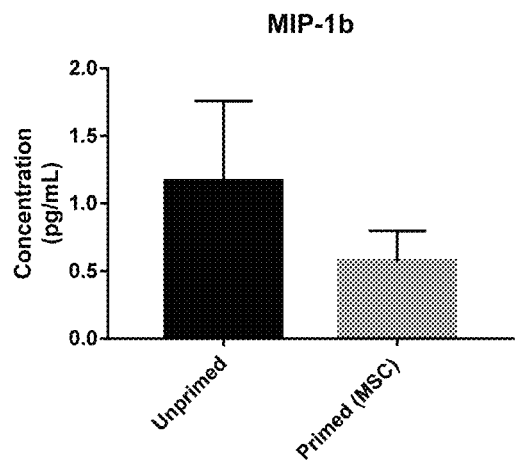
Figure 46M:
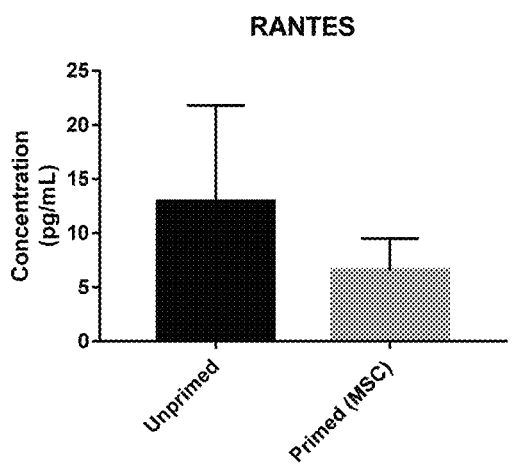
Figure 46N:
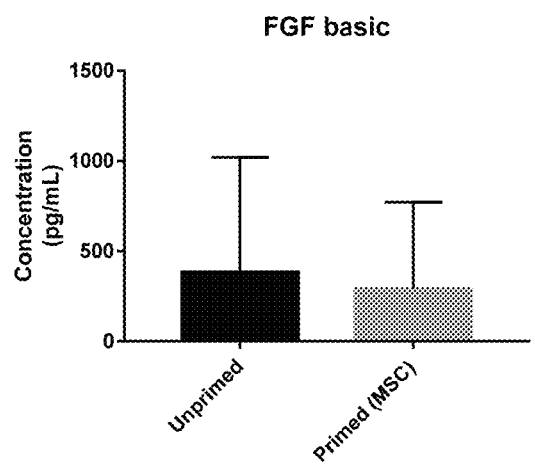
Figure 46O:
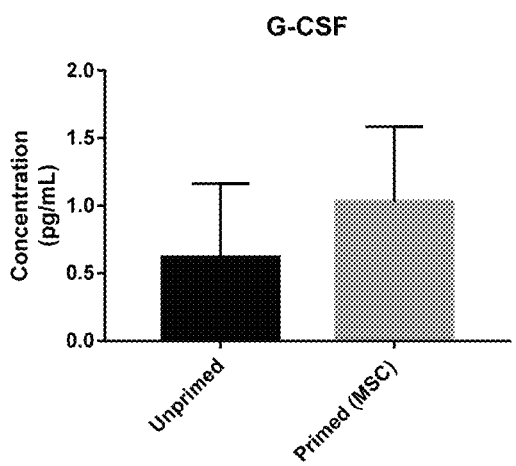
Figure 46P:
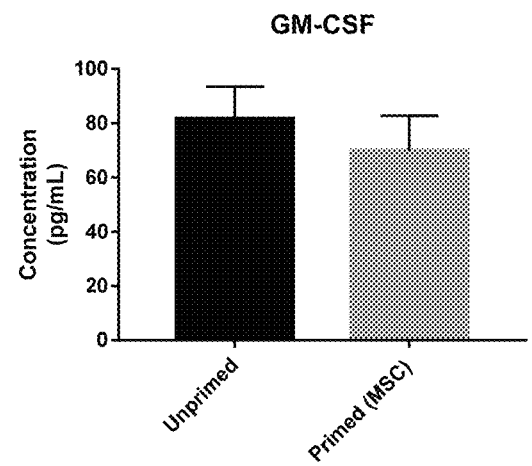
Figure 46Q:
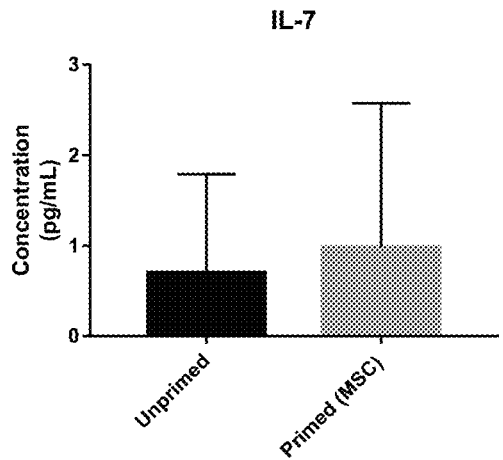
Figure 46R:
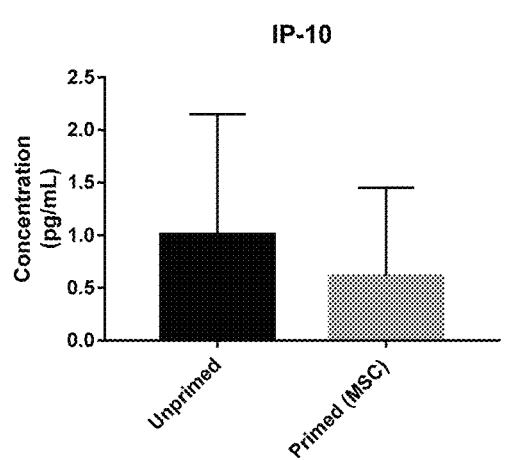
Figure 46S:
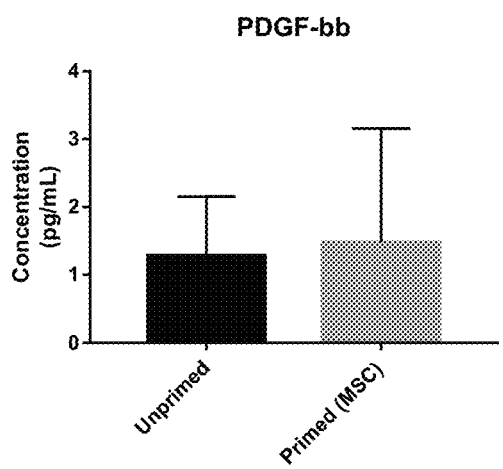
Figure 46T:
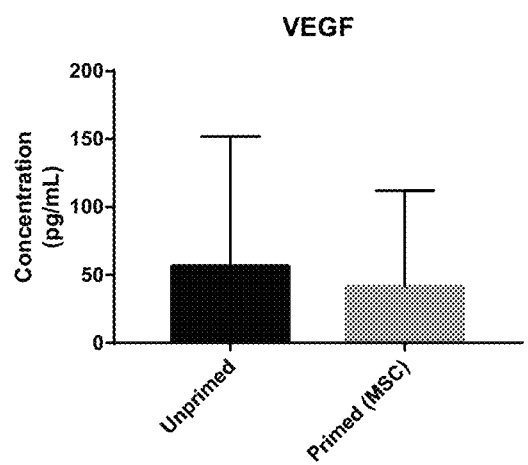
Figure 46U:
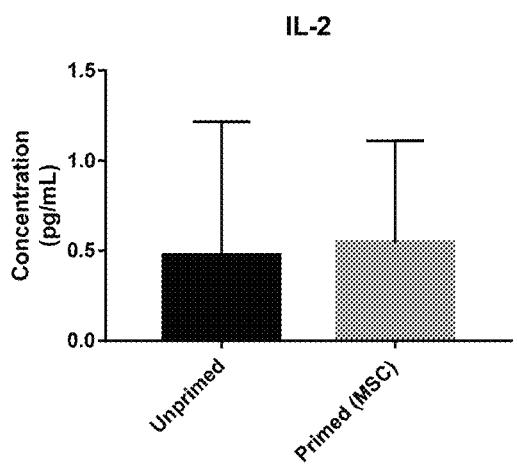
Figure 46V:
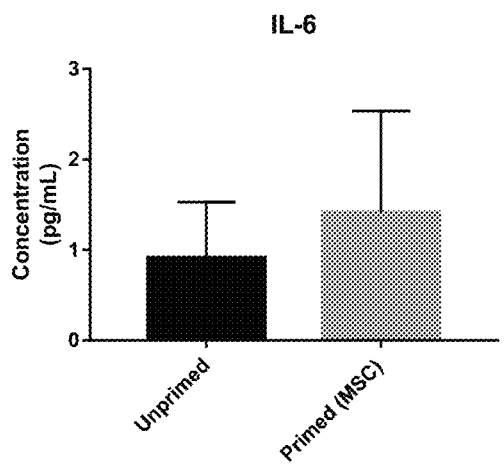

As shown in FIG. 46A-46VV, the cytokine profile of the red blood cell membranes was only very slightly altered by the 'priming' process, which in this instance was co-culture with MSCs (Mesenchymal stem cells). The red blood cell membrane secretion concentration of GRO-α was significantly increased following co-culture priming. Whilst the no analytes decreased significantly following co-culture priming. These results indicate that changes in the secretion profile of red blood cells following priming with MSCs is heavily dependent on the red blood cells being intact.

11.3. RBC Lysates

Whole blood was collected from healthy volunteers (n≥3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

Mesenchymal stem cells (MSCs) isolated from adipose tissue were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MSCs were seeded into T75 flasks at a concentration of $0.1 \times 10^6$ cells per mL of culture media and were incubated for 24 hours to ensure plate adherence (37° C., 5% $CO_2$). After incubation, the conditions as outlined in Table 10 were prepared using freshly isolated red blood cells. For co-culture with red blood cells the total volume of culture media in T75 flasks was 18 mL.

TABLE 10

Co-culture conditions for MSCs red blood cells (RBCs) at a ratio of 1:100 at 37° C., 5% $CO_2$ for 72 hours.

| Condition | Label | Flask size | MSCs seeded | Red blood cell number |
|---|---|---|---|---|
| MSCs:RBCs (1:100) | Primed | T75 | $1.8 \times 10^6$ | $180 \times 10^6$ |
| RBCs | Unprimed | T75 | — | $180 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were washed once with PBS and counted using a haematology analyser (Coulter Act Diff, Beckman Coulter).

The primed and unprimed red blood cells were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 47A:
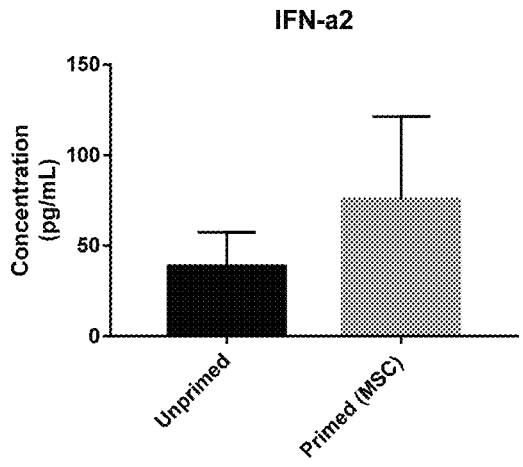
FIG. 47A-47VV is a series of graphs showing the concentration of proteins in red blood cells following co-culture for 3 days with (primed) or without (unprimed) mesenchymal stem cells (MSCs). Significant differences (p<0.05) were determined using Student's T-tests.
Figure 47B:
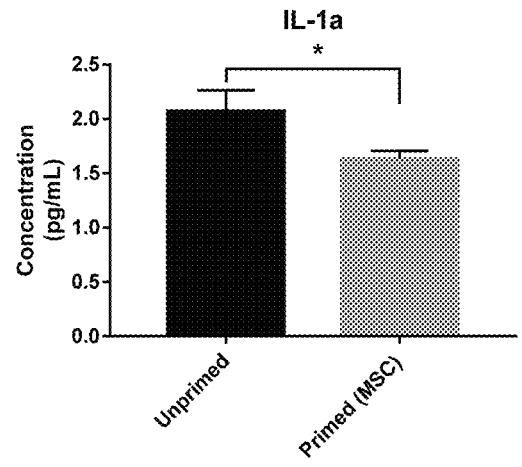
Figure 47C:
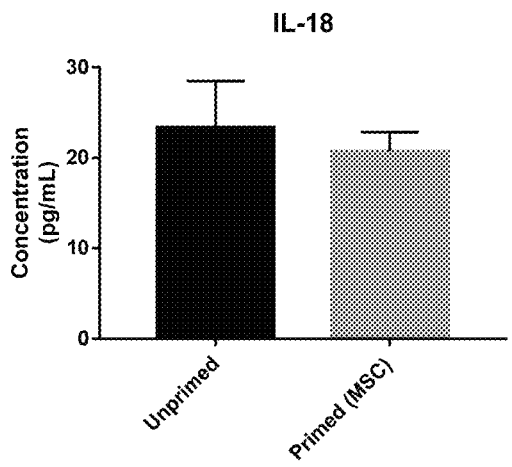
Figure 47D:
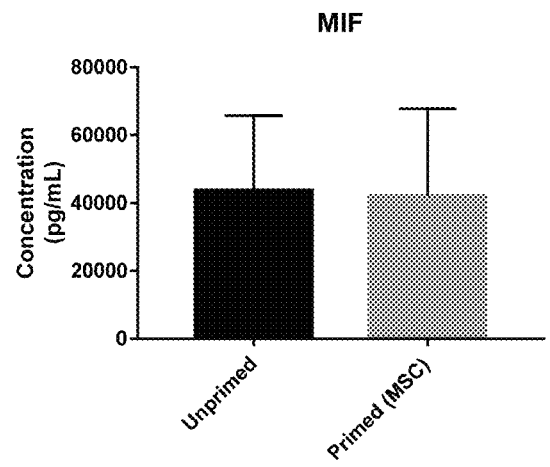
Figure 47E:
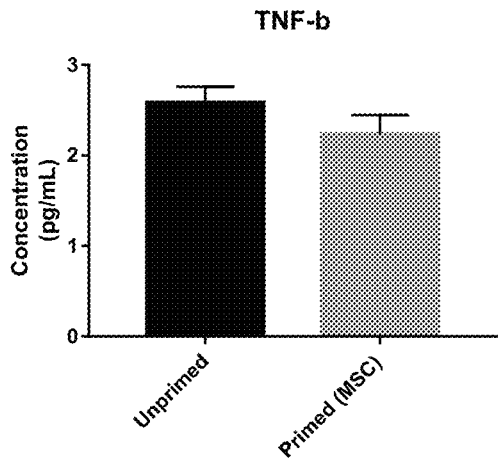
Figure 47F:
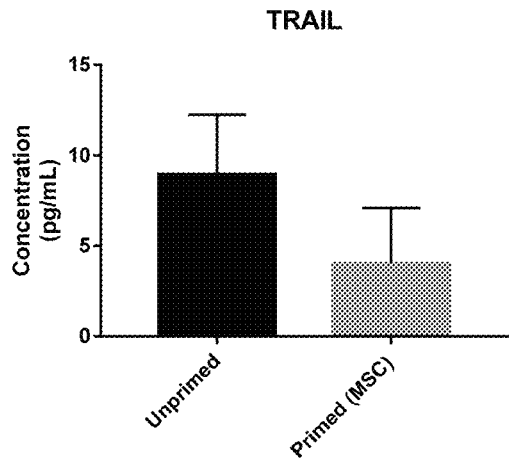
Figure 47G:
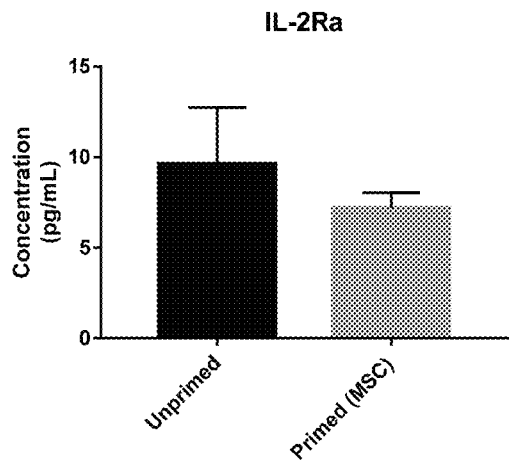
Figure 47H:
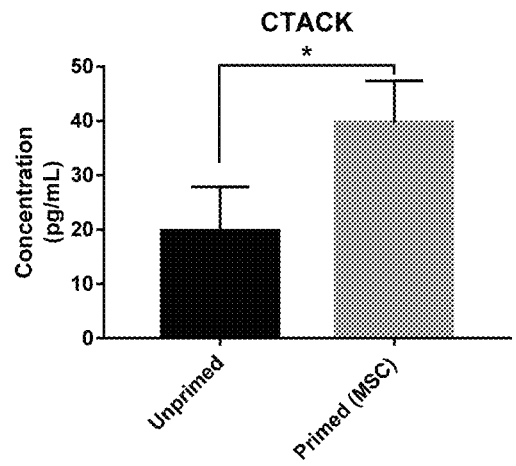
Figure 47I:
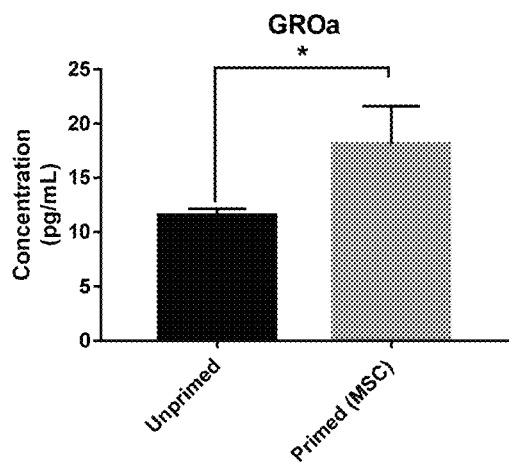
Figure 47J:
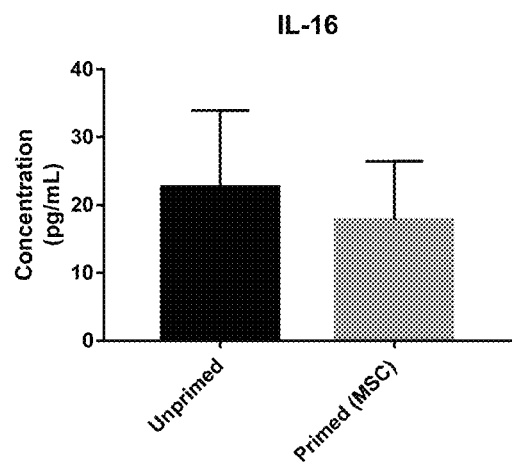
Figure 47K:
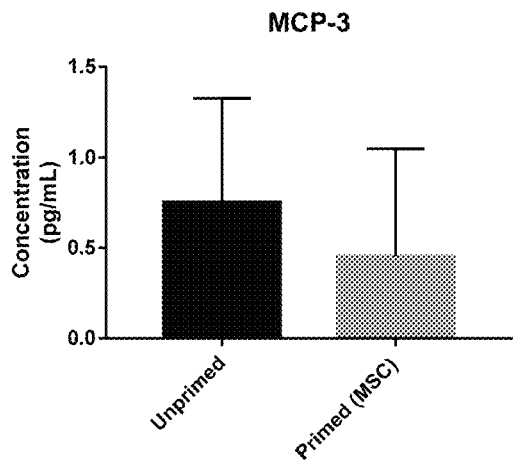
Figure 47L:
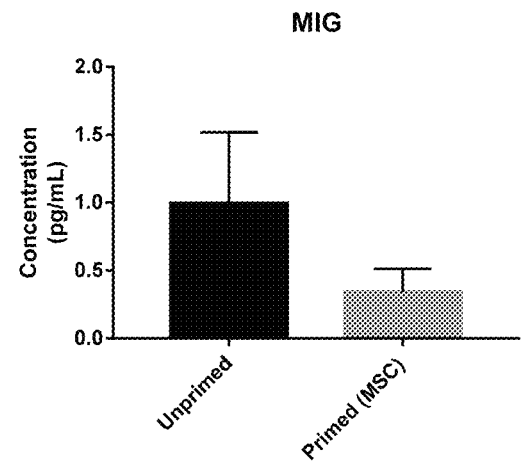
Figure 47M:
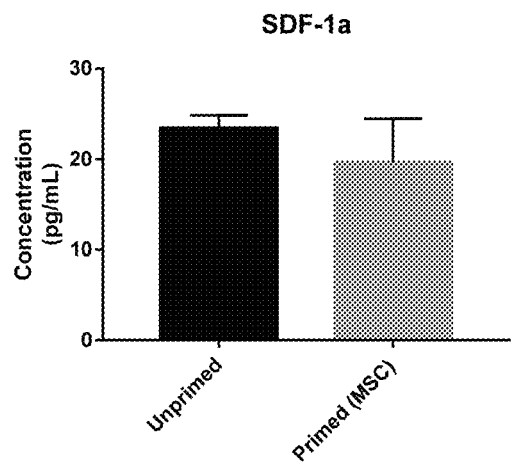
Figure 47N:
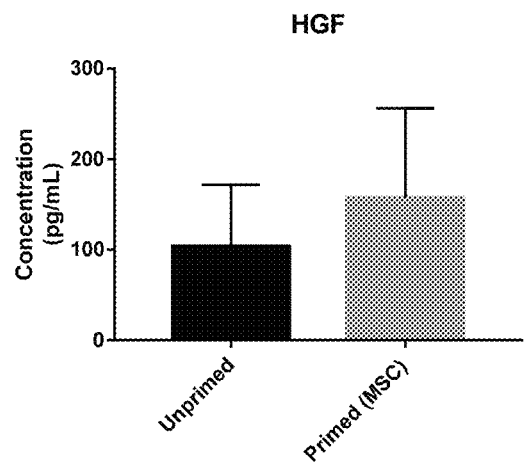
Figure 47O:
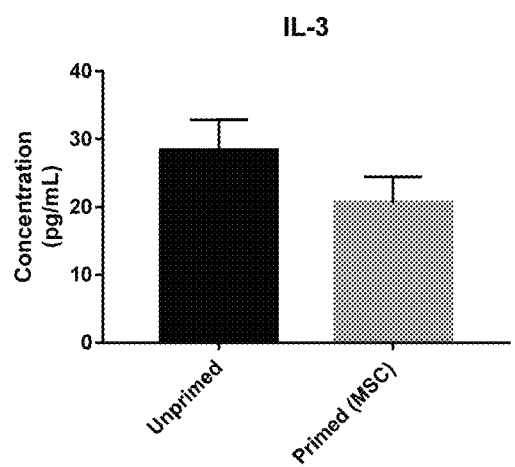
Figure 47P:
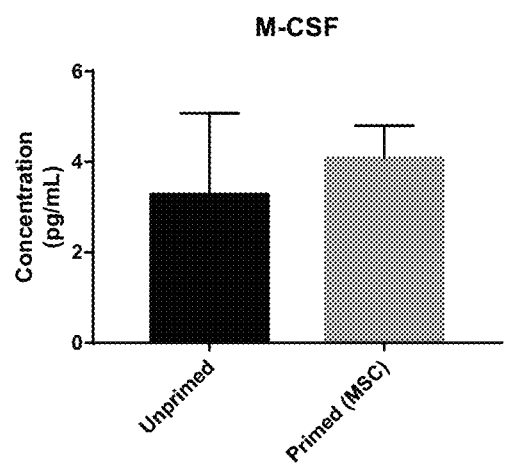
Figure 47Q:
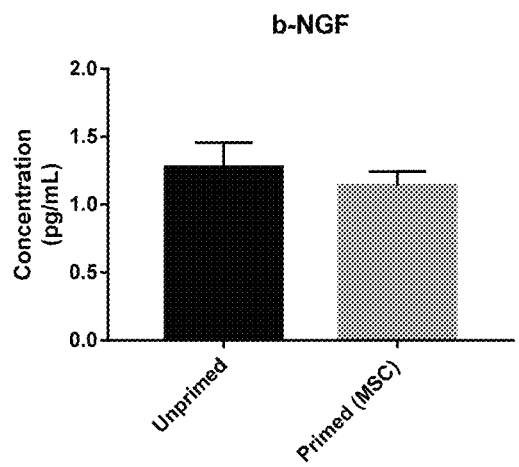
Figure 47R:
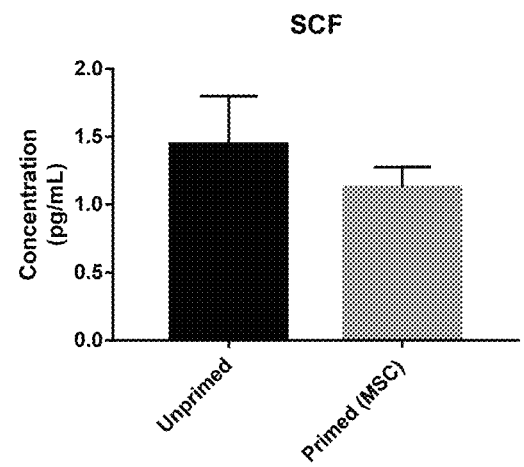
Figure 47S:
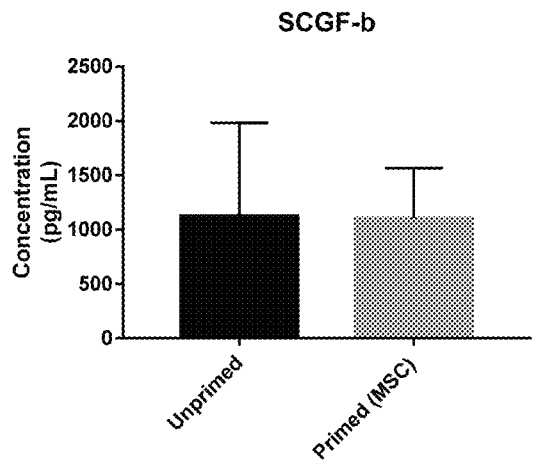
Figure 47T:
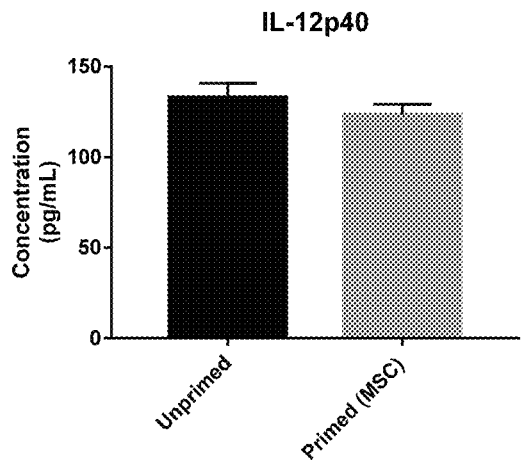
Figure 47U:
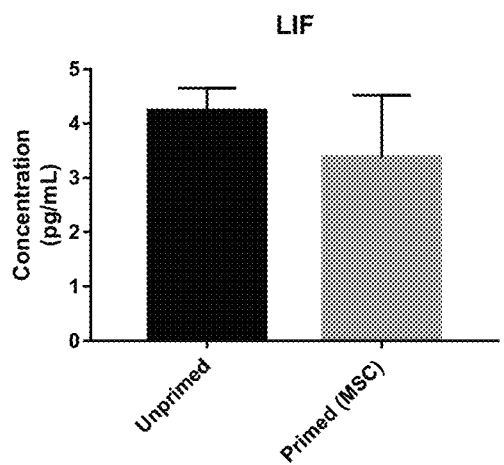
Figure 47V:
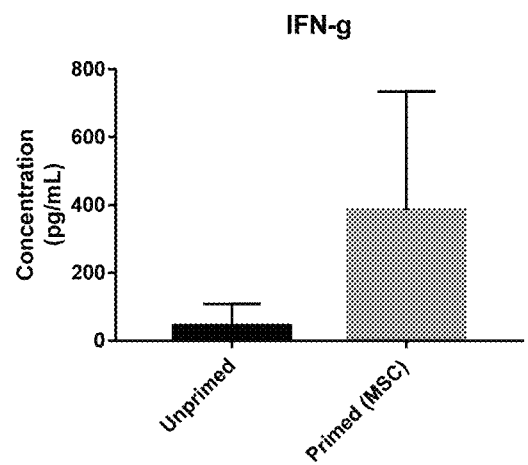
Figure 47W:
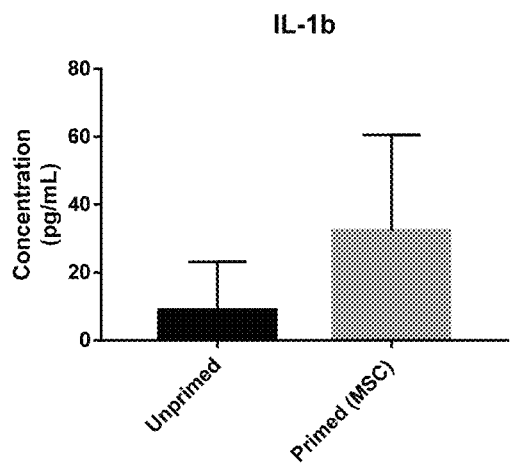
Figure 47X:
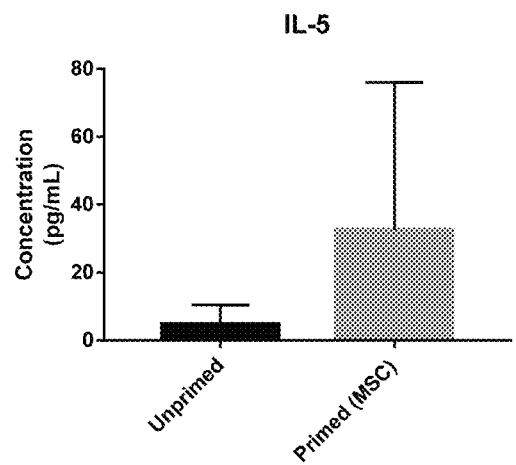
Figure 47Y:
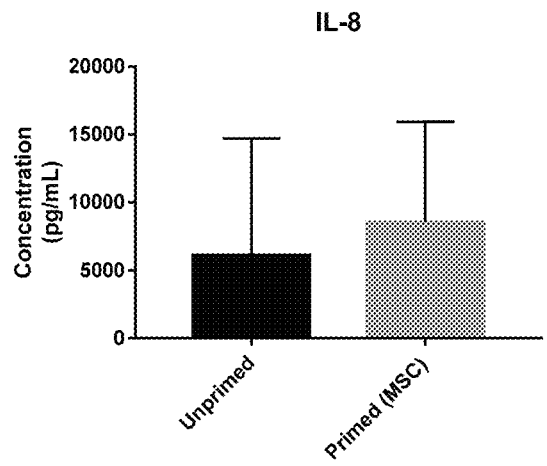
Figure 47Z:
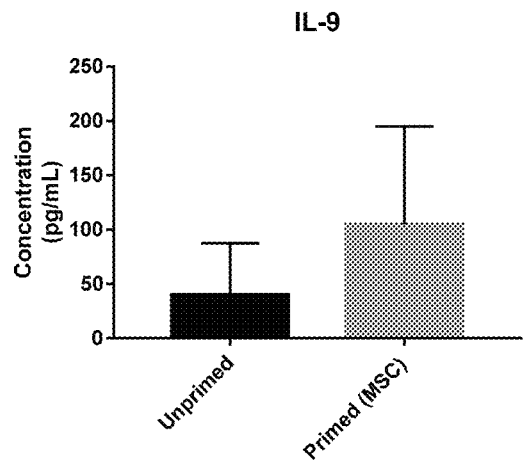
Figure 47A:
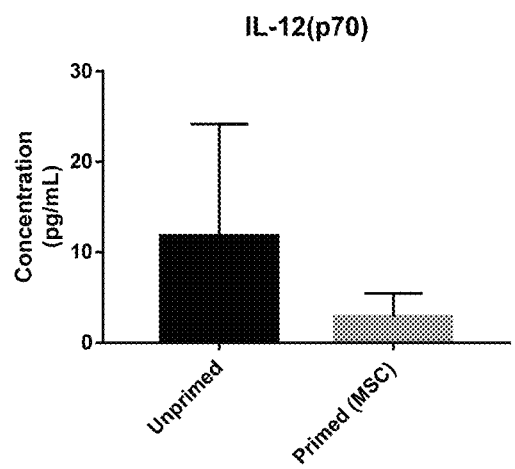
Figure 47B:
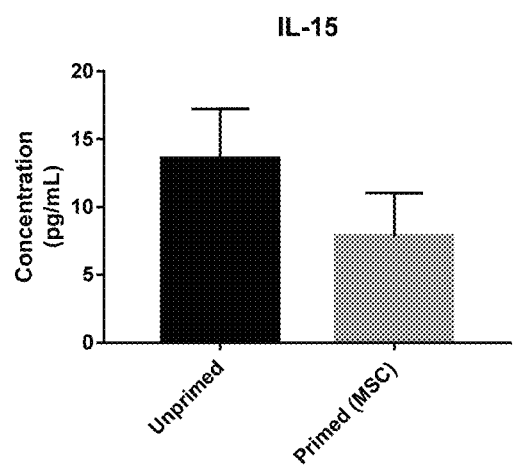
Figure 47C:
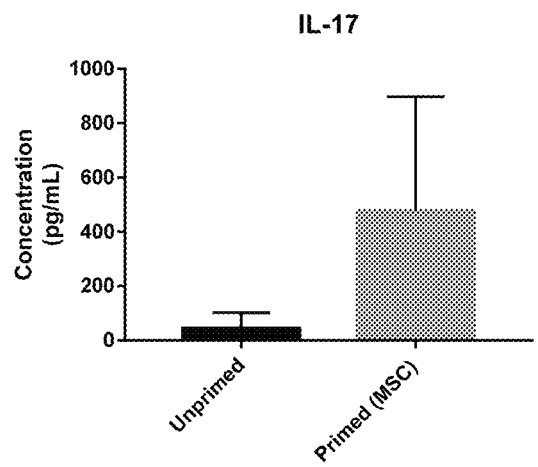
Figure 47D:
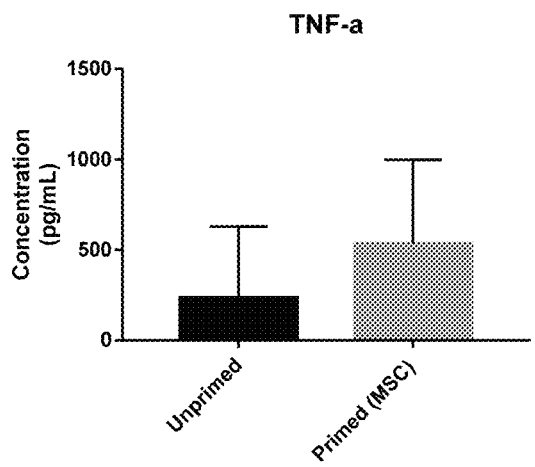
Figure 47E:
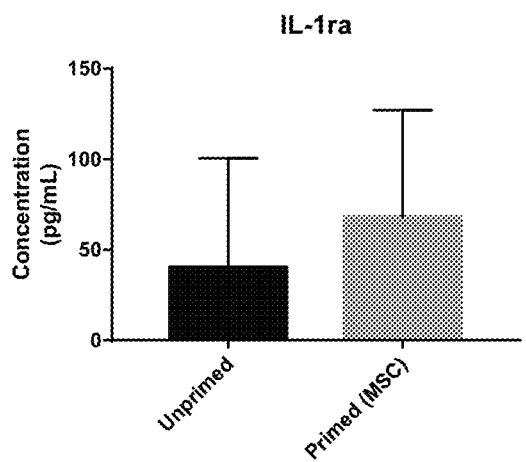
Figure 47F:
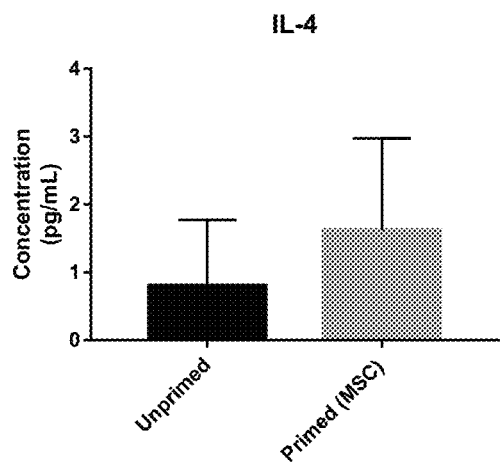
Figure 47G:
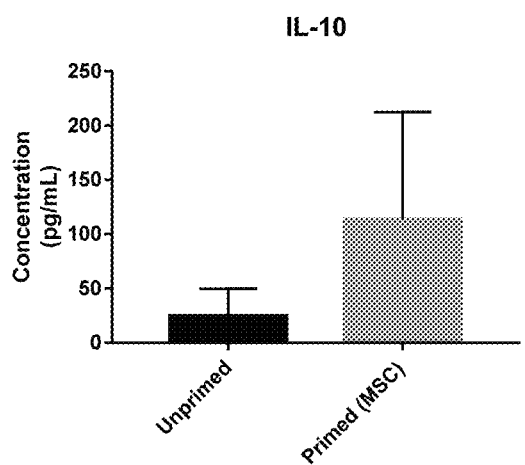
Figure 47H:
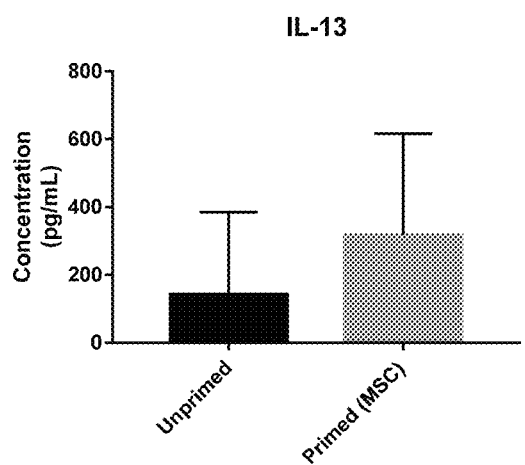
Figure 47I:
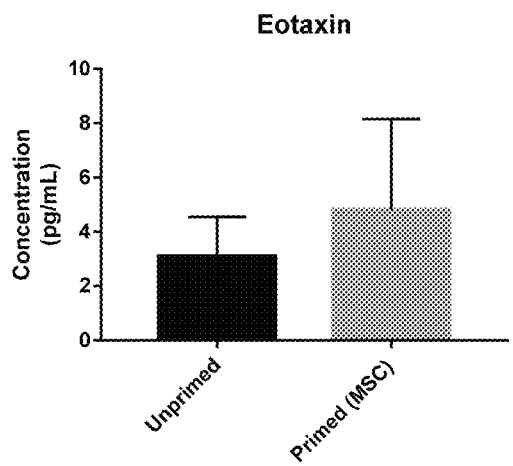
Figure 47J:
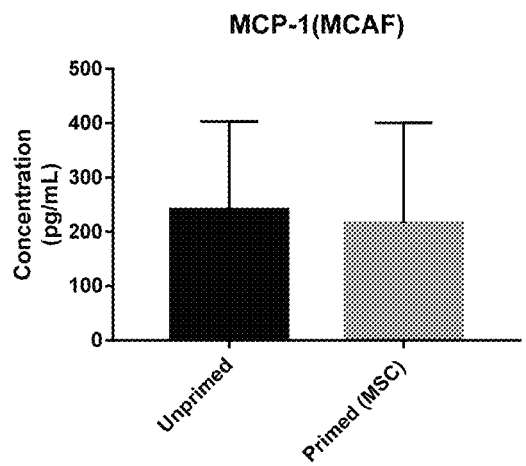
Figure 47K:
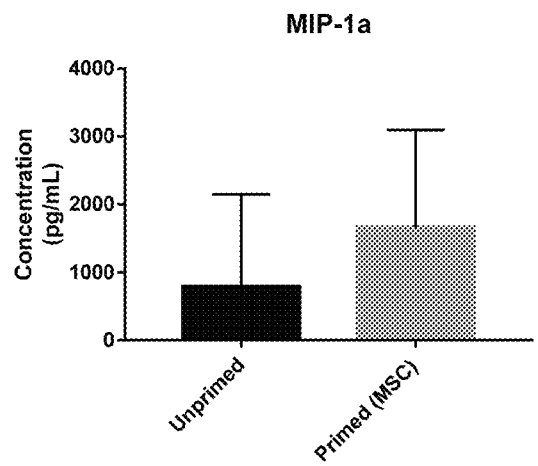
Figure 47L:
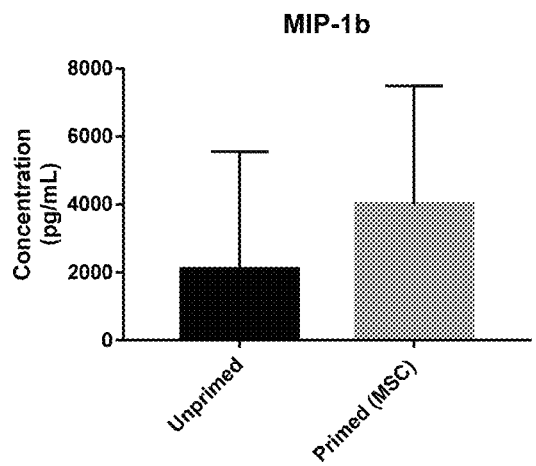
Figure 47M:
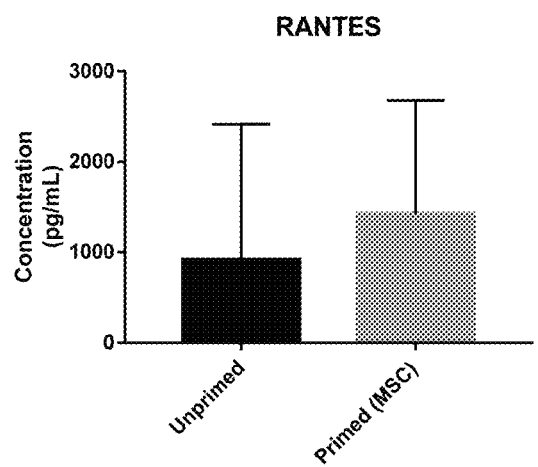
Figure 47N:
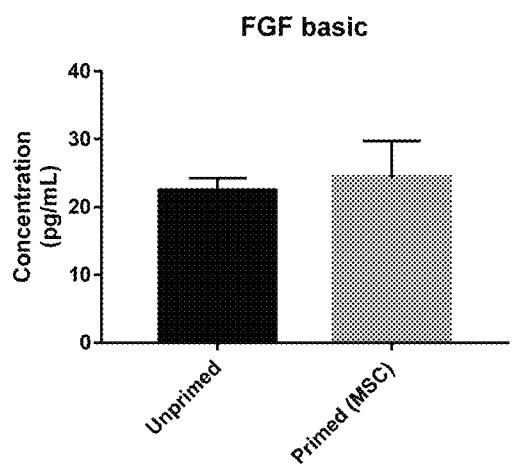
Figure 47O:
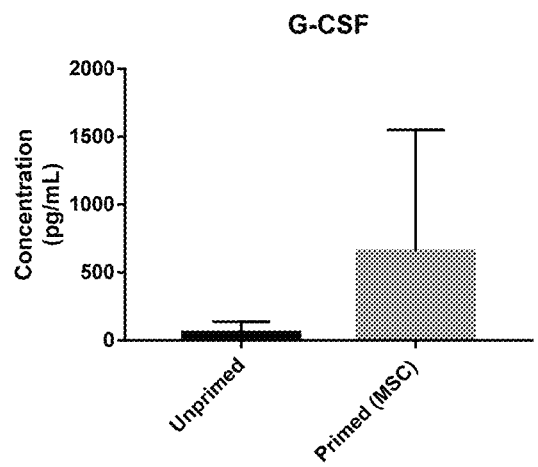
Figure 47P:
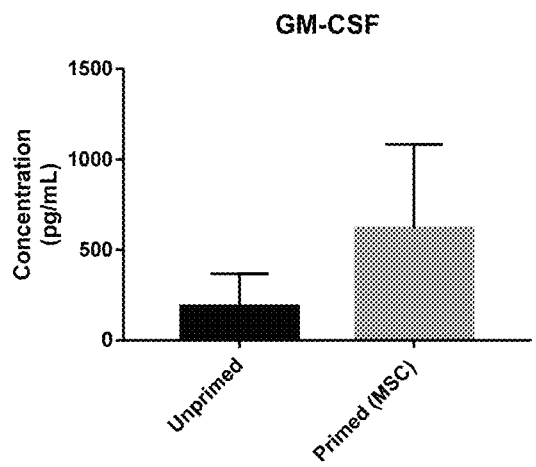
Figure 47Q:
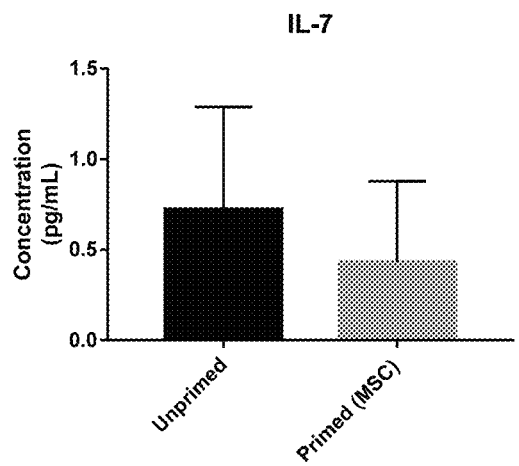
Figure 47R:
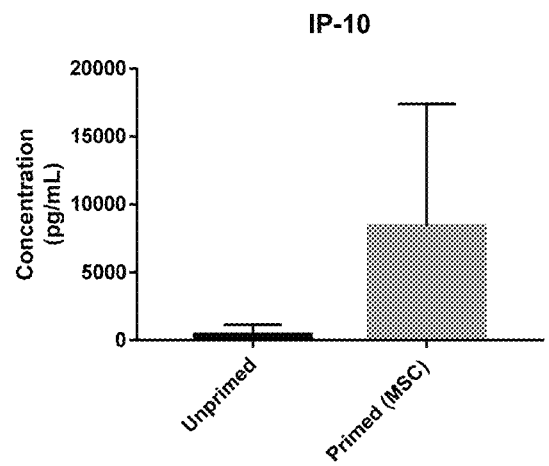
Figure 47S:
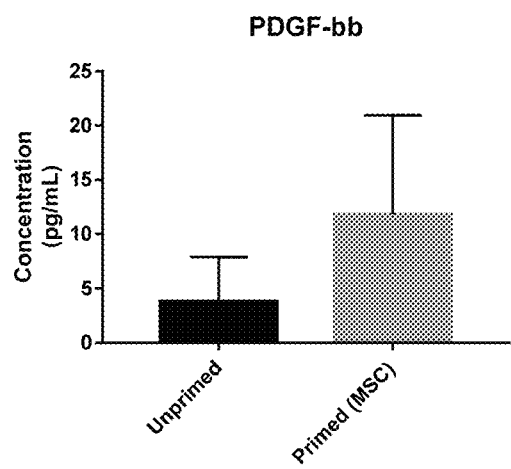
Figure 47T:
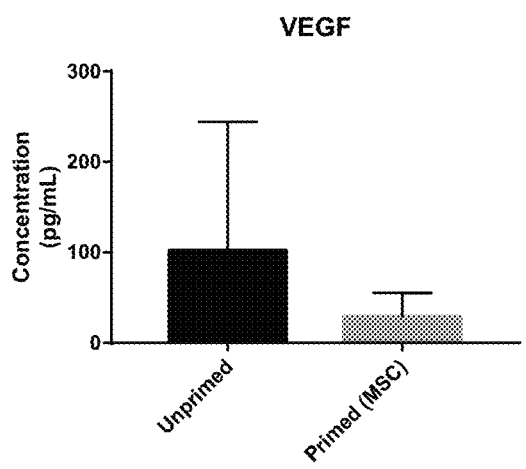
Figure 47U:
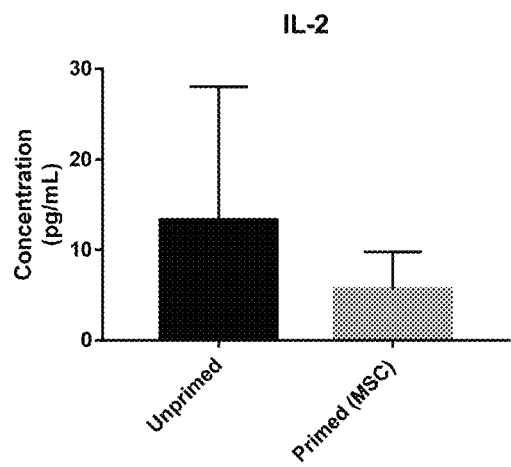
Figure 47V:
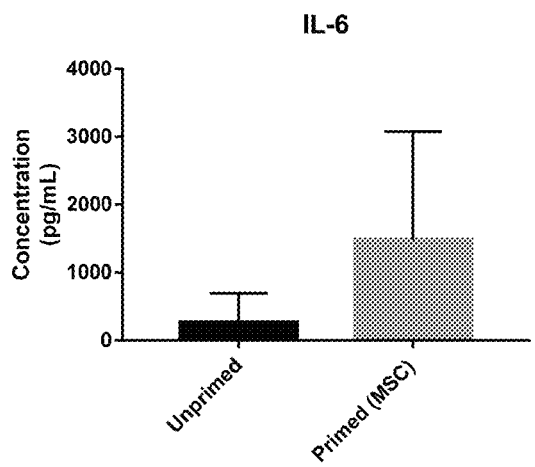

As shown in FIG. 47A-47VV, the cytokine profile of the red blood cells was altered by the 'priming' process, which in this instance was co-culture with mesenchymal stem cells (MSCs). The red blood cell concentration of analytes such as CTACK and GROa were significantly increased following co-culture priming. Whilst the level of IL-1a decreased significantly following co-culture priming. The results demonstrated that the cytokine profile of red blood cells was subject to change depending on their environment. Comparison of these results with the analysis of the cytokines released or secreted by red blood cells after priming indicated that the extended incubation of RBCs in PBS to generate a secretion profile was significantly more reproducible than the lysis procedure.

11.4. RBC Secretions

Whole blood was collected from healthy volunteers (n=3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

Mesenchymal stem cells (MSCs) isolated from adipose tissue were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MSCs were seeded into T75 flasks at a concentration of $0.1 \times 10^6$ cells per mL of culture media and were incubated for 24 hours to ensure plate adherence (37° C., 5% $CO_2$). After incubation, the conditions as outlined in Table 11 were prepared using freshly isolated red blood cells. For co-culture with red blood cells the total volume of culture media in T75 flasks was 18 mL.

TABLE 11

Co-culture conditions for MSCs and red blood cells (RBCs) at a ratio of 1:100 at 37° C., 5% $CO_2$ for 72 hours.

| Condition | Label | Flask size | MSCs seeded | Red blood cell number |
|---|---|---|---|---|
| MSCs:RBCs (1:100) | Primed | T75 | $2 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were washed once with PBS and counted using a haematology analyser (Coulter Act Diff, Beckman Coulter).

The red blood cells were then diluted in PBS to the equivalent of 400 million cells/mL. The red blood cells were then incubated in PBS for 24 hours, at 37° C. and 5% $CO_2$. After the incubation the red blood cells were removed by centrifugation (500 g, 10 minutes) the supernatants containing the red blood cell secretions were retained and analysed. Two multiplex assays were utilised. The 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 48A:
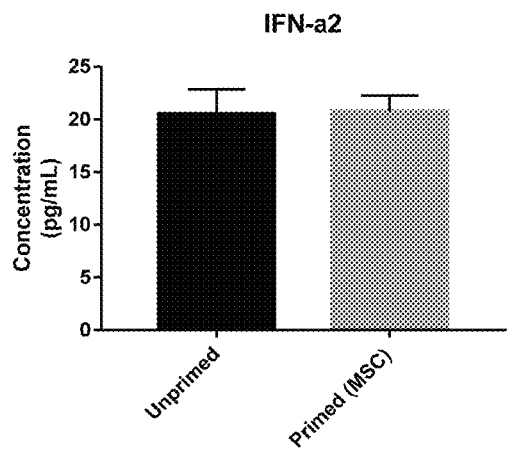
FIG. 48A-48VV is a series of graphs showing the concentration of proteins from red blood cells following co-culture for 3 days with (primed) or without (unprimed) mesenchymal stem cells (MSCs). Significant differences (p<0.05) were determined using Student's T-tests.
Figure 48B:
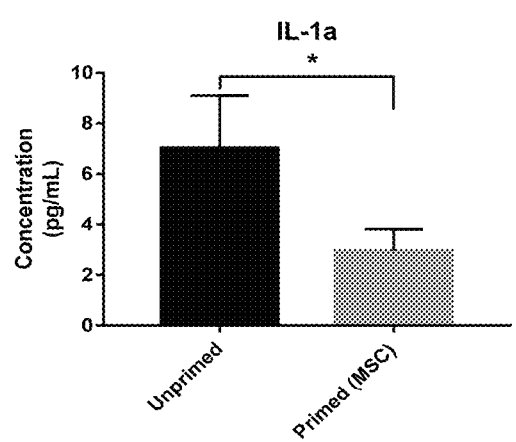
Figure 48C:
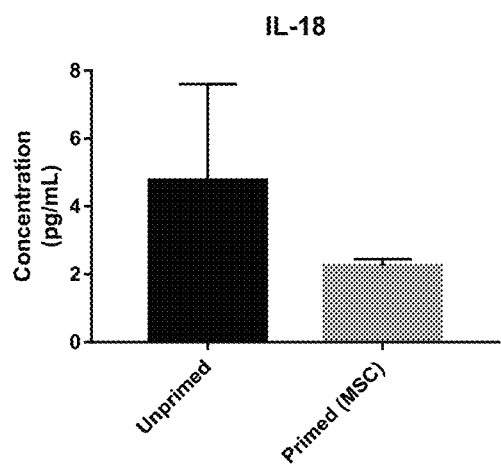
Figure 48D:
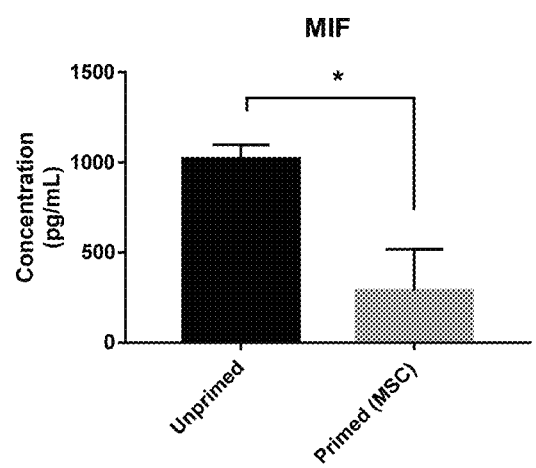
Figure 48E:
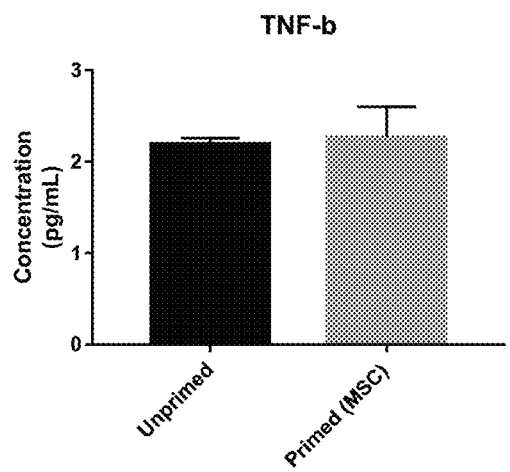
Figure 48F:
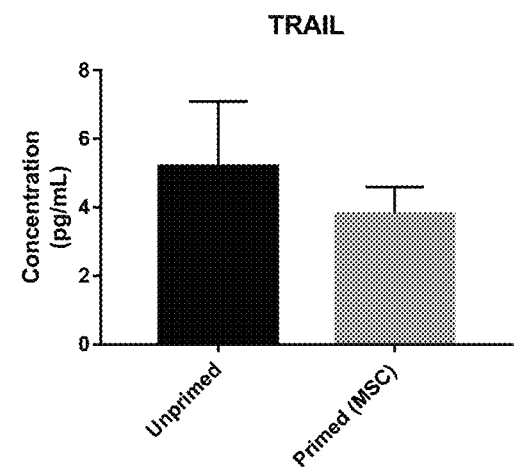
Figure 48G:
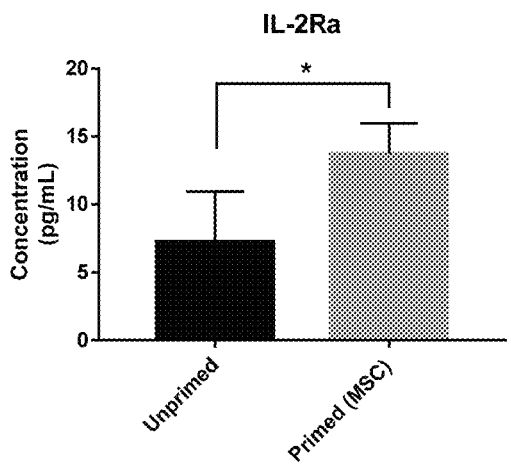
Figure 48H:
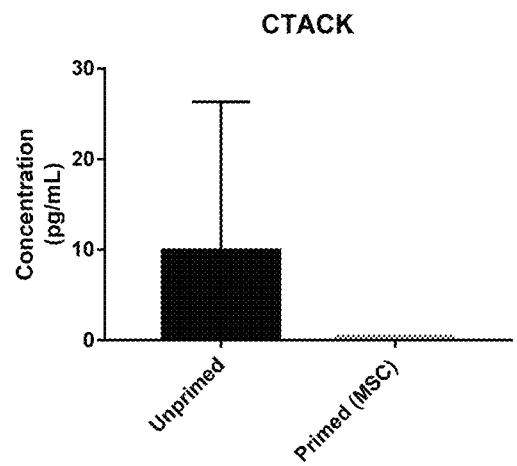
Figure 48I:
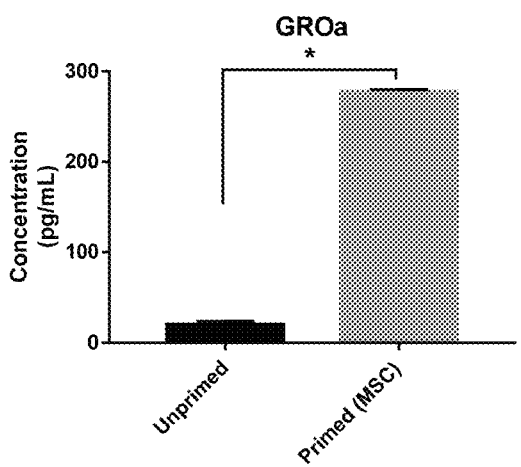
Figure 48J:
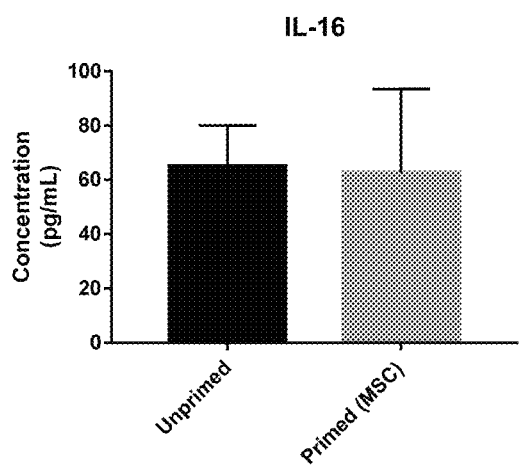
Figure 48K:
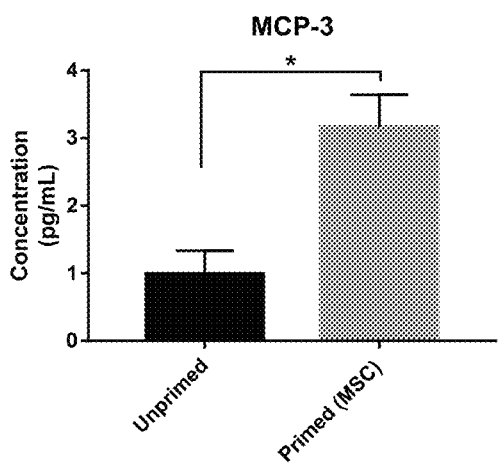
Figure 48L:
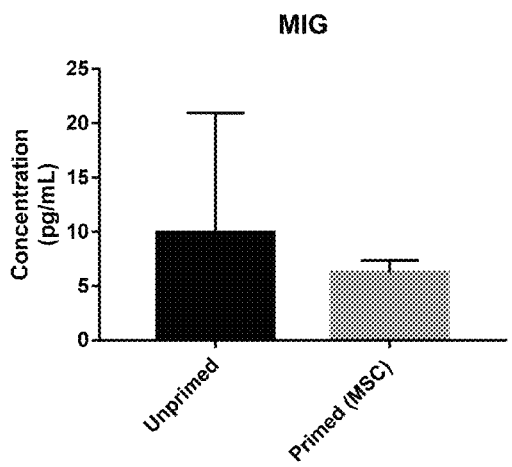
Figure 48M:
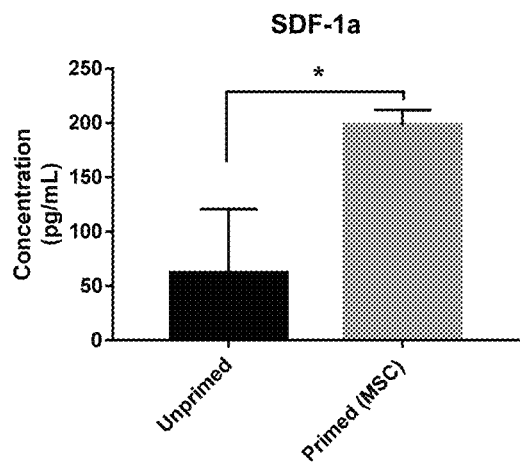
Figure 48N:
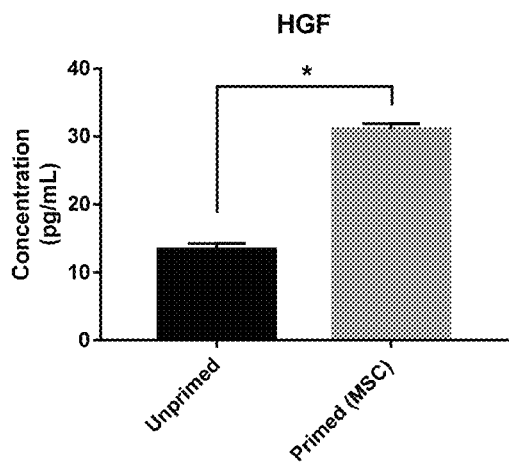
Figure 48O:
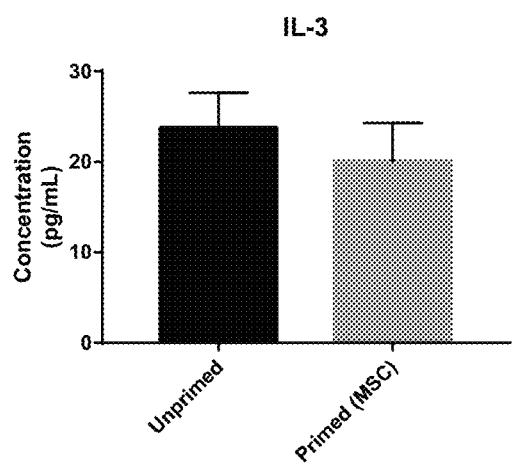
Figure 48P:
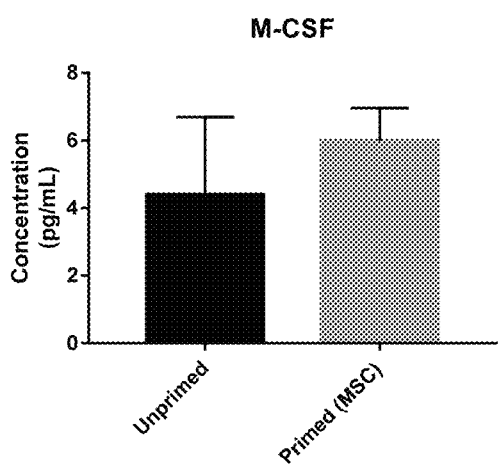
Figure 48Q:
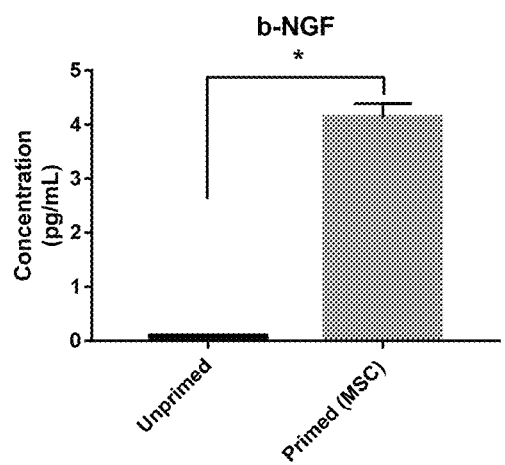
Figure 48R:
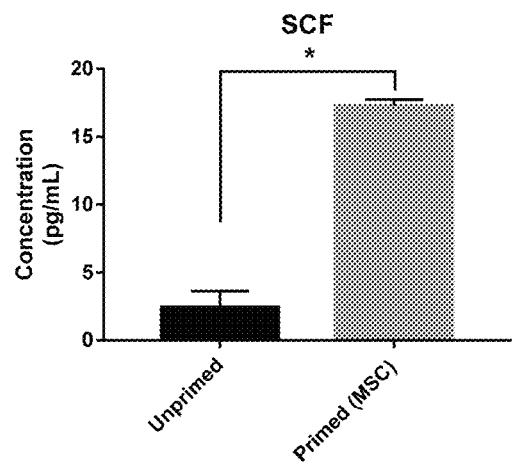
Figure 48S:
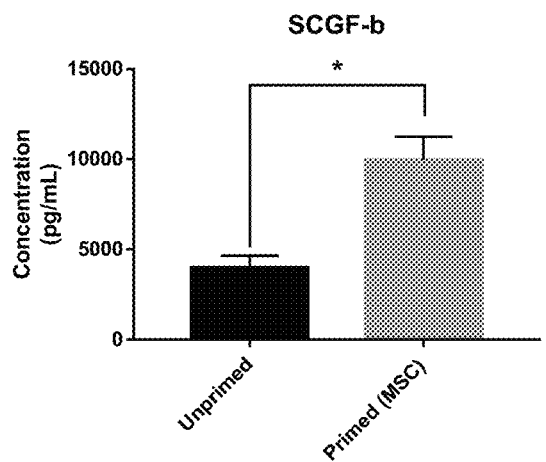
Figure 48T:
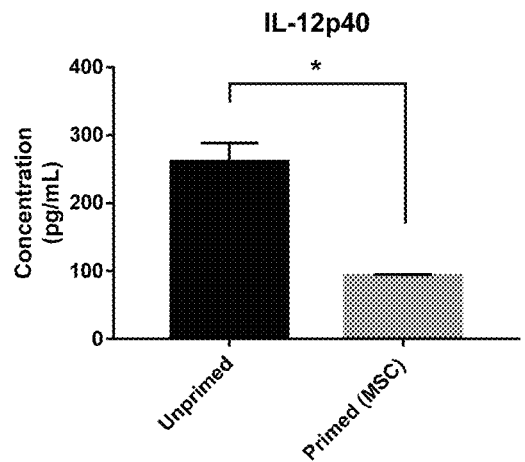
Figure 48U:
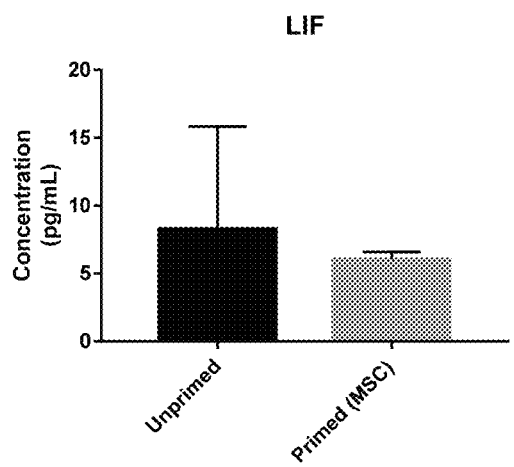
Figure 48V:
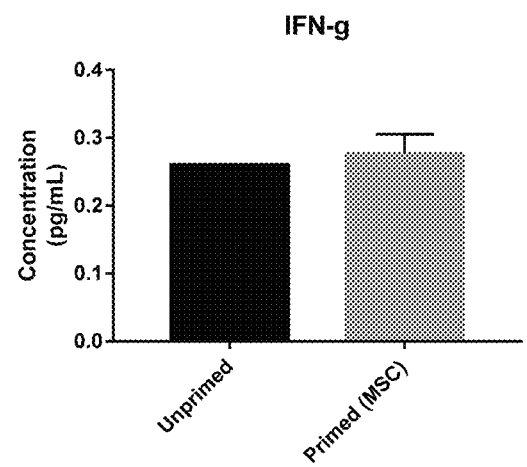
Figure 48W:
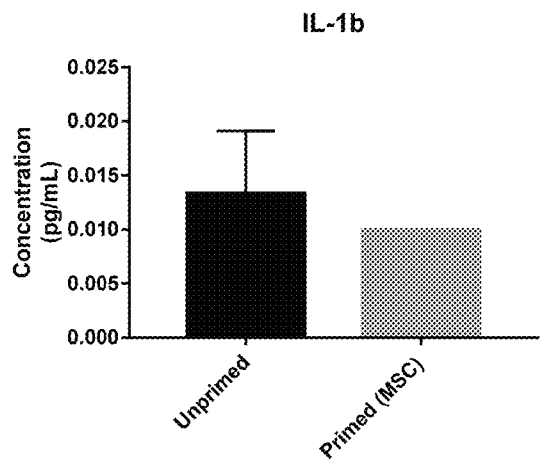
Figure 48X:
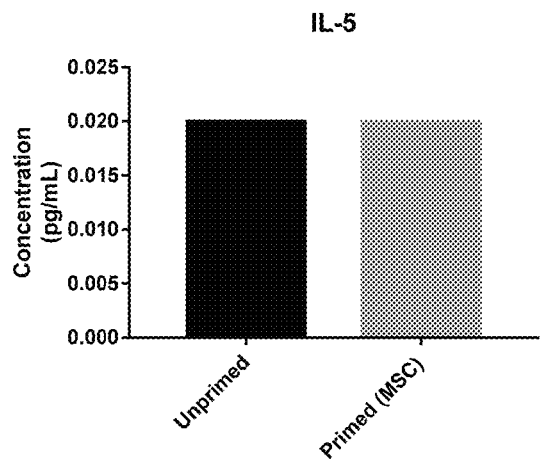
Figure 48Y:
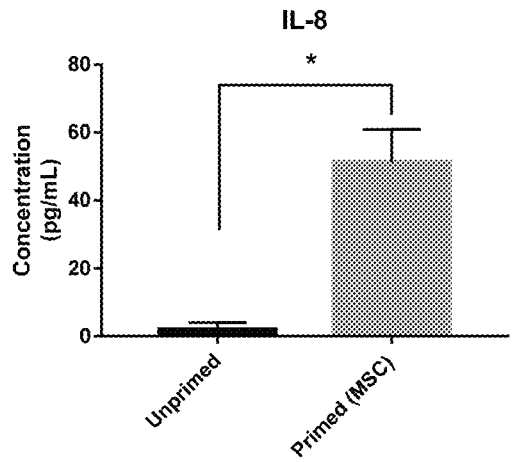
Figure 48Z:
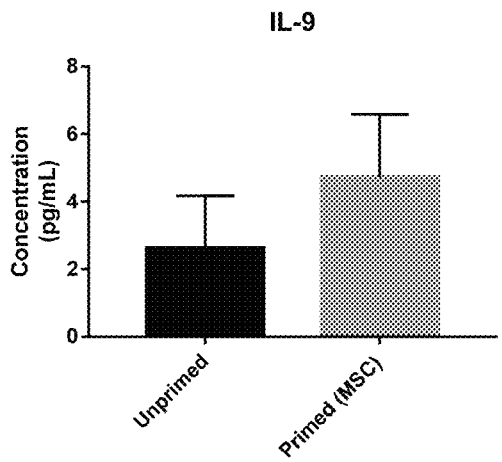
Figure 48A:
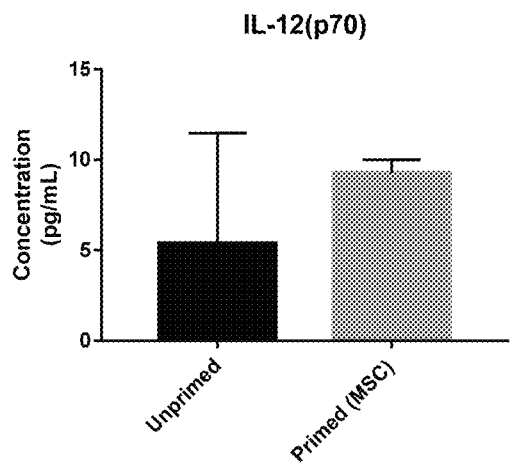
Figure 48B:
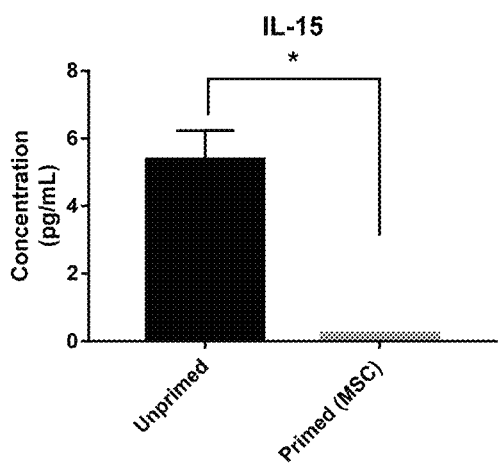
Figure 48C:
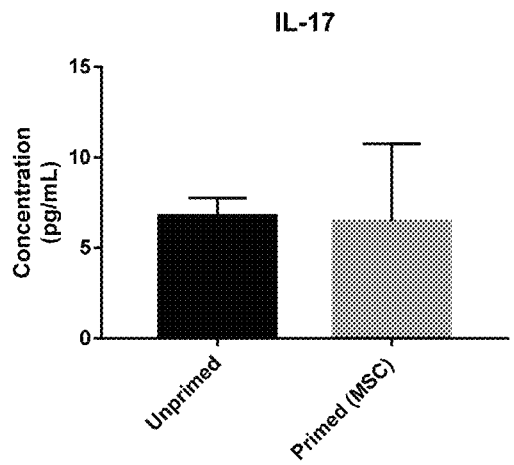
Figure 48D:
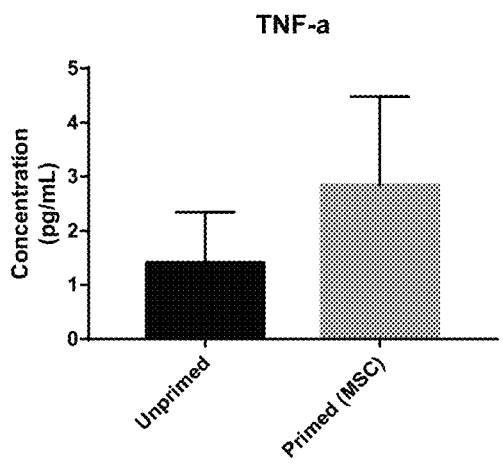
Figure 48E:
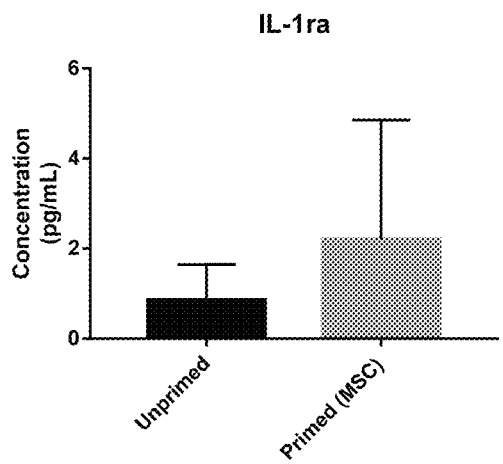
Figure 48F:
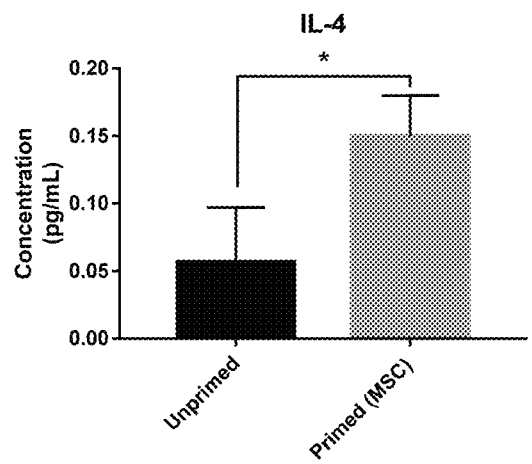
Figure 48G:
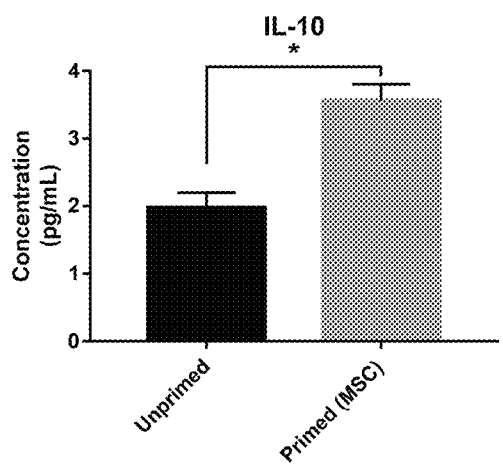
Figure 48H:
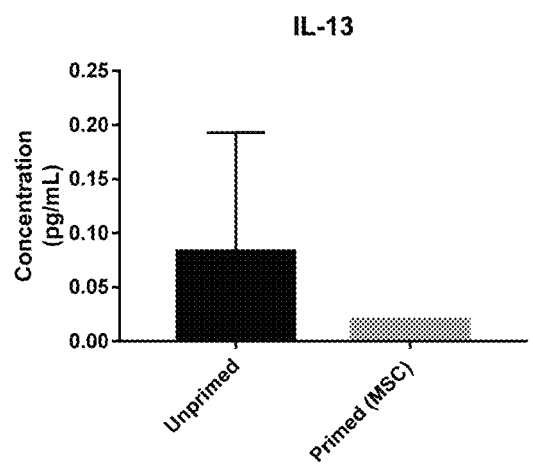
Figure 48I:
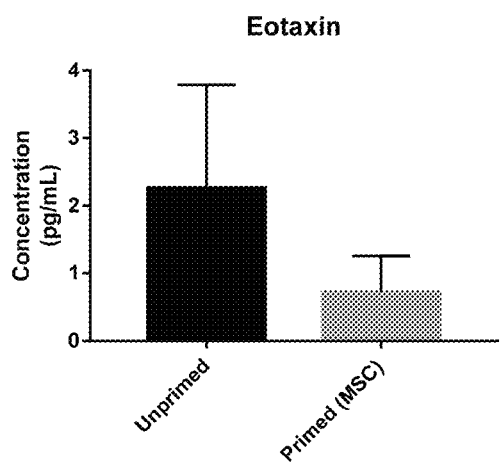
Figure 48J:
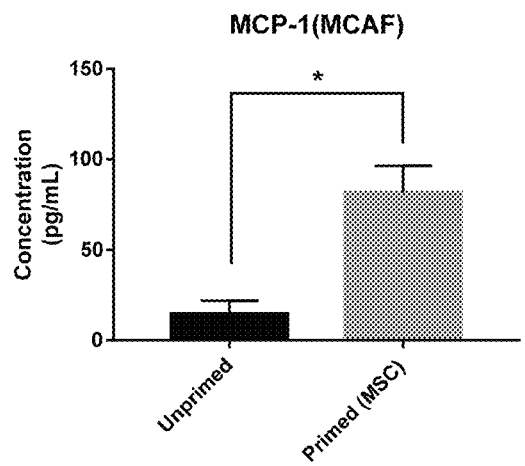
Figure 48K:
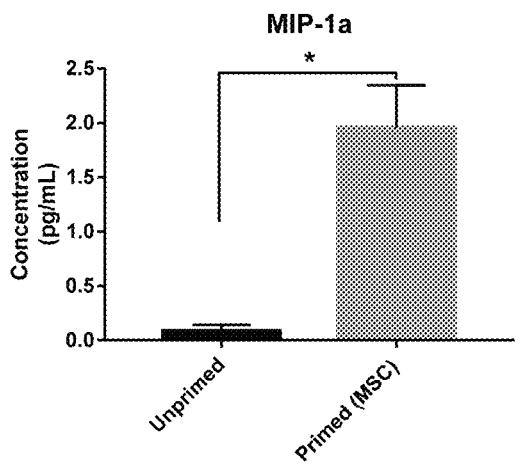
Figure 48L:
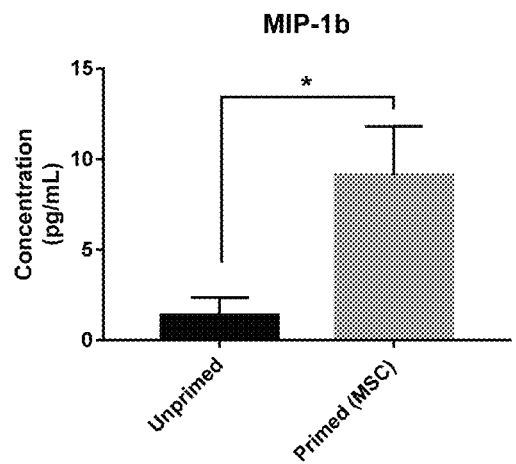
Figure 48M:
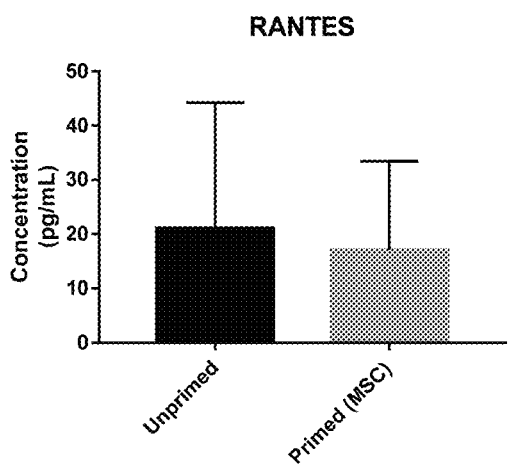
Figure 48N:
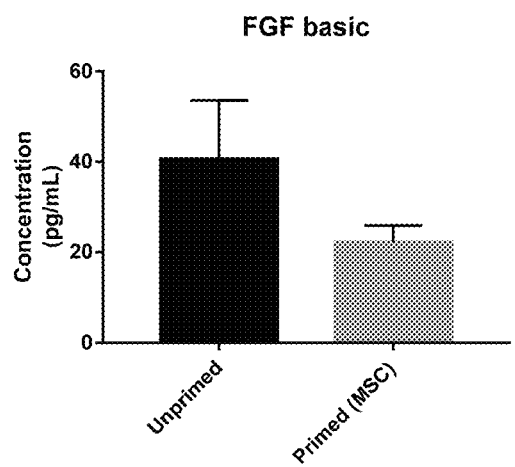
Figure 48O:
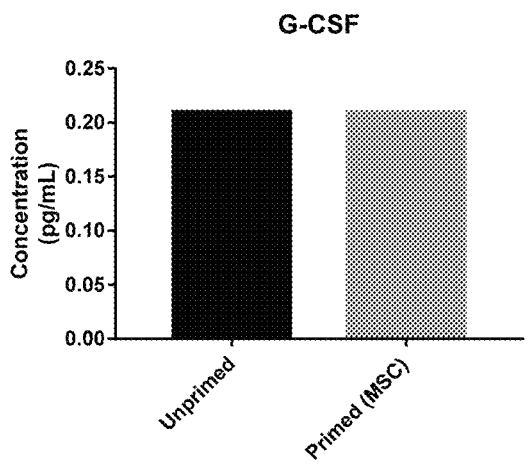
Figure 48P:
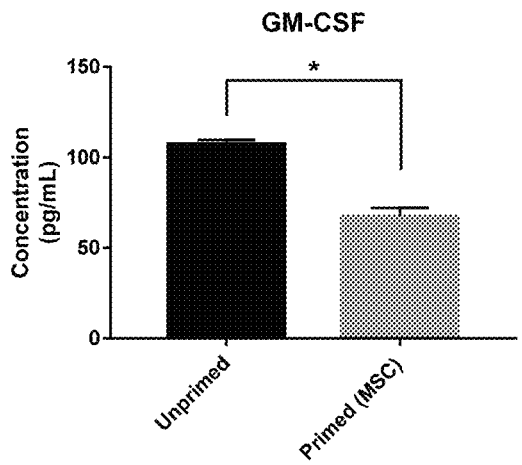
Figure 48Q:
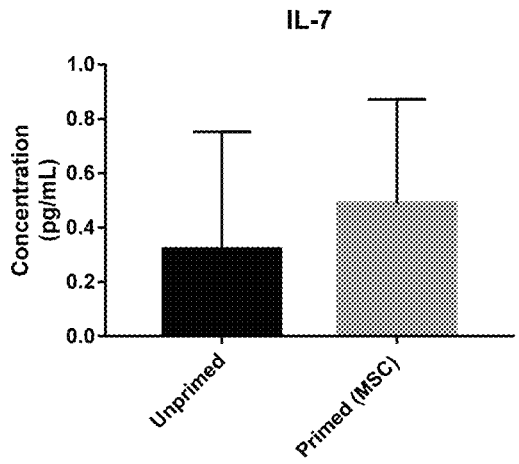
Figure 48R:
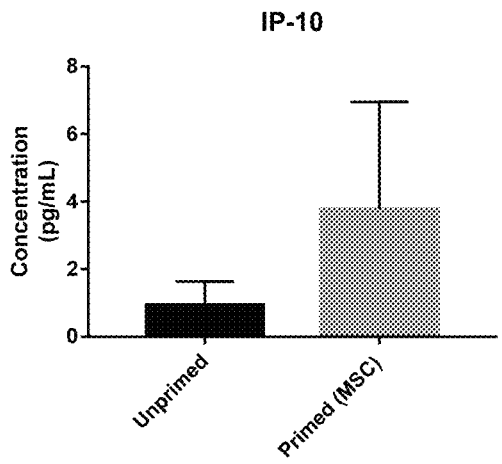
Figure 48S:
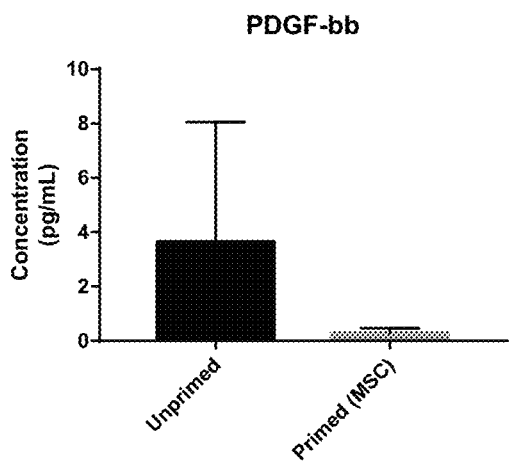
Figure 48T:
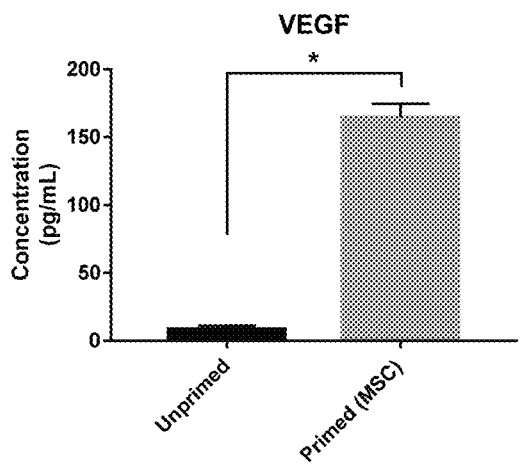
Figure 48U:
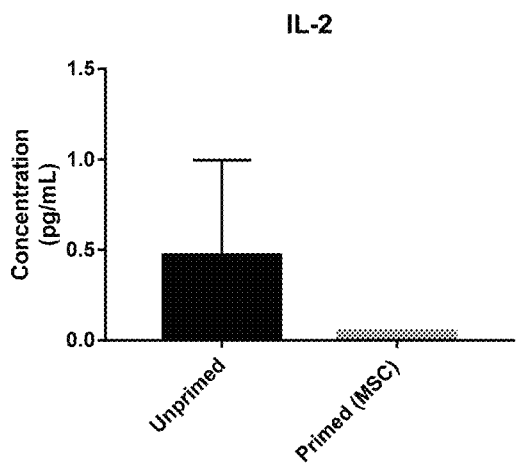
Figure 48V:
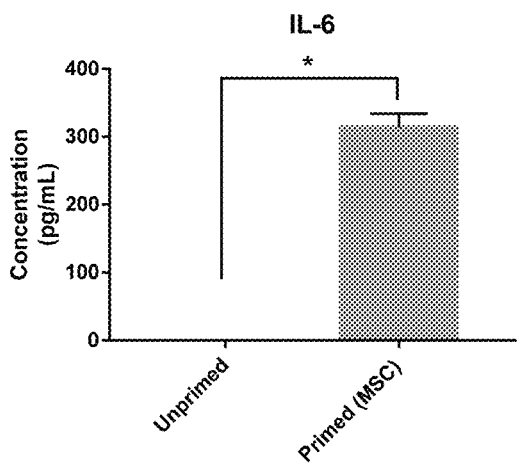

As shown in FIG. 48A-48VV, the cytokines released or secreted by red blood cells were altered by the 'priming' process, which in this instance was co-culture with MSCs (Mesenchymal stem cells). The red blood cell secretion concentration of proteins such as Gro-a, MCP-3, IL-2ra, SDF-1α, HGF, bNGF, SCF, SCGF-b, IL-8, 11-4, IL-10, MCP-1, MIP-1α, MIP-1b, VEGF and IL-6 were all significantly increased following co-culture priming. Whilst the levels of a few proteins such as IL-1a, MIF, IL-12(p40), IL-15, GM-CSF all decreased significantly following co-culture priming. The results demonstrated that the red blood cell cytokine secretion profile is subject to change depending on their environment. By incubating red blood cells in a protein rich environment, the cells were able to bind and release a wide range of cytokines.

Example 12. Red Blood Cells after Priming with MCF-7 Breast Cancer Cells

12.1 RBC Membranes

Whole blood was collected from healthy volunteers (n≥3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter)) and then suspended in dd$H_2$O to lyse the cells. This solution was vortexed and then centrifuged (15000 g, 20 minutes) to pellet the membranes. This process was repeated and the resulting pellet was suspended in PBS and used for priming experiments.

MCF-7 cells were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MCF-7 cells were seeded into T75 flasks at a concentration of $0.1 \times 10^6$ cells per mL of culture media and were incubated for 24 hours to ensure plate adherence (37° C., 5% $CO_2$). After incubation, the conditions as outlined in Table 12 were prepared using freshly isolated red blood cells. For co-culture with red blood cells the total volume of culture media in T75 flasks was 18 mL.

TABLE 12

Co-culture conditions for MCF-7 cells and red blood cells membranes at a ratio of 1:100 at 37° C., 5% $CO_2$ for 72 hours.

| Condition | Label | Flask size | MCF-7 cells seeded | Equivalent RBC membrane number |
|---|---|---|---|---|
| MCF-7 cells:RBC membranes (1:100) | Primed | T75 | $2 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cell membranes were isolated by centrifugation out of the conditioned media (15000 g, 20 minutes). Remaining particulates in the conditioned media were removed by centrifugation (2000 g, 10 minutes) after which it was stored at −80° C. The red blood cell membranes were washed once with PBS (15000 g, 20 minutes).

The red blood cell membranes were then diluted (based on the original number of red blood cells used) in PBS to the equivalent of the membranes from 400 million cells/mL. The primed and unprimed red blood cell membranes were subjected to 3 freeze-thaw cycles to ensure complete cellular lysis. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 49A:
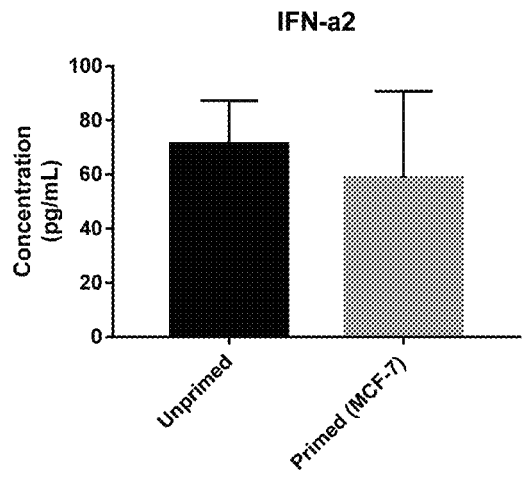
FIG. 49A-49VV is a series of graphs showing the concentration of proteins in red blood cell membranes following co-culture for 3 days with (primed) or without (unprimed) breast cancer cell line cells (MCF-7 cells). Significant differences (p<0.05) were determined using Student's T-tests.
Figure 49B:
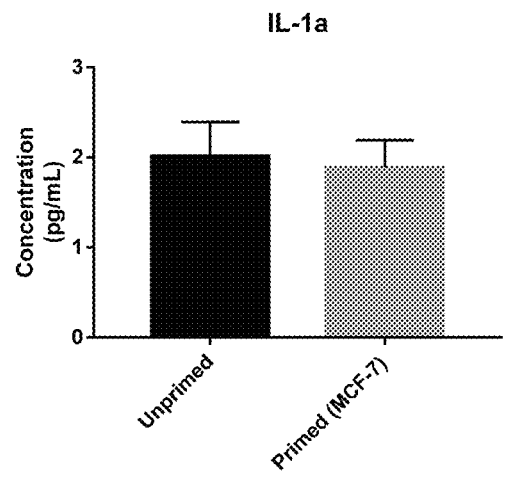
Figure 49C:
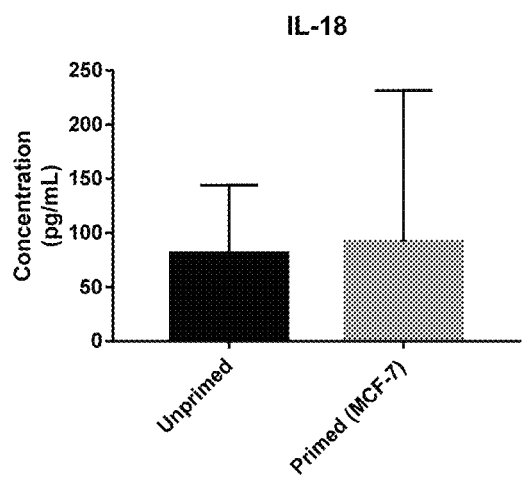
Figure 49D:
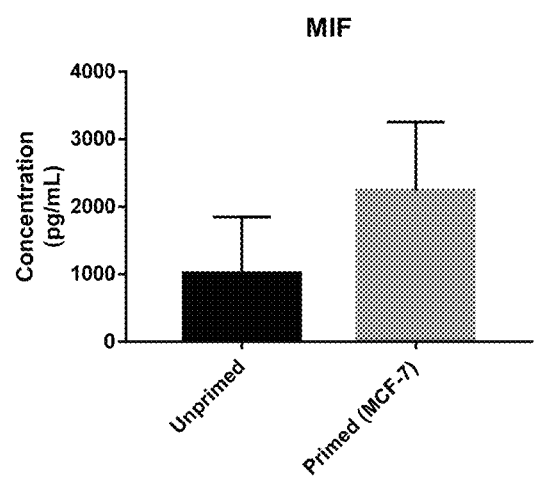
Figure 49E:
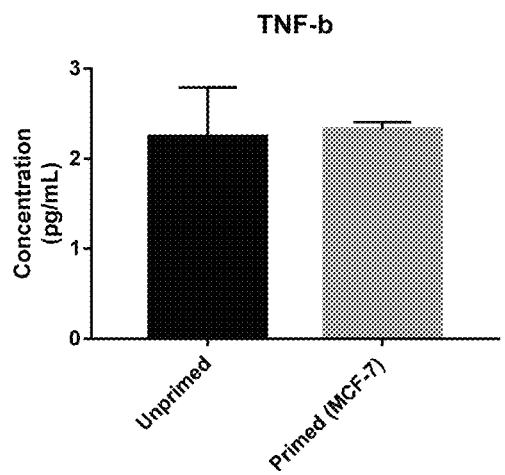
Figure 49F:
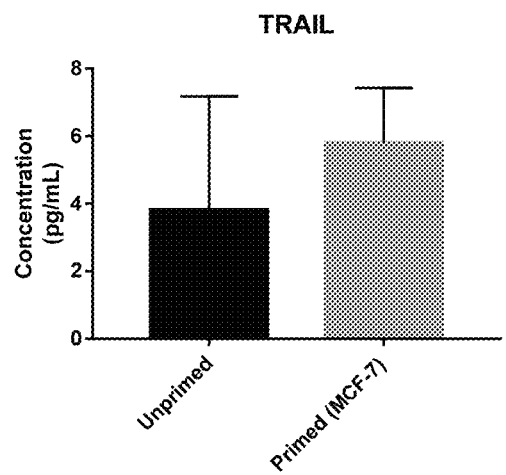
Figure 49G:
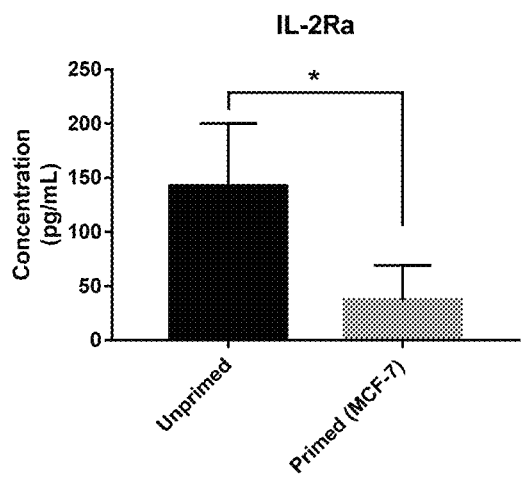
Figure 49H:
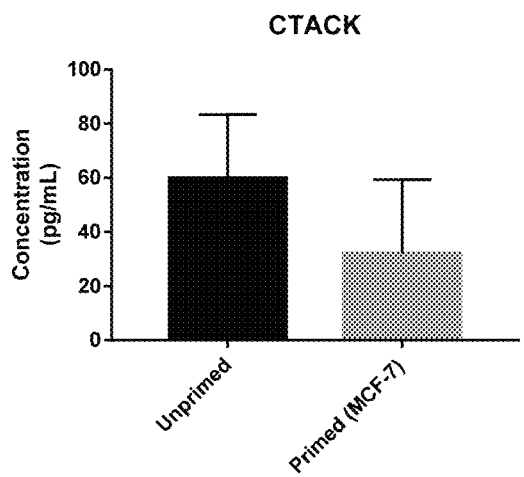
Figure 49I:
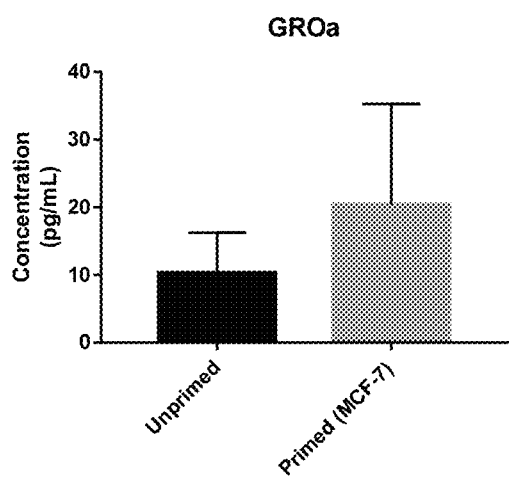
Figure 49J:
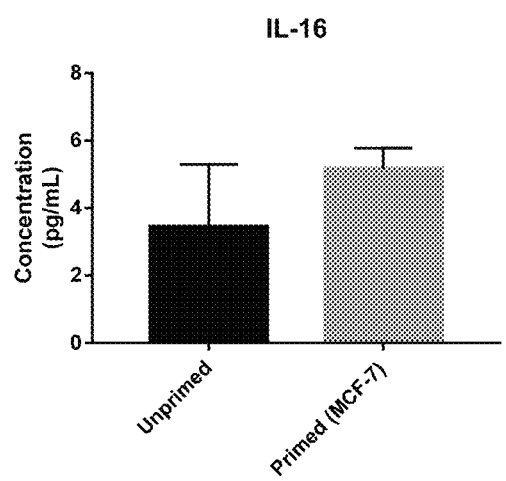
Figure 49K:
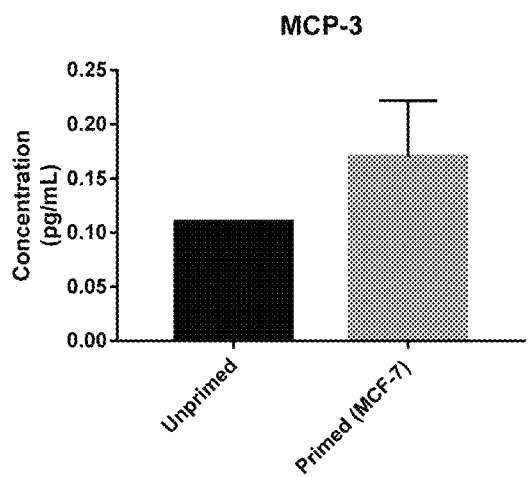
Figure 49L:
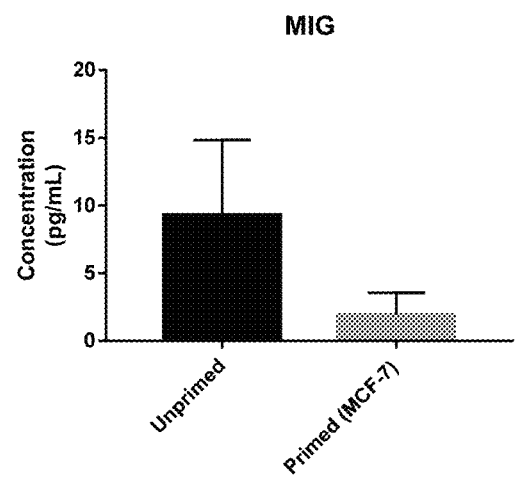
Figure 49M:
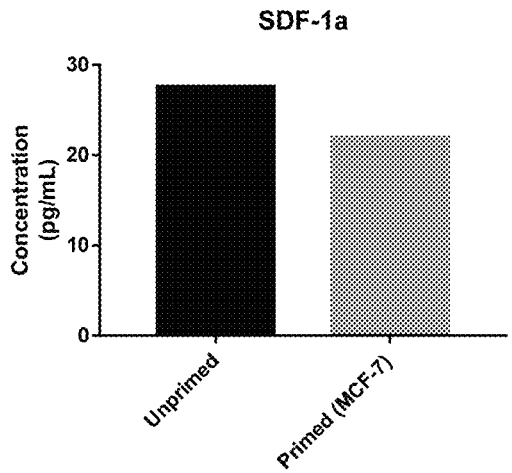
Figure 49N:
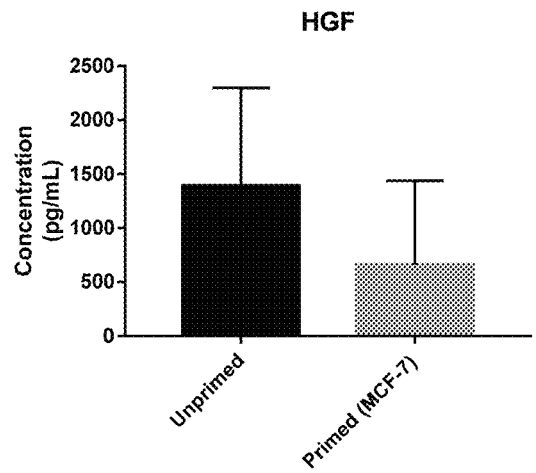
Figure 49O:
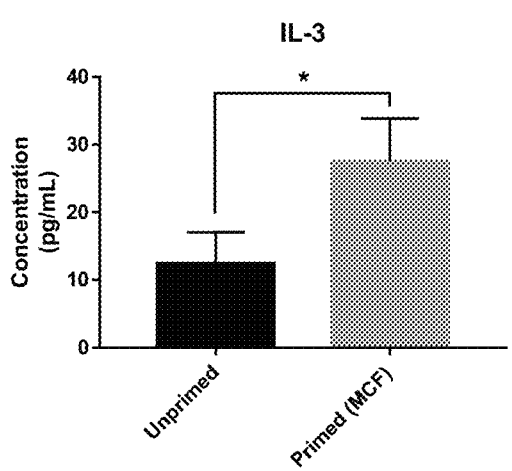
Figure 49P:
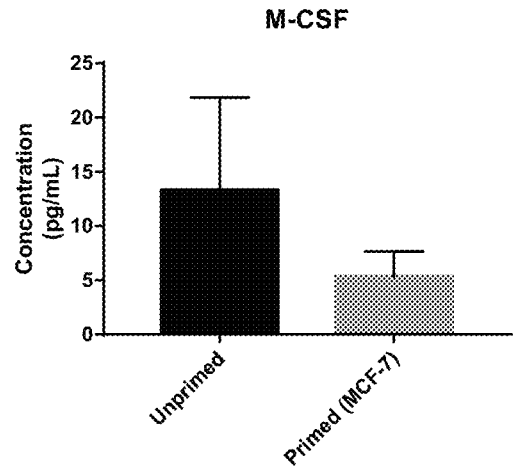
Figure 49Q:
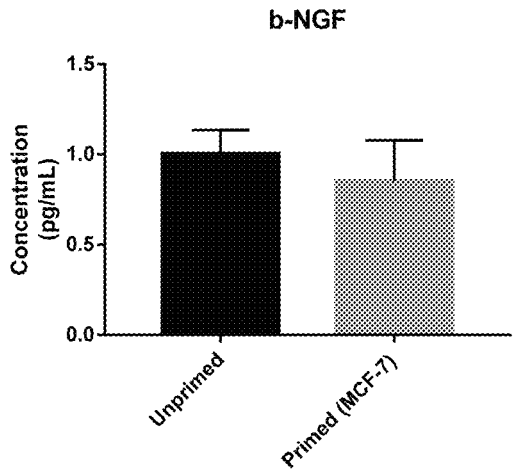
Figure 49R:
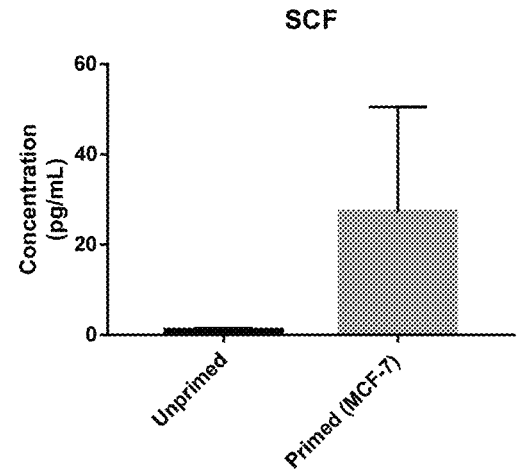
Figure 49S:
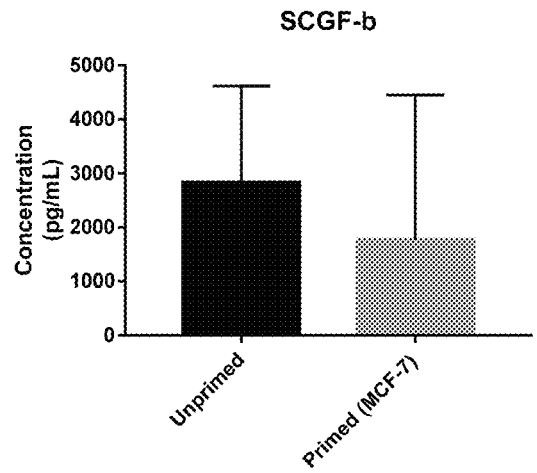
Figure 49T:
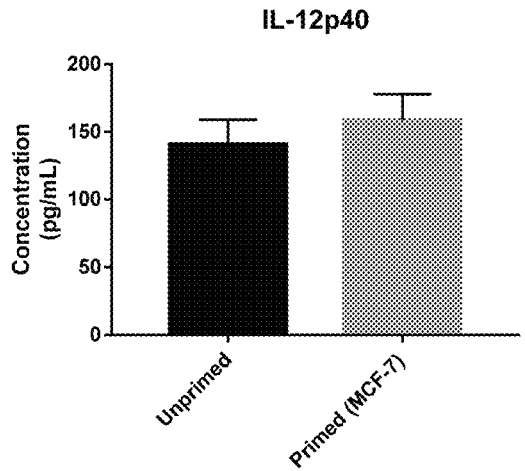
Figure 49U:
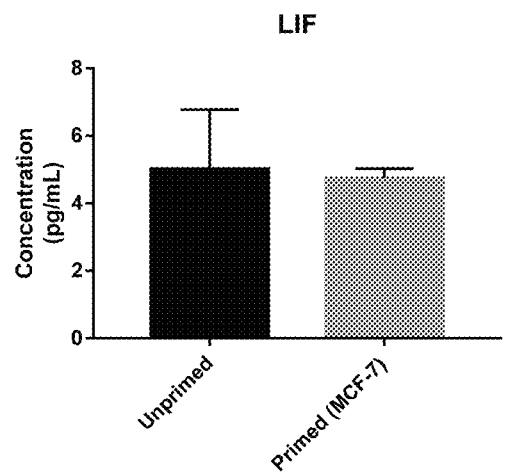
Figure 49V:
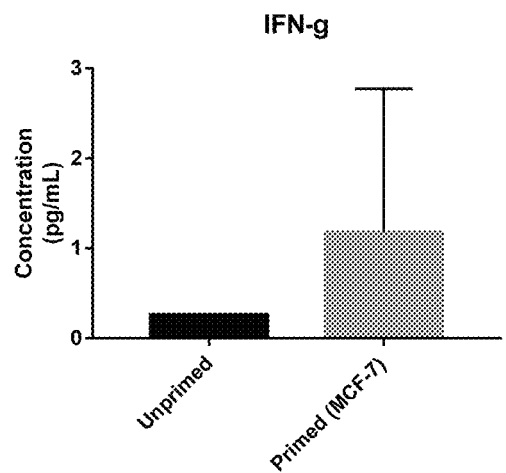
Figure 49W:
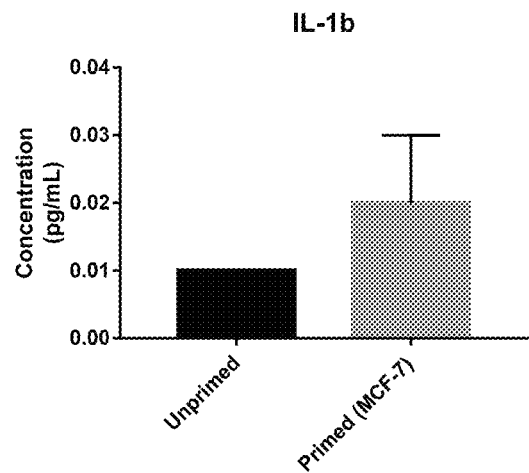
Figure 49X:
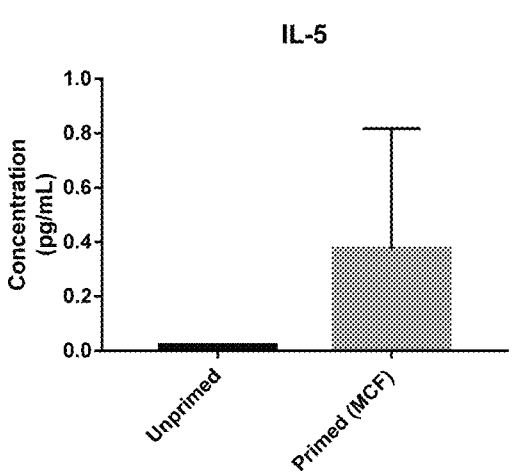
Figure 49Y:
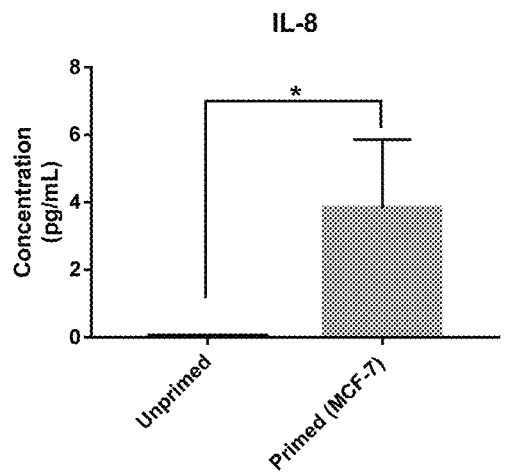
Figure 49Z:
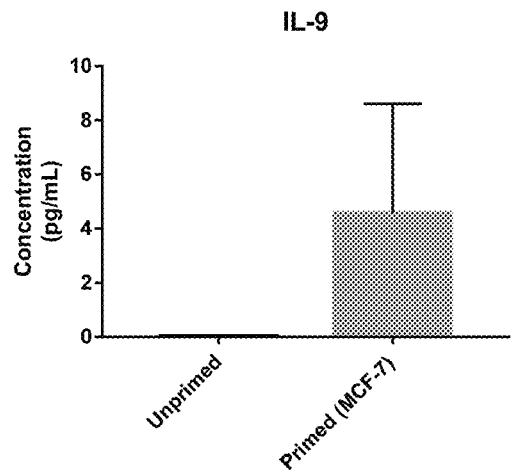
Figure 49A:
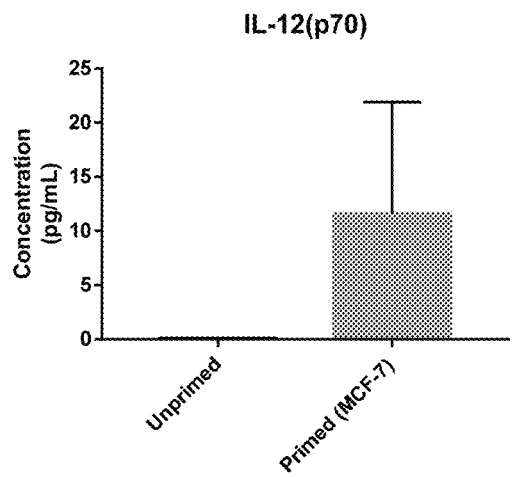
Figure 49B:
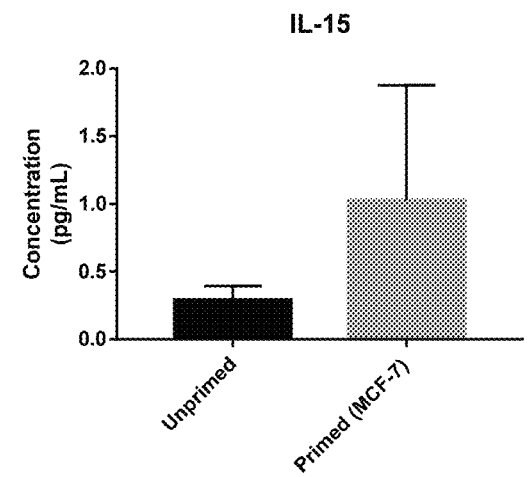
Figure 49C:
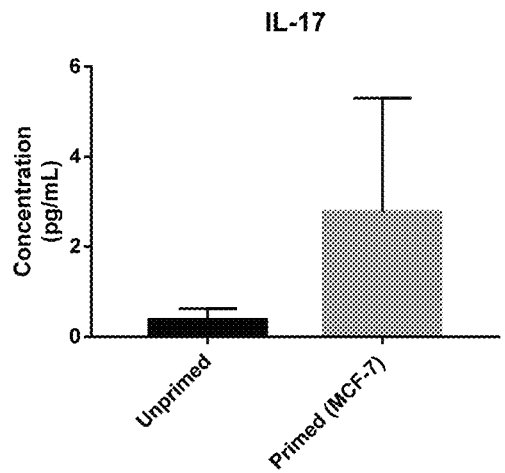
Figure 49D:
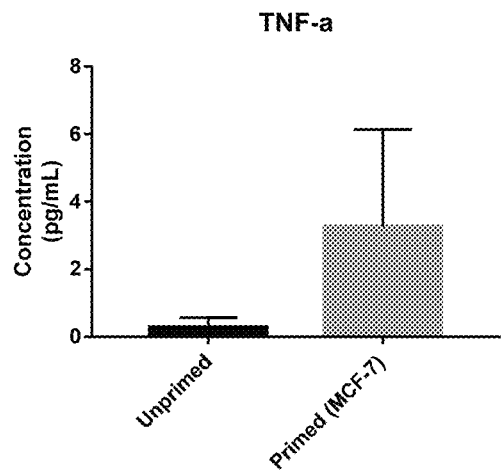
Figure 49E:
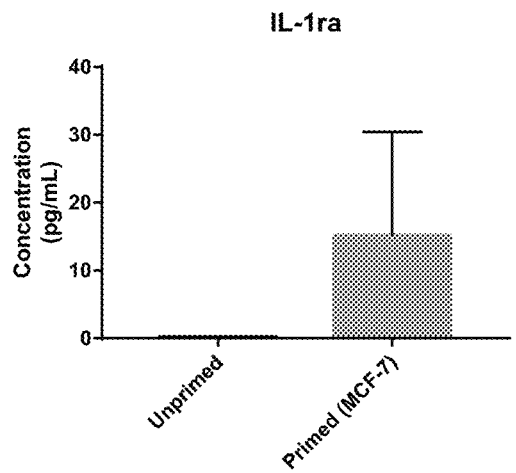
Figure 49F:
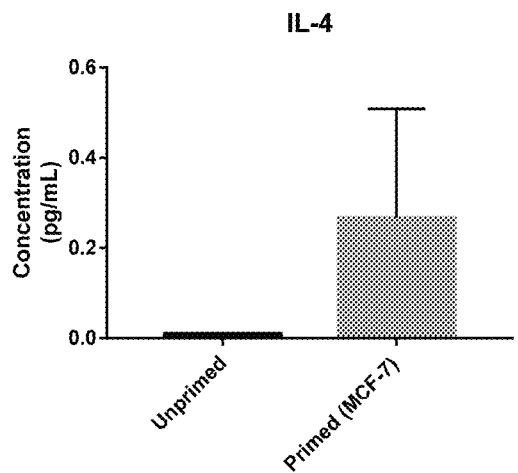
Figure 49G:
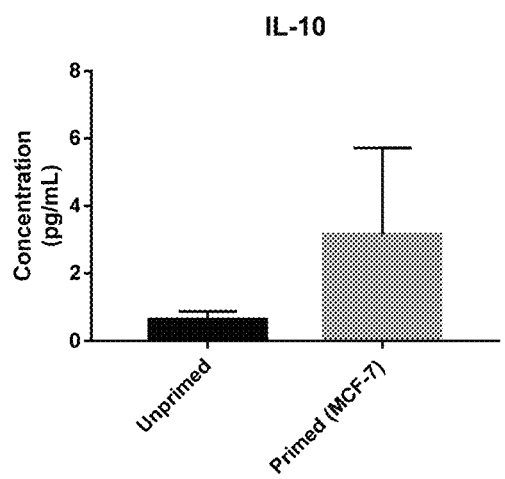
Figure 49H:
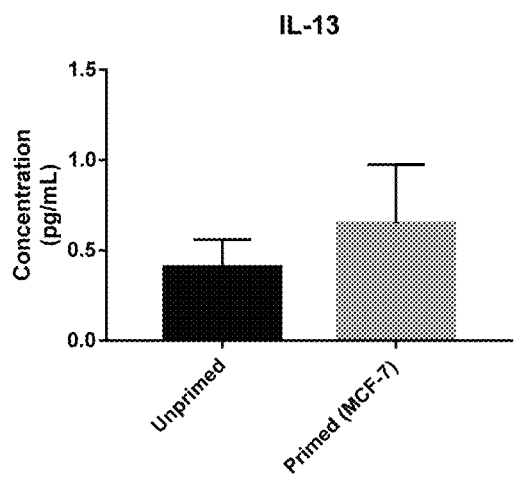
Figure 49I:
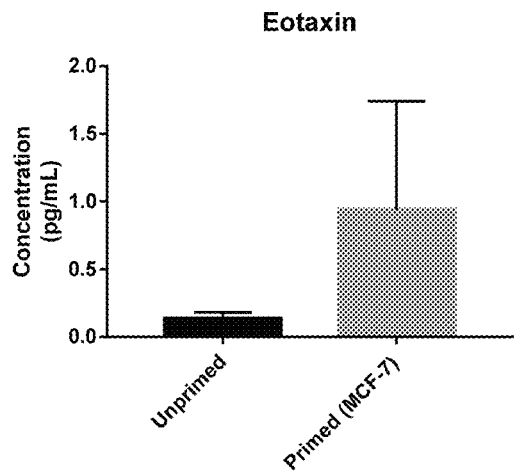
Figure 49J:
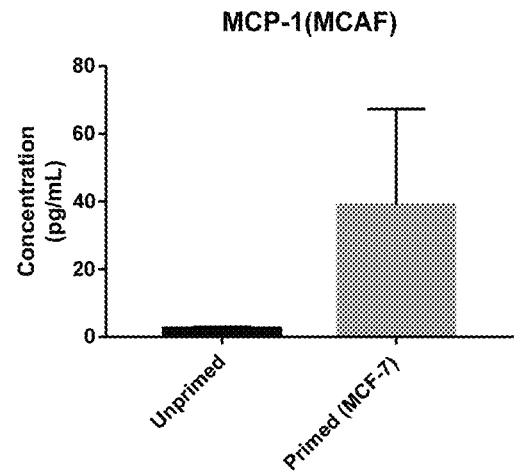
Figure 49K:
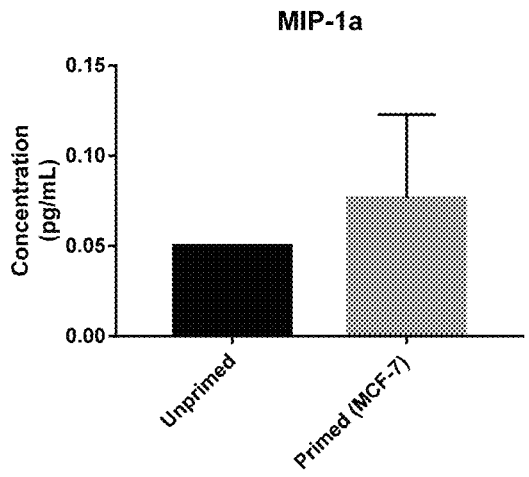
Figure 49L:
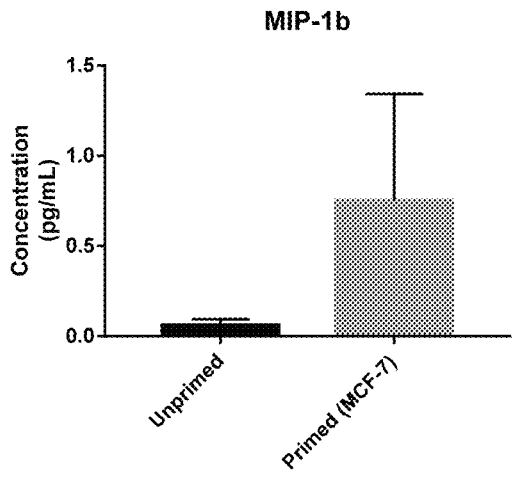
Figure 49M:
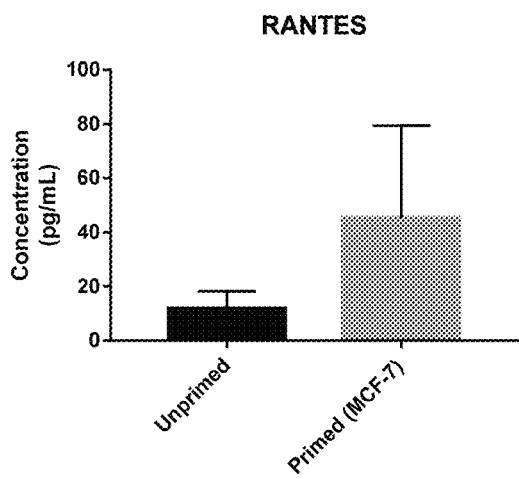
Figure 49N:
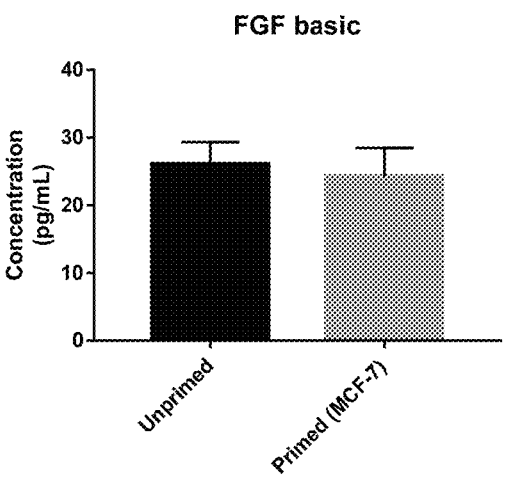
Figure 49O:
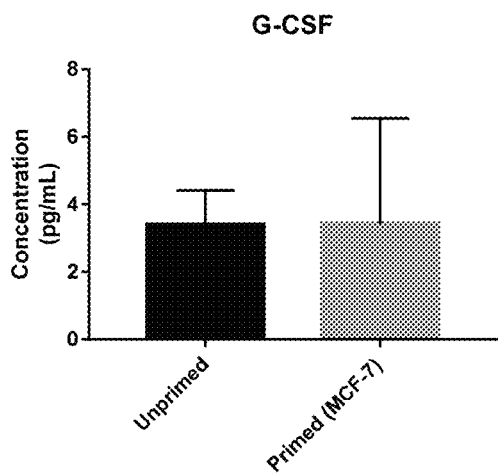
Figure 49P:
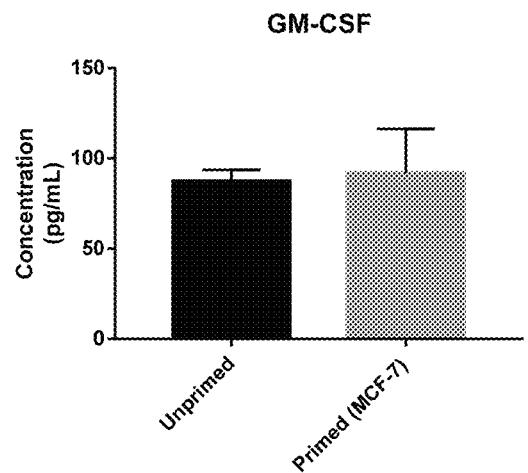
Figure 49Q:
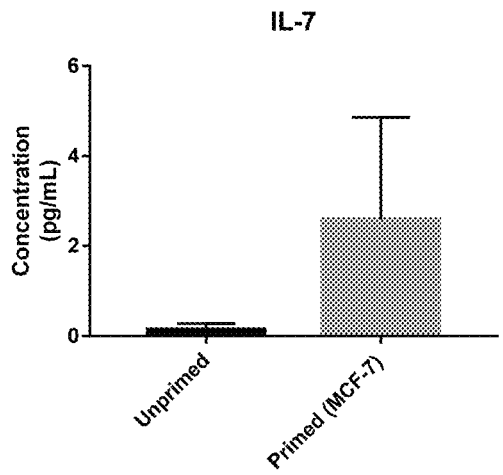
Figure 49R:
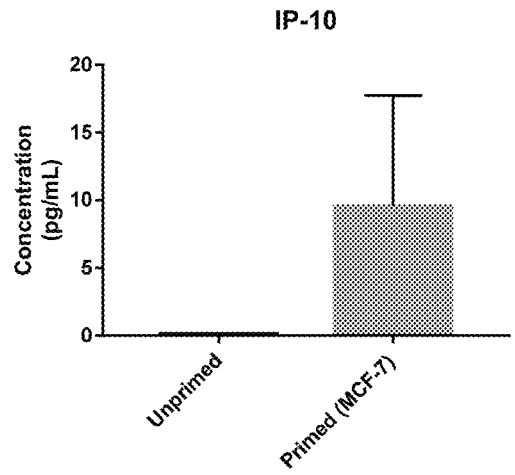
Figure 49S:
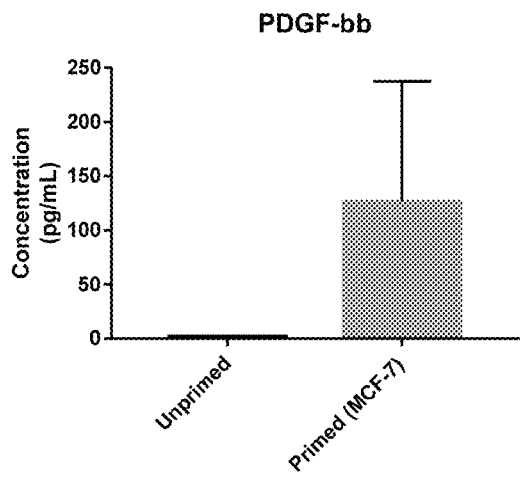
Figure 49T:
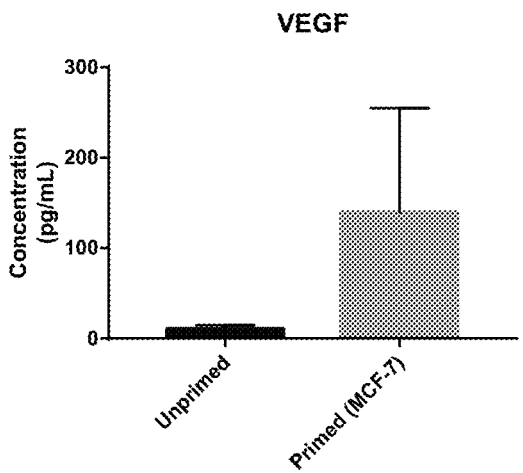
Figure 49U:
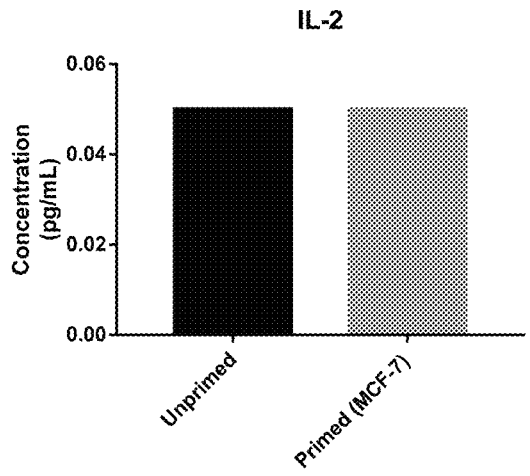
Figure 49V:
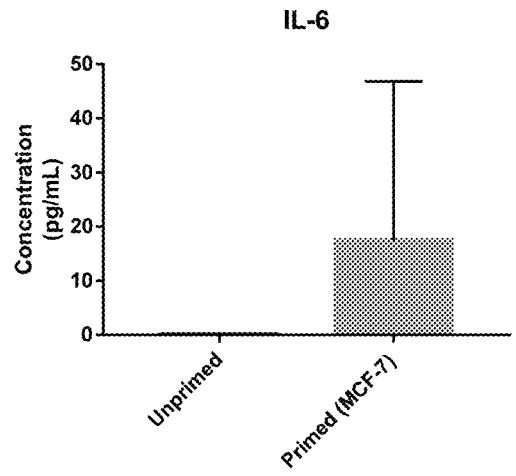

As shown in FIG. 49A-49VV, the cytokine profile of the red blood cell membranes were altered by the 'priming' process, which in this instance was co-culture with MCF-7 cells (breast cancer cell line). The red blood cell concentration of proteins such as IL-3, and IL-8 were significantly increased following co-culture priming. Whilst the level IL-2ra decreased significantly following co-culture priming. The results demonstrated that the cytokine profile of red blood cell membranes was subject to change depending on their environment. IL-3 was the only cytokine whose levels were also significantly changed after priming in the whole red blood cell lysis experiment, indicating that the membrane has different cytokine binding properties than the red blood cell as a whole.

12.2 Red Blood Cell Membrane Secretions

Whole blood was collected from healthy volunteers (n=3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then suspended in dd$H_2$O to lyse the cells. This solution was vortexed and then centrifuged (15000 g, 20 minutes) to pellet the membranes. This process was repeated and the resulting pellet was suspended in PBS and used for priming experiments.

MCF-7 cells were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MCF-7 cells were seeded into T75 flasks at a concentration of $0.1 \times 10^6$ cells per mL of culture media and were incubated for 24 hours to ensure plate adherence (37° C., 5% $CO_2$). After incubation, the conditions as outlined in Table 13 were prepared using freshly isolated red blood cells. For co-culture with red blood cells the total volume of culture media in T75 flasks was 18 mL.

TABLE 13

Co-culture conditions for MCF-7 cells and equivalent membranes from red blood cells (RBCs) at a ratio of 1:100 at 37° C., 5% $CO_2$ for 72 hours.

| Condition | Label | Flask size | MCF-7 cells seeded | Red blood cell derived membranes |
|---|---|---|---|---|
| MCF-7cells:RBC membranes (1:100) | Primed | T75 | $2 \times 10^6$ | $200 \times 10^6$ |
| RBC membranes | Unprimed | T75 | — | $200 \times 10^6$ |

Cells and membranes were then incubated for 72 hours at 37° C. with 5% $CO_2$. Following incubation, the red blood cell membranes were isolated by centrifugation out of the conditioned media (15000 g, 20 minutes). Any remaining particulates in the conditioned media were removed by centrifugation (2000 g, 10 minutes) after which it was stored at −80° C. The red blood cells membranes were washed once with PBS (15000 g, 20 minutes).

The red blood cell membranes were then diluted (based on the original number of red blood cells used) in PBS to the equivalent of the membranes from 400 million cells/mL. The membranes were then incubated in PBS for 24 hours, at 37° C. and 5% $CO_2$. After incubation the membranes were removed by centrifugation (15000 g, 20 minutes) the supernatants containing the red blood cell membrane secretions were retained and analysed. Two multiplex assays were utilised. The 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 50A:
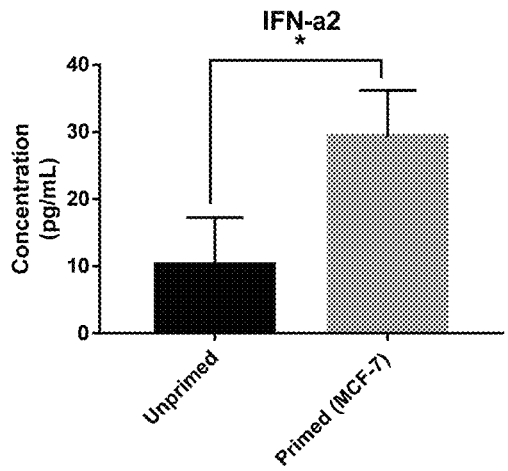
FIG. 50A-50VV is a series of graphs showing the concentration of proteins released by red blood cell membranes following co-culture for 3 days with or without (primed or unprimed) breast cancer cell line cells (MCF-7 cells). Significant differences (p<0.05) were determined using Student's T-tests.
Figure 50B:
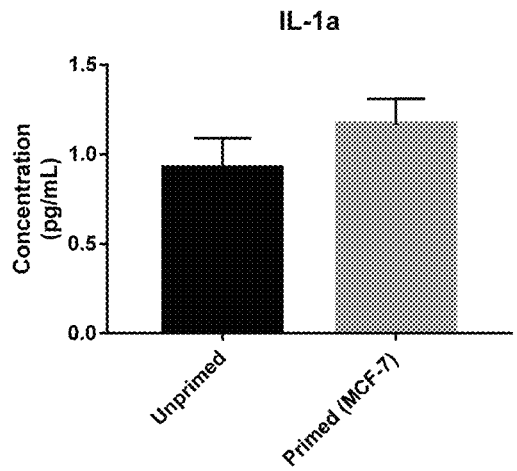
Figure 50C:
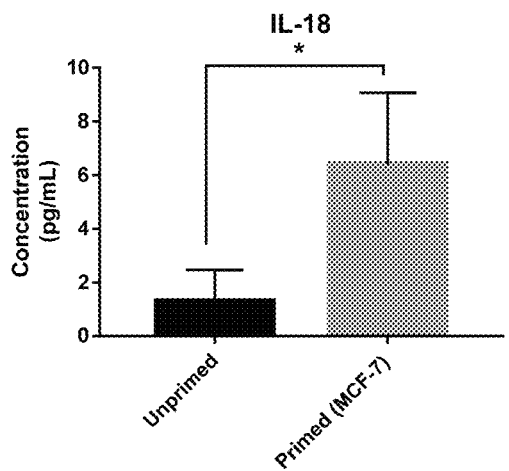
Figure 50D:
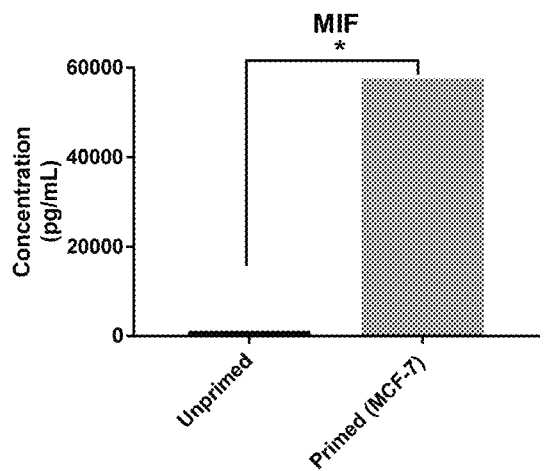
Figure 50E:
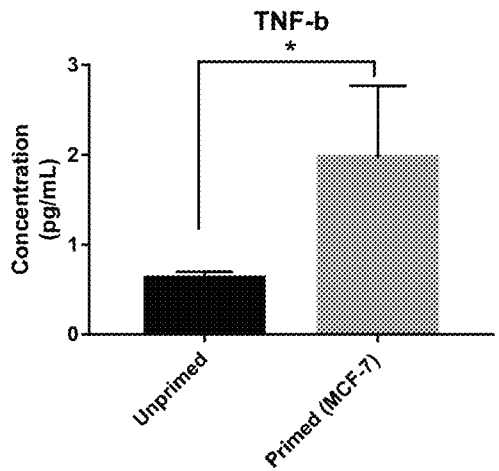
Figure 50F:
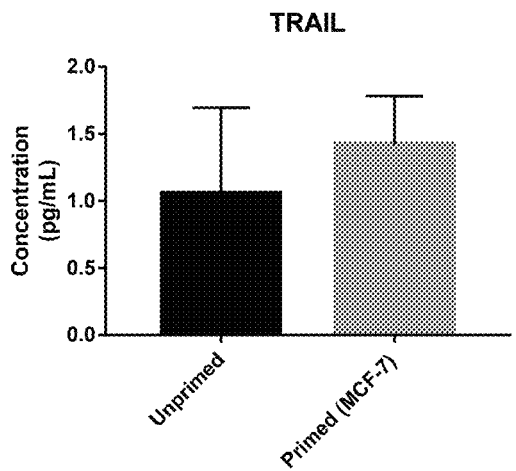
Figure 50G:
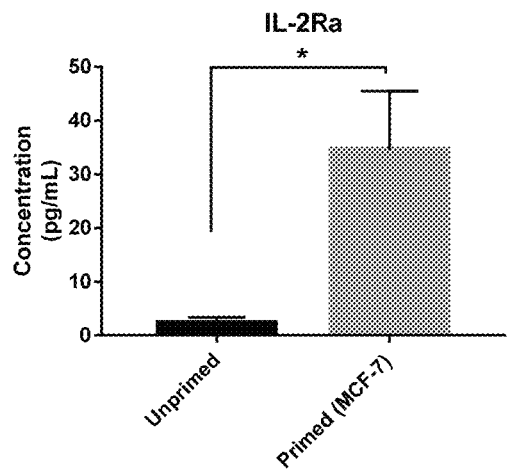
Figure 50H:
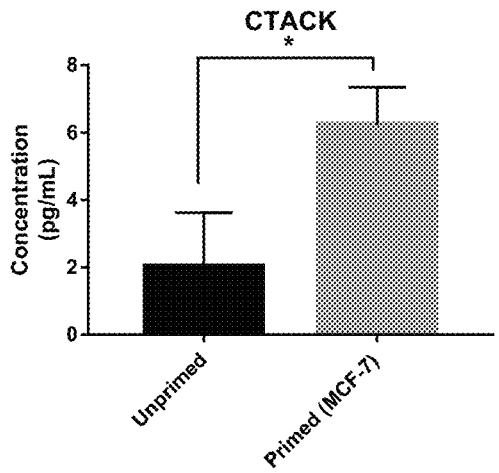
Figure 50I:
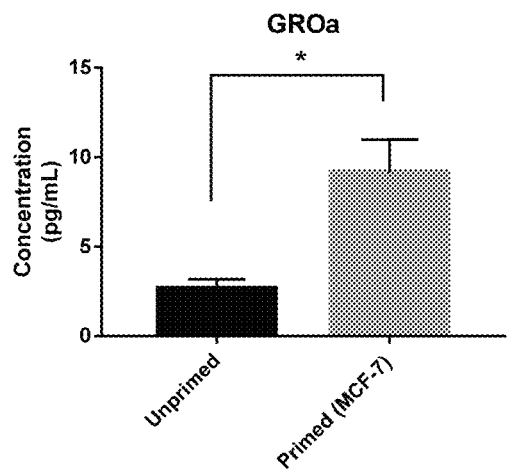
Figure 50J:
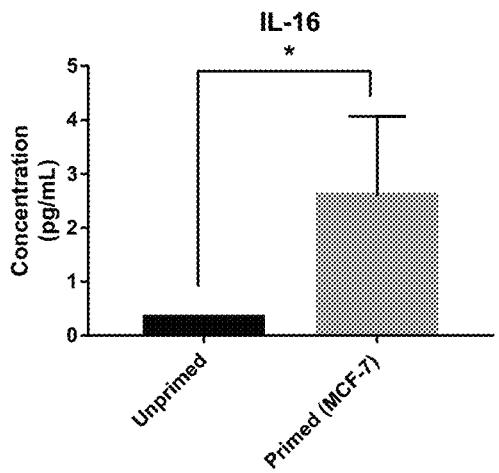
Figure 50K:
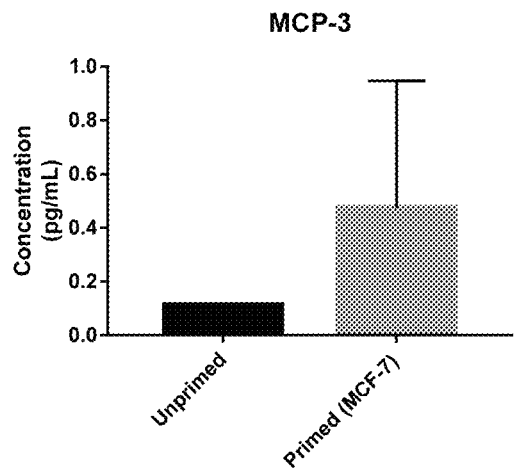
Figure 50L:
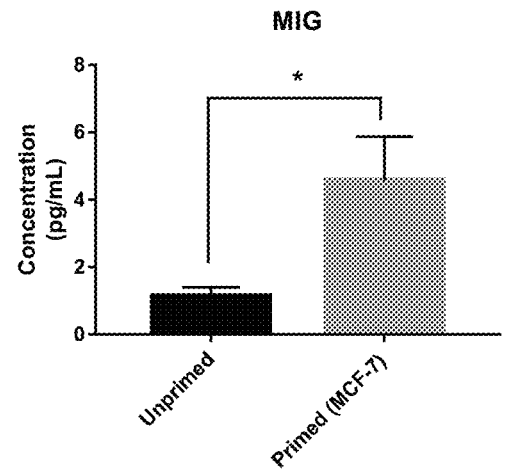
Figure 50M:
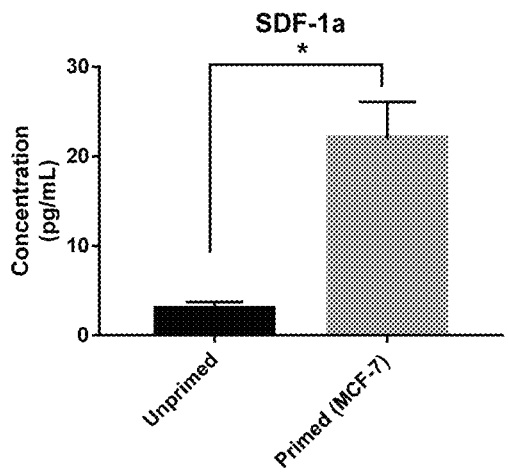
Figure 50N:
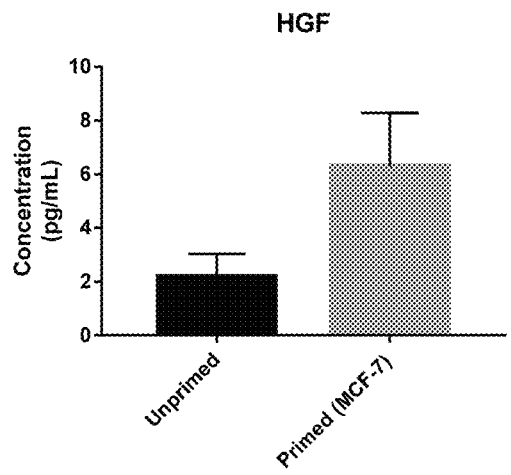
Figure 50O:
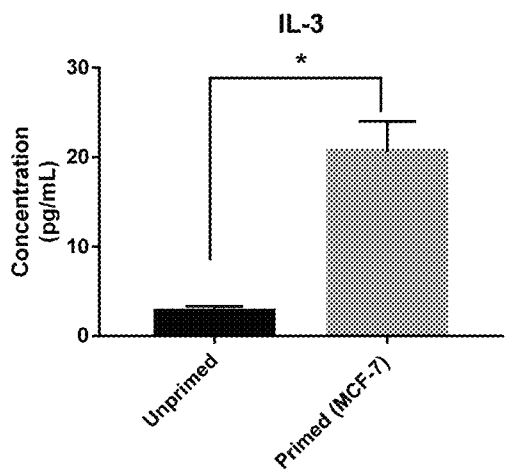
Figure 50P:
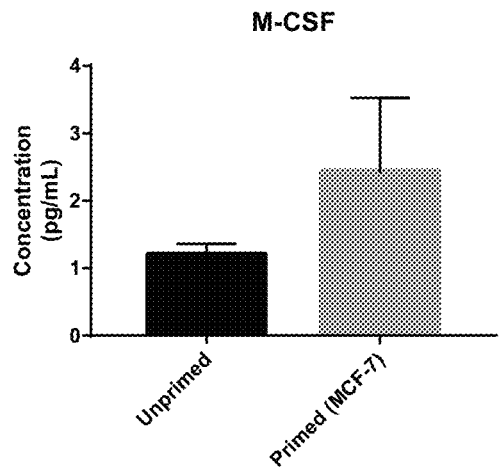
Figure 50Q:
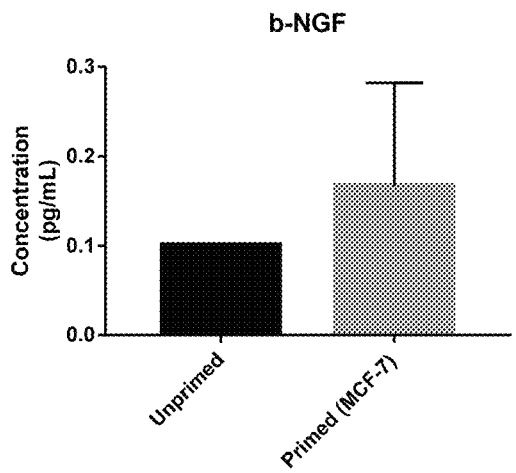
Figure 50R:
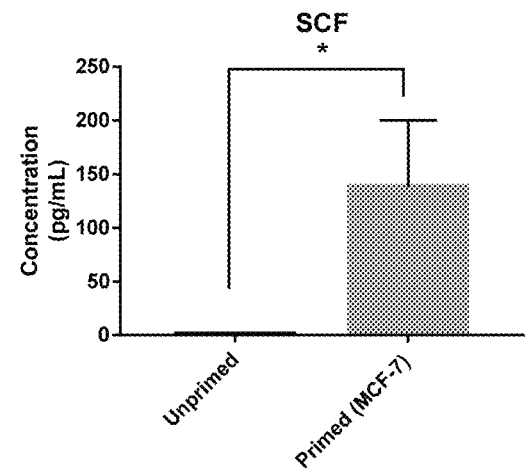
Figure 50S:
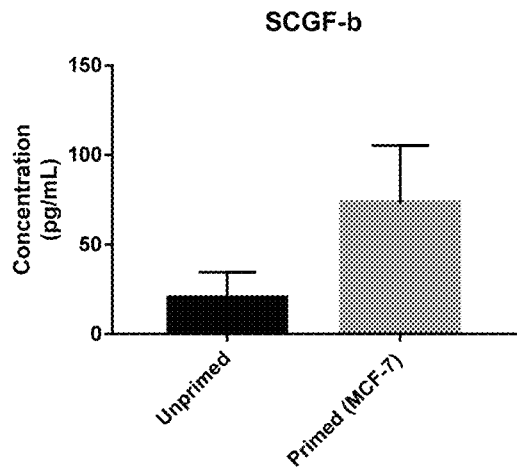
Figure 50T:
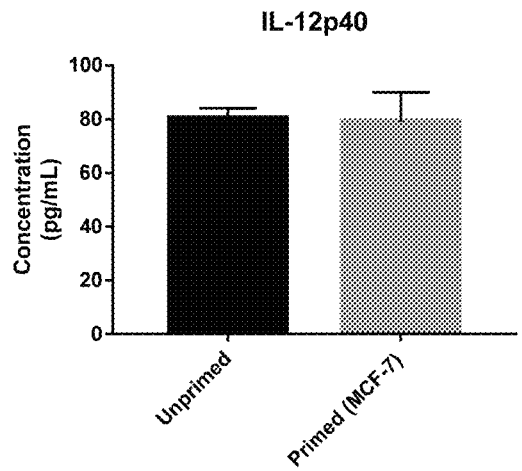
Figure 50U:
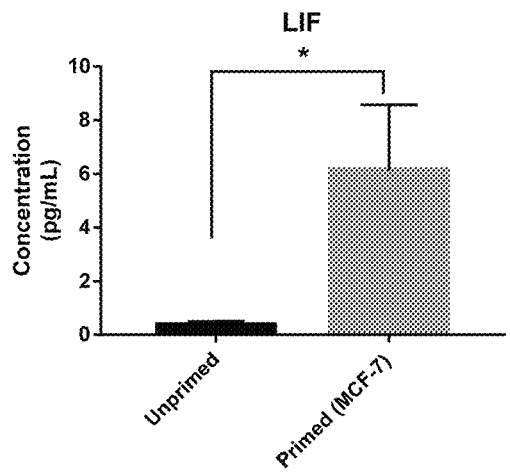
Figure 50V:
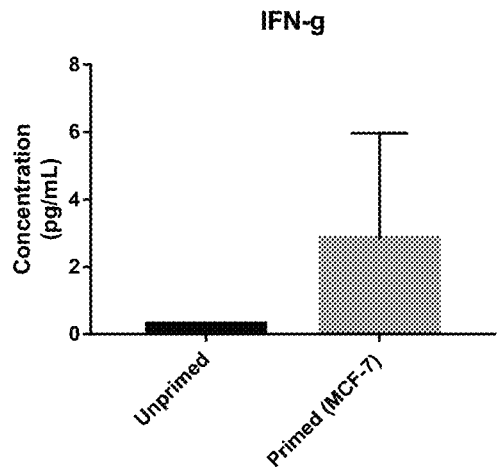
Figure 50W:
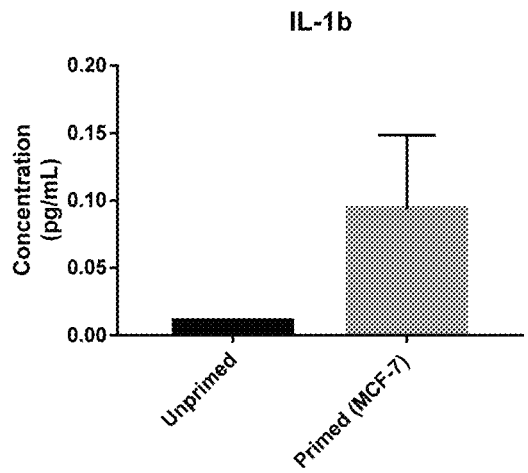
Figure 50X:
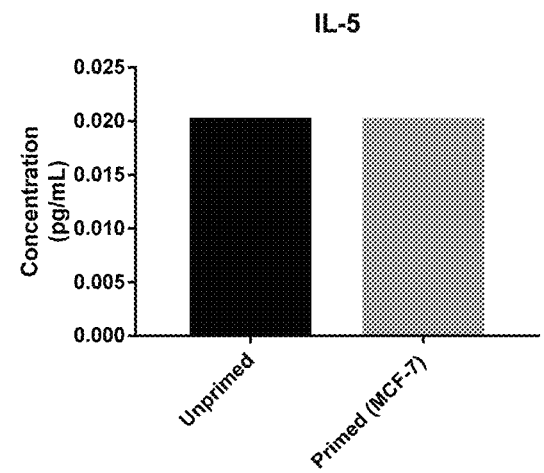
Figure 50Y:
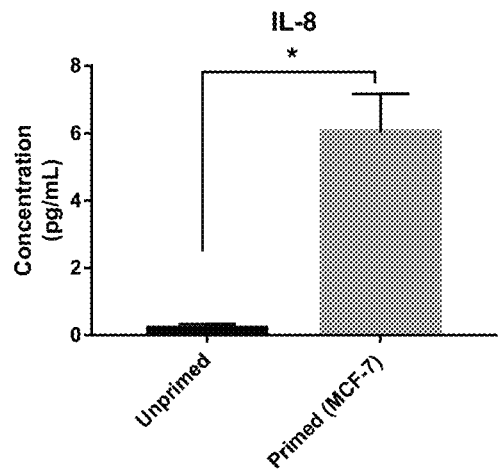
Figure 50Z:
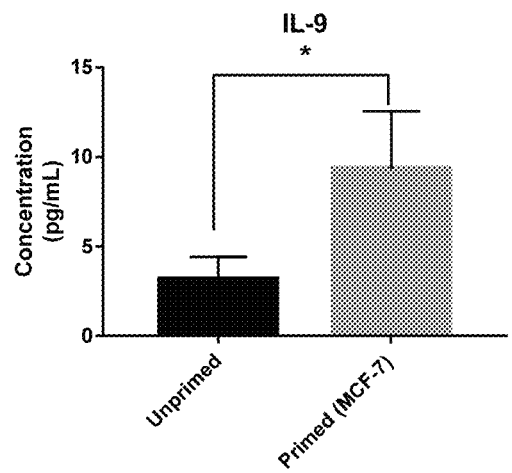
Figure 50A:
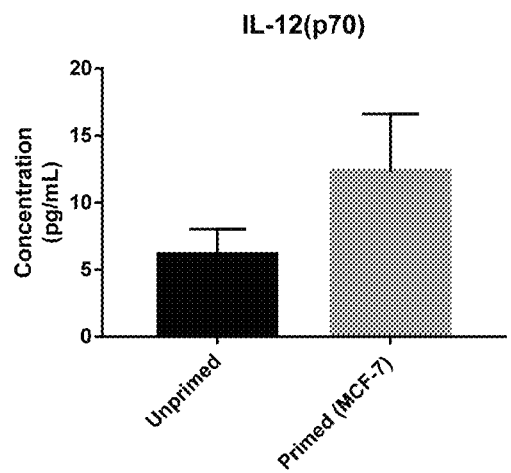
Figure 50B:
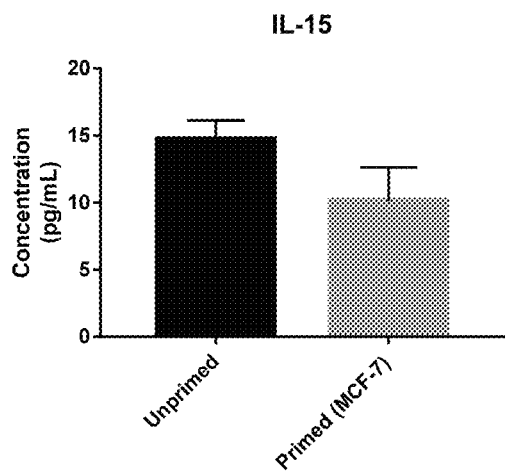
Figure 50C:
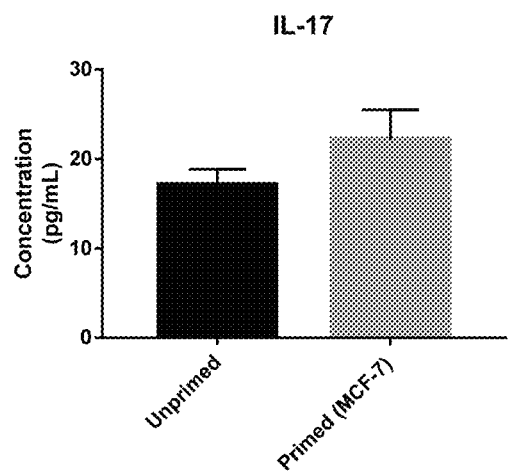
Figure 50D:
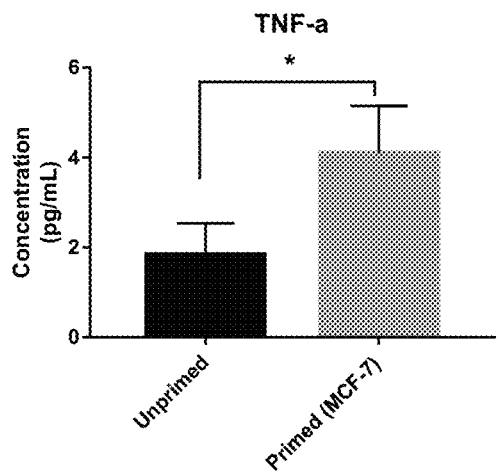
Figure 50E:
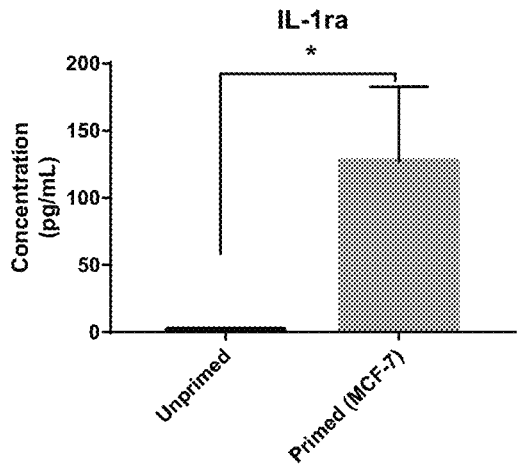
Figure 50F:
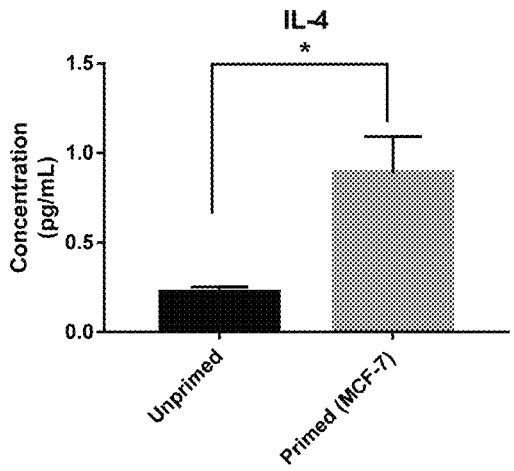
Figure 50G:
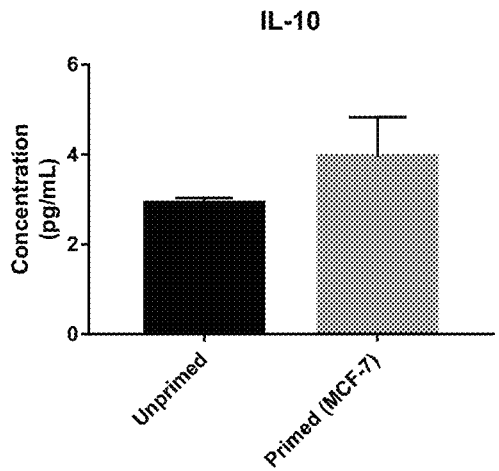
Figure 50H:
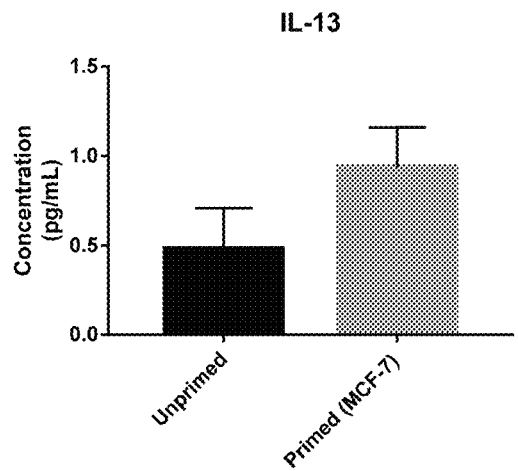
Figure 50I:
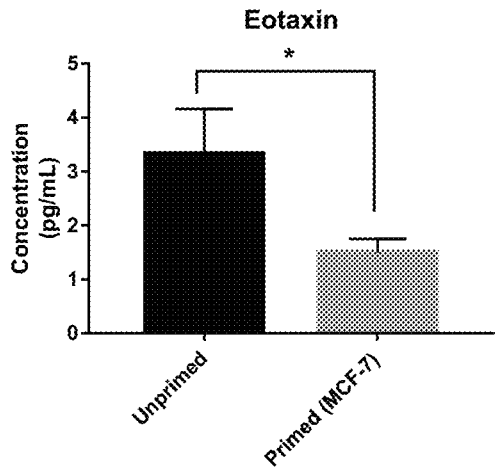
Figure 50J:
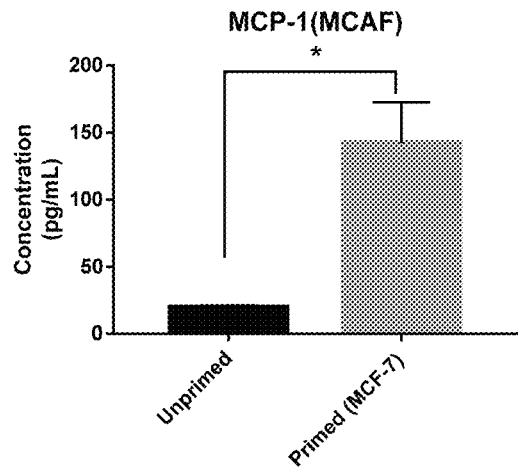
Figure 50K:
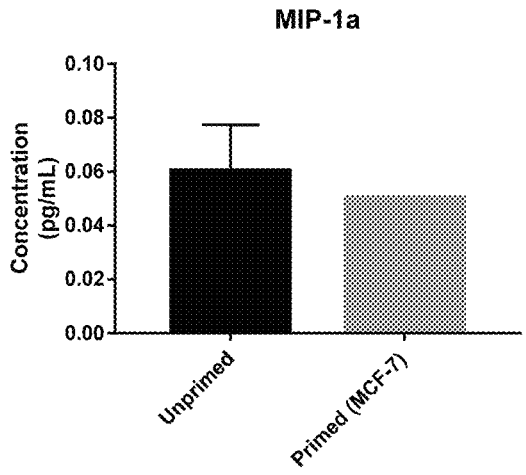
Figure 50L:
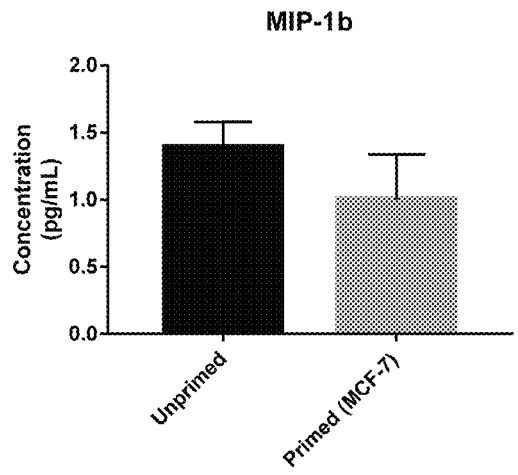
Figure 50M:
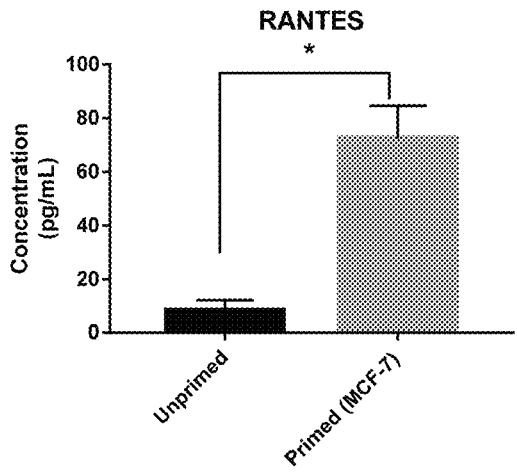
Figure 50N:
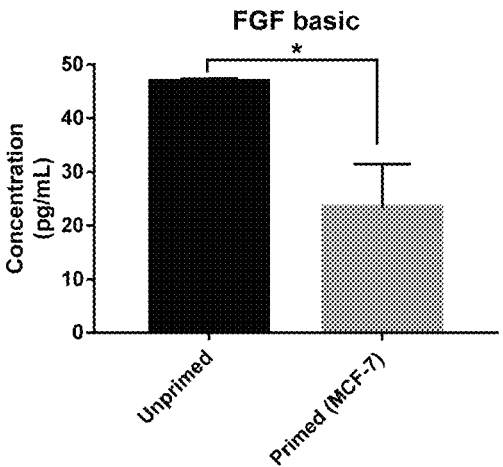
Figure 50O:
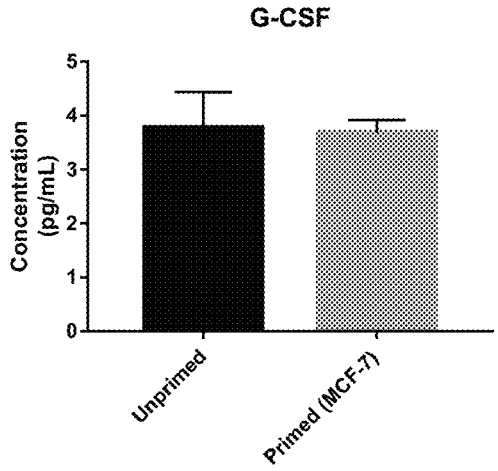
Figure 50P:
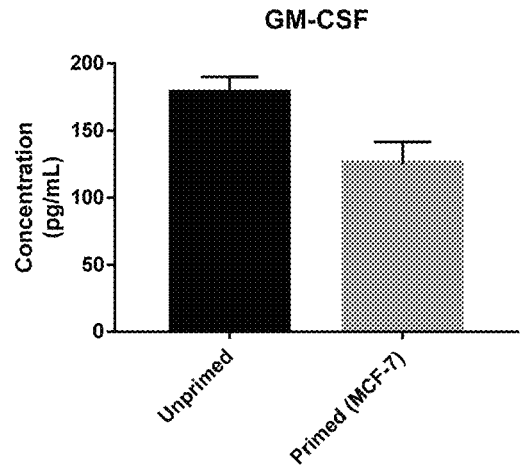
Figure 50Q:
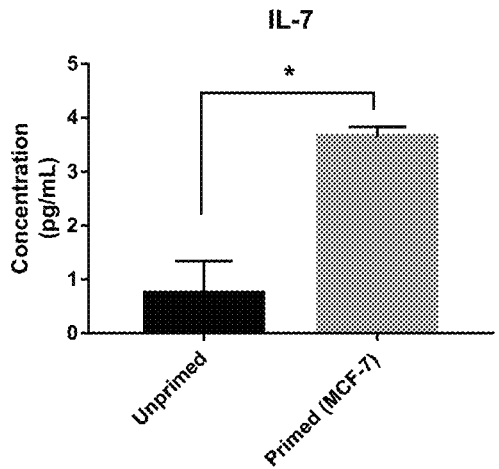
Figure 50R:
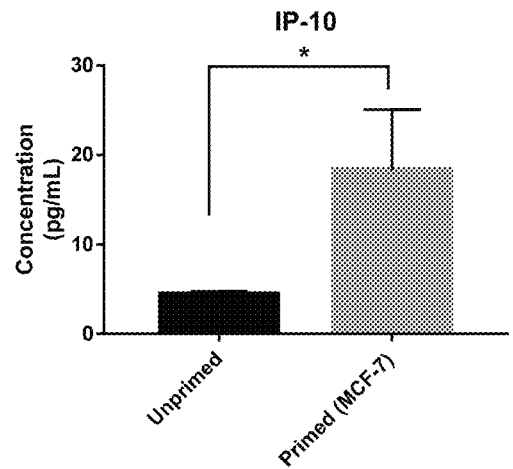
Figure 50S:
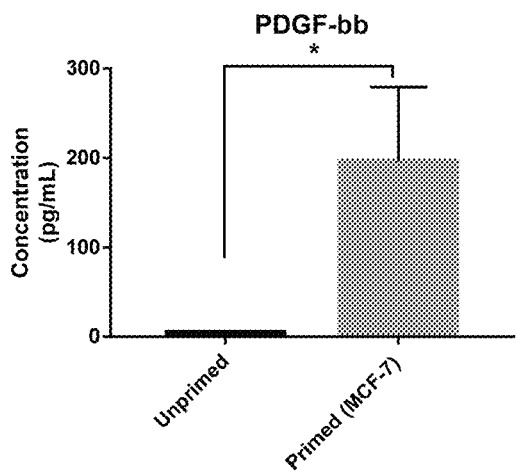
Figure 50T:
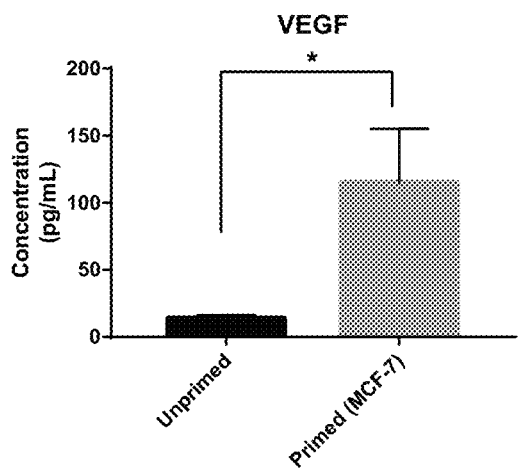
Figure 50U:
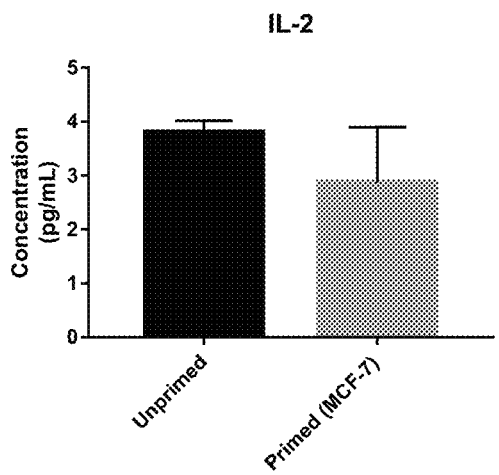
Figure 50V:
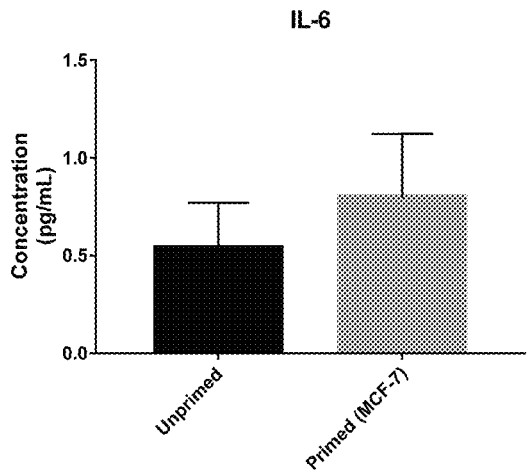

As shown in FIG. 50A-50VV, the cytokine secretion profile of the red blood cell membranes was altered by the 'priming' process, which in this instance was co-culture with MCF-7 cells (a breast cancer cell line). The red blood cell secretion concentration of proteins such as IFN-a2, IL-18, MIF, TNF-b, IL-2ra, CTACK, GRO-a, MIG, SDF-1α, IL-16, IL-3, LIF, IL-8, IL-9, TNF-a, IL-1ra, IL-4, MCP-1, RANTES, IL-7, IP-10, PDGF-bb, and VEGF were all significantly increased following co-culture priming. Whilst the levels of Eotaxin and FGF basic decreased significantly following co-culture priming. These results demonstrated that the red blood cell membrane contributes extensively to the changes in cytokine secretion profile of red blood cells when primed with MCF-7 cells.

12.3 RBC Lysates

Whole blood was collected from healthy volunteers (n≥3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

MCF-7 cells were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MCF-7 cells were seeded into T75 flasks at a concentration of $0.1 \times 10^6$ cells per mL of ADSC culture media and were incubated for 24 hours to ensure plate adherence (37° C., 5% $CO_2$). After incubation, the conditions as outlined in Table 14 were prepared using freshly isolated red blood cells. For co-culture with red blood cells the total volume of culture media in T75 flasks was 18 mL.

TABLE 14

Co-culture conditions for MCF-7 cells and red blood cells (RBCs) at a ratio of 1:100 at 37° C., 5% $CO_2$ for 72 hours.

| Condition | Label | Flask size | MCF-7 cells seeded | Red blood cell number |
|---|---|---|---|---|
| MCF-7 cells:RBCs (1:100) | Primed | T75 | $2.0 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were washed once with PBS and counted using a haematology analyser (Coulter Act Diff, Beckman Coulter).

The primed and unprimed red blood cells were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 51A:
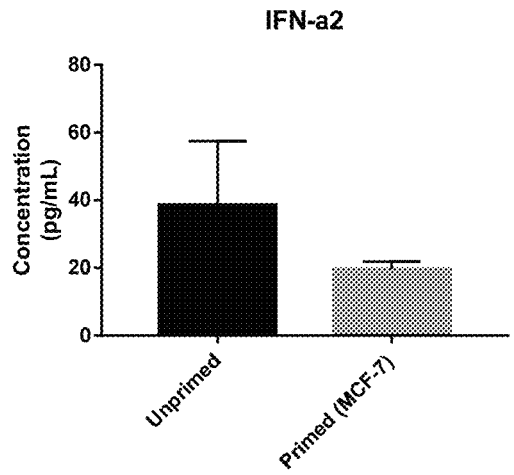
FIG. 51A-51VV is a series of graphs showing the concentration of proteins in red blood cells following co-culture for 3 days with (primed) or without (unprimed) breast cancer cell line cells (MCF-7 cells). Significant differences (p<0.05) were determined using Student's T-tests.
Figure 51B:
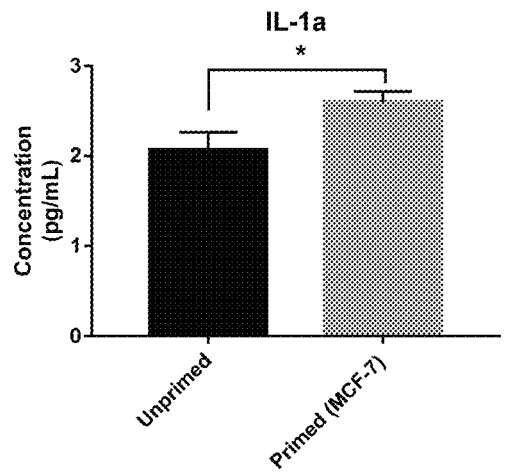
Figure 51C:
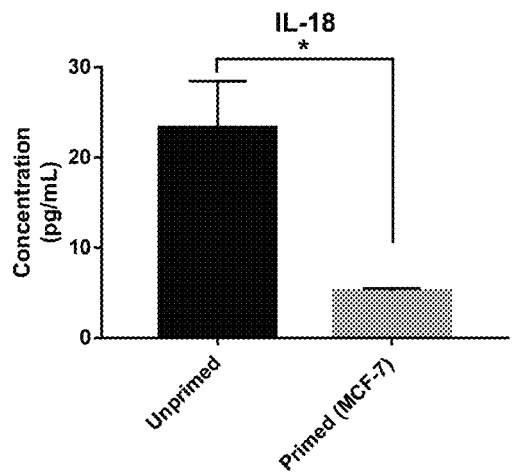
Figure 51D:
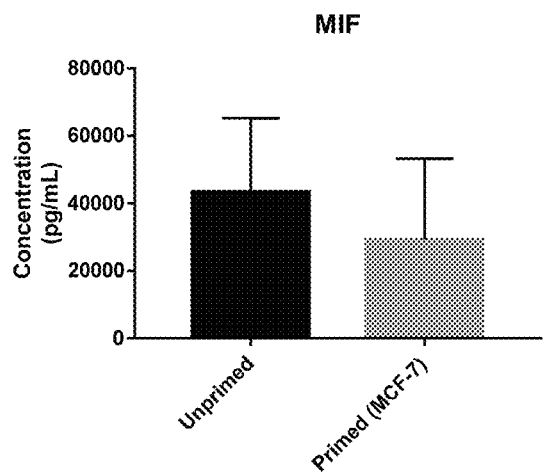
Figure 51E:
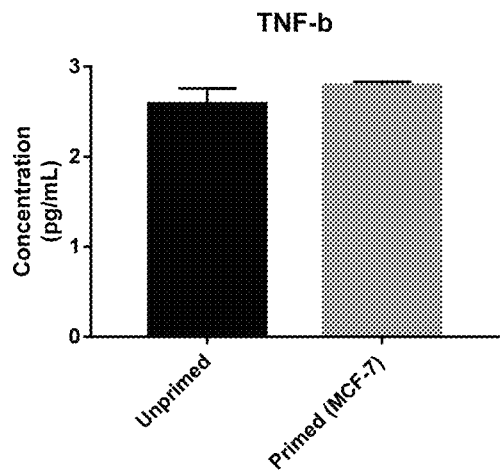
Figure 51F:
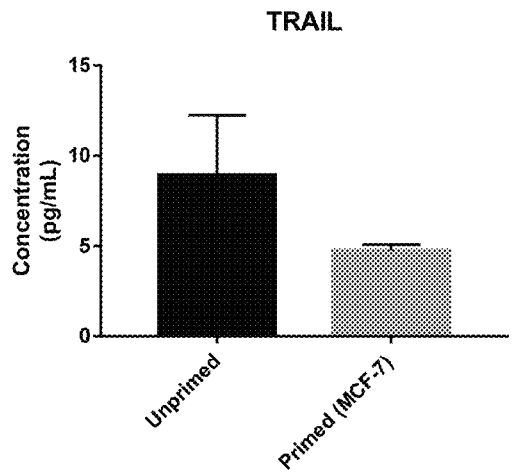
Figure 51G:
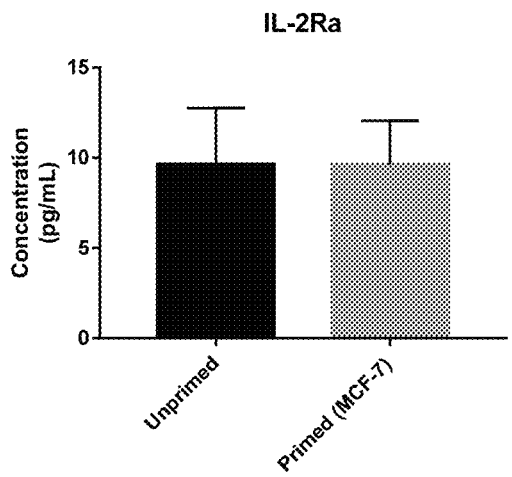
Figure 51H:
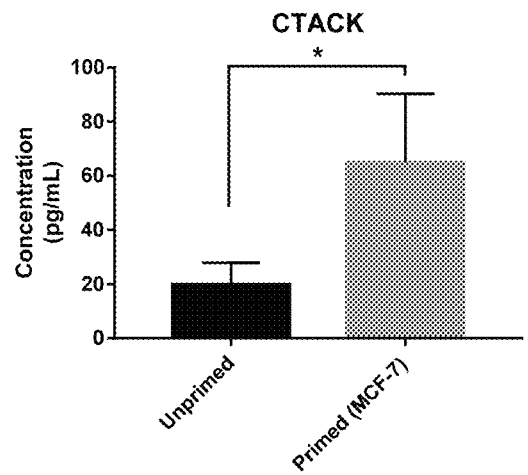
Figure 51I:
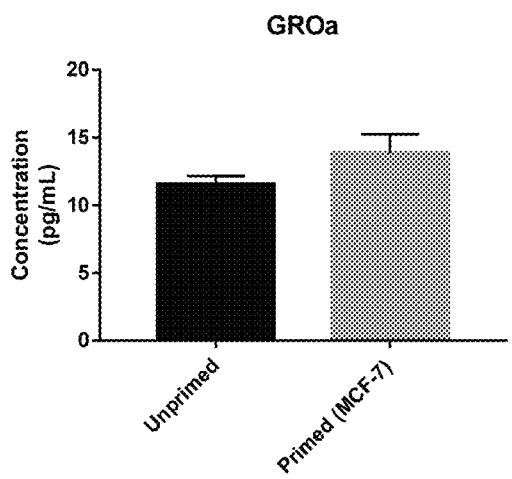
Figure 51J:
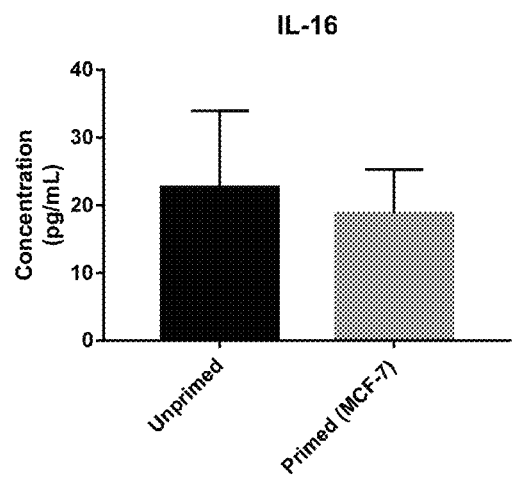
Figure 51K:
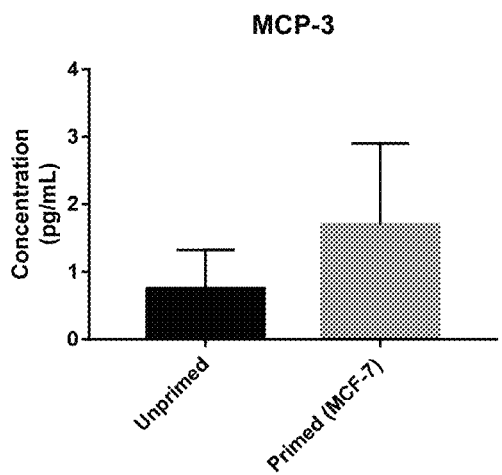
Figure 51L:
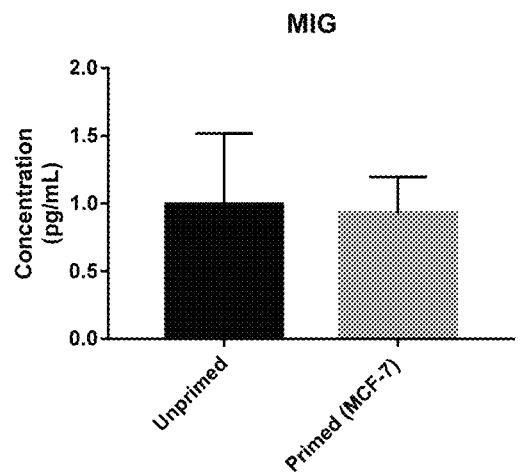
Figure 51M:
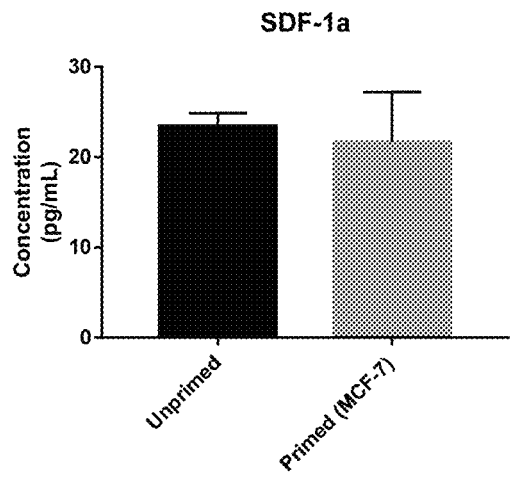
Figure 51N:
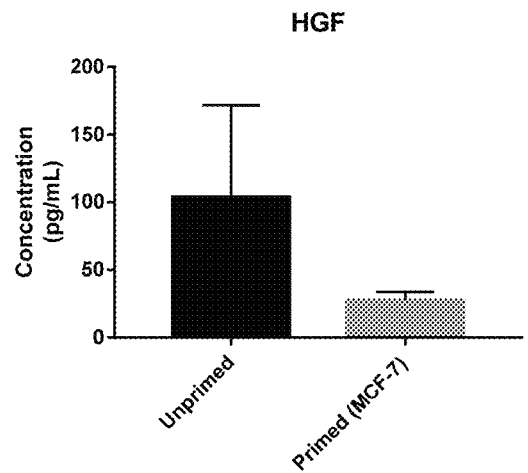
Figure 51O:
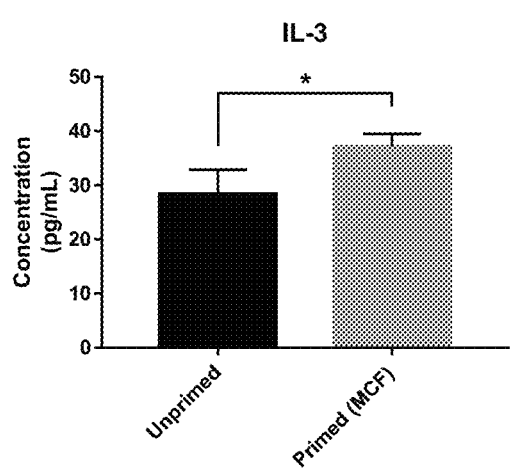
Figure 51P:
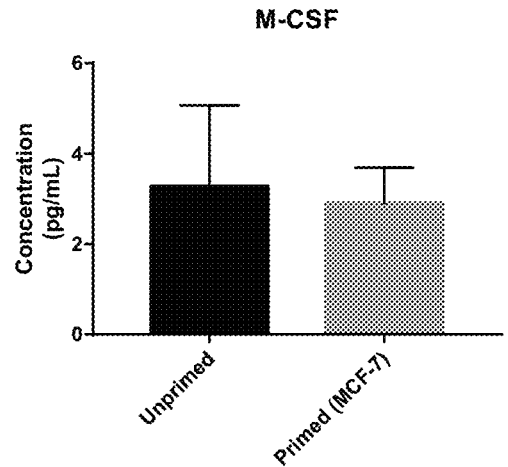
Figure 51Q:
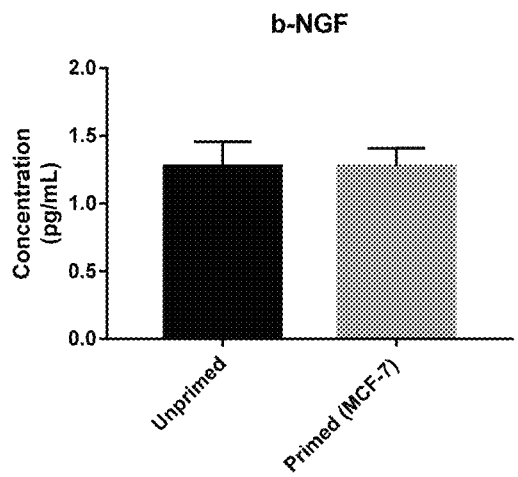
Figure 51R:
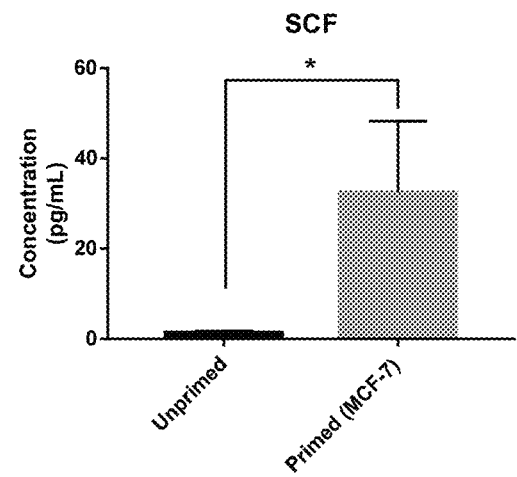
Figure 51S:
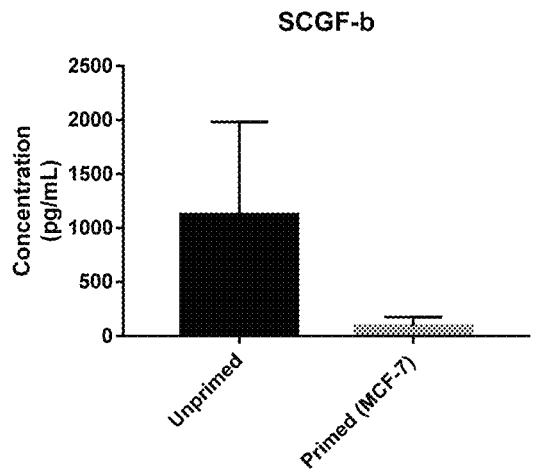
Figure 51T:
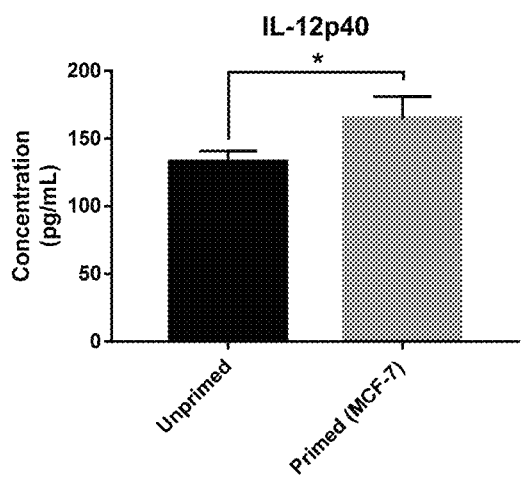
Figure 51U:
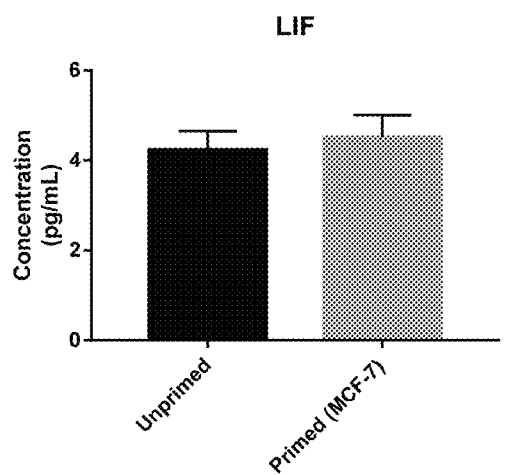
Figure 51V:
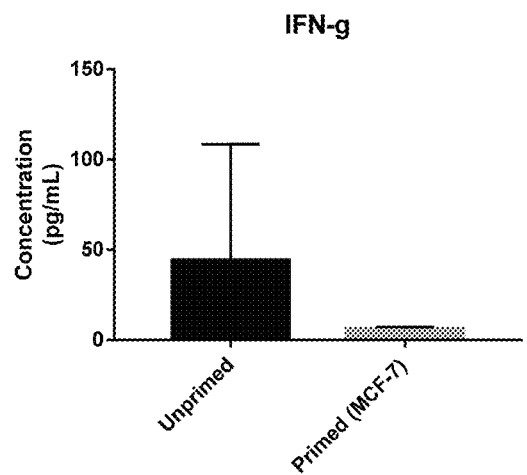
Figure 51W:
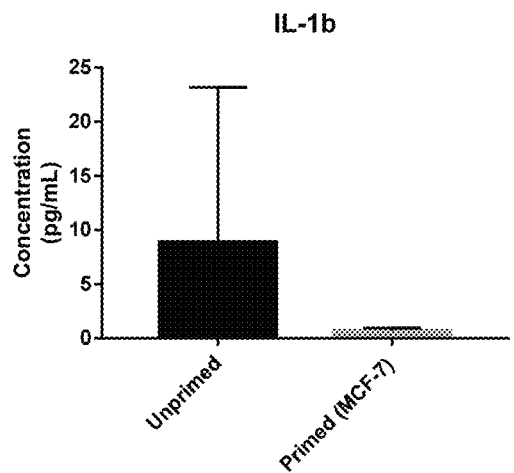
Figure 51X:
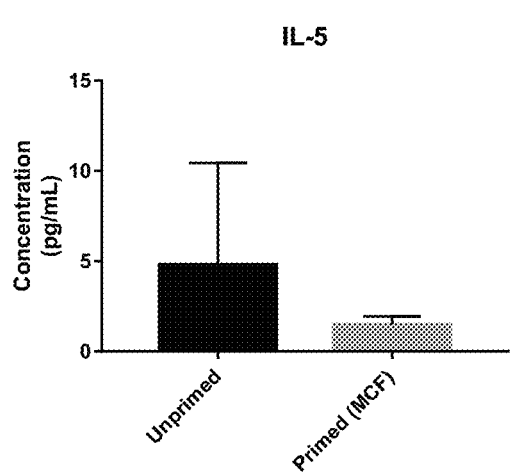
Figure 51Y:
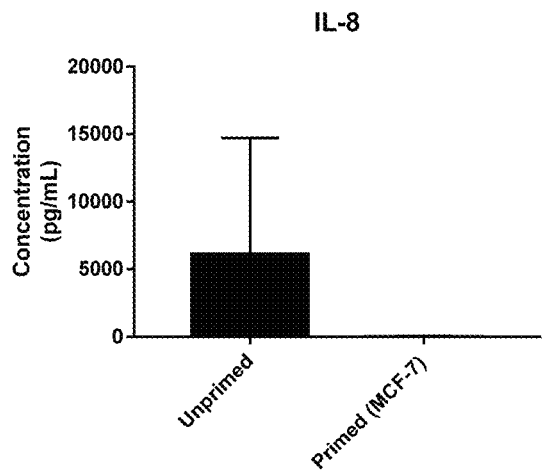
Figure 51Z:
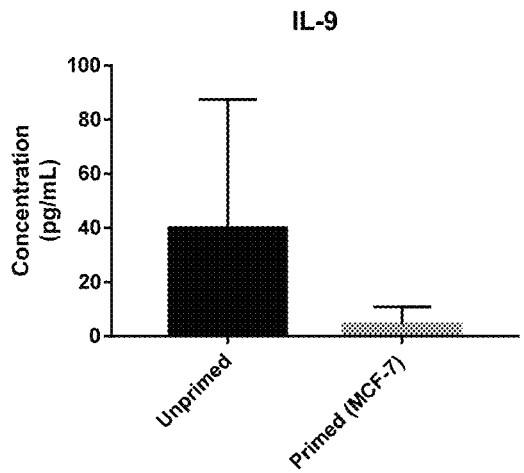
Figure 51A:
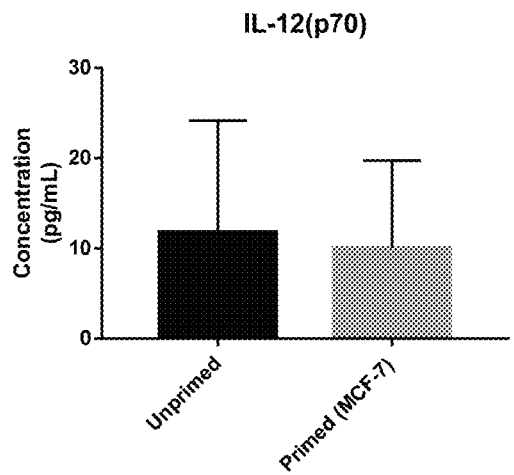
Figure 51B:
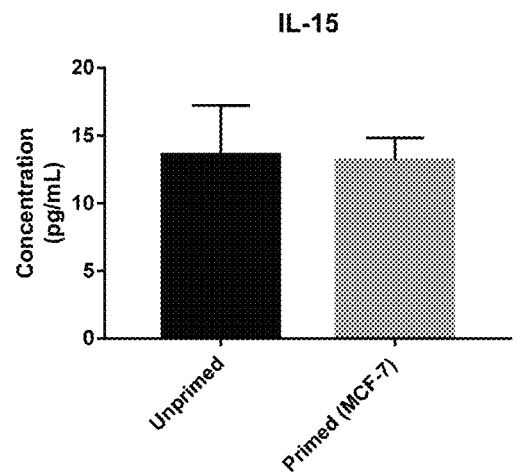
Figure 51C:
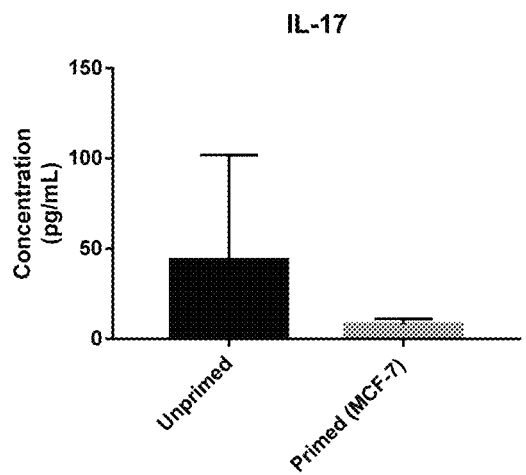
Figure 51D:
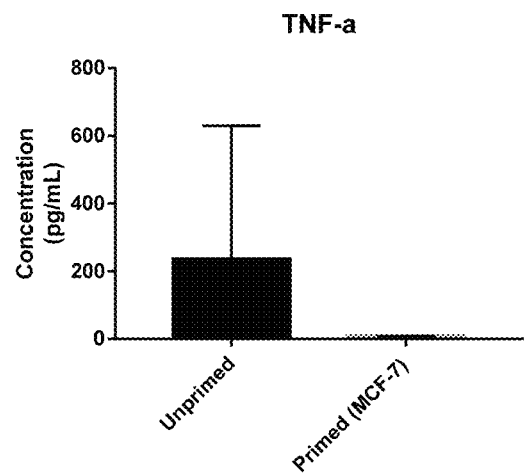
Figure 51E:
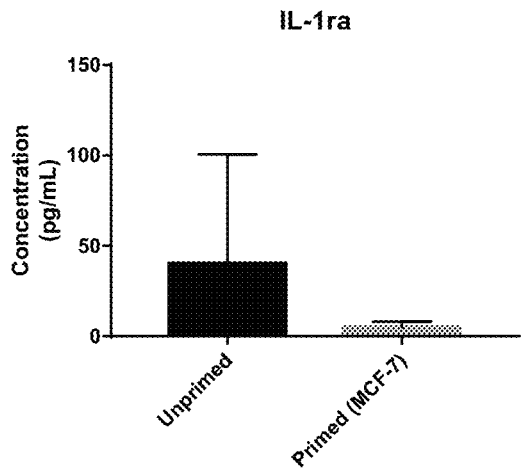
Figure 51F:
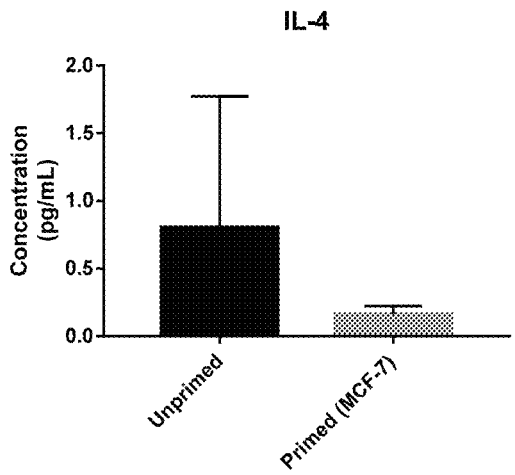
Figure 51G:
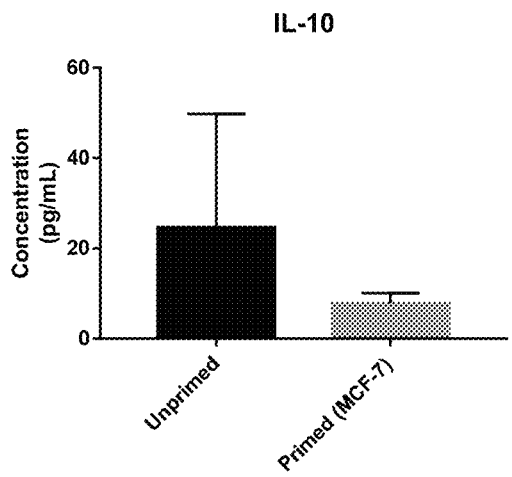
Figure 51H:
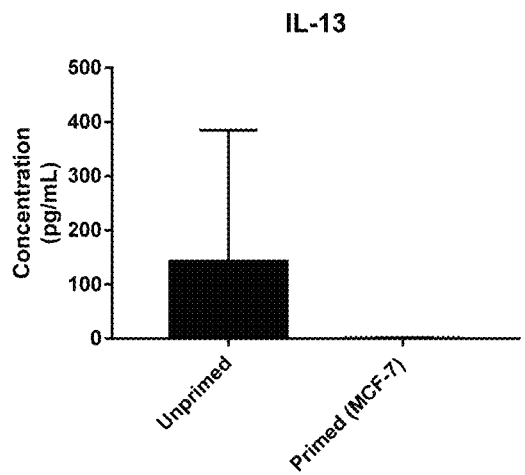
Figure 51I:
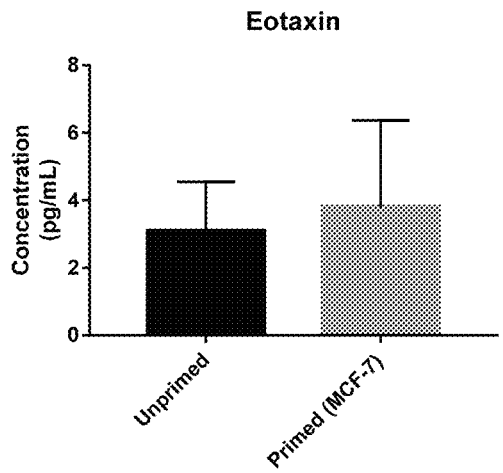
Figure 51J:
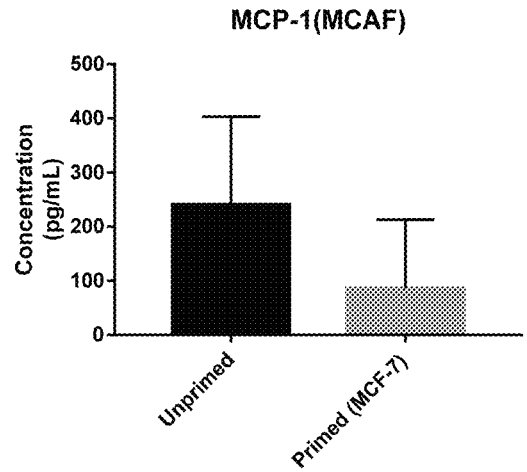
Figure 51K:
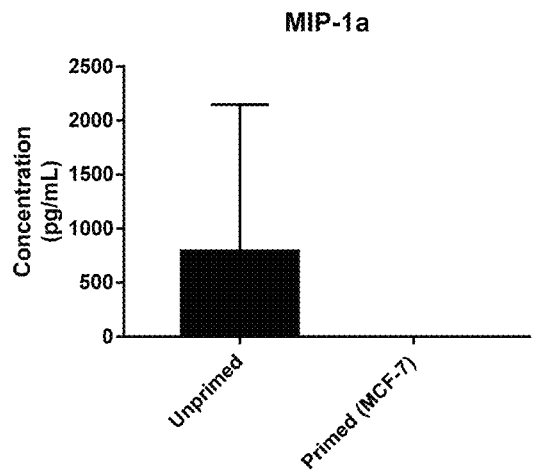
Figure 51L:
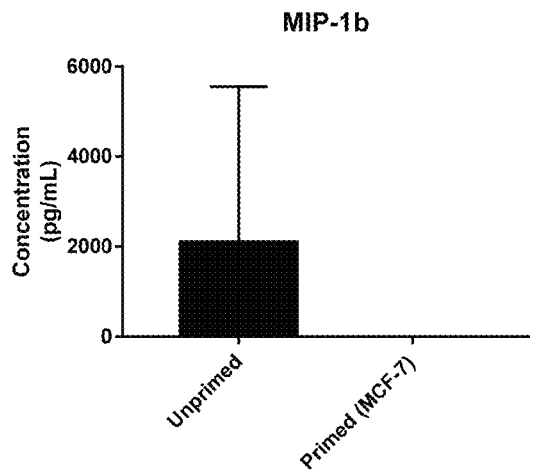
Figure 51M:
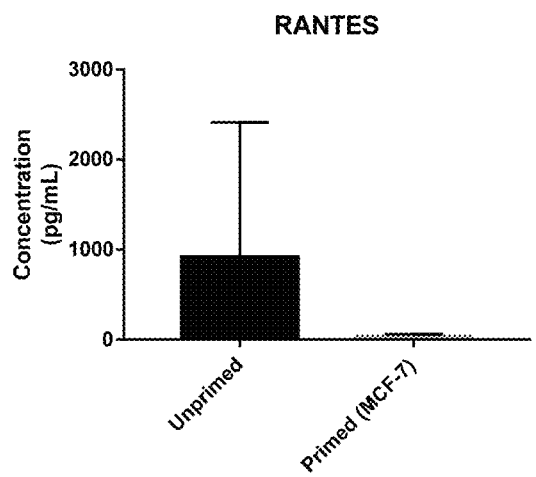
Figure 51N:
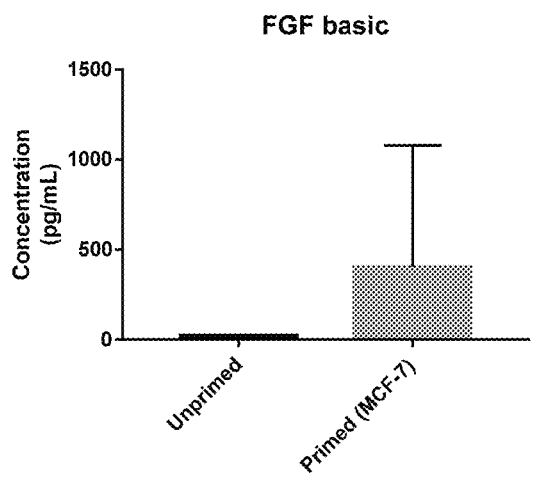
Figure 51O:
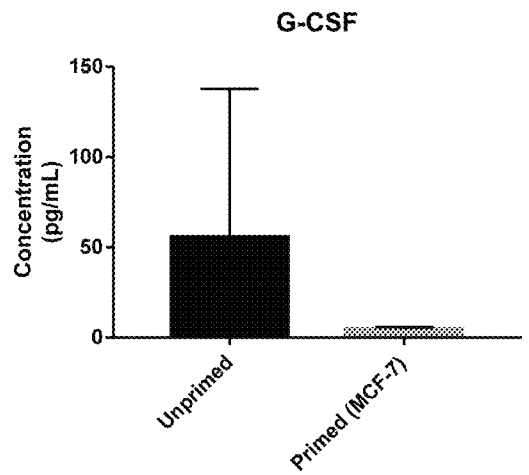
Figure 51P:
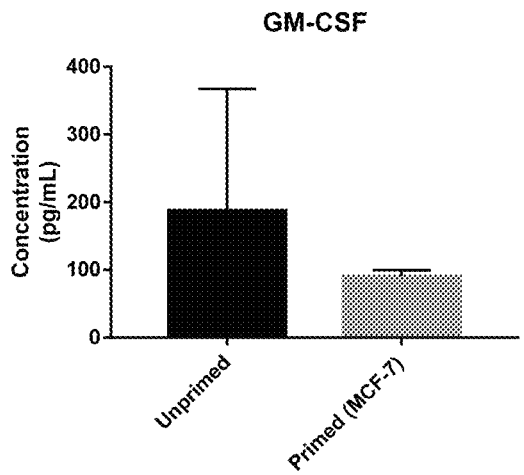
Figure 51Q:
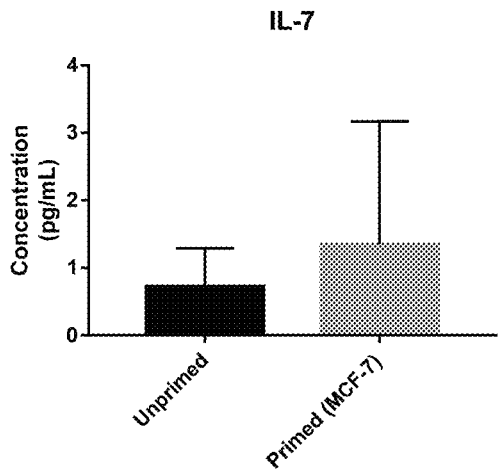
Figure 51R:
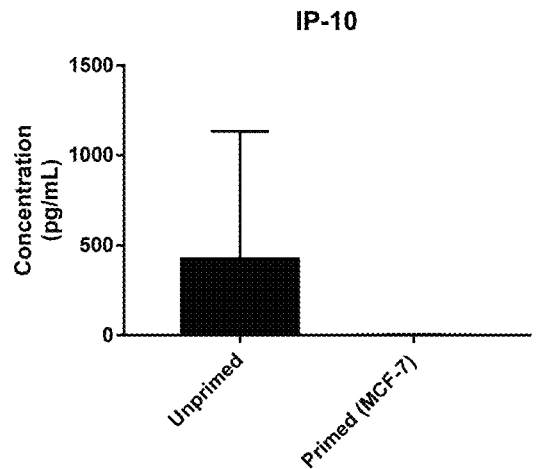
Figure 51S:
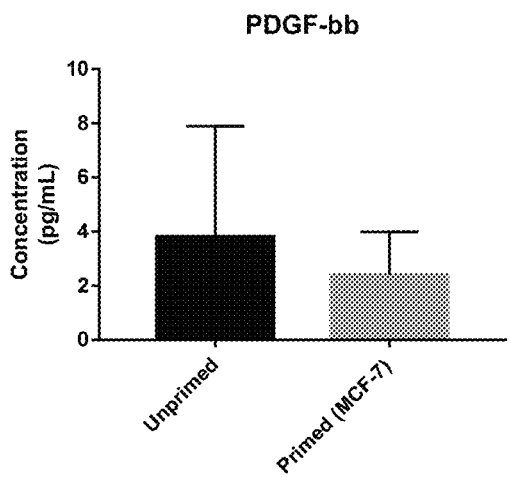
Figure 51T:
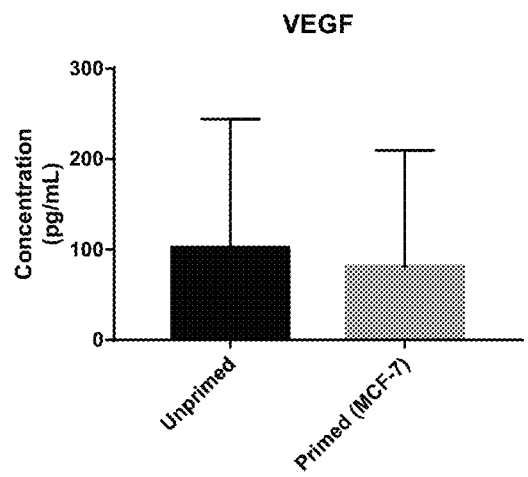
Figure 51U:
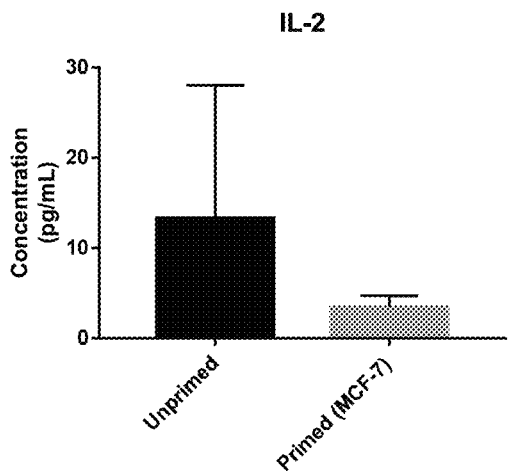
Figure 51V:
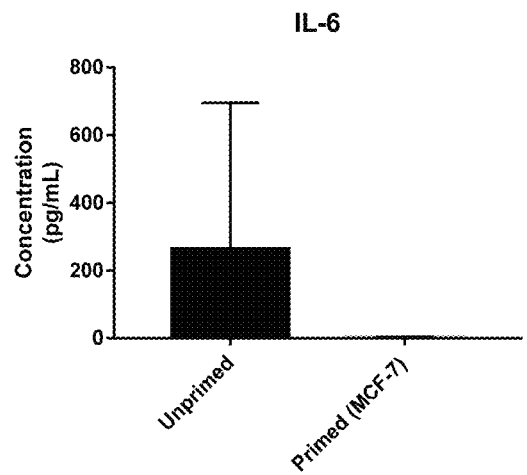

As shown in FIG. 51A-51VV, the cytokine profile of the red blood cells was altered by the 'priming' process, which in this instance was co-culture with MCF-7 (breast cancer cell line). The red blood cell concentration of proteins such as IL-1a, CTACK, IL3, and IL-12p40 were significantly increased following co-culture priming. Whilst the level of IL-18 decreased significantly following co-culture priming. The results demonstrated that the cytokine profile of red blood cells is subject to change depending on their environment. By incubating red blood cells in a protein rich environment, the cells were able to bind and release proteins. Comparison of these results with the analysis of the cytokines released or secreted by red blood cells after priming indicated that the extended incubation of RBCs in PBS to generate a secretion profile wa significantly more reproducible than the lysis procedure.

12.4. RBC Secretions

Whole blood was collected from healthy volunteers (n=3). Blood was collected from each volunteer by venepuncture (n≥3) directly into EDTA vacutainers ($k_2$EDTA vacutainers, BD Biosciences). All fractions of blood were collected and processed at room temperature within 4 hours of collection.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

MCF-7 cells were expanded in culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, MCF-7 cells were seeded into T75 flasks at a concentration of $0.1 \times 10^6$ cells per mL of ADSC culture media and were incubated for 24 hours to ensure plate adherence (37° C., 5% $CO_2$). After incubation, the conditions as outlined in Table 15 were prepared using freshly isolated red blood cells. For co-culture with red blood cells the total volume of culture media in T75 flasks was 18 mL.

TABLE 15

Co-culture conditions for MCF-7 cells and red blood cells (RBCs) at a ratio of 1:100 at 37° C., 5% $CO_2$ for 72 hours.

| Condition | Label | Flask size | MCF-7 cells seeded | Red blood cell number |
|---|---|---|---|---|
| MCF-7:RBCs (1:100) | Primed | T75 | $2 \times 10^6$ | $200 \times 10^6$ |
| RBCs | Unprimed | T75 | — | $200 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were washed once with PBS and counted using a haematology analyser (Coulter Act Diff, Beckman Coulter).

The red blood cells were then diluted in PBS to the equivalent of 400 million cells/mL. The red blood cells were then incubated in PBS for 24 hours, at 37° C. and 5% $CO_2$. After the incubation the red blood cells were removed by centrifugation (500 g, 10 minutes) the supernatant containing the red blood cell secretions were retained and analysed. Two multiplex assays were utilised. The 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-13, PDGF-BB, RANTES, TNF-α, and VEGF, and the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 52A:
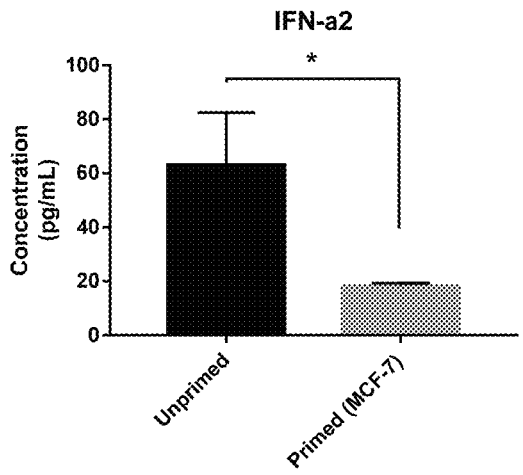
FIG. 52A-52VV is a series of graphs showing the concentration of released or secreted proteins from red blood cells following co-culture for 3 days with (primed) or without (unprimed) breast cancer cell line cells (MCF-7 cells). Significant differences (p<0.05) were determined using Student's T-tests.
Figure 52B:
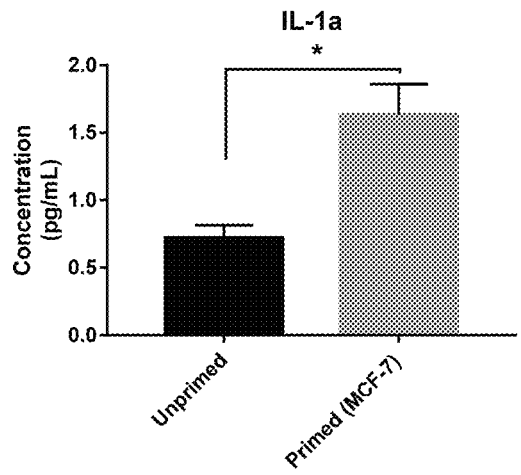
Figure 52C:
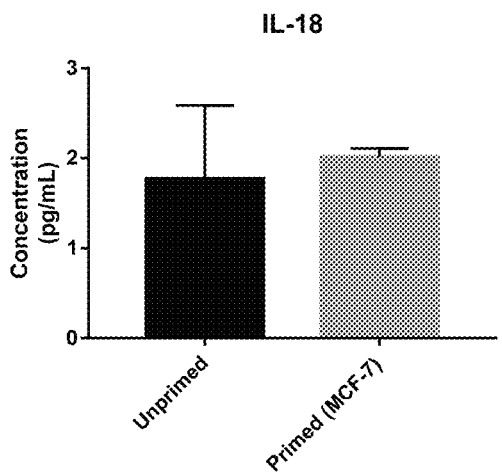
Figure 52D:
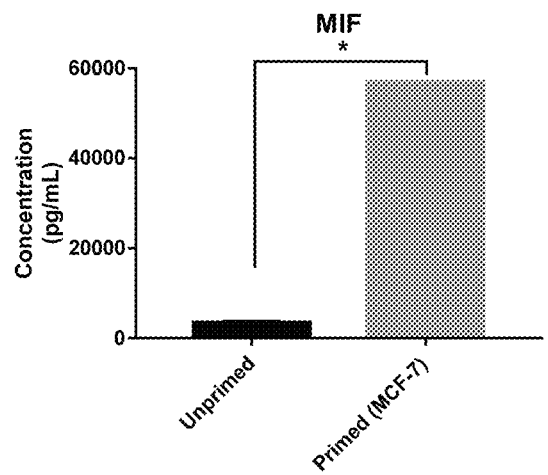
Figure 52E:
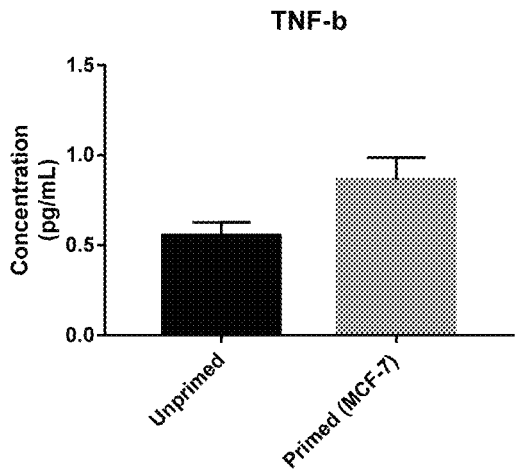
Figure 52F:
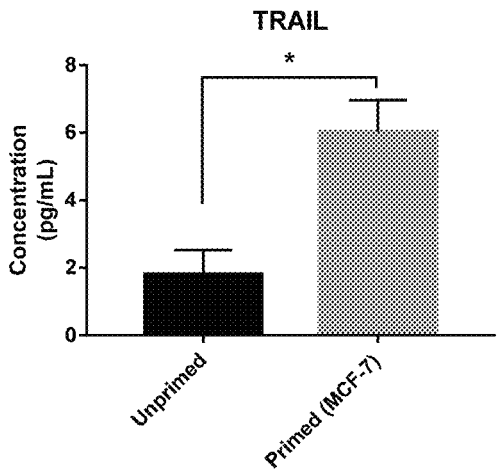
Figure 52G:
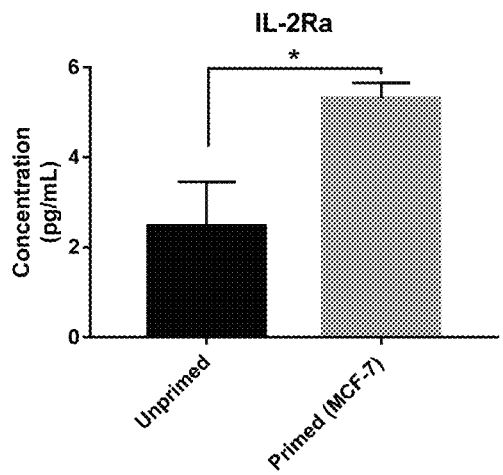
Figure 52H:
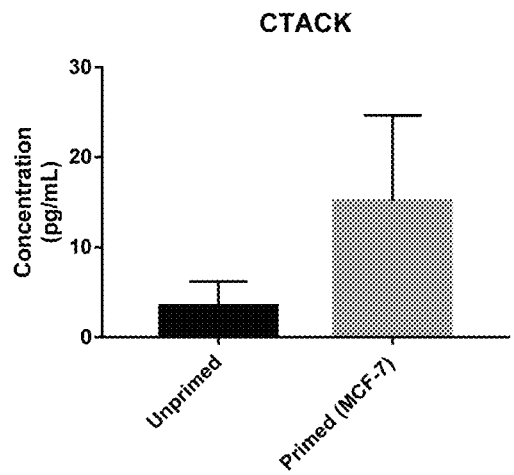
Figure 52I:
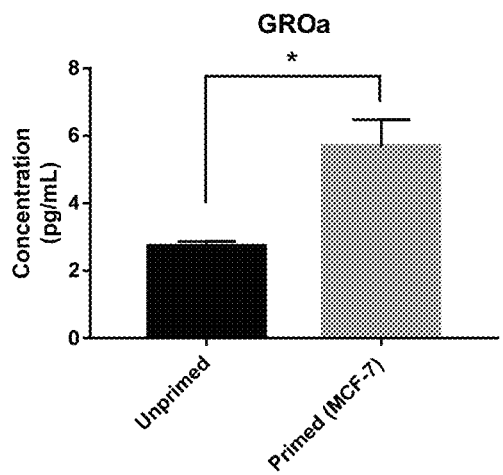
Figure 52J:
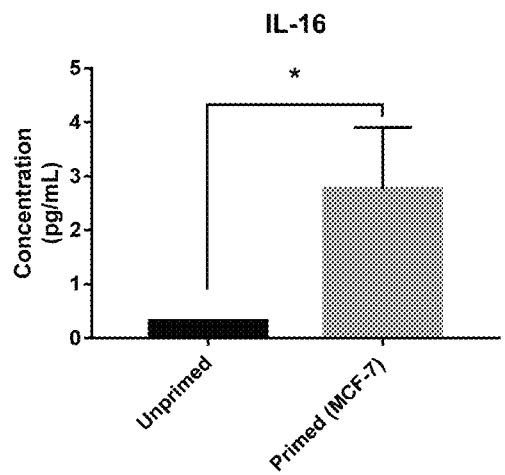
Figure 52K:
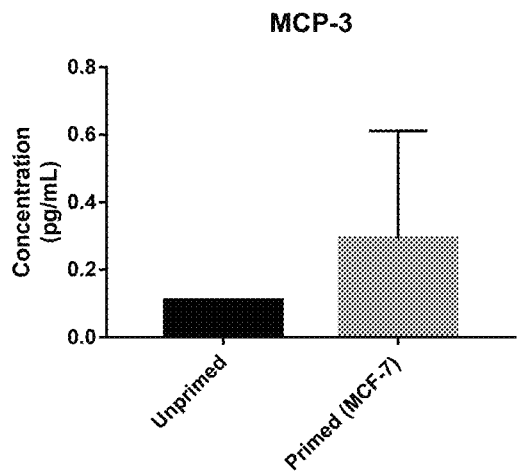
Figure 52L:
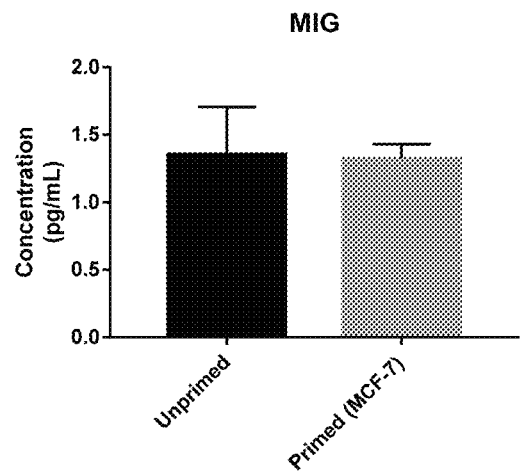
Figure 52M:
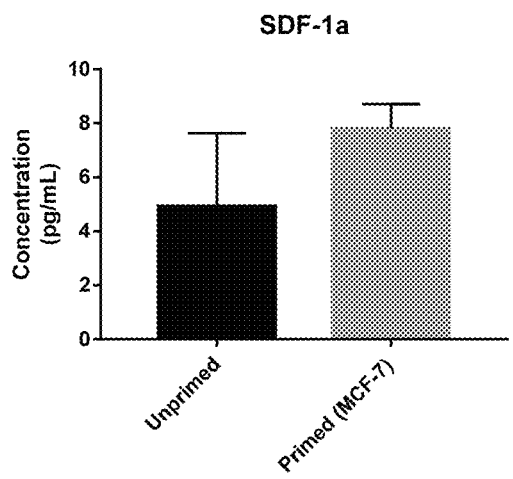
Figure 52N:
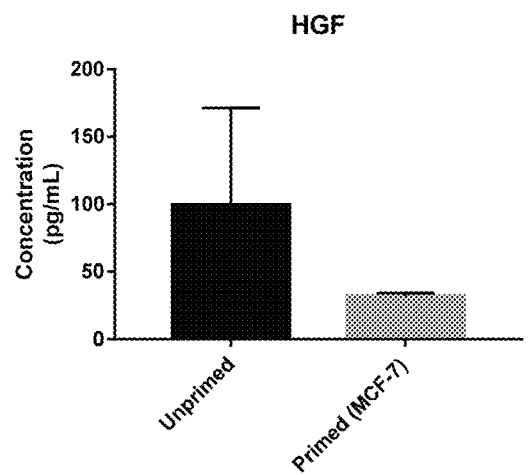
Figure 52O:
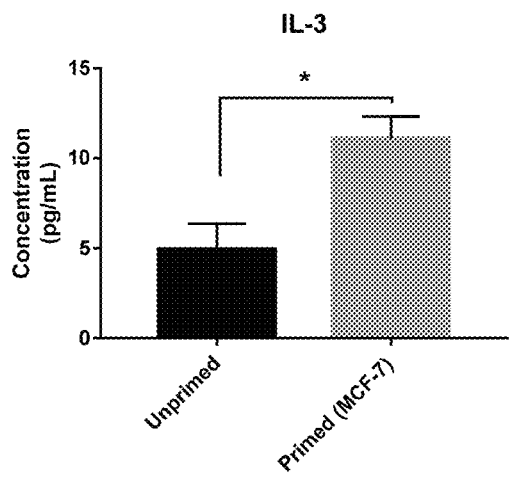
Figure 52P:
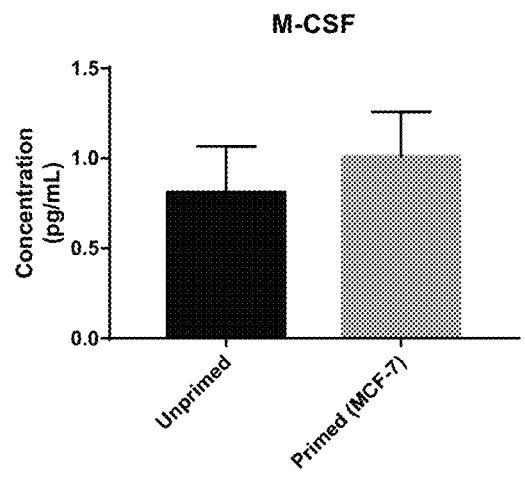
Figure 52Q:
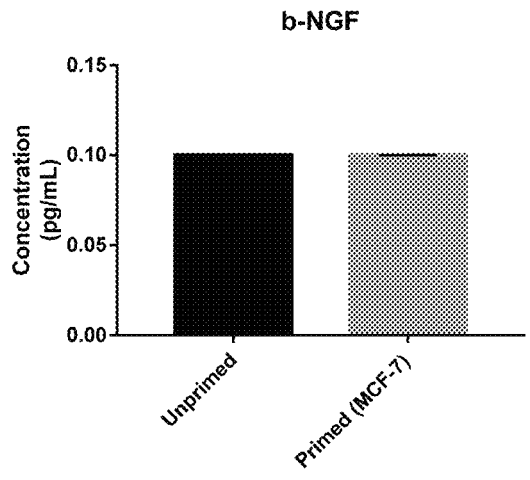
Figure 52R:
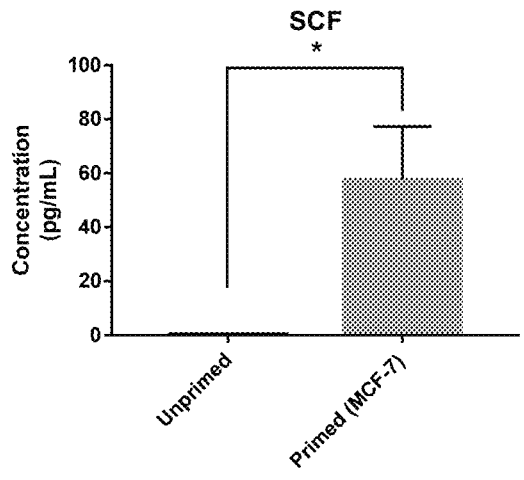
Figure 52S:
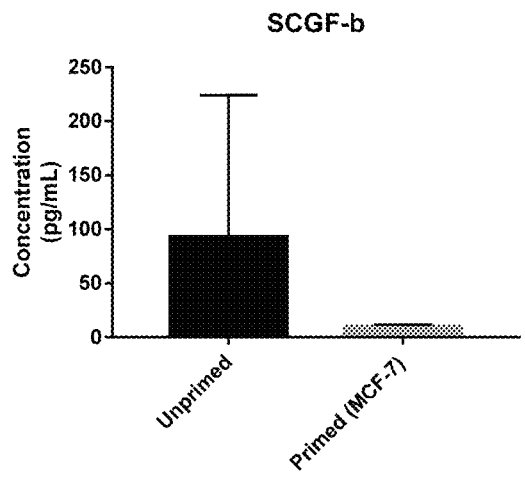
Figure 52T:
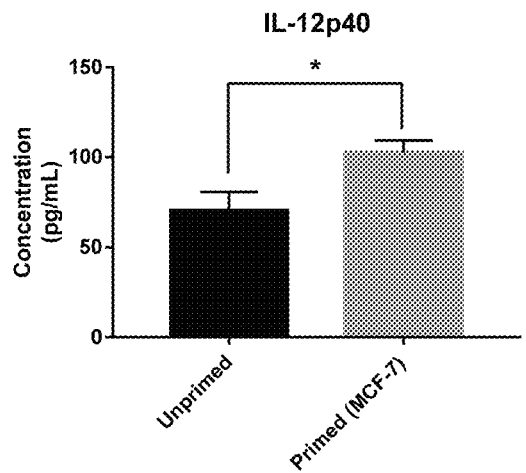
Figure 52U:
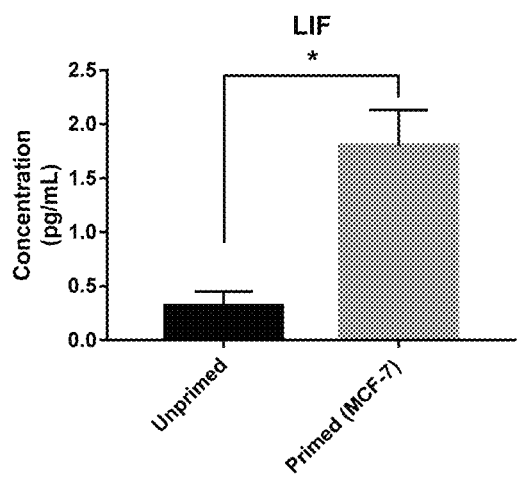
Figure 52V:
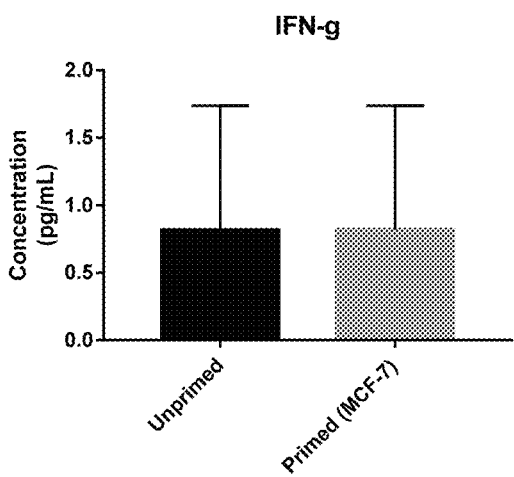
Figure 52W:
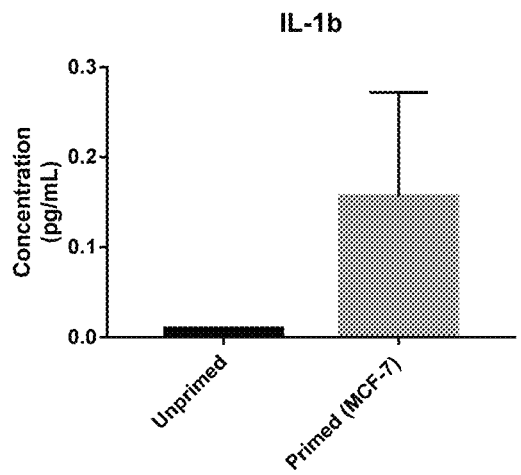
Figure 52X:
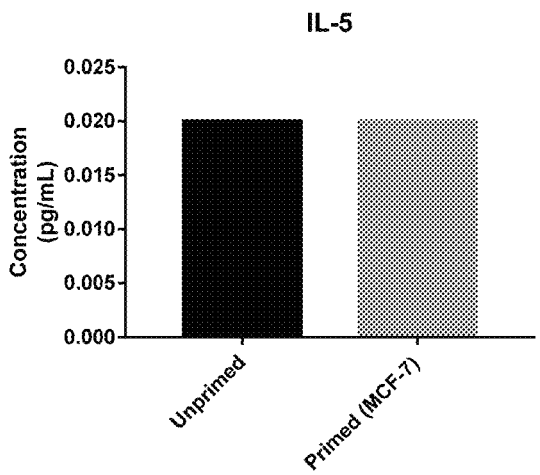
Figure 52Y:
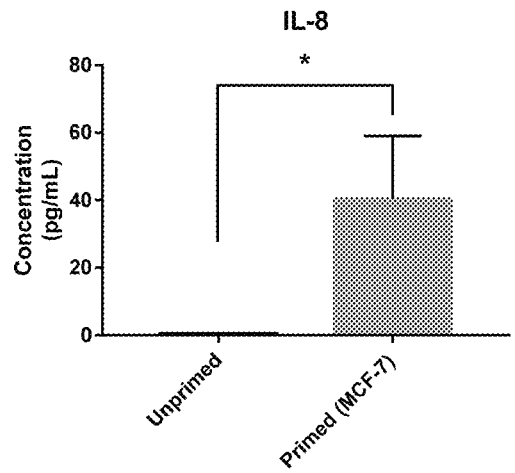
Figure 52Z:
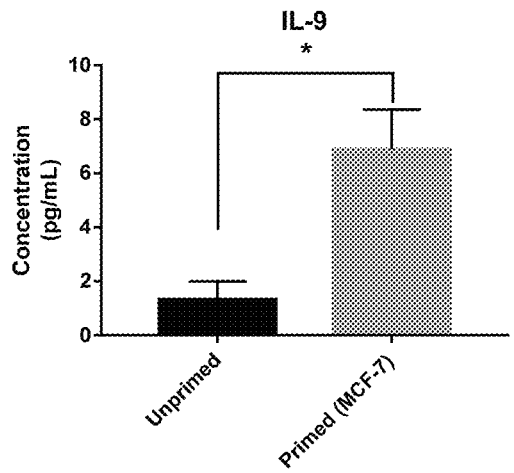
Figure 52A:
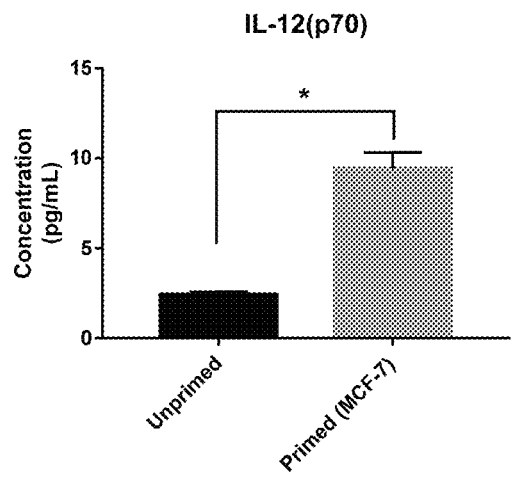
Figure 52B:
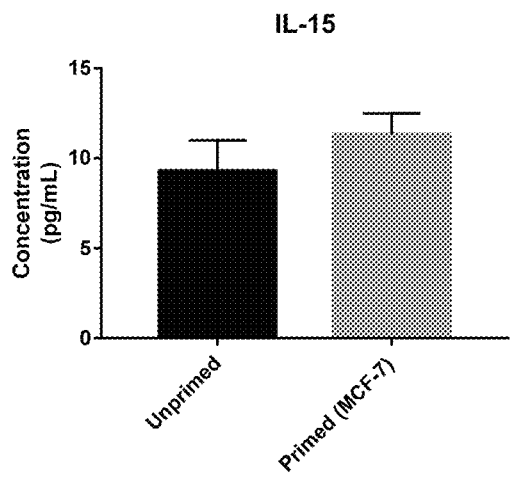
Figure 52C:
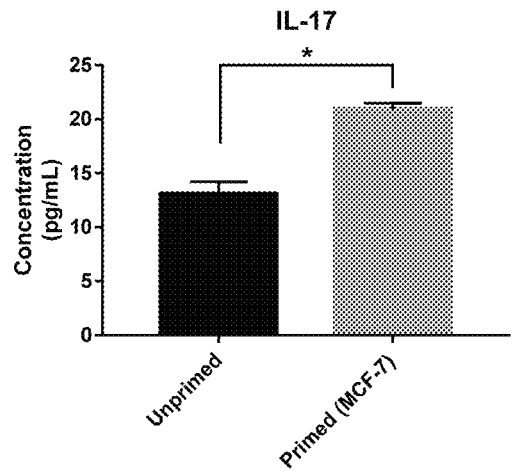
Figure 52D:
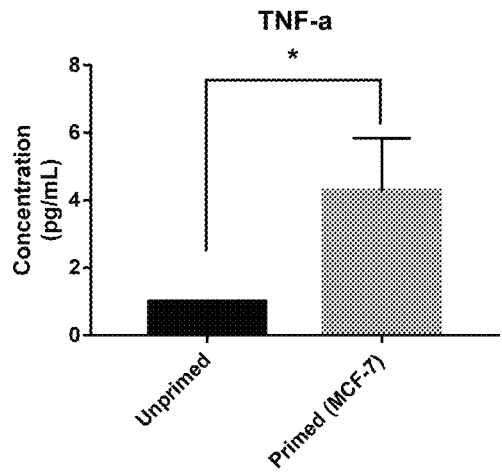
Figure 52E:
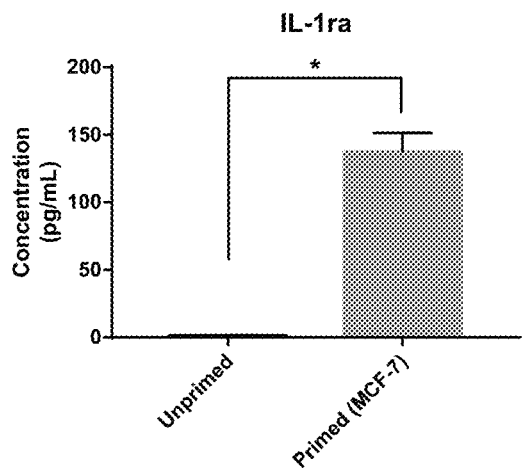
Figure 52F:
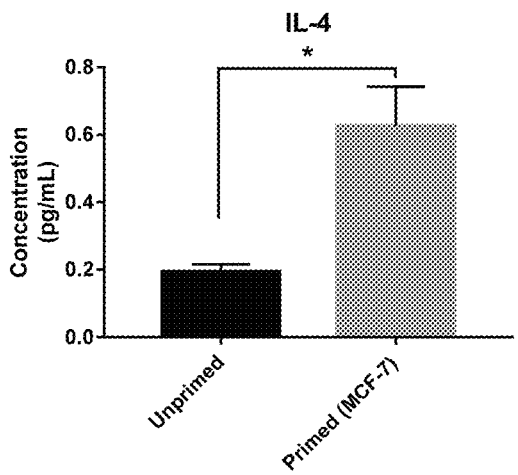
Figure 52G:
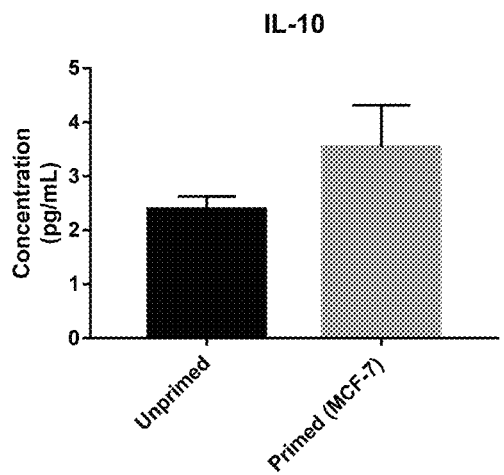
Figure 52H:
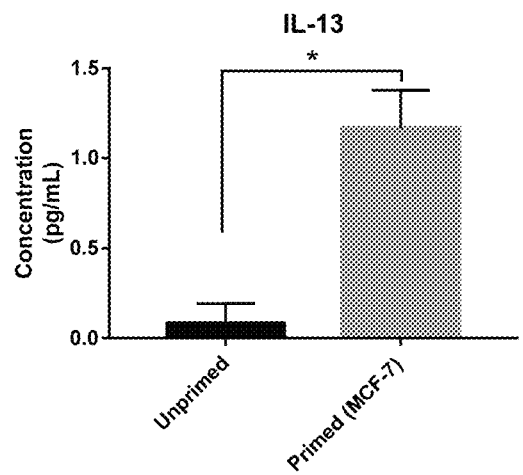
Figure 52I:
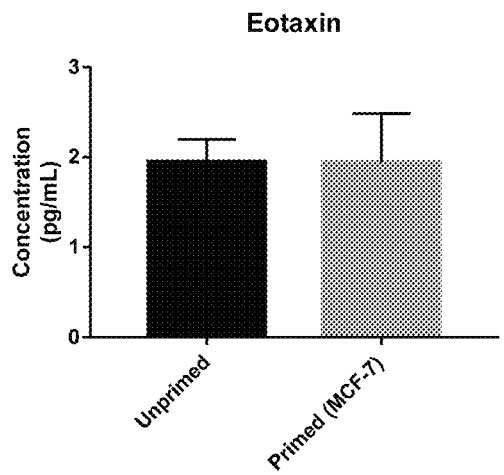
Figure 52J:
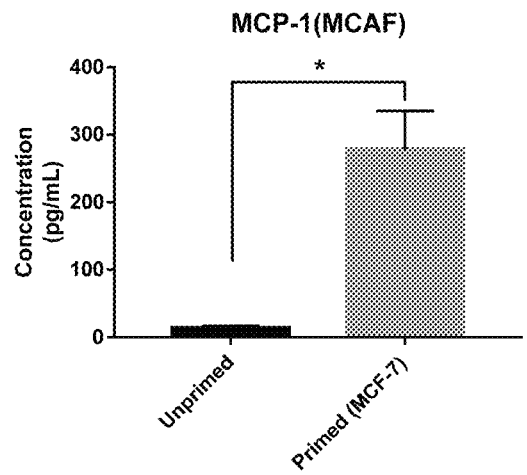
Figure 52K:
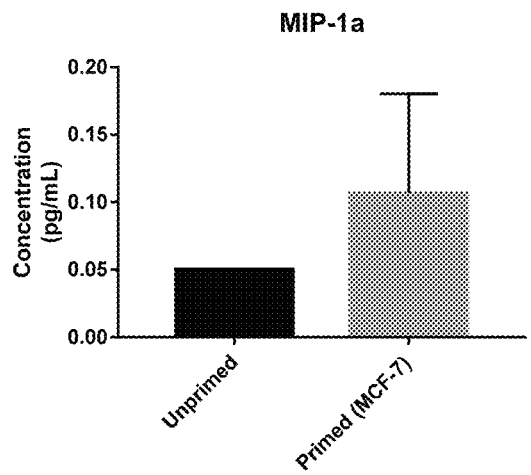
Figure 52L:
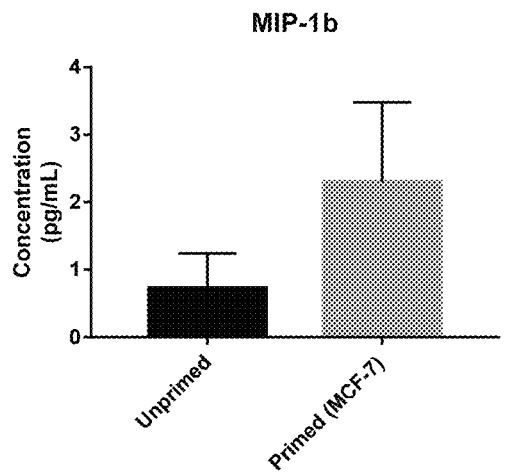
Figure 52M:
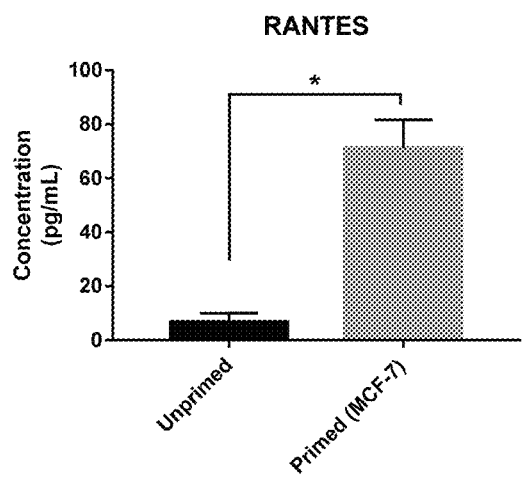
Figure 52N:
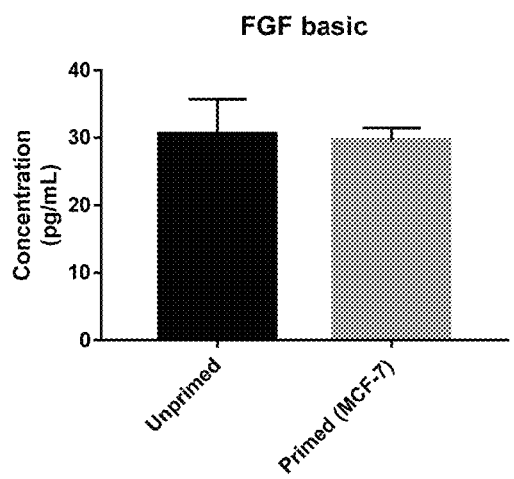
Figure 52O:
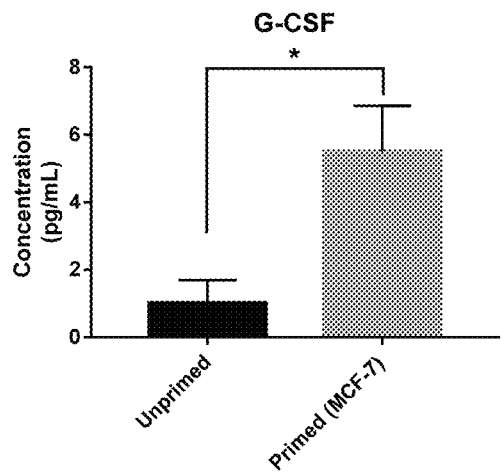
Figure 52P:
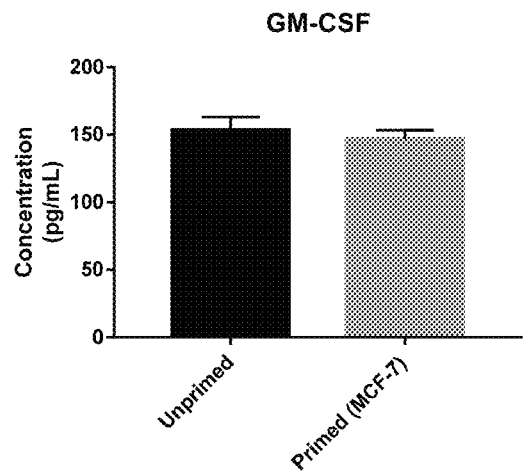
Figure 52Q:
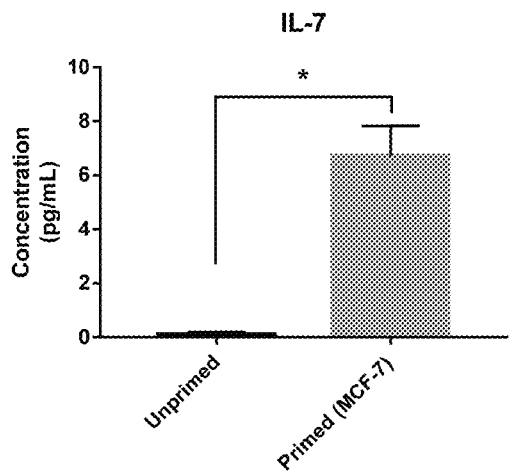
Figure 52R:
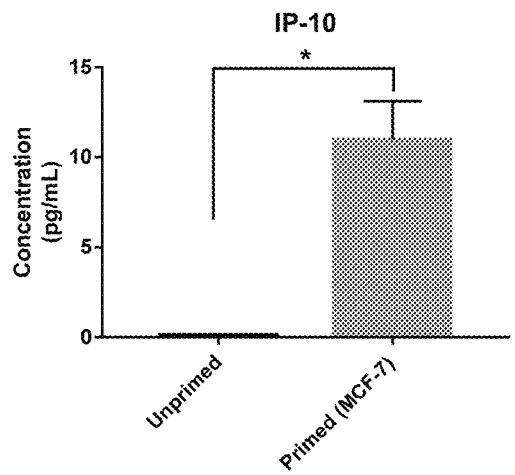
Figure 52S:
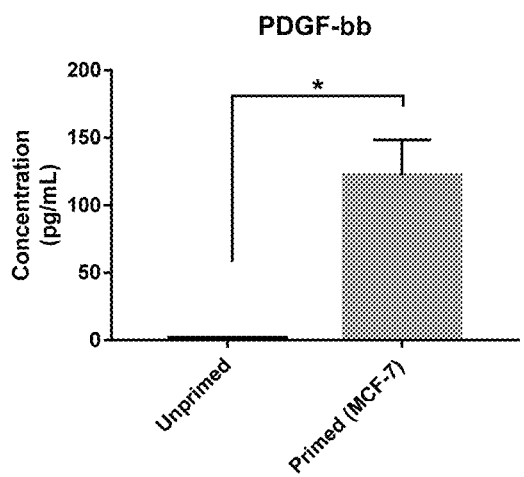
Figure 52T:
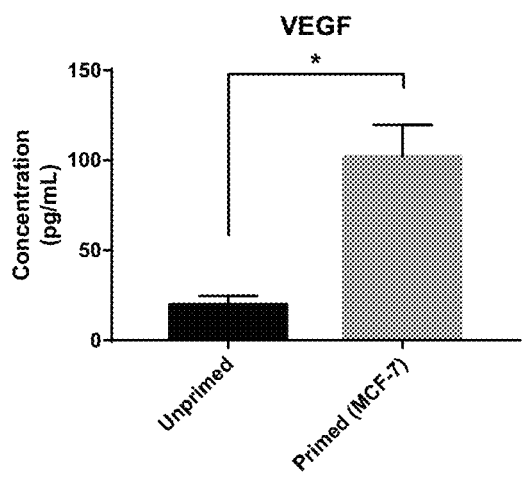
Figure 52U:
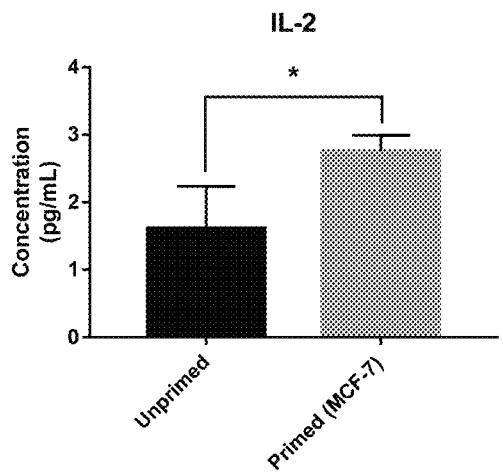
Figure 52V:
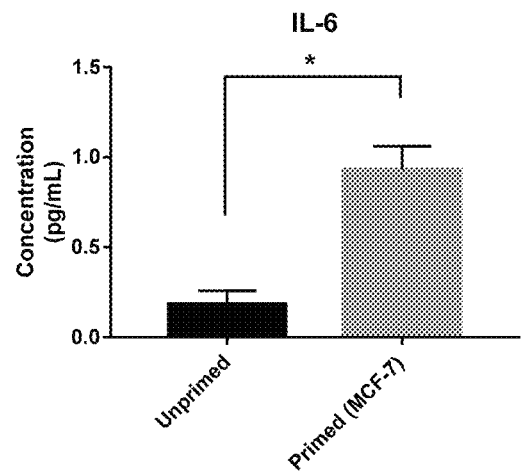

As shown in FIG. 52A-52VV, the cytokine secretion profile of the red blood cells was altered by the 'priming' process, which in this instance was co-culture with MCF-7 cells (a breast cancer cell line). The red blood cell secretion concentration of proteins such as IL-1a, MIF, TRAIL, IL-2ra, GRO-a, IL-16, IL-3, SCF, IL-12p40, LIF, IL-8, IL-9, IL-12p70, IL-17, TNF-a, IL-1ra, IL-4, IL-13, MCP-1, RANTES, G-CSF, IL-7, IP-10, PDGF-bb, VEGF, IL-2 and IL-6 were all significantly increased following co-culture priming. Whilst only the level of IFN-a2 decreased significantly following co-culture priming. These results demonstrated that the cytokine secretion profile of red blood cells is subject to change depending on their environment. By incubating red blood cells in a protein rich environment, the cells were able to bind and release proteins.

Example 13. Red Blood Cells after Priming with A549 Lung Cancer Cells

Whole blood was collected from healthy volunteers (n≥1). Blood was collected from each volunteer by venepuncture (n≥3) directly into EDTA vacutainers (k₂EDTA vacutainers, BD Biosciences). All fractions of blood were collected and processed at room temperature within 4 hours of collection. For multiplex analysis (BioPlex analysis) all samples were stored at −80° C. and were subjected to 3 freeze-thaw cycles at −80° C. to ensure complete cellular lysis prior to analysis.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then used for priming experiments.

A549 cells were expanded in A549 culture media (DMEM with 10% FBS and 1% antibiotic-antimycotic, v/v) at 37° C. and 5% $CO_2$. Cells were passaged twice a week when the cells reached confluence. Cells were counted using a haemocytometer and viability was determined with trypan blue staining.

For co-culture experiments, A549 cells were seeded into T75 flasks at a concentration of $0.1 \times 10^6$ cells per mL of ADSC culture media and were incubated for 24 hours to ensure plate adherence (37° C., 5% $CO_2$). After incubation, the conditions as outlined in Table 16 were prepared using freshly isolated red blood cells. For co-culture with red blood cells the total volume of culture media in T75 flasks was 18 mL.

TABLE 16

Co-culture conditions for A549 cells and red blood cells (RBCs) at a ratio of 1:100 at 37° C., 5% $CO_2$ for 72 hours.

| Condition | Label | Flask size | A549 cells seeded | Red blood cell number |
|---|---|---|---|---|
| A549 cells | | T75 | $1.8 \times 10^6$ | — |
| A549 cells: RBCs (1:100) | Primed | T75 | $1.8 \times 10^6$ | $180 \times 10^6$ |
| RBCs | Unprimed | T75 | — | $180 \times 10^6$ |

Cells were then incubated for 72 hours at 37° C. with 5% $CO_2$. Following incubation, the red blood cells were isolated by centrifugation out of the conditioned media (500 g, 10 minutes). Any remaining particulates in the conditioned media were removed by centrifugation (2000 g, 10 minutes) after which it was stored at −80° C. The red blood cells were washed once with PBS and counted using a haematology analyser (Coulter Act Diff, Beckman Coulter). The red blood cells were then frozen at −80° C. to produce lysates.

The primed and unprimed red blood cells were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-≈, TRAIL (Bio-Plex Pro 27-plex and 21-plex, Bio-Rad). The assays were performed according to manufacturer's instructions using an automated magnetic wash station (BioPlex Pro II, Bio-Rad) for the washing steps. The assays were run on the Luminex® 200™ system (Bio-Rad) and fluorescent values were collected. The calibration curve for each cytokine was analysed with 5 parametric logistic curve regression using BioPlex manager software (ver. 5.0, Bio-Rad, USA).

Figure 53A:
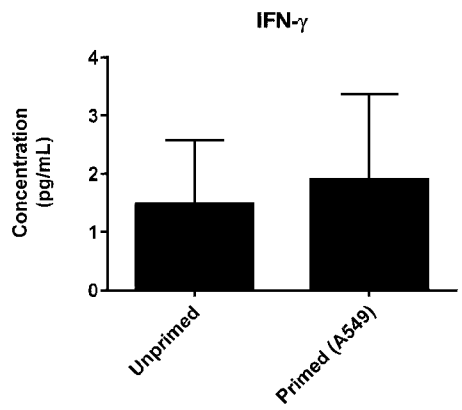
FIG. 53A-53UU is a series of graphs showing the concentration of proteins in red blood cells following co-culture for 3 days with (primed) or without (unprimed) a lung cancer cell line (A549 cells). Significant differences (p<0.05) were determined using Student's T-tests.
Figure 53B:
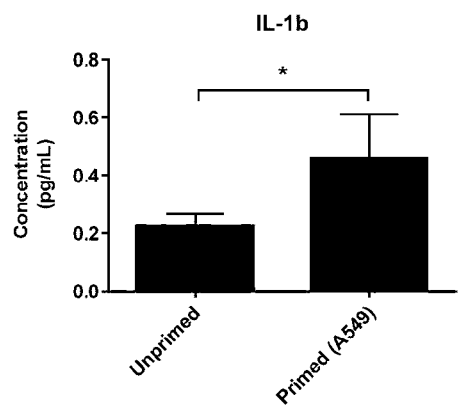
Figure 53C:
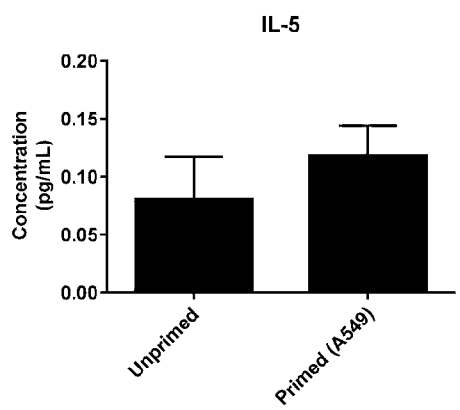
Figure 53D:
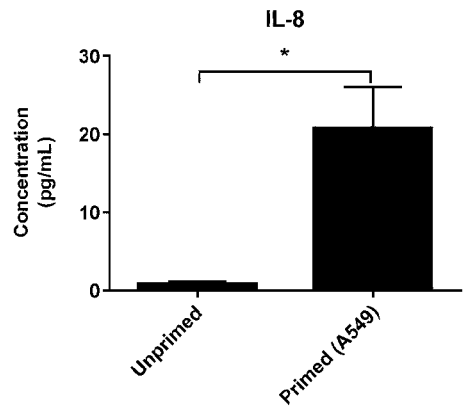
Figure 53E:
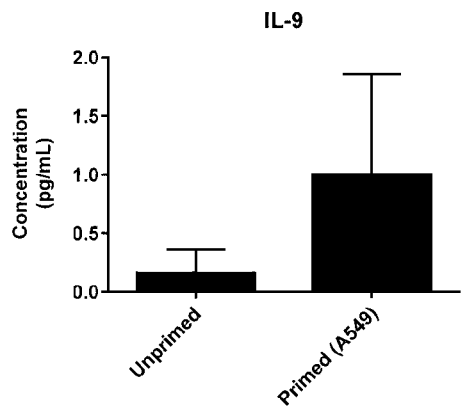
Figure 53F:
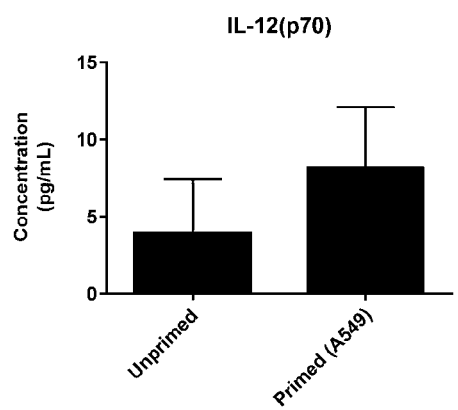
Figure 53G:
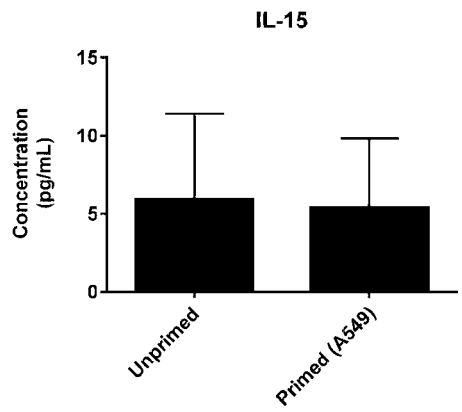
Figure 53H:
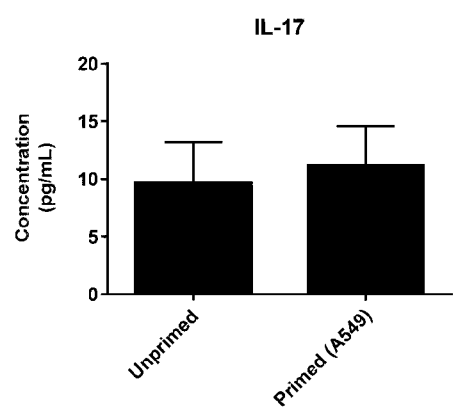
Figure 53I:
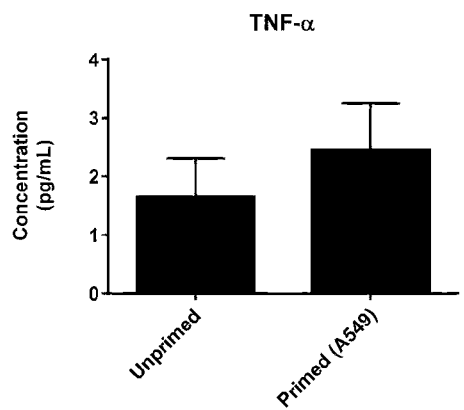
Figure 53J:
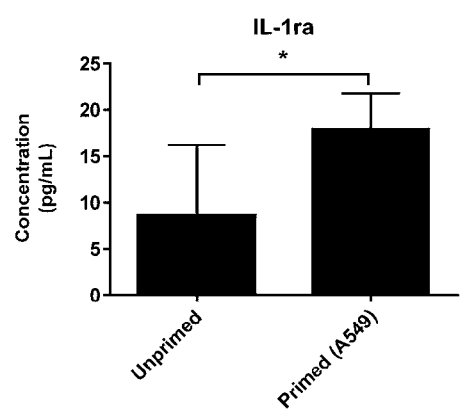
Figure 53K:
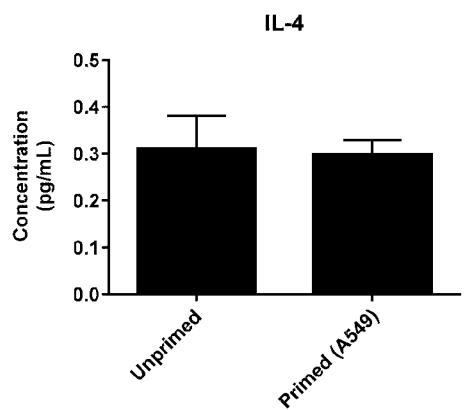
Figure 53L:
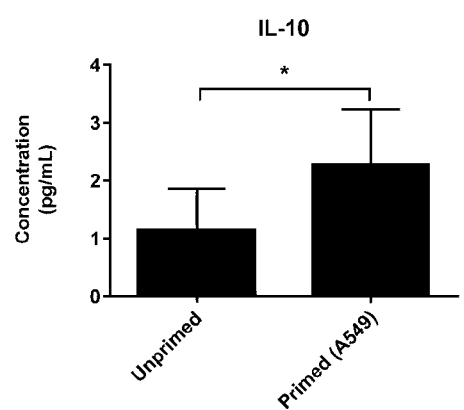
Figure 53M:
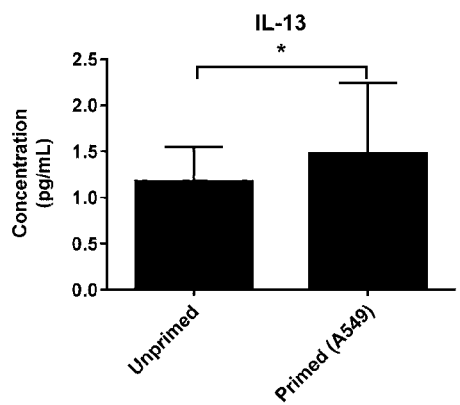
Figure 53N:
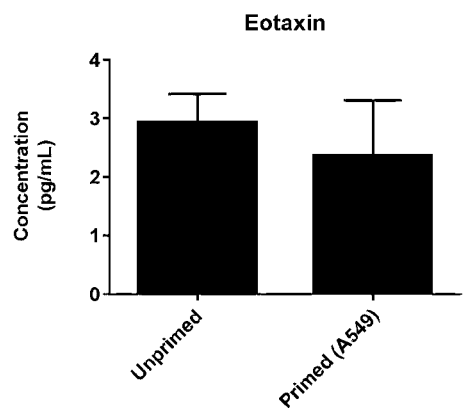
Figure 53O:
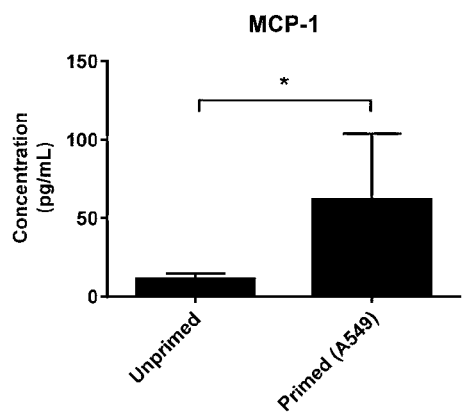
Figure 53P:
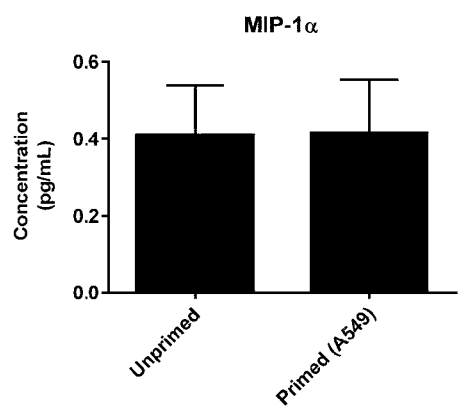
Figure 53Q:
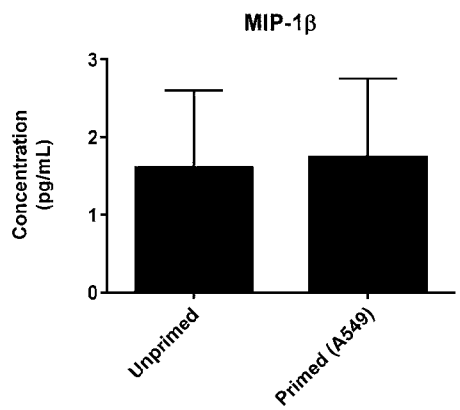
Figure 53R:
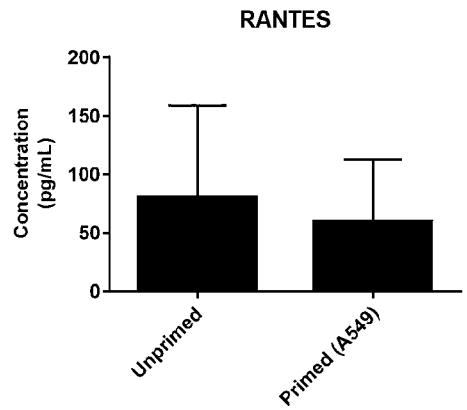
Figure 53S:
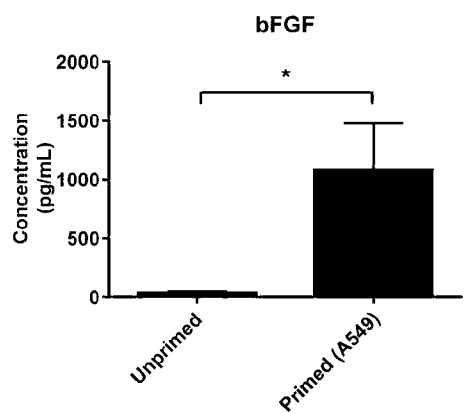
Figure 53T:
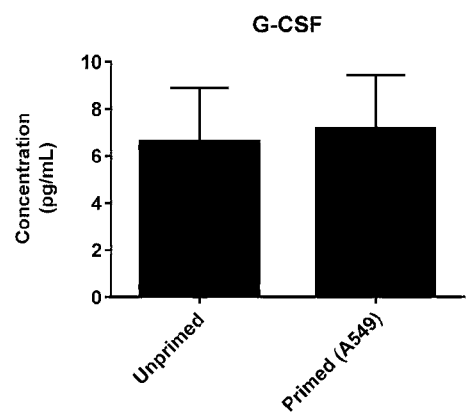
Figure 53U:
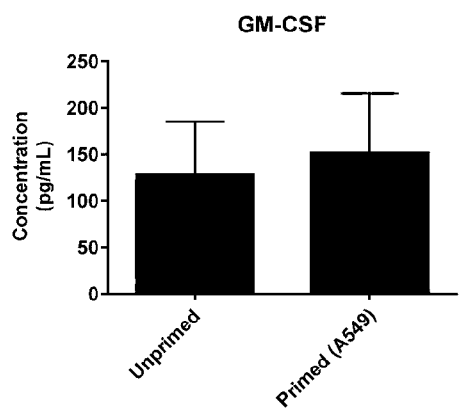
Figure 53V:
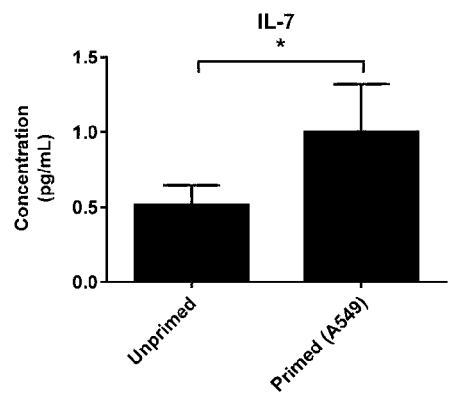
Figure 53W:
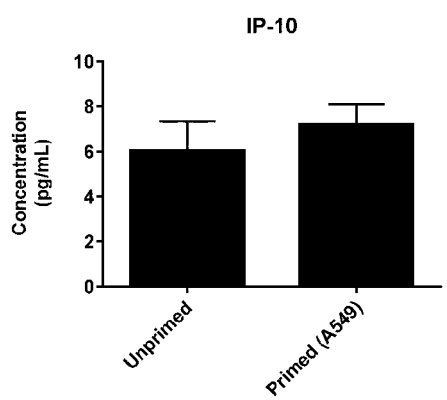
Figure 53X:
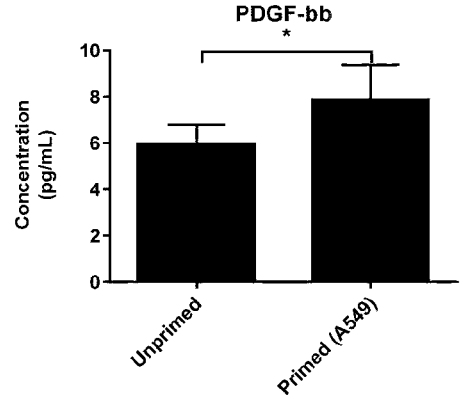
Figure 53Y:
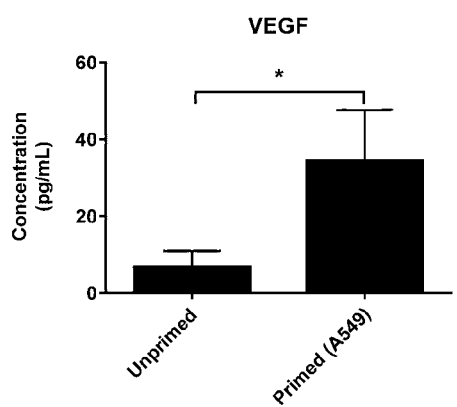
Figure 53Z:
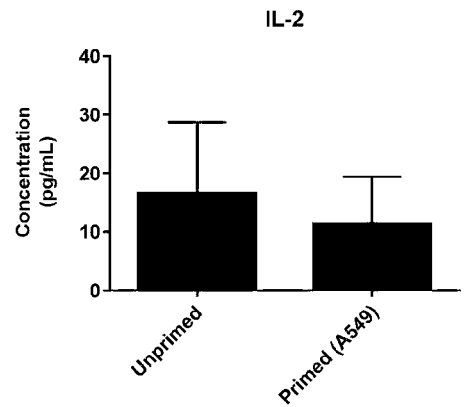
Figure 53A:
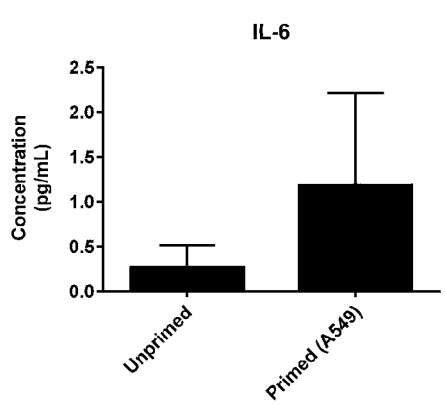
Figure 53B:
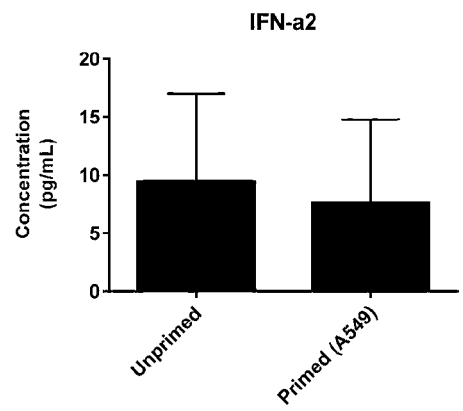
Figure 53C:
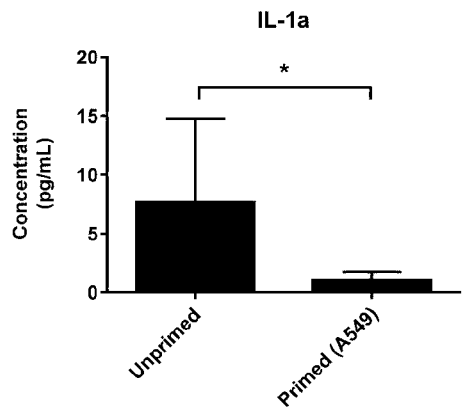
Figure 53D:
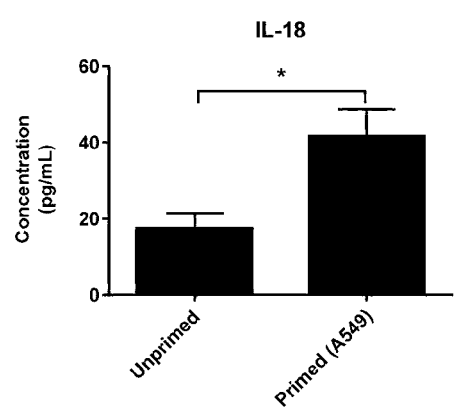
Figure 53E:
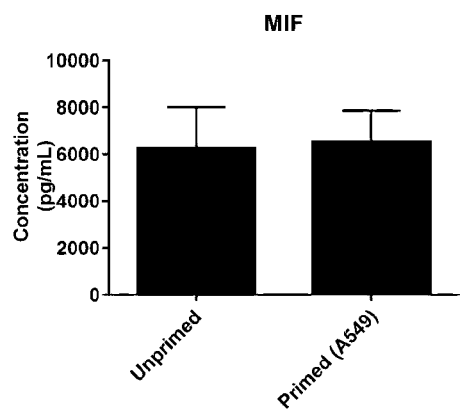
Figure 53F:
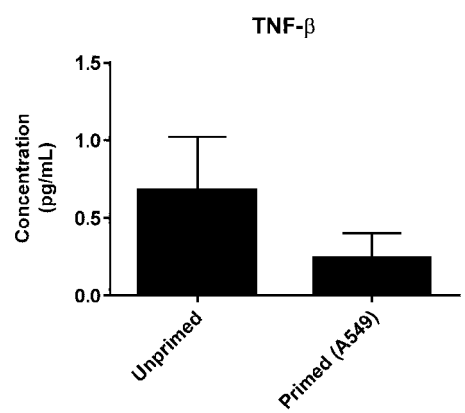
Figure 53G:
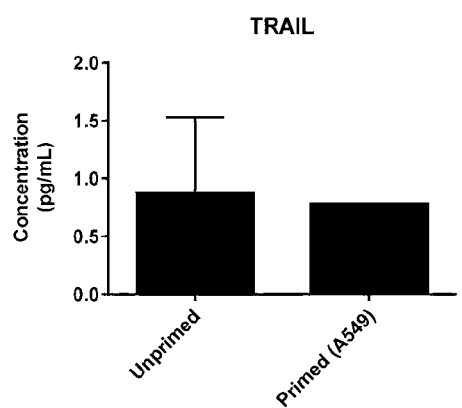
Figure 53H:
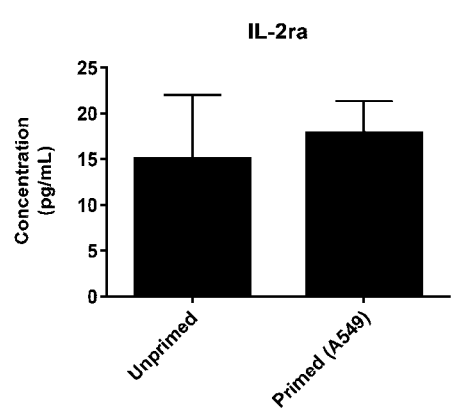
Figure 53I:
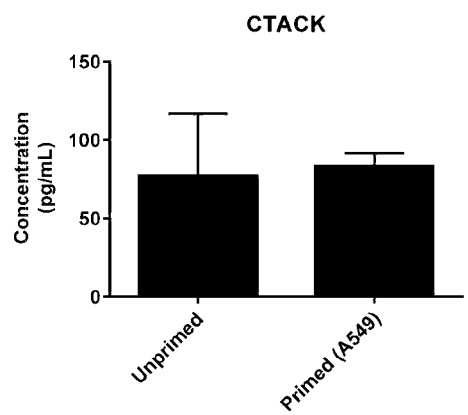
Figure 53J:
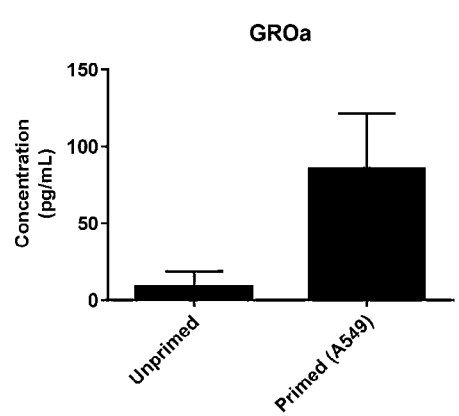
Figure 53K:
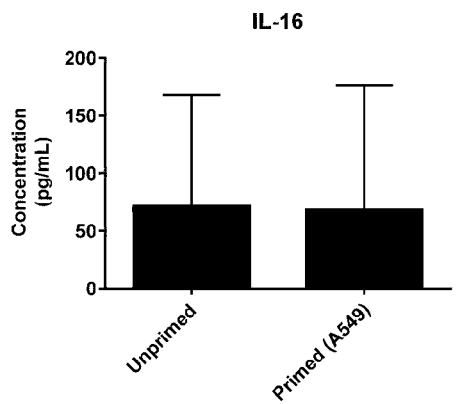
Figure 53L:
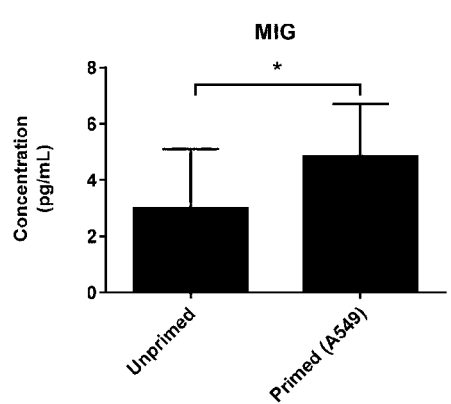
Figure 53M:
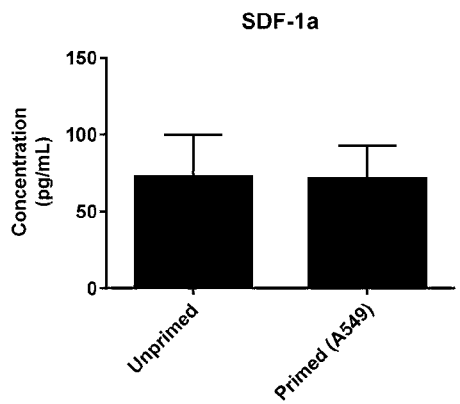
Figure 53N:
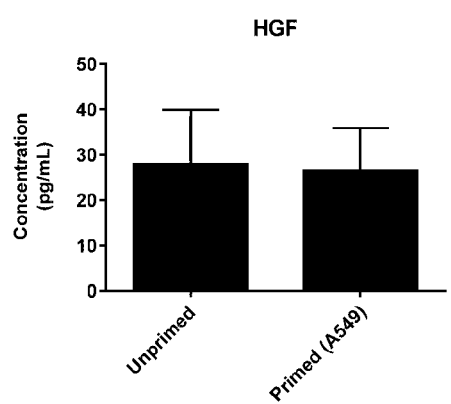
Figure 53O:
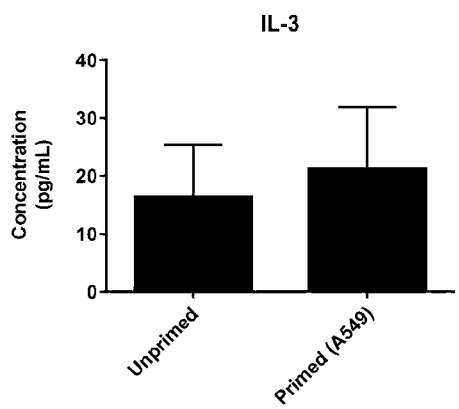
Figure 53P:
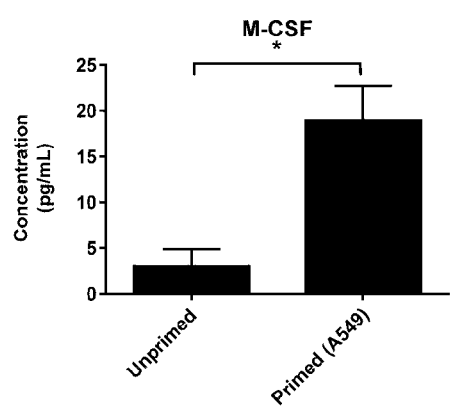
Figure 53Q:
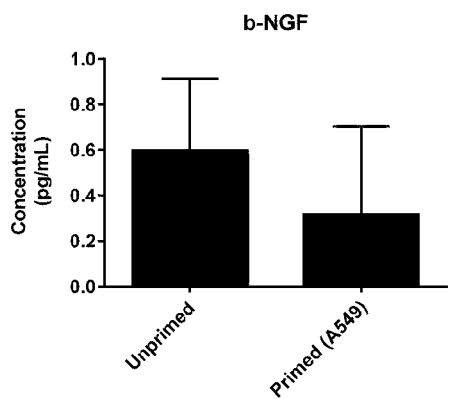
Figure 53R:
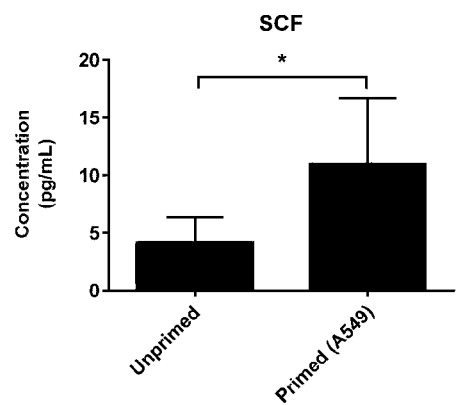
Figure 53S:
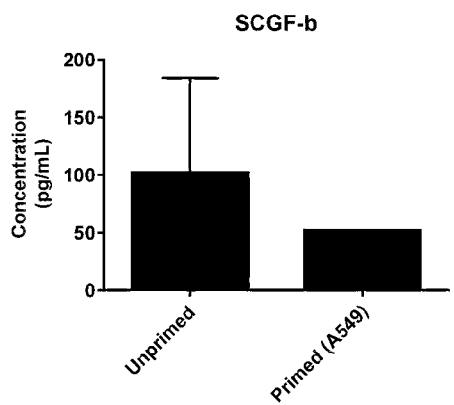
Figure 53T:
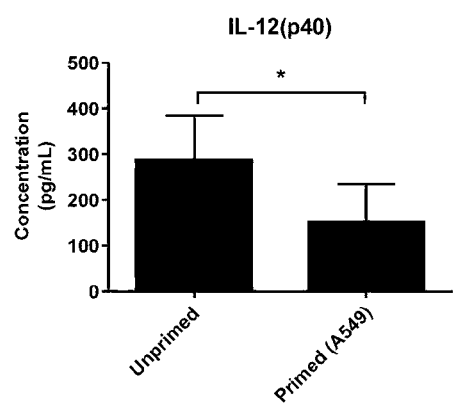
Figure 53U:
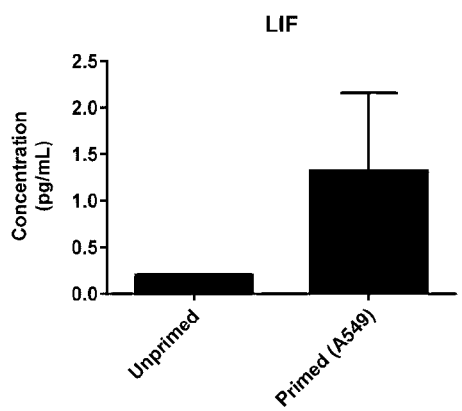

As shown in FIG. 53A-53UU, the cytokine profile of the red blood cells was altered by the 'priming' process, which in this instance was co-culture with A549 cells (lung cancer cell line). The red blood cell concentration of analytes such as IL-8, IL-10, and M-CSF were significantly increased following co-culture priming. Whilst the levels of a few analytes such as IL-1a and IL-12(p40) decreased significantly following co-culture priming. These results demonstrate that the cytokine profile of red blood cells is subject to change depending on their environment. By incubating red blood cells in a protein rich environment, the cells were able to bind and release analytes. The cytokine profile of red blood cells were also modulated (or primed) following incubation with mesenchymal stem cells (data already in priming patent).

Example 14. Other Exemplary Non-Limiting Embodiments

Further advantages of the claimed subject matter will become apparent from the following examples describing certain embodiments of the claimed subject matter.

1. A method for modulating the levels of at least one protein in a subject comprising:
   a.) producing primed red blood cells by contacting red blood cells with at least one agent or at least one condition that modulates the level of one or more red blood cell proteins; and
   b.) administering to the subject one or more primed red blood cell components selected from the group consisting of:
   (i) the primed red blood cells;
   (ii) supernatant obtained from incubation or culture of the primed red blood cells;
   (iii) lysate obtained from the primed red blood cells;
   (iv) membranes obtained from the primed red blood cells; and
   (v) red blood cell ghosts or membranes produced from the primed red blood cells,
   wherein administering the one or more primed red blood cell components to the subject modulates the levels of at least one protein in the subject.
2. The method of example 1, wherein the one or more primed red blood cell components are obtained during priming of the red blood cells and/or after priming of the red blood cells.
3. The method of example 2, wherein the red blood cells are obtained from the subject.
4. The method of example 2, wherein the red blood cells are not obtained from the subject.
5. The method of one or more of examples 1 to 4, wherein the one or more primed red blood cell components administered is the primed red blood cells.

6. The method of one or more of examples 1 to 4, wherein the one or more primed red blood cell components administered is the supernatant obtained from incubation or culture of the primed red blood cells.
7. The method of one or more of examples 1 to 4, wherein the one or more primed red blood cell components administered is lysate obtained from the primed red blood cells.
8. The method of one or more of examples 1 to 4, wherein the one or more primed red blood cell components administered is membranes obtained from the primed red blood cells.
9. The method of one or more of examples 1 to 4, wherein the one or more primed red blood cell components administered is red blood cell ghosts produced from the primed red blood cells.
10. The method of example 1, wherein the at least one agent is one or more agents selected from the group consisting of proteins, enzymes, nucleic acids, protease inhibitors, protein denaturation agents, RNA stabilisers, anticoagulants, and cells.
11. The method of example 10, wherein the at least one agent is selected from the group consisting of protease inhibitors, anti-coagulants, cancer cells, stem cells, and immune cells.
12. The method of example 1, wherein the at least one condition is shear stress, hypoxia, or hyperpoxia.
13. The method of one or more of examples 1 to 12, wherein the red blood cells are obtained from one or more sources selected from the group consisting of at least one subject, at least one cell bank, and at least one cell line.
14. The method of one or more of examples 1 to 12, wherein the subject is a human or a non-human mammal.
15. The method of one or more of examples 1 to 12, wherein the one or more primed red blood cell components are administered to the subject through one or more methods selected from the group consisting of systemically, locally, intravenously, subcutaneously, intraarticularly, intramuscularly, intrathecally, and intraperitoneally.
16. The method of one or more of examples 1 to 12, wherein the one or more red blood cell proteins are selected from the group consisting of chemokines, cytokines, growth factors, receptors, intracellular signal transmitters, hormones, nuclear transcription factors, neurotransmitters, extracellular matrix components, and enzymes.
17. The method of example 16, wherein the one or more red blood cell proteins are cytokines, chemokines, or growth factors.
18. A method of modulating the activity of target cells comprising:
    a.) producing primed red blood cells by contacting red blood cells with at least one agent or condition that modulates the level of one or more red blood cell proteins; and
    b.) mixing the target cells with one or more primed red blood cell components selected from the group consisting of:
    (i) the primed red blood cells;
    (ii) supernatant obtained from incubating or culturing the primed red blood cells;
    (iii) lysate obtained from the primed red blood cells;
    (iv) membranes obtained from the primed red blood cells; and
    (v) red blood cell ghosts or membranes produced from the primed red blood cells,
    wherein mixing the target cells with the one or more primed red blood cell components modulates the activity of the target cells.
19. The method of example 18, wherein the primed red blood cells modulate one or more activities of the target cells selected from the group consisting of cell signaling, immune response, cell development, cell growth, inhibition of cell growth, cell death, and cell repair.
20. The method of example 18, wherein the target cells are one or more selected from the group consisting of immune cells, immortalized cells, cancer cells, stem cells, endothelial cells, fibroblasts, and synovial cells.
21. The method of example 20, wherein the immune cells are one or more selected from the group consisting of T-lymphocytes, B-lymphocytes, monocytes, macrophages, dendritic cells, natural killer cells, neutrophils, eosinophils, and basophils.
22. The method of example 20, wherein the cancer cells are one or more selected from the group consisting of tumor cells, solid tumor cells, disseminated tumor cells, and/or cancerous blood cells.
23. The method of example 20, wherein the stem cells are one or more selected from the group consisting of totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, and mesenchymal stem cells.
24. The method of one or more of examples 18 to 23, wherein the mixing is a process selected from the group consisting of incubating, culturing, co-culturing, and combining the target cells with the primed red blood cells.
25. The method of one or more of examples 18 to 23, wherein the one or more primed red blood cell components administered is the primed red blood cells.
26. The method of one or more of examples 18 to 23, wherein the one or more primed red blood cell components administered is the supernatant obtained from incubation or culture of the primed red blood cells.
27. The method of one or more of examples 18 to 23, wherein the one or more primed red blood cell components administered is lysate obtained from the primed red blood cells.
28. The method of one or more of examples 15 to 20, wherein the one or more primed red blood cell components administered is membranes obtained from the primed red blood cells.
29. The method of one or more of examples 18 to 23, wherein the one or more primed red blood cell components administered is red blood cell ghosts produced from the primed red blood cells.
30. The method of example 24, wherein the target cells are from a subject.
31. The method of example 24, wherein the target cells are within a subject.
32. The method of one or more of examples 18 to 30, wherein the target cells are administered to a subject.
33. The method of one or more of examples 18 to 30, wherein one or more target cell components selected from the group consisting of target cells, target cell ghosts, target cell membranes, target cell lysates, target cell fractions, and supernatant produced by incubating or culturing target cells are administered to a subject.
34. The method of one or more of examples 18 to 30, wherein one or more of the primed red blood cells, primed red blood cell components, target cells and target cell components are administered to the subject.

35. The method of one or more of examples 18 to 30, wherein one or more of the primed red blood cells, primed red blood cell components, target cells or target cell components are administered to the subject by one or more routes selected from the group consisting of systemically, locally, intravenously, subcutaneously, intra-articularly, intramuscularly, intrathecally, and intraperitoneally.

36. The method of one or more of examples 18 to 35, wherein the subject has a disease or disorder.

37. A method of preventing, treating, or ameliorating a disease or disorder comprising administering to a subject in need thereof red blood cells or target cells produced according to one or more of examples 1 to 36.

38. The method of example 37, wherein the red blood cells or target cells are administered to the subject by one or more routes selected from the group consisting of systemically, locally, intravenously, subcutaneously, intra-articularly, intramuscularly, intrathecally, and intraperitoneally.

39. The method of example 37, wherein the subject is a human or non-human mammal.

40. The method of example 37, wherein the subject is a mammal, bird, fish, reptile, or amphibian.

41. The method of example 37, wherein the subject is a human, mouse, rat, hamster, ferret, gerbil, rabbit, monkey, chimpanzee, horse, pony, donkey, sheep, pig, chicken, goat, cat, or dog.

42. The method of example 37, wherein the disease or disorder is selected from the group consisting of cancer, infectious disease, organ failure, autoimmune disease, autoimmune disorders, inflammation, and immune deficiency.

43. A method of priming red blood cells comprising:
    a.) measuring the level of one of more proteins associated with the red blood cells;
    b.) contacting the red blood cells with at least one agent or at least one condition;
    c.) measuring the level of the one or more proteins associated with the red blood cells; and
    d.) comparing the level of the one or more proteins associated with the red blood cells before being contacted with the at least one agent or at least one condition with the level of the one or more proteins associated with the red blood cells after being contacted with the at least one agent or at least one condition,
    wherein a difference in the level of at least one of the one or more proteins associated with red blood cells indicates that the red blood cells have been primed.

44. The method of example 43, wherein the level of one or more proteins, two or more proteins, three of more proteins, four or more proteins, five or more proteins, six or more proteins, seven or more proteins, eight or more proteins, nine or more proteins, ten or more proteins, eleven or more proteins, twelve or more proteins, thirteen or more proteins, fourteen or more proteins, or fifteen or more proteins associated with red blood cells is measured.

45. The method of example 44, wherein the level of three of more proteins associated with red blood cells is measured.

46. The method of one or more of examples 43 to 48, wherein there is a difference in the level of at least one, at least two, at least three, at least four, at least five, at least six, at least seven, at least eight, at least nine, at least ten, at least eleven, at least twelve, at least thirteen, at least fourteen, or at least fifteen of the one or more proteins associated with the red blood cells.

47. The method of example 46, wherein there is a difference in the level of at least three proteins associated with the red blood cells.

48. The method of one or more of examples 43 to 47, wherein the difference in the level of the one or more proteins associated with red blood cells before being contacted with at least one agent or at least one condition compared to the level of the one or more proteins associated with red blood cells after being contacted with at least one agent or at least one conditions is determined by a statistical analysis selected from the group consisting of a Student's T test, an ANOVA test, a mixed-effects model, a Mann-Whitney test, a Wilcoxon rank sum, and a Spearmans rank correlation.

49. The method of one or more of examples 43 to 48, wherein there is an increase and/or decrease in the level of one or more of the proteins associated with red blood cells.

50. The method of one or more of examples 43 to 48, wherein there is an increase and/or decrease in the level of at least one of the one or more proteins associated with the red blood cells.

51. The method of one or more of examples 43 to 48, wherein there is an increase in the level of at least one of the one or more proteins associated with the red blood cells.

52. The method of one or more of examples 43 to 48, wherein there is a decrease in the level of at least one of the one or more proteins associated with the red blood cells.

53. The method of one or more of examples 43 to 48, wherein the level of the one or more proteins associated with red blood cells is measured using one or more antibodies.

54. The method of one or more of examples 43 to 48, wherein the one or more proteins are selected from the group consisting of chemokines, cytokines, growth factors, receptors, intracellular signal transmitters, hormones, nuclear transcription factors, neurotransmitters, and extracellular matrix components, and enzymes.

55. The method of example 54, wherein the one or more proteins are selected from the group consisting of chemokines, cytokines, and growth factors.

56. The method of one or more of examples 43 to 49, wherein the at least one agent is one or more agents selected from the group consisting of proteins, enzymes, nucleic acids, protease inhibitors, protein denaturation agents, RNA stabilizers, anticoagulants, and cells.

57. The method one or more of examples 43 to 49, wherein the at least one condition is shear stress, hypoxia, or hyperoxia.

58. The method of one or more of examples 43 to 57, wherein the primed red blood cells modulate the activity of one or more target cells.

59. The method of one or more of examples 43 to 58, wherein the primed red blood cells are administered to a subject.

60. A method for increasing or decreasing levels of a target protein on or within cells of a subject, the method comprising:
    treating red blood cells (RBC) to increase or decrease levels of a target protein present within the RBC and/or associated with a surface of the RBC, and administering to the subject one or more of:
(i) the RBC after said treating,
(ii) RBC lysate, RBC membranes, and/or RBC ghosts obtained from lysing the RBC during and/or after said treating,
(iii) cell wash obtained from washing the RBC during and/or after said treating,
(iv) culture supernatant obtained from a culture of the RBC generated during and/or after said treating,
(v) combinations of (i)-(iv);
to thereby increase or decrease the levels of the target protein on or within the cells.

61. The method according to example 60, wherein the RBC subjected to said treating are obtained from the subject.
62. The method according to example 60, wherein the RBC subjected to said treating are not obtained from the subject.
63. The method according to one more of examples 60 to 62, wherein the RBC administered to the subject are RBC ghosts.
64. The method according to one or more of examples 60 to 63, wherein said increasing or decreasing levels of a target protein induces or modulates: an immune response, cell development, cell growth, and/or cell repair in the subject.
65. The method according to example 64, wherein said increasing or decreasing levels of a target protein induces or modulates an immune response in the subject.
66. The method according to one or more of examples 60 to 65, wherein:
(i) the RBC
(ii) the RBC lysate, RBC membranes, and/or RBC ghosts
(iii) the cell wash
(iv) the culture supernatant, or
(v) combinations of (i)-(iv);
are administered to the subject systemically, locally, intravenously, subcutaneously, intra-articularly, intramuscularly, intrathecally, and/or intraperitoneally.
67. The method according to one or more of examples 60 to 66, wherein the subject is a mammalian subject, a human subject, or both.
68. A method for inducing or modulating the function of target cells, the method comprising:
treating RBC to increase or decrease levels of a target protein present within or associated with a surface of the RBC; and
mixing the target cells with one or more of:
(i) the RBC after said treating,
(ii) RBC lysate, RBC membranes, and/or RBC ghosts obtained from lysing the RBC during and/or after said treating,
(iii) cell wash obtained from washing the RBC during and/or after said treating,
(iv) culture supernatant obtained from a culture of the RBC generated during and/or after said treating,
(v) combinations of (i)-(iv);
to thereby induce or modulate the function of the target cells.
69. The method according to example 68, wherein the target cells are one or more of immune cells, cancer cells, stem cells, endothelial cells, fibroblasts, synovial cells, and/or myeloid cells.
70. The method according to example 69, wherein the immune cells are one or more of T lymphocytes, B lymphocytes, monocytes, macrophages, dendritic cells, natural killer cells, neutrophils, eosinophils, and/or basophils.
71. The method according to example 69, wherein the cancer cells are one or more of tumour cells, solid tumour cells, disseminated tumour cells, and/or cancerous blood cells.
72. The method according to example 69, wherein the stem cells are one or more of: totipotent stem cells, pluripotent stem cells, multipotent stem cells, tissue stem cells, embryonic stem cells, human embryonic stem cells (HeSC), somatic stem cells, hematopoietic stem cells (e.g. from umbilical cord blood, bone marrow), bone marrow stromal stem cells (skeletal stem cells), induced pluripotent stem cells (IPSO), epidermal stem cells, epithelial stem cells, mesenchymal stem cells, neural stem cells, mesenchymal stem cells, and/or combinations thereof.
73. The method according to example 69 or example 72, wherein the target cells are stem cells and said mixing primes the stem cells towards a specific cell lineage.
74. The method according to one or more of examples 68 to 73, further comprising administering to a subject suffering from or susceptible to developing a given disease or disorder:
(i) the target cells after said mixing,
(ii) target cell lysate, target cell membranes, and/or target cell ghosts obtained from lysing the target cells during and/or after said treating,
(i) cell wash obtained from washing the target cells during and/or after said treating,
(ii) culture supernatant obtained from a culture of the target cells generated during and/or after said treating,
(iii) combinations of (i)-(iv).
75. The method according to example 74, wherein:
(i) the target cells,
(ii) the target cell lysate, target cell membranes, and/or target cell ghosts,
(iii) the target cell wash,
(iv) the target cell culture supernatant, or
(v) combinations of (i)-(iv);
are administered to the subject systemically, locally, intravenously, subcutaneously, intra-artcularly, intramuscularly, intrathecally, and/or intraperitoneally.
76. The method according to example 74 or example 75, further comprising administering to the subject:
(i) the RBC,
(ii) the RBC lysate, RBC membranes, and/or RBC ghosts,
(iii) the cell wash,
(iv) the culture supernatant, or
(v) combinations of (i)-(iv).
77. 18. The method according to example 76, wherein:
(i) the RBC,
(ii) the RBC lysate, RBC membranes, and/or RBC ghosts,
(iii) the cell wash,
(iv) the culture supernatant, or
(v) combinations of (i)-(iv);
are administered to the subject systemically, locally, intravenously, subcutaneously, intra-artcularly, intramuscularly, intrathecally, and/or intraperitoneally.
78. The method according to example 76 or example 77, wherein:
(i) the target cells,
(ii) the target cell lysate, target cell membranes, and/or target cell ghosts,
(iii) the target cell wash,
(iv) the target cell culture supernatant, or
(v) combinations of (i)-(iv);
are administered to the subject locally, and
(i) the RBC,
(ii) the RBC lysate, RBC membranes, and/or RBC ghosts,
(iii) the cell wash, (iv) the culture supernatant, or
(v) combinations of (i)-(iv);
are administered to the subject systemically or locally.

79. The method according to one or more of examples 74 to 78, wherein the subject is a mammalian subject, a human subject, or both.
80. The method according to one or more of examples 74 to 80, wherein the subject is suffering from a tissue injury, cancer, an inflammatory disease or condition, or an immune disorder.
81. The method according to one or more of examples 68 to 80, wherein the RBC and/or the target cells are obtained from the subject.
82. The method according to one or more of examples 68 to 80, wherein the RBC and/or the target cells are not obtained from the subject.
83. The method according to one or more of examples 60 to 82, wherein said treating comprises one or more of:
    contacting the red blood cells with a protease inhibitor,
    contacting the red blood cells with an anticoagulant,
    lysing the red blood cells,
    subjecting the red blood cells to shear stress,
    treating the red blood cells with oxygen,
    depriving the red blood cells of oxygen.
84. The method according to example 83, wherein the protease inhibitor is selected from the group consisting of: aprotinin, leupeptin, α2-macroglobulin, antipain dihydrochloride, calpain inhibitor I, calpain inhibitor II, chymostatin, TLCK (CAS 131918-97-3), trypsin-inhibitor, Pefabloc SC (Roche), PMSF (C6H5CH2SO2F—Thermo Fisher Scientific), complete protease inhibitor cocktail (Roche), and combinations thereof.
85. The method according to example 83, wherein the anticoagulant is selected from the group consisting of: heparin, citrate, acid citrate dextrose, EDTA, and combinations thereof.
86. The method according to one or more of examples 60 to 85, wherein the target protein is one or more of: a cytokine, a chemokine, or a growth factor.
87. The method according to one or more of examples 60 to 86, wherein the target protein is an inflammatory cytokine or an inflammatory chemokine.
88. The method according to one or more of examples 60 to 87, wherein said levels of the target protein are increased.
89. The method according to example 88, wherein the target protein is selected from the group consisting of: CTACK, GRO-α, βFGF, G-CSF, CM-CSF, HGF, IFN-α2, IFN-γ, IL-1α, IL-1β, IL-2, IL-2rα, IL-3, IL-4, IL-5, IL-6, IL-7, IL-8, IL-9, IL-10, IL-12-40, IL-12p70, IL-13, IL-15, IL-16, IL-17, IL-18, IP-10, LIF, MCP-1, M-CSF, MIF, MIG, MIP-1α, MIP-1β, β-NGF, PDGF-bb, RANTES, SDF-1α, TNF-α, TNF-β, TRAIL, VEGF, and combinations thereof.
90. The method according to one or more of examples 60 to 87, wherein said levels of the target protein are decreased.
91. The method according to example 90, wherein the target protein is selected from the group consisting of: IFN-α2, IFN-γ, IL-1β, IL-8, IL-9, IL-12p70, IL-16, IL17, IL-18, MIF, TNF-α, IL-2rα, IL-4, CTACK, GRO-α, IL-18, MCP-1, MIP-1 GRO-α, MIP-1β, RANTES, SDF-1α, βFGF, G-CSF, GM-CSF, HGF, IL-3, IP-10, M-CSF, PDFG-bb, VEGF, IL-2, IL-6, IL-12p40, and combinations thereof.
92. The method according to one or more of examples 60 to 91, wherein the method is used as an adjunct therapy.
93. The method according to example 92, wherein the method is used as an adjunct therapy for treatment of tissue injury, cancer, an inflammatory disease or condition, and/or an immune disorder.

What is claimed is:

1. A method of modulating the activity of target cells comprising:
   a) producing primed red blood cells by contacting red blood cells with at least one agent that modulates the level of one or more proteins associated with the red blood cells, wherein the at least one agent is a cell, and wherein the one or more proteins associated with the red blood cells is selected from the group consisting of basic FGF, Eotaxin, G-CSF, GM-CSF, IFN-γ, IL1ra, IL-2, IL-4, IL-5, IL-6, IL-7, IL-8, IL-9, IL-10, IL-12 (p70), IL-13, IL-15, IL-17, IP-10, MCP-1, MIP-1α, MIP-1β, PDGF-BB, RANTES, TNF-α, VEGF, IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, and TRAIL;
   b) separating the primed red blood cells from the at least one agent; and
   c) mixing the target cells with one or more primed red blood cell components selected from the group consisting of:
      (i) the separated primed red blood cells;
      (ii) supernatant obtained from incubating or culturing the separated primed red blood cells;
      (iii) lysate obtained from the separated primed red blood cells;
      (iv) membranes obtained from the separated primed red blood cells; and
      (v) red blood cell ghosts produced from the separated primed red blood cells;
   wherein mixing the target cells with the one or more separated primed red blood cell components modulates the activity of the target cells.

2. The method of claim 1, wherein the primed red blood cells modulate one or more activities of the target cells selected from the group consisting of cell signaling, immune response, cell development, cell growth, cell death, inhibition of cell growth, and cell repair.

3. The method of claim 2, wherein the target cells are one or more selected from the group consisting of immune cells, immortalized cells, cancer cells, stem cells, endothelial cells, fibroblasts, and synovial cells.

4. The method of claim 1, wherein the target cells are from a subject.

5. The method of claim 1, wherein the modulated target cells or target cell components from said modulated target cells are administered to a subject.

6. The method of claim 5, wherein one or more of the modulated target cells or the target cell components from said modulated target cells are administered to the subject are selected from the group consisting of target cell ghosts, target cell membranes, target cell lysates, and supernatant produced by incubating or culturing target cells.

7. The method of claim 6, wherein said subject has a disease or disorder selected from the group consisting of cancer, infectious disease, organ failure, autoimmune disease, autoimmune disorders, inflammation, and immune deficiency.

8. The method of claim 7, wherein administration of the one or more of the modulated target cells or the target cell components from said modulated target cells treats the disease or disorder in said subject.

9. The method of claim 5, wherein one or more of the modulated target cells or the target cell components from said modulated target cells are administered to the subject by one or more routes selected from the group consisting of systemically, locally, intravenously, subcutaneously, intraarticularly, intramuscularly, intrathecally, and intraperitoneally.

10. The method of claim 5, wherein the subject has a disease or disorder selected from the group consisting of cancer, infectious disease, organ failure, autoimmune disease, autoimmune disorders, inflammation, and immune deficiency.

11. The method of claim 1, wherein the one of more proteins associated with the red blood cells is selected from the group consisting of basic FGF, Eotaxin, G-CSF, GM-CSF, IFN-γ, IL-1β, IL1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF.

12. The method of claim 1, wherein the one of more proteins associated with the red blood cells is selected from the group consisting of IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, and TRAIL.

13. The method of claim 1, wherein at least one of the one or more proteins associated with the red blood cells is selected from the group consisting of Eotaxin, GM-CSF, IFN-γ, IL-1ß, IL1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1ß, RANTES, TNF-α, IL-1α, IL-2Ra, IL-3, IL-12, IL-16, IL-18, CTACK, Gro-α, IFN-α2, LIF, MCP-3, M-CSF, MIF, MIG, SCF, SDF-1α, TNF-ß, and TRAIL.

14. The method of claim 13, wherein at least one of the one or more proteins associated with the red blood cells is selected from the group consisting of IFN-γ, IL-1ß, IL1ra, IL-2, IL-4, IL-5, IL-6, 11-7, IL-8, IL-9, IL-10, IL-12(p70), IL-13, IL-15, IL-17, IP-10, MCP-1, MIP-1α, MIP-1ß, RANTES, TNF-α, IL-1α, IL-2Ra, IL-3, IL12, IL-16, IL18, CTACK, Gro-α, IFN-α2, LIF, MCP-3, M-CSF, MIF, MIG, SCF, SDF-1α, TNF-ß, and TRAIL.

15. The method of claim 1, wherein at least one of the one or more proteins associated with the red blood cells is selected from the group consisting of basic FGF, G-CSF, IL1ra, IL-5, PDGF-BB, VEGF, HGF, β—NGF, and SCGF—β.

* * * * *